(12) United States Patent
Beaudenon-Huibregtse et al.

(10) Patent No.: US 9,080,215 B2
(45) Date of Patent: *Jul. 14, 2015

(54) MICRORNAS DIFFERENTIALLY EXPRESSED IN CERVICAL CANCER AND USES THEREOF

(71) Applicant: Asuragen, Inc., Austin, TX (US)

(72) Inventors: Sylvie Beaudenon-Huibregtse, Austin, TX (US); Emmanuel Labourier, Austin, TX (US); Laura Elizondo, Austin, TX (US)

(73) Assignee: Asuragen, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/735,760

(22) Filed: Jan. 7, 2013

(65) Prior Publication Data
US 2013/0184175 A1    Jul. 18, 2013

Related U.S. Application Data

(63) Continuation of application No. 12/209,822, filed on Sep. 12, 2008, now Pat. No. 8,361,714.

(60) Provisional application No. 60/972,646, filed on Sep. 14, 2007.

(51) Int. Cl.
*C12Q 1/68* (2006.01)

(52) U.S. Cl.
CPC ........ *C12Q 1/6886* (2013.01); *C12Q 2600/106* (2013.01); *C12Q 2600/112* (2013.01); *C12Q 2600/178* (2013.01)

(58) Field of Classification Search
USPC .................... 435/6, 91.1, 325, 375
See application file for complete search history.

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,876,187 A | 10/1989 | Duck et al. | 435/6 |
| 4,999,290 A | 3/1991 | Lee | 435/6 |
| 5,011,769 A | 4/1991 | Duck et al. | 435/6 |
| 5,188,934 A | 2/1993 | Menchen et al. | 435/6 |
| 5,256,555 A | 10/1993 | Milburn et al. | 435/195 |
| 5,260,191 A | 11/1993 | Yang | 435/6 |
| 5,262,311 A | 11/1993 | Pardee et al. | 435/91.2 |
| 5,366,860 A | 11/1994 | Bergot et al. | 435/6 |
| 5,432,272 A | 7/1995 | Benner | 536/25.3 |

(Continued)

FOREIGN PATENT DOCUMENTS

| | | |
|---|---|---|
| EP | 0416817 | 3/1991 |
| EP | 0870842 | 10/1998 |

(Continued)

OTHER PUBLICATIONS

Aaboe et al. "Vitronectin in human breast carcinomas," *Biochem. Biophys. Acta.*, 1638 (I): 72-82, 2003.

(Continued)

*Primary Examiner* — Terra C Gibbs
(74) *Attorney, Agent, or Firm* — Fulbright & Jaworski US LLP

(57) ABSTRACT

The present invention concerns methods and compositions for identifying a miRNA profile for a particular condition, such as cervical disease, and using the profile in assessing the condition of a patient.

19 Claims, 5 Drawing Sheets

(56) References Cited

U.S. PATENT DOCUMENTS

| | | | |
|---|---|---|---|
| 5,486,603 A | 1/1996 | Buhr | 536/24.3 |
| 5,538,848 A | 7/1996 | Livak et al. | 435/5 |
| 5,543,296 A | 8/1996 | Sobol et al. | 435/6 |
| 5,545,522 A | 8/1996 | Van Gelder et al. | 435/6 |
| 5,660,988 A | 8/1997 | Duck et al. | 435/6 |
| 5,723,591 A | 3/1998 | Livak et al. | 536/22.1 |
| 5,739,169 A | 4/1998 | Ocain et al. | 514/658 |
| 5,766,888 A | 6/1998 | Sobol et al. | 435/91.2 |
| 5,800,996 A | 9/1998 | Lee et al. | 435/6 |
| 5,801,005 A | 9/1998 | Cheever et al. | 435/724 |
| 5,801,155 A | 9/1998 | Kutyavin et al. | 514/44 |
| 5,824,311 A | 10/1998 | Greene et al. | 424/438.1 |
| 5,830,880 A | 11/1998 | Sedlacek et al. | 514/44 |
| 5,847,162 A | 12/1998 | Lee et al. | 549/227 |
| 5,859,221 A | 1/1999 | Cook et al. | 536/23.1 |
| 5,861,245 A | 1/1999 | McClelland et al. | 435/6 |
| 5,863,727 A | 1/1999 | Lee et al. | 435/6 |
| 5,871,697 A | 2/1999 | Rothberg et al. | 422/68.1 |
| 5,898,031 A | 4/1999 | Crooke | 435/172.3 |
| 5,925,517 A | 7/1999 | Tyagi et al. | 435/6 |
| 5,936,087 A | 8/1999 | Benson et al. | 546/33 |
| 5,942,398 A | 8/1999 | Tartaglia et al. | 435/6 |
| 5,945,526 A | 8/1999 | Lee et al. | 536/26.6 |
| 5,965,364 A | 10/1999 | Benner | 435/6 |
| 5,976,567 A | 11/1999 | Wheeler et al. | 424/450 |
| 5,998,203 A | 12/1999 | Matulic-Adamic et al. | 435/325 |
| 6,001,983 A | 12/1999 | Benner | 536/23.1 |
| 6,004,755 A | 12/1999 | Wang | 435/6 |
| 6,008,379 A | 12/1999 | Benson et al. | 549/224 |
| 6,020,481 A | 2/2000 | Benson et al. | 536/26.6 |
| 6,037,129 A | 3/2000 | Cole et al. | 435/6 |
| 6,040,138 A | 3/2000 | Lockhart et al. | 435/6 |
| 6,051,719 A | 4/2000 | Benson et al. | 548/416 |
| 6,057,105 A | 5/2000 | Hoon et al. | 435/6 |
| 6,084,102 A | 7/2000 | Kutyavin et al. | 548/100 |
| 6,096,314 A | 8/2000 | Cohen et al. | 424/185.1 |
| 6,103,476 A | 8/2000 | Tyagi et al. | 435/6 |
| 6,107,094 A | 8/2000 | Crooke | 435/455 |
| 6,111,095 A | 8/2000 | Benseler et al. | 536/25.3 |
| 6,132,997 A | 10/2000 | Shannon | 435/91.21 |
| 6,140,054 A | 10/2000 | Wittwer et al. | 435/6 |
| 6,140,500 A | 10/2000 | Yan et al. | 544/99 |
| 6,150,097 A | 11/2000 | Tyagi et al. | 435/6 |
| 6,153,737 A | 11/2000 | Manoharan et al. | 536/22.1 |
| 6,174,670 B1 | 1/2001 | Wittwer et al. | 435/6 |
| 6,184,037 B1 | 2/2001 | Rolland et al. | 435/455 |
| 6,191,278 B1 | 2/2001 | Lee et al. | 546/41 |
| 6,232,066 B1 | 5/2001 | Felder et al. | 435/6 |
| 6,238,869 B1 | 5/2001 | Kris et al. | 435/6 |
| 6,287,792 B1 | 9/2001 | Pardridge et al. | 435/7.5 |
| 6,344,316 B1 | 2/2002 | Lockhart et al. | 435/6 |
| 6,355,421 B1 | 3/2002 | Coull et al. | 435/6 |
| 6,383,752 B1 | 5/2002 | Agrawal et al. | 435/6 |
| 6,418,382 B2 | 7/2002 | Rothberg et al. | 702/20 |
| 6,435,245 B1 | 8/2002 | Sette et al. | 156/745 |
| 6,458,382 B1 | 10/2002 | Herweijer et al. | 424/450 |
| 6,458,533 B1 | 10/2002 | Felder et al. | 435/6 |
| 6,476,205 B1 | 11/2002 | Buhr | 536/23.1 |
| 6,485,901 B1 | 11/2002 | Gildea et al. | 435/5 |
| 6,506,559 B1 | 1/2003 | Fire et al. | 435/6 |
| 6,511,832 B1 | 1/2003 | Guarino et al. | 435/91.1 |
| 6,548,250 B1 | 4/2003 | Sorge | |
| 6,573,048 B1 | 6/2003 | VanAtta et al. | 435/6 |
| 6,573,099 B2 | 6/2003 | Graham | 435/455 |
| 6,586,218 B2 | 7/2003 | Milburn et al. | 435/195 |
| 6,586,219 B2 | 7/2003 | Milburn et al. | 435/195 |
| 6,589,743 B2 | 7/2003 | Sorge | 435/6 |
| 6,590,091 B2 | 7/2003 | Albagli et al. | 536/24.3 |
| 6,593,091 B2 | 7/2003 | Keys et al. | 435/6 |
| 6,596,490 B2 | 7/2003 | Dattagupta | 435/6 |
| 6,706,480 B1 | 3/2004 | Armour | 435/6 |
| 6,720,138 B2 | 4/2004 | Sharma et al. | 435/6 |
| 6,723,509 B2 | 4/2004 | Ach | 435/6 |
| 6,730,477 B1 | 5/2004 | Sun et al. | 435/6 |
| 6,787,335 B2 | 9/2004 | Salceda et al. | 435/69.1 |
| 6,797,471 B2 | 9/2004 | Katz et al. | 435/6 |
| 6,815,432 B2 | 11/2004 | Wheeler et al. | 514/44 |
| 6,858,225 B2 | 2/2005 | Semple et al. | 424/450 |
| 6,964,847 B1 | 11/2005 | Englert | 435/6 |
| 6,967,016 B2 | 11/2005 | Van Gemen et al. | 424/9.2 |
| 6,998,268 B2 | 2/2006 | Terada et al. | 435/455 |
| 7,001,724 B1 | 2/2006 | Greenfield | 435/6 |
| 7,005,261 B1 | 2/2006 | Lloyd et al. | 435/6 |
| 7,014,838 B2 | 3/2006 | Mueller et al. | 424/1.69 |
| 7,015,047 B2 | 3/2006 | Huang et al. | 436/526 |
| 7,056,704 B2 | 6/2006 | Tuschl et al. | 435/91.1 |
| 7,078,180 B2 | 7/2006 | Genetta | 435/7.23 |
| 7,078,196 B2 | 7/2006 | Tuschl et al. | 435/91.1 |
| 7,109,167 B2 | 9/2006 | Von Wronski et al. | 514/12 |
| 7,141,372 B2 | 11/2006 | Spivack et al. | 435/6 |
| 7,171,311 B2 | 1/2007 | Dai et al. | 702/219 |
| 7,192,586 B2 | 3/2007 | Bander | 424/155.1 |
| 7,205,105 B2 | 4/2007 | Afonina et al. | 435/6 |
| 7,232,806 B2 | 6/2007 | Tuschl et al. | 514/44 |
| 7,282,564 B2 | 10/2007 | Mello et al. | 530/350 |
| 7,297,480 B2 | 11/2007 | Vogt | 435/6 |
| 7,306,906 B2 | 12/2007 | Maruyama et al. | 435/6 |
| 7,307,067 B2 | 12/2007 | Sarnow et al. | 514/44 |
| 7,354,725 B2 | 4/2008 | Muraca | 435/7.1 |
| 7,365,058 B2 | 4/2008 | Stoffel et al. | 514/44 |
| 7,368,098 B2 | 5/2008 | Mueller et al. | 424/1.49 |
| 7,390,792 B2 | 6/2008 | Srivastava et al. | 514/44 |
| 7,402,389 B2 | 7/2008 | Mousses et al. | 435/6 |
| 7,452,987 B2 | 11/2008 | Giese et al. | 536/24.5 |
| 7,459,547 B2 | 12/2008 | Zamore et al. | 536/24.5 |
| 7,473,525 B2 | 1/2009 | Kreutzer et al. | 435/6 |
| 7,495,073 B2 | 2/2009 | Hsu et al. | 530/350 |
| 7,582,744 B2 | 9/2009 | Manoharan et al. | 536/24.5 |
| 7,592,441 B2 | 9/2009 | Bentwich et al. | 536/24.5 |
| 7,642,348 B2 | 1/2010 | Bentwich et al. | 536/24.5 |
| 7,655,785 B1 | 2/2010 | Bentwich | 536/24.1 |
| 7,683,036 B2 | 3/2010 | Esau et al. | 514/44 |
| 7,723,510 B1 | 5/2010 | Tuschl et al. | 536/24.5 |
| 2002/0006630 A1 | 1/2002 | Sirbasku | 514/1 |
| 2002/0037540 A1 | 3/2002 | Ali et al. | 424/1.49 |
| 2002/0065396 A1 | 5/2002 | Yang et al. | 424/1.49 |
| 2002/0065406 A1 | 5/2002 | Meyers | 435/6 |
| 2002/0068307 A1 | 6/2002 | Pluta et al. | 435/7.23 |
| 2002/0086356 A1 | 7/2002 | Tuschl et al. | 435/69.1 |
| 2002/0094546 A1 | 7/2002 | Shimkets et al. | 435/69.4 |
| 2002/0119156 A1 | 8/2002 | Chen et al. | 424/155.1 |
| 2002/0165189 A1 | 11/2002 | Crooke | 514/44 |
| 2003/0009295 A1 | 1/2003 | Markowitz et al. | 702/20 |
| 2003/0027783 A1 | 2/2003 | Zernicka-Goetz et al. | 514/44 |
| 2003/0031678 A1 | 2/2003 | Ali et al. | 424/185.1 |
| 2003/0033614 A1 | 2/2003 | French et al. | 800/3 |
| 2003/0084471 A1 | 5/2003 | Beach et al. | 800/278 |
| 2003/0099976 A1 | 5/2003 | Chang | 435/6 |
| 2003/0108923 A1 | 6/2003 | Tuschl et al. | 435/6 |
| 2003/0124114 A1 | 7/2003 | McIntire et al. | 424/94.63 |
| 2003/0157030 A1 | 8/2003 | Davis et al. | 424/46 |
| 2003/0170623 A1 | 9/2003 | Chen et al. | 435/6 |
| 2003/0175768 A1 | 9/2003 | Carson et al. | 435/6 |
| 2003/0180298 A1 | 9/2003 | Old et al. | 424/144.1 |
| 2003/0204322 A1 | 10/2003 | Loehrlein et al. | 702/20 |
| 2003/0215842 A1 | 11/2003 | Sledziewski et al. | 435/6 |
| 2004/0001841 A1 | 1/2004 | Nagavarapu et al. | 424/178.1 |
| 2004/0010001 A1 | 1/2004 | Au et al. | 514/283 |
| 2004/0029121 A1 | 2/2004 | Cottrell et al. | 435/6 |
| 2004/0029128 A1 | 2/2004 | Cottrell et al. | 435/6 |
| 2004/0053411 A1 | 3/2004 | Cullen et al. | 514/44 |
| 2004/0058373 A1 | 3/2004 | Winkler et al. | 435/91.2 |
| 2004/0063197 A1 | 4/2004 | Tilles et al. | 435/287.2 |
| 2004/0063654 A1 | 4/2004 | Davis et al. | 514/44 |
| 2004/0072164 A1 | 4/2004 | Maruyama et al. | 435/6 |
| 2004/0086504 A1 | 5/2004 | Sampath et al. | 424/143.1 |
| 2004/0110191 A1 | 6/2004 | Winkler et al. | 435/6 |
| 2004/0114800 A1 | 6/2004 | Ponomarev et al. | 382/173 |
| 2004/0115630 A1 | 6/2004 | Olek et al. | 435/6 |
| 2004/0115671 A1 | 6/2004 | Zlokovic et al. | 435/6 |
| 2004/0147027 A1 | 7/2004 | Troy et al. | 435/458 |
| 2004/0152112 A1 | 8/2004 | Croce et al. | 435/6 |
| 2004/0166511 A1 | 8/2004 | Clasina Timmermans et al. | 435/6 |

(56) References Cited

U.S. PATENT DOCUMENTS

| | | | |
|---|---|---|---|
| 2004/0175732 A1 | 9/2004 | Rana | 435/6 |
| 2004/0203145 A1 | 10/2004 | Zamore et al. | 435/375 |
| 2004/0214198 A1 | 10/2004 | Rana | 435/6 |
| 2004/0215651 A1 | 10/2004 | Markowitz et al. | 707/102 |
| 2004/0224337 A1 | 11/2004 | Foehr et al. | 435/6 |
| 2004/0229211 A1 | 11/2004 | Yeung | 435/5 |
| 2004/0236516 A1 | 11/2004 | Brandon | 702/20 |
| 2004/0243362 A1 | 12/2004 | Liebman | 703/2 |
| 2004/0259247 A1 | 12/2004 | Tuschl et al. | 435/375 |
| 2005/0020521 A1 | 1/2005 | Rana | 514/44 |
| 2005/0026278 A1 | 2/2005 | Tuschl et al. | 435/375 |
| 2005/0033030 A1 | 2/2005 | Lo et al. | 530/388.15 |
| 2005/0037362 A1 | 2/2005 | Remacle et al. | 435/6 |
| 2005/0059024 A1 | 3/2005 | Conrad | 435/6 |
| 2005/0065333 A1 | 3/2005 | Seth | 536/23.5 |
| 2005/0074788 A1 | 4/2005 | Dahlberg et al. | 435/6 |
| 2005/0075492 A1 | 4/2005 | Chen et al. | 536/23.1 |
| 2005/0095646 A1 | 5/2005 | Sherman | 435/7.1 |
| 2005/0112604 A1 | 5/2005 | Fujimoto et al. | 435/6 |
| 2005/0125161 A1 | 6/2005 | Cairney et al. | 702/20 |
| 2005/0130170 A1 | 6/2005 | Harvey et al. | 435/6 |
| 2005/0130172 A1 | 6/2005 | Beard et al. | 435/6 |
| 2005/0142556 A1 | 6/2005 | Hoon et al. | 435/6 |
| 2005/0153337 A1 | 7/2005 | Manoharan | 435/6 |
| 2005/0176018 A1 | 8/2005 | Thompson et al. | 435/6 |
| 2005/0181382 A1 | 8/2005 | Zamore et al. | 435/6 |
| 2005/0182005 A1 | 8/2005 | Tuschl et al. | 514/44 |
| 2005/0186586 A1 | 8/2005 | Zamore et al. | 435/6 |
| 2005/0208493 A1 | 9/2005 | Alon | 435/6 |
| 2005/0234006 A1 | 10/2005 | Tuschl et al. | 514/44 |
| 2005/0234007 A1 | 10/2005 | Tuschl et al. | 514/44 |
| 2005/0261218 A1 | 11/2005 | Esau et al. | 514/44 |
| 2005/0266418 A1 | 12/2005 | Chen et al. | 435/6 |
| 2005/0287539 A1 | 12/2005 | Pasloske et al. | 435/6 |
| 2006/0051768 A1 | 3/2006 | Hoon et al. | 435/6 |
| 2006/0078894 A1 | 4/2006 | Winkler et al. | 435/6 |
| 2006/0088521 A1 | 4/2006 | Mahadevan | 424/133.1 |
| 2006/0095980 A1 | 5/2006 | Petitte et al. | 800/19 |
| 2006/0105350 A1 | 5/2006 | Qiao et al. | 435/6 |
| 2006/0105360 A1 | 5/2006 | Croce et al. | 435/6 |
| 2006/0134639 A1 | 6/2006 | Huffel et al. | 435/6 |
| 2006/0134661 A1 | 6/2006 | Essner | 435/6 |
| 2006/0154275 A1 | 7/2006 | Sgarlato et al. | 435/6 |
| 2006/0165659 A1 | 7/2006 | Croce et al. | 424/93.2 |
| 2006/0183128 A1 | 8/2006 | Berlin et al. | 435/6 |
| 2006/0185026 A1 | 8/2006 | Sacktor et al. | 800/12 |
| 2006/0185027 A1 | 8/2006 | Bartel et al. | 800/14 |
| 2006/0189557 A1 | 8/2006 | Slack et al. | 514/44 |
| 2006/0195269 A1 | 8/2006 | Yeatman et al. | 702/20 |
| 2006/0210979 A1 | 9/2006 | Yang et al. | 435/6 |
| 2006/0247193 A1 | 11/2006 | Taira et al. | 514/44 |
| 2006/0252057 A1 | 11/2006 | Raponi et al. | 435/6 |
| 2006/0258566 A1 | 11/2006 | Von Wronski et al. | 514/7 |
| 2006/0271309 A1 | 11/2006 | Showe et al. | 702/20 |
| 2006/0292616 A1 | 12/2006 | Neely et al. | 435/6 |
| 2007/0003960 A1 | 1/2007 | Tuschl et al. | 435/6 |
| 2007/0003961 A1 | 1/2007 | Tuschl et al. | 435/6 |
| 2007/0003962 A1 | 1/2007 | Tuschl et al. | 435/6 |
| 2007/0003963 A1 | 1/2007 | Tuschl et al. | 435/6 |
| 2007/0009484 A1 | 1/2007 | Hunt et al. | 424/450 |
| 2007/0025997 A1 | 2/2007 | Nagavarapu et al. | 424/155.1 |
| 2007/0031840 A1 | 2/2007 | Klussmann et al. | 435/6 |
| 2007/0031873 A1 | 2/2007 | Wang et al. | 435/6 |
| 2007/0041934 A1 | 2/2007 | William et al. | 424/78.3 |
| 2007/0048758 A1 | 3/2007 | Lokhov et al. | 435/6 |
| 2007/0050146 A1 | 3/2007 | Bentwich et al. | 702/19 |
| 2007/0054287 A1 | 3/2007 | Bloch | 435/6 |
| 2007/0065844 A1 | 3/2007 | Golub et al. | 435/6 |
| 2007/0072204 A1 | 3/2007 | Hannon et al. | 435/6 |
| 2007/0093445 A1 | 4/2007 | Tuschl et al. | 514/44 |
| 2007/0099196 A1 | 5/2007 | Kauppinen et al. | 435/6 |
| 2007/0161004 A1 | 7/2007 | Brown et al. | 435/6 |
| 2007/0213292 A1 | 9/2007 | Stoffel et al. | 514/44 |
| 2007/0259827 A1 | 11/2007 | Aronin et al. | 514/44 |
| 2007/0287179 A1 | 12/2007 | Tuschl et al. | 435/455 |
| 2007/0299030 A1 | 12/2007 | Dmitrovsky et al. | 514/44 |
| 2008/0026951 A1 | 1/2008 | Brown et al. | 435/6 |
| 2008/0050744 A1 | 2/2008 | Brown et al. | 536/24.5 |
| 2008/0076674 A1 | 3/2008 | Litman et al. | 506/9 |
| 2008/0131878 A1 | 6/2008 | Latham et al. | 435/200 |
| 2008/0132461 A1 | 6/2008 | Tuschi et al. | 514/44 |
| 2008/0171667 A1 | 7/2008 | Brown et al. | 536/24.5 |
| 2008/0171715 A1 | 7/2008 | Brown et al. | 514/44 |
| 2008/0176766 A1 | 7/2008 | Brown et al. | 435/6 |
| 2008/0182237 A1 | 7/2008 | Bentwich et al. | 435/6 |
| 2008/0182245 A1 | 7/2008 | Brown et al. | 435/6 |
| 2008/0261908 A1 | 10/2008 | Croce et al. | 514/44 |
| 2008/0269147 A1 | 10/2008 | Tuschl et al. | 514/44 |
| 2008/0306006 A1 | 12/2008 | Croce | 514/12 |
| 2008/0306017 A1 | 12/2008 | Croce et al. | 514/44 |
| 2008/0306018 A1 | 12/2008 | Croce et al. | 514/44 |
| 2009/0029932 A1 | 1/2009 | Voinnet et al. | 514/44 |
| 2009/0092974 A1 | 4/2009 | Davison et al. | 435/91.1 |
| 2009/0186353 A1 | 7/2009 | Aharonov et al. | 435/6 |
| 2009/0186843 A1 | 7/2009 | Tuschl et al. | 514/44 |
| 2010/0087507 A1 | 4/2010 | Ochiya et al. | 514/44 |
| 2010/0144850 A1 | 6/2010 | Croce | 514/44 |
| 2010/0203544 A1 | 8/2010 | Croce et al. | 435/6 |
| 2010/0234241 A1 | 9/2010 | Croce et al. | 506/9 |
| 2010/0257618 A1 | 10/2010 | Croce et al. | 800/10 |
| 2010/0286232 A1 | 11/2010 | Schmittgen et al. | 514/44 |

FOREIGN PATENT DOCUMENTS

| | | |
|---|---|---|
| EP | 0921195 | 6/1999 |
| EP | 1 627 925 | 2/2006 |
| EP | 1352061 | 5/2006 |
| FR | 2877350 | 5/2006 |
| JP | 2005-296014 | 10/2005 |
| WO | WO 93/21329 | 10/1993 |
| WO | WO 97/27317 | 7/1997 |
| WO | WO 97/43450 | 11/1997 |
| WO | WO 97/45539 | 12/1997 |
| WO | WO 98/08973 | 3/1998 |
| WO | WO 99/21881 | 5/1999 |
| WO | WO 99/23256 | 5/1999 |
| WO | WO 99/36760 | 7/1999 |
| WO | WO 00/05409 | 2/2000 |
| WO | WO 00/24939 | 5/2000 |
| WO | WO 00/44895 | 8/2000 |
| WO | WO 00/56748 | 9/2000 |
| WO | WO 00/66604 | 11/2000 |
| WO | WO 00/75356 | 12/2000 |
| WO | WO 01/68255 | 9/2001 |
| WO | WO 01/75164 | 10/2001 |
| WO | WO 02/00169 | 1/2002 |
| WO | WO 02/64835 | 1/2002 |
| WO | WO 02/44321 | 6/2002 |
| WO | WO 03/020898 | 3/2003 |
| WO | WO 03/020931 | 3/2003 |
| WO | WO 03/022421 | 3/2003 |
| WO | WO 03/023058 | 3/2003 |
| WO | WO 03/029459 | 4/2003 |
| WO | WO 03/029485 | 4/2003 |
| WO | WO 03/040410 | 5/2003 |
| WO | WO 03/053586 | 7/2003 |
| WO | WO 03/066906 | 8/2003 |
| WO | WO 03/067217 | 8/2003 |
| WO | WO 03/076928 | 9/2003 |
| WO | WO 03/087297 | 10/2003 |
| WO | WO 03/091426 | 11/2003 |
| WO | WO 03/093810 | 11/2003 |
| WO | WO 03/100012 | 12/2003 |
| WO | WO 03/100448 | 12/2003 |
| WO | WO 2004/020085 | 3/2004 |
| WO | WO 2004/027093 | 4/2004 |
| WO | WO 2004/029212 | 4/2004 |
| WO | WO 2004/043387 | 5/2004 |
| WO | WO 2004/046324 | 6/2004 |
| WO | WO 2004/050125 | 6/2004 |
| WO | WO 2004/057017 | 7/2004 |
| WO | WO 2004/066183 | 8/2004 |
| WO | WO 2004/074509 | 9/2004 |
| WO | WO 2004/076622 | 9/2004 |

(56) References Cited

FOREIGN PATENT DOCUMENTS

| WO | WO 2005/013901 | 2/2005 |
|---|---|---|
| WO | WO 2005/078139 | 8/2005 |
| WO | WO 2005/079397 | 9/2005 |
| WO | WO 2005/116261 | 12/2005 |
| WO | WO 2005/118806 | 12/2005 |
| WO | WO 2006/028967 | 3/2006 |
| WO | WO 2006/033928 | 3/2006 |
| WO | WO 2006/101173 | 9/2006 |
| WO | WO 2006/113679 | 10/2006 |
| WO | WO 2006/119365 | 11/2006 |
| WO | WO 2006/128245 | 12/2006 |
| WO | WO 2006/135765 | 12/2006 |
| WO | WO 2006/137941 | 12/2006 |
| WO | WO 2007/016548 | 2/2007 |
| WO | WO 2007/033023 | 3/2007 |
| WO | WO 2007/073737 | 7/2007 |
| WO | WO 2007/081720 | 7/2007 |
| WO | WO 2007/081740 | 7/2007 |
| WO | WO 2007/087113 | 8/2007 |
| WO | WO 2008/014008 | 1/2008 |
| WO | WO 2008/095096 | 9/2008 |
| WO | WO 2008/136971 | 11/2008 |
| WO | WO 2008/137867 | 11/2008 |

OTHER PUBLICATIONS

Aagaard et al., "An inflammatory role for the mammalian carboxypeptidase inhibitor latexin: relationship to cystatins and the tumor suppressor TIG1," *Structure (Camb)*, 13: 309-317, 2005.
Abuharbeid et al., "The fibroblast growth factor-binding protein FGF-BP," *Int. J. Biochem. Cell Biol.*, 38(9):1463-1468, 2006.
Adams et al, "Infrequent mutation of TRAIL receptor 2 (TRAIL-R2/DR5) in transitional cell carcinoma of the bladder with 8p21 loss of heterozygosity," *Cancer Lett*. 220 (2): 137-144, 2005.
Akao et al., "*let-7* microRNA functions as a potential growth suppressor in human colon cancer cells," *Biol. Pharm. Bull*, 29(5):903-906, 2006.
Akao et al., "MicroRNAs 143 and 145 are possible common onco-microRNAs in human cancers," *Oncology Reports*, 16:845-850, 2006.
Akiba et al., "Expression and function of interleukin-8 in human hepatocellular carcinoma," *Int. J. Oncol.*, 18 (2): 257-264, 2001.
Alevizos et al., "Oral cancer in vivo gene expression profiling assisted by laser capture microdissection and microarray analysis," *Oncogene*, 20(43):6196-6204, 2001.
Allawi et al., "Quantitation of MicroRNAs using a modified Invader assay," *RNA*, 10:1153-1161, 2004.
Altucci and Gronemeyer, "The promise of retinoids to tight against cancer," *Nat. Rev. Cancer*, 1:181-193, 2001.
Altucci and Gronomeyer, "Retinoids and TRAIL: two cooperating actors to fight against cancer," *Vitam. Horm.*, 67:319-345, 2004.
Ambion, Inc., "mMessage mMachina®," High Yield Capped RNA Transcription Kit, Catalog #1340, 1344, 1348; pp. 1-8.
Ambion, Inc., "mMessage mMachine®," Instruction Manual, Catalog #1340, 1344, 1348; pp. 1-31.
Ambros et al., "A uniform system for microRNA annotation," *RNA*, 9(3;):277-279, 2003.
Ambros, "microRNAs: tiny regulators with great potential," *Cell*, 107(7):823-826, 2001.
Anatharaman and Aravind, "Evolutionary history, structural features and biochemical diversity of the N1pC/P60 superfamily of enzymes," *Genome Biol.*, 4: R11, 2003.
Ando et al., "Polo-like kinase 1 (Plk1) inhibits p53 function by physical interaction and phosphorylation," *J. Biol. Chem.*, 279 (24): 25549-25561, 2004.
Armour et al., "Measurement of locus copy number by hybridisation with amplifiable probes," *Nucleic Acids Research*, 28(2):605-609, 2000.
Association of Directors of Anatomic and Surgical Pathology, "Recommendations for the reporting of resected large intestinal carcinomas. Association of directors of anatomic and surgical pathology," *Am. J. Clin. Pathol.*, 106 (1): 12-15, 1996.
Astler and Coller, "The prognostic significance of direct extension of carcinoma of the colon and rectum," *Ann. Surg.*, 139: 846-852, 1954.
Asuragen, Inc. website, "Asuragen's DiscovArray miRNA Expression Profiling Service," located at http://www.asuragen.com/Services/solutions/discovarray.aspx, printed Mar. 6, 2009.
Baba et al., "Involvement of deregulated epiregulin expression in tumorigenesis in vivo through activated Ki-Ras signaling pathway in human colon cancer cells," *Cancer Res*, 60(24):6886-6889, 2000.
Bae et al., "MCL-1S, a splicing variant of the antiapoptotic BCL-2 family member MCL-1, encodes a proapoptotic protein possessing only the BH3 domain," *J. Biol. Chem.*, 275(33):25255-61, 2000.
Bagga et al., "Regulation by let-7 and lin-4 miRNAs results in target mRNA degradation," *Cell*, 122(4):553-563, 2005.
Bandres et al., "Identification by Real-time PCR of 13 mature microRNAs differentially expressed in colorectal cancer and non-tumoral tissues," *Mol. Cancer*, 5:29, 2006.
Bangoura et al,, "Expression of HIF-2alphaIEPAS1 in hepatocellular carcinoma," *World J. Gastroenterol*, 10(4):525-530, 2004.
Bartlett and Davis, "Effect of siRNA nuclease stability on the in vitro and in vivo kinetics of siRNA-mediated gene silencing," *Biotechnol. Bioeng.*, 97(4): 909-921, 2007.
Bartlett et al., "Impact of tumor-specific targeting on the biodistribution and efficacy of siRNA nanoparticles measured by multimodality in vivo imaging," 104(39):15549-15554, 2007.
Bartlett et al., "Insights into the kinetics of siRNA-mediated gene silencing from live-cell and live-animal bioluminescent imaging," *Nucleic Acids Research*, 34(1):322-333, 2006.
Barton et al., "Angiogenic protein expression in advanced epithelial ovarian cancer," *Clin. Cancer Res.*, 3 (9): 1579-1586, 1997.
Bellovin et al., "Reciprocal regulation of RhoA and RhoC characterizes the EMT and identifies RhoC as a prognostic marker of colon carcinoma," *Oncogene*, 25 (52): 6959-6967, 2006.
Bendtsen et al., "Feature-based prediction of non-classical and leaderless protein secretion," *Protein Eng. Des. Sel.*, 17: 349-356, 2004.
Bentwich et al., "Identification of hundreds of conserved and nonconserved human microRNAs," *Nat Genet.*, 37(7):766-770, 2005.
Berezikov et al, *Cell*, "Phylogenetic shadowing and computational identification of human microRNA genes," 120(1):21-24, 2005.
Billottet et al., "A selective inhibitor of the p110delta isoform of PI 3-kinase inhibits AML cell proliferation and survival and increases the cytotoxic effects of VP16," *Oncogene*, 25 (50): 6648-6659, 2006.
Birchmeier et al., "Met, metastasis, motility and more," *Nat Rev Mol Cell Biol*, 4(12):915-925, 2003.
Biswas et al., "Transforming growth factor beta receptor type II inactivation promotes the establishment and progression of colon cancer," *Cancer Res.*, 64 (14): 4687-4692, 2004.
Bilomsky et al., "Transformation suppressor protein Pdcd4 interferes with JNK-mediated phosphorylation of c-Jun and recruitment of the coactivator p300 by c-Jun," *Oncogene*, 23(45):7484-93, 2004.
Black et al., "Expression of cyclin D1, cyclin E, EGFR, UBE1L and K167 in paired benign and malignant lung tissues," *Lung Cancer*, 49:S289, Abstract P-650, 2005.
Blanc et al., "Wnt-5a gene expression in malignant human neuroblasts," *Cancer Lett.*, 228 (1-2): 117-123, 2005.
Boccaccio and Comoglio, "Invasive growth: a MET-driven genetic programme for cancer and stem cells," *Nat Rev Cancer*, 6(8):637-645, 2006.
Bodner-Adler et al., "Serum levels of angiogenin (ANG) in invasive cervical cancer and in cervical intraepithelial neoplasia (CIN)," *Anticancer Res.*, 21 (1B): 809-812, 2001.
Bostwick et al., "Amphiregulin expression in prostatic intraepithelial neoplasia and adenocarcinoma: a study of 93 cases," *Prostate*. 58(2):164-168, 2004.
Bottoni et al., "miR-15a and miR-16-1 Down-Regulation in Pituitary Adenomas" *J. Cell. Physiol.*, 204:280-285, 2005.
Boultwood et al., "Low expression of the putative tumour suppressor gene gravin in chronic myeloid leukaemia, myelodysplastic syndromes and acute myeloid leukaemia," *Br J Haematol*, 126(4):508-511, 2004.

(56) References Cited

OTHER PUBLICATIONS

Brazma and Vilo, "Gene expression data analysis," *FEBS Letters*, 480:17-24, 2000.
Brennecke et al., "Bantam encodes a developmentally regulated microRNA that controls cell proliferation and regulates the proapoptotic gene hid in *Drosophila*," *Cell*, 113:25-36, 2003.
Bustin et al., "Real-time reverse transcription PCR (qRT-PCR) and its potential use in clinical diagnosis," *Clinical Science*, 109:365-379, 2005.
Byrd et al., "Pretreatment cytogenetic abnormalities are predictive of induction success, cumulative incidence of relapse, and overall survival in adult patients with de novo acute myeloid leukemia: results from Cancer and Leukemia Group B (CALGB 8461)" *Blood*, 100:4325-4336, 2002.
Calin and Croce, "Genomics of chronic lymphocytic leukemia microRNAs as new players with clinical significance," *Seminars in Oncology*, 33(2):167-173, 2006.
Calin and Croce, "MicroRNA signatures in human cancers," *Nat Rev Cancer*, 6(11):857-866, 2006.
Calin and Croce, "MicroRNA—cancer connection: the beginning of a new tale," *Cancer Res.*, 66(15):7390-7394, 2006.
Calin and Croce, "MicroRNAs and chromosomal abnormalities in cancer cells," *Oncogene*, 25(46):6202-6210, 2006.
Cahn et al., "A MicroRNA signature associated with prognosis and progression in chronic lymphocytic leukemia," *New England Journal of Medicine*, 353(17):1793-1801, 2005.
Cahn et al., "Frequent deletions and down-regulation of micro-RNA genies miR15 and miR16 at 13q14 in chronic lymphocytic leukemia," *Proc. Natl. Acad. Sci. USA*, 99:15524-15529, 2002.
Carrano et al., "SKP2 is required for ubiquitin-mediated degradation of the CDK inhibitor p27," *Nat. Cell. Biol.*, 1 (4): 193-199, 1999.
Carreiras et at., "Expression and localization of alpha v integrins and their ligand vitronectin in normal ovarian epithelium and in ovarian carcinoma," *Gynecol. Oncol.*, 62 (2): 260-267, 1996.
Carreiras et al., "Human ovarian adenocarcinoma cells synthesize vitronectin and use it to organize their adhesion," *Gynecol. Oncol.*, 72 (3): 312-322, 1999.
Carrington and Ambros, "Role of MicroRNAs in Plant and Animal Development," *Science*; 301:336-338; 2003.
Casanova et al, "The class II tumor-suppressor gene RARRES3 is expressed in B cell lymphocytic leukemias and down-regulated with disease progression," *Leukemia*, 15 (10):1521-1526, 2001.
Castillo et al., "Amphiregulin contributes to the transformed phenotype of human hepatocellular carcinoma cells," *Cancer Res.*, 66(12):6129-6138, 2006.
Caudy et al., "Fragile X-related protein and VIG associate with the RNA interference machinery," *Genes & Development*, 16:2491-2496; 2002.
Chan et al., "Downregulation of ID4 by promoter hypermethylation in gastric adenocarcinoma," *Oncogene*, 22 (44): 6946-6953, 2003.
Chan et al, "MicroRNA-21 is an antiapoptotic factor in human glioblastoma cells," *Cancer Res.*, 65(14):6029-6033, 2005.
Chandler et al., "Prevalent expression of fibroblast growth factor (FGF) receptors and FGF2 in human tumor cell lines," *Int. J. Cancer*, 81(3):451-458, 1999.
Chang et al., "Elevated circulating level of osteopontin is associated with advanced disease state of non-small cell lung cancer," *Lung Cancer*, 57(3):373-380, 2007.
Chang et al., "MicroRNAs act sequentially and asymmetrically to control chemosensory laterality in the nematode," *Nature*, 430(7001):785-789, 2004.
Chang et al., "Transactivation of miR-34a by p53 broadly influences gene expression and promotes apoptosis," *Mol. Cell.*, 26(5):745-752, 2007.
Chen et al., "Identification of trophinin as an enhancer for cell invasion and a prognostic factor for early stage lung cancer," *European Journal of Cancer*, 43(4):782-790, 2007.
Chen et al., "Loss of PDCD4 expression in human lung cancer correlates with tumour progression and prognosis," *J. Pathol.*, 200(5):640-646, 2003.

Chen et al., "MicroRNAs modulate hematopoietic lineage differentiation," *Science*, 303(5654):83-86, 2004.
Chen et al., "Real-time quanitfication of microRNAs by stem-loop RT-PCR," *Nucleic Acids Research*, 33(20): e179 (13 printed pages), 2005.
Cheng et al, "Antisense inhibition of human miRNAs and indications for an involvement of miRNA in cell growth and apoptosis," *Nucleic Acids Res.*, 33(4):1290-1297, 2005.
Choi et al, "AKAP12/Gravin is inactivated by epigenetic mechanism in human gastric carcinoma and shows growth suppressor activity," *Oncogene*, 23(42):7095-7103, 2004.
Ciafre et at., "Extensive modulation of a set of microRNAs in primary glioblastoma," *Biochem. Biophys. Res. Commun.*, 334(4):1351-1358, 2005.
Cimmino et al., "miR-15 and miR-16 induce apoptosis by targeting BCL2," *Proceedings of the National Academy of Sciences of the USA*, 102(39):13944-13949, 2005.
Ciocca et al., "Heat shock portein hsp70 in patients with axillary lymph node-negative breast cancer: Prognostic implications," *Journal of the National Cancer Institute*, 85(7):570-574, 1993.
Claudio et al., "Expression of cell-cycle-regulated proteins pRb2/p130, p107, p27(kipl), p53, mdm-2, and Ki-67 (MIB-1) in prostatic gland adenocarcinoma," *Clin Cancer Res*, 8(6):1808-1815, 2002.
Cohen et al., "Expression of a down-regulated target, SSeCKS, reverses v-Jun-induced transformation of 10T1/2 murine fibroblasts," *Oncogene*, 20(2):141-146, 2001.
Coleman et al., "Superior 5' homogeneity of RNA from ATP-initiated transcription under T7 $\Phi$2.5 promoter," *Nucleic Acids Research*, 32(1):e14, 2004.
Cooper et al., "Molecular cloning of a new transforming gene from a chemically transformed human cell line," *Nature*, 311(5981):29-33, 1984.
Croci et al., "inhibition of connective tissue growth factor (CTGF/CCN2) expression decreases the survival and myogenic differentiation of human rhabdomyosarcoma cells," *Cancer Res.*, 64(5):1730-1736, 2004.
Cross et at., "25-Hydroxyvitamin D (3)-lalpha-hydroxylase and vitamin D receptor gene expression in human colonic mucosa is elevated during early cancerogenesis," *Steroids*, 66:287-292, 2001.
Cully et al., "Transforming acidic coiled coil 1 promotes transformation and mammary tumorigenesis," *Cancer Res.*, 65(22):10363-10370, 2005.
Danilkovitch-Miagkova and Zbar, "Dysregulation of Met receptor tyrosine kinase activity in invasive tumors," *J Clin Invest*, 109(7):863-867, 2002.
D'Antonio et al., "Transfoming growth factor alpha, amphiregulin and cripto-1 are frequently expressed in advanced human ovarian carcinomas," *Int. J. Oncol.*, 21(5):941-948, 2002.
Database Emb, "Human DNA related to regulating mammalian cells using miRNAs Seq 471," EBI Database Accession No. ADR83569, Dec. 2, 2004.
Davalos et al., "High EPHB2 mutation rate in gastric but not endometrial tumors with microsatellite instability," *Oncogene*, 26 (2): 308-311, 2006.
Davis et al., "Modeling of repeated-batch transcription for production of RNA," *Journal of Biotechnology*, 71:25-37, 1999.
De Candia et al., "Id4 messenger RNA and estrogen receptor expression: inverse correlation in human normal breast epithelium and carcinoma," *Hum. Pathol.*, 37 (8): 1032-1041, 2006.
De Nigris et al., "Induction of ETS-1 and ETS-2 transcription factors is required for thyroid cell transformation," *Cancer Res.*, 61 (5): 2267-2275, 2001.
Dean et al., "The human met oncogene is related to the tyrosine kinase oncogenes," *Nature*, 318(6044):385-388, 1985.
Denli and Harmon., "RNAi: an ever-growing puzzle," *Trends Biochem. Sci.*, 28:196, 2003.
Devine et al., "Serum markers CASA, CEA, CYFRA, TPS, and NSE in lung cancer," *Lung Cancer*, Abstract, 11:37, 1994.
Diederichs and Haber, "Sequence variations of microRNAs in human cancer: Alterations in predicted secondary structure do not affect processing," *Cancer Res.*, 66(12):6097-0104, 2006.

(56) References Cited

OTHER PUBLICATIONS

DiSepio et al., "Identification and characterization of a retinoid-induced class II tumor suppressor/growth regulatory gene," *Proc. Natl. Acad. Sci. USA*, 95: 14811-14815, 1998.

Doench and Sharp, "Specificity of microRNA target selection in translational repression," *Genes Dev*, 18(5):504-11, 2004.

Doench et al., "siRNAs can function as miRNAs," *Genes & Dev*, 17:438-442, 2003.

Dong et al., "Telomerase: regulation, function and transformation," *Crit Rev Oncol Hematol* 54(2):85-93, 2005.

Donnellan and Chetty, "Cyclin D1 and human neoplasia," *Mol Pathol*, 51(1):1-7, 1998.

Dostie et al., "Numerous microRNPs in neuronal cells containing novel microRNAs," *RNA*, 9:180-186; 2003.

Duvic et al., "Expression of a retinoid-inducible tumor suppressor, tazarotene-inducible gene-3 is decreased in psoriasis and skin cancer," *Clin. Cancer Res*., 6 (8): 3249-3259, 2000.

Duvic et al, "Tazarotene-induced gene 3 is suppressed in basal cell carcinomas and reversed in vivo by tazarotene application," *J. Invest. Dermatol.*, 121: 902-909, 2003.

Ebert et al., "Induction and expression of amphiregulin in human pancreatic cancer," *Cancer Res*., 54(15):3959-3962, 1994.

Eferl et al., "Liver tumor development. c-Jun antagonizes the proapoptotic activity of p53," *Cell*, 112 (2): 181-192, 2003.

Einama et al., "High-level Skp2 expression in pancreatic ductal adenocarcinoma: correlation with the extent of lymph node metastasis, higher histological grade, and poorer patient outcome," *Pancreas*, 32(4):376-381, 2006.

Esau et al., "MicroRNA-143 regulates adipocyte differentiation," *Journal of Biological Chemistry*, 279(50):52361-52365, 2004.

Esquela-Kerscher and Slack, "Oncomirs—microRNAs with a role in cancer," *Nat Rev Cancer*, 6(4):259-269, 2006.

Ezzat et al., "Dual inhibition of RET and FGFR4 restrains medullary thyroid cancer cell growth," *Clin. Cancer Res.*, 11 (3): 1336-1341, 2005.

Faried et al., "RhoA and RhoC proteins promote both cell proliferation and cell invasion of human oesophageal squamous cell carcinoma cell lines in vitro and in vivo," *Eur. J. Cancer*; 42 (10): 1455-1465, 2006.

Fay et al., "Analysis of CUL-5 expression in breast epithelial cells, breast cancer cell lines, normal tissues and tumor tissues," *Mol. Cancer*, 2:40, 2003.

Feldman and Feldman, "The development of androgen-independent prostate cancer," *Nat. Rev. Cancer*, 1(1):34-45, 2001.

Fernandez et al., "The matrix metalloproteinase-9/neutrophil gelatinase-associated lipocalin complex plays a role in breast tumor growth and is present in the urine of breast cancer patients," *Clin. Cancer Res.*, 11(15):5390-5395, 2005.

Fesik, "Promoting apoptosis as a strategy for cancer drug discovery," *Nat Rev Cancer*, 5(11):876-885, 2005.

Firth and Baxter, "Cellular actions of the insulin-like growth factor binding proteins," *Endocrin. Rev.*, 23 (6): 824-854, 2002.

Fontana et al, "MicroRNA's 17-5p-20a-106a control monocytopeiesis through AML1 targeting and M-CSF receptor upregulation," *Nature Cell Biology*, 9(7):775-787, 2007.

Freelove and Walling, "Pancreatic cancer: diagnosis and management," *Am. Fam. Physician*, 73(3):485-492, 2006.

Fujiwara et al., "Isolation of a candidate tumor suppressor gene on chromosome 8p21.3-p22 that is homologous to an extracellular domain of the PDGF receptor beta gene," *Oncogene*, 10(5):891-895, 1995.

Galardi et al., "miR-221 and miR-222 expression affects the proliferation potential of human prostate carcinoma cell lines by targeting p27Kip1," *J. Biol. Chem*, 282(32):23716-23724, 2007.

Gao et al., "Frequent loss of PDCD4 expression in human glioma: possible role in the tumorigenesis of glioma," *Oncol. Rep.*, 17(1):123-128, 2007.

Garzon et al., "MicroRNA fingerprints during human megakaryocytopoiesis," *Proc. Natl. Acad. Sci. USA*, 103(13):5078-5083, 2006.

Garzon et al., "MicroRNA signatures associated with cytogenetics and outcome in acute myeloid leukemia. Session Type: Oral Session," *Blood*, 108(11): 49A, Abstract #151, 2006.

Giannakakis et al., "miRNA genetic alterations in human cacners," *Expert opinion on biological therapy*, 7(9):1375-1386, 2007.

Goke et al., "Progammed cell death protein 4 suppresses CDK1/cdc2 via induction of p21(Waf1/Cip1)," *Am. J. Physiol. Cell Physiol.*, 287(6):C1541-6, 2004.

Grandori et al., "The Myc/Max/Mad network and the transcriptional control of cell behavior," *Annu. Rev. Cell. Dev. Biol.*, 16: 653-699, 2000.

Grenier et al., "Cyfra 21-1, a new marker for lung cancer," *Nucl. Med. Biol.*, 21(3):471-476, 1994.

Griffiths-Jones et al., "miRBase: microRNA sequences, targets and gene nomenclature," *Nucleic Acids Res.*, 34 (Database Issue):D140-D144, 2006.

Grimwade, "The clinical significance of cytogenetic abnormalities in acute myeloid leukaemia," *Best. Pract. Res. Clin.Haematol*., 14:497-529, 2001.

Grishok et al., "Genes and mechanisms related to RNA interference regulate expression of the small temporal RNAs that control *C. elegans* developmental timing," *Cell*, 106:23-34, 2001.

Grosshans et al., "The temporal patterning microRNA let-7 regulates several transcription factors at the larval to adult transition in *C. elegans*," *Dev. Cell*, 8(3):321-330, 2005.

Gstaiger et al., "Skp2 is oncogenic and overexpressed in human cancers," *Proc. Natl. Acad. Sci. USA*, 98(9):5043-5048, 2001.

Guda and Subramaniam, "TARGET: a new method for predicting protein subcellular localization in eukaryotes," *Bioinformatics*, 21: 3963-3969, 2005.

Guo et al., "Reduced expression of EphB2 that parallels invasion and metastasis in colorectal tumours," *Carcinogenesis*, 27(3):454-464, 2006.

Gurevich, "Preparative in vitro mRNA synthesis using SP6 and T7 RNA polymerases," *Anal Biochem.*, 195(2):207-213, 1991.

Ha et al., "A bulged lin-4/lin-14 RNA duplex is sufficient for *Caenorhabditis elegans* lin-14 temporal gradient formation," *Genes Dev.*, 10, 3041-3050, 1996.

Hajnal et al., "Subtaction cloning of H-rev107, a gene specifically expressed in H-ras resistant fibroblasts," *Oncogene*, 9: 479-490, 1994.

Hamamura et al., "Ganglioside GD3 promotes cell growth and invasion through p130Cas and paxillin in malignant melanoma cells," *Proc Natl Acad Sci U S A*, 102(31):11041-11046, 2005.

Hanahan and Weinberg, "The hallmarks of cancer," *Cell*, 100(1):57-70, 2000.

Hannigan et al., "Integrin-linked kinase: a cancer therapeutic target unique among its ILK," *Nat Rev Cancer*, 5(1):51-63, 2005.

Hardenbol et al.,"Multiplexed genotyping with sequence-tagged molecular inversion probes," *Nat Biotechnol*, 21(6):673-678, 2003.

Hartmann et al., "Oxia-induced up-regulation of angiogenin in human malignant melanoma," *Cancer Res.*, 59 (7): 1578-1583, 1999.

He et al., "A microRNA polycistron as a potential human oncogene," *Nature*, 435(7043):828-833, 2005.

He et al., "The role of microRNA genes in papillary thyroid carcinoma," *Proc. Natl. Acad. Sci. USA*, 102(52):19075-19080, 2005.

Hishikawa et al., "Connective tissue growth factor induces apoptosis in human breast cancer cell line MCF-7," *J. Biol. Chem.*, 274(52):37461-37466, 1999.

Holmquist-Mengeibier et al., "Recruitment of HIF-1alpha and HIF-2alpha to common target genes is differentially regulated in neuroblastoma: HIF-2alpha promotes an agressive phenotype," *Cancer Cell*, 10(5):413-423, 2006.

Huang et al., "Cloning and characterization of a novel retinoid-inducible gene 1 (RIG1) deriving from human gastric cancer cells," *Mol. Cell. Endocrinol.*, 159: 15-24, 2000.

Huang et al., "Skp2 inhibits FOXO1 in tumor suppression through ubiquitin-mediated degradation," *Proc. Natl. Acad. Sci. USA*, 102(5):1649-1654, 2005.

Huang et al., "Skp2 overexpression is highly representative of intrinsic biological aggressiveness and independently associated with poor prognosis in primary localized myxofibrosarcomas," *Clin. Cancer Res*., 12 (2): 487-498, 2006.

(56) References Cited

OTHER PUBLICATIONS

Huang et al., "The retinoid-inducible gene I: effect on apoptosis and mitogen-activated kinase signal pathways," *Anticancer Res.*, 22: 799-804, 2002.
Huang et al., "Wnt5a expression is associated with the tumor proliferation and the stromal vascular endothelial growth factor—an expression in non-small-cell lung cancer," *J. Clin. Oncol.*, 23 (34): 8765-8773, 2005.
Hutvagner and Zamore, "A microRNA in a multiple-turnover RNAi enzyme complex," *Science*, 297(5589):2056-2060, 2002.
Hutvagner et al, "Sequence-specific inhibition of small RNA function," *PLoS Biol.* 2(4):E98, 2004.
Huusko et al, "Nonsense-mediated decay microarray analysis identifies mutations of EPHB2 in human prostate cancer," *Nat. Genet.*, 36 (9): 979-983, 2004.
Hynes and Lane, "ERBB receptors and cancer: the complexity of targeted inhibitors," *Nat Rev Cancer*, 5(5):341-354, 2005.
Illmer et al, "MiRNA expression signatures in actue myeloid leukemia are predictors for patient outcome. Session Type: Oral Session," *Blood*, 108(11): 49A, Abstract #152, 2006.
Ishikawa et al., "Increases of amphiregulin and transforming growth factor-alpha in serum as predictors of poor response to gefitinib among patients with advanced non-small cell lung cancers," *Cancer Res.*, 65(20):9176-9184, 2005.
Ito et al., "Decreased expression of cyclin G2 is significantly linked to the malignant transformation of papillary carcinoma of the thyroid," *Anticancer Res.*, 23(3B):2335-2338, 2003.
Ito et al,, "Decreased expression of p107 is correlated with anaplastic transformation in papillary carcinoma of the thyroid," *Anticancer Res.*, 23(5A):3819-3824, 2003.
Ito et al., "Expression of ets-1 and ets-2 in colonic neoplasms," *Anticancer Res.*, 22 (3). 1581-1584, 2002.
Ito et al,, "Expression of p8 protein in medullary thyroid carcinoma," *Anticancer Res.*, 25 (5): 3419-3423, 2005.
Jaakkola et di, "Amplification of fgfr4 gene in human breast and gynecological cancers," *Int. J. Cancer*, 54 (3): 378-382, 1993.
Jaattela, "Over-expression of hsp70 confers tumorigenicity to mouse fibrosarcoma cells," *Int. J. Cancer*, 60(5):689-693, 1995.
Jansen et al., "Characterization of programmed cell death 4 in multiple human cancers reveals a novel enhancer of drug sensitivity," *Mol. Cancer Ther*., 3(2):103-110, 2004.
Jansen et al., "Epidermal expression of the translation inhibitor progammed cell death 4 suppresses tumorigenesis," *Cancer Res.*, 65(14):6034-41, 2005.
Jemal et al., "Cancer statistics, 2007," *CA Cancer J. Clin.*, 57:43-66, 2007.
Jemielity et al., "Novel 'anti-reverse' cap analogs with superior translational properties," *RNA*, 9(9):1108-1122, 2003.
Jiang et al., "Decreased expression of type II tumor suppressor gene RARRES3 in tissues of hepatocellular carcinoma and cholangiocarcinoma," *World J. Gastroenterol.*, 11: 948-953, 2005.
Jiang et al., "RNA silencing of S-phase kinase-interacting protein 2 inhibits proliferation and centrosome amplification in lung cancer cells," *Oncogene*, 24(21):3409-3418, 2005.
Jin et al., "Tumorigenic transformation by CPI-17 through inhibition of a merlin phosphatase," *Nature*, 442 (7102): 576-579, 2006.
Jing et al., "Tazarotene-induced gene 1 (TIG1) expression in prostate carcinomas and its relationship to tumorigenicity," *J. Natl. Cancer Inst.*, 94: 482-490, 2002.
Johnson et al., "RAS is regulated by the let-7 microRNA family," *Cell*, 120:635-647, 2005.
Jönsson et al., "Loss of Wnt-5a protein is associated with early relapse in invasive ductal breast carcinomas," *Cancer Res.*, 62 (2): 409-416, 2002.
Jubb et al., "EphB2 is a prognostic factor in colorectal cancer," *Clin. Cancer Res.*, 11 (14): 5181-5187, 2005.
Kabbarah et al, "Expression Profiling of Mouse Endometrial Cancers Microdissected from Ethanol-Fixed, Paraffin-Embedded Tissues," *Am. J. Pathology*, 162:755-762, 2003.

Kallay et al., "Vitamin D receptor activity and prevention of colonic hyperproliferation and oxidative stress," *Food Chem. Toxicol.*, 40: 1191-1196, 2002.
Kamata et al., "High expression of skp2 correlates with poor prognosis in endometrial endometrioid adenocarcinoma," *J. Cancer Res. Clin. Oncol.*, 131(9):591-596, 2005.
Kato, "Adaptor-tagged competitive PCR: a novel method for measuring relative gene expression," *Nucleic Acids Research*, Oxford University Press, Surrey, GB, 25(22):4694-4696, 1997.
Kaufmann et al,, "Elevated expression of the apoptotic regulator Mcl-1 at the time of leukemic relapse," *Blood*, 91(3):991-1000, 1998.
Keen and Taylor, "Aurora-kinase inhibitors as anticancer agents," *Nat. Rev. Cancer*; 4(12):927-936, 2004.
Kern et al., "Application of a fed-batch system to produce RNA by in vitro transcription," *Biotechnol. Prog.*, 15:174-184, 1999.
Kern et al., "Application of solution equilibrium analysis to in vitro RNA transcription," *Biotechnol. Prog.*, 13:747-756, 1997.
Kim et al., "Genomics of microRNA," *Trends in Genetics*, 22:165-173, 2006.
Kim et al., "Identification of many microRNAs that copurify with polyribosomes in mammalian neurons," *Proc. Natl. Acad. Sci., USA*, 101:360-365, 2004.
Kiriakidou et al., "A combined computational-experimental approach predicts human microRNA targets," *Genes Dev.* 18(10):1165-78, 2004.
Kirikoshi et al., "Up-regulation of Frizzled-7 (FZD7) in human gastric cancer," *Int. J. Oncol.*, 19 (1): 111-115, 2001.
Kita et al., "Modulation of polygulutamine-induced cell death by genes identified by expression profiling," *Human Molecular Genetics*, 11(19):2279-2287, 2002.
Kitadai et al., "Expression of amphiregulin, a novel gene of the epidermal growth factor family, in human gastric carcinomas," *Jpn. J. Cancer Res.*, 84(8):879-884, 1993.
Kleer et al., "RhoC GTPase expression as a potential marker of lymph node metastasis in squamous cell carcinomas of the head and neck," *Clin. Cancer Res.*, 12 (15): 4485-4490, 2006.
Kohno and Pouyssegur, "Pharmacological inhibitors of the ERK signaling pathway: application as anticancer drugs," *Progress in Cell Cycle Research,*. (Meijer, L., Jezequel, A., and Roberge, M., Eds), Chapter 22, vol. 5:219-224, 2003.
Koivunen et al., "Protein kinase C (PKC) family in cancer progression," *Cancer Lett*, 235(1):1- 10, 2006.
Koivunen et al., "Protein kinase C alpha/beta inhibitor Go6976 promotes formation of cell junctions and inhibits invasion of urinary bladder carcinoma cells," *Cancer Res*, 64(16):5693-5701, 2004.
Kokko et al., "EPHB2 germline variants in patients with colorectal cancer or hyperplastic polyposis,"*BMC Cancer*, 6: 145, 2006.
Komatsu et al, "Increased expression of S100A6 (Calcyclin), a calcium-binding protein of the S100 family, in human colorectal adenocarcinomas," *Clin. Cancer Res.*, 6: 172-177, 2000.
Komiya et al., "PRLTS gene alterations in human prostate cancer," *Jpn. J. Cancer Res.*, 88(4):389-393, 1997.
Krek et al., "Combinatorial microRNA target predictions," *Nature Genet.*, 37:495-500, 2005.
Krichevsky et al., "A microRNA array reveals extensive regulation of microRNAs during brain development," *RNA*, 9(10):1274-1281, 2003.
Kubista et al., "Light-up probe based real-time Q-PCR," *SPIE*, 4264:53-58, 2001.
Kwong et al., "Silencing of the retinoid response gene TIG1 by promoter hypermethylation in nasopharyngeal carcinoma," *Int. J. Cancer*, 113 (3): 386-392, 2005.
L'hote and Knowles, "Cell responses to FGFR3 signalling: growth, differentiation and apoptosis," *Exp. Cell. Res.*, 304 (2): 417-431, 2005.
Labourier et al., "Improving in vitro transcription for large scale sytnthesis of human quality capped RNA," *Ambion Diagnostics, RNA Healthcare Solutions*, Eukaryotic mRNA Processing meeting, Cold Spring Harbor Laboratory, Cold Spring Harbor, NY, Aug. 2003.
Lagos-Quintana et al., "Identification of novel genes coding for small expressed RNAs," *Science*, 294(5543):853-858, 2001.

(56) References Cited

OTHER PUBLICATIONS

Lao et al., "Multiplexing RT-PCR for the detection of multiple miRNA species in small samples," *Biochemical and Biophysical Research Communications*, 343:85-89, 2006.

Lau et al., "An abundant class of tiny RNAs with probable regulatory roles in *Caenorhabditis elegans*," *Science*, 294(5543):858-862, 2001.

Lee and Ambros, "An extensive class of small RNAs in *Caenorhabditis elegans*," *Science*, 294(5543):862-864, 2001.

Lee et al., "A protein reacted with anti-vitronectin antibody accumulates in tumors derived from B16F10 melanoma cells," *Cell Struct. Funct.*, 23 (4): 193-199, 1998.

Lee et al, "Ectopic expression of neutrophil gelatinase-associated lipocalin suppresses the invasion and liver metastasis of colon cancer cells," *Int. J. Cancer*, 118(10):2490-2497, 2006.

Lee et al., "Expression profiling identities stroma- and tumor-related microRNAs in pancreatic cancer," 97$^{th}$ Annual AACR, Washington D.C., Abstract No. 5725, 2006.

Lee et al, "MicroRNA maturation: stepwise processing and subcellular localization," *EMBO J.*, 21(17):4663-4670, 2002.

Lee et al., "The nuclear RNase III Drosha initiates microRNA processing," *Nature*, 425(6956):415-419, 2003.

Leprince et al., "A putative second cell-derived oncogene of the avian leukaemia retrovirus E26," *Nature*, 306 (5941): 395-397, 1983.

Leris et al., "WNT5A expression in human breast cancer," *Anticancer Res.*, 25 (2a): 731-734, 2005.

Lewis et al, "Prediction of mammalian microRNA targets," *Cell*, 115(7):787-798, 2003.

Li et al., "Overexpression of ETS2 in human esophageal squamous cell carcinoma," *World J. Gastroenterol.*, 9 (2): 205-208, 2003.

Lim et al, "Microarray analysis shows that some microRNAs downregulate large numbers of target mRNAs," *Nature*, 433(7027):769-773, 2005.

Lim et al, "The microRNAs of *Caenorhabditis elegans*," *Genes and Development*, 17:991- 1008, 2003.

Lin and Gelman, "Reexpression of the major protein kinase C substrate, SSeCKS, suppresses v-src-induced morphological transformation and tumorigenesis," *Cancer Res*, 57(11):2304-2312, 1997.

Lin et al., "Connective tissue growth factor inhibits metastasis and acts as an independent prognostic marker in colorectal cancer," *Gastroenterology*, 128(1):9-23, 2005.

Lin et al., "The *C. elegans hunchback* homolog, *hbl-1*, controls temporal patterning and is a probable microRNA target," *Dev. Cell*, 4(5):639-650, 2003.

Linsley et al, "Transcripts targeted by the microRNA-16 family cooperatively regulate cell cycle progression," *Molecular and Cellular Biology*, 27(6):2240-2252, 2007.

Liu and Matsuura, "Inhibition of Smad antiproliferative function by CDK phosphorylation," *Cell Cycle*, 4(1):63-66, 2005.

Liu et al., "CpG island methylation and expression of the secreted frizzled-related protein gene family in chronic lymphocytic leukemia," *Cancer Res.*, 66 (2): 653-658, 2006.

Liu et al., "An oligonucleotide microchip for genome-wide micronRNA profiling in human and mouse tissue," *Proc. Nat. Acad. Sci. USA*, 101:9740-9744, 2004.

Liu et al., "FoxM1B is overexpressed in human glioblastomas and critically regulates the tumorigenicity of glioma cells," *Cancer Res.*, 66 (7): 3593-3602, 2006.

Lo et al., "High resolution allelotype of microdissected primary nasopharyngeal carcinoma," *Cancer Res.*, 60: 3348-3353, 2000.

Lo Vasco et al., "Inositide-specific phospholipase c beta1 gene deletion in the progression of myelodysplastic syndrome to acute myeloid leukemia," *Leukemia*, 18 (6): 1122-1126, 2004.

Lu et at., "MicroRNA expression profiles classify human cancers," *Nature*, 435(7043):834-838, 2005.

Lucke et al., "Inhibiting mutations in the transforming growth factor beta type 2 receptor in recurrent human breast cancer," *Cancer Res*, 61(2):482-485, 2001.

Maki et al., "Avian sarcoma virus 17 carries the jun oncogene," *Proc. Natl. Acad. Sci. USA*, 84 (9): 2848-2852, 1987.

Manion and Hockenbery, "Targeting Bcl-2-related proteins in cancer therapy," *Cancer Biol Ther*, 2(4 Suppl 1):S105-114, 2003.

Marcucci et al., "Prognostic factors and outcome of core binding factor acute myeloid leukemia patients with t(8;21) differ from those of patients with inv(16): a Cancer and Leukemia Group B study," *J.Clin.Oncol.*, 23:5705-5717, 2005.

Markowitz et al., "Inactivation of the type II TGF-beta receptor in colon cancer cells with microsatellite instability," *Science*, 268(5215):1336-1338, 1995.

Markowitz, "TGF-beta receptors and DNA repair genes, coupled targets in a pathway of human colon carcinogenesis," *Biochim. Biophys. Acta.*, 1470 (1): M13-20, 2000.

Marks, "Thioredoxin in cancer—role of histone deacetylase inhibitors," *Semin. Cancer Biol.*, 16(6):436-443, 2006.

Martello et al., "MicroRNA control of nodal signaling," *Nature*, 449(7159):183-188, 2007.

Martin and Keller, "Tailing and 3'-end labeling of RNA with yeast poly(A) polymerase and various nucleotides," *RNA*, 4(2):226-230, 1998.

Martin et al., "Molecular profiling of cervical neoplasia," *Expert Review of Molecular Diagnostics*, 6(2):217-229, 2006.

Martinez, "Identification of differentially expressed genes in HPV associated cancers using gene expression, tissue, and microRNA microarrays," Dissertation Abstract, University of Pittsburg, 2007.

Massague et al., "TGFbeta signaling in growth control, cancer, and heritable disorders," *Cell*, 103 (2): 295-309, 2000.

Matoba et al., "Gene expression in mouse cerebellum during its development," *Gene*, 241 :125-131, 2000.

Matoba et al., "Gene expression profiling of mouse postnatal cerebellar development," *Physiol. Genomics*, 4:155-164, 2000.

McManus, "MicroRNAs and cancer," *Seminars in Cancer Biology*, 13:253-258, 2003.

Meister et al., "Sequence-specific inhibition of microRNA- and siRNA-induced RNA silencing," *RNA*, 10(3):544-50, 2004.

Meng et al., "Involvement of human micro-rna in growth and response to chemotherapy in human cholangiocarcinoma cell lines," *Gastroenterology*, 130(7):2113-2129, 2006.

Merle et al., "Functional consequences of frizzled-7 receptor overexpression in human hepatocellular carcinoma," *Gastroenterology*, 127 (4): 110-1122, 2004.

Metzler et al., "High Expression of Precursor MicroRNA-155/B/C RNA in Children with Burkitt Lymphoma," *Genes, Chromosomes, & Cancer* 39:167-169; 2004.

Michael et al., "Reduced accumulation of specific microRNAs in colorectal neoplasia," *Mol. Cancer Res.*, 1:882-891, 2003.

Miyake et al., "Increased angiogenin expression in the tumor tissue and serum of urothelial carcinoma patients is related to disease progression and recurrence," *Cancer*, 86 (2): 316-324, 1999.

Mizunuma et al., "The LIM-only protein, LMO4, and the LIM domain-binding protein, LDB1, expression in squamous cell carcinomas of the oral cavity," *Br J Cancer*, 88(10):1543-1548, 2003.

Mohanty and Kushner, "Polynucleotide phosphorylase functions both as a 3'-5' exonuclease and a poly(A) polymerase in *Escherichia coli*," *PNAS*, 97:11966-11971; 2000.

Moller et al., "Expression of APO-1 (CD95), a member of the NGF/TNF receptor superfamily, in normal and neoplastic colon epithelium," *Int J Cancer*, 57(3):371-377, 1994.

Montero et al., "Angiogenin expression and prognosis in primary breast carcinoma," *Clin, Cancer Res.*, 4 (9): 2161-2168, 1998.

Mori et al., "A genome-wide search identifies epigenetic silencing of somatostatin, tachykinin-1, and 5 other genes in colon cancer," *Gastroenterology*, 131(3):797-808, 2006.

Mrozek et al., "Clinical relevance of mutations and gene-expression changes in adult acute myeloid leukemia with normal cytogenetics: are we ready for a prognostically prioritized molecular classification?," *Blood*, 06-001149v1, 2006.

Mundt et al., "On the regulation and function of human polo-like kinase 1 (PLK1): effects of overexpression on cell cycle progression," *Biochem Biophys Res Common*, 239(2):377-385, 1997.

Muralidhar et al., "Global microRNA profiles in cervical squamous cell carcinoma depend on Drosha expression levels," *J. Pathol.*, 212:368-377, 2007.

(56) References Cited

OTHER PUBLICATIONS

Nagpal et al., "Tazaratone-induced gen 1 (TIG1), a novel retinoic acid receptor-responsive gene in skin," *J. Invest. Dermatol.*,. 106 (2): 269-274, 1996.

Nakada et al., "The phosphorylation of EphB2 receptor regulates migration and invasion of human glioma cells," *Cancer Res.*, 64 (9): 3179-3185, 2004.

Nelson et al., "Microarray-based, high-throughput gene expression profiling of microRNAs," *Nature Methods*, 1(2):1-7, 2004.

Nesbit et al., "MYC oncogenes and human neoplastic disease," *Oncogene*, 18 (19): 3004-3016, 1999.

O'Donnel et al., "c-Myc-regulated microRNA's modulcate E2F1 expression," *Nature*, 435(7043):839-4843, 2005.

Office Action issued in European Application No. 02720894.1, mailed Jul. 11, 2007.

Office Action issued in European Application No. 05804851.3, mailed Jul. 30, 2008.

Office Action issued in European Application No. 05804851.3, mailed Dec. 21, 2007.

Office Action issued in European Application No. 05815286.9, mailed Apr. 3, 2008.

Office Action issued in European Application No. 05858321.2, mailed Apr. 11, 2008.

Office Action issued in U.S. Appl. No. 10/632,534, mailed Jul. 11, 2006.

Office Action issued in U.S. Appl. No. 10/632,534, mailed Mar. 29, 2007.

Office Action issued in U.S. Appl. No. 10/632,534, mailed Mar. 24, 2006.

Office Action issued in U.S. Appl. No. 10/632,539, mailed Apr. 17, 2007.

Office Action issued in U.S. Appl. No. 10/632,539, mailed Jul. 27, 2006.

Office Action issued in U.S. Appl. No. 10/632,539, mailed Mar. 27, 2006.

Office Action issued in U.S. Appl. No. 10/880,350, mailed Feb. 21, 2006.

Office Action issued in U.S. Appl. No. 10/880,350, mailed Oct. 4, 2006.

Office Action issued in U.S. Appl. No. 10/880,350, mailed Sep. 10, 2007.

Office Action issued in U.S. Appl. No. 10/963,415, mailed Aug. 2, 2007.

Office Action issued in U.S. Appl. No. 10/963,415, mailed Apr. 13, 2007.

Office Action issued in U.S. Appl. No. 10/963,415, mailed Mar. 17, 2008.

Office Action issued in U.S. Appl. No. 11/141,707, mailed Feb. 9, 2009.

Office Action issued in U.S. Appl. No. 11/141,707, mailed Jul. 17, 2008.

Office Action issued in U.S. Appl. No. 11/141,707, mailed May 15, 2007.

Office Action issued in U.S. Appl. No. 11/141,707, mailed Oct. 17, 2007.

Office Action issued in U.S. Appl. No. 11/567,082, mailed Jan. 27, 2009.

Office Action issued in U.S. Appl. No. 11/567,082, mailed Jul. 21, 2008.

Office Action issued in U.S. Appl. No. 11/567,082, mailed Jul. 3, 2007.

Office Action issued in U.S. Appl. No. 11/567,082, mailed Nov. 13, 2007.

Office Action issued in U.S. Appl. No. 11/837,490, mailed Aug. 6, 2008.

Office Action issued in U.S. Appl. No. 11/837,490, mailed Jan. 13, 2009.

Office Action issued in U.S. Appl. No. 11/837,494, mailed Jan. 15, 2009.

Office Action issued in U.S. Appl. No. 11/837,494, mailed Mar. 5, 2009.

Office Action issued in U.S. Appl. No. 11/837,494, mailed Oct. 30, 2008.

Office Action issued in U.S. Appl. No. 11/837,495, mailed Mar. 5, 2009.

Office Action issued in U.S. Appl. No. 11/837,495, mailed Oct. 30, 2008.

Office Action issued in U.S. Appl. No. 11/837,498, mailed Jan. 15, 2009.

Office Action issued in U.S. Appl. No. 11/837,498, mailed Oct. 29, 2008.

Olsen and Ambros, "The lin-4 regulatory RNA controls developmental timing in *Caenorhabditis elegans* by blocking LIN-14 protein synthesis after the initiation of translation," *Dev. Biol.*, 216:671, 1999.

Ovcharenko et al., "High-throughput RNAi screening in vitro: from cell lines to primary cells," *RNA*, 11(6):985-93, 2005.

Palleres et al., "Structure of human carboxypeptidase A4: with its endogenous protein inhibitor, latexin," *Proc. Natl. Acad. Sci. USA*, 102: 3978-3983, 2005.

Parkin et al., "Global cancer statistics, 2002," *CA Cancer J. Clin.*, 55(2):74-108, 2005.

Pasquinelli and Ruvkun, "Control of developmental timing by micrornas and their targets," *Ann. Rev. Cell Dev. Biol.*, 18:495-513, 2002.

Pasquineili et al., "Reverse 5' caps in RNAs made in vitro by phage RNA polymerases," *RNA*, 1:957-967, 1995.

PCT International Preliminary Report on Patentability and Written Opinion, issued in International Application No. PCT/US2005/018826, mailed Dec. 7, 2006.

PCT International Preliminary Report on Patentability and Written Opinion, issued in International Application No. PCT/US2005/022710, mailed Jan. 18, 2007.

PCT International Preliminary Report on Patentability and Written Opinion, issued in International Application No. PCT/US2005/036799, mailed Apr. 26, 2007.

PCT International Preliminary Report on Patentability and Written Opinion, issued in International Application No. PCT/US2005/041162, mailed Dec. 6, 2007.

PCT International Search Report and Written Opinion, issued in International Application No. PCT/US2005/036799, mailed Jun. 22, 2006.

PCT International Search Report and Written Opinion, issued in International Application No. PCT/US2005/022710, mailed Oct. 7, 2005.

PCT International Search Report and Written Opinion, issued in International Application No. PCT/US2005/041162, mailed Nov. 16, 2007.

PCT International Search Report and Written Opinion, issued in International Application No. PCT/US2007/078859, mailed Mar. 25. 2008.

PCT International Search Report and Written Opinion, issued in International Application No. PCT/US2007/078894, mailed Apr. 14, 2008.

PCT International Search Report and Written Opinion, issued in International Application No. PCT/US2007/078936, mailed Apr. 14, 2008.

PCT International Search Report and Written Opinion, issued in International Application No. PCT/US2007/086396, mailed May 30, 2008.

PCT International Search Report and Written Opinion, issued in International Application No. PCT/US2007/087021, mailed Sep. 3, 2008.

PCT International Search Report and Written Opinion, issued in International Application No. PCT/US2007/087037, mailed Jan. 12, 2009.

PCT International Search Report and Written Opinion, issued in International Application No. PCT/US2007/087038, mailed Oct. 17, 2008.

PCT International Search Report and Written Opinion, issued in International Application No. PCT/US2007/089206, mailed Aug. 26, 2008.

(56) References Cited

OTHER PUBLICATIONS

PCT International Search Report and Written Opinion, issued in International Application No. PCT/US2007/087029, mailed Jan. 13, 2009.
PCT International Search Report and Written Opinion, issued in International Application No. PCT/US2007/087031, mailed Jan. 13, 2009.
PCT International Search Report and Written Opinion, issued in International Application No. PCT/US2007/087033, mailed Jan. 13, 2009.
PCT International Search Report and Written Opinion, issued in International Application No. PCT/US2008/080318, mailed Feb. 9, 2009.
PCT International Search Report, issued in International Application No. PCT/US2002/003169, mailed Feb. 17, 2003.
PCT Invitation to Pay Additional Fees and Partial International Search, issued in International Application No. PCT/US2005/018826, mailed Mar. 20, 2006.
PCT Invitation to Pay Additional Fees and Partial International Search, issued in International Application No. PCT/US2005/041162, mailed Aug. 31, 2007.
PCT Invitation to Pay Additional Fees and Partial International Search, issued in International Application No. PCT/US2007/087031, mailed Sep. 10, 2008.
PCT Invitation to Pay Additional Fees and Partial International Search, issued in International Application No. PCT/US2007/087033, mailed Sep. 5, 2008.
PCT Invitation to Pay Additional Fees and Partial International Search, issued in International Application Nb. PCT/US2007/087029, mailed Sep. 10, 2008.
PCT Invitation to Pay Additional Fees and Partial International Search, issued in International Application No. PCT/US2007/078859, mailed Jan. 28, 2008.
PCT Invitation to Pay Additional Fees and Partial International Search, issued in International Application No. PCT/US2007/078894, mailed Feb. 11, 2008.
PCT Invitation to Pay Additional Fees and Partial International Search, issued in International Application No. PCT/US2007/078936, mailed Feb. 5, 2008.
PCT Invitation to Pay Additional Fees and Partial International Search, issued in International Application No. PCT/US2007/087021, mailed Jul. 10, 2008.
PCT Invitation to Pay Additional Fees and Partial International Search, issued in International Application No. PCDUS20077087037, mailed Aug. 25, 2008.
PCT Invitation to Pay Additional Fees and Partial International Search, issued in International Application No. PCT/US2007/087038, mailed Jul. 16, 2008.
PCT Invitation to Pay Additional Fees and Partial International Search, issued in International Application No. PCT/US2007/089206, mailed Jul. 7, 2008.
PCT Invitation to Pay Additional Fees and Partial International Search, issued in International Application No. PCT/US2008/076246, mailed Dec. 30, 2008.
Petit et al., "LHFP, a novel translocation partner gene of HMGIC in a lipoma, is a member of a new family of LHFP-like genes," *Genomics*, 57 (3): 438-441, 1999.
Phillips et al., "Antisense RNA amplification: A linear amplification method for analyzing the mRNA populaion," *Methods, a Companion to Methods in Enzymology*, 10(3):283-288, 1996.
Ree et al., "Expression of a novel tactor in human breast cancer cells with metastatic potential," *Cancer Res.*, 59 (18): 4675-4680, 1999.
Reimer et al., "Altered regulation of cyclin G in human breast cancer and its specific localization at replication foci in response to DNA damage in p53+/+ cells," *J. Biol. Chem.*, 274 (16): 11022-11029, 1999.
Reinhart et al. "The 21-nucleotide let-7 RNA regulates developmental timing in *Caenorhabditis elegans*," *Nature*, 403:901-906, 2000.
Rickert et al., "Multiplexed Real-Time PCR Using Universal Reporters," *Clin. Chem.*, 50(9):1680-1683, 2004.

Rosenkilde and Schwartz, "The chemokine system—a major regulator of angiogenesis in health and disease," *Apmis*, 112(7-8):481-495, 2004.
Rossi et al., "Identification of inactivating mutations in the JAK1, SYNJ2, and CLPTM1 genes in prostate cancer cells using inhibition of nonsense-mediated decay and microarray analysis," *Cancer Genet. Cytogenet.*, 161 (2): 97-103, 2005.
Rubin and Gutmann, "Neurofibromatosis type 1—a model for nervous system tumour formation?," *Nat Rev Cancer*, 5(7):557-564, 2005.
Ruth et al., "RhoC promotes human melanoma invasion in a PI3K/Akt-dependent pathway," *J. Invest. Dermatol.*, 126 (4): 862-868, 2006.
Sacchi et al., "Hu-ets-1 and Hu-ets-2 genes are transposed in acute leukemias with (4;11) and (8;21) translocations," *Science*, 231 (4736): 379-382, 1986.
Saigusa et al., "Overexpressed Skp2 within 5p amplification detected by array-based comparative genomic hybridization is associated with poor prognosis of glioblastomas," *Cancer Sci*, 96(10):676-683, 2005.
Saitoh et al., "Frequent up-regulation of WNT5A mRNA in primary gastric cancer," *Int. J. Mol. Med.*, 9 (5): 515-519, 2002.
Sakai et al., "Microarray hybridization with fractionated cDNA: enhanced identification of differentially expressed genes," *Analytical Biochemistry*, 287(1):32-37, 2000.
Sampson and Uhlenbeck, "Bichemical and physical characterization of an unmodified yeast phenylalanine transfer RNA transcribed in vitro," *Proc. Natl. Acad. Sci., USA*, 85(4):1033-1037, 1988.
Sanger Institute, miRBase::Sequences—Stem-loop sequence MI0000268, Sep. 2008, located at http://microRNA.sanger.ac.ukm, printed on Dec. 23, 2008.
Sanger Institute, "miRBase" *miRBase Sequence Database*, located at http://microrna.sanger.ac.uk/, printed Jan. 21, 2009.
Schenborn and Stecha, "Ribo m$^7$G cap analog: A reagent for preparing in vitro capped transcripts", *Promega Notes*, 74:18-20, 2000.
Scherr et al., "Lentrivirus-mediated antagomir expression for specific inhibition of miRNA function," *Nucleic Acids Research*, 35(22):e149, 2007.
Schouten et al., "Relative quantification of 40 nucleic acid sequences by multiplex ligation-dependent probe amplification," *Nucleic Acids Research*, 30(12):e57, 2002.
Schulze-Bergkamen et al., "Suppression of Mcl-1 via RNA interference sensitizes human hepatocellular carcinoma cells towards apoptosis induction," *BMC Cancer*, 6:232, 2006.
Seggerson et al., "Two genetic circuits repress the *Caenorhabditis elegans* heterochronic gene lin-28 after translation initiation," *Dev. Biol.*, 243:215, 2002.
Sementchenko et al, "ETS2 function is required to maintain the transfomied state of human prostate cancer cells," *Oncogene*, 17 (22): 2883-2888, 1998.
Shah et al, "FGFR4 overexpression in pancreatic cancer is mediated by an intronic enhancer activated by HNF1alpha," *Oncogene*, 21 (54): 8251-8261, 2002.
Shelly et al., "Epiregulin is a potent pan-ErbB ligand that preferentially activates heterodimeric receptor complexes," *J. Biol. Chem.*, 273 (17): 10496-10505, 1998.
Shelton et al., "MicroRNAs and Human Cancer," Abstract submitted for a Cold Spring Symposium in early Jun. 2006—71$^{st}$ Symposium: Regulatory RNAs.
Shi et al., "Facile means for quantifying microRNA expression by real-time PCR," *BioTechniques*, 39(4):519-524, 2005.
Shibahara et al., "Down-regulation of Skp2 is correlated with p27-associated cell cycle arrest induced by phenylacetate in human prostate cancer cells," *Anticancer Res.*, 25 (3b): 1881-1888, 2005.
Shigemasa et al., "Increased MCL-1 expression is associated with poor prognosis in ovarian carcinomas," *Jpn. J. Cancer Res.*, 93(5):542-550, 2002.
Shimo et al., "Connective tissue growth factor as a major angiogenic agent that is induced by hypoxia in a human breast cancer cell line," *Cancer Lett.*, 174(1):57-64, 2001.
Shimoyama et al., "Increased serum angiogenin concentration in colorectal cancer is correlated with cancer progression," *Clin. Cancer Res.*, 5 (5): 1125-1130, 1999.

(56) References Cited

OTHER PUBLICATIONS

Shingara et al., "An optimized isolation and labeling platform for accurate microRNA expression profiling," *RNA*, 11:1461-1470, 2005.
Shuldiner et al., "RNA template-specific polymerase chain reaction RS-PCR a novel strategy to reduce dramatically false positives," *Gene*, 91(1):139-142, 1990.
Shyu at al,, "RARRES3 expression positively con-elated to tumour differentiation in tissues of colorectal adenocarcinoma," *Br. J. Cancer*, 89 (1): 146-151, 2003.
Si et al., "miR-21-mediated tumor growth," *Oncogene*, 1-5, 2006.
Simpson et al., "Altered expression of Erg and Ets-2 transcription factors is associated with genetic changes at 21q22.2-22.3 in immortal and cervical carcinoma cell lines," *Oncogene*, 14 (18): 2149-2157, 1997.
Sirera et al., "The analysis of serum DNA concentration by means of hTERT quantification: A useful prognostic factor in advanced non-small cell lung cancer (NSCLC)," *Lung Cancer*, 49:S74, Abstract PD-026, 2005.
Skotzko at al., "Retroviral vector-mediated gene transfer of antisense cyclin G1 (CYCG1) inhibits proliferation of human osteogenic sarcoma cells," *Cancer Res.*, 55 (23): 5493-5498, 1995.
Slack et al., "The lin-41 RBCC gene acts in the *C. elegans* heterochronic pathway between the let-7 regulatory RNA and the LIN-29 transcription factor," *Molec. Cell*, 5(4):659-669, 2000.
Slack, "Control of developmental timing by microRNAs," believed at the time of the filing of this form to have been presented by Frank Slack at Santa Cruz in Aug. 2004.
Slack, "Control of Development by microRNAs," believed at the time of the filing of this form to have been presented by Frank Slack at IIT Bombay on Jan. 28, 2004.
Slack, "Control of Development by microRNAs," believed at the time of the filing of this form to have been presented by Frank Slack at Keystone miRNAs on Apr. 15, 2005.
Slack, "Control of Development by microRNAs," believed at the time of the filing of this form to have been presented by Frank Slack at UCT on Feb. 17, 2004.
Slack, "Control of Development by microRNAs," believed at the time of the filing of this form to have been presented by Frank Slack at UNMC on Mar. 29, 2004.
Slack, "MicroRNA control of oncogene expression," believed at the time of the filing of this form to have been presented by Frank Slack at Slack GTBIO on Nov. 8, 2004.
Slack, "MicroRNAs and cancer," believed at the time of the filing of this form to have presented by Frank Slack at University of Puerto Rico Bayamon on Sep. 22, 2004.
Slack, "Multiple, dynamic microRNA ribonucleoprotein complexes with select microRNA cargos in *C. elegans*," believed at the time of the filing of this form to have been presented by Frank Slack at Gordon on Jun. 8, 2004.
Slack, "Small RNA genes as potential causes and treatments of cancer," believed at the time of tile filing of this form to have been presented by Frank Slack at Jaslok on Feb. 1, 2004.
Slack, "Temporal patterning and biological timing," believed at the time of the filing of this form to have been presented by Frank Slack at Dartmouth on Mar. 19, 2004.
Smith et al., "Exclusive amplification of cDNA template (EXACT) RT-PCR to avoid amplifying contaminating genomic pseudogenes,"*BioTechniques*, 31(4): 776-778, 780 782, 2001.
Smith et al, "Malignant transformation of mammalian cells initiated by constitutive expression of the polo-like kinase," *Biochem Biophys Res Commun*, 234(2):397-405, 1997.
Sparmann and Bar-Sagi, "Ras-induced interleukin-8 expression plays a critical role in tumor growth and angiogenesis," *Cancer Cell*, 6(5):447-458, 2004.
Stepinski et al., "Synthesis and properties of mRNAs containing the novel 'anti-reverse' cap analogs 7-methyl(3'O-methyl)GpppG and 7-methyl(e'deoxy)GpppG," *RNA*, 7:1486-1495, 2001.
Stone et al., "Isolation of a human prostate carcinoma cell line (DU 145)," *Int. J. Cancer*, 21 (3): 274-281, 1978.

Strebhardt and Ullrich, "Targeting polo-like kinase 1 for cancer therapy," *Nat. Rev. Cancer*, 6 (4): 321-330, 2006.
Sturniolo et al., "A novel tumor suppressor protein promotes keratinocyte terminal differentiation via activation of type I transglutaminase," *J. Biol. Chem.*, 278 (48): 48066-48073, 2003.
Su et al,. "Overexpression of p8 is inversely correlated with apoptosis in pancreatic cancer," *Clin. Cancer Res.*, 7 (5): 1320-1324, 2001.
Sueoka et al., "Detection of plasma hnRNP B1 mRNA, a new cancer biomarker, in lung cancer patients by quantitative real-time polymerase chain reaction," *Lung Cancer*, 48(1):77-83, 2005.
Sui et al., "Clinical significance of Skp2 expression, alone and combined with Jab1 and p27 in epithelial ovarian tumors," *Oncol. Rep.*, 15 (4): 765-771, 2006.
Sum et al., "Overexpression of LMO4 induces mammary hyperplasia, promotes cell invasion, and is a predictor of poor outcome in breast cancer," *Proc. Nati Acad Sci U S A*, 102(21):7659-7664, 2005.
Sum et al., "The LIM domain protein LMO4 interacts with the cofactor CtIP and the tumor suppressor BRCA1 and inhibits BRCA1 activity," *J Biol Chem*, 277(10):7849-7856, 2002.
Sunpaweravong et al., "Epidermal growth factor receptor and cyclin D1 are independently amplified and overexpressed in esophageal squamous cell carcinoma," *J Cancer Res Clin Oncol*, 131(2):111-119, 2005.
Szafranska et al., "A unique microRNA molecular signature for pancreatic carcinoma," AACR-Pancreatic Cancer: Early Detection and Novel Therapeutics, Chapel Hill, NC, Jun. 26-27, 2006.
Takainizawa et al., "Reduced expression of the let-7 microRNAs in human lung cancers in association with shortened postoperative survival," *Cancer Research*, 64:3753-3756, 2004.
Takanami, "'The prognostic value of overexpression of Skp2 mRNA in non-small cell lung cancer.," *Oncol. Rep.*, 13 (4): 727-731, 2005.
Takimoto et al., "Genetic alterations in the retinoblastoma protein-related p107 gene in human hematologic malignancies," *Biochem Biophys Res Commun*, 251(1):264-268, 1998.
Tanaka et al., "A novel frizzled gene identified in human esophageal carcinoma mediates APC/beta-catenin signals," *Proc. Natl. Acad. Sci. USA*, 95 (17): 10164-10169, 1998.
Taniwaki et al., "Gene expression profiles of small-cell lung cancers: molecular signatures of lung cancer," *Int J Oncol*, 29(3):567-575, 2006.
Tassi et al., "Enhancement of fibroblast growth factor (FGF) activity by an FGF-binding protein," *J. Biol. Chem.*, 276(43):40247-40253, 2001.
Tazawa et al., "Tumor-suppressive *miR-34a* induces senescence-like growth arrest through modulation of the E2F pathway in human colon cancer cells," *PNAS*, 104(39):15472-15477, 2007.
Thøgersen et al., "A subclass of HER1 ligands are prognostic markers for survival in bladder cancer patients," *Cancer Res.*, 61 (16): 6227-6233, 2001.
Tomasini-Johansson et al., "Vitronectin in colorectal adenocarcinoma—synthesis by stromal cells in culture," *Exp. Cell. Res.*, 214 (1): 303-312, 1994.
Toning et al., "Increased expression of heparin binding EGF (HB-EGF), amphiregulin, TGF alpha and epiregulin in androgen-independent prostate cancer cell lines," *Anticancer Res.*, 20 (1a): 91-95, 2000.
Toyoda et al., "Distribution of mRNA for human epiregulin, a differentially expressed member of the epidermal growth factor family," *Biochem J*, 326 (Pt 1):69-75, 1997.
Traub et aL, "Prognostic impact of Skp2 and p27 in human breast cancer.," *Breast Cancer Res. Treat.*, 99 (2): 185-191, 2006.
Tsai et al., "RIG1 inhibits the Ras/mitogen-activated protein kinase pathway by suppressing the activation of Ras.," *Cell Signal*, 18 (3): 349-358, 2006.
U.S. Appl. No. 11/273,640, entitled "Methods and compositions involving miRNA and miRNA inhibitors molecules," by David Brown el al., filed Nov. 14, 2005.
U.S. Appl. No. 11/855,792, entitled "Methods of normalization in microRNA detection assays," by Gary Latham et al., filed Sep. 14, 2007.

(56) References Cited

OTHER PUBLICATIONS

U.S. Appl. No. 11/857,948, entitled "MicroRNAs differentially expressed in pancreatic diseases and uses thereof," by Emmanuel Labourier et al., filed Sep. 19, 2007.
U.S. Appl. No. 11/967,639, entitled "Functions and targets of LET-7 micro RNAs," by Charles Johnson et al., filed Dec. 31, 2007.
U.S. Appl. No. 11/967,663, entitled "miR-16 regulated genes and pathways as targets for therapeutic intervention," by Mike Byrom et al., filed Dec. 31, 2007.
U.S. Appl. No. 12/112,291, entitled "miR-20 Regulated Genes and Pathways as Targets for Therapeutic Intervention," by Andreas Bader et al., filed Apr. 30, 2008.
U.S. Appl. No. 12/120,388, entitled "miR-21 regulated genes and pathways as targets for therapeutic intervention," by Andreas Bader et al., filed May 14, 2008.
U.S. Appl. No. 12/124,394, entitled "miR-200 Regulated Genes and Pathways as Targets for Therapeutic Intervention," by Andreas Bader et al., filed May 21, 2008.
U.S. Appl. No. 12/125,412, entitled "miR-143 regulated genes and pathways as targets for therapeutic intervention," by Andreas Bader et al., filed May 22, 2008.
U.S. Appl. No. 12/125,675, entitled "miR-126 regulated genes and pathways as targets for therapeutic intervention," by Andreas Bader et al., filed May 22, 2008.
U.S. Appl. No. 12/134,932, entitled "miR-134 Regulated Genes and Pathways as Targets for Therapeutic Intervention," by Andreas Bader et al., filed Jun. 6, 2008.
U.S. Appl. No. 12/167,492, entitled "miR-15, miR-26, miR-31, miR-145, miR-147, miR-188, miR-215, miR-216, miR-331, mmu-miR-292-3P regulated genes and pathways as targets for therapeutic intervention," by Andreas Bader et al., filed Jul. 3, 2008.
U.S. Appl. No. 12/253,718, entitled "MicroRNAs differentially expressed in lung diseases and uses thereof," by Gary J. Lathan et al., filed Oct. 17, 2008.
U.S. Appl. No. 12/325,917, entitled "miR-124 Regulated Genes and Pathways as Targets for Therapeutic Intervention," by Andreas Bader et al., filed Dec. 1, 2008.
U.S. Appl. No. 12/340,329, entitled "miR-10 Regulated Genes and Pathways as Targets fur Therapeutic Intervention," by Ovcharenko et al., filed Dec. 19, 2008.
U.S. Appl. No. 12/368,053, entitled "miRNAs Differentially Expressed in Lymph Nodes from Cancer Patients," by Sylvie Beaudenon et al., filed Feb. 9, 2009.
U.S. Appl. No. 12/398,852, entitled "MicroRNA markers for recurrence of colorectal cancer," by Elizabeth Mambo et al., filed Mar. 5, 2009.
U.S. Appl. No. 12/412,087, entitled "Compositions and methods related to miR-16 and therapy of prostate cancer," by Fumitaka Takeshita et al., filed Mar. 26, 2009.
U.S. Appl. No. 12/420,634, entitled "Methods and compositions for diagnosing and modulating human papillomavirus (HPV)," by Sylvie Beaudenon-Huibregtse, filed Apr. 8, 2009.
U.S. Appl. No. 12/437,899, entitled "Compositions and methods related to miRNA modulation of neovascularization or angiogenesis," by Jikui Shen et al., filed May 8, 2009.
U.S. Appl. No. 60/575,743, entitled "Methods and compositions involving MicroRNA," by David Brown et al., filed May 28, 2004.
U.S. Appl. No. 60/649,584, entitled "Methods and compositions involving MicroRNA," by David Brown et al., filed Feb. 3, 2005.
U.S. Appl. No. 60/650,807, entitled "Compositions and methods involving MDA-7 and COX-2 inhibitors for the treatment of cancer," by Sunil Chada et al., filed Feb. 8, 2005.
U.S. Appl. No. 60/906,028, entitled "Prostate cancer specific miRNAs," by David Brown, filed Mar. 9, 2007.
U.S. Appl. No. 61/113,385, entitled "Methods and compositions involving miRNAs in cancer stem cells," by Lubna Patrawala et al., filed Nov. 11, 2008.
Uhm et al., "Vitronectin, a glioma-derived extracellular matrix protein, protects tumor cells from apoptotic death," *Clin. Cancer Res.*, 5 (6): 1587-1594, 1999.

Ulisse et al., "Expression of Aurora kinases in human thyroid carcinoma cell lines and tissues," *Int. J. Cancer*, 119 (2): 275-282, 2006.
Vargas-Roig et al., "Heat shock protein expression and drug resistance in breast cancer patients treated with induction chemotherapy," *Cancer Detection and Prevention*, 21(5):441-451, 1997.
Vella et al., "Architecture of a validated microRNA::target interaction," *Chem. Biol.*, 11(12):1619-1623, 2004.
Vella et al., "The C. elegans microRNA let-7 binds to imperfect let-7 complementary sites from the lin-41 3'UTR," *Genes Dev.*, 18(2):132-7, 2004.
Visvader et al., "The LIM domain gene LMO4 inhibits differentiation of mammary epithelial cells in vitro and is overexpressed in breast cancer," *Proc Natl Acad Sci U S A*, 98(25):14452-14457, 2001.
Volinia et al., "A microRNA expression signature of human solid tumors defines cancer gene targets," *Proc. Natl. Acad. Sci. USA*, 103(7):2257-2261, 2006.
Volloch and Sherman, "Oncogenic potential of Hsp72," *Oncogene*, 18(24):3648-3651, 1999.
Vos et al., "RASSF2 is a novel K-Ras-specific effector and potential tumor suppressor," *J Biol Chem*, 278(30):28045-28051, 2003.
Wade, "Transcriptional control at regulatory checkpoints by histone deacetylases: molecular connections between cancer and chromatin," *Hum. Mol. Genet.*, 10(7):693-698, 2001.
Wang et al., "Identification of rat lung-specific microRNAs by micoRNA microarray: valuable discoveries for the facilitation of lung research," *BMC Genomics*, 8:29-42, 2007.
Weeraratna et al., "Wnt5a signaling directly affects cell motility and invasion of metastatic melanoma," *Cancer Cell*, 1 (3): 279-288, 2002.
Weinstein, "Disorders in cell circuitry during multistage carcinogenesis, the role of homeostasis," *Carcinogenesis*, 21 (5): 857-864, 2000.
Weiss and Bohmann, "Deregulated repression of c-Jun provides a potential link to its role in tumorigenesis," *Cell Cycle*, 3 (2): 111-113, 2004.
Welsh et al., "Fingerprinting genomes using PCR with arbitrary primers," *Nucleic Acids Research*, Oxford university Press, Surrey, GB, 18(24):7213-7218, 1990.
Welsh et al., "Nucleic acid fingerprinting by PCR-based methods: applications to problems in aging and mutagenesis," *Mutation Research*, 338(1-6):215-229, 1995.
Wheeler and Ridley, "Why three Rho proteins? RhoA, RhoB, RhoC, and cell motility," *Exp. Cell. Res.*, 301 (1): 43-49, 2004.
Whitcombe et al., "A homogeneous fluorescence assay for PCR amplicons: its application to real-time, single-tube genotyping," *Clin, Chem.*, 44(5):918-923, 1998.
Whitcombe et al., "Advances in approaches to DNA-based diagnostics," *Curr. Opin. Biotechnol.*, 9(6):602-608, 1998.
Wikman et al., "Identification of differentially expressed genes in pulmonary adenocarcinoma by using cDNA array," *Oncogene*, 21(37):5804-5813, 2002.
Wood et al., "DNA microarray analysis of vitamin D-induced gene expression in a human colon carcinoma cell line," *Physiol. Genomics*, 17 (2): 122-129, 2004.
Wooster and Weber, "Breast and ovarian cancer," *N. Engl. J. Med.*, 348(23):2339-2347, 2003.
Wu et al., "Expression of Ephb2 and Ephb4 in breast carcinoma," *Pathol. Oncol. Res.*, 10 (1): 26-33, 2004.
Wu et al., "MicroRNA and cancer: current status and prospective," *International Journal of Cancer*, 120:953-960, 2006.
Wu et al., "p107 Expression in colorectal tumours rises during carcinogenesis and falls during Invasion," *Eur J Cancer*, 38(14):1838-1848, 2002.
Wu et al., "RARRES1 expression is significantly related to tumour differentiation and staging in colorectal adenocarcinoma," *Eur. J. Cancer*, 42(4):557-565, 2006.
Wu et al., "RhoC induces differential expression of genes involved in invasion and metastasis in MCF10A breast cells," *Breast Cancer Res., Treat.*, 84 (1); 3-12, 2004.
Wu et al., "The prognostic impact of EphB2/B4 expression on patients with advanced ovarian carcinoma," *Gynecol. Oncol.*, 102 (1): 15-21, 2006.
Wyatt et al., "Synthesis and purification of large amounts of RNA oligonucleotides," *Biotechniques*, 11(6):764-769, 1991.

(56) References Cited

OTHER PUBLICATIONS

Wyttenbach et al., "Polyglutamine expansions cause decreased CRE-mediated transcription and early gene expression changes prior to cell death in an inducible cell model of Huntington's disease," *Human Molecular Genetics*, 10(17):1829-1845, 2001.

Xia et al., "Positive expression of HIF-2alpha/EPAS1 in invasive bladder cancer," *Urology*, 59(5):774-778, 2002.

Xia et al., "Regulation of vascular endothelial growth factor transcription by endothelial PAS domain protein 1 (EPAS1) and possible involvement of EPAS1 in the angiogenesis of renal cell carcinoma," *Cancer*, 91(8):1429-1436, 2001.

Xia et al., "The Src-suppressed C kinase substrate, SSeCKS, is a potential metastasis inhibitor in prostate cancer," *Cancer Res*, 61(14):5644-5651, 2001.

Xie et al., "Negative feedback regulation of Dicer-Like1 in *Arahidopsis* by microRNA-guided mRNA degradation," *Current Biology*, 13:784-789, 2003.

Xie, et al., "Systematic discovery of regulatory motifs in human promoters and 3' UTRs by comparison of several mammals," *Nature*, 434(7031):338-345, 2005.

Xu et al., "The *Drosophila* microRNA Mir-14 suppresses cell death and is required for normal fat metabolism," *Curr. Biol.*, 13:790-795, 2003.

Yanaihara et al., "Unique microRNA molecular profiles in lung cancer diagnosis and prognosis," *Cancer Cell*, 9:189-198, 2006.

Yang et al,, "Differential expression of CCAAT/enhancer-binding protein-delta (c/EBPdelta) in rat androgen-dependent tissues and human prostate cancer," *J. Androl.*, 22 (3): 471-480, 2001.

Yang et al., "Smad3 reduces susceptibility to hepatocarcinoma by sensitizing hepatocytes to apoptosis through downreguiation of Bc1-2," *Cancer Cell*, 9(6):445-457, 2006.

Yang et al ,"Stromal expression of connective tissue growth factor promotes angiogenesis and prostate cancer tumorigenesis," *Cancer Res.*, 65(19):8887-8895, 2005.

Yang et al., "The transformation suppressor Pdcd4 is a novel eukaryotic translation initiation factor 4A binding protein that inhibits translation," *Mol. Cell Biol.*, 23(1):26-37, 2003.

Yang et al, "Tumorigenesis suppressor Pdcd4 down-regulates mitogen-activated protein kinase kinase kinase kinase 1 expression to suppress colon carcinoma cell invasion," *Mol Cell Biol*, 26(4):1297-1306, 2006.

Yao et al, "RhoC GTPase is required for PC-3 prostate cancer cell invasion but not motility," *Oncogene*, 25 (16): 2285-2296, 2006.

Yoon and De Micheli, "Prediction of regulatory modules comprising microRNs and target genes," *Bioinformatics*, 21(Suppl.2):ii93-ii100, 2005.

Yoshida et al., "The clinical significance of Cyclin B1 and Wee1 expression in non-small-cell lung cancer," *Ann Oncol*, 15(2):252-256, 2004.

Yoshimura et al., "Prognostic impact of hypoxia-inducible factors 1alpha and 2alpha in colorectal cancer patients: correlation with tumor angiogenesis and cyclooxygenase-2 expression," *Clin. Cancer Res.*, 10(24):8554-8560, 2004.

Yoshioka et al,. "A role for LIM kinase in cancer invasion," *Proc. Natl. Acad. Sci. USA*, 100 (12): 7247-7252, 2003.

Youssef et al, "Hypermethylation and silencing of the putative tumor suppressor, Tazarotene-induced gene 1 in human cancers," *Cancer Res.*, 64 (7): 2411-2417, 2004.

Yu et al,. "Global assessment of promoter methylation in a mouse model of cancer identifies ID4 as a putative tumor-suppressor gene in human leukemia," *Nat. Genet.*, 37 (3): 265-274, 2005.

Zangemeister-Wittke and Huwiler, "Antisense targeting of Mcl-1 has therapeutic potential in gastric cancer," *Cancer Biol. Ther.*, 5(10):1355-1356, 2006.

Zeng et al, "Both natural and designed micro RNAs can inhibit the expression of cognate mRNAs when expressed in human cells," *Mol Cell*. 9, 1327-33, 2002.

Zeng et al, "MicroRNAs and small interfering RNAs can inhibit mRNA expression by similar mechanisms," *Proc. Natl. Acad. Sci.* 100: 9779-9784, 2003.

Zhang et al, "Involvement of programmed cell death 4 in transforming growth factor-beta1-induced apoptosis in human hepatocellular carcinoma," *Oncogene*, 25(45):6101-6112, 2006.

Zhang et al., "Methylation of the retinoid response gene TIG1 in prostate cancer correlates with methylation of the retinoic acid receptor beta gene," *Oncogene*, 23 (12): 2241-2249, 2004.

Zhao et al, "Cyclin G1 has growth inhibitory activity linked to the ARF-Mdm2-p53 and pRb tumor suppressor pathways," *Mol Cancer Res*, 1(3):195-206, 2003.

Zhu et al, "MicroRNA targets the tumor suppressor gene tropomyosin I (TIPM1)" *The Journal of Biological Chemistry*, 282(19):14328-14336, 2007.

Zhu et al., "Epiregulin is Up-regulated in pancreatic cancer and stimulates pancreatic cancer cell growth," *Biochem. Biophys. Res. Commun.*, 273 (3): 1019-1024, 2000.

Zimmerman et al., "Technical aspects of quantitative competitive PCR," *Biotechniques*, 21(2):268-270, 1996.

Calin et al., "Human microRNA genes are frequently located at fragile sites and genomic regions involved in cancers," *PNAS*, 101(9):2999-3004, 2004.

Cao et al., "A functional study of miR-124 in the developing neural tube," *Genes & Development*, 21(5):531-536, 2007.

Conaco et al., "Reciprocal actions of REST and a microRNA promote neuronal identity," *PNAS*, 103(7):2422-2427, 2006.

Decision on Appeal, Appeal 2008-002253, issued in U.S. Appl. No. 10/880,350, decided May 29, 2009.

Karginov et al, "A biochemical approach to identifying microRNA targets," *PNAS*, 104(49):19291-19296, 2007.

Lujambio et al., "Genetic unmasking of an epigenetically silenced microRNA in human cancer cells," *Cancer Research*, 67(4):1424-1429, 2007.

Makeyev et al., "The microRNA miR-124 promotes neuronal differentiation by triggering brain-specific alternative pre-mRNA splicing," *Molecular Cell*, 27(3):435-448, 2007.

Nakamura et al., "March-II is a syntaxin-6-binding protein involved in endosomal trafficking," *Molecular Biology of the Cell*, 16(4):1696-1710, 2005.

Office Action issued in U.S. Appl. No. 09154092.2, mailed May 7, 2009.

Office Action issued in U.S. Appl. No. 10/963,415, mailed Mar. 9, 2009.

Office Action issued in U.S. Appl. No. 11/141,707, mailed Jun. 19, 2009.

Office Action issued in U.S. Appl. No. 11/273,640, mailed Jun. 26, 2009.

Office Action issued in U.S. Appl. No. 11/837,487, mailed Mar. 25, 2009.

Office Action issued in U.S. Appl. No. 11/837,498, mailed Apr. 30, 2009.

Office Action issued in U.S. Appl. No. 11/857,948, mailed Jun. 4, 2009.

Office Action issued in U.S. Appl. No. 11/967,639, mailed May 14, 2009.

Office Action issued in U.S. Appl. No. 11/967,639, mailed Mar. 13, 2009.

PCT International Preliminary Report on Patentability, issued in International Application No. PCT/US2007/078894, mailed Apr. 2, 2009.

PCT International Preliminary Report on Patentability, issued in International Application No. PCT/US2007/078936, mailed Apr. 2, 2009.

PCT International Preliminary Report on Patentability, issued in International Application No. PCT/US2007/078859, mailed Apr. 2, 2009.

PCT International Search Report and Written Opinion, issued in International Application No. PCT/US2008/076246, mailed Feb. 27, 2009.

PCT Invitation to Pay Additional Fees and Partial International Search, issued in International Application No. PCT/US2008/085178, mailed May 8, 2009.

Tang et al., "PS 7-2 microrna expression profile in cervical cancer and its derived cell lines," 23rd *International Papillomavirus Conference and Clinical Workshop*, Prague, Czech Republic, Sep. 1-7, 2006.

(56) References Cited

OTHER PUBLICATIONS

Visvanathan et al., "The microRNA miR-124 antagonizes the antineural REST/SCP1 pathway during embryonic CNS development," *Genes & Development*, 21(7):744-749, 2007.
Wang and Wang, "Systematic identification of microRNA functions by combining target prediction and expression profiling," *Nucleic Acids Research*, 34(5):1646-1652, 2006.
"Poster Abstracts," *Annals of Surgical Oncology*, 15(Suppl 1):33-64, 2008.
Agrawal and Syngal, "Colon cancer screening strategies," *Curr Opin Gastroenterol*, 21(1):59- 63, 2005.
Aoki et al., "Proteasomal degradation of the FoxO1 transcriptional regulator in cells transformed by the P3k and Akt oncoproteins," *Proc Natl Acad Sci U S A*, 101(37):13613-13617, 2004.
Austin and Cook, "Increased expression of Mcl-1 is required for protection against serum starvation in phosphatase and tensin homologue on chromosome 10 null mouse embryonic fibroblasts, but repression of Bim is favored in human glioblastomas," *J Bol Chem*, 280(39):33280-33288, 2005.
Bader and Vogt, "An essential role for protein synthesis in oncogenic cellular transformation," *Oncogene*, 23(18):3145-3150, 2004.
Bader et al.," Oncogenic PI3K deregulates transcription and translation," *Nat Rev Cancer*, 5(12):921-929, 2005.
Baffa et al., "MicroRNA expression profiling of human metastatic cancers identities cancer gene targets," *J. Pathol.*, Epub Ahead of Print, 2009.
Bai et al,, "Downregulation of selective MicroPNAs in trigeminal ganglion neurons following inflammatory muscle pain," *Mol Pain*, 3:15, 2007.
Bartel et al,, "Alternative and aberrant splicing of MDM2 mRNA in human cancer," *Cancer Cell*, 2(1):9-15, 2002.
Beeram et al., "Raf: a strategic target for therapeutic development against cancer," *J Clin Oncol*, 23(27):6771-6790, 2005.
Bell and Dutta, "DNA replication in eukaryotic cells," *Annu Rev Biochem*, 71:333-374, 2002.
Bello et al., "Androgen responsive adult human prostatic epithelial cell lines immortalized by human papillomavirus 18," *Carcinogenesis*, 18(6):1215-1223, 1997.
Bertagnolli et al., "Sentinel node staging of resectable colon cancer: results of a multicenter study," Ann. Surg., 240(4).624-630, 2004.
Blobe et al., "Functional roles for the cytoplasmic domain of the type III transforming growth factor beta receptor in regulating transforming growth factor beta signaling," *J Biol Chem*, 276(27):24627-24637, 2001.
Brothman et al., "Metastatic properties of the human prostatic cell line, PPC-1, in athymic nude mice," *J Urol.*, 145(5):1088-1091, 1991.
Calin et al., "MicroRNA profiling reveals distinct signatures in B cell chronic lymphocytic leukemias," *Proc Natl Acad Sci USA*, 101(32):11755-11760, 2004.
Carter and Brunet, "FOXO transcription factor," *Curr Biol*, 17(4):R113-114, 2007.
Caselitz et al., "Malignant melanomas contain only the vimentin type of intermediate filaments," *Virchows Arch A Pathol Anat Histopathol*, 400(1):43-51, 1983.
Chendrimada et al., "MicroRNA silencing through RISC recruitment of eIF6," *Nature*, 447(7146):823-828, 2007.
Chieffi et al., "Aurora B expression directly correlates with prostate cancer malignancy and influence prostate cell proliferation," *Prostate*, 66(3):326-333, 2006.
Chmielarz et al., "Prognostic factors for the time of occurrence and dynamics of distant metastases and local recurrences after radical treatment in patients with rectal cancer," *Med Sci Monit.*, 7(6):1263-1269, 2001.
Churg, "Immunohistochemical staining for vimentin and keratin in malignant mesothelioma," *Am J Surg Pathol*, 9(5):360-365, 1985.
Cipriano and Chen, "Insensitivity to growth inhibition by TGF-beta1 correlates with a lack of inhibition of the CDK2 activity in prostate carcinoma cells," *Oncogene*, 17(12):1549-1556, 1998.

Coello et al,, "Prognostic significance of micrometastasis in non-small-cell lung cancer," *Clin. Lung Cancer*, 5:214-225, 2004.
Cohen et al., "Prognosis of node-positive colon cancer," *Cancer*, 67(7):1859-1861, 1991.
Coll et al., "Molecular cloning of the avian acute transforming retrovirus MH2 reveals a novel cell-derived sequence (v-mil) in addition to the myc oncogene," *Embo J*, 2(12):2189-2194, 1983.
Costello et al, "Cyclin-dependent kinase 6 (CDK6) amplification in human gliomas identified using two-dimensional separation of genomic DNA," *Cancer Res*, 57(7):1250-1254, 1997.
Cox et al. ,"Significance of sentinel lymph node micrometastases in human breast cancer,", *J. Am. Coll. Surg.*, 206(2):261-268, 2008.
Dahl et al., "Identification of sentinel nodes in patients with colon cancer," *Eur. J. Surg. Oncol.*, 31(4):381-385, 2005.
Davison et al., "Analyzing micro-RNA expression using microarrays," *Meth. Enzymol.*, 411:14-34, 2006.
D'Cunha et cd., "Poor correspondence between clinical and pathologic staging in stage 1 non-small cell lung cancer: results from CALGB 9761, a prospective trial," *Lung Cancer*, 48:241-246, 2005.
De Boer et al., "Micrometastases and isolated tumor cells: relevant and robust or rubbish? (MIRROR): preliminary results of the MIRROR study from the Dutch breast cancer trialists' group (BOOG)," *San Antonio Breast Cancer Symposium*, Abstract 23, 2008.
Dillon et al., "An April to remember: novel TNF ligands as therapeutic targets," *Nat Rev Drug Discov*, 5(3):235-246, 2006.
Dittmer, "The biology of the Ets1 proto-oncogene," *Mol Cancer*, 2:29, 2003.
Dyer and Bremner, "The search for the retinoblastoma cell of origin," *Nat Rev Cancer*, 5(2):91-101, 2005.
Egle et al., "Bim is a suppressor of Myc-induced mouse B cell leukemia," *Proc Natl Acad Sci U S A*, 101(16):6164-6169, 2004.
Egloff et al., "Cychn B1 and other cyclins as tumor antigens in immunosurveillance and immunotherapy of cancer," *Cancer Res*, 66(1):6-9, 2006.
Esser et al., "The role of sentinel lymph node mapping in staging of colon and rectal cancer," *Dis Colon Rectum*, 44(6):850-856, 2001.
European Search Report and Search Opinion issued in European Application No. 09154092.2. mailed Aug. 12, 2009.
Fakharzadeh et al., "Tumorigenic potential associated with enhanced expression of a gene that is amplified in a mouse tumor cell line," *Embo J*, 10(6):1565-1569, 1991.
Ferris et al., "Molecular staging of cervical lymph nodes in squamous cell carcinoma of the head and neck," *Cancer Res.*, 65:2147-2156, 2005.
Gerald and Haber, "The EWS-WT1 gene fusion in desmoplastic small round cell tumor," *Semin Cancer Biol*, 15(3):197-205, 2005.
Gillanders et al., "Molecular detection of micrometastatic breast cancer in histopathology-negative axillary lymph nodes correlates with traditional predictors of prognosis: an interim analysis of a prospective multi-institutional cohort study," *Ann. Surg.*, 239:828-840, 2004.
Gilles et al., "Vimentin expression in cervical carcinomas: association with invasive and migratory potential," *J Pathol*, 180(2):175-180, 1996.
Gipponi et al., "Sentinel lymph node as a new marker for therapeutic planning in breast cancer patients," *J. Surg. Oncol.*, 85(3):102-111, 2004.
Gomez-Bougie et al., "The imbalance between Bim and Mcl-1 expression controls the survival of human myeloma cells," *Eur J Immunol*, 34(11):3156-3164, 2004.
Gonzalez et al., "Oncogenic activity of Cdc6 through repression of the INK4/ARF locus," *Nature*, 440(7084):702-706, 2006.
Goyns et al., "The c-ets-1 proto-oncogene is rearranged in some cases of acute lymphoblastic leukaemia," *Br J Cancer*, 56(5):611-613, 1987.
Hayette et al., "In B-cell chronic lymphocytic leukemias, 7q21 translocations lead to overexpression of the CDK6 gene," *Blood*, 102(4):1549-1550, 2003.
Ho et al., "Quantification of colorectal cancer micrometastases in lymph nodes by nested and real-time reverse transcriptase-PCR analysis for carcinoembryonic antigen," *Clin. Cancer Res.*, 10(17):5777-5784, 2004.

(56) References Cited

OTHER PUBLICATIONS

Hodge et al., "The role of IL-6 and STAT3 in inflammation and cancer," *Eur J. Cancer*, 41(16):2502-2512, 2005.
Hoeflich et al., "Insulin-like growth factor-binding protein 2 in tumorigenesis: protector or promoter?" *Cancer Res*, 61(24):8601-8610, 2001.
Hofer et al., "The role of metastasis-associated protein 1 in prostate cancer progression," *Cancer Res*, 64(3):825-829, 2004.
Horoszewicz et al., "The LNCaP cell line—a new model for studies on human prostatic carcinoma," *Prog Clin Biol Res.*, 37:115-32, 1980.
Houston and O'Connell, "The Fas signalling pathway and its role in the pathogenesis of cancer," *Carr Opin Pharmacol*, 4(4):321-326, 2004.
Houvenaeghel et al., "Micrometastases in sentinel lymph node in a multicentric study: predictive factors of nonsentinel lymph node involvement—Groupe des Chirurgiens de la Federation des Centres de Lutte Contre le Cancer," *J. Clin. Oncol.*, 24:1814-1822, 2006.
Hsu et al., "BOD (Bcl-2-related ovarian death gene) is an ovarian BH3 domain-containing proapoptotic Bcl-2 protein capable of dimerization with diverse antiapoptotic Bcl-2 members," *Mol Endocrinol*, 12(9):1432-1440, 1998.
Huber et al., "Variance stabilization applied to microarray data calibration and to the quantification of differential expression," *Bioinformatics*, 18:Suppl 1:S96-104, 2002.
Hughes et al., "A rapid, fully automated, molecular-based assay accurately analyzes sentinel lymph nodes for the presence of metastatic breast cancer," *Ann. Surg.*, 243:389-398, 2006.
Iorio et al., "MicroRNA gene expression deregnation in human breast cancer," *Cancer Res*, 65(16):7065-7070, 2005.
Islam et al., "Vimentin expression in human squamous carcinoma cells: relationship with phenotypic changes and cadherin-based cell adhesion," *J Cell Biochem*, 78(1):141-150, 2000.
Jackson and Foster, "The enigmatic protein kinase Cdelta: complex roles in cell proliferation and survival," *Faseb J*, 18(6):627-636, 2004.
Jang et al., "MTA1 overexpression correlates significantly with tumor grade and angiogenesis in human breast cancers," *Cancer Sci*, 97(5):374-379, 2006.
Janknecht, "EWS-ETS oncoproteins: the linchpins of Ewing tumors," *Gene*, 363:1-14, 2005.
Jansen et al., "Two unrelated cell-derived sequences in the genome of avian leukemia and carcinoma inducing retrovirus MH2," *Embo J*, 2(11):1969-1975, 1983.
Kahn et al., "Increased levels of the FoxM1 transcription factor accelerate development and progression of prostate carcinomas in both TRAMP and LADY transgenic mice," *Cancer Res*, 66(3):1712-1720, 2006.
Kalinichenko et al., "Foxm1b transcription factor is essential for development of hepatocellular carcinomas and is negatively regulated by the p19ARF tumor suppressor," *Genes Dev*, 18(7):830-850, 2004.
Kammula et al., "Serial follow-up and the prognostic significance of reverse transcriptase-polymerase chain reaction—staged sentinel lymph nodes from melanoma patients." *J. Clin. Oncol.*, 22:3989-3996, 2004.
Kapsimali et al., "MicroRNAs show a wide diversity of expression profiles in the developing and mature central nervous system," *Genome Biol*, 8(8):R173, 2007.
Karakaidos et al, "Overexpression of the replication licensing regulators hCdt1 and hCdc6 characterizes a subset of non-small-cell lung carcinomas: synergistic effect with mutant p53 on tumor growth and chromosomal instability—evidence of E2F-1 transcriptional control over hCdt1," *Am J Pathol*, 165(4):1351-1365, 2004.
Karin et al., "NF-kappaB in cancer: from innocent bystander to major culprit," *Nat Rev Cancer*, 2(4):301-310, 2002.
Kastan and Lim, "The many substrates and functions of ATM," *Nat Rev Mol Cell Biol*, 1(3):179-186, 2000.

Kim et al., "The Forkhead Box m1 transcription factor stimulates the proliferation of tumor cells during development of lung cancer," *Cancer Res*, 66(4):2153-2161, 2006.
Kiriakidou et al., "An mRNA m7G cap binding-like motif within human Ago2 represses translation," *Cell*, 129(6):1141-1151, 2007.
Kops et al., "On the road to cancer: aneuploidy and the mitotic checkpoint," *Nat Rev Cancer*, 5(10):773-785. 2005.
Kristjánsdóttir and Rudolph, "Cdc25 phosphatases and cancer," *Chem Biol*, 11(8):1043-1051, 2004.
Kuehbacher et al., "Targeting microRNA expression to regulate angiogenesis," *Trends Pharmacol Sci.*, 29(1):12-15, 2008.
Kuhajda, "Fatty acid synthase and cancer: new application of an old pathway," *Cancer Res*, 66(12):5977-5980, 2006.
Lagos-Quintana et al., "New microRNAs from mouse and human," *RNA*, 9(2):175-179, 2003.
Lam et al., "Expression of p19INK4d, CDK4, CDK6 in glioblastoma multiforme," *Br J Neurosurg*, 14(1):28-32, 2000.
Lee et al., "Altered microRNA expression in cervical carcinomas," *Clin Cancer Res*, 14(9):2535-2542, 2008.
Li et al., "Apoptosis of non-small-cell lung cancer cell lines after paclitaxel treatment involves the BH3-only proapoptotic protein Bim," *Cell Death Differ*, 12(3):292-303, 2005.
Li et al.,"PDGF-D is a potent transforming and angiogenic growth factor," *Oncogene*, 22(10):1501-1510, 2003.
Liang et al., "Chacterization of microRNA expression profiles in normal human tissues," *BMC Genomics*, 8:166, 2007.
Liu and Erikson, "Polo-like kinase (Plk)1 depletion induces apoptosis in cancer cells," *Proc Natl Acad Sci U S A*, 100(10):5789-5794, 2003.
Lukiw, "Micro-RNA speciation in fetal, adult and Alzheimer's diseasehippocampus," *Neuroreport*, 18(3):297-300, 2007.
Ma et al., "Tumour invasion and metastasis initiated by microRNA-10b in breast cancer," *Nature*, 449(7163):682-688, 2007.
Malumbres and Barbacid, "To cycle or not to cycle: a critical decision in cancer," *Nat Rev Cancer*, 1(3):222-231, 2001.
Marone et al., "Analysis of cyclin E and CDK2 in ovarian cancer: gene amplification and RNA overexpression," *Int J Cancer*, 75(1):34-39, 1998.
McInroy and Määttä, "Down-regulation of vimentin expression inhibits carcinoma cell migration and adhesion," *Biochem Biophys Res Commun*, 360(1):109-114, 2007.
Mendrzyk et al., "Genomic and protein expression profiling identifies CDK6 as novel independent prognostic marker in medulloblastoma," *J Clin Oncol*, 23(34):8853-8862, 2005.
Mishima et al., "RT-PCR-based analysis of microRNA (miR-1 and -124) expression in mouse CNS," *Brain Res*, 1131(1):37-43, Epub Dec. 19, 2006. 2007.
Momand et al., "The MDM2 gene amplification database," *Nucleic Acids Res*, 26(15):3453-3459, 1998.
Morton et al., "Sentinel-node biopsy or nodal observation in melanoma," *N. Engl. J. Med*., 355(13):1307-1317, 2006.
Morton et al., "Technical details of intraoperative lymphatic mapping for early stage melanoma," *Arch Surg*, 127(4):392-399, 1992.
Murphy et al., "p16INK4A, CDC6, and MCM5: predictive biomarkers in cervical preinvasive neoplasia and cervical cancer," *J Clin Pathol*, 58(5):525-534, 2005.
Nauert et al., "Gravin, an autoantigen recognized by serum from myasthenia gravis patients, is a kinase scaffold protein, " *Curr Biol*, 7(1):52-62, 1997.
Nerlov, "C/EBPalpha mutations in acute myeloid leukaemias," *Nat Rev Cancer*, 4(5):394-400, 2004.
Ngan et al., "Quantitative evaluation of vimentin expression in tumour stroma of colorectal cancer," *Br J Cancer*, 96(6):986-992, 2007.
Nordgård et al., "Quantitative RT-PCR detection of tumor cells in sentinel lymph nodes isolated from colon cancer patients with an ex vivo approach," *Annals of Surgery*, 249(4):602-607, 2009.
Öberg et al., "Detection of occult tumour cells in lymph nodes of colorectal cancer patients using real-time quantitative RT-PCR for CEA and CK20 mRNAS," *Int. J. Cancer*, 111(1):101-110, 2004.
O'Connor et al., "Bim: a novel member of the Bcl-2 family that promotes apoptosis," *Embo J*, 17(2):384-395, 1998.

(56) References Cited

OTHER PUBLICATIONS

Office Action issued in U.S. Appl. No. 11/837,490, mailed Aug. 18, 2009.
Office Action issued in U.S. Appl. No. 11/953,606, mailed Aug. 10, 2009.
Ohlsson et al., "Biomarker selection for detection of occult tumour cells in lymph nodes of colorectal cancer patients using real-time quantitative RT-PCR," *Br. J. Cancer*, 95(2):218-225, 2006.
Ohsaki et al., "Antitumor activity of magainin analogues against human lung cancer cell lines," *Cancer Res*, 52(13):3534-3538, 1992.
Ollila et al., "Metastatic melanoma cells in the sentinel node cannot be ignored," *J. Am. Coll. Surg.*, 208(5):924-929, 2009.
Paik et al., "FoxOs are lineage-restricted redundant tumor suppressors and regulate endothelial cell homeostasis," *Cell*, 128(2):309-323, 2007.
Paramo et al., "Validation of sentinel node mapping in patients with colon cancer," *Ann Surg Oncol*, 9(6):550-554, 2002.
Payton and Coats, "Cyclin E2, the cycle continues," *Int J Biochem Cell Biol*, 34(4):315-320, 2002.
Payton et al., "Deregulation of cyclin E2 expression and associated kinase activity in primary breast tumors," *Oncogene*, 21(55):8529-8534, 2002.
PCT International Preliminary Report on Patentability and Written Opinion, issued in International Application No. PCT/US2007/087033, mailed Jun. 18, 2009.
PCT International Preliminary Report on Patentability and Written Opinion, issued in International Application No. PCT/US2007/087031, mailed Jun. 18, 2009.
PCT International Preliminary Report on Patentability and Written Opinion, issued in International Application No. PCT/US2007/087029, mailed Jun. 18, 2009.
PCT International Preliminary Report on Patentability and Written Opinion, issued in International Application No. PCT/US2007/087037, mailed Jun. 18, 2009.
PCT International Preliminary Report on Patentability and Written Opinion, issued in International Application No. PCT/US2007/086396, mailed Jun. 18, 2009.
PCT International Preliminary Report on Patentability and Written Opinion, issued in International Application No. PCT/US2007/087021, mailed Jun. 18, 2009.
PCT International Preliminary Report on Patentability and Written Opinion, issued in International Application No. PCT/US2007/089206, mailed Jun. 18, 2009.
PCT International Preliminary Report on Patentability and Written Opinion, issued in International Application No. PCT/US2007/087038, mailed Jun. 18, 2009.
PCT International Search Report and Written Opinion, issued in International Application No. PCT/US2008/085178, mailed Aug. 21, 2009.
PCT International Search Report and Written Opinion, issued in International Application No. PCT/US2009/033556, mailed Aug. 4, 2009.
PCT Invitation to Pay Additional Fees and Partial International Search, issued in international Application No. PCT/US2009/043361, mailed Jul. 22, 2009.
PCT Invitation to Pay Additional Fees and Partial international Search, issued in International Application No. PCT/US2009/036195, mailed Jul. 2, 2009.
PCT Invitation to Pay Additional Fees and Partial International Search, issued in international Application No. PCT/US2009/033556, mailed Jun. 5, 2009.
Pendas et al, "Worldwide experience with lymphatic mapping for invasive breast cancer," *Semin. Oncol.*, 31(3):318-323, 2004.
Phan et al., "Sentinel lymph node biopsy for melanoma: indications and rationale," *Cancer Control*, 16(3):234-239, 2009.
Pietras et al., "PDGF receptors as cancer drug targets," *Cancer Cell*, 3(5):439-443, 2003.
Pretlow et al, "K-ras mutations in putative preneoplastic lesions in human colon," *J. Natl Cancer Inst.*, 85(24):2004-2007, 1993.
Qian et al., "Expression profiling of CD34+ hematopoietic stem/progenitor cells reveals distinct subtypes of therapy-related acute myeloid leukemia," *Proc Natl Acad Sci U S A*, 99(23):14925-14930, 2002.
Chuan et al., "The evolution of lymph node assessment in breast cancer," *Journal of Surgical Oncology*, 2008.
Rapp et al., "Structure and biological activity of v-raf, a unique oncogene transduced by a retrovirus," *Proc Natl Acad Sci U S A*, 80(14):4218-4222, 1983.
Redston et al., "Analysis of micrometastatic disease in sentinel lymph nodes from resectable colon cancer: results of Cancer and Leukemia Group B Trial 80001," *J. Clin. Oncol.*, 24(6):878-883, 2006.
Reintgen et al., "Sentinel Node Biopsy in Breast Cancer: An Overview," *Breast J.*, 6(5):299- 305, 2000.
Reshmi and Pillai, "Beyond HPV: oncomirs as new players in cervical cancer," *FEBS Letters*, 582:4113-4116, 2008.
Roberts et al., "Interpretive disparity among pathologists in breast sentinel lymph node evaluation," *Am. J. Surg.*, 180:324-329, 2003.
Rous, "A sarcoma of the fowl transmissible by an agent separable from the tumor cells," *J Exp Med*, 13:397-411, 1911.
Ryan et al., "MicroRNAs of the mammalian eye display distinct and overlapping tissue specificity," *Molecular Vision*, 12:1175-1184, 2006.
Saha et al., "Historical review of lymphatic mapping in gastrointestinal malignancies," *Ann Surg Oncol*, 11(3 Suppl):245S-249S, 2004.
Saha et al., "Ultrastaging of colorectal cancer by sentinel lymph node mapping technique—a multicenter trial," *Ann. Surg. Oncol.*, 8(9 Suppl):94S-98S, 2001.
Sasaki et al., "Expression of the MTA1 mRNA in advanced lung cancer," *Lung Cancer*, 35(2):149-154, 2002.
Schepeler et al., "Diagnostic and prognostic microRNAs in stage II colon cancer," *Cancer Research*, 68(15):6416-6424 2008.
Schetter et al., "MicroRNA expression profiles associated with prognosis and therapeutic outcome in colon adenocarcinoma," *JAMA*, 299(4):425-436, 2008.
Schorr et al., "Lymphatic spread and microinvolvement in adenocarcinoma of the esophago-gastric junction," *J Slug. Oncol.*, 94:307-315, 2006.
Schuster and Porse, "C/EBPalpha: a tumour suppressor in multiple tissues?" *Biochim Biophys Acta*, 1766(1):88-103, 2006.
Scoggins et al., "Prospective multi-institutional study of reverse transcriptase polymerase chain reaction for molecular staging of melanoma," *J Clin. Oncol.*, 24:2849-2857, 2006.
Semple and Duncker, "ORC-associated replication factors as biomarkers for cancer," *Biotechnol Adv*, 22(8):621-631, 2004.
Shen et al., "MicroRNAs regulate ocular neovascularization," *Molecular Therapy*, 16(7):1208-1216, 2008.
Shen et al., "Suppression of ocular neovascularization with siRNa targeting VEGF receptor 1," *Gene Therapy*, 13:225-234, 2006.
Sherr and McCormick, "The RB and p53 pathways in cancer," *Cancer Cell*, 2(2):103-112, 2002.
Sherr and Roberts, "CDK inhibitors: positive and negative regulators of G1-phase progression," *Genes Dev*, 13(12):1501-1512, 1999.
Singh et al., "Overexpression of vimentin: role in the invasive phenotype in an androgen-independent model of prostate cancer," *Cancer Res*, 63(9):2306-2311, 2003.
Slaby et al., "Altered expression of miR-21, miR-31, miR-143 and miR-145 is related to clinicopathologic features of colorectal cancer," *Oncology*, 72(5-6):397-402, 2007.
Smirnova et al., "Regulation of miRNA expression during neural cell specification," *Eur J Neurosci*, 21(6):1469-1477, 2005.
Smith et al., "Overexpression of aurora B kinase (AURKB) in primary non-small cell lung carcinoma is frequent, generally driven from one allele, and correlates with the level of genetic instability," *Br J Cancer*, 93(6):719-729, 2005.
Sommers et al., "Loss of epithelial markers and acquisition of vimentin expression in adriamycin- and vinblastine-resistant human breast cancer cell lines," *Cancer Res*, 52(19):5190-5197, 1992.
Stehelin et al., "DNA related to the transforming gene(s) of avian sarcoma viruses is present in normal avian DNA," *Nature*, 260(5547):170-173, 1976.

(56) References Cited

OTHER PUBLICATIONS

Swanson et al., "The prognosis of T3N0 colon cancer is dependent on the number of lymph nodes examined," *Ann. Surg. Oncol.*, 10(1):65-71, 2003.
Tagawa et al., "Genome-wide array-based CGH for mantle cell lymphoma: identification of homozygous deletions of the proapoptotic gene BIM," *Oncogene*, 24(8):1348-1358, 2005.
Takeuchi et al., "Prognostic significance of molecular upstaging of paraffin-embedded sentinel lymph nodes in melanoma patients," *J. Clin. Oncol.*, 22:2671-2680, 2004.
Toh et al., "A novel candidate metastasis-associated gene, mta1, differentially expressed in highly metastatic mammary adenocarcinoma cell lines. cDNA cloning, expression, and protein analyses," *J Biol Chem*, 269(37):22958-22963, 1994.
Toll et al., "Overexpression of metastasis-associated MTA1 mRNA in invasive oesophageal carcinomas," *Br J Cancer*, 79(11-12):1723-1726, 1999.
Toh et al., "Overexpression of the MTA1 gene in gastrointestinal carcinomas: correlation with invasion and metastasis," *Int J Cancer*, 74(4):459-463, 1997.
Tsai et al., "Correlation of intrinsic chemoresistance of ‚non-small-cell lung cancer cell lines with HER-2/neu gene expression but not with ras gene mutations," *J Natl Cancer Inst*, 85(11):897-901, 1993.
Turner et al., "Hallmarks of 'BRCAness' in sporadic cancers," *Nat Rev Cancer*, 4(10):814-819, 2004.
Tuveson et al., "BRAF as a potential therapeutic target in melanoma and other malignancies," *Cancer Cell*, 4(2):95-98, 2003.
Upton et al., "Expression of vimentin in surgically resected adenocarcinomas and large cell carcinomas of lung," *Am J Surg Pathol*, 10(8):560-567, 1986.
Vanhaesebroeck et aL, "Phosphoinositide 3-kinases: a conserved family of signal transducers," *Trends Biochem Sci*, 22(7):267-272, 1997.
Vogt et al., "Triple layer control: phosphorylation, acetylation and uhiquitination of FOXO proteins," *Cell Cycle*, 4(7):908-913, 2005.
Wagner and Sondak, "The sentinel lymph node: more than just another blue lymph node," *Cancer*, 97(8):1821-1823, 2003.
Wang et al., "Aberrant expression of oncogenic and tumor-suppressive microRNAs in cervical cancer is required for cancer cell growth," *PLoS One*, 3(7):e2557, 2008.
Wang et al., "Increased levels of forkhead box M1B transcription factor in transgenic mouse hepatocytes prevent age-related proliferation defects in regenerating liver," *Proc Natl Acad Sci U S A*, 98(20):11468-11473, 2001.
Wang et al., "Oncogenic HPV infection interrupts the expression of tumor-suppressive miR-34a through viral oncoprotein E6," *RNA*, 15(4):637-647, 2009.
Weil et al., "Targeting the kinesin Eg5 to monitor siRNA transfection in mammalian cells," *Biotechniques*, 33(6):1244-1248, 2002.
Wiemer, "The role of microRNAs in cancer: no small matter," *Eur J Cancer*, 43(10):1529-1544, 2007.
Wong et al., "Number of nodes examined and staging accuracy in colorectal carcinoma," *J. Clin. Oncol.*, 17(9):2896-2900, 1999.
Wood et al., "One hundred consecutive cases of sentinel lymph node mapping in early colorectal carcinoma: detection of missed micrometastases," *J. Gastrointest Surg.*, 6(3):322-330, 2002.
Xi et al., "A combination of molecular markers accurately detects lymph node metastasis in non-small cell lung cancer patients," *Clin. Cancer Res.*, 12:2484-2491, 2006.
Xi et al., "Identification of mRNA markers for molecular staging of lymph nodes in colorectal cancer," *Clin. Chem.*, 52(3):520-523, 2006.
Xi et al, "Molecular staging of lymph nodes from patients with esophageal adenocarcinorna," *Clin. Cancer Res.*, 11:1099-1109, 2005.
Yamamoto et al., "Cdk2/cdc2 expression in colon carcinogenesis and effects of cdk2/cdc2 inhibitor in colon cancer cells," *Int J Oncol*, 13(2):233-239, 1998.
Yeatman, "A renaissance for SRC," *Nat Rev Cancer*, 4(6):470-480, 2004.
Vi et al., "The association of the expression of MTA1, nm23H1 with the invasion, metastasis of ovarian carcinoma," *Chin Med Sci J*, 18(2):87-92, 2003.
Yu et al., "Crosstalk between cancer and immune cells: role of STAT3 in the tumour microenvironment," *Nat Rev Immunol*, 7(1):41-51, 2007.
Zhang et al., "Enhancement of hematopoietic stem cell repopulating capacity and self-renewal in the absence of the transcription factor C/EBP alpha," *Immunity*, 21(6):853-863, 2004.
"Human miRNA targets," for "mmu-miR-126-3p" Apr. 2005 version, accessed and retrieved from miRanda webserver at www.microrna.org and http://cbio.mskcc.org/cgi-bin/mirnaviewer, on Dec. 31, 2009. p. 1 of the 23 print-out pages included.
Aiello et al., "Suppression of retinal neovascularization in vivo by inhibition of vascular endothelial growth factor (VEGF) using soluble VEGF-receptor chimeric proteins," *Proc. Natl. Acad. Sci. USA*. 92(23):10457-10461, 1995.
Bedell et al., "Amplification of human papillomavirus genomes in vitro is dependent on epithelial differentiation," *J Virol.*, 65(5):2254-60, 1991.
Bommer et al., "p53-mediated activation of miRNA34 candidate tumor-suppressor genes," *Current Biology*, 17:1298-1307, mailed 2007.
Bonei et al., "The *miR-15a-miR-16-1* cluster controls prostate cancer by targeting multiple oncogenic activities," *Nature Medicine*, 14(11):1271-1277, 2008.
Bosch and de Sanjosé, "The epidemiology of human papillomavirus infection and cervical cancer," *Dis Markers.*, 23(4):213-27, 2007
Brown and Regillo, "Anti-VEGF agents in the treatment of neovascular age-related macular degeneration: applying clinical trial results to the treatment of everyday patients," *Am. J. Ophthalmol.*, 144(4):627-637, 2007.
Bullinger et al., "Gene expression profiling in acute myeloid leukemia," *Journal of Clinical Oncology*, 23(26):6296-6305, 2005.
Cai et al., "Human papillomavirus genotype 31 does not express detectable microRNA levels during latent or productive virus replication," *J. Virol.*, 80(21):10890-3, 2006.
Campochiaro and Hackett, "Ocular neovascularization: a valuable model system," *Oncogene*, 22(42):6537-6548, 2003.
Clifford et al., "Human papillomavirus types in invasive cervical cancer worldwide: a meta-analysis," *Br. J. Cancer*, 88(1):63-73, 2003.
Cogliano et al., "Carcinogenicity of human papillomaviruses," *Lancet Oncol.*, 6(4):204, 2005.
Costinean et al., "Pre-B cell proliferation and lymphoblastic leukemia/high-grade lymphoma in E µ-miR155 transgenic mice," *Proc. Natl. Acad. Sci. USA*, 103(18):7024-7029, 2006.
Cox, "Epidemiology and natural history of HPV," *J. Fam. Pract.*, Suppl:3-9, 2006.
Crnogorac-Jurcevic et al., "Proteomic analysis of chronic pancreatitis and pancreatic adenocarcinoma," *Gastroenterology*, 129:1454-1463, 2005.
Cummins and Velculescu, "Implications of micro-RNA profiling for cancer diagnosis," *Oncogene*, 25(46):6220-6227, 2006.
Dews et al., "Augmentation of tumor angiogenesis by a Myc-activated microRNA cluster," *Nat. Genet.*, 38(9):1060-1065, 2006.
D'Souza et al., "Case-control study of human papillomavirus and oropharyngeal cancer," *New Engl. J. Med.*, 356:1944-1956, 2007.
European Search Report issued in European Application No. 09154092.2, mailed Aug. 12, 2009.
Fazi et al., "A minicircuitry comprised of microRNA-223 and transcription factors NFI-A and C/EBPα regulates human granulopoiesis," *Cell*, 123:819-831, 2005.
Folkman, "Successful treatment of an angiogenic disease," *N Engl J Med* 320:1211-1212, 1989.
Griffiths-Jones et al., "miRBase: tools for microRNA genomics," *Nucl. Acids Res.*, 36 (Database Issue):D154-D158, 2008.
Han et al., "Cyclin D I expression in human prostate carcinoma cell lines and primary tumors," *The Prostate*, 35:95-101, 1998.
Harfe, "MicroRNAs in vertebrate development," *Curr. Opin. Genet. Dev.*, 15(4):410-5, 2005.

(56) References Cited

OTHER PUBLICATIONS

Hayashita et al., "A polycistronic microRNA cluster, *miR-17-92*, is overexpressed in human lung cancers and enhances cell proliferation," *Cancer Res.*, 65(21):9628-9632, 2005.

He et al., "A microRNA component of the p53 tumour suppressor network," *Nature*, 447(7148):1130-1134, 2007.

Hermeking, "p53 enters the microRNA world," *Cancer Cell*, 12(5):414-418, 2007.

Hornstein et al., "The microRNA *mir-196* acts upstream of Hoxb8 and Shh in limb development," *Nature*, 438:671-674, 2005.

Houbaviy et al., "Embryonic stem cell-specific micro-RNAs," *Developmental Cell*, 5:351-358, 2001.

Hummel et al., "Differentiation-induced and constitutive transcription of human papillomavirus type 31b in cell lines containing viral episomes," *J. Virol.*, 66(10):6070-80, 1992.

Ji et al., "Restoration of tumor suppressor miR-34 inhibits human p53-mutant gastric cancer tumorspheres," *BMC Cancer*, 8:266, 2008.

John et al., "Human microRNA targets," *PLOS Biology*, 2(11):1862-1879, 2004.

Jopling et al., "Modulation of hepatitis C virus RNA abundance by a liver-specific MicroRNA," *Science*, 309(5740):1577-81, 2005.

Kayed et al., "Hedgehog signaling in the normal and diseased pancreas," *Pancreas*, 32(2):119-129, 2006.

Kwak et al., "VEGF is major stimulator in model of choroidal neovascularization," *Invest. Ophthalmol. Vis. Sci.*, 41(10):3158-3164, 2000.

Lagos-Quintana et al., "Identification of tissue-specific microRNAs from mouse," *Current Biology*, 35-739, 2002.

Lecellier et al., "A cellular microRNA mediates antiviral defense in human cells," *Science*, 308(5721):557-60, 2005.

Lee et al., "The *C. elegans* heterochronic gene *lin-4* encodes small RNAs with antisense complementarity to *lin-14*," *Cell*, 75(5):843-854, 1993.

Lewis et al., "Conserved seed pairing, often flanked by adenosines, indicates that thousands of human genes are microRNA targets," *Cell*, 120:15-20, 2005.

Lilja et al., "Prostate-specific antigen and prostate cancer: prediction, detection and monitoring," *Nat. Rev. Cancer*, 8(4):268-278, 2008.

Lima e Silva et al., "The SDF-1/CXCR4 ligand/receptor pair is an important contributor to several types of ocular neovascularization," *FASEB J.*, 21(12):3219-3230, 2007.

Lui et al., "Patterns of known and novel small RNAs in human cervical cancer," *Cancer Res.*, 67(13):6031-6043, 2007.

Mahato et al., "Modulation of gene expression by antisense and antigen oligodeoxynucleotides and small interfering RNA," *Expert Opinion on Drug Delivery*, 2(1):3-28, 2005.

Mammalian Gene Collection (MGC) Program Team, "Generation and initial analysis of more than 15,000 full-length human and mouse cDNA sequences," *PNAS*, 99(26):16899-16903, 2002.

Martinez et al., "Human papiliomavirus type 16 reduces the expression of microRNA-218 in cervical carcinoma cells," *Oncogene*, 27:2575-2582, 2008.

Mattie et al., "Optimized high throughput microRNA expression profiling provides novel biomarker assessment of clinical prostate and breast cancer biopsies," *Mol. Cancer*, 5:24, 2006.

Michael and Oren, "The p53-Mdm2 module and the ubiquitin system," *Semin. Cancer Biol.* 13:49-58, 2003.

Miller et al., "Vascular endothelial growth factor/vascular permeability factor is temporally and spatially correlated with ocular angiogenesis in a primate mode," *Am. J. Pathol.*, 145(3):574-584, 1994.

Minakuchi el al., "Atelocollagen-mediated synthetic small interfering RNA delivery for effective gene silencing in vitro and in vivo," *Nucleic Acids Research*, 32(13):e109, 2004.

Office Action issued in Australian Application No. 2005250432, mailed Dec. 1, 2009.

Office Action issued in European Application No. 07871689.1, mailed Dec. 15, 2009.

Office Action issued in European Application No. 07871690.9, mailed Dec. 14, 2009.

Office Action issued in European Application No. 07871691.7, mailed Dec. 14, 2009.

Office Action issued in European Application No. 07871693.3, mailed Dec. 9, 2009.

Office Action issued in European Application No. 07871694.1, mailed Dec. 10, 2009.

Office Action issued in European Application No. 07871756.8, mailed Oct. 20, 2009.

Office Action issued in U.S. Appl. No. 11/141,707, mailed Jan. 6, 2010.

Office Action issued in U.S. Appl. No. 11/273,640, mailed Nov. 20, 2009.

Office Action issued in U.S. Appl. No. 11/567,082, mailed Sep. 30, 2009.

Office Action issued in U.S. Appl. No. 11/837,487, mailed Sep. 15, 2009.

Office Action issued in U.S. Appl. No. 11/837,488, mailed Feb. 19, 2010.

Office Action issued in U.S. Appl. No. 11/837,494, mailed Jan. 5, 2010.

Office Action issued in U.S. Appl. No. 11/837,495, mailed Jan. 5, 2010.

Office Action issued in U.S. Appl. No. 11/837,498, mailed Nov. 20, 2009.

Office Action issued in U.S. Appl. No. 11/857,948, mailed Nov. 3, 2009.

Office Action issued in U.S. Appl. No. 11/953,606, mailed Jan. 8, 2010.

Office Action issued in U.S. Appl. No. 11/967,663, mailed Feb. 12, 2010.

Office Action issued in U.S. Appl. No. 11/967,663, mailed Oct. 1, 2009.

Office Action issued in U.S. Appl. No. 12/112,291, mailed Nov. 16, 2009.

Office Action issued in U.S. Appl. No. 12/120,388, mailed Feb. 19, 2010.

Office Action issued in U.S. Appl. No. 12/124,394, mailed Feb. 5, 2010.

Office Action issued in U.S. Appl. No. 12/124,394, mailed Nov. 6 2009.

Office Action issued in U.S. Appl. No. 12/125,412, mailed Feb. 16, 2010.

Office Action issued in U.S. Appl. No. 12/125,412, mailed Nov. 12, 2009.

Office Action issued in U.S. Appl. No. 12/125,675, mailed Sep. 10, 2009.

Office Action issued in U.S. Appl. No. 12/134,932, mailed Nov. 12, 2009.

Office Action issued in U.S. Appl. No. 12/167,492, mailed Feb. 12, 2010.

Ozaki et at., "Blockade of vascular endothelial cell growth factor receptor signaling is sufficient to completely prevent retinal neovascularization," *Am. J. Pathol.*, 156(2):697-707, 2000.

PCT International Preliminary Report on Patentability issued in International Application No. PCT/US2007/078952, mailed Feb. 11, 2010.

PCT International Preliminary Report on Patentability issued in International Application No. PCT/US2008/066025, mailed Dec. 23, 2009.

PCT International Search Report and Written Opinion issued in International Application No. PCT/US2009/036195, mailed Sep. 4, 2009.

PCT International Search Report and Written Opinion issued in International Application No. PCT/US2009/039935, mailed Sep. 17, 2009.

PCT International Search Report and Written Opinion issued in International Application No. PCT/US2008/066025, mailed Sep. 16, 2009.

PCT International Search Report and Written Opinion issued in International Application No. PCT/US2007/078952, mailed Jan. 26, 2010.

(56) References Cited

OTHER PUBLICATIONS

PCT International Search Report and Written Opinion issued in International Application No. PCT/US2009/043361, mailed Nov. 4, 2009.
PCT Invitation to Pay Additional Fees issued in International Application No. PCT/US2007/078952, mailed Sep. 22, 2009.
PCT Invitation to Pay Additional Fees issued in International Application No. PCT/US2008/087762, mailed Nov. 9, 2009.
Pohseno et at., "MicroRNAs modulate the angiogenic properties of HUVECs," *Blood* 108(9):3068-3071, 2006.
Porkka et at., "MicroRNA expression profiling in prostate cancer," *Cancer Res.*, 67(13):6130-6135, 2007.
Rader et al., "In vitro differentiation of epithelial cells from cervical neoplasias resembles in vivo lesions," *Oncogene*, 5(4):571-6, 1990.
Rosenfeld et al., "Ranibizumab: Phase III clinical trial results," *Ophthahmol. Clin. North Am.* 19(3):361-372, 2006.
Saiz et al., "MicroRNA expression profiling in acute myelogenous leukemia," *Blood, ASH Annual Meeting Abstracts*, 104:320a, Abstract No. 1131, Poster board number session 285-I, 2004.
Scaria et al., "Host-virus genome interactions: macro roles for microRNAs," *Cell Microbiol.*, (12):2784-94 2007.
Scaria et al., "Host-virus interaction: a new role for microRNAs," *Retrovirology*, 3:68, 2006.
Scherer and Rossi, "Approaches for the sequence-specific knockdown of mRNA," *Nat. Biotechnol.*, 21(12):1457-1465, 2003.
Scott et al., "BCL2 antisense reduces prostate cancer cell survival following irradiation," *Cancer Biotherapy & Radiopharmaceuticals*, 17(6):4641-656, 2002.
Segal et al., "A module map showing conditional activity of expression modules in cancer," *Nature Genetics*, 36(10):1090-1098, 2004.
Sellner et al., "Reverse transcriptase inhibits Taq polymerase activity," *Nucleic Acids Research*, 20(7):1487-1490, 1992.
Sevignani et al., "Mammalian microRNAs: a small world for fine-tuning gene expression," *Mamm. Genome*, 17(3):189-202, 2006.
Shen et al., "Oxidative damage in age-related macular degeneration," *Histol. Histopathol.* 22(12):1301-1308, 2007.
Si et al,, "miR-21—mediated tumor growth," *Oncogene*, 26(19):2799-2803, 2007.
Smith et al., "Human papillomavirus type distribution in invasive cervical cancer and high-grade cervical lesions: a meta-analysis update," *Int. J. Cancer*, 121(3):621-32, 2007.
Smith et al., "Oxygen-induced retinopathy in the mouse," *Invest, Ophthalmol. Vis. Sci.* 35(1):101-111, 1994.
Sun et al., "Development of a micro-array to detect human and mouse microRNAs and characterization of expression in human organs," *Nucleic Acids Research*, 32(22):e188, 2004.
Sun et al., "Downregulation of CCND1 and CDK6 by miR-34a induces cell cycle arrest," *FEBS Letters*, 582:1564-1568, 2008.
Szafranska et al., "MicroRNA expression alterations are linked to tumorigenesis and non-neoplastic processes in pancreatic ductal adenocarcinoma," *Oncogene*, 26:4442-4452, 2007.
Takei et al., "A small interfering RNA targeting vascular endothelial growth factor as cancer therapeutics," *Cancer Research*, 64:3365-3370, 2004.
Tricoli et al., "MicroRNA: potential for cancer detection, diagnosis, and prognosis," *Cancer Res.*, 67(10):4553-4555, 2007.
Voorhoeve et al., "A genetic screen implicates miRNA-372 and miRNA-373 as oncogenes in testicular germ cell tumors," *Cell*, 124(6):1169-1181, 2006.
Walboomers et al., "Human papillomavirus is a necessary cause of invasive cervical cancer worldwide," *J. Pathol.*, 189(1):12-9, 1999.
White et al., "Treatment of pulmonary hensangiomatosis with recombinant interferon alfa-2a," *N Engl J Med* 320:1197-1200, 1989.
Wiemer, "The role of microRNAs in cancer: no small matter," *Eur. J. Cancer*, 43(10):1529-44, 2007.
Wilson and Laimins, "Differentiation of HPV-containing cells using organotypic "raft" culture or methylcellulose," *Methods Mol. Med.*, 119:157-69, 2005.

Yamato et al., "New highly potent and specific E6 and E7 siRNAs for treatment of HPV16 positive cervical cancer," *Cancer Gene Therapy*, 15:140-153, 2008.
Yang et al., "Dicer is required for embryonic angiogenesis during mouse development," *J. Biol. Chem.* 280(10):9330-9335, 2005.
Zhang et al., "microRNAs as oncogenes and tumor suppressors," *Dev. Biol.*, 302(1):1-12, 2007.
Al-Hajj et al., "Prospective identification of tumorigenic breast cancer cells," *Proc. Natl. Acad. Sci. U S A*, 100(7):3983-8, 2003.
Bao et al., "Glioma stem cells promote radioresistance by preferential activation of the DNA damage response," *Nature*, 444(7120):756-60, 2006.
Bartel, "MicroRNAs: genomics, biogenesis, mechanism, and function," *Cell*, 116:281-297, 2004.
Basturk et al., "MicroRNA expression in androgen independent and metastatic prostate cancer," *Modern Pathology*, Abstract No. 669, 21(Suppl. 1):148A, 2008.
Beier et al., "CD133(+) and CD133(−) glioblastoma-derived cancer stem cells show differential growth characteristics and molecular profiles," *Cancer Res.*, 67(9):4010-5, 2007.
Ben-Porath et al., "An embryonic stem cell-like gene expression signature in poorly differentiated aggressive human tumors," *Nat. Genet.*, 40(5):499-507, 2008.
Berman et al., "Medulloblastoma growth inhibition by hedgehog pathway blockade," *Science*, 297(5586):1559-61, 2002.
Birnie et al., "Gene expression profiling of human prostate cancer stem cells reveals a pro-inflammatory phenotype and the importance of extracellular matrix interactions," *Genome Biol.*, 9(5):R83. [Epub ahead of print], 2008.
Blower et al., "MicroRNAs moduaIte the chemosensitivity of tumor cells," *Mol Cancer Ther*, 7(1):1-9, 2008.
Bonci et al., "The miR-15A/miR-16-1 cluster controls prostate cancer progression by targeting multiple oncogenic activities," *European Urology Supplements*, Abstract No. 802, 7(3):271, 2008.
Bourguignon et al., "Hyaluronan-CD44 interaction activates stem cell marker Nanog, Stat-3-mediated MDR1 gene expression, and ankyrin-regulated multidrug efflux in breast and ovarian tumor cells," *J. Biol. Chem.*, 283(25): 17635-51, 2008.
Bussing et al.,"*let-7* microRNAs in development, stem cells and cancer," *Trends in Molecular Medicine*, 14(9):400-409, 2008.
Clement et al., "HEDGEHOG-GLI1 signaling regulates human glioma growth, cancer stem cell self-renewal, and tumorigenicity," *Curr, Biol.*, 17(2): 165-72, 2007.
Collins et al., "Prospective identification of tumorigenic prostate cancer stem cells," *Cancer Res.*, 65(23):10946-51, 2005.
Cummins et al., "The colorectal microRNAome," *Proc. Natl. Acad. Sci. USA*, 103(10):3687-3692, 2006.
Dai et al., "Prostate cancer induces bone metastasis through Wnt-induced bone morphogenetic protein-dependent and independent mechanisms," *Cancer Res.*, 68(14): 5785-94, 2008.
Declaration of Dr. David P. Bartel under 37 C.F.R. 1.132, submitted in U.S. App. No. 10/913,288, 2009.
Dontu et al., "In vitro propagation and transcriptional profiling of human mammary stem/progenitor cells," *Genes Dev.*, 17:1253-70, 2003.
Doyle and Ross, "Multidrug resistance mediated by the breast cancer resistance protein BCRP (ABCG2)," *Oncogene*, 22(47):7340-58, 2003.
Dröge and Davey, "Do cells *let-7* determine stemness?" *Cell Stem Cell*, 2(1):8-9, 2008.
Dylla et al., "Colorectal cancer stem cells are enriched in xenogeneic tumors following chemotherapy," *PLoS One*, 3(6):e2428, 13 pages, 2008.
Engelmann et al., "MCF7 side population cells with characteristics of cancer stem/progenitor cells express the tumor antigen MUC1," *Cancer Res.*, 68(7):2419-26, 2008.
Esquela-Kerscher et al., "The *let-7* microRNA reduces tumor growth in mouse models of lung cancer," *Cell Cycle*, 7(6):759-764, 2008.
Fan et al., "Hedgehog signaling promotes prostate xenograft tumor growth," *Endocrinology*, 145: 3961-3970, 2004.
Fan et al., "Notch pathway inhibition depletes stem-like cells and blocks engraftment in embryonal brain tumors," *Cancer Res.*, 66(15): 7445-52, 2006.

(56) References Cited

OTHER PUBLICATIONS

Francipane et al., "Crucial role of interleukin-4 in the survival of colon cancer stem cells," *Cancer Res.*, 68 (11):4022-4025, 2008.
Ginestier et al., "ALDH1 is a marker of normal and malignant human mammary stein cells and a predictor of poor clinical outcome," *Cell Stem Cell*, 1(5):555-567, 2007.
Goodell et al., "isolation and functional properties of murine hematopoietic stem cells that are replicating in vivo," *J. Exp. Med.*, 183(4):1797-806, 1996.
Gu et at., "Prostate cancer cells with stem cell characteristics reconstitute the original human tumor in vivo," *Cancer Res.*, 67(10):4807-15, 2007.
Hambardzumyan et al., "PI3K pathway regulates survival of cancer stem cells residing in the perivascular niche following radiation in medulloblastoma in vivo," *Genes Dev.*, 22(4):436-48, 2008.
Hermann et al., "Distinct populations of cancer stem cells determine tumor growth and metastatic activity in human pancreatic cancer," *Cell Stem Cell*, 1(3):313-23, 2007.
Hirschmann-Jax et al., "A distinct "side population" of cells with high drug efflux capacity in human tumor cells," *Proc. Natl. Acad. Sci. USA*, 101:14228-33, 2004.
Ho et al., "MDR1 and BCRP1 expression in leukemic progenitors correlates with chemotherapy response in acute myeloid leukemia," *Exp. Hematol.*, 36(4): 433-42, 2008.
Hurt et al., "CD44+ CD24(−) prostate cells are early cancer progenitor/stem cells that provide a model for patients with poor prognosis," *Br. J. Cancer*, 98(4):756-65, 2008.
Ibarn et al., "A role for microRNAs in maintenance of mouse mammary epithelial progenitor cells", *Genes Dev.*, 21(24):3238-3243, 2007.
Isbam et al., "Association of numerous micro-RNAs ( μRNAs) with prostate cancer initiation and progression," *European Urology Supplements*, Abstract No. 429, 6(2):130, 2007.
Jamieson et al, "Granulocyte-macrophage progenitors as candidate leukemic stem cells in blast-crisis CML," *N. Engl. J. Med.*, 351(7):657-67, 2004.
Jiang et al., "Real-time expression profiling of microRNA precursors in human cancer cell lines," *Nucleic Acids Research*, 33(17):5394-5403, 2005.
Johnson et al., "The *let-7* microRNA represses cell proliferation pathways in human cells," *Cancer Res*, 67(16):7713-7722, 2007.
Karhadkar et al., "Hedgehog signalling in prostate regeneration, neoplasia and metastasis," *Nature*, 431(7009):707-12, 2004.
Keshet et al., "MDR1 expression identifies human melanoma stem cells," *Biochem. Biophys. Res. Commun.*, 368(4):930-6, 2008.
Konopleva et al., "Mechanisms of apoptosis sensitivity and resistance to the BH3 mimetic ABT-737 in acute myeloid leukemia," *Cancer Cell*, 10(5):375-88, 2006.
Kumar et al., "Suppression of non-small cell lung tumor development by the *let-7* microRNA family," *PNAS*, 105(10):3903-3908, 2008.
Lanza et al., "mRNA/microRNA gene expression profile in microsatellite, unstable colorectal cancer," *Molec Cancer*, 6:54, 2007.
Lechner et al., "Nestin-positive progenitor cells derived from adult human pancreatic islets of Langerhans contain side population (SP) cells defined by expression of the ABCG2 (BCRP1) ATP-binding cassette transporter," *Biochem. Biophys. Res. Commun.*, 293(2):670-674, 2002.
Leong and Gao, "The Notch pathway in prostate development and cancer," *Differentiation*, 76(6): 699-716, 2008.
Lessard and Sauvageau, "Bmi-1 determines the proliferative capacity of normal and leukaemic stern cells," *Nature*, 423(6937):255-60, 2003.
Li et al., "Evidence that transgenes encoding components of the Wnt signaling pathway preferentially induce mammary cancers from progenitor cells," *Proc Natl Acad Sci USA*, 100(26):15853-8, 2003.
Li et al., "Intrinsic resistance of tumorigenic breast cancer cells to chemotherapy," *J. Natl. Cancer Inst.*, 100(9):672-9, 2008.
Li et al., "Mutant TNFalpha negatively regulates human breast cancer stem cells from MCF7 in vitro," *Cancer Biol. Ther.*, 6(9):1480-9, 2007.
Liu et al., "Functional studies of BCL11A: characterization of the conserved BCL11A-XL splice variant and its interaction with BCL6 in nuclear paraspeckles of germinal center B cells," *Mol. Cancer*, 5:18, 2006.
Liu et al., "Hedgehog signaling and Bmi-1 regulate self-renewal of normal and malignant human mammary stem cells," *Cancer Res.*, 66(12):6063-71, 2006.
Liu et al., "Sex-determining region Y box 4 is a transforming oncogene in human prostate cancer cells," *Cancer Res.*, 66(8):4011-9, 2006.
Liu et al., "The prognostic role of a gene signature from tumorigenic breast-cancer cells," *N. Engl. J. Med.*, 356(3):217-26, 2007.
Lu et al., "Defined culture conditions of human embryonic stem cells,"*Proc. Natl. Acad. Sci. USA*, 103(15): 5688-93, 2006.
Maitland & Collins, "Prostate cancer stem cells: a new target for therapy", *J Clin Oncol.*, 26(17):2862-70, 2008. (Abstract).
Malanchi et al., "Cutaneous cancer stem cell maintenance is dependent on beta-catenin signalling," *Nature*, 452(7187):650-3, 2008.
Miki & Rhim, "Prostate cell cultures as in vitro models for the study of normal stem cells and cancer stem cells", *Prost. Can. Prost. Dis.*, 11:32-39, 2008.
Miki et al., "Identification of putative stem cell markers, CD133 and CXCR4, in hTERT-immortalized primary nonmalignant and malignant tumor-derived human prostate epithelial cell lines and in prostate cancer specimens," *Cancer Res.*, 67(7):3153-61, 2007.
Nykänen et al., "ATP requirements and small interfering RNA structure in the RNA interference pathway," *Cell*, 107:309-321, 2001.
Office Action issued in European Application No. 05858321.2., mailed Apr. 16, 2010.
Office Action issued in European Application No. 09154092.2, mailed Apr. 1, 2010.
Office Action issued in U.S. Appl. No. 11/141,707, mailed Mar. 11, 2010.
Office Action issued in U.S. Appl. No. 11/273,640, mailed May 5, 2010.
Office Action issued in U.S. Appl. No. 11/837,487, mailed May 28, 2010.
Office Action issued in U.S. Appl. No. 11/837,490, mailed Apr. 9, 2010.
Office Action issued in U.S. Appl. No. 11/837,498, mailed May 7, 2010.
Office Action issued in U.S. Appl. No. 11/857,948, mailed May 25, 2010.
Office Action issued in U.S. Appl. No. 11/967,639, mailed May 14, 2010.
Office Action issued in U.S. Appl. No. 11/967,639, mailed Mar. 24, 2010.
Office Action issued in U.S. Appl. No, 12/112,291, mailed Mar. 1, 2010.
Office Action issued in U.S. Appl. No. 12/125,675, mailed Apr. 22, 2010.
Office Action issued in U.S. Appl. No. 12/134,932, mailed Mar. 24, 2010.
Office Action issued in U.S. Appl. No. 12/325,917, mailed May 3, 2010.
Office Action issued in U.S. Appl. No. 12/420,634. mailed May 6, 2010.
Patrawala et al., "Hierarchical organization of prostate cancer cells in xenograft tumors: the CD44+alpha2beta1+ cell population is enriched in tumor-initiating cells," *Cancer Res.*, 67(14):6796-805, 2007.
Patrawala et al., "Highly purified CD44+ prostate cancer cells from xenografi human tumors are enriched in tumorigenic and metastatic progenitor cells," *Oncogene*, 25(12):1696-708, 2006.
Patrawala et al., "MicroRNAs in prostate cancer stem cells", AACR Cancer Stem Cell Special Conference—Los Angeles, Feb. 12-15, 2008.
Patrawala et al., "Side population is enriched in tnmorigenic, stem-like cancer cells, whereas ABCG2+ and ABCG2− cancer cells are similarly tumorigenic," *Cancer Res.*, 65(14):6207-19, 2005.

(56) References Cited

OTHER PUBLICATIONS

PCT International Preliminary Report on Patentability issued in International Application No. PCT/US2008/076246, mailed Mar. 16, 2010.
PCT International Search Report and Written Opinion issued in International Application No. PCT/US2008/087762, mailed Mar. 16, 2010.
PCT International Search Report and Written Opinion issued in international Application No. PCT/US2009/038399, mailed Mar. 3, 2010.
PCT International Search Report and Written Opinion issued in International Application No. PCT/US2009/064015, mailed May 11, 2010.
Peacock et al, "Hedgehog signaling maintains a tumor stem cell compartment in multiple myeloma," *Proc. Natl. Acad. Sci. USA*, 104(10):4048-53, 2007.
Peng et al., "Overexpression of microRNA let-7c in prostate cancer," *Modern Pathology*, Abstract No. 788, 20 (Suppl. 2):169A, 2007.
Reiter and Sawyers, "Xenograft models and the molecular biology of human prostate cancer," In :*Prostate Cancer: Biology, Genetics, and the New Therapeutics*, Totowa, NJ, 163-173, 2001.
Richardson et al., "CD133, a novel marker for human prostatic epithelial stem cells," *J Cell Sci*, 117(Pt 16):3539-45, 2004.
Schwarz et al., "Asymmetry in the assembly of the RNAi enzyme complex," *Cell*, 115:199-208, 2003.
Shepherd et al., "Expression profiling of CD133+ and CD133− epithelial cells from human prostate," *Prostate*, 68(9):1007-1024, 2008.
Shipitsin et al., "Molecular definition of breast tumor heterogeneity," *Cancer Cell*, 11(3):259-73, 2007.
Singh et al., "Identification of a cancer stem cell in human brain tumors," *Cancer Res.*, 63(18):5821-8, 2003.
Sinner et al., "Sox17 and Sox4 differentially regulate beta-catenin/T-cell factor activity and proliferation of colon carcinoma cells," *Mol. Cell Biol.*, 27(22):7802-15, 2007.
Takeshita et al., "Systemic delivery of synthetic microRNA-16 inhibits the growth of metastatic prostate tumors via downregulation of multiple cell-cycle genes," *Molecular Therapy*, 18(1):181-187, 2010.
Tang et al., "Prostate cancer stem/progenitor cells: identification, characterization, and implications," *Mol. Carcinog.*, 46(1):1-14, 2007.
Tang et al., "Transforming growth factor-beta can suppress tumorigenesis through effects on the putative cancer stem or early progenitor cell and committed progeny in a breast cancer xenograft model," Cancer Res., 67(18):8643-52, 2007.
Thiyagarajan et al., "Role of GLI2 transcription factor in growth and tumorigenicity of prostate cells," *Cancer Res.*, 67(22):10642-6, 2007.
Tijsterman and Plasterk, "Dicers at RISC: the mechanism of RNAi," *Cell*, 117:1-4, 2004.
Tockman et al., "Considerations in bringing a cancer biomarker to clinical application," *Cancer Research*, 52:2711s-2718s, 1992.
Prang et al., "Regression of murine lung tumors by the *let-7* microRN," *Oncogene*, 29(11):1580-1587, Epub 2009.
U.S. Appl. No. 10/778,908, entitled "Anti-microRNA oligonucleotide molecules," by Thomas Tuschl et al., filed Feb. 13, 2004.
U.S. Appl. No. 60/869,295 entitled "MicroRNAs Differentially Expressed in Leukemia and Uses Thereof" by Tim Davison, et al., submitted Dec. 8, 2006.
Vemieulen et al., "Single-cell cloning of colon cancer stem cells reveals a multi-lineage differentiation capacity," *PNAS*, 105(360):13427-13432, 2008.
Vezina & Bushman, "Hedgehog signaling in prostate growth and benign prostate hyperplasia," *Curr. Urol. Rep.*, 8(4): 275-80, 2007.
Wang & Dick, "Cancer stem cells:lessons from leukemia", *Trends Cell Biol.*, 15(9):494-501, 2005.
Wang et al., "Pten deletion leads to the expansion of a prostatic stem/progenitor cell subpopulation and tumor initiation," *Proc. Natl. Acad. Sci. USA*, 103(5):1480-1485, 2006.

Watabe et al., "Growth, regeneration, and tumorigenesis of the prostate activates the PSCA promoter," *Proc Natl Acad Sci USA*, 99(1):401-6, 2002.
Weidhaas et al., "MicroRNAs as potential agents to alter esistance to cytotoxic anticancer therapy," *Cancer Res*, 67(23):11111-11116, 2007.
Willert et al., "Wnt proteins are lipid-modified and can act as stem cell growth factors," *Nature*, 423(6938):448-52, 2003.
Xi et al, "Differentially regulated micro-RNAs and actively translated messenger RNA transcripts by tumor suppressor p53 in colon cancer," *Clin Cancer Res.*, 12:2014-2024, 2006b.
Xi et al., "Prognostic Values of microRNAs in Colorectal Cancer," *Biomark Insights*, 2:113-121, 2006a.
Yang et al., "Significance of CD90+ cancer stein cells in human liver cancer," *Cancer Cell*, 13(2):153-66, 2008.
Yu et al., "*let-7* regulates self renewal and tumorigenicity of breast cancer cells," *Cell*, 131:1109-1123, 2007.
Zhang et al., "Identification and characterization of ovarian cancer-initiating cells from primary human tumors," *Cancer Res.*, 68(11):4311-20, 2008.
Zhang et al., "NANOGP8 is a retrogene expressed in cancers," *FEBS J.*, 273(8):1723-30, 2006.
Zhou et al., "Activation of the PTEN/mTOR/STAT3 pathway in breast cancer stem-like cells is required for viability and maintenance," *Proc. Natl. Acad. Sci. USA*, 104(41):16158-63, 2007.
Zhou et al., "The ABC transporter Bcrp1/ABCG2 is expressed in a wide variety of stem cells and is a molecular determinant of the side-population phenotype," *Nat. Med.*, 7(9):1028-1034, 2001.
Agrawal and Kandimalla, "Antisense therapeutics: is it as simple as complementary base recognition," *Molecular Medicine Today*, 6:72-81, 2000.
Benlloch et al., "Role of CEA, PLUNC and CK19 mRNA expression in lymph nodes from resected stage I non-small cell lung cancer (NSCLC) patients as markers of occult micrometastasis: A pilot study," *Lung Cancer*, Abstract No. P-649, 49(1):S289, 2005.
Chirila et al., "The use of synthetic polymers for delivery of therapeutic antisense oligodeoxynucleondes," *Biomaterials*, 23:321-342, 2002.
Crooke, "Progress in antisense technology," *Anna. Rev. Med.*, 55:61-95, 2004.
Jang et al., "Gene delivery from polymer scaffolds for tissue engineering," *Expert Rev. Medical Devices*, 1(1):127-138, 2004.
Logsdon et al., "Molecular profiling of pancreatic adenocarcinoma and chronic pancreatitis identifies multiple genes differentially regulated in pancreatic cancer." *Cancer Research*, 63:2649-2657, 2003.
Office Action issued in Australian Application No. 2005250432, mailed Aug. 25, 2010.
Office Action issued in European Application No. 07871756.8, mailed Jun. 30, 2010.
Office Action issued in European Application No. 08770269.2, mailed Jul. 30, 2010.
Office Action issued in U.S. Appl. No. 11/141,707, mailed Sep. 2, 2010.
Office Action issued in U.S. Appl. No. 11/837,495, mailed Sep. 2, 2010.
Office Action issued in U.S. Appl. No. 11/857,948, mailed Aug. 24, 2010.
Office Action issued in U.S. Appl. No. 11/953,606, mailed Jul. 1, 2010.
Office Action issued in U.S. Appl. No. 12/120,388, mailed Jul. 21, 2010.
Office Action issued in U.S. Appl. No. 12/167,492, mailed Aug. 12, 2010.
Office Action issued in U.S. Appl. No. 12/253,718, mailed Jun. 11, 2010.
Office Action issued in U.S. Appl. No. 12/325,917, mailed Jul. 28, 2010.
Office Action issued in U.S. Appl. No. 12/368,053, mailed Aug. 19, 2010.
Office Action issued in U.S. Appl. No. 12/420,634, mailed Aug. 30, 2010.
Office Action issued in U.S. Appl. No. 12/616,616, mailed Aug. 13. 2010.

(56) References Cited

OTHER PUBLICATIONS

Opalinska and Gewirtz, "Nucleic-acid therapeutics: basic principles and recent applications," *Nature Reviews*, 1:503-514, 2002.
PCT International Preliminary Report on Patentability and Written Opinion issued in International Application No. PCT/US2008/080318, mailed Apr. 29, 2010.
PCT International Preliminary Report on Patentability and Written Opinion issued in International Application No. PCT/US2008/085178, mailed Jun. 10, 2010.
PCT International Preliminary Report on Patentability and Written Opinion issued in International Application No. PCT/US2008/087762, mailed Jul. 1, 2010.
PCT International Search Report and Written Opinion issued in International Application No. PCT/US2009/064015, mailed Jul. 26, 2010.
Peracchi, "Prospects for antiviral ribozymes and deoxyribozymes," *Rev. Med. Virol.*, 14:47-64, 2004.
Office Communication, issued European Patent Application No. 08 831 073.5, dated Aug. 16. 2010.
Extended European Search Report issued in European Application No. 10183451.3, mailed Jan. 12, 2011.
Extended European Search Report issued in European Application No. 10183456.2, mailed Jan. 12, 2011.
Extended European Search Report issued in European Application No. 10183481.0, mailed Jan. 7, 2011.
Extended European Search Report issued in European Application No. 10183538.7, mailed Jan. 12, 2011.
Extended European Search Report issued in European Application No. 10183560.1, mailed Jan. 7, 2011.
Extended European Search Report issued in European Application No. 10183567.6, mailed Jan. 7, 2011,
Extended European Search Report issued in European Application No. 10183589.0, mailed Jan. 7, 2011.
Extended European Search Report issued in European Application No. 10183611.2, mailed Jan. 7, 2011,
Notice of Allowance issued in U.S. Appl. No. 11/141,707, mailed Oct. 4, 2010.
Notice of Allowance issued in U.S. Appl. No. 11/837,495, mailed Dec. 2, 2010.
Office Action issued in European Application No. 05 858 321.2, mailed Apr. 16, 2010.
Office Action issued in European Application No. 07 871 691.7, mailed Oct. 28, 2010.
Office Action issued in European Application No. 07 871 693.3, mailed Oct. 18, 2010.
Office Action issued in European Application No. 09 154 092.2, mailed Nov. 10, 2010.
Office Action issued in Japanese Application No. 2007-515415, mailed Jan. 26, 2011 (and English language translation thereof).
Office Action issued in U.S. Appl. No. 11/837,487, mailed Nov. 22, 2010.
Office Action issued in U.S. Appl. No. 11/837,488, mailed Feb. 15. 2011.
Office Action issued in U.S. Appl. No. 11/837,494, mailed Dec. 9, 2010.
Office Action issued in U.S. Appl. No. 11/857,948, mailed Jan. 26, 2011.
Office Action issued in U.S. Appl. No. 11/953,606, mailed Oct. 1, 2010.
Office Action issued in U.S. Appl. No. 12/125,675, mailed Jan. 28, 2011.
Office Action issued in U.S. Appl. No. 12/125,675, mailed Oct. 14, 2010.
Office Action issued in U.S. Appl. No. 12/134,932, mailed Feb. 24, 2011.
Office Action issued in U.S. Appl. No. 12/134,932, mailed Nov. 4, 2010.
Office Action issued in U.S. Appl. No. 12/167,492, mailed Feb. 25, 2011.
Office Action issued in U.S. Appl. No. 12/253,718, mailed Nov. 1, 2010..
Office Action issued in U.S. Appl. No. 12/325,917, mailed Feb. 14, 2011.
Office Action issued in U.S. Appl. No. 12/340,329, mailed Sep. 28, 2010.
Office Action issued in U.S. Appl. No. 12/368,053, mailed Dec. 21, 2010.
PCT International Preliminary Report on Patentability issued in International Application No. PCT/US2009/033556, mailed Aug. 19, 2010.
PCT International Preliminary Report on Patentability issued in International Application No. PCT/US2009/036195, mailed Sep. 16, 2010.
PCT International Preliminary Report on Patentability issued in International Application No. PCT/US2009/038399, mailed Oct. 7, 2010.
PCT International Preliminary Report on Patentability issued in International Application No. PCT/US2009/039935, mailed Oct. 21, 2010.
PCT International Preliminary Report on Patentability issued in International Application No. PCT/US2009/043361, mailed Nov. 18, 2010.
Suh et al., "Human embryonic stem cells express a unique set of microRNAs" *Developmental Biology*, 270:488-498, 2004.
Takeshita et al., "Efficient delivery of small interfering RNA to bone-metastatic tumors by using atelocollagen in vivo," *PNAS*, 102(34):12177-12182, 2005.
Extended European Search Report issued in European Application No. 10183577.5, mailed Feb. 14, 2011.
Extended European Search Report issued in European Application No. 10183543.7, mailed Feb. 4, 2011.
Extended European Search Report issued in European Application No. 10183534.5, mailed Feb. 15, 2011.
Extended European Search Report issued in European Application No. 10183525.4, mailed Feb. 7, 2011.
Extended European Search Report issued in European Application No. 10183596.5, mailed Feb. 14, 2011.
Extended European Search Report issued in European Application No. 10183490.1, mailed Feb. 4, 2011.
Extended European Search Report issued in European Application No. 10183515.5, mailed Feb. 7, 2011.
Extended European Search Report issued in European Application No. 10183462.0, mailed Feb. 4, 2011.
Extended European Search Report issued in European Application No. 10183470.3, mailed Feb. 3, 2011.
Extended European Search Report issued in European Application No. 10183639.3, mailed Mar. 2, 2011.
Mourelatos et al.,"miRNPs: a novel class of ribonucleoproteins containing numerous microRNAs," *Genes & Development*, 16:720-728, 2002.
Notice of Allowance issued in U.S. Appl. No. 11/837,490, mailed Apr. 1, 2011.
Office Action issued in Australian Application No. 2005250432, mailed Mar. 29, 2011.
Office Action issued in Australian Application No. 2005333165, mailed Feb. 7, 2011.
Office Action issued in Chinese Application No. 200780050263.1, mailed Mar. 28, 2011, and English language translation thereof.
Office Action issued in European Application No. 08831073.5, mailed Feb. 25, 2011.
Office Action issued in European Application No. 09717913.9, mailed Mar. 7, 2011.
Office Action issued in U.S. Appl. No. 12/398,852, mailed Mar. 7, 2011.
Office Action issued in U.S. Appl. No. 12/437,899, mailed Mar. 7, 2011.
Mansfield et al., "MicroRNA-responsive 'sensor' transgenes uncover Hox-like and other developmentally regulated patterns of vertebrate microRNA expression," *Nature Genetics*, 36(10):1079-1083, 2004.
Office Action issued in Australian Application No. 2005250432, mailed Jun. 10, 2011.

(56) References Cited

OTHER PUBLICATIONS

Office Action issued in Chinese Application No. 200780050263.1, issued Mar. 28, 2011.

Office Action issued in European Application No. 07 814 937.4, mailed Apr. 8, 2011.

Office Action issued in European Application No. 09 154 092.2, mailed Mar. 30, 2011.

Office Action issued in Japanese Application No. 2007-541398, dated Mar. 28, 2011.

Office Action issued in U.S. Appl. No. 12/167,492, mailed Jun. 7, 2011.

Office Action issued in U.S. Appl. No. 12/253,718, mailed Apr. 22, 2011.

Office Action issued in U.S. Appl. No. 12/325,917, mailed Apr. 22, 2011.

Office Action issued in U.S. Appl. No. 12/368,053, mailed Jun. 22, 2011.

Office Action issued in U.S. Appl. No. 12/412,087, mailed Apr. 22, 2011.

Office Action issued in U.S. Appl. No. 12/420,634, mailed Apr. 29, 2011.

Afanasyeva et al., "New miRNAs cloned from neuroblastoina," *BMC Genomics*, 9(1):52, 2008.

Barnetson et al., "Genetic analysis of multiple sporadic colon carcinomas from a single patient," *Int J Colorectal Dis*, 15:83-86, 2000.

Braasch et al., "RNA interference in mammalian cells by chemically-modified RNA," *Biochemistry*, 42:7967-7975, 2003.

Brioschi et al., "Down-regulation of microRNAs 222/221 in acute myelogenous leukemia with deranged core-binding factor subunits," *Neoplasia*, 12(11):866-876, 2010.

Burdy et al., "Identifying patients with T3-T4 node-negative colon cancer at high risk of recurrence," *Dis Colon Rectum*, 44:1682-1688, 2001.

Chiaretti et al., "Gene expression profiling identifies a subset of adult T-cell acute lymphoblastic leukemia with myeloid-like gene features and over-expression of miR-223," *Haematologica*, 95(7):1114-1121, 2010.

Extended European Search Report issued in European Application No. 10181713.8, mailed Jun. 24, 2011.

Extended European Search Report issued in European Application No. 10181728.6, mailed Jul. 8, 2011.

Extended European Search Report issued in European Application No. 10181821.9, mailed Jul. 29, 2011.

Honma et al., "The role of atelocollagen-based cell transfection array in high-throughput screening of gene functions and in drug discovery," *Current Drug Discovery Technologies*, 1(4):287-294, 2004.

Kasashima et al., "Altered expression profiles of microRNAs during TPA-induced differentiation of HL-60 cells," *Biochemical and Biophysical Research Communications*, 322(2):403-410, 2004.

Mi et al., "MicroRNA expression signatures accurately discriminate acute lymphoblastic leukemia from acute myeloid leukemia," *PNAS*, 104(50):19971-19976, 2007.

Nikiforova et al., "MicroRNA expression profiling of thyroid tumors: biological significance and diagnostic utility," 93(5):1600-1608, 2008.

Office Action issued in U.S. Appl. No. 11/273,640, mailed Jul. 26, 2011.

Office Action issued in U.S. Appl. No. 12/398,852, mailed Aug. 11, 2011.

Office Action issued in U.S. Appl. No. 12/412,087, mailed Aug. 18, 2011.

Office Action issued in U.S. Appl. No. 12/437,899, mailed Jun. 29, 2011.

Schorr et al., "Modulation of gene expression by lentiviral-mediated delivery of small interfering RNA," *Cell Cycle*, 2(3):251-257, 2003.

MICRORNAS DIFFERENTIALLY EXPRESSED IN CERVICAL CANCER AND USES THEREOF

This application is a divisional of co-pending U.S. patent application Ser. No. 12/209,822 filed Sep. 12, 2008, which claims priority to U.S. Provisional Application Ser. No. 60/972,646 filed Sep. 14, 2007, both of which are incorporated herein by reference in their entirety.

BACKGROUND OF THE INVENTION

I. Field of the Invention

The present invention relates generally to the field of molecular biology. More particularly, it concerns methods and compositions involving microRNA (miRNAs) molecules. Certain aspects of the invention include applications for miRNAs in diagnostics, therapeutics, and prognostics of cervical cancer.

II. Background

In 2001, several groups used a cloning method to isolate and identify a large group of "microRNAs" (miRNAs) from *C. elegans, Drosophila*, and humans (Lagos-Quintana et al., 2001; Lau et al., 2001; Lee and Ambros, 2001). Several hundred miRNAs have been identified in plants and animals—including humans—which do not appear to have endogenous siRNAs. Thus, while similar to siRNAs, miRNAs are distinct.

miRNAs thus far observed have been approximately 21-22 nucleotides in length, and they arise from longer precursors, which are transcribed from non-protein-encoding genes. See review of Carrington et al. (2003). The precursors form structures that fold back on themselves in self-complementary regions; they are then processed by the nuclease Dicer (in animals) or DCL1 (in plants) to generate the short double-stranded miRNA. One of the miRNA strands is incorporated into a complex of proteins and miRNA called the RNA-induced silencing complex (RISC). The miRNA guides the RISC complex to a target mRNA, which is then cleaved or translationally silenced, depending on the degree of sequence complementarity of the miRNA to its target mRNA. Currently, it is believed that perfect or nearly perfect complementarity leads to mRNA degradation, as is most commonly observed in plants. In contrast, imperfect base pairing, as is primarily found in animals, leads to translational silencing. However, recent data suggest additional complexity (Bagga et al., 2005; Lim et al., 2005), and mechanisms of gene silencing by miRNAs remain under intense study.

Recent studies have shown that expression levels of numerous miRNAs are associated with various cancers (reviewed in Esquela-Kerscher and Slack, 2006; Calin and Croce, 2006). miRNAs have also been implicated in regulating cell growth and cell and tissue differentiation—cellular processes that are associated with the development of cancer.

Cervical cancer is the second most common cause of cancer in women worldwide (Pisani et al., 2002; Parkin et al., 2005). About 470,000 new cases are diagnosed and approximately 230,000 women die of cervical cancer every year (Pisani et al., 1999). While the majority (~80%) of these new cases and deaths occur in developing countries, it is estimated that approximately 3,700 women will die from invasive cervical cancer in the United States in 2007 (Jemal et al., 2007).

Epidemiological and molecular studies have demonstrated that human papillomaviruses (HPVs) are the etiological agents of the vast majority (99.7%) of cervical cancers and their intraepithelial precursors (Pisani, et al., 2002; Parkin et al., 2005; zur Hausen, 2002). Approximately, fifty HPV types infect the anogenital tract including the uterine cervix (Pisani, et al., 2002; Parkin et al., 2005). "High-risk" HPV types are associated with intraepithelial lesions that can progress into invasive carcinomas. Among these, HPV 16 and HPV 18 are associated with 50% and 20%, respectively, of cervical squamous cell carcinomas (Bosch and de Sanjose, 2002; zur Hausen, 2002; Clifford et al., 2003). Other high-risk HPV types (31, 33, 35, 39, and 45 among others) are found in 20-30% of cervical cancers (Bosch and de Sanjose, 2002; zur Hausen, 2002; Clifford et al., 2003). High-risk HPV types are also associated with 25% of head and neck tumors, in particular tumors of the mouth, tonsils, esophagus and larynx (Gillison et al., 2000; Rose et al., 2006).

Cytological examination of cervical smears with Papanicolaou staining (Pap smears) is the screening method universally accepted for early detection of cervical cancer and its precursors. Pap smear screening has been very effective in reducing cervical cancer incidence and mortality. Abnormal pap smear results include mild dysplasias referred to as low-grade squamous intraepithelial lesions (LSIL) and moderate to severe dysplasias referred to as high-grade squamous intraepithelial lesions (HSIL). A Pap smear with LSIL or HSIL indicates a need for further examination and possible treatment. In one study (ALTS Group, 2000), over 80% of LSILs were found to be positive for HPV; however, almost 50% of LSILs will regress to normal. HSILs are generally considered to be pre-cancerous in nature and indicate more aggressive treatment. In addition, as many as 3 million Pap smears are classified as inconclusive in the U.S. every year, and cervical cancer is still a significant public health problem. Pap smear screening is imperfect due, in part, to sampling and staining errors, resulting in false-negatives. It is estimated that ~17% of cervical cancers develop in women with previous false-negative Pap smears. It is also estimated that approximately 9% of cervical cancers develop in women with previous true-negative Pap tests.

As an adjunct to cytology screening, The United States Food and Drug Administration has approved a nucleic acid hybridization test for HPV for all women over 30 years old and as triage for women with inconclusive Pap smears. However, several problems associated with this assay include variable assay sensitivity, the inability to genotype certain strains of HPV, and the inability to detect about half of the high risk HPV types associated with cervical cancer (Begeron et al., 2000; de Cremoux et al., 2006).

A need exists for additional diagnostic assays that can assess the condition of cervical tissue in general and accurately distinguish pre-cancerous or cancerous tissue from non-cancerous tissue in particular.

SUMMARY OF THE INVENTION

Embodiments of the invention include compositions and methods of identifying miRNAs that are differentially expressed or mis-regulated in various states of normal, pre-cancerous, cancerous, and/or abnormal tissues, including but not limited to normal cervical tissue, pre-cancerous diseased cervical tissue (e.g., low-grade squamous intraepithelial lesions (LSIL) and high-grade squamous intraepithelial lesions (HSIL)), squamous cell carcinoma, cervical cancer (e.g., cervical squamous cell carcinoma), squamous cell carcinoma of the vulva and vagina, penile intraepithelial lesions, anal cancer, cancers of the digestive tract, oral cancers, a subset of head and neck cancers, and tonsil cancer. In certain aspects, the cancers are related to or a result of HPV infection. In other aspects a subject known or at risk of infection with HPV can be monitored. In still a further aspect, a subject can be monitored periodically, e.g. miRNA assays can be conducted in conjunction with pap smears or non-invasive procedures or procedures with limited invasiveness (e.g., swabbing or flushing and the like). The method of sampling is not intended to be a limiting factor and is at the discretion of the care giver. Further, the invention describes a method for diagnosing normal, pre-cancerous, and cancerous tissues or cells, including but not limited to cervical squamous intraepithelial lesions and cervical cancer based on determining levels (increased or decreased) of selected miRNAs in patient-derived samples. Samples may be obtained and/or analyzed from patients, including but not limited to patients having or suspected of having pre-cancerous cervical lesion or cervical cancer, or a patient suspected of having one or the other condition.

The term "miRNA" is used according to its ordinary and plain meaning and refers to a microRNA molecule found in eukaryotes that is involved in RNA-based gene regulation. See, e.g., Carrington et al., 2003, which is hereby incorporated by reference. Individual miRNAs in a variety of organisms have been identified, sequenced, and given names. Names of miRNAs and their sequences related to the present invention are provided herein.

It is understood that a "synthetic nucleic acid" of the invention means that the nucleic acid does not have a chemical structure or sequence of a naturally occurring nucleic acid or is made by non-natural processes. Consequently, it will be understood that the term "synthetic miRNA" refers to a "synthetic nucleic acid" that functions as or inhibits the functions of an miRNA, at least in part, in a cell or under physiological conditions.

While many of the embodiments of the invention involve synthetic miRNAs or synthetic nucleic acids, in some embodiments of the invention, the nucleic acid molecule(s) need not be "synthetic." In certain embodiments, a non-synthetic miRNA employed in methods and compositions of the invention may have all or part of the sequence and structure of a naturally occurring miRNA precursor or the mature miRNA. For example, non-synthetic miRNAs used in methods and compositions of the invention may not have one or more modified nucleotides or nucleotide analogs. In these embodiments, the non-synthetic miRNA may or may not be recombinantly produced. In particular embodiments, the nucleic acid in methods and/or compositions of the invention is specifically a synthetic miRNA; though in other embodiments, the invention specifically involves a non-synthetic miRNA and not a synthetic miRNA. Any embodiments discussed with respect to the use of synthetic miRNAs can be applied with respect to non-synthetic miRNAs, and vice versa.

It will be understood that the term "naturally occurring" refers to something found in an organism without any intervention by a person; it could refer to a naturally-occurring wildtype or mutant molecule. In some embodiments a synthetic miRNA molecule does not have the sequence of a naturally occurring miRNA molecule. In other embodiments, a synthetic miRNA molecule may have the sequence of a naturally occurring miRNA molecule, but the chemical structure of the molecule, particularly in the part unrelated specifically to the precise sequence (non-sequence chemical structure) differs from chemical structure of the naturally occurring miRNA molecule with that sequence. In some cases, the synthetic miRNA has both a sequence and non-sequence chemical structure that are not found in a naturally-occurring miRNA. Moreover, the sequence of the synthetic molecules will identify which miRNA is effectively being provided or inhibited; the endogenous miRNA will be referred to as the "corresponding miRNA." Corresponding miRNA sequences that can be used in the context of the invention include, but are not limited to, all or a portion of those sequences in SEQ ID NOs: 1-562, as well as any other of miRNA sequence, miRNA precursor sequence, or any complementary sequence. In some embodiments, the sequence is or is derived from or contains all or part of a sequence identified in Table 1 below to target a particular miRNA (or set of miRNAs) or mRNA (or set of mRNA).

TABLE 1

Example listing of miRNA evaluated.

| miR | Sequence | Ref. | SEQ ID NO |
|---|---|---|---|
| ambi-miR-7027 | AAAUGGUGCCCUAGUGACUAC | 1 | SEQ ID NO: 1 |
| ambi-miR-7029 | GGAAACCGUUACCAUUACUGAGU | 1 | SEQ ID NO: 2 |
| ambi-miR-7039 | GCCGAGACUAGAGUCACAUCCUG | 1 | SEQ ID NO: 3 |
| ambi-miR-7062 | UCUCUGGGCCUGUGUCUUAGGC | 2, 3 | SEQ ID NO: 4 |
| ambi-miR-7066 | GUCAUACACGGCUCUCCUCUCU | 2, 3 | SEQ ID NO: 5 |
| ambi-miR-7068-1 | ACACACCUGGUUAACCUCU | 1 | SEQ ID NO: 6 |
| ambi-miR-7070 | UAUGUCUGCUGACCAUCACC | 1 | SEQ ID NO: 7 |
| ambi-miR-7074 | CCACAGCACUGCCUGGUCAGA | 1 | SEQ ID NO: 8 |
| ambi-miR-7075 | CUGGUUUCACAUGGUGGCUUAGAU | 1 | SEQ ID NO: 9 |
| ambi-miR-7079 | AAUUGCACGGUAUCCAUCUGUA | 2, 3 | SEQ ID NO: 10 |
| ambi-miR-7083 | GCAGUCCAUGGGCAUAUACAC | | SEQ ID NO: 11 |
| ambi-miR-7085 | ACAAGUCAGGCUCUUGGGACCU | 1 | SEQ ID NO: 12 |
| ambi-miR-7100 | UCAUCGUCUCAAAUGAGUCU | 2, 3 | SEQ ID NO: 13 |
| ambi-miR-7101 | CAAGCUCGCUUCUAUGGGUCU | 1 | SEQ ID NO: 14 |

TABLE 1-continued

Example listing of miRNA evaluated.

| miR | Sequence | Ref. | SEQ ID NO |
|---|---|---|---|
| hsa-asg-10202_st2 | GGGCCCUGGCUCCAUCUCCUUU | 1 | SEQ ID NO: 15 |
| hsa-asg-10278_st2 | UAUAGAUUUAAAUACGUAUGUA | 1 | SEQ ID NO: 16 |
| hsa-asg-10674_st1 | GACAGCACGACACUGCCUUCAU | 1 | SEQ ID NO: 17 |
| hsa-asg-10883_st1 | UGCCUGUCUACACUUGCUGUGC | 1 | SEQ ID NO: 18 |
| hsa-asg-11181_st1 | UGGCCUUGGGUCAGAGAGGGCU | 1 | SEQ ID NO: 19 |
| hsa-asg-11199_st2 | CCCUCGAGGAGCUCACAGUCUA | 1 | SEQ ID NO: 20 |
| hsa-asg-11688_st1 | CCUCAGCUGUGUUCUUGGUAUC | 1 | SEQ ID NO: 21 |
| hsa-asg-11883_st1 | GGAACGGCUUCAUACAGGAGUU | 1 | SEQ ID NO: 22 |
| hsa-asg-11938_st1 | GGGCAGAGAGCAAGAAGUAUCA | 1 | SEQ ID NO: 23 |
| hsa-asg-12325_st2 | UGCUGAGGGGCAGAGAUCAGAC | 1 | SEQ ID NO: 24 |
| hsa-asg-12346_st2 | UGGAUGGAGGUUGAGAGGGCUG | 1 | SEQ ID NO: 25 |
| hsa-asg-12356_st1 | UGGCGGUGGAGAGAGGGAAUGU | 1 | SEQ ID NO: 26 |
| hsa-asg-12964_st2 | UGGUUUUUGGUUUCCAGAGCAG | 1 | SEQ ID NO: 27 |
| hsa-asg-13166_st2 | AAUCAUUCACGGACAACACUUU | 1 | SEQ ID NO: 28 |
| hsa-asg-13189_st1 | UGAGGGGCAGAGAGCGAGACUUU | 1 | SEQ ID NO: 29 |
| hsa-asg-13230_st2 | CUGGUUUCACAUGGUGGCUUAGAU | 1 | SEQ ID NO: 30 |
| hsa-asg-13237_st1 | ACACUCAAACUGCUGAC | 1 | SEQ ID NO: 31 |
| hsa-asg-13254_st1 | UAUGUCUGCUGACCAUCACC | 1 | SEQ ID NO: 32 |
| hsa-asg-13279_st1 | UGACCGAUUUCUCCUGGUGUUCAGA | 1 | SEQ ID NO: 33 |
| hsa-asg-13284_st1 | UUAGGGCCCUGGCUCCAUCUCC | 1 | SEQ ID NO: 34 |
| hsa-asg-13297_st1 | UACCCAGAGCAUGCAGUGUGAA | 1 | SEQ ID NO: 35 |
| hsa-asg-13304_st2 | CUUGGCACCUAGCAAGCACUCA | 1 | SEQ ID NO: 36 |
| hsa-asg-13308_st2 | CACUAGAUUGUGAGCUCCUGGA | 1 | SEQ ID NO: 37 |
| hsa-asg-13613_st2 | UUUCCACAGGAUGGUGGGGGGG | 1 | SEQ ID NO: 38 |
| hsa-asg-13966_st2 | CUGGCUCUUAAAGGCACGAGAG | 1 | SEQ ID NO: 39 |
| hsa-asg-14172_st1 | AAACAUGGUUCCGUCAAGCACC | 1 | SEQ ID NO: 40 |
| hsa-asg-14176_st1 | ACAAGUCAGGCUCUUGGGACCU | 1 | SEQ ID NO: 41 |
| hsa-asg-14230_st1 | UUGGGAACAUUUUGCAUGUA | 1 | SEQ ID NO: 42 |
| hsa-asg-2027_st1 | GAGCUGGUAAAAUGGAACCAAA | 1 | SEQ ID NO: 43 |
| hsa-asg-2301_st2 | UACUUCAGAAUCUCCAGGAGUA | 1 | SEQ ID NO: 44 |
| hsa-asg-279_st2 | UGCUUGGCACCUAGCAAGCACU | 1 | SEQ ID NO: 45 |
| hsa-asg-2919_st1 | AUUUCAGUGGAGUGAAGUUCAG | 1 | SEQ ID NO: 46 |
| hsa-asg-3038_st2 | UGUAGCAGGCCAGAGAAUGAGG | 1 | SEQ ID NO: 47 |
| hsa-asg-3145_st1 | AAGCUCACAGUCUAGUUGUGUU | 1 | SEQ ID NO: 48 |
| hsa-asg-3376_st1 | CGAGGUUGCCCUUUGUAUAUUC | 1 | SEQ ID NO: 49 |
| hsa-asg-3597_st2 | GCAUUUGCUGGUGGUGGCAGGG | 1 | SEQ ID NO: 50 |
| hsa-asg-3711_st2 | GGGAUGGGCAAGGUAGAACUCA | 1 | SEQ ID NO: 51 |
| hsa-asg-4557_st2 | CAGAUUCGAUUCUAGGGGAAUA | 1 | SEQ ID NO: 52 |

TABLE 1-continued

Example listing of miRNA evaluated.

| miR | Sequence | Ref. | SEQ ID NO |
|---|---|---|---|
| hsa-asg-4564_st2 | CAGGUGAGGUUCUUGGGAGCCU | 1 | SEQ ID NO: 53 |
| hsa-asg-5021_st1 | UAUGUCUGCUGACCAUCACCUU | 1 | SEQ ID NO: 54 |
| hsa-asg-522_st1 | AAUGGAUUUGUAGGAGGAAGGG | 1 | SEQ ID NO: 55 |
| hsa-asg-5304_st1 | ACUAGAUUGUGAGCUCCUGGAG | 1 | SEQ ID NO: 56 |
| hsa-asg-5617_st1 | UAUGUAACAUGGUCCACUAACU | 1 | SEQ ID NO: 57 |
| hsa-asg-562_st1 | UGCAGUCCAUGGGCAUAUACAC | 1 | SEQ ID NO: 58 |
| hsa-asg-5740_st2 | UCAGGUGGCCAGGUGCAUAUCU | 1 | SEQ ID NO: 59 |
| hsa-asg-6758_st1 | UUUGAUGAGAACAUCUGGGGCC | 1 | SEQ ID NO: 60 |
| hsa-asg-6951_st2 | CAGGAACAGCAGGGUUGUGAGG | 1 | SEQ ID NO: 61 |
| hsa-asg-7023_st2 | GAAAGCUGUGUUGGAGAGGCAG | 1 | SEQ ID NO: 62 |
| hsa-asg-7465_st2 | AACCGUGGCUUUCGAUUGUUAC | 1 | SEQ ID NO: 63 |
| hsa-asg-7472_st2 | AGAGGUUGCCCUUGGUGAAUUC | 1 | SEQ ID NO: 64 |
| hsa-asg-8067_st2 | UGGAGACGCGGCCCUGUUGGAG | 1 | SEQ ID NO: 65 |
| hsa-asg-8411_st2 | UUUCUAGGGCACAGACAGUGCA | 1 | SEQ ID NO: 66 |
| hsa-asg-8477_st1 | GGGAGCCAGGAAGUAUUGAUGU | 1 | SEQ ID NO: 67 |
| hsa-asg-924_st1 | CCUGCUAUGCCAACAUAUUGCC | 1 | SEQ ID NO: 68 |
| hsa-asg-9681_st1 | UUGGGAACAUUUUGCAUGUAUA | 1 | SEQ ID NO: 69 |
| hsa-asg-9687_st1 | UUGGGGACAUUUUGCAUUCAUA | 1 | SEQ ID NO: 70 |
| hsa-asg-9696_st1 | UCAAAACGUGAGGCGCUGCUAU | 1 | SEQ ID NO: 71 |
| hsa-asg-9920_st1 | UGUUUUUGGGGUGGGUGGCCC | 1 | SEQ ID NO: 72 |
| hsa-cand206_st1 | UAACAUGGUCCACUAACUCUC | 4 | SEQ ID NO: 73 |
| hsa-cand207_st1 | UGGGAUGGUAAACCGCUUCUU | 4 | SEQ ID NO: 74 |
| hsa-cand283_st1 | UGGGAGAAGGCUGUUUACUCU | 4 | SEQ ID NO: 75 |
| hsa-cand317_st1 | UGCCAACAUAUUGCCAUCUUU | 4 | SEQ ID NO: 76 |
| hsa-cand345_st1 | AGCCAGGAAGUAUUGAUGUUU | 4 | SEQ ID NO: 77 |
| hsa-cand720_st1 | UGUCAGAGGUGACAGGGGCCA | 4 | SEQ ID NO: 78 |
| hsa-let-7a | UGAGGUAGUAGGUUGUAUAGUU | 2, 3 | SEQ ID NO: 79 |
| hsa-let-7b | UGAGGUAGUAGGUUGUGUGGUU | 2, 3 | SEQ ID NO: 80 |
| hsa-let-7c | UGAGGUAGUAGGUUGUAUGGUU | 2, 3 | SEQ ID NO: 81 |
| hsa-let-7d | AGAGGUAGUAGGUUGCAUAGU | 2, 3 | SEQ ID NO: 82 |
| hsa-let-7e | UGAGGUAGGAGGUUGUAUAGU | 2, 3 | SEQ ID NO: 83 |
| hsa-let-7f | UGAGGUAGUAGAUUGUAUAGUU | 2, 3 | SEQ ID NO: 84 |
| hsa-let-7g | UGAGGUAGUAGUUUGUACAGU | 2, 3 | SEQ ID NO: 85 |
| hsa-let-7i | UGAGGUAGUAGUUUGUGCUGU | 2, 3 | SEQ ID NO: 86 |
| hsa-miR-1 | UGGAAUGUAAAGAAGUAUGUA | 2, 3 | SEQ ID NO: 87 |
| hsa-miR-100 | AACCCGUAGAUCCGAACUUGUG | 2, 3 | SEQ ID NO: 88 |
| hsa-miR-101 | UACAGUACUGUGAUAACUGAAG | 2, 3 | SEQ ID NO: 89 |
| hsa-miR102_st2 | AAUGCACCUGGGCAAGGAUUCA | 5 | SEQ ID NO: 90 |

TABLE 1-continued

Example listing of miRNA evaluated.

| miR | Sequence | Ref. | SEQ ID NO |
|---|---|---|---|
| hsa-miR-103 | AGCAGCAUUGUACAGGGCUAUGA | 2, 3 | SEQ ID NO: 91 |
| hsa-miR-105 | UCAAAUGCUCAGACUCCUGU | 2, 3 | SEQ ID NO: 92 |
| hsa-miR-106a | AAAAGUGCUUACAGUGCAGGUAGC | 2, 3 | SEQ ID NO: 93 |
| hsa-miR-106b | UAAAGUGCUGACAGUGCAGAU | 2, 3 | SEQ ID NO: 94 |
| hsa-miR-107 | AGCAGCAUUGUACAGGGCUAUCA | 2, 3 | SEQ ID NO: 95 |
| hsa-miR-10a | UACCCUGUAGAUCCGAAUUUGUG | 2, 3 | SEQ ID NO: 96 |
| hsa-miR-10b | UACCCUGUAGAACCGAAUUUGU | 2, 3 | SEQ ID NO: 97 |
| hsa-miR-122a | UGGAGUGUGACAAUGGUGUUUGU | 2, 3 | SEQ ID NO: 98 |
| hsa-miR-124a | UUAAGGCACGCGGUGAAUGCCA | 2, 3 | SEQ ID NO: 99 |
| hsa-miR-125a | UCCCUGAGACCCUUUAACCUGUG | 2, 3 | SEQ ID NO: 100 |
| hsa-miR-125b | UCCCUGAGACCCUAACUUGUGA | 2, 3 | SEQ ID NO: 101 |
| hsa-miR-126 | CAUUAUUACUUUUGGUACGCG | 2, 3 | SEQ ID NO: 102 |
| hsa-miR-126-AS | CGCGUACCAAAAGUAAUAAUG | 2, 3 | SEQ ID NO: 103 |
| hsa-miR-127 | UCGGAUCCGUCUGAGCUUGGCU | 2, 3 | SEQ ID NO: 104 |
| hsa-miR-128a | UCACAGUGAACCGGUCUCUUUU | 2, 3 | SEQ ID NO: 105 |
| hsa-miR-129 | CUUUUUGCGGUCUGGGCUUGC | 2, 3 | SEQ ID NO: 106 |
| hsa-miR-130a | CAGUGCAAUGUUAAAAGGGCAU | 2, 3 | SEQ ID NO: 107 |
| hsa-miR-130b | CAGUGCAAUGAUGAAAGGGCAU | 2, 3 | SEQ ID NO: 108 |
| hsa-miR-132 | UAACAGUCUACAGCCAUGGUCG | 2, 3 | SEQ ID NO: 109 |
| hsa-miR-133a | UUGGUCCCCUUCAACCAGCUGU | 2, 3 | SEQ ID NO: 110 |
| hsa-miR-133b | UUGGUCCCCUUCAACCAGCUA | 2, 3 | SEQ ID NO: 111 |
| hsa-miR-134 | UGUGACUGGUUGACCAGAGGG | 2, 3 | SEQ ID NO: 112 |
| hsa-miR-135a | UAUGGCUUUUUAUUCCUAUGUGA | 2, 3 | SEQ ID NO: 113 |
| hsa-miR-135b | UAUGGCUUUUCAUUCCUAUGUG | 2, 3 | SEQ ID NO: 114 |
| hsa-miR-136 | ACUCCAUUUGUUUUGAUGAUGGA | 2, 3 | SEQ ID NO: 115 |
| hsa-miR-137 | UAUUGCUUAAGAAUACGCGUAG | 2, 3 | SEQ ID NO: 116 |
| hsa-miR-138 | AGCUGGUGUUGUGAAUC | 2, 3 | SEQ ID NO: 117 |
| hsa-miR-139 | UCUACAGUGCACGUGUCU | 2, 3 | SEQ ID NO: 118 |
| hsa-miR-140 | AGUGGUUUUACCCUAUGGUAG | 2, 3 | SEQ ID NO: 119 |
| hsa-miR-141 | UAACACUGUCUGGUAAAGAUGG | 2, 3 | SEQ ID NO: 120 |
| hsa-miR-142-3p | UGUAGUGUUUCCUACUUUAUGGA | 2, 3 | SEQ ID NO: 121 |
| hsa-miR-142-5p | CAUAAAGUAGAAAGCACUAC | 2, 3 | SEQ ID NO: 122 |
| hsa-miR-143 | UGAGAUGAAGCACUGUAGCUCA | 2, 3 | SEQ ID NO: 123 |
| hsa-miR-144 | UACAGUAUAGAUGAUGUACUAG | 2, 3 | SEQ ID NO: 124 |
| hsa-miR-145 | GUCCAGUUUUCCCAGGAAUCCCUU | 2, 3 | SEQ ID NO: 125 |
| hsa-miR-146a | UGAGAACUGAAUUCCAUGGGUU | 2, 3 | SEQ ID NO: 126 |
| hsa-miR-147 | GUGUGUGGAAAUGCUUCUGC | 2, 3 | SEQ ID NO: 127 |
| hsa-miR-148a | UCAGUGCACUACAGAACUUUGU | 2, 3 | SEQ ID NO: 128 |

TABLE 1-continued

Example listing of miRNA evaluated.

| miR | Sequence | Ref. | SEQ ID NO |
|---|---|---|---|
| hsa-miR-148b | UCAGUGCAUCACAGAACUUUGU | 2, 3 | SEQ ID NO: 129 |
| hsa-miR-149 | UCUGGCUCCGUGUCUUCACUCC | 2, 3 | SEQ ID NO: 130 |
| hsa-miR-150 | UCUCCCAACCCUUGUACCAGUG | 2, 3 | SEQ ID NO: 131 |
| hsa-miR-151 | ACUAGACUGAAGCUCCUUGAGG | 2, 3 | SEQ ID NO: 132 |
| hsa-miR-152 | UCAGUGCAUGACAGAACUUGGG | 2, 3 | SEQ ID NO: 133 |
| hsa-miR-153 | UUGCAUAGUCACAAAAGUGA | 2, 3 | SEQ ID NO: 134 |
| hsa-miR-154 | UAGGUUAUCCGUGUUGCCUUCG | 2, 3 | SEQ ID NO: 135 |
| hsa-miR-155 | UUAAUGCUAAUCGUGAUAGGGG | 2, 3 | SEQ ID NO: 136 |
| hsa-miR157_st2 | AGCACCAUGCAGUCCAUGGGCA | 5 | SEQ ID NO: 137 |
| hsa-miR-15a | UAGCAGCACAUAAUGGUUUGUG | 2, 3 | SEQ ID NO: 138 |
| hsa-miR-15b | UAGCAGCACAUCAUGGUUUACA | 2, 3 | SEQ ID NO: 139 |
| hsa-miR-16 | UAGCAGCACGUAAAUAUUGGCG | 2, 3 | SEQ ID NO: 140 |
| hsa-miR-17-3p | ACUGCAGUGAAGGCACUUGU | 2, 3 | SEQ ID NO: 141 |
| hsa-miR-17-5p | CAAAGUGCUUACAGUGCAGGUAGU | 2, 3 | SEQ ID NO: 142 |
| hsa-miR-181a | AACAUUCAACGCUGUCGGUGAGU | 2, 3 | SEQ ID NO: 143 |
| hsa-miR-181b | AACAUUCAUUGCUGUCGGUGGG | 2, 3 | SEQ ID NO: 144 |
| hsa-miR-181c | AACAUUCAACCUGUCGGUGAGU | 2, 3 | SEQ ID NO: 145 |
| hsa-miR-182 | UUUGGCAAUGGUAGAACUCACA | 2, 3 | SEQ ID NO: 146 |
| hsa-miR-182-AS | UGUGAGUUCUACCAUUGCCAAA | 2, 3 | SEQ ID NO: 147 |
| hsa-miR-183 | UAUGGCACUGGUAGAAUUCACUG | 2, 3 | SEQ ID NO: 148 |
| hsa-miR-184 | UGGACGGAGAACUGAUAAGGGU | 2, 3 | SEQ ID NO: 149 |
| hsa-miR-185 | UGGAGAGAAAGGCAGUUC | 2, 3 | SEQ ID NO: 150 |
| hsa-miR-186 | CAAAGAAUUCUCCUUUUGGGCUU | 2, 3 | SEQ ID NO: 151 |
| hsa-miR-187 | UCGUGUCUUGUGUUGCAGCCG | 2, 3 | SEQ ID NO: 152 |
| hsa-miR-188 | CAUCCCUUGCAUGGUGGAGGGU | 2, 3 | SEQ ID NO: 153 |
| hsa-miR-189 | GUGCCUACUGAGCUGAUAUCAGU | 2, 3 | SEQ ID NO: 154 |
| hsa-miR-18a | UAAGGUGCAUCUAGUGCAGAUA | 2, 3 | SEQ ID NO: 155 |
| hsa-miR-18b | UAAGGUGCAUCUAGUGCAGUUA | 2, 3 | SEQ ID NO: 156 |
| hsa-miR-190 | UGAUAUGUUUGAUAUAUUAGGU | 2, 3 | SEQ ID NO: 157 |
| hsa-miR-191 | CAACGGAAUCCCAAAAGCAGCU | 2, 3 | SEQ ID NO: 158 |
| hsa-miR-192 | CUGACCUAUGAAUUGACAGCC | 2, 3 | SEQ ID NO: 159 |
| hsa-miR-193a | AACUGGCCUACAAAGUCCCAG | 2, 3 | SEQ ID NO: 160 |
| hsa-miR-193b | AACUGGCCCUCAAAGUCCCGCUUU | 2, 3 | SEQ ID NO: 161 |
| hsa-miR-194 | UGUAACAGCAACUCCAUGUGGA | 2, 3 | SEQ ID NO: 162 |
| hsa-miR-195 | UAGCAGCACAGAAAUAUUGGC | 2, 3 | SEQ ID NO: 163 |
| hsa-miR-196a | UAGGUAGUUUCAUGUUGUUGG | 2, 3 | SEQ ID NO: 164 |
| hsa-miR-196b | UAGGUAGUUUCCUGUUGUUGG | 2, 3 | SEQ ID NO: 165 |
| hsa-miR-197 | UUCACCACCUUCUCCACCCAGC | 2, 3 | SEQ ID NO: 166 |

TABLE 1-continued

Example listing of miRNA evaluated.

| miR | Sequence | Ref. | SEQ ID NO |
|---|---|---|---|
| hsa-miR-198 | GGUCCAGAGGGGAGAUAGG | 2, 3 | SEQ ID NO: 167 |
| hsa-miR-199a | CCCAGUGUUCAGACUACCUGUUC | 2, 3 | SEQ ID NO: 168 |
| hsa-miR-199a-AS | GAACAGGUAGUCUGAACACUGGG | 2, 3 | SEQ ID NO: 169 |
| hsa-miR-199b | CCCAGUGUUUAGACUAUCUGUUC | 2, 3 | SEQ ID NO: 170 |
| hsa-miR-19a | UGUGCAAAUCUAUGCAAAACUGA | 2, 3 | SEQ ID NO: 171 |
| hsa-miR-19b | UGUGCAAAUCCAUGCAAAACUGA | 2, 3 | SEQ ID NO: 172 |
| hsa-miR-200a | CAUCUUACCGGACAGUGCUGGA | 2, 3 | SEQ ID NO: 173 |
| hsa-miR-200b | UAAUACUGCCUGGUAAUGAUGAC | 2, 3 | SEQ ID NO: 174 |
| hsa-miR-200c | UAAUACUGCCGGGUAAUGAUGG | 2, 3 | SEQ ID NO: 175 |
| hsa-miR-202-AS | UUUUCCCAUGCCCUAUACCUCU | 2, 3 | SEQ ID NO: 176 |
| hsa-miR-203 | GUGAAAUGUUUAGGACCACUAG | 2, 3 | SEQ ID NO: 177 |
| hsa-miR-204 | UUCCCUUUGUCAUCCUAUGCCU | 2, 3 | SEQ ID NO: 178 |
| hsa-miR-205 | UCCUUCAUUCCACCGGAGUCUG | 2, 3 | SEQ ID NO: 179 |
| hsa-miR-206 | UGGAAUGUAAGGAAGUGUGUGG | 2, 3 | SEQ ID NO: 180 |
| hsa-miR-208 | AUAAGACGAGCAAAAAGCUUGU | 2, 3 | SEQ ID NO: 181 |
| hsa-miR-20a | UAAAGUGCUUAUAGUGCAGGUAG | 2, 3 | SEQ ID NO: 182 |
| hsa-miR-21 | UAGCUUAUCAGACUGAUGUUGA | 2, 3 | SEQ ID NO: 183 |
| hsa-miR-210 | CUGUGCGUGUGACAGCGGCUGA | 2, 3 | SEQ ID NO: 184 |
| hsa-miR-211 | UUCCCUUUGUCAUCCUUCGCCU | 2, 3 | SEQ ID NO: 185 |
| hsa-miR-212 | UAACAGUCUCCAGUCACGGCC | 2, 3 | SEQ ID NO: 186 |
| hsa-miR-213 | ACCAUCGACCGUUGAUUGUACC | 2, 3 | SEQ ID NO: 187 |
| hsa-miR-214 | ACAGCAGGCACAGACAGGCAG | 2, 3 | SEQ ID NO: 188 |
| hsa-miR-215 | AUGACCUAUGAAUUGACAGAC | 2, 3 | SEQ ID NO: 189 |
| hsa-miR-216 | UAAUCUCAGCUGGCAACUGUG | 2, 3 | SEQ ID NO: 190 |
| hsa-miR-217 | UACUGCAUCAGGAACUGAUUGGAU | 2, 3 | SEQ ID NO: 191 |
| hsa-miR-218 | UUGUGCUUGAUCUAACCAUGU | 2, 3 | SEQ ID NO: 192 |
| hsa-miR-219 | UGAUUGUCCAAACGCAAUUCU | 2, 3 | SEQ ID NO: 193 |
| hsa-miR-22 | AAGCUGCCAGUUGAAGAACUGU | 2, 3 | SEQ ID NO: 194 |
| hsa-miR-220 | CCACACCGUAUCUGACACUUU | 2, 3 | SEQ ID NO: 195 |
| hsa-miR-221 | AGCUACAUUGUCUGCUGGGUUUC | 2, 3 | SEQ ID NO: 196 |
| hsa-miR-222 | AGCUACAUCUGGCUACUGGGUCUC | 2, 3 | SEQ ID NO: 197 |
| hsa-miR-223 | UGUCAGUUUGUCAAAUACCCC | 2, 3 | SEQ ID NO: 198 |
| hsa-miR-224 | CAAGUCACUAGUGGUUCCGUUUA | 2, 3 | SEQ ID NO: 199 |
| hsa-miR-23a | AUCACAUUGCCAGGGAUUUCC | 2, 3 | SEQ ID NO: 200 |
| hsa-miR-23b | AUCACAUUGCCAGGGAUUACC | 2, 3 | SEQ ID NO: 201 |
| hsa-miR-24 | UGGCUCAGUUCAGCAGGAACAG | 2, 3 | SEQ ID NO: 202 |
| hsa-miR-25 | CAUUGCACUUGUCUCGGUCUGA | 2, 3 | SEQ ID NO: 203 |
| hsa-miR-26a | UUCAAGUAAUCCAGGAUAGGC | 2, 3 | SEQ ID NO: 204 |

TABLE 1-continued

Example listing of miRNA evaluated.

| miR | Sequence | Ref. | SEQ ID NO |
|---|---|---|---|
| hsa-miR-26b | UUCAAGUAAUUCAGGAUAGGUU | 2, 3 | SEQ ID NO: 205 |
| hsa-miR-27a | UUCACAGUGGCUAAGUUCCGC | 2, 3 | SEQ ID NO: 206 |
| hsa-miR-27b | UUCACAGUGGCUAAGUUCUGC | 2, 3 | SEQ ID NO: 207 |
| hsa-miR-28 | AAGGAGCUCACAGUCUAUUGAG | 2, 3 | SEQ ID NO: 208 |
| hsa-miR-296 | AGGGCCCCCCUCAAUCCUGU | 2, 3 | SEQ ID NO: 209 |
| hsa-miR-299-3p | UAUGUGGGAUGGUAAACCGCUU | 2, 3 | SEQ ID NO: 210 |
| hsa-miR-299-5p | UGGUUUACCGUCCCACAUACAU | 2, 3 | SEQ ID NO: 211 |
| hsa-miR-29a | UAGCACCAUCUGAAAUCGGUU | 2, 3 | SEQ ID NO: 212 |
| hsa-miR-29b | UAGCACCAUUUGAAAUCAGUGUU | 2, 3 | SEQ ID NO: 213 |
| hsa-miR-29c | UAGCACCAUUUGAAAUCGGU | 2, 3 | SEQ ID NO: 214 |
| hsa-miR-301 | CAGUGCAAUAGUAUUGUCAAAGC | 2, 3 | SEQ ID NO: 215 |
| hsa-miR-302a | UAAACGUGGAUGUACUUGCUUU | 2, 3 | SEQ ID NO: 216 |
| hsa-miR-302b | ACUUUAACAUGGAAGUGCUUUCU | 2, 3 | SEQ ID NO: 217 |
| hsa-miR-302b-AS | AGAAAGCACUUCCAUGUUAAAGU | 2, 3 | SEQ ID NO: 218 |
| hsa-miR-302c | UUUAACAUGGGGGUACCUGCUG | 2, 3 | SEQ ID NO: 219 |
| hsa-miR-302c-AS | CAGCAGGUACCCCCAUGUUAAA | 2, 3 | SEQ ID NO: 220 |
| hsa-miR-302d | UAAGUGCUUCCAUGUUUGAGUGU | 2, 3 | SEQ ID NO: 221 |
| hsa-miR-30a-3p | CUUUCAGUCGGAUGUUUGCAGC | 2, 3 | SEQ ID NO: 222 |
| hsa-miR-30a-5p | UGUAAACAUCCUCGACUGGAAG | 2, 3 | SEQ ID NO: 223 |
| hsa-miR-30b | UGUAAACAUCCUACACUCAGCU | 2, 3 | SEQ ID NO: 224 |
| hsa-miR-30c | UGUAAACAUCCUACACUCUCAGC | 2, 3 | SEQ ID NO: 225 |
| hsa-miR-30d | UGUAAACAUCCCCGACUGGAAG | 2, 3 | SEQ ID NO: 226 |
| hsa-miR-30e-3p | CUUUCAGUCGGAUGUUUACAGC | 2, 3 | SEQ ID NO: 227 |
| hsa-miR-30e-5p | UGUAAACAUCCUUGACUGGA | 2, 3 | SEQ ID NO: 228 |
| hsa-miR-31 | GGCAAGAUGCUGGCAUAGCUG | 2, 3 | SEQ ID NO: 229 |
| hsa-miR-32 | UAUUGCACAUUACUAAGUUGC | 2, 3 | SEQ ID NO: 230 |
| hsa-miR-320 | AAAAGCUGGGUUGAGAGGGCGAA | 2, 3 | SEQ ID NO: 231 |
| hsa-miR-323 | GCACAUUACACGGUCGACCUCU | 2, 3 | SEQ ID NO: 232 |
| hsa-miR-324-3p | CCACUGCCCCAGGUGCUGCUGG | 2, 3 | SEQ ID NO: 233 |
| hsa-miR-324-5p | CGCAUCCCCUAGGGCAUUGGUGU | 2, 3 | SEQ ID NO: 234 |
| hsa-miR-325 | CCUAGUAGGUGUCCAGUAAGUGU | 2, 3 | SEQ ID NO: 235 |
| hsa-miR-326 | CCUCUGGGCCCUUCCUCCAG | 2, 3 | SEQ ID NO: 236 |
| hsa-miR-328 | CUGGCCCUCUCUGCCCUUCCGU | 2, 3 | SEQ ID NO: 237 |
| hsa-miR-329 | AACACACCUGGUUAACCUCUUU | 2, 3 | SEQ ID NO: 238 |
| hsa-miR-33 | GUGCAUUGUAGUUGCAUUG | 2, 3 | SEQ ID NO: 239 |
| hsa-miR-330 | GCAAAGCACACGGCCUGCAGAGA | 2, 3 | SEQ ID NO: 240 |
| hsa-miR-331 | GCCCCUGGGCCUAUCCUAGAA | 2, 3 | SEQ ID NO: 241 |
| hsa-miR-335 | UCAAGAGCAAUAACGAAAAAUGU | 2, 3 | SEQ ID NO: 242 |

TABLE 1-continued

Example listing of miRNA evaluated.

| miR | Sequence | Ref. | SEQ ID NO |
|---|---|---|---|
| hsa-miR-337 | UCCAGCUCCUAUAUGAUGCCUUU | 2, 3 | SEQ ID NO: 243 |
| hsa-miR-338 | UCCAGCAUCAGUGAUUUUGUUGA | 2, 3 | SEQ ID NO: 244 |
| hsa-miR-339 | UCCCUGUCCUCCAGGAGCUCA | 2, 3 | SEQ ID NO: 245 |
| hsa-miR-340 | UCCGUCUCAGUUACUUUAUAGCC | 2, 3 | SEQ ID NO: 246 |
| hsa-miR-342 | UCUCACACAGAAAUCGCACCCGUC | 2, 3 | SEQ ID NO: 247 |
| hsa-miR-345 | UGCUGACUCCUAGUCCAGGGC | 2, 3 | SEQ ID NO: 248 |
| hsa-miR-346 | UGUCUGCCCGCAUGCCUGCCUCU | 2, 3 | SEQ ID NO: 249 |
| hsa-miR-34a | UGGCAGUGUCUUAGCUGGUUGUU | 2, 3 | SEQ ID NO: 250 |
| hsa-miR-34b | UAGGCAGUGUCAUUAGCUGAUUG | 2, 3 | SEQ ID NO: 251 |
| hsa-miR-34c | AGGCAGUGUAGUUAGCUGAUUGC | 2, 3 | SEQ ID NO: 252 |
| hsa-miR-361 | UUAUCAGAAUCUCCAGGGGUAC | 2, 3 | SEQ ID NO: 253 |
| hsa-miR-365 | UAAUGCCCCUAAAAAUCCUUAU | 2, 3 | SEQ ID NO: 254 |
| hsa-miR-367 | AAUUGCACUUUAGCAAUGGUGA | 2, 3 | SEQ ID NO: 255 |
| hsa-miR-368 | ACAUAGAGGAAAUUCCACGUUU | 2, 3 | SEQ ID NO: 256 |
| hsa-miR-369-3p | AAUAAUACAUGGUUGAUCUUU | 2, 3 | SEQ ID NO: 257 |
| hsa-miR-369-5p | AGAUCGACCGUGUUAUAUUCGC | 2, 3 | SEQ ID NO: 258 |
| hsa-miR-370 | GCCUGCUGGGGUGGAACCUGG | 2, 3 | SEQ ID NO: 259 |
| hsa-miR-371 | GUGCCGCCAUCUUUUGAGUGU | 2, 3 | SEQ ID NO: 260 |
| hsa-miR-372 | AAAGUGCUGCGACAUUUGAGCGU | 2, 3 | SEQ ID NO: 261 |
| hsa-miR-373 | ACUCAAAAUGGGGCGCUUUCC | 2, 3 | SEQ ID NO: 262 |
| hsa-miR-373-AS | GGAAAGCGCCCCCAUUUUGAGU | 2, 3 | SEQ ID NO: 263 |
| hsa-miR-374 | UUAUAAUACAACCUGAUAAGUG | 2, 3 | SEQ ID NO: 264 |
| hsa-miR-375 | UUUGUUCGUUCGGCUCGCGUGA | 2, 3 | SEQ ID NO: 265 |
| hsa-miR-376a | GGUAGAUUCUCCUUCUAUGAG | 2, 3 | SEQ ID NO: 266 |
| hsa-miR-377 | AUCACACAAAGGCAACUUUUGU | 2, 3 | SEQ ID NO: 267 |
| hsa-miR-378 | CUCCUGACUCCAGGUCCUGUGU | 2, 3 | SEQ ID NO: 268 |
| hsa-miR-379 | UGGUAGACUAUGGAACGUA | 2, 3 | SEQ ID NO: 269 |
| hsa-miR-380-3p | UAUGUAAUAUGGUCCACAUCUU | 2, 3 | SEQ ID NO: 270 |
| hsa-miR-380-5p | UGGUUGACCAUAGAACAUGCGC | 2, 3 | SEQ ID NO: 271 |
| hsa-miR-381 | UAUACAAGGGCAAGCUCUCUGU | 2, 3 | SEQ ID NO: 272 |
| hsa-miR-382 | GAAGUUGUUCGUGGUGGAUUCG | 2, 3 | SEQ ID NO: 273 |
| hsa-miR-383 | AGAUCAGAAGGUGAUUGUGGCU | 2, 3 | SEQ ID NO: 274 |
| hsa-miR-384 | AUUCCUAGAAAUUGUUCAUA | 2, 3 | SEQ ID NO: 275 |
| hsa-miR-410 | AAUAUAACACAGAUGGCCUGU | 2, 3 | SEQ ID NO: 276 |
| hsa-miR-411 | UAGUAGACCGUAUAGCGUACG | 2, 3 | SEQ ID NO: 277 |
| hsa-miR-412 | ACUUCACCUGGUCCACUAGCCGU | 2, 3 | SEQ ID NO: 278 |
| hsa-miR-422a | CUGGACUUAGGGUCAGAAGGCC | 2, 3 | SEQ ID NO: 279 |
| hsa-miR-422b | CUGGACUUGGAGUCAGAAGGCC | 2, 3 | SEQ ID NO: 280 |

TABLE 1-continued

Example listing of miRNA evaluated.

| miR | Sequence | Ref. | SEQ ID NO |
|---|---|---|---|
| hsa-miR-423 | AGCUCGGUCUGAGGCCCCUCAG | 2, 3 | SEQ ID NO: 281 |
| hsa-miR-424 | CAGCAGCAAUUCAUGUUUUGAA | 2, 3 | SEQ ID NO: 282 |
| hsa-miR-425 | AAUGACACGAUCACUCCCGUUGA | 2, 3 | SEQ ID NO: 283 |
| hsa-miR-429 | UAAUACUGUCUGGUAAAACCGU | 2, 3 | SEQ ID NO: 284 |
| hsa-miR-432 | UCUUGGAGUAGGUCAUUGGGUGG | 2, 3 | SEQ ID NO: 285 |
| hsa-miR-432-AS | CCACCCAAUGACCUACUCCAAGA | 2, 3 | SEQ ID NO: 286 |
| hsa-miR-433 | AUCAUGAUGGGCUCCUCGGUGU | 2, 3 | SEQ ID NO: 287 |
| hsa-miR-448 | UUGCAUAUGUAGGAUGUCCCAU | 2, 3 | SEQ ID NO: 288 |
| hsa-miR-449 | UGGCAGUGUAUUGUUAGCUGGU | 2, 3 | SEQ ID NO: 289 |
| hsa-miR-450 | UUUUUGCGAUGUGUUCCUAAUA | 2, 3 | SEQ ID NO: 290 |
| hsa-miR-452 | UGUUUGCAGAGGAAACUGAGAC | 2, 3 | SEQ ID NO: 291 |
| hsa-miR-452-AS | GUCUCAGUUUCCUCUGCAAACA | 2, 3 | SEQ ID NO: 292 |
| hsa-miR-455 | UAUGUGCCUUUGGACUACAUCG | 2, 3 | SEQ ID NO: 293 |
| hsa-miR-485-3p | GUCAUACACGGCUCUCCUCUCU | 2, 3 | SEQ ID NO: 294 |
| hsa-miR-485-5p | AGAGGCUGGCCGUGAUGAAUUC | 2, 3 | SEQ ID NO: 295 |
| hsa-miR-487a | AAUCAUACAGGGACAUCCAGUU | 2, 3 | SEQ ID NO: 296 |
| hsa-miR-487b | AAUCGUACAGGGUCAUCCACUU | 2, 3 | SEQ ID NO: 297 |
| hsa-miR-488 | CCCAGAUAAUGGCACUCUCAA | 2, 3 | SEQ ID NO: 298 |
| hsa-miR-489 | AGUGACAUCACAUAUACGGCAGC | 2, 3 | SEQ ID NO: 299 |
| hsa-miR-490 | CAACCUGGAGGACUCCAUGCUG | 2, 3 | SEQ ID NO: 300 |
| hsa-miR-491 | AGUGGGGAACCCUUCCAUGAGGA | 2, 3 | SEQ ID NO: 301 |
| hsa-miR-492 | AGGACCUGCGGGACAAGAUUCUU | 2, 3 | SEQ ID NO: 302 |
| hsa-miR-493 | UUGUACAUGGUAGGCUUUCAUU | 2, 3 | SEQ ID NO: 303 |
| hsa-miR-493-3p | UGAAGGUCUACUGUGUGCCAG | 2, 3 | SEQ ID NO: 304 |
| hsa-miR-493-5p | UGAAGGUCUACUGUGUGCCAG | 2, 3 | SEQ ID NO: 305 |
| hsa-miR-494 | UGAAACAUACACGGGAAACCUCUU | 2, 3 | SEQ ID NO: 306 |
| hsa-miR-495 | AAACAAACAUGGUGCACUUCUUU | 2, 3 | SEQ ID NO: 307 |
| hsa-miR-496 | AUUACAUGGCCAAUCUC | 2, 3 | SEQ ID NO: 308 |
| hsa-miR-497 | CAGCAGCACACUGUGGUUUGU | 2, 3 | SEQ ID NO: 309 |
| hsa-miR-498 | UUUCAAGCCAGGGGGCGUUUUUC | 2, 3 | SEQ ID NO: 310 |
| hsa-miR-499 | UUAAGACUUGCAGUGAUGUUUAA | 2, 3 | SEQ ID NO: 311 |
| hsa-miR-500 | AUGCACCUGGGCAAGGAUUCUG | 2, 3 | SEQ ID NO: 312 |
| hsa-miR-501 | AAUCCUUUGUCCCUGGGUGAGA | 2, 3 | SEQ ID NO: 313 |
| hsa-miR-502 | AUCCUUGCUAUCUGGGUGCUA | 2, 3 | SEQ ID NO: 314 |
| hsa-miR-503 | UAGCAGCGGGAACAGUUCUGCAG | 2, 3 | SEQ ID NO: 315 |
| hsa-miR-504 | AGACCCUGGUCUGCACUCUAU | 2, 3 | SEQ ID NO: 316 |
| hsa-miR-505 | GUCAACACUUGCUGGUUUCCUC | 2, 3 | SEQ ID NO: 317 |
| hsa-miR-506 | UAAGGCACCCUUCUGAGUAGA | 2, 3 | SEQ ID NO: 318 |

TABLE 1-continued

Example listing of miRNA evaluated.

| miR | Sequence | Ref. | SEQ ID NO |
|---|---|---|---|
| hsa-miR-507 | UUUUGCACCUUUUGGAGUGAA | 2, 3 | SEQ ID NO: 319 |
| hsa-miR-508 | UGAUUGUAGCCUUUUGGAGUAGA | 2, 3 | SEQ ID NO: 320 |
| hsa-miR-509 | UGAUUGGUACGUCUGUGGGUAGA | 2, 3 | SEQ ID NO: 321 |
| hsa-miR-510 | UACUCAGGAGAGUGGCAAUCACA | 2, 3 | SEQ ID NO: 322 |
| hsa-miR-511 | GUGUCUUUUGCUCUGCAGUCA | 2, 3 | SEQ ID NO: 323 |
| hsa-miR-512-3p | AAGUGCUGUCAUAGCUGAGGUC | 2, 3 | SEQ ID NO: 324 |
| hsa-miR-512-5p | CACUCAGCCUUGAGGGCACUUUC | 2, 3 | SEQ ID NO: 325 |
| hsa-miR-513 | UUCACAGGGAGGUGUCAUUUAU | 2, 3 | SEQ ID NO: 326 |
| hsa-miR-514 | AUUGACACUUCUGUGAGUAG | 2, 3 | SEQ ID NO: 327 |
| hsa-miR-515-3p | GAGUGCCUUCUUUUGGAGCGU | 2, 3 | SEQ ID NO: 328 |
| hsa-miR-515-5p | UUCUCCAAAAGAAAGCACUUUCUG | 2, 3 | SEQ ID NO: 329 |
| hsa-miR-516-3p | UGCUUCCUUUCAGAGGGU | 2, 3 | SEQ ID NO: 330 |
| hsa-miR-517a | AUCGUGCAUCCCUUUAGAGUGUU | 2, 3 | SEQ ID NO: 331 |
| hsa-miR-517-AS | AACACUCUAAAGGGAUGCACGAU | 2, 3 | SEQ ID NO: 332 |
| hsa-miR-518a | AAAGCGCUUCCCUUUGCUGGA | 2, 3 | SEQ ID NO: 333 |
| hsa-miR-518b | CAAAGCGCUCCCCUUUAGAGGU | 2, 3 | SEQ ID NO: 334 |
| hsa-miR-518c | CAAAGCGCUUCUCUUUAGAGUG | 2, 3 | SEQ ID NO: 335 |
| hsa-miR-518c-AS | CACUCUAAAGAGAAGCGCUUUG | 2, 3 | SEQ ID NO: 336 |
| hsa-miR-518d | CAAAGCGCUUCCCUUUGGAGC | 2, 3 | SEQ ID NO: 337 |
| hsa-miR-518e | AAAGCGCUUCCCUUCAGAGUGU | 2, 3 | SEQ ID NO: 338 |
| hsa-miR-518f | AAAGCGCUUCUCUUUAGAGGA | 2, 3 | SEQ ID NO: 339 |
| hsa-miR-518f-AS | UCCUCUAAAGAGAAGCGCUUU | 2, 3 | SEQ ID NO: 340 |
| hsa-miR-519b | AAAGUGCAUCCUUUUAGAGGUUU | 2, 3 | SEQ ID NO: 341 |
| hsa-miR-519c | AAAGUGCAUCUUUUUAGAGGAU | 2, 3 | SEQ ID NO: 342 |
| hsa-miR-519d | CAAAGUGCCUCCCUUUAGAGUGU | 2, 3 | SEQ ID NO: 343 |
| hsa-miR-519e | AAAGUGCCUCCUUUUAGAGUGU | 2, 3 | SEQ ID NO: 344 |
| hsa-miR-519e-AS | ACACUCUAAAAGGAGGCACUUU | 2, 3 | SEQ ID NO: 345 |
| hsa-miR-520a | AAAGUGCUUCCCUUUGGACUGU | 2, 3 | SEQ ID NO: 346 |
| hsa-miR-520a-AS | ACAGUCCAAAGGGAAGCACUUU | 2, 3 | SEQ ID NO: 347 |
| hsa-miR-520b | AAAGUGCUUCCUUUUAGAGGG | 2, 3 | SEQ ID NO: 348 |
| hsa-miR-520c | AAAGUGCUUCCUUUUAGAGGGUU | 2, 3 | SEQ ID NO: 349 |
| hsa-miR-520d | AAAGUGCUUCUCUUUGGUGGGUU | 2, 3 | SEQ ID NO: 350 |
| hsa-miR-520d-AS | AACCCACCAAAGAGAAGCACUUU | 2, 3 | SEQ ID NO: 351 |
| hsa-miR-520e | AAAGUGCUUCCUUUUUGAGGG | 2, 3 | SEQ ID NO: 352 |
| hsa-miR-520h | ACAAAGUGCUUCCCUUUAGAGU | 2, 3 | SEQ ID NO: 353 |
| hsa-miR-521 | AACGCACUUCCCUUUAGAGUGU | 2, 3 | SEQ ID NO: 354 |
| hsa-miR-522 | AAAAUGGUUCCCUUUAGAGUGUU | 2, 3 | SEQ ID NO: 355 |
| hsa-miR-523 | AACGCGCUUCCCUAUAGAGGG | 2, 3 | SEQ ID NO: 356 |

TABLE 1-continued

Example listing of miRNA evaluated.

| miR | Sequence | Ref. | SEQ ID NO |
|---|---|---|---|
| hsa-miR-524 | GAAGGCGCUUCCCUUUGGAGU | 2, 3 | SEQ ID NO: 357 |
| hsa-miR-524-AS | ACUCCAAAGGGAAGCGCCUUC | 2, 3 | SEQ ID NO: 358 |
| hsa-miR-525 | CUCCAGAGGGAUGCACUUUCU | 2, 3 | SEQ ID NO: 359 |
| hsa-miR-525-AS | AGAAAGUGCAUCCCUCUGGAG | 2, 3 | SEQ ID NO: 360 |
| hsa-miR-526b | CUCUUGAGGGAAGCACUUUCUGUU | 2, 3 | SEQ ID NO: 361 |
| hsa-miR-526b-AS | AACAGAAAGUGCUUCCCUCAAGAG | 2, 3 | SEQ ID NO: 362 |
| hsa-miR-526c | CUCUAGAGGGAAGCGCUUUCUGUU | 2, 3 | SEQ ID NO: 363 |
| hsa-miR-527 | CUGCAAAGGGAAGCCCUUUCU | 2, 3 | SEQ ID NO: 364 |
| hsa-miR-539 | GGAGAAAUUAUCCUUGGUGUGU | 2, 3 | SEQ ID NO: 365 |
| hsa-miR-542-5p | UCGGGGAUCAUCAUGUCACGAG | 2, 3 | SEQ ID NO: 366 |
| hsa-miR-565 | GGCUGGUCGCGAUGUCUGUUU | 2, 3 | SEQ ID NO: 367 |
| hsa-miR-574 | CACGCUCAUGCACACACCCAC | 2, 3 | SEQ ID NO: 368 |
| hsa-miR-585 | UGGGCGUAUCUGUAUGCUA | 2, 3 | SEQ ID NO: 369 |
| hsa-miR-594_st2 | CCCAUCUGGGGUGGCCUGUGACUUU | 2, 3 | SEQ ID NO: 370 |
| hsa-miR-598 | UACGUCAUCGUUGUCAUCGUCA | 2, 3 | SEQ ID NO: 371 |
| hsa-miR-628 | UCUAGUAAGAGUGGCAGUCG | 2, 3 | SEQ ID NO: 372 |
| hsa-miR-654 | UGGUGGGCCGCAGAACAUGUGC | 2, 3 | SEQ ID NO: 373 |
| hsa-miR-7 | UGGAAGACUAGUGAUUUUGUUG | 2, 3 | SEQ ID NO: 374 |
| hsa-miR-9 | UCUUUGGUUAUCUAGCUGUAUGA | 2, 3 | SEQ ID NO: 375 |
| hsa-miR-92 | UAUUGCACUUGUCCCGGCCUG | 2, 3 | SEQ ID NO: 376 |
| hsa-miR-93 | AAAGUGCUGUUCGUGCAGGUAG | 2, 3 | SEQ ID NO: 377 |
| hsa-miR-95 | UUCAACGGGUAUUUAUUGAGCA | 2, 3 | SEQ ID NO: 378 |
| hsa-miR-96 | UUUGGCACUAGCACAUUUUUGC | 2, 3 | SEQ ID NO: 379 |
| hsa-miR-98 | UGAGGUAGUAAGUUGUAUUGUU | 2, 3 | SEQ ID NO: 380 |
| hsa-miR-99a | AACCCGUAGAUCCGAUCUUGUG | 2, 3 | SEQ ID NO: 381 |
| hsa-miR-99b | CACCCGUAGAACCGACCUUGCG | 2, 3 | SEQ ID NO: 382 |
| hsa-miR-9-AS | UCAUACAGCUAGAUAACCAAAGA | 2, 3 | SEQ ID NO: 383 |
| mmu-let-7d-AS | ACUAUGCAACCUACUACCUCU | 2, 3 | SEQ ID NO: 384 |
| mmu-miR-101b | UACAGUACUGUGAUAGCUGAAG | 2, 3 | SEQ ID NO: 385 |
| mmu-miR-106a | CAAAGUGCUAACAGUGCAGGUA | 2, 3 | SEQ ID NO: 386 |
| mmu-miR-129-3p | AAGCCCUUACCCCAAAAAGCAU | 2, 3 | SEQ ID NO: 387 |
| mmu-miR-140-AS | CUACCAUAGGGUAAAACCACUG | 2, 3 | SEQ ID NO: 388 |
| mmu-miR-151 | CUAGACUGAGGCUCCUUGAGG | 2, 3 | SEQ ID NO: 389 |
| mmu-miR-155 | UUAAUGCUAAUUGUGAUAGGGG | 2, 3 | SEQ ID NO: 390 |
| mmu-miR-17-3p | ACUGCAGUGAGGGCACUUGUA | 2, 3 | SEQ ID NO: 391 |
| mmu-miR-192 | CUGACCUAUGAAUUGACA | 2, 3 | SEQ ID NO: 392 |
| mmu-miR-199b | CCCAGUGUUUAGACUACCUGUUC | 2, 3 | SEQ ID NO: 393 |
| mmu-miR-201 | UACUCAGUAAGGCAUUGUUCU | 2, 3 | SEQ ID NO: 394 |

TABLE 1-continued

Example listing of miRNA evaluated.

| miR | Sequence | Ref. | SEQ ID NO |
|---|---|---|---|
| mmu-miR-202 | AGAGGUAUAGCGCAUGGGAAGA | 2, 3 | SEQ ID NO: 395 |
| mmu-miR-207 | GCUUCUCCUGGCUCUCCUCCCUC | 2, 3 | SEQ ID NO: 396 |
| mmu-miR-211 | UUCCCUUUGUCAUCCUUUGCCU | 2, 3 | SEQ ID NO: 397 |
| mmu-miR-215 | AUGACCUAUGAUUUGACAGAC | 2, 3 | SEQ ID NO: 398 |
| mmu-miR-217 | UACUGCAUCAGGAACUGACUGGAU | 2, 3 | SEQ ID NO: 399 |
| mmu-miR-290 | CUCAAACUAUGGGGGCACUUUUU | 2, 3 | SEQ ID NO: 400 |
| mmu-miR-291-3p | AAAGUGCUUCCACUUUGUGUGCC | 2, 3 | SEQ ID NO: 401 |
| mmu-miR-291-5p | CAUCAAAGUGGAGGCCCUCUCU | 2, 3 | SEQ ID NO: 402 |
| mmu-miR-292-3p | AAGUGCCGCCAGGUUUUGAGUGU | 2, 3 | SEQ ID NO: 403 |
| mmu-miR-292-5p | ACUCAAACUGGGGGCUCUUUUG | 2, 3 | SEQ ID NO: 404 |
| mmu-miR-293 | AGUGCCGCAGAGUUUGUAGUGU | 2, 3 | SEQ ID NO: 405 |
| mmu-miR-294 | AAAGUGCUUCCCUUUUGUGUGU | 2, 3 | SEQ ID NO: 406 |
| mmu-miR-295 | AAAGUGCUACUACUUUUGAGUCU | 2, 3 | SEQ ID NO: 407 |
| mmu-miR-297 | AUGUAUGUGUGCAUGUGCAUG | 2, 3 | SEQ ID NO: 408 |
| mmu-miR-298 | GGCAGAGGAGGGCUGUUCUUCC | 2, 3 | SEQ ID NO: 409 |
| mmu-miR-300 | UAUGCAAGGGCAAGCUCUCUUC | 2, 3 | SEQ ID NO: 410 |
| mmu-miR-322 | AAACAUGAAGCGCUGCAACA | 2, 3 | SEQ ID NO: 411 |
| mmu-miR-325 | CCUAGUAGGUGCUCAGUAAGUGU | 2, 3 | SEQ ID NO: 412 |
| mmu-miR-329 | AACACACCCAGCUAACCUUUUU | 2, 3 | SEQ ID NO: 413 |
| mmu-miR-330 | GCAAAGCACAGGGCCUGCAGAGA | 2, 3 | SEQ ID NO: 414 |
| mmu-miR-337 | UUCAGCUCCUAUAUGAUGCCUUU | 2, 3 | SEQ ID NO: 415 |
| mmu-miR-341 | UCGAUCGGUCGGUCGGUCAGU | 2, 3 | SEQ ID NO: 416 |
| mmu-miR-344 | UGAUCUAGCCAAAGCCUGACUGU | 2, 3 | SEQ ID NO: 417 |
| mmu-miR-345 | UGCUGACCCCUAGUCCAGUGC | 2, 3 | SEQ ID NO: 418 |
| mmu-miR-346 | UGUCUGCCCGAGUGCCUGCCUCU | 2, 3 | SEQ ID NO: 419 |
| mmu-miR-34b | UAGGCAGUGUAAUUAGCUGAUUG | 2, 3 | SEQ ID NO: 420 |
| mmu-miR-350 | UUCACAAAGCCCAUACACUUUCA | 2, 3 | SEQ ID NO: 421 |
| mmu-miR-351 | UCCCUGAGGAGCCCUUUGAGCCUG | 2, 3 | SEQ ID NO: 422 |
| mmu-miR-376a | AUCGUAGAGGAAAAUCCACGU | 2, 3 | SEQ ID NO: 423 |
| mmu-miR-376b | AUCAUAGAGGAACAUCCACUUU | 2, 3 | SEQ ID NO: 424 |
| mmu-miR-380-3p | UAUGUAGUAUGGUCCACAUCUU | 2, 3 | SEQ ID NO: 425 |
| mmu-miR-383 | AGAUCAGAAGGUGACUGUGGCU | 2, 3 | SEQ ID NO: 426 |
| mmu-miR-384 | AUUCCUAGAAAUUGUUCACA | 2, 3 | SEQ ID NO: 427 |
| mmu-miR-409 | GAAUGUUGCUCGGUGAACCCCUU | 2, 3 | SEQ ID NO: 428 |
| mmu-miR-411 | AACACGGUCCACUAACCCUCAGU | 2, 3 | SEQ ID NO: 429 |
| mmu-miR-424 | CAGCAGCAAUUCAUGUUUUGGA | 2, 3 | SEQ ID NO: 430 |
| mmu-miR-429 | UAAUACUGUCUGGUAAUGCCGU | 2, 3 | SEQ ID NO: 431 |
| mmu-miR-7b | UGGAAGACUUGUGAUUUUGUU | 2, 3 | SEQ ID NO: 432 |

TABLE 1-continued

Example listing of miRNA evaluated.

| miR | Sequence | Ref. | SEQ ID NO |
|---|---|---|---|
| rno-miR-151-AS | CCUCAAGGAGCCUCAGUCUAGU | 2, 3 | SEQ ID NO: 433 |
| rno-miR-20-AS | UAAAGUGCUUAUAGUGCAGGUAG | 2, 3 | SEQ ID NO: 434 |
| rno-miR-297 | AUGUAUGUGUGCAUGUAUGCAUG | 2, 3 | SEQ ID NO: 435 |
| rno-miR-327 | CCUUGAGGGGCAUGAGGGU | 2, 3 | SEQ ID NO: 436 |
| rno-miR-333 | GUGGUGUGCUAGUUACUUUU | 2, 3 | SEQ ID NO: 437 |
| rno-miR-336 | UCACCCUUCCAUAUCUAGUCU | 2, 3 | SEQ ID NO: 438 |
| rno-miR-343 | UCUCCCUCCGUGUGCCCAGA | 2, 3 | SEQ ID NO: 439 |
| rno-miR-344 | UGAUCUAGCCAAAGCCUGACCGU | 2, 3 | SEQ ID NO: 440 |
| rno-miR-346 | UGUCUGCCUGAGUGCCUGCCUCU | 2, 3 | SEQ ID NO: 441 |
| rno-miR-347 | UGUCCCUCUGGGUCGCCCA | 2, 3 | SEQ ID NO: 442 |
| rno-miR-349 | CAGCCCUGCUGUCUUAACCUCU | 2, 3 | SEQ ID NO: 443 |
| rno-miR-352 | AGAGUAGUAGGUUGCAUAGUA | 2, 3 | SEQ ID NO: 444 |
| rno-miR-421 | GGCCUCAUUAAAUGUUUGUUG | 2, 3 | SEQ ID NO: 445 |
| rno-miR-7-AS | AACAAAAUCACUAGUCUUCCA | 2, 3 | SEQ ID NO: 446 |
| hsa-let-7d* | CUAUACGACCUGCUGCCUUUCU | 2 | SEQ ID NO: 447 |
| hsa-let-7e* | CUAUACGGCCUCCUAGCUUUCC | 2 | SEQ ID NO: 448 |
| hsa-miR-100* | CAAGCUUGUAUCUAUAGGUAUG | 2 | SEQ ID NO: 449 |
| hsa-miR-101* | CAGUUAUCACAGUGCUGAUGCU | 2 | SEQ ID NO: 450 |
| hsa-miR-106b* | CCGCACUGUGGGUACUUGCUGC | 2 | SEQ ID NO: 451 |
| hsa-miR-10b* | ACAGAUUCGAUUCUAGGGGAAU | 2 | SEQ ID NO: 452 |
| hsa-miR-125a-5p | UCCCUGAGACCCUUUAACCUGUGA | 2 | SEQ ID NO: 453 |
| hsa-miR-125b-2* | UCACAAGUCAGGCUCUUGGGAC | 2 | SEQ ID NO: 454 |
| hsa-miR-126* | CAUUAUUACUUUUGGUACGCG | 2 | SEQ ID NO: 455 |
| hsa-miR-127-3p | UCGGAUCCGUCUGAGCUUGGCU | 2 | SEQ ID NO: 456 |
| hsa-miR-129-3p | AAGCCCUUACCCCAAAAAGCAU | 2 | SEQ ID NO: 457 |
| hsa-miR-135a | UAUGGCUUUUUAUUCCUAUGUGA | 2 | SEQ ID NO: 458 |
| hsa-miR-136 | ACUCCAUUUGUUUUGAUGAUGGA | 2 | SEQ ID NO: 459 |
| hsa-miR-136* | CAUCAUCGUCUCAAAUGAGUCU | 2 | SEQ ID NO: 460 |
| hsa-miR-139-5p | UCUACAGUGCACGUGUCUCCAG | 2 | SEQ ID NO: 461 |
| hsa-miR-140-3p | UACCACAGGGUAGAACCACGG | 2 | SEQ ID NO: 462 |
| hsa-miR-140-5p | CAGUGGUUUUACCCUAUGGUAG | 2 | SEQ ID NO: 463 |
| hsa-miR-141* | CAUCUUCCAGUACAGUGUUGGA | 2 | SEQ ID NO: 464 |
| hsa-miR-142-3p | UGUAGUGUUUCCUACUUUAUGGA | 2 | SEQ ID NO: 465 |
| hsa-miR-142-5p | CAUAAAGUAGAAAGCACUACU | 2 | SEQ ID NO: 466 |
| hsa-miR-143* | GGUGCAGUGCUGCAUCUCUGGU | 2 | SEQ ID NO: 467 |
| hsa-miR-144 | UACAGUAUAGAUGAUGUACU | 2 | SEQ ID NO: 468 |
| hsa-miR-144* | GGAUAUCAUCAUAUACUGUAAG | 2 | SEQ ID NO: 469 |
| hsa-miR-145* | GGAUUCCUGGAAAUACUGUUCU | 2 | SEQ ID NO: 470 |

TABLE 1-continued

Example listing of miRNA evaluated.

| miR | Sequence | Ref. | SEQ ID NO |
|---|---|---|---|
| hsa-miR-146b-5p | UGAGAACUGAAUUCCAUAGGCU | 2 | SEQ ID NO: 471 |
| hsa-miR-151-3p | CUAGACUGAAGCUCCUUGAGG | 2 | SEQ ID NO: 472 |
| hsa-miR-154* | AAUCAUACACGGUUGACCUAUU | 2 | SEQ ID NO: 473 |
| hsa-miR-15b* | CGAAUCAUUAUUUGCUGCUCUA | 2 | SEQ ID NO: 474 |
| hsa-miR-17 | CAAAGUGCUUACAGUGCAGGUAG | 2 | SEQ ID NO: 475 |
| hsa-miR-181c | AACAUUCAACCUGUCGGUGAGU | 2 | SEQ ID NO: 476 |
| hsa-miR-181d | AACAUUCAUUGUUGUCGGUGGGU | 2 | SEQ ID NO: 477 |
| hsa-miR-183* | GUGAAUUACCGAAGGGCCAUAA | 2 | SEQ ID NO: 478 |
| hsa-miR-193a-5p | UGGGUCUUUGCGGGCGAGAUGA | 2 | SEQ ID NO: 479 |
| hsa-miR-195* | CCAAUAUUGGCUGUGCUGCUCC | 2 | SEQ ID NO: 480 |
| hsa-miR-197 | UUCACCACCUUCUCCACCCAGC | 2 | SEQ ID NO: 481 |
| hsa-miR-199a-5p | CCCAGUGUUCAGACUACCUGUUC | 2 | SEQ ID NO: 482 |
| hsa-miR-199b-3p | ACAGUAGUCUGCACAUUGGUUA | 2 | SEQ ID NO: 483 |
| hsa-miR-199b-5p | CCCAGUGUUUAGACUAUCUGUUC | 2 | SEQ ID NO: 484 |
| hsa-miR-20a* | ACUGCAUUAUGAGCACUUAAAG | 2 | SEQ ID NO: 485 |
| hsa-miR-21* | CAACACCAGUCGAUGGGCUGU | 2 | SEQ ID NO: 486 |
| hsa-miR-212 | UAACAGUCUCCAGUCACGGCC | 2 | SEQ ID NO: 487 |
| hsa-miR-214* | UGCCUGUCUACACUUGCUGUGC | 2 | SEQ ID NO: 488 |
| hsa-miR-24-1* | UGCCUACUGAGCUGAUAUCAGU | 2 | SEQ ID NO: 489 |
| hsa-miR-26b* | CCUGUUCUCCAUUACUUGGCUC | 2 | SEQ ID NO: 490 |
| hsa-miR-28-3p | CACUAGAUUGUGAGCUCCUGGA | 2 | SEQ ID NO: 491 |
| hsa-miR-28-5p | AAGGAGCUCACAGUCUAUUGAG | 2 | SEQ ID NO: 492 |
| hsa-miR-29a* | ACUGAUUUCUUUUGGUGUUCAG | 2 | SEQ ID NO: 493 |
| hsa-miR-29b-1* | GCUGGUUUCAUAUGGUGGUUUAGA | 2 | SEQ ID NO: 494 |
| hsa-miR-29b-2* | CUGGUUUCACAUGGUGGCUUAG | 2 | SEQ ID NO: 495 |
| hsa-miR-29c* | UGACCGAUUUCUCCUGGUGUUC | 2 | SEQ ID NO: 496 |
| hsa-miR-30a | UGUAAACAUCCUCGACUGGAAG | 2 | SEQ ID NO: 497 |
| hsa-miR-30a* | CUUUCAGUCGGAUGUUUGCAGC | 2 | SEQ ID NO: 498 |
| hsa-miR-30b* | CUGGGAGGUGGAUGUUUACUUC | 2 | SEQ ID NO: 499 |
| hsa-miR-30c-2* | CUGGGAGAAGGCUGUUUACUCU | 2 | SEQ ID NO: 500 |
| hsa-miR-31* | UGCUAUGCCAACAUAUUGCCAU | 2 | SEQ ID NO: 501 |
| hsa-miR-32 | UAUUGCACAUUACUAAGUUGCA | 2 | SEQ ID NO: 502 |
| hsa-miR-329 | AACACACCUGGUUAACCUCUUU | 2 | SEQ ID NO: 503 |
| hsa-miR-330-3p | GCAAAGCACACGGCCUGCAGAGA | 2 | SEQ ID NO: 504 |
| hsa-miR-337-3p | CUCCUAUAUGAUGCCUUUCUUC | 2 | SEQ ID NO: 505 |
| hsa-miR-337-5p | GAACGGCUUCAUACAGGAGUU | 2 | SEQ ID NO: 506 |
| hsa-miR-345 | GCUGACUCCUAGUCCAGGGCUC | 2 | SEQ ID NO: 507 |
| hsa-miR-361-5p | UUAUCAGAAUCUCCAGGGGUAC | 2 | SEQ ID NO: 508 |

TABLE 1-continued

Example listing of miRNA evaluated.

| miR | Sequence | Ref. | SEQ ID NO |
|---|---|---|---|
| hsa-miR-369-5p | AGAUCGACCGUGUUAUAUUCGC | 2 | SEQ ID NO: 509 |
| hsa-miR-374a | UUAUAAUACAACCUGAUAAGUG | 2 | SEQ ID NO: 510 |
| hsa-miR-374b | AUAUAAUACAACCUGCUAAGUG | 2 | SEQ ID NO: 511 |
| hsa-miR-374b* | CUUAGCAGGUUGUAUUAUCAUU | 2 | SEQ ID NO: 512 |
| hsa-miR-375 | UUUGUUCGUUCGGCUCGCGUGA | 2 | SEQ ID NO: 513 |
| hsa-miR-376b | AUCAUAGAGGAAAAUCCAUGUU | 2 | SEQ ID NO: 514 |
| hsa-miR-376c | AACAUAGAGGAAAUUCCACGU | 2 | SEQ ID NO: 515 |
| hsa-miR-377* | AGAGGUUGCCCUUGGUGAAUUC | 2 | SEQ ID NO: 516 |
| hsa-miR-410 | AAUAUAACACAGAUGGCCUGU | 2 | SEQ ID NO: 517 |
| hsa-miR-424* | CAAAACGUGAGGCGCUGCUAU | 2 | SEQ ID NO: 518 |
| hsa-miR-425 | AUCGGGAAUGUCGUGUCCGCCC | 2 | SEQ ID NO: 519 |
| hsa-miR-431* | CAGGUCGUCUUGCAGGGCUUCU | 2 | SEQ ID NO: 520 |
| hsa-miR-450a | UUUUGCGAUGUGUUCCUAAUAU | 2 | SEQ ID NO: 521 |
| hsa-miR-451 | AAACCGUUACCAUUACUGAGUU | 2 | SEQ ID NO: 522 |
| hsa-miR-455-3p | GCAGUCCAUGGGCAUAUACAC | 2 | SEQ ID NO: 523 |
| hsa-miR-455-5p | UAUGUGCCUUUGGACUACAUCG | 2 | SEQ ID NO: 524 |
| hsa-miR-483-3p | UCACUCCUCUCCUCCCGUCUU | 2 | SEQ ID NO: 525 |
| hsa-miR-486-5p | UCCUGUACUGAGCUGCCCCGAG | 2 | SEQ ID NO: 526 |
| hsa-miR-488 | UUGAAAGGCUAUUUCUUGGUC | 2 | SEQ ID NO: 527 |
| hsa-miR-490-3p | CAACCUGGAGGACUCCAUGCUG | 2 | SEQ ID NO: 528 |
| hsa-miR-497 | CAGCAGCACACUGUGGUUUGU | 2 | SEQ ID NO: 529 |
| hsa-miR-499-5p | UUAAGACUUGCAGUGAUGUUU | 2 | SEQ ID NO: 530 |
| hsa-miR-501-5p | AAUCCUUUGUCCCUGGGUGAGA | 2 | SEQ ID NO: 531 |
| hsa-miR-505* | GGGAGCCAGGAAGUAUUGAUGU | 2 | SEQ ID NO: 532 |
| hsa-miR-512-3p | AAGUGCUGUCAUAGCUGAGGUC | 2 | SEQ ID NO: 533 |
| hsa-miR-513c | UUCUCAAGGAGGUGUCGUUUAU | 2 | SEQ ID NO: 534 |
| hsa-miR-517* | CCUCUAGAUGGAAGCACUGUCU | 2 | SEQ ID NO: 535 |
| hsa-miR-539 | GGAGAAAUUAUCCUUGGUGUGU | 2 | SEQ ID NO: 536 |
| hsa-miR-542-3p | UGUGACAGAUUGAUAACUGAAA | 2 | SEQ ID NO: 537 |
| hsa-miR-543 | AAACAUUCGCGGUGCACUUCUU | 2 | SEQ ID NO: 538 |
| hsa-miR-574-3p | CACGCUCAUGCACACACCCACA | 2 | SEQ ID NO: 539 |
| hsa-miR-602 | GACACGGGCGACAGCUGCGGCCC | 2 | SEQ ID NO: 540 |
| hsa-miR-628-5p | AUGCUGACAUAUUUACUAGAGG | 2 | SEQ ID NO: 541 |
| hsa-miR-629* | GUUCUCCCAACGUAAGCCCAGC | 2 | SEQ ID NO: 542 |
| hsa-miR-630 | AGUAUUCUGUACCAGGGAAGGU | 2 | SEQ ID NO: 543 |
| hsa-miR-650 | AGGAGGCAGCGCUCUCAGGAC | 2 | SEQ ID NO: 544 |
| hsa-miR-654-3p | UAUGUCUGCUGACCAUCACCUU | 2 | SEQ ID NO: 545 |
| hsa-miR-654-5p | UGGUGGGCCGCAGAACAUGUGC | 2 | SEQ ID NO: 546 |

TABLE 1-continued

Example listing of miRNA evaluated.

| miR | Sequence | Ref. | SEQ ID NO |
|---|---|---|---|
| hsa-miR-655 | AUAAUACAUGGUUAACCUCUUU | 2 | SEQ ID NO: 547 |
| hsa-miR-656 | AAUAUUAUACAGUCAACCUCU | 2 | SEQ ID NO: 548 |
| hsa-miR-744 | UGCGGGGCUAGGGCUAACAGCA | 2 | SEQ ID NO: 549 |
| hsa-miR-766 | ACUCCAGCCCCACAGCCUCAGC | 2 | SEQ ID NO: 550 |
| hsa-miR-768-3p | UCACAAUGCUGACACUCAAACUGCUGAC | 2 | SEQ ID NO: 551 |
| hsa-miR-873 | GCAGGAACUUGUGAGUCUCCU | 2 | SEQ ID NO: 552 |
| hsa-miR-885-5p | UCCAUUACACUACCCUGCCUCU | 2 | SEQ ID NO: 553 |
| hsa-miR-886-3p | CGCGGGUGCUUACUGACCCUU | 2 | SEQ ID NO: 554 |
| hsa-miR-886-5p | CGGGUCGGAGUUAGCUCAAGCGG | 2 | SEQ ID NO: 555 |
| hsa-miR-889 | UUAAUAUCGGACAACCAUUGU | 2 | SEQ ID NO: 556 |
| hsa-miR-93* | ACUGCUGAGCUAGCACUUCCCG | 2 | SEQ ID NO: 557 |
| hsa-miR-940 | AAGGCAGGGCCCCCGCUCCCC | 2 | SEQ ID NO: 558 |
| hsa-miR-944 | AAAUUAUUGUACAUCGGAUGAG | 2 | SEQ ID NO: 559 |
| hsa-miR-96 | UUUGGCACUAGCACAUUUUUGCU | 2 | SEQ ID NO: 560 |
| hsa-miR-99a* | CAAGCUCGCUUCUAUGGGUCUG | 2 | SEQ ID NO: 561 |
| hsa-miR-99b* | CAAGCUCGUGUCUGUGGGUCCG | 2 | SEQ ID NO: 562 |

1 Bentwich et al, 2005;
2 miRBase;
3 Griffiths-Jones et al., 2006;
4 Berezikov et al., 2005;
5 Xie et al., 2005

In some embodiments, it may be useful to know whether a cell expresses a particular miRNA endogenously or whether such expression is affected under particular conditions or a particular disease state. Thus, in some embodiments of the invention, methods include assaying a cell or a sample containing a cell for the presence of one or more miRNA. In other aspects, a sample may comprise RNA or nucleic acid isolated from a tissue or cells of a patient or reference. Consequently, in some embodiments, methods include a step of generating an miRNA profile for a sample. The term "miRNA profile" refers to a set of data regarding the expression pattern for a plurality of miRNAs (e.g., one or more miRNA from Table 1) in the sample; it is contemplated that the miRNA profile can be obtained using a set of miRNAs, using for example nucleic acid amplification or hybridization techniques well known to one of ordinary skill in the art. It is contemplate the any one or subset of the miRNA listed in this application can be included or excluded from the claimed invention.

In some embodiments of the invention, an miRNA profile is generated by steps that include: (a) labeling miRNA in the sample; (b) hybridizing miRNA to a number of probes, or amplifying a number of miRNA, and (c) determining miRNA hybridization to the probes or detection of miRNA amplification products, wherein an miRNA profile is generated. See U.S. Provisional Patent Application 60/575,743 and the U.S. Provisional Patent Application 60/649,584, and U.S. patent application Ser. No. 11/141,707, all of which are hereby incorporated by reference.

Methods of the invention involve diagnosing a patient based on an miRNA expression or expression profile. In certain embodiments, the presence, absence, elevation, or reduction in the level of expression of a particular miRNA or set of miRNA in a cell is correlated with a disease state compared to the expression level of that miRNA or set of miRNAs in a normal cell. This correlation allows for diagnostic methods to be carried out when the expression level of an miRNA is measured in a biological sample being assessed and then compared to the expression level of a normal cell. It is specifically contemplated that miRNA profiles for patients, particularly those suspected of having a particular disease or condition such as a pre-cancerous cervical lesion or a cervical cancer, can be generated by evaluating any miRNA or sets of the miRNAs discussed in this application. The miRNA profile that is generated from the patient will be one that provides information regarding the particular disease or condition. In many embodiments, the miRNA profile is generated using miRNA hybridization or amplification, (e.g., array hybridization or RT-PCR). In certain aspects, a miRNA profile can be used in conjunction with other diagnostic tests, such as serum protein profiles.

Embodiments of the invention include methods for diagnosing, prognosing, and/or assessing a condition in a patient comprising measuring an expression profile of one or more miRNAs in a sample from the patient. The difference in the expression profile in the sample from the patient and a reference expression profile, such as an expression profile from a normal or non-pathologic sample or a reference (e.g., a reference sample or a digital reference), is indicative of a pathologic, disease, or cancerous condition. An miRNA or probe set comprising or identifying a segment of a corresponding miRNA can include all or part of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 125, 150, 175, 200, 250, 300, 350, 400, 500, 550 to 562 or any integer or range derivable there between, of a miRNA or a probe or its complement listed in Table 1. It is contemplate the any one or subset of the miRNA listed in this application can be included or excluded from the claimed invention.

In certain aspects, the methods for diagnosing a condition in a patient comprise measuring an expression profile of one or more miRNAs, from Table 1, in a sample from the patient, wherein the difference between the expression profile in the sample from the patient and an expression profile of a normal sample or a reference is indicative of a pathological condition.

In a further aspect, the methods for diagnosing a condition in a patient comprises measuring an expression profile of one or more miRNAs in a sample from the patient, wherein the difference between the expression profile of the sample from the patient and an expression profile of a reference is indicative of a cervical tissue disease, or condition; wherein the miRNA is one or more of hsa-let-7a, hsa-let-7b, hsa-let-7c, hsa-let-7i, hsa-miR-100, hsa-miR-101, hsa-miR-106a, hsa-miR-125a, hsa-miR-125b, hsa-miR-126-AS, hsa-miR-127, hsa-miR-130a, hsa-miR-134, hsa-miR-142-3p, hsa-miR-143, hsa-miR-145, hsa-miR-148b, hsa-miR-149, hsa-miR-151, hsa-miR-152, hsa-miR-154, hsa-miR-15a, hsa-miR-15b, hsa-miR-16, hsa-miR-17-5p, hsa-miR-181a, hsa-miR-185, hsa-miR-186, hsa-miR-187, hsa-miR-192, hsa-miR-193a, hsa-miR-195, hsa-miR-196a, hsa-miR-196b, hsa-miR-199a, hsa-miR-199a-AS, hsa-miR-199b, hsa-miR-19a, hsa-miR-20a, hsa-miR-203, hsa-miR-205, hsa-miR-21, hsa-miR-214, hsa-miR-215, hsa-miR-22, hsa-miR-221, hsa-miR-223, hsa-miR-23b, hsa-miR-24, hsa-miR-25, hsa-miR-26a, hsa-miR-26b, hsa-miR-299-5p, hsa-miR-29b, hsa-miR-29c, hsa-miR-302c-AS, hsa-miR-30a-3p, hsa-miR-30a-5p, hsa-miR-30b, hsa-miR-30c, hsa-miR-30e-3p, hsa-miR-30e-5p, hsa-miR-31, hsa-miR-320, hsa-miR-324-3p, hsa-miR-335, hsa-miR-338, hsa-miR-342, hsa-miR-34a, hsa-miR-361, hsa-miR-365, hsa-miR-367, hsa-miR-368, hsa-miR-370, hsa-miR-374, hsa-miR-376a, hsa-miR-379, hsa-miR-381, hsa-miR-423, hsa-miR-424, hsa-miR-450, hsa-miR-7, hsa-miR-93, hsa-miR-95, hsa-miR-96, hsa-miR-99a, hsa-miR-99b, ambi-miR-7027, ambi-miR-7029, hsa-miR-509, hsa-miR-193b, ambi-miR-7039, hsa-miR-526b, hsa-miR-498, hsa-miR-452, ambi-miR-7062, ambi-miR-7070, hsa-miR-497, ambi-miR-7079, ambi-miR-7083, ambi-miR-7085, hsa-miR-503, or ambi-miR-7101 or complements thereof.

In a particular aspect, hsa-miR-205, hsa-miR-196b, hsa-miR-203, hsa-miR-503, hsa-miR-196a, hsa-miR-99a, hsa-miR-187, ambi-miR-7083 and/or ambi-miR-7101, or any combination or complement thereof being expressed or having an increased expression or upregulated expression when compared with expression in a non-cervical reference sample, is indicative of cervical tissue. In another aspect, a decrease in expression or down-regulation of hsa-miR-7 and/or hsa-miR-215 is also indicative of a cervical tissue.

In still further aspects of the invention, the methods for diagnosing a condition in a patient comprise measuring an expression profile of one or more miRNAs in a sample or a cervix sample from the patient believed to be pre-cancerous or cancerous or contain pre-cancerous or cancerous cells, wherein the difference between the expression profile in the sample from the patient and an expression profile of normal adjacent tissue (NAT) or a reference tissue is indicative of a disease or condition; wherein the miRNA is one or more miRNA listed in Table 1. It is contemplate the any one or subset of the miRNA listed in this application can be included or excluded from the claimed invention.

In still further aspects of the invention, the methods for diagnosing a condition in a patient comprise measuring an expression profile of one or more miRNAs in a cervix sample from a patient believed to be precancerous or cancerous, or contain precancerous or cancerous cells, or from a patient suspected of having or at risk of developing a pre-cancerous or cancerous condition, wherein the difference between the expression profile in the sample from the patient and an expression profile of normal cervix (NCX) or normal adjacent tissue (NAT) or a reference tissue is indicative of a disease or condition; herein the miRNA is one or more of hsa-let-7a, hsa-let-7b, hsa-let-7c, hsa-let-7d, hsa-let-7e, hsa-let-7f, hsa-let-7g, hsa-let-7i, hsa-miR-1, hsa-miR-100, hsa-miR-101, hsa-miR-106a, hsa-miR-106b, hsa-miR-10a, hsa-miR-10b, hsa-miR-124a, hsa-miR-125a, hsa-miR-125b, hsa-miR-126, hsa-miR-126-AS, hsa-miR-127, hsa-miR-130a, hsa-miR-130b, hsa-miR-133a, hsa-miR-134, hsa-miR-135b, hsa-miR-139, hsa-miR-140, hsa-miR-141, hsa-miR-142-5p, hsa-miR-143, hsa-miR-145, hsa-miR-146a, hsa-miR-149, hsa-miR-150, hsa-miR-152, hsa-miR-153, hsa-miR-154, hsa-miR-155, hsa-miR-15b, hsa-miR-16, hsa-miR-17-5p, hsa-miR-18a, hsa-miR-181a, hsa-miR-181b, hsa-miR-182, hsa-miR-183, hsa-miR-185, hsa-miR-186, hsa-miR-187, hsa-miR-189, hsa-miR-190, hsa-miR-195, hsa-miR-196a, hsa-miR-196b, hsa-miR-199a, hsa-miR-199a-AS, hsa-miR-199b, hsa-miR-20a, hsa-miR-200a, hsa-miR-200b, hsa-miR-200c, hsa-miR-203, hsa-miR-204, hsa-miR-205, hsa-miR-21, hsa-miR-210, hsa-miR-214, hsa-miR-215, hsa-miR-218, hsa-miR-223, hsa-miR-224, hsa-miR-23b, hsa-miR-24, hsa-miR-25, hsa-miR-26a, hsa-miR-26b, hsa-miR-27b, hsa-miR-28, hsa-miR-296, hsa-miR-299-5p, hsa-miR-29a, hsa-miR-29b, hsa-miR-29c, hsa-miR-302d, hsa-miR-30a-3p, hsa-miR-30a-5p, hsa-miR-30b, hsa-miR-30d, hsa-miR-31, hsa-miR-320, hsa-miR-324-3p, hsa-miR-325, hsa-miR-328, hsa-miR-330, hsa-miR-335, hsa-miR-339, hsa-miR-361, hsa-miR-365, hsa-miR-368, hsa-miR-370, hsa-miR-373-AS, hsa-miR-376a, hsa-miR-377, hsa-miR-379, hsa-miR-381, hsa-miR-382, hsa-miR-423, hsa-miR-424, hsa-miR-429, hsa-miR-450, hsa-miR-92, hsa-miR-93, hsa-miR-95, hsa-miR-98, hsa-miR-99a, hsa-miR-99b, hsa-miR-520d, hsa-miR-518b, ambi-miR-7029, hsa-miR-491, hsa-miR-515-5p, hsa-miR-498, ambi-miR-7062, hsa-miR-432, hsa-miR-495, ambi-miR-7066, ambi-miR-7068-1, ambi-miR-7070, hsa-miR-492, hsa-miR-497, ambi-miR-7074, ambi-miR-7075, hsa-miR-501, ambi-miR-7079, ambi-miR-7083, ambi-miR-7085, hsa-miR-500, hsa-miR-513, hsa-miR-505, ambi-miR-7100, or ambi-miR-7101, hsa-miR-133b, hsa-miR-455, hsa-asg-5021_st1, hsa-asg-13254_st1, hsa-asg-14176 st1, hsa-miR-487b, hsa-miR-411, hsa-miR-574, hsa-miR-542-5p, hsa-asg-5617_st1, hsa-asg-14172_st1, hsa-asg-13304_st2, hsa-asg-13297_st1, hsa-miR157_st2, hsa-cand317_st1, hsa-miR-329, hsa-asg-10202_st2, hsa-miR-369-5p, hsa-asg-13284_st1, hsa-asg-9687_st1, hsa-miR-433, hsa-miR-565, hsa-asg-562_st1, hsa-asg-279_st2, hsa-asg-8411_st2, hsa-asg-7472_st2, hsa-asg-13279_st1, hsa-miR-487a, hsa-cand206_st1, hsa-cand345_st1, hsa-asg-9696_st1, hsa-miR-485-3p, hsa-asg-13166_st2, hsa-miR-594_st2, hsa-miR-299-3p, hsa-asg-924_st1, hsa-miR-539, hsa-asg-10883_st1, hsa-miR-585, hsa-miR-493-5p, hsa-asg-12964_st2, hsa-asg-4557_st2, hsa-asg-10674_st1, hsa-asg-14230_st1, hsa-asg-9681_st1, hsa-miR-628, hsa-asg-13237_st1, hsa-asg-13230_st2, hsa-miR-493-3p, hsa-miR-654, hsa-asg-2919_st1, hsa-asg-8067_st2, hsa-asg-11199_st2, hsa-asg-12346_st2, hsa-asg-11883_st1, hsa-miR102_st2, hsa-asg-2027_st1, hsa-asg-3711_st2, hsa-asg-3145_st1, hsa-asg- 7465_st2, hsa-asg-3376_st1, hsa-cand283_st1, hsa-asg-2301_st2, hsa-cand207_st1, hsa-miR-598, hsa-asg-10278_st2, hsa-miR-18b, hsa-asg-11181_st1, hsa-asg-7023_st2, hsa-asg-3597_st2, hsa-asg-5304_st1, hsa-asg-11688_st1, hsa-cand720_st1, hsa-asg-13308_st2, hsa-asg-3038_st2, hsa-asg-13966_st2, hsa-asg-13189_st1, hsa-asg-11938_st1, hsa-asg-5740_st2, hsa-asg-8477_st1, hsa-asg-12325_st2, hsa-asg-12356_st1, hsa-asg-6758_st1, hsa-asg-522_st1, hsa-asg-4564_st2, hsa-asg-6951_st2, hsa-asg-9920_st1, hsa-asg-13613_st2, hsa-miR-184, hsa-miR-503, hsa-miR-485-5p, hsa-miR-494, hsa-miR-504, hsa-miR-211, hsa-miR-99b, hsa-miR-499, hsa-miR-422b, hsa-miR-338, hsa-miR-422a, hsa-miR-331, hsa-miR-489, hsa-miR-324-5p, hsa-miR-151, hsa-miR-17-3p, hsa-miR-340, hsa-miR-194, hsa-let-7d*, hsa-let-7e*, hsa-miR-100*, hsa-miR-101*, hsa-miR-106b*, hsa-miR-10b*, hsa-miR-125a-5p, hsa-miR-125b-2*, hsa-miR-126*, hsa-miR-127-3p, hsa-miR-129-3p, hsa-miR-135a, hsa-miR-136, hsa-miR-136*, hsa-miR-139-5p, hsa-miR-140-3p, hsa-miR-140-5p, hsa-miR-141*, hsa-miR-142-3p, hsa-miR-143*, hsa-miR-144, hsa-miR-144*, hsa-miR-145*, hsa-miR-146b-5p, hsa-miR-151-3p, hsa-miR-154*, hsa-miR-15b*, hsa-miR-17, hsa-miR-181c, hsa-miR-181d, hsa-miR-183*, hsa-miR-193a-5p, hsa-miR-195*, hsa-miR-197, hsa-miR-199a-5p, hsa-miR-199b-3p, hsa-miR-199b-5p, hsa-miR-20a*, hsa-miR-21*, hsa-miR-212, hsa-miR-214*, hsa-miR-24-1*, hsa-miR-26b*, hsa-miR-28-3p, hsa-miR-28-5p, hsa-miR-29a*, hsa-miR-29b-1*, hsa-miR-29b-2*, hsa-miR-29c*, hsa-miR-30a, hsa-miR-30a*, hsa-miR-30b*, hsa-miR-30c-2*, hsa-miR-31*, hsa-miR-32, hsa-miR-330-3p, hsa-miR-337-3p, hsa-miR-337-5p, hsa-miR-345, hsa-miR-361-5p, hsa-miR-374a, hsa-miR-374b, hsa-miR-374b*, hsa-miR-375, hsa-miR-376b, hsa-miR-376c, hsa-miR-377*, hsa-miR-410, hsa-miR-424*, hsa-miR-425, hsa-miR-431*, hsa-miR-450a, hsa-miR-451, hsa-miR-455-3p, hsa-miR-455-5p, hsa-miR-483-3p, hsa-miR-486-5p, hsa-miR-488, hsa-miR-490-3p, hsa-miR-499-5p, hsa-miR-501-5p, hsa-miR-505*, hsa-miR-512-3p, hsa-miR-513c, hsa-miR-517*, hsa-miR-542-3p, hsa-miR-543, hsa-miR-574-3p, hsa-miR-602, hsa-miR-628-5p, hsa-miR-629*, hsa-miR-630, hsa-miR-650, hsa-miR-654-3p, hsa-miR-654-5p, hsa-miR-655, hsa-miR-656, hsa-miR-744, hsa-miR-766, hsa-miR-768-3p, hsa-miR-873, hsa-miR-885-5p, hsa-miR-886-3p, hsa-miR-886-5p, hsa-miR-889, hsa-miR-93*, hsa-miR-940, hsa-miR-944, hsa-miR-96, hsa-miR-99a*, hsa-miR-99b*, or complements thereof.

In certain aspects, the reduced expression or down regulation of hsa-miR-1, hsa-miR-100, hsa-miR-125b, hsa-miR-125b-2*, hsa-miR-133a, hsa-miR-133b, hsa-miR-134, hsa-miR-135a, hsa-miR-139-5p, hsa-miR-136*, hsa-miR-143*, hsa-miR-154, hsa-miR-204, hsa-miR-211, hsa-miR-218, hsa-miR-224, hsa-miR-143, hsa-miR-145, hsa-miR-145*, hsa-miR-299-3p, hsa-miR-299-5p, hsa-miR-368, hsa-miR-99a, hsa-miR-195, hsa-miR-337-3p, hsa-miR-337-5p, hsa-miR-375, hsa-miR-376a, hsa-miR-376c, hsa-miR-379, hsa-miR-381, hsa-miR-410, hsa-miR-411, hsa-miR-424, hsa-miR-451, hsa-miR-455-5p, hsa-miR-495, hsa-miR-497, hsa-miR-517*, hsa-miR-654-3p, hsa-miR-885-5p, hsa-miR-886-5p, hsa-miR-99a*, ambi-miR-7101 and/or ambi-miR-7029 or a complement thereof relative to normal adjacent tissue or a normal cervix tissue reference is indicative of a cancerous condition or tissue. In other aspects, the increased or upregulation of hsa-miR-21, hsa-miR-21*hsa-miR-31, hsa-miR-31*, hsa-miR-135b, hsa-miR-141, hsa-miR-182, hsa-miR-183, hsa-miR-203, hsa-miR-205, hsa-miR-224, hsa-miR-141, hsa-miR-944, hsa-miR-96, and/or hsa-miR-182 or complement thereof relative to normal adjacent tissue or a normal cervix tissue reference is indicative of a cancerous condition or cancerous tissue.

In a still further aspect, the reduced expression or down regulation of hsa-miR-1, hsa-miR-133a, hsa-miR-204, hsa-miR-218, hsa-miR-143, hsa-miR-368, hsa-miR-99a, hsa-miR-100, hsa-miR-195, hsa-miR-376a, hsa-miR-424, hsa-miR-497, hsa-miR-299_5p, hsa-miR-154, hsa-miR-134, ambi-miR-7101 and/or ambi-miR-7029 or complement thereof relative to normal cervix tissue is indicative of a cancerous condition or tissue. In other aspects, the increased or upregulation of hsa-miR-205, hsa-miR-183, hsa-miR-31, hsa-miR-224, hsa-miR-182, hsa-miR-21 and/or hsa-miR-203 or complement thereof relative to normal cervix tissue is indicative of a cancerous condition or cancerous tissue.

In yet still further aspects of the invention, the reduced expression or down regulation of hsa-miR-133b, hsa-miR-455, hsa-asg-5021_st1, hsa-asg-13254_st1, hsa-asg-14176_st1, hsa-miR-487b, hsa-miR-411, hsa-miR-574, hsa-miR-542-5p, hsa-asg-5617_st1, hsa-asg-14172_st1, hsa-asg-13304_st2, hsa-asg-13297_st1, hsa-miR157_st2, hsa-miR-329, hsa-asg-10202_st2, hsa-miR-369-5p, hsa-asg-13284_st1, hsa-asg-9687_st1, hsa-miR-433, hsa-miR-565, hsa-asg-562_st1, hsa-asg-279_st2, hsa-asg-8411_st2, hsa-asg-7472_st2, hsa-asg-13279_st1, hsa-miR-487a, hsa-cand206 st1, hsa-cand345_st1, hsa-asg-9696_st1, hsa-miR-485-3p, hsa-asg-13166_st2, hsa-miR-594_st2, hsa-miR-299-3p, hsa-miR-539, hsa-asg-10883_st1, hsa-miR-585, hsa-miR-493-5p, hsa-asg-12964_st2, hsa-asg-4557_st2, hsa-asg-10674_st1, hsa-asg-14230_st1, hsa-asg-9681_st1, hsa-miR-628, hsa-asg-13237_st1, hsa-asg-13230_st2, hsa-miR-493-3p, hsa-miR-654, hsa-asg-33_st1, hsa-asg-8067_st2, hsa-asg-11199_st2, hsa-asg-12346_st2, hsa-asg-11883_st1, hsa-miR102_st2, hsa-asg-2027_st1, hsa-asg-3145_st1, hsa-asg-7465_st2, hsa-asg-3376_st1, hsa-cand283_st1, hsa-asg-2301_st2, hsa-cand207_st1, hsa-miR-598, hsa-asg-10278_st2, hsa-asg-11181_st1, hsa-asg-7023_st2, hsa-asg-3597_st2, hsa-asg-5304_st1, hsa-cand720_st1, hsa-asg-13308_st2, hsa-asg-3038_st2, hsa-asg-13966_st2, hsa-asg-13189_st1, hsa-asg-11938_st1, hsa-asg-5740_st2, hsa-asg-8477_st1, hsa-asg-12325_st2, hsa-asg-12356_st1, hsa-asg-6758_st1, hsa-asg-522_st1, hsa-asg-4564_st2, hsa-asg-6951_st2, hsa-asg-9920_st1, hsa-asg-13613_st2, hsa-miR-184, hsa-miR-503, hsa-miR-485-5p, hsa-miR-494, hsa-miR-504, hsa-miR-211, hsa-miR-99b, hsa-miR-499, hsa-miR-422b, hsa-miR-338, hsa-miR-422a, hsa-miR-331, hsa-miR-489, hsa-miR-324-5p, hsa-miR-151, hsa-miR-17-3p, hsa-miR-340, and/or hsa-miR-194 or complement thereof relative to normal cervix tissue is indicative of a cancerous condition or tissue. In other aspects, the increased or upregulation of hsa-asg-11688 st1, hsa-miR-18b, hsa-miR-18a, hsa-asg-3711_st2, hsa-miR-183, hsa-asg-2919_st1, hsa-asg-924_st1, and/or hsa-cand317_st1, or complement thereof relative to normal cervix tissue is indicative of a cancerous condition or cancerous tissue.

In yet still further aspects of the invention, the reduced expression or down regulation of hsa-let-7d*, hsa-let-7e*, hsa-miR-100*, hsa-miR-101*, hsa-miR-106b*, hsa-miR-10b*, hsa-miR-125a-5p, hsa-miR-125b-2*, hsa-miR-126*, hsa-miR-127-3p, hsa-miR-129-3p, hsa-miR-135a, hsa-miR-136, hsa-miR-136*, hsa-miR-139-5p, hsa-miR-140-3p, hsa-miR-140-5p, hsa-miR-141*, hsa-miR-142-3p, hsa-miR-143*, hsa-miR-144, hsa-miR-144*, hsa-miR-145*, hsa-miR-146b-5p, hsa-miR-151-3p, hsa-miR-154*, hsa-miR-15b*, hsa-miR-17, hsa-miR-181c, hsa-miR-181d, hsa-miR-183*, hsa-miR-193a-5p, hsa-miR-195*, hsa-miR-197, hsa-miR-199a-5p, hsa-miR-199b-3p, hsa-miR-199b-5p, hsa-miR- 20a*, hsa-miR-212, hsa-miR-214*, hsa-miR-24-1*, hsa-miR-26b*, hsa-miR-28-3p, hsa-miR-28-5p, hsa-miR-29a*, hsa-miR-29b-1*, hsa-miR-29b-2*, hsa-miR-29c*, hsa-miR-30a, hsa-miR-30a*, hsa-miR-30b*, hsa-miR-30c-2*, hsa-miR-32, hsa-miR-330-3p, hsa-miR-337-3p, hsa-miR-337-5p, hsa-miR-345, hsa-miR-361-5p, hsa-miR-374a, hsa-miR-374b, hsa-miR-374b*, hsa-miR-375, hsa-miR-376b, hsa-miR-376c, hsa-miR-377*, hsa-miR-410, hsa-miR-424*, hsa-miR-425, hsa-miR-431*, hsa-miR-450a, hsa-miR-451, hsa-miR-455-3p, hsa-miR-455-5p, hsa-miR-483-3p, hsa-miR-486-5p, hsa-miR-488, hsa-miR-490-3p, hsa-miR-499-5p, hsa-miR-501-5p, hsa-miR-505*, hsa-miR-512-3p, hsa-miR-513c, hsa-miR-517*, hsa-miR-542-3p, hsa-miR-543, hsa-miR-574-3p, hsa-miR-602, hsa-miR-628-5p, hsa-miR-629*, hsa-miR-630, hsa-miR-650, hsa-miR-654-3p, hsa-miR-654-5p, hsa-miR-655, hsa-miR-656, hsa-miR-744, hsa-miR-766, hsa-miR-768-3p, hsa-miR-873, hsa-miR-885-5p, hsa-miR-886-3p, hsa-miR-886-5p, hsa-miR-889, hsa-miR-93*, hsa-miR-940, hsa-miR-99a*, and/or hsa-miR-99b* or complement thereof relative to normal cervix tissue is indicative of a cancerous condition or tissue. In other aspects, the increased or upregulation of hsa-miR-31*, hsa-miR-96, hsa-miR-21*, and/or hsa-miR-944 or complement thereof relative to normal cervix tissue is indicative of a cancerous condition or cancerous cells or cancerous tissue.

In certain aspects, the expression of one or more of hsa-miR-1, hsa-miR-15b, hsa-miR-133a, hsa-miR-143, hsa-miR-205, hsa-miR-21, hsa-miR-204, hsa-miR-195, hsa-miR-100, hsa-miR-99a, hsa-miR-368, and/or hsa-miR-183 or complement thereof, including various combinations thereof, are assessed to determine if a target sample is cancerous. In other aspects, hsa-miR-16 can be used as reference. Embodiments of the invention include analysis of miR expression by amplification assays. In certain aspects, the PCR assay is quantitative PCR and in particular real time quantitative reverse transcription PCR (qRT-PCR).

In yet still further aspects of the invention, the methods for diagnosing a condition in a patient comprise measuring an expression profile of one or more miRNAs in a cervix sample from the patient suspected of having a cancerous condition, (e.g., cervical squamous cell carcinoma) wherein the difference between the expression profile in the sample from the patient and an expression profile of normal tissue or a reference tissue is indicative of a cancerous disease or condition; wherein the miRNA is one or more of hsa-miR-1, hsa-miR-100, hsa-miR-133a, hsa-miR-134, hsa-miR-143, hsa-miR-154, hsa-miR-182, hsa-miR-183, hsa-miR-195, hsa-miR-204, hsa-miR-205, hsa-miR-21, hsa-miR-218, hsa-miR-224, hsa-miR-299-5p, hsa-miR-31, hsa-miR-368, hsa-miR-376a, hsa-miR-424, hsa-miR-99a, ambi-miR-7029, hsa-miR-497, ambi-miR-7101, hsa-miR-133b, hsa-miR-455, hsa-asg-5021_st1, hsa-asg-13254_st1, hsa-asg-14176_st1, hsa-miR-487b, hsa-miR-411, hsa-miR-574, hsa-miR-542-5p, hsa-asg-5617_st1, hsa-asg-14172_st1, hsa-asg-13304_st2, hsa-asg-13297_st1, hsa-miR157_st2, hsa-cand317_st1, hsa-miR-329, hsa-asg-10202_st2, hsa-miR-369-5p, hsa-asg-13284_st1, hsa-asg-9687_st1, hsa-miR-433, hsa-miR-565, hsa-asg-562_st1, hsa-asg-279_st2, hsa-asg-8411_st2, hsa-asg-7472_st2, hsa-asg-13279_st1, hsa-miR-487a, hsa-cand206 st1, hsa-cand345_st1, hsa-asg-9696_st1, hsa-miR-485-3p, hsa-asg-13166_st2, hsa-miR-594_st2, hsa-miR-299-3p, hsa-asg-924_st1, hsa-miR-539, hsa-asg-10883_st1, hsa-miR-184, hsa-miR-503, hsa-miR-485-5p, hsa-miR-494, hsa-miR-504, hsa-miR-211, hsa-miR-99b, or a complement thereof.

In certain aspects of the invention, the methods for diagnosing a condition in a patient comprise measuring an expression profile of one or more miRNAs in a cervix sample from the patient suspected of having a precancerous condition (e.g., cervical squamous intraepithelial lesion (SIL), also known as cervical intraepithelial neoplasias), wherein the difference between the expression profile in the sample from the patient and an expression profile of normal tissue or a reference is indicative of a disease or condition; wherein the miRNA is one or more of hsa-miR-1, hsa-miR-133a, hsa-miR-124a, hsa-miR-187, hsa-miR-204, hsa-miR-145, hsa-miR-143, hsa-miR-325, hsa-miR-500, hsa-miR-196a, hsa-miR-125a, hsa-miR-376a, hsa-miR-505, hsa-miR-100, hsa-miR-99a, hsa-miR-141, hsa-miR-200a, ambi-miR-7029, hsa-miR-223, hsa-miR-205, hsa-miR-146a, hsa-miR-429, hsa-miR-200b, hsa-miR-182, hsa-miR-142-5p, hsa-miR-203, hsa-miR-21, hsa-miR-31, or hsa-miR-513 or complement thereof. In certain aspects, decreased expression, in a patient sample, of hsa-miR-1, hsa-miR-133a, hsa-miR-124a, hsa-miR-187, hsa-miR-204, hsa-miR-145, hsa-miR-143, hsa-miR-325, hsa-miR-500, hsa-miR-196a, hsa-miR-125a, hsa-miR-376a, hsa-miR-505, hsa-miR-100, and/or hsa-miR-99a or complements thereof are indicative of SIL. Increased expression of hsa-miR-141, hsa-miR-200a, ambi-miR-7029, hsa-miR-233, hsa-miR-205, hsa-miR-146a, hsa-miR-429, hsa-miR-200b, hsa-miR-182, hsa-miR-142-5p, hsa-miR-203, hsa-miR-21, hsa-miR-513, and/or hsa-miR-31 can be indicative of SIL.

Other embodiments of the invention use the cycle threshold (Ct) values to distinguish between pre-cancerous or cancerous tissue and normal tissues. Ct values may be determined for one or more of the miRNA listed in Table 1 or their complements. In certain aspects, the Ct values for miR-1, miR-21, or both miR-1 and miR-21 can be used to distinguish between pre-cancerous or cancerous cervical samples or tissues and normal or non-cancerous tissues.

A sample may be taken from a patient having or suspected of having a disease or pathological condition. A sample may also comprise nucleic acids or RNA isolated from a tissue or cell sample from a patient. In certain aspects, the sample can be, but is not limited to tissue (e.g., biopsy, particularly fine needle biopsy), blood, serum, plasma, or cervical samples (e.g., pap smear or punch biopsy). The sample can be fresh, frozen, fixed (e.g., formalin fixed), or embedded (e.g., paraffin embedded) tissues or cells. In a particular aspect, the sample is a cervical sample or nucleic acid or RNA isolated therefrom.

Methods of the invention can be used to diagnose or assess a pathological condition. In certain aspect, the condition is a non-cancerous condition, such as pre-cancerous cervical lesion. In other aspects the condition is a cancerous condition, such as cervical cancer.

The methods can further comprise one or more steps including: (a) obtaining a sample from the patient, (b) isolating nucleic acids from the sample, (c) labeling the nucleic acids isolated from the sample, and (d) hybridizing the labeled nucleic acids to one or more probes or primers. Nucleic acids of the invention include one or more nucleic acid comprising at least one segment having a sequence or complementary sequence of one or more of the miRNA sequences in Table 1. In certain aspects, the nucleic acids identify one or more miRNAs listed in Table 1. Nucleic acids of the invention are typically coupled to a support. Such supports are well known to those of ordinary skill in the art and include, but are not limited to glass, plastic, metal, or latex. In particular aspects of the invention, the support can be planar or in the form of a bead or other geometric shapes or configurations.

Certain embodiments of the invention include determining expression of one or more miRNA by using an amplification assay or a hybridization assay, a variety of which are well known to one of ordinary skill in the art. In certain aspects, an amplification assay can be a quantitative amplification assay, such as quantitative RT-PCR or the like. In still further aspects, a hybridization assay can include in situ hybridization, array hybridization assays or solution hybridization assays.

Aspects of the invention can be used to diagnose or assess a patient's condition. For example, the methods can be used to screen for a pathological condition, assess prognosis of a pathological condition, stage a pathological condition, or assess response of a pathological condition to therapy.

Embodiments of the invention concern nucleic acids that perform the activities of or inhibit endogenous miRNAs when introduced into cells. In certain aspects, nucleic acids are synthetic or non-synthetic miRNA. Sequence-specific miRNA inhibitors can be used to inhibit sequentially or in combination the activities of one or more endogenous miRNAs in cells, as well those genes and associated pathways modulated by the endogenous miRNA.

The present invention concerns, in some embodiments, short nucleic acid molecules that function as miRNAs or as inhibitors of miRNA in a cell. The term "short" refers to a length of a single polynucleotide that is 5, 10, 15, 20, 25, 50, 100, or 150 nucleotides or fewer, including all integers or range derivable there between.

The present invention also concerns kits containing compositions of the invention or compositions to implement methods of the invention. In some embodiments, kits can be used to evaluate one or more miRNA molecules. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 200, 300, 400, 500 or more miRNA probes, miRNA molecules or miRNA inhibitors, or any range and combination derivable therein. In some embodiments, there are kits for evaluating or modulating miRNA activity in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using miRNA probes or primers, synthetic miRNAs, nonsynthetic miRNAs, and/or miRNA inhibitors of the invention for therapeutic, prognostic, or diagnostic applications are also included as part of the invention. Specifically contemplated are any such molecules corresponding to any miRNA reported to influence biological activity, such as those discussed herein.

In certain aspects, negative and/or positive control synthetic miRNAs and/or miRNA inhibitors are included in some kit embodiments. The control molecules can be used to verify transfection efficiency and/or control for transfection-induced changes in cells.

It is contemplated that any method or composition described herein can be implemented with respect to any other method or composition described herein and that different embodiments may be combined. It is specifically contemplated that any methods and compositions discussed herein with respect to miRNA molecules or miRNA may be implemented with respect to synthetic miRNAs to the extent the synthetic miRNA is exposed to the proper conditions to allow it to become a mature miRNA under physiological circumstances. The claims originally filed are contemplated to cover claims that are multiply dependent on any filed claim or combination of filed claims.

It is also contemplated that any one or more of the miRNA listed, particularly in Table 1, may be specifically excluded from any particular set or subset of miRNA or nucleic acid.

Any embodiment of the invention involving specific miRNAs by name is contemplated also to cover embodiments involving miRNAs whose sequences are at least 70, 75, 80, 81, 82, 83, 84, 85, 86, 87, 88, 89, 90, 91, 92, 93, 94, 95, 96, 97, 98% identical to the mature sequence of the specified miRNA. This also includes the various fragments of these miRNA or nucleic acid sequences.

Embodiments of the invention include kits for analysis of a pathological sample by assessing miRNA profile for a sample comprising, in suitable container means, two or more miRNA probes, wherein the miRNA probes detect one or more of the miRNAs described in Table 1. The kit can further comprise reagents for labeling miRNA in the sample. The kit may also include the labeling reagents include at least one amine-modified nucleotide, poly(A) polymerase, and poly(A) polymerase buffer. Labeling reagents can include an amine-reactive dye.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

It will be understood that shorthand notations are employed such that a generic description of an miRNA refers to any of its gene family members (distinguished by a number or sequence similarity), unless otherwise indicated. It is understood by those of skill in the art that a "gene family" refers to a group of genes having the same or similar miRNA coding sequence. Typically, members of a gene family are identified by a number following the initial designation; however some family members are identified by sequence similarity, for example see the various miRNA databases. For example, miR-16-1 and miR-16-2 are members of the miR-16 gene family and "mir-7" refers to miR-7-1, miR-7-2 and miR-7-3. Moreover, unless otherwise indicated, a shorthand notation refers to related miRNAs (distinguished by a letter). Thus, "let-7," for example, refers to let-7a-1, let7-a-2, let-7b, let-7c, let-7d, let-7e, let-7f-1, and let-7f-2." Exceptions to this shorthand notations will be otherwise identified.

It will be understand that the term "providing" an agent is used to include "administering" the agent to a patient.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
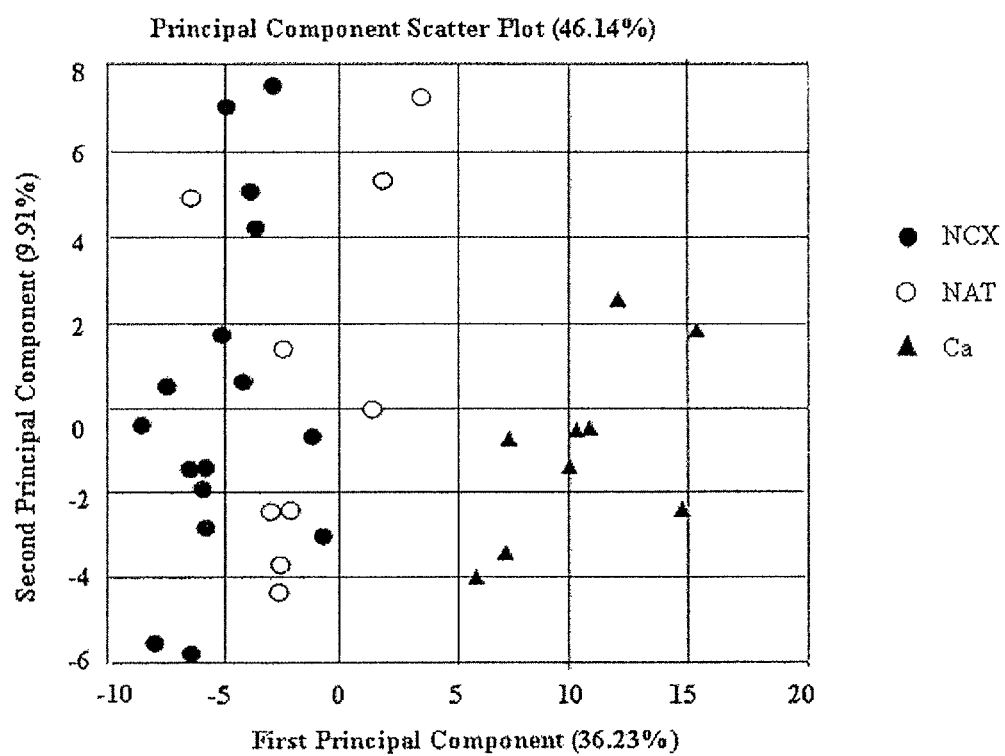
FIG. 1 Principal Component Analysis of miRNAs expressed in normal cervix sample (NCX), cancerous cervix samples (Ca), and paired normal adjacent cervix samples (NAT).

The present invention is directed to compositions and methods relating to preparation and characterization of miRNAs, as well as use of miRNAs for therapeutic, prognostic, and diagnostic applications, particularly those methods and compositions related to assessing and/or identifying cervical diseases and conditions.

I. CANCEROUS AND PRECANCEROUS CONDITIONS

As mentioned above, cervical cancer is the second most common cause of cancer in women worldwide (Pisani et al., 2002; Parkin et al., 2005). About 470,000 new cases are diagnosed and approximately 230,000 women die of cervical cancer every year (Pisani et al., 1999). While the majority (~80%) of these new cases and deaths occur in developing countries, it is estimated that approximately 3,700 women will die from invasive cervical cancer in the United States in 2007 (Jemal et al., 2007).

Cytological examination of cervical smears with Papanicolaou staining (Pap smear) is the screening method universally accepted for early detection of cervical cancer and its precursors. Pap smear screening programs have been very effective in reducing cervical cancer incidence and have reduced mortality rates by 60% among women aged 30 and over. However, even in those countries where these programs are routinely used, cervical cancer is still a significant public health problem. The Bethesda system categorizes Pap smear results as negative, ASC-US (atypical squamous cells of undetermined significance), ASCU-H (atypical squamous cells, cannot exclude high grade lesion), LSIL (low grade squamous intraepithelial lesion), HSIL (high grade intraepithelial lesion) and carcinoma. While guidelines and protocols for the management of women diagnosed with ASC-H, LSIL, HSIL and cancer are well established, the ASC-US entity is a significant problem for clinicians. The morphological criteria for ASC-US are suggestive, resulting in great variations in reported rates for ASC-US between laboratories. Approximately 3 million Pap smears are classified as ASC-US every year in the US, and the predictive value is very low. Although most Pap tests indicating ASC-US will revert spontaneously, it is estimated that in 5 to 15% of cases ASC-US Pap tests might already correspond to high grade SIL at histology. The ASC-US category is thus a source of confusion to both physicians and patients due to uncertainties that can lead to either the risk of false-positive diagnosis and unnecessary treatment or the risk of missing bona-fide lesions.

Epidemiological and molecular studies have demonstrated that human papillomaviruses (HPVs) are the etiological agents of the vast majority (99.7%) of cervical cancers and their intraepithelial precursors (Pisani, et al., 2002; Parkin et al., 2005; zur Hausen, 2002). About a dozen HPV types (including types 16, 18, 31 and 45) are called "high-risk" types because they can lead to cervical cancer, as well as anal cancer, vulvar cancer, and penile cancer. Several types of HPV, particularly type 16, have been found to be associated with oropharyngeal squamous-cell carcinoma, a form of head and neck cancer. HPV-induced cancers often have viral sequences integrated into the cellular DNA. Some of the HPV "early" genes, such as E6 and E7, are known to act as oncogenes that promote tumor growth and malignant transformation.

II. miRNA MOLECULES

MicroRNA molecules ("miRNAs") are generally 21 to 22 nucleotides in length, though lengths of 19 and up to 23 nucleotides have been reported. The miRNAs are each processed from a longer precursor RNA molecule ("precursor miRNA"). Precursor miRNAs are transcribed from non-protein-encoding genes. The precursor miRNAs have two regions of complementarity that enables them to form a stem-loop- or fold-back-like structure, which is cleaved in animals by a ribonuclease III-like nuclease enzyme called Dicer. The processed miRNA is typically a portion of the stem.

The processed miRNA (also referred to as "mature miRNA") become part of a large complex to down-regulate a particular target gene. Examples of animal miRNAs include those that imperfectly basepair with the target, which halts translation (Olsen et al., 1999; Seggerson et al., 2002). siRNA molecules also are processed by Dicer, but from a long, double-stranded RNA molecule. siRNAs are not naturally found in animal cells, but they can direct the sequence-specific cleavage of an mRNA target through a RNA-induced silencing complex (RISC) (Denli et al., 2003).

The nucleic acid molecules are typically synthetic. The term "synthetic" means the nucleic acid molecule is isolated and not identical in sequence and/or chemical structure to a naturally-occurring nucleic acid molecule, such as an endogenous precursor miRNA or miRNA molecule. While in some embodiments, nucleic acids of the invention do not have an entire sequence that is identical to a sequence of a naturally-occurring nucleic acid, such molecules may encompass all or part of a naturally-occurring sequence. It is contemplated, however, that a synthetic nucleic acid administered to a cell may subsequently be modified or altered in the cell such that its structure or sequence is the same or similar as non-synthetic or naturally occurring nucleic acid, such as a mature miRNA sequence. For example, a synthetic nucleic acid may have a sequence that differs from the sequence of a precursor miRNA, but that sequence may be altered once in a cell to be the same as an endogenous, processed miRNA. The term "isolated" means that the nucleic acid molecules of the invention are initially separated from different (in terms of sequence or structure) and unwanted nucleic acid molecules such that a population of isolated nucleic acids is at least about 90% homogenous, and may be at least about 95, 96, 97, 98, 99, or 100% homogenous with respect to other polynucleotide molecules. In many embodiments of the invention, a nucleic acid is isolated by virtue of it having been synthesized in vitro separate from endogenous nucleic acids in a cell. It will be understood, however, that isolated nucleic acids may be subsequently mixed or pooled together in a variety of combinations.

In certain aspects, synthetic miRNA of the invention are RNA or RNA analogs. miRNA inhibitors may be DNA or RNA, or analogs thereof. miRNA and miRNA inhibitors of the invention are typically "synthetic nucleic acids."

In some embodiments, there is a recombinant or synthetic miRNA having a length of between 17 and 130 residues. The present invention concerns miRNA molecules that are, are at least, or are at most 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 140, 145, 150, 160, 170, 180, 190, 200 or more residues in length, including any integer or any range derivable therein, be it synthetic or non-synthetic.

In certain embodiments, synthetic miRNA have (a) an "miRNA region" whose sequence from 5' to 3' is identical to all or a segment of a mature miRNA sequence, and (b) a "complementary region" whose sequence from 5' to 3' is between 60% and 100% complementary to the miRNA sequence. The term "miRNA region" refers to a region on the synthetic miRNA that is at least 75, 80, 85, 90, 95, or 100% identical, including all integers there between, to all or part of the sequence of a mature, naturally occurring miRNA sequence. In certain embodiments, the miRNA region is or is at least 90, 91, 92, 93, 94, 95, 96, 97, 98, 99, 99.1, 99.2, 99.3, 99.4, 99.5, 99.6, 99.7, 99.8, 99.9 or 100% identical to the sequence of a naturally-occurring miRNA.

The term "complementary region" refers to a region of a synthetic miRNA that is or is at least 60% complementary to a corresponding naturally occurring miRNA sequence. The complementary region is or is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% complementary to its corresponding naturally occurring miRNA, or any range derivable therein. With single polynucleotide sequences, there can be a hairpin loop structure as a result of chemical bonding between the miRNA region and the complementary region. In other embodiments, the complementary region is on a different nucleic acid molecule than the miRNA region, in which case the complementary region is on the complementary strand and the miRNA region is on the active or functional strand.

In other embodiments of the invention, there are synthetic nucleic acids that are miRNA inhibitors. An miRNA inhibitor is between about 17 to 25 nucleotides in length and comprises a 5' to 3' sequence that is at least 90% complementary to the 5' to 3' sequence of a mature miRNA. In certain embodiments, an miRNA inhibitor molecule is 17, 18, 19, 20, 21, 22, 23, 24, or 25 nucleotides in length, or any range derivable therein. Moreover, an miRNA inhibitor has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA, particularly a mature, naturally occurring miRNA. One of skill in the art could use a portion of a sequence that is complementary to the sequence of a mature miRNA as the sequence for an miRNA inhibitor. Moreover, that portion of a sequence can be altered so that it is still 90% complementary to the sequence of a mature miRNA.

In some embodiments of the invention, a synthetic miRNA contains one or more design elements. These design elements include, but are not limited to: (i) a replacement group for the phosphate or hydroxyl of the nucleotide at the 5' terminus of the complementary region; (ii) one or more sugar modifications in the first or last 1 to 6 residues of the complementary region; or (iii) noncomplementarity between one or more nucleotides in the last 1 to 5 residues at the 3' end of the complementary region and the corresponding nucleotides of the miRNA region.

In certain embodiments, a synthetic miRNA has a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. In particular embodiments, the replacement group is biotin, an amine group, a lower alkylamine group, an acetyl group, 2'O-Me (2'oxygen-methyl), DMTO (4,4'-dimethoxytrityl with oxygen), fluorescein, a thiol, or acridine, though other replacement groups are well known to those of skill in the art and can be used as well. This design element can also be used with an miRNA inhibitor.

Additional embodiments concern a synthetic miRNA having one or more sugar modifications in the first or last 1 to 6 residues of the complementary region (referred to as the "sugar replacement design"). In certain cases, there is one or more sugar modifications in the first 1, 2, 3, 4, 5, 6 or more residues of the complementary region, or any range derivable therein. In additional cases, there can be one or more sugar modifications in the last 1, 2, 3, 4, 5, 6 or more residues of the complementary region, or any range derivable therein. It will be understood that the terms "first" and "last" are with respect to the order of residues from the 5' end to the 3' end of the region. In particular embodiments, the sugar modification is a 2'O-Me modification. In further embodiments, there is one or more sugar modifications in the first or last 2 to 4 residues of the complementary region or the first or last 4 to 6 residues of the complementary region. This design element can also be used with an miRNA inhibitor. Thus, an miRNA inhibitor can have this design element and/or a replacement group on the nucleotide at the 5' terminus, as discussed above.

In other embodiments of the invention, there is a synthetic miRNA in which one or more nucleotides in the last 1 to 5 residues at the 3' end of the complementary region are not complementary to the corresponding nucleotides of the miRNA region ("noncomplementarity") (referred to as the "noncomplementarity design"). The noncomplementarity may be in the last 1, 2, 3, 4, and/or 5 residues of the complementary miRNA. In certain embodiments, there is non-complementarity with at least 2 nucleotides in the complementary region.

It is contemplated that synthetic miRNA of the invention have one or more of the replacement, sugar modification, or noncomplementarity designs. In certain cases, synthetic RNA molecules have two of them, while in others these molecules have all three designs in place.

The miRNA region and the complementary region may be on the same or separate polynucleotides. In cases in which they are contained on or in the same polynucleotide, the miRNA molecule will be considered a single polynucleotide. In embodiments in which the different regions are on separate polynucleotides, the synthetic miRNA will be considered to be comprised of two polynucleotides.

When the RNA molecule is a single polynucleotide, there is a linker region between the miRNA region and the complementary region. In some embodiments, the single polynucleotide is capable of forming a hairpin loop structure as a result of bonding between the miRNA region and the complementary region. The linker constitutes the hairpin loop. It is contemplated that in some embodiments, the linker region is, is at least, or is at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues in length, or any range derivable therein. In certain embodiments, the linker is between 3 and 30 residues (inclusive) in length.

In addition to having an miRNA region and a complementary region, there may be flanking sequences as well at either the 5' or 3' end of the region. In some embodiments, there is or is at least 1, 2, 3, 4, 5, 6, 7, 8, 9, 10 nucleotides or more, or any range derivable therein, flanking one or both sides of these regions.

A. Nucleic Acids

The present invention concerns miRNAs that can be labeled or amplified, used in array analysis, or employed in diagnostic, therapeutic, or prognostic applications, particularly those related to diseases and conditions of the cervix. The RNA may have been endogenously produced by a cell, or been synthesized or produced chemically or recombinantly. They may be isolated and/or purified. The term "miRNA," unless otherwise indicated, refers to the processed RNA, after it has been cleaved from its precursor. Table 1 indicates which SEQ ID NO correspond to a mature miRNA sequence. The name of the miRNA is often abbreviated and referred to without a hsa-, mmu-, or rno- prefix and will be understood as such, depending on the context. Unless otherwise indicated, miRNAs referred to in the application are human sequences identified as mir-X or let-X, where X is a number and/or letter.

In certain embodiments, a miRNA is designated with a "5P" or "3P" suffix. "5P" indicates that the mature miRNA derives from the 5' end of the precursor and a corresponding "3P" indicates that it derives from the 3' end of the precursor, as described on the world wide web at sanger.ac.uk. Moreover, in some embodiments, a miRNA is used that does not correspond to a known human miRNA. It is contemplated that these non-human miRNA probes may be used in embodiments of the invention or that there may exist a human miRNA that is homologous to the non-human miRNA. While the invention is not limited to human miRNA, in certain embodiments, miRNA from human cells or a human biological sample is evaluated. In other embodiments, any mammalian cell, biological sample, or preparation thereof may be employed.

In some embodiments of the invention, methods and compositions involving miRNA may concern miRNA and/or other nucleic acids. Nucleic acids may be, be at least, or be at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length. Such lengths cover the lengths of processed miRNA, miRNA probes, precursor miRNA, miRNA containing vectors, control nucleic acids, and other probes and primers. In many embodiments, miRNA sequences are 19-24 nucleotides in length, while miRNA probes are 19-35 nucleotides in length, depending on the length of the processed miRNA and any flanking regions added. miRNA precursors are generally between 62 and 110 nucleotides in humans.

Nucleic acids, and mimetics thereof, of the invention may have regions of identity or complementarity to another nucleic acid. It is contemplated that the region of complementarity or identity can be at least 5 contiguous residues, though it is specifically contemplated that the region is, is at least, or is at most 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous nucleotides. It is further understood that the length of complementarity within a precursor miRNA or between a miRNA probe and a miRNA or a miRNA gene are such lengths. Moreover, the complementarity may be expressed as a percentage, meaning that the complementarity between a nucleic acid and its target is 90% or greater over the length of the nucleic acid. In some embodiments, complementarity is or is at least 90%, 95% or 100%. In particular, such lengths may be applied to any nucleic acid comprising a nucleic acid sequence identified in any of SEQ ID NO:1 through SEQ ID NO:562 or any other sequence disclosed herein. Each of these SEQ ID NOs is disclosed herein. The commonly used name of the miRNA is given (with its identifying source in the prefix, for example, "hsa" for human sequences) and the processed miRNA sequence. Moreover, a lowercase letter in the table below may or may not be lowercase; for example, hsa-mir-130b can also be referred to as miR-130B. The term "miRNA probe" refers to a nucleic acid probe that can identify a particular miRNA or structurally related miRNAs.

It is understood that a miRNA is derived from genomic sequences or a gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "recombinant" may be used and this generally refers to a molecule that has been manipulated in vitro or that is a replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary. miRNA probes or nucleic acids of the invention can include, can be or can be at least 60, 65, 70, 75, 80, 85, 90, 95, 96, 97, 98, 99 or 100% complementary to their target.

As used herein, "hybridization," "hybridizes," or "capable of hybridizing" is understood to mean the forming of a double or triple stranded molecule or a molecule with partial double or triple stranded nature. The term "anneal" as used herein is synonymous with "hybridize." The term "hybridization," "hybridize(s)," or "capable of hybridizing" encompasses hybridization under "stringent condition(s)" or "high stringency" and "low stringency" or "low stringency condition(s)."

As used herein "stringent condition(s)" or "high stringency" are those conditions that allow hybridization between or within one or more nucleic acid strand(s) containing complementary sequence(s), but preclude hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.5 M NaCl at temperatures of about 42° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

1. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moiety. Preferred alkyl (e.g., alkyl, carboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

2. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

3. Nucleotides

As used herein, a "nucleotide" refers to a nucleoside further comprising a "backbone moiety." A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

4. Nucleic Acid Analogs

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652, 099 and 5,763,167, which describe nucleic acids incorporating fluorescent analogs of nucleosides found in DNA or RNA, particularly for use as fluorescent nucleic acids probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified 2'-deoxyfuranosyl moieties) used in nucleic acid detection; U.S. Pat. No. 5,446, 137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3'-5' internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466, 786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probe; U.S. Pat. Nos. 5,378,825, 5,777, 092, 5,623,070, 5,610,289 and 5,602,240, which describe oligonucleotides with three or four atom linker moiety replacing phosphodiester backbone moiety used for improved nuclease resistance, cellular uptake, and regulating RNA expression; U.S. Pat. No. 5,858,988, which describes hydrophobic carrier agent attached to the 2'-O position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA; enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; U.S. Pat. Nos. 5,637, 683, 6,251,666 (L-nucleotide substitutions), and 5,480,980 (7-deaza-2' deoxyguanosine nucleotides and nucleic acid analogs thereof).

5. Modified Nucleotides

Labeling methods and kits of the invention specifically contemplate the use of nucleotides that are both modified for attachment of a label and can be incorporated into a miRNA molecule. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Modified nucleotides for use in the invention are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments, are alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, Biosearch Technologies and NEN. Functional groups may be prepared according to ways known to those of skill in the art, including the representative information found in U.S. Pat. Nos. 4,404,289; 4,405,711; 4,337,063 and 5,268,486, and U.K. Patent 1,529,202, which are all incorporated by reference.

Amine-modified nucleotides are used in several embodiments of the invention. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N6-(4-amino)butyl-dATP, N6-(6-amino)butyl-dATP, N4-[2,2-oxy-bis-(ethylamine)]-dCTP; N6-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

B. Preparation of Nucleic Acids

A nucleic acid may be made or prepared by any technique known to one of ordinary skill in the art, such as for example, chemical synthesis, enzymatic production or biological production. It is specifically contemplated that nucleic acids of the invention are chemically synthesized.

In some embodiments of the invention, miRNAs are recovered or isolated from a biological sample. The miRNA may be recombinant or it may be natural or endogenous to the cell (produced from the cell's genome). It is contemplated that a biological sample may be treated in a way so as to enhance the recovery of small RNA molecules such as miRNA. U.S. patent application Ser. No. 10/667,126 describes such methods and it is specifically incorporated by reference herein. Generally, methods involve lysing cells with a solution having guanidinium and a detergent.

Alternatively, nucleic acid synthesis is performed according to standard methods. See, for example, Itakura and Riggs (1980). Additionally, U.S. Pat. Nos. 4,704,362, 5,221,619, and 5,583,013 each describe various methods of preparing synthetic nucleic acids. Non-limiting examples of a synthetic nucleic acid (e.g., a synthetic oligonucleotide), include a nucleic acid made by in vitro chemically synthesis using phosphotriester, phosphite, or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al., 2001, incorporated herein by reference).

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method polynucleotides phosphorylase method and by solid-phase chemistry. The diester method was the first to be developed to a usable state, primarily by Khorana and co-workers. (Khorana, 1979). The basic step is the joining of two suitably protected deoxynucleotides to form a dideoxynucleotide containing a phosphodiester bond.

The main difference between the diester and triester methods is the presence in the latter of an extra protecting group on the phosphate atoms of the reactants and products (Itakura et al., 1975). Purification's are typically done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide phosphorylase method is an enzymatic method of DNA synthesis that can be used to synthesize many useful oligonucleotides (Gillam et al., 1978; Gillam et al., 1979). Under controlled conditions, polynucleotide phosphorylase adds predominantly a single nucleotide to a short oligonucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-phase methods draw on technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage and Lyer, 1992) has become by far the most widely used coupling chemistry for the synthesis of oligonucleotides. Phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant methods for producing nucleic acids in a cell are well known to those of skill in the art. These include the use of vectors (viral and non-viral), plasmids, cosmids, and other vehicles for delivering a nucleic acid to a cell, which may be the target cell (e.g., a cancer cell) or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference.

In certain embodiments, the present invention concerns nucleic acid molecules that are not synthetic. In some embodiments, the nucleic acid molecule has a chemical structure of a naturally occurring nucleic acid and a sequence of a naturally occurring nucleic acid, such as the exact and entire sequence of a single stranded primary miRNA (see Lee 2002), a single-stranded precursor miRNA, or a single-stranded mature miRNA. In addition to the use of recombinant technology, such non-synthetic nucleic acids may be generated chemically, such as by employing technology used for creating oligonucleotides.

C. Isolation of Nucleic Acids

Nucleic acids may be isolated using techniques well known to those of skill in the art, though in particular embodiments, methods for isolating small nucleic acid molecules, and/or isolating RNA molecules can be employed. Chromatography is a process often used to separate or isolate nucleic acids from protein or from other nucleic acids. Such methods can involve electrophoresis with a gel matrix, filter columns, alcohol precipitation, and/or other chromatography. If miRNA from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

Methods may involve the use of organic solvents and/or alcohol to isolate nucleic acids, particularly miRNA used in methods and compositions of the invention. Some embodiments are described in U.S. patent application Ser. No. 10/667,126, which is hereby incorporated by reference. Generally, this disclosure provides methods for efficiently isolating small RNA molecules from cells comprising: adding an alcohol solution to a cell lysate and applying the alcohol/lysate mixture to a solid support before eluting the RNA molecules from the solid support. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column has worked particularly well for such isolation procedures.

In specific embodiments, miRNA isolation processes include: a) lysing cells in the sample with a lysing solution comprising guanidinium, wherein a lysate with a concentration of at least about 1 M guanidinium is produced; b) extracting miRNA molecules from the lysate with an extraction solution comprising phenol; c) adding to the lysate an alcohol solution for form a lysate/alcohol mixture, wherein the concentration of alcohol in the mixture is between about 35% to about 70%; d) applying the lysate/alcohol mixture to a solid support; e) eluting the miRNA molecules from the solid support with an ionic solution; and, f) capturing the miRNA molecules. Typically the sample is dried down and resuspended in a liquid and volume appropriate for subsequent manipulation.

D. Labels and Labeling Techniques

In some embodiments, the present invention concerns miRNA that are labeled. It is contemplated that miRNA may first be isolated and/or purified prior to labeling. This may achieve a reaction that more efficiently labels the miRNA, as opposed to other RNA in a sample in which the miRNA is not isolated or purified prior to labeling. In many embodiments of the invention, the label is non-radioactive. Generally, nucleic acids may be labeled by adding labeled nucleotides (one-step process) or adding nucleotides and labeling the added nucleotides (two-step process).

1. Labeling Techniques

In some embodiments, nucleic acids are labeled by catalytically adding to the nucleic acid an already labeled nucleotide or nucleotides. One or more labeled nucleotides can be added to miRNA molecules. See U.S. Pat. No. 6,723,509, which is hereby incorporated by reference.

In other embodiments, an unlabeled nucleotide or nucleotides is catalytically added to a miRNA, and the unlabeled nucleotide is modified with a chemical moiety that enables it to be subsequently labeled. In embodiments of the invention, the chemical moiety is a reactive amine such that the nucleotide is an amine-modified nucleotide. Examples of amine-modified nucleotides are well known to those of skill in the art, many being commercially available such as from Ambion, Sigma, Jena Bioscience, and TriLink.

One issue for labeling miRNA is how to label the already existing molecule. The present invention concerns the use of an enzyme capable of using a di- or tri-phosphate ribonucleotide or deoxyribonucleotide as a substrate for its addition to a miRNA. Moreover, in specific embodiments, it involves using a modified di- or tri-phosphate ribonucleotide, which is added to the 3' end of a miRNA. Enzymes capable of adding such nucleotides include, but are not limited to, poly(A) polymerase, terminal transferase, and polynucleotide phosphorylase. Terminal transferase catalyzes the addition of nucleotides to the 3' terminus of a nucleic acid. Polynucleotide phosphorylase can polymerize nucleotide diphosphates without the need for a primer.

2. Labels

Labels on miRNA or miRNA probes may be colorimetric (includes visible and UV spectrum, including fluorescent), luminescent, enzymatic, or positron emitting (including radioactive). The label may be detected directly or indirectly. Radioactive labels include $^{125}I$, $^{32}P$, $^{33}P$, and $^{35}S$. Examples of enzymatic labels include alkaline phosphatase, luciferase, horseradish peroxidase, and β-galactosidase. Labels can also be proteins with luminescent properties, e.g., green fluorescent protein and phicoerythrin.

The colorimetric and fluorescent labels contemplated for use as conjugates include, but are not limited to, Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and TOTAB. Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides are available from Molecular Probes, and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences, such as Cy3-UTP and Cy5-UTP.

Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP.

It is contemplated that nucleic acids may be labeled with two different labels. Furthermore, fluorescence resonance energy transfer (FRET) may be employed in methods of the invention (e.g., Klostermeier et al., 2002; Emptage, 2001; Didenko, 2001, each incorporated by reference).

Alternatively, the label may not be detectable per se, but indirectly detectable or allowing for the isolation or separation of the targeted nucleic acid. For example, the label could be biotin, digoxigenin, polyvalent cations, chelator groups and the other ligands, include ligands for an antibody.

3. Visualization Techniques

A number of techniques for visualizing or detecting labeled nucleic acids are readily available. Such techniques include, microscopy, arrays, Fluorometry, Light cyclers or other real time PCR machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al., 1997), spectroscopy, capillary gel electrophoresis (Cummins et al., 1996), spectroscopy; mass spectroscopy; radiological techniques; and mass balance techniques.

When two or more differentially detectable labels are employed, fluorescent resonance energy transfer (FRET) techniques may be employed to characterize association of one or more nucleic acid. Furthermore, a person of ordinary skill in the art is well aware of ways of visualizing, identifying, and characterizing labeled nucleic acids, and accordingly, such protocols may be used as part of the invention. Examples of tools that may be used also include fluorescent microscopy, a BioAnalyzer, a plate reader, Storm (Molecular Dynamics), Array Scanner, FACS (fluorescent activated cell sorter), or any instrument that has the ability to excite and detect a fluorescent molecule.

III. ARRAY PREPARATION AND SCREENING

A. Array Preparation

The present invention concerns the preparation and use of miRNA arrays or miRNA probe arrays. The arrays can be ordered macroarrays or microarrays of nucleic acid molecules (probes) that are fully or nearly complementary or identical to a plurality of miRNA molecules or precursor miRNA molecules and are positioned on a support or support material in a spatially separated organization. Macroarrays are typically a support (e.g., sheets of nitrocellulose or nylon) upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample. A variety of different array devices in which a plurality of distinct nucleic acid probes are stably associated with the surface of a solid support are known to those of skill in the art. Useful substrates or supports for arrays include nylon, glass, metal, plastic, and silicon. Such arrays may vary in a number of different ways, including average probe length, sequence or types of probes, nature of bond between the probe and the array surface, e.g. covalent or non-covalent, and the like. The labeling and screening methods of the present invention and the arrays are not limited in its utility with respect to any parameter except that the probes detect miRNA; consequently, methods and compositions may be used with a variety of different types of miRNA arrays.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940;

5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 2, 20, 25, 50, 80, 100 or more different probes. It is contemplated that they may contain 1000, 16,000, 65,000, 250,000 or 1,000,000 or more different probes. The probes can be directed to targets in one or more different organisms or cell types. The oligonucleotide probes range from 5 to 50, 5 to 45, 10 to 40, 9 to 34, or 15 to 40 nucleotides in length in some embodiments. In certain embodiments, the oligonucleotide probes are 5, 10, 15, 20 to 20, 25, 30, 35, 40 nucleotides in length including all integers and ranges there between.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols are disclosed above, and include information found in WO 9743450; WO 03023058; WO 03022421; WO 03029485; WO 03067217; WO 03066906; WO 03076928; WO 03093810; WO 03100448A1, all of which are specifically incorporated by reference.

B. Sample Preparation

It is contemplated that the miRNA of a wide variety of samples can be analyzed using the arrays, index of miRNA probes, or array technology described herein and known to the skilled artisan. While endogenous miRNA is contemplated for use with compositions and methods of the invention, recombinant miRNA—including nucleic acids that are complementary or identical to endogenous miRNA or precursor miRNA—can also be handled and analyzed as described herein. Samples may be biological samples, in which case, they can be from biopsy, fine needle aspirates, exfoliates, scrappings, blood, tissue, organs, or any sample containing or constituting biological cells of interest. In certain embodiments, samples may be, but are not limited to, fresh, frozen, fixed, formalin fixed, paraffin embedded, or formalin fixed and paraffin embedded. Alternatively, the sample may not be a biological sample, but be a chemical mixture, such as a cell-free reaction mixture (which may contain one or more biological enzymes).

C. Hybridization

After an array or a set of miRNA probes is prepared and the miRNA in the sample is labeled, the population of target nucleic acids is contacted with the array or probes under hybridization conditions, where such conditions can be adjusted, as desired, to provide for an optimum level of specificity in view of the particular assay being performed. Suitable hybridization conditions are well known to those of skill in the art and reviewed in Sambrook et al. (2001) and WO 95/21944. Of particular interest in many embodiments is the use of stringent conditions during hybridization. Stringent conditions are known to those of skill in the art.

It is specifically contemplated that a single array or set of probes may be contacted with multiple samples. The samples may be labeled with different labels to distinguish the samples. For example, a single array can be contacted with a tumor tissue sample labeled with Cy3, and normal tissue sample labeled with Cy5. Differences between the samples for particular miRNAs corresponding to probes on the array can be readily ascertained and quantified.

The small surface area of the array permits uniform hybridization conditions, such as temperature regulation and salt content. Moreover, because of the small area occupied by the high density arrays, hybridization may be carried out in extremely small fluid volumes (e.g., about 250 µl or less, including volumes of about or less than about 5, 10, 25, 50, 60, 70, 80, 90, 100 µl or any range derivable therein). In small volumes, hybridization may proceed very rapidly.

D. Differential Expression Analyses

Arrays of the invention can be used to detect differences between two samples. Specifically contemplated applications include identifying and/or quantifying differences between miRNA from a sample that is normal and from a sample that is not normal or contains abnormal components, between a cancerous condition and a non-cancerous condition, or between two differently treated samples. Also, miRNA may be compared between a sample believed to be susceptible to a particular disease or condition and one believed to be not susceptible or resistant to that disease or condition. A sample that is not normal is one exhibiting phenotypic trait(s) of a disease or condition or one believed to be not normal with respect to that disease or condition. Phenotypic traits include symptoms of or susceptibility to a disease or condition of which a component is or may or may not be genetic or caused by a hyperproliferative or neoplastic cell or cells.

An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., Science, 251:767-777 (1991), each of which is incorporated by reference in its entirety for all purposes. These arrays may generally be produced using mechanical synthesis methods or light directed synthesis methods which incorporate a combination of photolithographic methods and solid phase synthesis methods. Techniques for the synthesis of these arrays using mechanical synthesis methods are described in, e.g., U.S. Pat. No. 5,384, 261, incorporated herein by reference in its entirety for all purposes. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, which are hereby incorporated in their entirety for all purposes. Arrays may be packaged in such a manner as to allow for diagnostics or other manipulation of an all inclusive device, see for example, U.S. Pat. Nos. 5,856,174 and 5,922,591 incorporated in their entirety by reference for all purposes. See also U.S. patent application Ser. No. 09/545, 207, filed Apr. 7, 2000 for additional information concerning arrays, their manufacture, and their characteristics, which is incorporated by reference in its entirety for all purposes.

Particularly arrays can be used to evaluate samples with respect to diseases or conditions that include, but are not limited to pre-cancerous cervical lesion or cervical cancer.

Cancers that may be evaluated by methods and compositions of the invention include cancer cells particularly from the uterus or cervix, but may also include cells and cancer cells from the bladder, blood, bone, bone marrow, brain, breast, colon, esophagus, gastrointestine, gum, head, kidney, liver, lung, nasopharynx, neck, ovary, prostate, skin, stomach, testis, or tongue. miRNA can be evaluated in precancers, such as metaplasia, dysplasia, and hyperplasia.

It is specifically contemplated that the invention can be used to evaluate differences between stages of disease, such as between hyperplasia, neoplasia, pre-cancer and cancer, or between a primary tumor and a metastasized tumor.

Moreover, it is contemplated that samples that have differences in the activity of certain pathways may also be compared. These pathways include those involving the following factors: antibody response, apoptosis, calcium/NFAT signaling, cell cycle, cell migration, cell adhesion, cell division, cytokines and cytokine receptors, drug metabolism, growth factors and growth factor receptors, inflammatory response, insulin signaling, NFκ-B signaling, angiogenesis, adipogenesis, cell adhesion, viral infection, bacterial infection, senescence, motility, glucose transport, stress response, oxidation, aging, telomere extension, telomere shortening, neural transmission, blood clotting, stem cell differentiation, G-Protein Coupled Receptor (GPCR) signaling, and p53 misregulation.

Cellular pathways that may be profiled also include but are not limited to the following: any adhesion or motility pathway including but not limited to those involving cyclic AMP, protein kinase A, G-protein couple receptors, adenylyl cyclase, L-selectin, E-selectin, PECAM, VCAM-1, α-actinin, paxillin, cadherins, AKT, integrin-α, integrin-β, RAF-1, ERK, PI-3 kinase, vinculin, matrix metalloproteinases, Rho GTPases, p85, trefoil factors, profilin, FAK, MAP kinase, Ras, caveolin, calpain-1, calpain-2, epidermal growth factor receptor, ICAM-1, ICAM-2, cofilin, actin, gelsolin, RhoA, RAC1, myosin light chain kinase, platelet-derived growth factor receptor or ezrin; any apoptosis pathway including but not limited to those involving AKT, Fas ligand, NFκB, caspase-9, PI3 kinase, caspase-3, caspase-7, ICAD, CAD, EndoG, Granzyme B, Bad, Bax, Bid, Bak, APAF-1, cytochrome C, p53, ATM, Bcl-2, PARP, Chk1, Chk2, p21, c-Jun, p73, Rad51, Mdm2, Rad50, c-Abl, BRCA-1, perforin, caspase-4, caspase-8, caspase-6, caspase-1, caspase-2, caspase-10, Rho, Jun kinase, Jun kinase kinase, Rip2, lamin-A, lamin-B1, lamin-B2, Fas receptor, $H_2O_2$, Granzyme A, NADPH oxidase, HMG2, CD4, CD28, CD3, TRADD, IKK, FADD, GADD45, DR3 death receptor, DR4/5 death receptor, FLIPs, APO-3, GRB2, SHC, ERK, MEK, RAF-1, cyclic AMP, protein kinase A, E2F, retinoblastoma protein, Smac/Diablo, ACH receptor, 14-3-3, FAK, SODD, TNF receptor, RIP, cyclin-D1, PCNA, Bcl-XL, PIP2, PIP3, PTEN, ATM, Cdc2, protein kinase C, calcineurin, IKKα, IKKβ, IKKγ, SOS-1, c-FOS, Traf-1, Traf-2, Iκβ or the proteasome; any cell activation pathway including but not limited to those involving protein kinase A, nitric oxide, caveolin-1, actin, calcium, protein kinase C, Cdc2, cyclin B, Cdc25, GRB2, SRC protein kinase, ADP-ribosylation factors (ARFs), phospholipase D, AKAP95, p68, Aurora B, CDK1, Eg7, histone H3, PKAc, CD80, PI3 kinase, WASP, Arp2, Arp3, p16, p34, p20, PP2A, angiotensin, angiotensin-converting enzyme, protease-activated receptor-1, protease-activated receptor-4, Ras, RAF-1, PLCβ, PLCγ, COX-1, G-protein-coupled receptors, phospholipase A2, IP3, SUMO1, SUMO 2/3, ubiquitin, Ran, Ran-GAP, Ran-GEF, p53, glucocorticoids, glucocorticoid receptor, components of the SWI/SNF complex, RanBP1, RanBP2, importins, exportins, RCC1, CD40, CD40 ligand, p38, IKKα, IKKβ, NFκB, TRAF2, TRAF3, TRAF5, TRAF6, IL-4, IL-4 receptor, CDK5, AP-1 transcription factor, CD45, CD4, T cell receptors, MAP kinase, nerve growth factor, nerve growth factor receptor, c-Jun, c-Fos, Jun kinase, GRB2, SOS-1, ERK-1, ERK, JAK2, STAT4, IL-12, IL-12 receptor, nitric oxide synthase, TYK2, IFNγ, elastase, IL-8, epithelins, IL-2, IL-2 receptor, CD28, SMAD3, SMAD4, TGFβ or TGFβ receptor; any cell cycle regulation, signaling or differentiation pathway including but not limited to those involving TNFs, SRC protein kinase, Cdc2, cyclin B, Grb2, Sos-1, SHC, p68, Aurora kinases, protein kinase A, protein kinase C, Eg7, p53, cyclins, cyclin-dependent kinases, neural growth factor, epidermal growth factor, retinoblastoma protein, ATF-2, ATM, ATR, AKT, CHK1, CHK2, 14-3-3, WEE1, CDC25 CDC6, Origin Recognition Complex proteins, p15, p16, p27, p21, ABL, c-ABL, SMADs, ubiquitin, SUMO, heat shock proteins, Wnt, GSK-3, angiotensin, p73 any PPAR, TGFα, TGFβ, p300, E6-AP, Hect-E3s, MDM2, GADD45, Notch, cdc34, BRCA-1, BRCA-2, SKP1, the proteasome, CUL1, E2F, p107, steroid hormones, steroid hormone receptors, IκBα, IκBβ, Sin3A, heat shock proteins, Ras, Rho, ERKs, IKKs, PI3 kinase, Bcl-2, Bax, PCNA, MAP kinases, dynein, RhoA, PKAc, cyclin AMP, FAK, PIP2, PIPS, integrins, thrombopoietin, Fas, Fas ligand, PLK3, MEKs, JAKs, STATs, acetylcholine, paxillin calcineurin, p38, importins, exportins, Ran, Rad50, Rad51, DNA polymerase, RNA polymerase, Ran-GAP, Ran-GEF, NuMA, Tpx2, RCC1, Sonic Hedgehog, Crm1, Patched (Ptc-1), MPF, CaM kinases, tubulin, actin, kinetochore-associated proteins, centromere-binding proteins, telomerase, TERT, PP2A, c-MYC, insulin, T cell receptors, B cell receptors, CBP, IKβ, NFκB, RAC1, RAF1, EPO, diacylglycerol, c-Jun, c-Fos, Jun kinase, hypoxia-inducible factors, GATA4, β-catenin, α-catenin, calcium, arrestin, survivin, caspases, procaspases, CREB, CREM, cadherins, PECAMs, corticosteroids, colony-stimulating factors, calpains, adenylyl cyclase, growth factors, nitric oxide, transmembrane receptors, retinoids, G-proteins, ion channels, transcriptional activators, transcriptional coactivators, transcriptional repressors, interleukins, vitamins, interferons, transcriptional corepressors, the nuclear pore, nitrogen, toxins, proteolysis, or phosphorylation; or any metabolic pathway including but not limited to those involving the biosynthesis of amino acids, oxidation of fatty acids, biosynthesis of neurotransmitters and other cell signaling molecules, biosynthesis of polyamines, biosynthesis of lipids and sphingolipids, catabolism of amino acids and nutrients, nucleotide synthesis, eicosanoids, electron transport reactions, ER-associated degradation, glycolysis, fibrinolysis, formation of ketone bodies, formation of phagosomes, cholesterol metabolism, regulation of food intake, energy homeostasis, prothrombin activation, synthesis of lactose and other sugars, multi-drug resistance, biosynthesis of phosphatidylcholine, the proteasome, amyloid precursor protein, Rab GTPases, starch synthesis, glycosylation, synthesis of phoshoglycerides, vitamins, the citric acid cycle, IGF-1 receptor, the urea cycle, vesicular transport, or salvage pathways. It is further contemplated that nucleic acids molecules of the invention can be employed in diagnostic and therapeutic methods with respect to any of the above pathways or factors. Thus, in some embodiments of the invention, a miRNA may be differentially expressed with respect to one or more of the above pathways or factors. In certain aspects, the pathways or cellular elements involved or effected by HPV infection can be assessed, evaluated, and/or monitored, e.g., hTERT, E6TP1, MCMI, Bak, and PDZ domain-containing proteins such as Scribble, h-Dlg, MAGI-1, MAGI-3, and MUPP1.

Phenotypic traits also include characteristics such as susceptibility or receptivity to particular drugs or therapeutic treatments (drug efficacy), and risk of drug toxicity. Samples that differ in these phenotypic traits may also be evaluated using the arrays and methods described.

In certain embodiments, miRNA profiles may be generated to evaluate and correlate those profiles with pharmacokinetics. For example, miRNA profiles may be created and evaluated for patient tumor and blood samples prior to the patient's being treated or during treatment to determine if there are miRNAs whose expression correlates with the outcome of the patient. Identification of differential miRNAs can lead to a diagnostic assay involving them that can be used to evaluate tumor and/or blood samples to determine what drug regimen the patient should be provided. In addition, it can be used to identify or select patients suitable for a particular clinical trial. If a miRNA profile is determined to be correlated with drug efficacy or drug toxicity that may be relevant to whether that patient is an appropriate patient for receiving the drug or for a particular dosage of the drug.

In addition to prognostic assays, samples from patients with a variety of diseases can be evaluated to determine if different diseases can be identified based on blood miRNA levels. A diagnostic assay can be created based on the profiles that doctors can use to identify individuals with a disease or who are at risk to develop a disease. Alternatively, treatments can be designed based on miRNA profiling. Examples of such methods and compositions are described in the U.S. Provisional Patent Application Ser. No. 60/683,736 entitled "Methods and Compositions Involving miRNA and miRNA Inhibitor Molecules" filed on May 23, 2005, which is hereby incorporated by reference in its entirety.

E. Other Assays

In addition to the use of arrays and microarrays, it is contemplated that a number of difference assays could be employed to analyze miRNAs, their activities, and their effects. Such assays include, but are not limited to, nucleic amplification, polymerase chain reaction, quantitative PCR, RT-PCR, in situ hybridization, Northern hybridization, hybridization protection assay (HPA) (GenProbe), branched DNA (bDNA) assay (Chiron), rolling circle amplification (RCA), single molecule hybridization detection (US Genomics), Invader assay (ThirdWave Technologies), and/or Bridge Litigation Assay (Genaco).

IV. THERAPEUTIC METHODS

Methods of the invention include reducing or eliminating activity of one or more miRNAs in a cell comprising introducing into a cell an miRNA inhibitor; or supplying or enhancing the activity of one or more miRNAs in a cell. The present invention also concerns inducing certain cellular characteristics by providing to a cell a particular nucleic acid, such as a specific synthetic miRNA molecule or a synthetic miRNA inhibitor molecule. However, in methods of the invention, the miRNA molecule or miRNA inhibitor need not be synthetic. They may have a sequence that is identical to a naturally occurring miRNA or they may not have any design modifications. In certain embodiments, the miRNA molecule and/or an miRNA inhibitor are synthetic, as discussed herein.

The particular nucleic acid molecule provided to the cell is understood to correspond to a particular miRNA in the cell, and thus, the miRNA in the cell is referred to as the "corresponding miRNA." In situations in which a named miRNA molecule is introduced into a cell, the corresponding miRNA will be understood to be the induced miRNA. It is contemplated, however, that the miRNA molecule introduced into a cell is not a mature miRNA but is capable of becoming a mature miRNA under the appropriate physiological conditions. In cases in which a particular corresponding miRNA is being inhibited by a miRNA inhibitor, the particular miRNA will be referred to as the targeted miRNA. It is contemplated that multiple corresponding miRNAs may be involved. In particular embodiments, more than one miRNA molecule is introduced into a cell. Moreover, in other embodiments, more than one miRNA inhibitor is introduced into a cell. Furthermore, a combination of miRNA molecule(s) and miRNA inhibitor(s) may be introduced into a cell.

Methods include identifying a cell or patient in need of inducing those cellular characteristics. Also, it will be understood that an amount of a synthetic nucleic acid that is provided to a cell or organism is an "effective amount," which refers to an amount needed to achieve a desired goal, such as inducing a particular cellular characteristic(s).

In certain embodiments of the methods include providing or introducing to a cell a nucleic acid molecule corresponding to a mature miRNA in the cell in an amount effective to achieve a desired physiological result.

Moreover, methods can involve providing synthetic or nonsynthetic miRNA molecules. It is contemplated that in these embodiments, methods may or may not be limited to providing only one or more synthetic miRNA molecules or only on or more nonsynthetic miRNA molecules. Thus, in certain embodiments, methods may involve providing both synthetic and nonsynthetic miRNA molecules. In this situation, a cell or cells are most likely provided a synthetic miRNA molecule corresponding to a particular miRNA and a nonsynthetic miRNA molecule corresponding to a different miRNA. Furthermore, any method including a list of miRNAs using Markush group language may be articulated without the Markush group language and a disjunctive article (i.e., or) instead, and vice versa.

In some embodiments, there is a method for reducing or inhibiting cell proliferation in a cell comprising introducing into or providing to the cell an effective amount of (i) an miRNA inhibitor molecule or (ii) a synthetic or nonsynthetic miRNA molecule that corresponds to an miRNA sequence. In certain embodiments the methods involves introducing into the cell an effective amount of (i) an miRNA inhibitor molecule having a 5' to 3' sequence that is at least 90% complementary to all or part of the 5' to 3' sequence of one or more mature miRNA of Table 1.

Certain embodiments of the invention include methods of treating a pre-cancerous cervical lesion or a cancerous cervical condition. In one aspect, the method comprises contacting a cervical cell with one or more nucleic acid, synthetic miRNA, or miRNA comprising at least one nucleic acid segment having all or a portion of a miRNA sequence. The segment may be 5, 6, 7, 8, 9, 10, 11, 12, 13, 14, 15, 16, 17, 18, 19, 20, 21, 22, 23, 24, 25, 30 or more nucleotides or nucleotide analog, including all integers there between. An aspect of the invention includes the modulation of a miRNA or a mRNA within a target cell, such as a cervical cell.

Typically, an endogenous gene, miRNA or mRNA is modulated in the cell. In particular embodiments, the nucleic acid sequence comprises at least one segment that is at least 70, 75, 80, 85, 90, 95, or 100% identical in nucleic acid sequence to one or more miRNA sequence listed in Table 1. Modulation of the expression or processing of an endogenous gene, miRNA, or mRNA can be through modulation of the processing of an mRNA, such processing including transcription, transportation and/or translation with in a cell. Modulation may also be effected by the inhibition or enhancement of miRNA activity with a cell, tissue, or organ. Such processing may effect the expression of an encoded product or the stability of the mRNA. In still other embodiments, a nucleic acid sequence can comprise a modified nucleic acid sequence.

In particular embodiments, the cervical cell is a cervical cancer cell. Methods of the invention can further comprise administering a second therapy, such as chemotherapy, radiotherapy, surgery, or immunotherapy. The nucleic acid can be transcribed from a nucleic acid vector, such as a plasmid vector or a viral vector.

Methods of treating a pre-cancerous or cancerous cervical condition include contacting or administering to a cervical cell one or more nucleic acid comprising a miRNA sequence, wherein expression of an endogenous miRNA is modulated in the cervical cell; where the miRNA sequence is at least 70, 75, 80, 85% or more identical to one or more of the sequences identified in Table 1. In certain aspects, the activity of those miRNAs indicated as having increased expression in a pre-cancerous or cancerous tissue is decreased. In a further aspect, the miRNA activity of those miRNA indicated as having decreased expression in a pre-cancerous or cancerous tissue is increased.

In certain aspects, one or more miRNA sequence may include or comprise a modified nucleobase or nucleic acid sequence.

The methods may further comprise administering a second therapy. The second therapy can be, but is not limited to chemotherapy, radiotherapy, surgery, or immunotherapy.

In still further aspects, one or more miRNA are transcribed from a nucleic acid vector, such as a plasmid or viral vector.

In certain aspects, a subject is administered: one or more nucleic acid possessing a function of an miRNA having a nucleic acid segment having at least 80, 85, 90, 95, 97, 98, 99, or 100% nucleic acid sequence identity to those miRNA decreased or down-regulated in a disease or condition to be treated.

In certain aspects, a subject is administered: one or more miRNA inhibitors having a nucleic acid segment having at least 80, 85, 90, 95, 97, 98, 99, or 100% nucleic acid sequence identity to those miRNA increased or up-regulated in a disease or condition to be treated.

Synthetic nucleic acids can be administered to the subject or patient using modes of administration that are well known to those of skill in the art, particularly for therapeutic applications. It is particularly contemplated that a patient is human or any other mammal or animal.

It will be understood in methods of the invention that a cell or other biological matter such as an organism (including patients) can be provided an miRNA or miRNA molecule corresponding to a particular miRNA by administering to the cell or organism a nucleic acid molecule that functions as the corresponding miRNA once inside the cell. The form of the molecule provided to the cell may not be the form that acts as an miRNA once inside the cell. Thus, it is contemplated that in some embodiments, biological matter is provided a synthetic miRNA or a nonsynthetic miRNA, such as one that becomes processed into a mature and active miRNA once it has access to the cell's miRNA processing machinery. In certain embodiments, it is specifically contemplated that the miRNA molecule provided to the biological matter is not a mature miRNA molecule but a nucleic acid molecule that can be processed into the mature miRNA once it is accessible to miRNA processing machinery. The term "nonsynthetic" in the context of miRNA means that the miRNA is not "synthetic," as defined herein. Furthermore, it is contemplated that in embodiments of the invention that concern the use of synthetic miRNAs, the use of corresponding nonsynthetic miRNAs is also considered an aspect of the invention, and vice versa.

In other embodiments, the methods involve reducing cell viability comprising introducing into or providing to the cell an effective amount of (i) an miRNA inhibitor molecule or (ii) a synthetic or nonsynthetic miRNA molecule that corresponds to an miRNA sequence. Methods for inducing apoptosis have a number of therapeutic applications including, but not limited to, the treatment of pre-cancer or cancer.

The present invention also concerns using miRNA compositions to treat diseases or conditions or to prepare therapeutics for the treatment of diseases or conditions. It is contemplated that 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 more miRNA (or any range derivable therein) may be used for these embodiments. In certain embodiments, methods involve one or more miRNA inhibitors and/or an miRNA molecules corresponding to any of these miRNAs, particularly for the treatment or prevention of cancer. Cancer includes, but is not limited to, malignant cancers, tumors, metastatic cancers, unresectable cancers, chemo- and/or radiation-resistant cancers, and terminal cancers.

In certain embodiments, methods also include targeting an miRNA to modulate in a cell or organism. The term "targeting an miRNA to modulate" or "targeting an miRNA" means a nucleic acid of the invention will be employed so as to modulate the selected miRNA. In some embodiments the modulation is achieved with a synthetic or non-synthetic miRNA that corresponds to the targeted miRNA, which effectively provides the targeted miRNA to the cell or organism (positive modulation). In other embodiments, the modulation is achieved with an miRNA inhibitor, which effectively inhibits the targeted miRNA in the cell or organism (negative modulation).

In some embodiments, the miRNA targeted to be modulated is an miRNA that affects a disease, condition, or pathway. In certain embodiments, the miRNA is targeted because a treatment can be provided by negative modulation of the targeted miRNA. In other embodiments, the miRNA is targeted because a treatment can be provided by positive modulation of the targeted miRNA.

In certain methods of the invention, there is a further step of administering the selected miRNA modulator to a cell, tissue, organ, or organism (collectively "biological matter") in need of treatment related to modulation of the targeted miRNA or in need of the physiological or biological results discussed herein (such as with respect to a particular cellular pathway or result, such as a decrease in cell viability). Consequently, in some methods of the invention there is a step of identifying a patient in need of treatment that can be provided by the miRNA modulator(s). It is contemplated that an effective amount of an miRNA modulator can be administered in some embodiments. In particular embodiments, there is a therapeutic benefit conferred on the biological matter, where a "therapeutic benefit" refers to an improvement in the one or more conditions or symptoms associated with a disease or condition or an improvement in the prognosis, duration, or status with respect to the disease. It is contemplated that a therapeutic benefit includes, but is not limited to, a decrease in pain, a decrease in morbidity, a decrease in a severity or duration of a symptom. For example, with respect to cancer, it is contemplated that a therapeutic benefit can be inhibition of tumor growth, prevention of metastasis, reduction in number of metastases, inhibition of cancer cell proliferation, inhibition of cancer cell proliferation, induction of cell death in cancer cells, inhibition of angiogenesis near cancer cells, induction of apoptosis of cancer cells, reduction in pain, reduction in risk of recurrence, induction of chemo- or radiosensitivity in cancer cells, prolongation of life, palliation of symptoms related to the condition, and/or delay of death directly or indirectly related to a cancer.

Furthermore, it is contemplated that the miRNA compositions may be provided as part of a therapy to a patient, in conjunction with traditional therapies or preventative agents. Moreover, it is contemplated that any method discussed in the context of therapy may be applied as a preventative measure, particularly in a patient identified to be potentially in need of the therapy or at risk of the condition or disease for which a therapy is needed.

In addition, methods of the invention concern employing one or more nucleic acids corresponding to an miRNA and a therapeutic drug. The nucleic acid can enhance the effect or efficacy of the drug, reduce any side effects or toxicity, modify its bioavailability, and/or decrease the dosage or frequency needed. In certain embodiments, the therapeutic drug is a cancer therapeutic. Consequently, in some embodiments, there is a method of treating cancer in a patient comprising administering to the patient the cancer therapeutic and an effective amount of at least one miRNA molecule that improves the efficacy of the cancer therapeutic or protects non-cancer cells. Cancer therapies also include a variety of combination therapies with both chemical and radiation based treatments. Combination chemotherapies include but are not limited to, for example, bevacizumab, cisplatin (CDDP), carboplatin, EGFR inhibitors (gefitinib and cetuximab), procarbazine, mechlorethamine, cyclophosphamide, camptothecin, COX-2 inhibitors (e.g., celecoxib) ifosfamide, melphalan, chlorambucil, busulfan, nitrosurea, dactinomycin, daunorubicin, doxorubicin (adriamycin), bleomycin, plicomycin, mitomycin, etoposide (VP 16), tamoxifen, raloxifene, estrogen receptor binding agents, taxol, taxotere, gemcitabien, navelbine, farnesyl-protein transferase inhibitors, transplatinum, 5-fluorouracil, vincristin, vinblastin and methotrexate, or any analog or derivative variant of the foregoing.

Generally, inhibitors of miRNAs can be given to achieve the opposite effect as compared to when nucleic acid molecules corresponding to the mature miRNA are given. Similarly, nucleic acid molecules corresponding to the mature miRNA can be given to achieve the opposite effect as compared to when inhibitors of the miRNA are given. For example, miRNA molecules that increase cell proliferation can be provided to cells to increase proliferation or inhibitors of such molecules can be provided to cells to decrease cell proliferation. The present invention contemplates these embodiments in the context of the different physiological effects observed with the different miRNA molecules and miRNA inhibitors disclosed herein. These include, but are not limited to, the following physiological effects: increase and decreasing cell proliferation; increasing or decreasing apoptosis; increasing or decreasing transformation; increasing or decreasing cell viability; activating, stimulating or suppressing cellular pathways; reduce or increase viable cell number; and increase or decrease number of cells at a particular phase of the cell cycle. Methods of the invention are generally contemplated to include providing or introducing one or more different nucleic acid or mimetic molecules corresponding to one or more different miRNA molecules. It is contemplated that the following, at least the following, or at most the following number of different nucleic acid molecules may be provided or introduced: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. This also applies to the number of different miRNA molecules that can be provided or introduced into a cell.

V. KITS

Any of the compositions described herein may be comprised in a kit. In a non-limiting example, reagents for isolating miRNA, labeling miRNA, and/or evaluating a miRNA population using an array, nucleic acid amplification, and/or hybridization can be included in a kit, as well reagents for preparation of samples from cervical samples or other sample that have been, may have been, exposed to, or suspected of being infected with HPV. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. In certain aspects, the kit can include amplification reagents. In other aspects, the kit may include various supports, such as glass, nylon, polymeric beads, and the like, and/or reagents for coupling any probes and/or target nucleic acids. It may also include one or more buffers, such as reaction buffer, labeling buffer, washing buffer, or a hybridization buffer, compounds for preparing the miRNA probes, and components for isolating miRNA. Other kits of the invention may include components for making a nucleic acid array comprising miRNA, and thus, may include, for example, a solid support.

Kits for implementing methods of the invention described herein are specifically contemplated. In some embodiments, there are kits for preparing miRNA for multi-labeling and kits for preparing miRNA probes and/or miRNA arrays. In these embodiments, kit comprise, in suitable container means, 1, 2, 3, 4, 5, 6, 7, 8, 9, 10, 11, 12 or more of the following: (1) poly(A) polymerase; (2) unmodified nucleotides (G, A, T, C, and/or U); (3) a modified nucleotide (labeled or unlabeled); (4) poly(A) polymerase buffer; (5) at least one microfilter; (6) label that can be attached to a nucleotide; (7) at least one miRNA probe; (8) reaction buffer; (9) a miRNA array or components for making such an array; (10) acetic acid; (11) alcohol; and (12) solutions for preparing, isolating, enriching, and purifying miRNAs or miRNA probes or arrays. Other reagents include those generally used for manipulating RNA, such as formamide, loading dye, ribonuclease inhibitors, and DNase.

In specific embodiments, kits of the invention include an array containing miRNA probes, as described in the application. An array may have probes corresponding to all known miRNAs of an organism or a particular tissue or organ in particular conditions, or to a subset of such probes. The subset of probes on arrays of the invention may be or include those identified as relevant to a particular diagnostic, therapeutic, or prognostic application. For example, the array may contain one or more probes that is indicative or suggestive of (1) a disease or condition, (2) susceptibility or resistance to a particular drug or treatment; (3) susceptibility to toxicity from a drug or substance; (4) the stage of development or severity of a disease or condition (prognosis); and (5) genetic predisposition to a disease or condition.

For any kit embodiment, including an array, there can be nucleic acid molecules that contain or can be used to amplify a sequence that is a variant of, identical to or complementary to all or part of any of SEQ ID NOS: 1-562. In certain embodiments, a kit or array of the invention can contain one or more probes for the miRNAs identified by SEQ ID NOS: 1-562. Any nucleic acid discussed above may be implemented as part of a kit.

The components of the kits may be packaged either in aqueous media or in lyophilized form. The container means of the kits will generally include at least one vial, test tube, flask, bottle, syringe or other container, into which a component may be placed, and preferably, suitably aliquotted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried power. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 μg or at least or at most those amounts of dried dye are provided in kits of the invention. The dye may then be resuspended in any suitable solvent, such as DMSO.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

Such kits may also include components that facilitate isolation of the labeled miRNA. It may also include components that preserve or maintain the miRNA or that protect against its degradation. Such components may be RNAse-free or protect against RNAses. Such kits generally will comprise, in suitable means, distinct containers for each individual reagent or solution.

Kits of the invention may also include one or more of the following: Control RNA; nuclease-free water; RNase-free containers, such as 1.5 ml tubes; RNase-free elution tubes; PEG or dextran; ethanol; acetic acid; sodium acetate; ammonium acetate; guanidinium; detergent; nucleic acid size marker; RNase-free tube tips; and RNase or DNase inhibitors.

It is contemplated that such reagents are embodiments of kits of the invention. Such kits, however, are not limited to the particular items identified above and may include any reagent used for the manipulation or characterization of miRNA.

VI. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

RNA from Cervical Specimens and Cell Lines

Paired tissue samples from nine squamous cell carcinomas (Ca) and nine normal adjacent regions (NAT) of the uterine cervix from the same patients and three squamous intraepithelial lesions (SIL) of the cervix were purchased from ProteoGenex (Culver City, Calif., USA). Total RNA was extracted from these tissue samples using the mirVana™ miRNA Isolation Kit (Ambion; Austin, Tex., USA) according to the manufacturer's protocol. Additional samples used in the study included purified total RNA from sixteen normal cervical tissue specimens (NCX) (FirstChoice® Human Cervix Total RNA, Ambion). In addition, total RNA was purified from cells of four squamous cell carcinoma-derived cervical cell lines (SW756, C4-1, CaSki, SiHa) and from an adenocarcinoma-derived cervical cell line (HeLa), using the mirVana™ miRNA Isolation Kit (Ambion) according to the manufacturer's protocol. In all cases, purified total RNA was quantified using a NanoDrop® ND-1000 spectrophotometer (NanoDrop Technologies; Wilmington, Del., USA). Tables 2, 3, and 4, below, show information regarding the nine matched Ca/NAT cervical samples (Table 2), the sixteen normal cervical samples (NCX, Table 3), and the cervical cell lines (CL) (Table 4)

TABLE 2

Tissue Sample Pathology Report for Nine Pairs of Cancerous (Ca) and Normal Adjacent Cervical Tissue (NAT) Samples. HPV; human papillomavirus.

| Sample | Age | Ethnicity | Histological Diagnosis | TNM Staging Score (Greene et al., 2002) | HPV 16/18 Status |
|---|---|---|---|---|---|
| Ca1 | 52 | Caucasian | SCC | T1N1M0 | 16 |
| NAT1 | | | normal | NA | negative |
| Ca2 | 32 | Caucasian | SCC, poorly differentiated | T1bN0M0 | 18 |
| NAT2 | | | normal | NA | 16 |
| Ca3 | 47 | Caucasian | SCC, non-keratinizing | T1aN1M0 | 16 |
| NAT3 | | | normal | NA | 16 |
| Ca4 | 45 | Caucasian | SCC, moderately differentiated | T1aN1M0 | 16 |
| NAT4 | | | normal | NA | negative |
| Ca5 | 29 | Caucasian | SCC, poorly differentiated | T1a2N0M0 | 18 |
| NAT5 | | | normal | NA | 18 |
| Ca6 | 55 | Caucasian | SCC, moderately differentiated | T3aN1M0 | negative |
| NAT6 | | | normal | NA | negative |

TABLE 2-continued

Tissue Sample Pathology Report for Nine Pairs of
Cancerous (Ca) and Normal Adjacent Cervical Tissue
(NAT) Samples. HPV; human papillomavirus.

| Sample | Patient Information | | Histological Diagnosis | TNM Staging Score (Greene et al., 2002) | HPV 16/18 Status |
|---|---|---|---|---|---|
| | Age | Ethnicity | | | |
| Ca7 | 40 | Caucasian | SCC, moderately differentiated | T2aN1M0 | 16 + 18 |
| NAT7 | | | normal | NA | negative |
| Ca8 | 44 | Caucasian | SCC, well to poorly differentiated | T1a2N0M0 | 16 |
| NAT8 | | | normal | NA | 16 |
| Ca9 | 39 | Caucasian | SCC, poorly differentiated | T3aN0M0 | 18 |
| NAT9 | | | normal | NA | negative |

TABLE 3

Patient Information for Sixteen Normal Cervical
Tissue (NCX) Samples. HPV; human papillomavirus

| Sample | Patient Age | Patient Ethnicity | HPV 16/18 Status |
|---|---|---|---|
| NCX1 | 45 | Caucasian | negative |
| NCX2 | 78 | Caucasian | negative |
| NCX3 | 72 | Caucasian | negative |
| NCX4 | 36 | Unknown | negative |
| NCX5 | 46 | Caucasian | negative |
| NCX6 | 48 | Caucasian | negative |
| NCX7 | 31 | Caucasian | negative |
| NCX8 | 48 | African American | negative |
| NCX9 | 45 | African American | negative |
| NCX10 | 56 | Caucasian | negative |
| NCX11 | 57 | Caucasian | 18 |
| NCX12 | 65 | Caucasian | 18 |
| NCX13 | 57 | Caucasian | negative |
| NCX14 | 52 | African American | negative |
| NCX15 | 47 | African American | negative |
| NCX16 | 53 | Caucasian | negative |

TABLE 4

Histology and HPV (human papillomavirus) Status for Five Cervical
Cancer-Derived Cell Lines. SCC, squamous cell carcinoma.

| Cell Line | Histology | HPV 16/18 Status |
|---|---|---|
| HeLa | Adenocarcinoma | 18 |
| SW756 | SCC | 18 |
| C4-1 | SCC | 18 |
| CaSki | SCC | 16 |
| SiHa | SCC | 16 |

Example 2 miRNA Expression in the Normal Cervix

The inventors first evaluated miRNA expression in normal cervical tissue samples. miRNA expression profiling was performed as previously described (Shingara et al., 2005) except that the miRNA fractions recovered from 20 µg total RNA were labeled with Cy5 (GE Healthcare Life Sciences; Piscataway, N.J., USA). To isolate miRNA fractions, total RNA samples were fractionated and purified using the flashPAGE™ fractionator and reagents (catalog #—AM13100; Ambion) according to the manufacturer's recommendations. Labeled miRNAs were hybridized to mirVana miRNA Bioarrays V1 (Ambion) according to the manufacturer's instructions. The arrays contained 377 individual miRNA probes, including 281 human miRNAs from the mirBase Sequence Database (microrna.sanger.ac.uk) (Griffiths-Jones et al., 2006), 33 new human miRNAs (Ambi-miRs) and 63 mouse or rat miRNAs from the mirBase Sequence Database.

Following hybridization, the arrays were scanned using the Axon® GenePix 400B scanner and associated GenePix software (Molecular Devices Corporation; Sunnyvale, Calif., USA). Raw array data were normalized with the variance stabilization method (VSN) (Huber et al., 2002). VSN is a global normalization process that stabilizes the variance evenly across the entire range of expression and utilizes calibration of signal followed by transformation of data to a generalized natural logarithmic space in lieu of the traditional logarithm base 2 transformation. Absolute values and differences in VSN transformed expression are denoted by H and ΔH, respectively, and were used for all subsequent data analyses. Differences in normalized expression values between samples (ΔH) were transformed to a generalized fold change via exponentiation base e. These values exhibit a compression for small differences in expression. For each array, the minimum observable threshold was determined by examining the foreground minus background median intensities for 'EMPTY' spots. The minimum threshold was defined as 5% symmetric trimmed mean plus 2 standard deviations across all 'EMPTY' spots on an individual array. For an overview of miRNA processing and analysis, see Davison et al., (2006).

The inventors first characterized miRNA expression profiles from 16 normal cervix specimens (Table 5). Approximately 200 miRNAs were detected above background signal (Mean (NCX)>2.87). These included 171 human miRNAs, 17 miRNAs previously identified in mouse or rat, and 15 new human miRNAs (Ambi-miR-7027, -7029, -7039, -7058, -7068-1, -7070, -7075, -7076, -7079, -7081, -7083, -7085, -7100, -7101, and -7105). Pair-wise t-test comparison analyses revealed no statistically significant differences in cervical miRNA expression between Caucasian (n=11) and African-American (n=4) patients or between older (over 50 years of age) and younger (less than 50 years of age) patients.

TABLE 5

Normalized Array Data for Sixteen Normal Cervix Tissue Samples (NCX1-NCX16). TV,
threshold value, miRNAs > TV, number of miRNAs expressed at greater than threshold
value. %, percentage of miRNAs expressed at greater than threshold value.

| | NCX 1 | NCX 2 | NCX 3 | NCX 4 | NCX 5 | NCX 6 | NCX 7 | NCX 8 | NCX 9 |
|---|---|---|---|---|---|---|---|---|---|
| TV | 3.37 | 3.28 | 3.22 | 3.16 | 2.90 | 2.03 | 1.83 | 2.41 | 2.82 |
| miRNAs > TV | 182 | 185 | 182 | 187 | 202 | 260 | 286 | 232 | 208 |
| % | 48.31 | 49.09 | 48.31 | 49.61 | 53.51 | 69.09 | 75.84 | 61.56 | 55.06 |

TABLE 5-continued

Normalized Array Data for Sixteen Normal Cervix Tissue Samples (NCX1-NCX16). TV, threshold value, miRNAs > TV, number of miRNAs expressed at greater than threshold value. %, percentage of miRNAs expressed at greater than threshold value.

| miR Name | | | | | | | | | |
|---|---|---|---|---|---|---|---|---|---|
| hsa-let-7a | 10.98 | 11.24 | 11.01 | 10.78 | 11.14 | 10.60 | 10.39 | 10.69 | 11.03 |
| hsa-let-7b | 11.35 | 11.03 | 11.26 | 10.78 | 11.19 | 10.60 | 10.39 | 10.69 | 11.07 |
| hsa-let-7c | 11.16 | 11.09 | 11.18 | 10.78 | 11.19 | 10.60 | 10.39 | 10.69 | 11.04 |
| hsa-let-7d | 9.31 | 9.73 | 9.72 | 9.99 | 9.88 | 9.69 | 10.17 | 9.84 | 9.98 |
| hsa-let-7e | 8.20 | 8.05 | 8.24 | 8.47 | 8.31 | 8.37 | 8.52 | 8.31 | 8.40 |
| hsa-let-7f | 7.89 | 8.67 | 8.60 | 8.69 | 8.58 | 8.47 | 9.22 | 8.87 | 9.08 |
| hsa-let-7g | 8.13 | 8.63 | 8.51 | 8.79 | 8.76 | 8.69 | 8.92 | 8.91 | 9.02 |
| hsa-let-7i | 8.46 | 8.50 | 8.53 | 8.76 | 8.63 | 8.75 | 8.92 | 8.69 | 8.89 |
| hsa-miR-1 | 3.68 | 5.01 | 5.90 | 5.54 | 5.17 | 5.03 | 5.98 | 5.62 | 6.34 |
| hsa-miR-100 | 9.02 | 9.02 | 9.28 | 9.42 | 9.34 | 9.25 | 9.28 | 9.21 | 9.22 |
| hsa-miR-101 | 3.40 | 3.95 | 3.97 | 4.29 | 4.35 | 4.90 | 5.15 | 4.57 | 4.96 |
| hsa-miR-103 | 8.28 | 8.17 | 8.27 | 8.65 | 8.41 | 8.67 | 8.53 | 8.26 | 8.43 |
| hsa-miR-105 | 1.67 | 1.41 | 1.55 | 1.64 | 1.95 | 1.70 | 1.58 | 1.57 | 2.10 |
| hsa-miR-106a | 7.21 | 7.57 | 7.53 | 7.50 | 7.46 | 7.80 | 7.48 | 7.57 | 7.50 |
| hsa-miR-106b | 6.19 | 6.32 | 6.39 | 6.19 | 6.37 | 6.83 | 6.66 | 6.37 | 6.56 |
| hsa-miR-107 | 8.20 | 8.19 | 8.15 | 8.55 | 8.42 | 8.61 | 8.43 | 8.26 | 8.41 |
| hsa-miR-10a | 6.53 | 6.66 | 6.86 | 7.50 | 7.73 | 7.69 | 7.77 | 7.36 | 7.30 |
| hsa-miR-10b | 7.27 | 7.50 | 7.64 | 8.13 | 8.26 | 8.18 | 8.13 | 8.05 | 7.91 |
| hsa-miR-122a | 3.56 | 3.17 | 3.59 | 2.80 | 3.16 | 2.99 | 3.09 | 3.88 | 3.46 |
| hsa-miR-124a | 3.45 | 2.55 | 2.36 | 3.69 | 5.04 | 4.42 | 4.18 | 3.41 | 2.60 |
| hsa-miR-125a | 8.64 | 8.32 | 8.93 | 9.34 | 9.27 | 8.90 | 9.07 | 8.30 | 8.83 |
| hsa-miR-125b | 10.14 | 9.87 | 10.25 | 10.70 | 10.65 | 10.40 | 10.33 | 10.27 | 10.17 |
| hsa-miR-126 | 9.45 | 9.36 | 9.34 | 9.57 | 9.35 | 9.32 | 9.63 | 9.46 | 9.50 |
| hsa-miR-126-AS | 4.96 | 5.22 | 5.24 | 5.63 | 5.45 | 5.50 | 6.31 | 5.77 | 5.62 |
| hsa-miR-127 | 4.52 | 3.88 | 4.27 | 4.62 | 4.53 | 5.21 | 4.85 | 4.82 | 4.72 |
| hsa-miR-128a | 5.03 | 4.91 | 5.43 | 5.70 | 5.46 | 5.44 | 5.36 | 5.03 | 5.21 |
| hsa-miR-129 | 2.70 | 2.55 | 2.74 | 2.66 | 2.64 | 2.62 | 2.35 | 2.84 | 2.38 |
| hsa-miR-130a | 7.31 | 7.31 | 7.45 | 7.40 | 8.00 | 8.57 | 8.41 | 7.54 | 7.64 |
| hsa-miR-130b | 4.69 | 4.88 | 4.53 | 4.68 | 4.87 | 5.07 | 5.13 | 4.86 | 4.76 |
| hsa-miR-132 | 5.31 | 5.73 | 5.53 | 5.87 | 5.41 | 5.89 | 5.77 | 5.97 | 5.60 |
| hsa-miR-133a | 6.29 | 6.08 | 7.68 | 7.68 | 7.46 | 7.27 | 7.10 | 7.16 | 7.34 |
| hsa-miR-134 | 5.02 | 4.64 | 4.87 | 5.09 | 4.90 | 5.31 | 5.34 | 5.00 | 5.31 |
| hsa-miR-135a | 2.36 | 1.28 | 1.55 | 2.42 | 2.13 | 2.16 | 3.19 | 2.38 | 2.10 |
| hsa-miR-135b | 1.42 | 1.77 | 1.89 | 1.88 | 2.08 | 1.82 | 1.77 | 1.70 | 2.24 |
| hsa-miR-136 | 2.36 | 0.04 | 2.61 | 1.64 | 2.13 | 1.58 | 1.71 | 1.43 | 2.29 |
| hsa-miR-137 | 2.57 | 2.73 | 1.73 | 1.96 | 1.68 | 2.10 | 2.96 | 2.32 | 2.64 |
| hsa-miR-138 | 1.90 | 2.67 | 2.61 | 2.00 | 2.02 | 2.38 | 2.09 | 2.35 | 2.49 |
| hsa-miR-139 | 5.02 | 3.51 | 3.99 | 4.92 | 4.63 | 4.88 | 5.37 | 5.00 | 5.35 |
| hsa-miR-140 | 4.53 | 5.11 | 4.85 | 4.97 | 4.92 | 4.97 | 5.52 | 5.10 | 5.18 |
| hsa-miR-141 | 5.76 | 6.07 | 5.39 | 5.38 | 5.96 | 6.99 | 6.82 | 5.87 | 5.93 |
| hsa-miR-142-3p | 3.61 | 3.31 | 3.41 | 2.82 | 2.84 | 2.51 | 3.03 | 3.12 | 3.23 |
| hsa-miR-142-5p | 3.40 | 3.74 | 3.59 | 3.55 | 3.97 | 3.22 | 3.70 | 3.90 | 3.47 |
| hsa-miR-143 | 10.20 | 10.26 | 10.37 | 10.58 | 10.75 | 10.21 | 10.39 | 10.45 | 10.38 |
| hsa-miR-144 | 1.42 | 0.78 | 1.55 | 1.23 | 1.53 | 1.54 | 1.51 | 1.09 | 1.99 |
| hsa-miR-145 | 11.35 | 11.23 | 11.36 | 10.78 | 11.19 | 10.60 | 10.39 | 10.69 | 11.07 |
| hsa-miR-146a | 5.81 | 6.21 | 5.60 | 6.39 | 6.04 | 6.15 | 5.59 | 6.27 | 5.66 |
| hsa-miR-147 | 2.19 | 2.83 | 2.56 | 2.16 | 2.60 | 1.86 | 1.95 | 2.16 | 1.56 |
| hsa-miR-148a | 6.33 | 6.63 | 6.40 | 6.41 | 7.01 | 6.57 | 7.13 | 6.64 | 6.67 |
| hsa-miR-148b | 3.73 | 4.12 | 4.28 | 4.61 | 4.47 | 3.95 | 4.99 | 3.81 | 4.58 |
| hsa-miR-149 | 4.19 | 4.16 | 3.84 | 4.17 | 4.28 | 4.26 | 4.06 | 4.00 | 3.80 |
| hsa-miR-150 | 6.07 | 6.09 | 6.47 | 6.37 | 6.00 | 6.17 | 6.01 | 5.95 | 5.85 |
| hsa-miR-151 | 5.82 | 5.65 | 5.74 | 6.06 | 5.92 | 5.98 | 5.84 | 5.95 | 5.76 |
| hsa-miR-152 | 7.21 | 7.04 | 6.85 | 7.30 | 7.12 | 7.26 | 7.41 | 6.89 | 7.19 |
| hsa-miR-153 | 2.70 | 2.67 | 1.97 | 2.16 | 2.13 | 2.38 | 2.86 | 2.51 | 2.73 |
| hsa-miR-154 | 5.07 | 4.57 | 4.76 | 4.92 | 4.98 | 5.73 | 5.49 | 5.10 | 5.13 |
| hsa-miR-155 | 5.21 | 5.58 | 5.73 | 5.67 | 5.36 | 5.51 | 5.25 | 5.82 | 5.08 |
| hsa-miR-15a | 6.02 | 6.42 | 6.43 | 6.36 | 6.78 | 6.75 | 6.93 | 6.79 | 6.74 |
| hsa-miR-15b | 6.45 | 6.83 | 6.83 | 7.02 | 7.07 | 6.87 | 7.06 | 6.55 | 6.70 |
| hsa-miR-16 | 9.60 | 9.59 | 9.57 | 9.80 | 10.01 | 9.71 | 9.73 | 9.62 | 9.64 |
| hsa-miR-17-3p | 4.06 | 4.23 | 3.87 | 4.34 | 4.44 | 4.95 | 4.49 | 4.39 | 4.17 |
| hsa-miR-17-5p | 7.28 | 7.43 | 7.41 | 7.31 | 7.37 | 7.60 | 7.28 | 7.40 | 7.39 |
| hsa-miR-18a | 4.20 | 4.75 | 4.39 | 3.53 | 3.77 | 4.95 | 4.56 | 4.03 | 4.67 |
| hsa-miR-181a | 6.58 | 6.64 | 6.87 | 6.94 | 7.15 | 6.48 | 7.30 | 6.14 | 6.58 |
| hsa-miR-181b | 5.78 | 5.80 | 6.03 | 6.23 | 6.39 | 6.24 | 6.26 | 5.88 | 5.81 |
| hsa-miR-181c | 3.48 | 3.74 | 3.94 | 4.17 | 4.24 | 4.26 | 4.37 | 4.11 | 3.86 |
| hsa-miR-182 | 5.29 | 5.48 | 4.79 | 4.90 | 5.48 | 5.19 | 5.21 | 4.96 | 4.36 |
| hsa-miR-182-AS | 0.78 | 2.55 | 2.04 | 0.91 | 1.53 | 1.78 | 1.61 | 1.48 | 2.33 |
| hsa-miR-183 | 3.12 | 3.59 | 1.64 | 3.15 | 3.29 | 3.32 | 3.18 | 2.65 | 1.88 |
| hsa-miR-184 | 3.94 | 3.92 | 3.41 | 3.65 | 3.31 | 3.53 | 3.57 | 3.81 | 3.76 |
| hsa-miR-185 | 5.49 | 5.66 | 5.50 | 5.35 | 5.42 | 5.94 | 5.75 | 5.67 | 5.75 |
| hsa-miR-186 | 3.48 | 4.19 | 4.33 | 4.08 | 4.18 | 4.19 | 4.81 | 4.54 | 4.83 |
| hsa-miR-187 | 4.58 | 4.56 | 4.89 | 6.35 | 5.60 | 5.62 | 5.44 | 5.35 | 5.78 |
| hsa-miR-188 | 3.64 | 3.37 | 3.20 | 3.10 | 3.29 | 3.55 | 3.39 | 3.72 | 3.11 |
| hsa-miR-189 | 3.81 | 4.11 | 4.30 | 4.78 | 4.74 | 4.82 | 4.83 | 4.66 | 4.35 |

TABLE 5-continued

Normalized Array Data for Sixteen Normal Cervix Tissue Samples (NCX1-NCX16). TV, threshold value, miRNAs > TV, number of miRNAs expressed at greater than threshold value. %, percentage of miRNAs expressed at greater than threshold value.

| | | | | | | | | | |
|---|---|---|---|---|---|---|---|---|---|
| hsa-miR-190 | 1.29 | 1.41 | 1.89 | 2.26 | 1.61 | 1.82 | 1.86 | 1.38 | 1.21 |
| hsa-miR-191 | 7.92 | 7.31 | 7.75 | 8.45 | 8.18 | 8.39 | 8.16 | 7.96 | 7.92 |
| hsa-miR-192 | 4.26 | 3.97 | 4.57 | 4.26 | 4.61 | 4.61 | 4.49 | 4.85 | 4.48 |
| hsa-miR-193a | 4.09 | 4.22 | 4.73 | 4.25 | 4.14 | 5.01 | 4.29 | 3.61 | 3.97 |
| hsa-miR-194 | 4.51 | 4.73 | 4.69 | 4.87 | 5.10 | 4.97 | 4.93 | 5.26 | 4.97 |
| hsa-miR-195 | 8.99 | 9.12 | 9.16 | 9.26 | 9.26 | 9.42 | 9.19 | 9.20 | 9.27 |
| hsa-miR-196a | 4.45 | 4.61 | 4.94 | 5.18 | 5.09 | 5.18 | 5.27 | 5.20 | 5.01 |
| hsa-miR-196b | 6.29 | 6.26 | 6.36 | 6.88 | 6.63 | 7.05 | 7.10 | 6.80 | 6.45 |
| hsa-miR-197 | 5.04 | 4.49 | 4.91 | 5.35 | 5.19 | 4.81 | 4.82 | 4.73 | 4.82 |
| hsa-miR-198 | 4.77 | 4.79 | 4.64 | 4.22 | 4.45 | 4.10 | 4.42 | 4.97 | 4.58 |
| hsa-miR-199a | 8.46 | 8.34 | 8.73 | 8.96 | 8.78 | 8.82 | 8.79 | 8.69 | 8.64 |
| hsa-miR-199a-AS | 8.61 | 8.70 | 8.53 | 9.27 | 8.98 | 8.75 | 9.08 | 9.27 | 9.14 |
| hsa-miR-199b | 6.90 | 7.06 | 6.96 | 6.46 | 6.98 | 6.81 | 7.33 | 7.19 | 6.94 |
| hsa-miR-19a | 3.51 | 3.84 | 3.81 | 3.53 | 4.19 | 4.63 | 5.07 | 4.46 | 4.64 |
| hsa-miR-19b | 7.46 | 7.56 | 7.65 | 7.68 | 7.82 | 7.93 | 7.99 | 7.77 | 7.84 |
| hsa-miR-20a | 6.01 | 6.54 | 6.32 | 6.38 | 6.22 | 6.74 | 6.46 | 6.60 | 6.45 |
| hsa-miR-200a | 6.48 | 6.73 | 5.80 | 6.18 | 6.51 | 7.24 | 7.36 | 6.90 | 6.53 |
| hsa-miR-200b | 7.39 | 7.51 | 6.90 | 7.41 | 7.60 | 7.79 | 7.88 | 7.72 | 7.35 |
| hsa-miR-200c | 8.46 | 8.65 | 8.07 | 8.23 | 8.44 | 8.60 | 8.50 | 8.19 | 8.13 |
| hsa-miR-203 | 8.93 | 10.08 | 8.13 | 7.18 | 6.45 | 7.41 | 7.04 | 6.65 | 6.75 |
| hsa-miR-204 | 3.61 | 3.59 | 5.08 | 5.30 | 4.86 | 5.30 | 4.98 | 5.43 | 4.75 |
| hsa-miR-205 | 9.40 | 10.01 | 8.28 | 7.79 | 7.89 | 7.90 | 7.75 | 7.49 | 7.65 |
| hsa-miR-206 | 2.64 | 3.01 | 3.08 | 3.22 | 2.81 | 2.97 | 3.24 | 3.80 | 2.93 |
| hsa-miR-208 | 1.79 | 1.28 | 1.73 | 1.74 | 1.53 | 1.93 | 1.54 | 1.48 | 2.15 |
| hsa-miR-21 | 8.95 | 9.54 | 8.92 | 9.18 | 9.08 | 9.30 | 9.30 | 9.69 | 9.69 |
| hsa-miR-210 | 6.26 | 6.59 | 5.68 | 5.20 | 5.33 | 6.49 | 5.43 | 5.06 | 5.74 |
| hsa-miR-211 | 2.10 | 2.67 | 1.08 | 1.79 | 2.81 | 2.70 | 2.37 | 2.51 | 1.82 |
| hsa-miR-212 | 2.57 | 3.21 | 3.14 | 3.43 | 3.21 | 2.94 | 3.31 | 3.06 | 2.42 |
| hsa-miR-213 | 1.79 | 1.98 | 1.36 | 2.26 | 2.34 | 2.19 | 2.11 | 2.20 | 2.46 |
| hsa-miR-214 | 8.01 | 7.60 | 8.21 | 8.83 | 8.30 | 8.44 | 8.34 | 8.16 | 8.31 |
| hsa-miR-215 | 1.16 | 1.77 | 1.17 | 1.96 | 2.08 | 2.07 | 2.14 | 2.29 | 2.20 |
| hsa-miR-216 | 0.56 | 1.41 | 2.41 | 1.92 | 2.24 | 2.00 | 1.80 | 1.87 | 1.82 |
| hsa-miR-217 | 2.28 | 3.28 | 1.81 | 1.83 | 1.75 | 2.07 | 1.98 | 1.79 | 1.76 |
| hsa-miR-218 | 5.26 | 5.60 | 5.45 | 5.70 | 5.78 | 5.72 | 6.25 | 5.91 | 5.98 |
| hsa-miR-219 | 1.90 | 1.88 | 2.18 | 2.66 | 2.02 | 2.43 | 2.32 | 2.65 | 2.05 |
| hsa-miR-22 | 8.37 | 8.41 | 7.86 | 8.45 | 8.37 | 8.87 | 8.59 | 8.80 | 8.61 |
| hsa-miR-220 | 1.03 | 2.25 | 1.89 | 1.59 | 1.61 | 1.66 | 1.68 | 1.95 | 1.99 |
| hsa-miR-221 | 8.19 | 8.43 | 8.35 | 8.43 | 8.56 | 8.51 | 8.15 | 8.37 | 8.31 |
| hsa-miR-222 | 7.58 | 7.63 | 7.72 | 8.06 | 8.32 | 7.89 | 7.61 | 7.90 | 7.50 |
| hsa-miR-223 | 5.90 | 7.26 | 6.14 | 6.69 | 6.42 | 5.77 | 6.27 | 6.50 | 6.09 |
| hsa-miR-224 | 5.89 | 6.45 | 5.64 | 5.91 | 5.76 | 5.58 | 5.83 | 5.63 | 5.76 |
| hsa-miR-23a | 9.38 | 9.55 | 9.22 | 9.62 | 9.62 | 9.45 | 9.69 | 9.38 | 9.48 |
| hsa-miR-23b | 9.91 | 9.92 | 9.70 | 10.21 | 10.18 | 10.02 | 10.12 | 9.73 | 9.89 |
| hsa-miR-24 | 9.85 | 9.80 | 9.54 | 10.04 | 9.84 | 10.08 | 9.83 | 9.80 | 9.73 |
| hsa-miR-25 | 6.14 | 6.52 | 6.49 | 6.63 | 6.62 | 6.59 | 6.72 | 6.57 | 6.75 |
| hsa-miR-26a | 10.83 | 10.75 | 10.98 | 10.78 | 11.12 | 10.60 | 10.39 | 10.69 | 10.81 |
| hsa-miR-26b | 6.65 | 7.34 | 7.43 | 7.86 | 7.64 | 7.61 | 8.35 | 8.06 | 7.87 |
| hsa-miR-27a | 8.67 | 9.02 | 8.56 | 8.78 | 8.76 | 8.72 | 8.92 | 8.63 | 8.86 |
| hsa-miR-27b | 8.96 | 9.13 | 9.03 | 9.49 | 9.42 | 9.32 | 9.45 | 9.02 | 9.14 |
| hsa-miR-28 | 5.50 | 5.79 | 5.91 | 6.26 | 6.07 | 5.96 | 6.27 | 6.03 | 6.21 |
| hsa-miR-296 | 2.91 | 3.06 | 2.56 | 2.51 | 2.56 | 2.57 | 2.23 | 2.46 | 2.46 |
| hsa-miR-299-5p | 4.88 | 4.61 | 4.79 | 5.00 | 4.74 | 4.96 | 5.16 | 4.88 | 5.18 |
| hsa-miR-29a | 9.23 | 9.18 | 9.26 | 9.11 | 9.33 | 9.58 | 9.67 | 9.40 | 9.49 |
| hsa-miR-29b | 6.40 | 6.70 | 6.47 | 6.58 | 6.80 | 7.61 | 7.57 | 7.30 | 7.34 |
| hsa-miR-29c | 5.97 | 6.56 | 6.69 | 5.95 | 6.66 | 7.26 | 7.61 | 6.84 | 7.07 |
| hsa-miR-301 | 1.67 | 1.88 | 2.24 | 1.88 | 2.64 | 3.29 | 3.26 | 1.95 | 2.60 |
| hsa-miR-302a | 2.28 | 2.48 | 2.36 | 2.08 | 2.19 | 2.36 | 1.98 | 2.13 | 2.20 |
| hsa-miR-302b | 1.16 | 2.41 | 2.56 | 1.54 | 1.37 | 1.78 | 1.54 | 1.66 | 1.42 |
| hsa-miR-302b-AS | 1.29 | 2.25 | 0.89 | 1.74 | 1.13 | 1.50 | 1.74 | 1.52 | 1.88 |
| hsa-miR-302c | 2.19 | 1.88 | 1.73 | 1.83 | 2.02 | 1.86 | 1.86 | 1.57 | 1.63 |
| hsa-miR-302c-AS | 3.77 | 3.51 | 4.06 | 2.45 | 2.19 | 3.59 | 2.94 | 4.53 | 4.20 |
| hsa-miR-302d | 1.90 | 1.28 | 2.93 | 1.88 | 2.29 | 1.66 | 1.86 | 1.75 | 1.69 |
| hsa-miR-30a-3p | 3.77 | 3.76 | 3.69 | 4.23 | 4.58 | 4.31 | 4.43 | 4.52 | 4.27 |
| hsa-miR-30a-5p | 7.85 | 7.82 | 7.81 | 8.36 | 8.26 | 8.69 | 8.46 | 8.33 | 8.33 |
| hsa-miR-30b | 6.67 | 6.72 | 7.00 | 7.81 | 7.60 | 7.44 | 7.86 | 7.78 | 7.45 |
| hsa-miR-30c | 7.47 | 7.29 | 7.42 | 7.90 | 8.00 | 7.71 | 7.76 | 7.71 | 7.44 |
| hsa-miR-30d | 7.93 | 7.77 | 7.93 | 8.39 | 8.07 | 8.39 | 8.24 | 8.28 | 8.38 |
| hsa-miR-30e-3p | 3.75 | 4.02 | 3.92 | 4.15 | 4.14 | 3.98 | 4.35 | 4.28 | 4.16 |
| hsa-miR-30e-5p | 7.17 | 7.32 | 7.15 | 7.50 | 7.47 | 8.05 | 7.85 | 7.58 | 7.65 |
| hsa-miR-31 | 8.00 | 8.31 | 7.21 | 6.75 | 6.86 | 7.84 | 7.02 | 6.87 | 7.03 |
| hsa-miR-32 | 1.79 | 1.77 | 2.47 | 2.19 | 2.13 | 2.13 | 2.09 | 2.06 | 1.94 |
| hsa-miR-320 | 8.38 | 8.31 | 8.58 | 8.40 | 8.56 | 8.51 | 8.44 | 8.23 | 8.32 |
| hsa-miR-323 | 2.86 | 2.25 | 2.30 | 2.39 | 2.02 | 2.66 | 2.51 | 2.41 | 2.10 |
| hsa-miR-324-3p | 5.75 | 5.30 | 5.76 | 6.10 | 5.74 | 6.02 | 5.52 | 5.89 | 5.76 |
| hsa-miR-324-5p | 2.70 | 3.10 | 3.66 | 3.32 | 3.14 | 3.78 | 3.32 | 3.35 | 3.46 |
| hsa-miR-325 | 2.28 | 2.41 | 2.74 | 2.19 | 2.29 | 2.16 | 2.11 | 2.80 | 1.42 |

TABLE 5-continued

Normalized Array Data for Sixteen Normal Cervix Tissue Samples (NCX1-NCX16). TV, threshold value, miRNAs > TV, number of miRNAs expressed at greater than threshold value. %, percentage of miRNAs expressed at greater than threshold value.

| | | | | | | | | | |
|---|---|---|---|---|---|---|---|---|---|
| hsa-miR-326 | 2.70 | 2.41 | 2.52 | 2.54 | 2.78 | 2.36 | 2.16 | 2.32 | 2.98 |
| hsa-miR-328 | 3.43 | 2.93 | 3.77 | 3.94 | 3.91 | 3.82 | 3.61 | 4.02 | 3.33 |
| hsa-miR-33 | 1.90 | 1.77 | 0.21 | 1.54 | 1.61 | 2.19 | 2.16 | 1.75 | 1.82 |
| hsa-miR-330 | 2.64 | 3.21 | 2.78 | 2.94 | 2.71 | 3.07 | 2.66 | 2.78 | 2.76 |
| hsa-miR-331 | 5.22 | 5.08 | 5.32 | 5.18 | 5.15 | 5.31 | 5.21 | 4.96 | 5.15 |
| hsa-miR-335 | 3.64 | 4.34 | 4.50 | 5.05 | 4.72 | 4.79 | 5.37 | 4.48 | 4.79 |
| hsa-miR-337 | 2.81 | 2.78 | 2.70 | 1.92 | 1.61 | 1.74 | 2.14 | 2.26 | 2.42 |
| hsa-miR-338 | 2.57 | 2.67 | 2.52 | 1.54 | 2.34 | 2.70 | 3.27 | 2.65 | 3.02 |
| hsa-miR-339 | 5.17 | 4.48 | 5.09 | 5.17 | 4.98 | 5.07 | 5.06 | 4.79 | 4.98 |
| hsa-miR-340 | 0.78 | 1.28 | 2.99 | 2.23 | 2.24 | 2.13 | 2.19 | 2.26 | 2.60 |
| hsa-miR-342 | 7.00 | 7.07 | 7.25 | 7.77 | 7.39 | 7.31 | 7.24 | 7.35 | 7.31 |
| hsa-miR-345 | 4.28 | 3.70 | 4.02 | 4.81 | 4.65 | 4.83 | 4.73 | 4.65 | 4.18 |
| hsa-miR-346 | 2.10 | 1.98 | 2.30 | 2.12 | 2.48 | 1.97 | 1.80 | 2.10 | 1.88 |
| hsa-miR-34a | 7.72 | 7.46 | 7.62 | 7.21 | 7.72 | 7.93 | 7.40 | 7.44 | 7.28 |
| hsa-miR-34b | 3.96 | 4.06 | 4.59 | 3.80 | 4.45 | 6.40 | 5.19 | 4.85 | 4.83 |
| hsa-miR-34c | 2.43 | 3.34 | 3.14 | 2.64 | 3.56 | 6.55 | 4.86 | 4.70 | 4.12 |
| hsa-miR-361 | 6.81 | 6.75 | 6.82 | 7.35 | 7.09 | 7.27 | 7.07 | 6.85 | 6.89 |
| hsa-miR-365 | 3.30 | 2.97 | 3.22 | 3.43 | 3.76 | 3.63 | 4.29 | 3.77 | 3.57 |
| hsa-miR-367 | 1.79 | 1.15 | 1.46 | 2.12 | 1.68 | 1.74 | 1.58 | 1.48 | 0.55 |
| hsa-miR-368 | 7.00 | 6.94 | 6.77 | 7.08 | 6.79 | 7.38 | 7.60 | 7.28 | 7.36 |
| hsa-miR-369-3p | 1.16 | 0.90 | 0.98 | 1.54 | 1.82 | 1.70 | 2.21 | 1.57 | 2.10 |
| hsa-miR-370 | 5.17 | 4.89 | 5.13 | 4.17 | 4.32 | 4.23 | 4.54 | 4.79 | 4.47 |
| hsa-miR-371 | 1.55 | 2.48 | 1.46 | 1.33 | 1.89 | 1.58 | 1.54 | 1.79 | 1.28 |
| hsa-miR-372 | 2.19 | 2.25 | 1.55 | 1.07 | 1.53 | 1.37 | 1.64 | 1.79 | 1.42 |
| hsa-miR-373 | 1.55 | 2.83 | 1.08 | 1.74 | 1.95 | 1.78 | 1.89 | 1.95 | 1.69 |
| hsa-miR-373-AS | 4.09 | 3.74 | 3.17 | 3.39 | 3.33 | 3.44 | 3.61 | 3.30 | 2.98 |
| hsa-miR-374 | 1.55 | 2.67 | 2.78 | 2.86 | 3.07 | 3.07 | 3.90 | 3.46 | 3.38 |
| hsa-miR-375 | 4.28 | 4.15 | 4.52 | 4.83 | 4.90 | 5.48 | 5.00 | 4.97 | 4.72 |
| hsa-miR-376a | 5.00 | 5.21 | 5.04 | 5.21 | 4.84 | 5.55 | 6.39 | 5.70 | 5.64 |
| hsa-miR-377 | 3.51 | 3.54 | 3.47 | 3.06 | 3.19 | 3.94 | 4.44 | 3.46 | 4.26 |
| hsa-miR-378 | 3.75 | 3.88 | 3.95 | 3.96 | 4.34 | 4.47 | 4.19 | 4.12 | 3.72 |
| hsa-miR-379 | 5.72 | 5.30 | 5.07 | 5.67 | 5.39 | 5.77 | 5.80 | 5.87 | 5.63 |
| hsa-miR-380-3p | 0.36 | 2.08 | 2.74 | 1.49 | 1.53 | 1.45 | 1.71 | 1.33 | 1.21 |
| hsa-miR-380-5p | 1.67 | 1.28 | 1.27 | 2.04 | 1.53 | 1.58 | 1.77 | 1.24 | 2.24 |
| hsa-miR-381 | 4.26 | 4.08 | 4.23 | 4.48 | 4.21 | 5.23 | 4.92 | 4.51 | 4.61 |
| hsa-miR-382 | 4.65 | 4.61 | 4.42 | 4.47 | 4.21 | 4.68 | 5.02 | 4.35 | 4.86 |
| hsa-miR-383 | 1.79 | 2.83 | 2.61 | 1.96 | 2.24 | 2.13 | 2.23 | 2.65 | 2.49 |
| hsa-miR-384 | 2.01 | 1.41 | 0.34 | 1.33 | 1.89 | 1.32 | 1.51 | 0.82 | 1.07 |
| hsa-miR-422a | 3.96 | 4.93 | 4.99 | 5.53 | 5.72 | 5.83 | 5.75 | 5.91 | 4.68 |
| hsa-miR-422b | 6.39 | 6.57 | 6.68 | 6.68 | 6.90 | 7.08 | 6.78 | 6.85 | 6.30 |
| hsa-miR-423 | 6.08 | 5.89 | 6.31 | 6.64 | 6.63 | 6.19 | 6.21 | 6.09 | 5.89 |
| hsa-miR-424 | 5.11 | 5.92 | 5.92 | 5.65 | 6.53 | 6.02 | 7.16 | 5.84 | 5.88 |
| hsa-miR-425 | 3.92 | 3.56 | 3.49 | 4.27 | 3.97 | 4.23 | 4.15 | 4.02 | 4.07 |
| hsa-miR-429 | 4.63 | 5.03 | 4.42 | 4.96 | 5.08 | 5.46 | 5.72 | 5.43 | 4.72 |
| hsa-miR-448 | 0.78 | 2.61 | 1.46 | 1.18 | 1.75 | 1.82 | 1.58 | 1.79 | 1.21 |
| hsa-miR-449 | 2.19 | 2.17 | 1.46 | 2.54 | 2.64 | 4.39 | 3.12 | 2.93 | 1.82 |
| hsa-miR-450 | 2.86 | 1.77 | 2.99 | 2.45 | 2.43 | 2.75 | 3.39 | 2.63 | 2.33 |
| hsa-miR-7 | 2.70 | 3.34 | 2.24 | 2.64 | 2.71 | 2.41 | 3.14 | 2.98 | 3.02 |
| hsa-miR-9 | 0.36 | 2.88 | 3.02 | 2.04 | 1.89 | 2.03 | 2.61 | 2.49 | 2.33 |
| hsa-miR-9-AS | 2.95 | 3.76 | 3.11 | 3.29 | 3.07 | 3.30 | 4.02 | 3.85 | 3.70 |
| hsa-miR-92 | 6.97 | 6.60 | 7.16 | 7.20 | 7.06 | 7.32 | 6.96 | 6.84 | 7.11 |
| hsa-miR-93 | 6.75 | 7.05 | 7.03 | 7.07 | 6.99 | 7.10 | 6.89 | 6.74 | 6.77 |
| hsa-miR-95 | 3.27 | 3.76 | 3.22 | 3.15 | 3.31 | 3.22 | 3.42 | 3.38 | 3.31 |
| hsa-miR-96 | 3.48 | 3.84 | 2.96 | 3.11 | 3.56 | 3.59 | 4.14 | 3.44 | 3.86 |
| hsa-miR-98 | 5.14 | 5.32 | 5.57 | 5.71 | 5.65 | 5.42 | 6.05 | 5.87 | 5.86 |
| hsa-miR-99a | 9.85 | 9.75 | 10.19 | 10.21 | 10.22 | 10.10 | 10.13 | 10.08 | 10.16 |
| hsa-miR-99b | 7.04 | 7.03 | 7.48 | 7.73 | 7.49 | 7.60 | 7.30 | 7.42 | 7.49 |
| mmu-let-7d-AS | 1.03 | 1.03 | 2.41 | 1.39 | 1.53 | 1.97 | 1.68 | 2.06 | 2.87 |
| mmu-miR-101b | 0.67 | 1.28 | 1.08 | 2.45 | 2.24 | 2.66 | 2.63 | 2.16 | 1.88 |
| mmu-miR-106a | 6.64 | 6.96 | 6.82 | 6.79 | 6.66 | 7.03 | 6.77 | 6.91 | 6.81 |
| mmu-miR-129-3p | 1.79 | 1.03 | 3.14 | 2.76 | 2.43 | 2.19 | 1.95 | 2.23 | 2.49 |
| mmu-miR-140-AS | 7.12 | 6.80 | 7.06 | 7.36 | 7.27 | 7.47 | 7.30 | 7.18 | 7.20 |
| mmu-miR-151 | 3.61 | 3.48 | 3.87 | 4.74 | 4.63 | 4.46 | 4.74 | 4.77 | 3.96 |
| mmu-miR-155 | 0.67 | 3.21 | 3.66 | 3.10 | 2.71 | 3.03 | 3.45 | 4.09 | 2.95 |
| mmu-miR-17-3p | 0.90 | 3.01 | 2.61 | 3.08 | 3.25 | 3.59 | 3.39 | 3.15 | 2.98 |
| mmu-miR-192 | 3.66 | 4.12 | 4.48 | 4.04 | 4.44 | 4.45 | 4.42 | 4.67 | 4.33 |
| mmu-miR-199b | 5.60 | 6.01 | 6.38 | 6.33 | 6.50 | 6.90 | 6.63 | 6.63 | 6.51 |
| mmu-miR-201 | 0.27 | 1.15 | 2.82 | 1.44 | 1.68 | 1.74 | 1.77 | 1.38 | 2.05 |
| mmu-miR-202 | 4.42 | 4.71 | 4.38 | 3.57 | 3.49 | 3.46 | 3.61 | 4.13 | 4.24 |
| mmu-miR-207 | 3.00 | 2.17 | 2.56 | 2.19 | 2.71 | 2.16 | 2.03 | 2.13 | 1.99 |
| mmu-miR-211 | 1.67 | 2.25 | 1.97 | 1.23 | 1.61 | 1.62 | 1.51 | 1.83 | 0.93 |
| mmu-miR-215 | 2.19 | 1.15 | 1.73 | 1.59 | 2.02 | 1.66 | 1.68 | 1.62 | 2.05 |
| mmu-miR-217 | 0.56 | 2.33 | 2.18 | 1.49 | 1.68 | 1.89 | 1.71 | 1.66 | 1.99 |
| mmu-miR-290 | 2.95 | 3.24 | 3.11 | 2.82 | 2.87 | 2.84 | 2.91 | 3.21 | 3.05 |
| mmu-miR-291-3p | 2.01 | 2.17 | 1.73 | 1.79 | 1.89 | 1.62 | 1.47 | 1.62 | 1.35 |
| mmu-miR-291-5p | 2.64 | 2.25 | 2.24 | 2.00 | 2.02 | 1.89 | 2.11 | 2.13 | 1.63 |

TABLE 5-continued

Normalized Array Data for Sixteen Normal Cervix Tissue Samples (NCX1-NCX16). TV, threshold value, miRNAs > TV, number of miRNAs expressed at greater than threshold value. %, percentage of miRNAs expressed at greater than threshold value.

| | | | | | | | | | |
|---|---|---|---|---|---|---|---|---|---|
| mmu-miR-292-3p | 0.56 | 2.61 | 3.14 | 1.92 | 1.95 | 2.10 | 1.80 | 2.03 | 2.10 |
| mmu-miR-292-5p | 2.43 | 2.08 | 2.24 | 2.19 | 2.34 | 2.07 | 2.39 | 2.68 | 2.46 |
| mmu-miR-293 | 2.51 | 2.33 | 1.81 | 1.74 | 2.29 | 1.70 | 1.71 | 1.99 | 1.35 |
| mmu-miR-294 | 2.01 | 1.53 | 1.36 | 2.36 | 2.60 | 2.07 | 2.26 | 2.03 | 1.99 |
| mmu-miR-295 | 2.36 | 2.08 | 2.04 | 1.92 | 1.68 | 1.54 | 1.61 | 1.70 | 1.63 |
| mmu-miR-297 | 0.90 | 1.15 | 1.81 | 1.79 | 1.68 | 1.37 | 1.83 | 1.91 | 1.63 |
| mmu-miR-298 | 4.90 | 4.64 | 4.63 | 4.32 | 4.29 | 4.03 | 4.31 | 4.70 | 4.58 |
| mmu-miR-300 | 2.81 | 3.06 | 2.96 | 3.23 | 3.16 | 3.59 | 3.61 | 3.15 | 3.05 |
| mmu-miR-322 | 2.95 | 0.78 | 1.97 | 1.83 | 2.02 | 1.70 | 1.74 | 1.52 | 1.35 |
| mmu-miR-424 | 3.73 | 4.76 | 4.98 | 4.57 | 5.47 | 4.96 | 5.98 | 4.63 | 4.66 |
| mmu-miR-325 | 2.10 | 2.61 | 1.97 | 1.88 | 1.68 | 1.86 | 1.95 | 2.06 | 2.24 |
| mmu-miR-329 | 2.01 | 2.48 | 2.89 | 1.83 | 2.08 | 1.97 | 1.80 | 2.10 | 2.46 |
| mmu-miR-330 | 2.10 | 2.67 | 1.89 | 2.08 | 1.89 | 2.16 | 1.89 | 1.91 | 1.49 |
| mmu-miR-337 | 2.10 | 1.53 | 2.41 | 1.64 | 1.75 | 1.89 | 2.03 | 1.91 | 1.63 |
| mmu-miR-341 | 3.23 | 2.41 | 3.06 | 2.19 | 2.29 | 2.19 | 2.23 | 2.23 | 2.24 |
| mmu-miR-344 | 0.56 | 0.56 | 1.81 | 1.49 | 1.45 | 1.74 | 1.44 | 1.43 | 1.99 |
| mmu-miR-345 | 2.57 | 2.25 | 2.52 | 2.84 | 2.81 | 2.43 | 2.49 | 2.49 | 2.60 |
| mmu-miR-346 | 0.36 | 1.41 | 1.73 | 2.90 | 2.56 | 1.86 | 2.14 | 2.13 | 2.20 |
| mmu-miR-34b | 2.28 | 2.08 | 2.66 | 1.96 | 2.60 | 4.42 | 3.66 | 3.30 | 2.76 |
| mmu-miR-350 | 2.86 | 2.93 | 1.81 | 1.79 | 2.08 | 1.70 | 1.64 | 1.70 | 1.88 |
| mmu-miR-351 | 2.57 | 1.53 | 2.30 | 1.96 | 2.24 | 2.10 | 2.03 | 1.95 | 1.94 |
| mmu-miR-376a | 2.81 | 3.10 | 2.18 | 2.80 | 2.90 | 3.25 | 3.99 | 3.38 | 3.21 |
| mmu-miR-376b | 1.79 | 3.21 | 2.04 | 2.08 | 1.82 | 2.07 | 2.09 | 2.20 | 2.42 |
| mmu-miR-380-3p | 3.12 | 2.08 | 2.70 | 2.51 | 2.39 | 2.48 | 2.58 | 2.93 | 2.57 |
| mmu-miR-383 | 3.00 | 2.55 | 3.08 | 1.96 | 1.89 | 2.25 | 2.09 | 2.38 | 1.42 |
| mmu-miR-384 | 0.18 | 0.67 | 0.89 | 1.74 | 1.53 | 1.41 | 1.54 | 1.57 | 2.42 |
| mmu-miR-409 | 5.08 | 4.57 | 4.49 | 4.76 | 4.25 | 4.88 | 5.18 | 4.83 | 5.12 |
| hsa-miR-410 | 3.08 | 3.01 | 2.66 | 2.98 | 2.99 | 3.38 | 3.61 | 3.48 | 3.49 |
| mmu-miR-411 | 3.04 | 2.83 | 2.24 | 2.80 | 2.81 | 2.31 | 3.03 | 2.51 | 2.98 |
| hsa-miR-412 | 1.16 | 0.78 | 2.36 | 1.92 | 1.29 | 1.62 | 1.64 | 1.83 | 1.69 |
| mmu-miR-429 | 1.16 | 2.08 | 1.73 | 2.08 | 2.02 | 1.82 | 1.98 | 1.87 | 1.88 |
| mmu-miR-7b | 2.75 | 1.98 | 2.47 | 2.30 | 2.13 | 1.86 | 1.98 | 1.99 | 2.38 |
| rno-miR-151-AS | 7.21 | 6.98 | 7.12 | 7.34 | 7.23 | 7.24 | 7.25 | 6.98 | 7.19 |
| rno-miR-20-AS | 1.67 | 2.78 | 2.78 | 2.12 | 1.95 | 1.58 | 1.58 | 1.66 | 2.10 |
| rno-miR-297 | 1.03 | 1.15 | 2.11 | 1.59 | 1.13 | 1.70 | 1.61 | 1.19 | 1.42 |
| rno-miR-327 | 3.56 | 3.86 | 3.64 | 3.19 | 3.21 | 2.79 | 3.19 | 3.74 | 3.63 |
| rno-miR-333 | 2.28 | 1.88 | 2.47 | 1.88 | 1.89 | 1.93 | 1.74 | 1.87 | 1.99 |
| rno-miR-336 | 4.01 | 3.10 | 2.78 | 3.23 | 3.39 | 4.06 | 3.06 | 3.39 | 3.83 |
| rno-miR-343 | 2.19 | 1.53 | 2.61 | 2.16 | 2.19 | 1.89 | 1.68 | 1.66 | 1.28 |
| rno-miR-344 | 0.90 | 1.15 | 1.55 | 0.97 | 1.68 | 1.54 | 1.61 | 1.57 | 1.88 |
| rno-miR-346 | 2.81 | 1.98 | 2.86 | 3.01 | 3.49 | 1.93 | 1.64 | 2.06 | 1.42 |
| rao-miR-347 | 2.86 | 0.90 | 1.64 | 2.54 | 1.95 | 2.00 | 2.32 | 2.38 | 2.57 |
| rno-miR-349 | 0.67 | 0.56 | 0.56 | 1.74 | 2.19 | 1.50 | 1.68 | 1.14 | 1.69 |
| rno-miR-352 | 5.14 | 5.41 | 5.70 | 5.95 | 5.78 | 5.55 | 6.30 | 5.91 | 5.85 |
| rno-miR-421 | 1.90 | 1.98 | 0.64 | 1.88 | 1.75 | 1.66 | 1.58 | 1.70 | 2.42 |
| rno-miR-7-AS | 1.03 | 1.65 | 2.66 | 2.90 | 2.84 | 2.03 | 2.86 | 2.10 | 2.33 |
| hsa-miR-522 | 2.01 | 2.33 | 2.66 | 1.33 | 1.21 | 1.50 | 1.68 | 1.99 | 1.99 |
| hsa-miR-519b | 0.90 | 2.17 | 2.04 | 1.79 | 1.89 | 1.93 | 1.61 | 1.48 | 2.20 |
| hsa-miR-520c | 0.56 | 2.41 | 1.27 | 2.42 | 1.89 | 1.62 | 1.74 | 1.52 | 1.49 |
| hsa-miR-519e | 1.42 | 0.90 | 0.98 | 1.74 | 2.02 | 1.62 | 1.54 | 1.52 | 1.35 |
| hsa-miR-519d | 1.55 | 2.61 | 1.46 | 1.64 | 2.39 | 2.00 | 1.68 | 1.79 | 2.20 |
| hsa-miR-520b | 2.19 | 2.25 | 1.08 | 1.64 | 1.61 | 1.50 | 1.61 | 1.52 | 1.35 |
| hsa-miR-519c | 2.10 | 1.28 | 1.46 | 1.39 | 1.89 | 1.66 | 1.54 | 1.43 | 1.76 |
| hsa-miR-526b-AS | 1.67 | 2.73 | 1.17 | 1.28 | 1.61 | 1.66 | 1.40 | 1.19 | 1.82 |
| hsa-miR-520e | 1.03 | 2.33 | 2.41 | 1.64 | 1.75 | 1.82 | 1.61 | 1.99 | 2.53 |
| hsa-miR-520a | 0.78 | 0.78 | 1.46 | 1.44 | 1.75 | 1.58 | 1.47 | 1.70 | 1.76 |
| hsa-miR-520d | 1.16 | 2.41 | 1.97 | 1.69 | 1.68 | 1.82 | 1.86 | 1.99 | 1.94 |
| hsa-miR-520h | 2.28 | 2.73 | 1.64 | 2.00 | 1.75 | 1.32 | 1.44 | 1.70 | 2.05 |
| hsa-miR-517a | 1.55 | 2.41 | 1.08 | 2.00 | 1.82 | 1.78 | 1.68 | 2.03 | 2.24 |
| hsa-miR-518e | 1.55 | 1.98 | 2.30 | 1.33 | 0.97 | 1.58 | 1.61 | 1.33 | 1.69 |
| hsa-miR-521 | 2.51 | 2.41 | 2.52 | 1.69 | 1.45 | 1.78 | 1.77 | 1.43 | 2.24 |
| hsa-miR-523 | 2.36 | 2.17 | 2.18 | 1.44 | 1.29 | 1.58 | 1.64 | 1.52 | 2.10 |
| hsa-miR-518f | 1.79 | 1.65 | 1.81 | 1.59 | 1.68 | 1.82 | 1.61 | 1.75 | 1.76 |
| hsa-miR-518c | 1.79 | −0.02 | 3.17 | 2.64 | 1.68 | 1.74 | 1.47 | 1.29 | 2.10 |
| hsa-miR-518b | 2.01 | 1.65 | 0.72 | 2.36 | 2.34 | 1.97 | 1.68 | 1.83 | 1.88 |
| hsa-miR-518d | 1.42 | 2.17 | 1.17 | 2.19 | 1.75 | 1.70 | 1.47 | 1.52 | 0.86 |
| hsa-miR-525-AS | 1.16 | 1.65 | 0.56 | 1.18 | 1.37 | 1.50 | 1.40 | 1.09 | 1.42 |
| hsa-miR-524 | 2.28 | 2.55 | 1.27 | 1.92 | 1.75 | 1.58 | 1.80 | 1.66 | 1.63 |
| hsa-miR-518a | 0.27 | 1.53 | 2.04 | 1.39 | 1.45 | 1.41 | 1.26 | 1.48 | 1.82 |
| hsa-miR-515-3p | 1.55 | 2.41 | 2.66 | 1.44 | 2.19 | 1.58 | 1.64 | 1.83 | 1.42 |
| hsa-miR-516-3p | 2.57 | 1.03 | 2.70 | 1.83 | 1.58 | 1.77 | 1.95 | 2.20 | |
| ambi-miR-7026 | 0.90 | 1.41 | 1.89 | 1.69 | 1.95 | 1.58 | 1.44 | 1.29 | 1.35 |
| ambi-miR-7027 | 3.37 | 3.21 | 2.61 | 3.33 | 3.16 | 3.76 | 3.51 | 3.43 | 2.95 |
| hsa-miR-512-3p | 1.67 | 2.25 | 2.74 | 2.33 | 2.13 | 1.93 | 1.64 | 2.29 | 2.53 |
| ambi-miR-7029 | 6.16 | 6.97 | 7.49 | 6.33 | 7.72 | 7.62 | 7.77 | 7.24 | 7.71 |
| hsa-miR-491 | 4.16 | 3.82 | 3.90 | 3.64 | 3.66 | 3.88 | 3.85 | 3.93 | 3.74 |

TABLE 5-continued

Normalized Array Data for Sixteen Normal Cervix Tissue Samples (NCX1-NCX16). TV, threshold value, miRNAs > TV, number of miRNAs expressed at greater than threshold value. %, percentage of miRNAs expressed at greater than threshold value.

| | | | | | | | | | |
|---|---|---|---|---|---|---|---|---|---|
| hsa-miR-506 | 2.01 | 2.25 | 2.04 | 1.69 | 1.13 | 1.82 | 2.03 | 1.87 | 2.20 |
| hsa-miR-514 | 0.90 | 1.88 | 0.56 | 1.39 | 1.53 | 1.62 | 1.54 | 1.43 | 1.00 |
| hsa-miR-509 | 2.75 | 2.25 | 1.89 | 2.00 | 1.89 | 2.07 | 1.98 | 2.03 | 2.46 |
| hsa-miR-508 | 1.16 | 2.08 | 0.98 | 1.54 | 1.75 | 1.86 | 1.58 | 1.95 | 1.14 |
| hsa-miR-507 | 2.75 | 1.41 | 1.55 | 1.74 | 1.61 | 1.78 | 1.51 | 1.38 | 1.63 |
| ambi-miR-7036 | 2.36 | 1.41 | 2.30 | 2.86 | 3.12 | 2.91 | 3.09 | 3.44 | 3.39 |
| hsa-miR-193b | 6.95 | 6.73 | 6.58 | 7.07 | 6.98 | 7.03 | 6.97 | 6.68 | 6.59 |
| ambi-miR-7038-1 | 2.95 | 2.08 | 1.36 | 1.44 | 2.24 | 1.86 | 1.74 | 2.23 | 2.15 |
| ambi-miR-7039 | 5.20 | 5.21 | 4.80 | 4.51 | 4.16 | 4.69 | 3.91 | 4.46 | 4.66 |
| hsa-miR-488 | 2.36 | 1.65 | 2.56 | 1.59 | 1.68 | 1.78 | 1.68 | 1.91 | 1.99 |
| hsa-miR-510 | 2.64 | 1.65 | 2.56 | 1.59 | 1.89 | 1.62 | 1.71 | 2.03 | 1.69 |
| hsa-miR-517-AS | 2.19 | 2.25 | 1.55 | 2.08 | 2.19 | 1.70 | 1.83 | 1.83 | 1.99 |
| hsa-miR-518f-AS | 2.28 | 2.25 | 2.04 | 1.88 | 2.08 | 1.45 | 1.37 | 1.62 | 1.69 |
| hsa-miR-518c-AS | 4.09 | 3.46 | 3.61 | 3.13 | 3.23 | 3.14 | 3.32 | 3.70 | 3.44 |
| hsa-miR-526c | 0.56 | 1.28 | 0.72 | 1.74 | 1.75 | 1.74 | 1.86 | 1.70 | 1.94 |
| hsa-miR-526b | 2.28 | 1.88 | 3.08 | 2.16 | 2.39 | 2.13 | 2.16 | 3.21 | 2.53 |
| hsa-miR-520a-AS | 1.29 | 0.56 | 0.56 | 1.74 | 1.21 | 1.66 | 1.64 | 1.14 | 2.10 |
| hsa-miR-525 | 1.29 | 1.15 | 2.11 | 1.83 | 1.75 | 2.03 | 2.03 | 2.38 | 1.76 |
| hsa-miR-524-AS | 2.64 | 2.33 | 2.74 | 2.82 | 2.13 | 2.36 | 1.98 | 2.13 | 2.73 |
| hsa-miR-520d-AS | 2.64 | 0.37 | 0.56 | 2.12 | 1.89 | 1.86 | 1.92 | 1.91 | 1.28 |
| hsa-miR-527 | 3.00 | 2.41 | 2.47 | 2.08 | 2.39 | 1.97 | 2.14 | 2.29 | 2.33 |
| hsa-miR-515-5p | 1.79 | 1.15 | 1.46 | 1.79 | 2.34 | 1.66 | 1.33 | 1.57 | 1.88 |
| hsa-miR-519e-AS | 1.03 | 1.53 | 2.56 | 1.79 | 1.95 | 1.66 | 1.77 | 2.16 | 1.63 |
| ambi-miR-7054 | 2.10 | 2.48 | 1.17 | 1.28 | 1.53 | 1.54 | 1.68 | 1.66 | 1.49 |
| ambi-miR-7055 | 1.55 | 1.03 | 2.36 | 2.23 | 2.02 | 2.00 | 1.86 | 2.03 | 2.24 |
| hsa-miR-498 | 1.42 | 1.53 | 2.18 | 2.54 | 2.29 | 2.25 | 2.43 | 2.26 | 2.67 |
| hsa-miR-513 | 3.54 | 4.20 | 3.57 | 3.92 | 4.09 | 4.12 | 3.87 | 5.23 | 4.14 |
| ambi-miR-7058 | 6.06 | 5.90 | 6.26 | 6.07 | 6.24 | 5.58 | 6.00 | 5.71 | 5.86 |
| ambi-miR-7059-1 | 2.01 | 1.88 | 2.04 | 1.54 | 1.75 | 1.54 | 1.74 | 1.48 | 2.20 |
| hsa-miR-452 | 5.30 | 5.18 | 4.43 | 4.77 | 4.77 | 5.01 | 5.05 | 4.83 | 4.61 |
| hsa-miR-493 | 2.36 | 1.53 | 2.56 | 2.42 | 2.39 | 2.38 | 3.10 | 2.54 | 2.46 |
| ambi-miR-7062 | 3.20 | 2.73 | 2.04 | 2.42 | 2.34 | 2.51 | 2.23 | 2.35 | 2.49 |
| hsa-miR-432 | 5.05 | 4.78 | 4.91 | 5.02 | 4.77 | 5.07 | 5.36 | 5.19 | 5.09 |
| hsa-miR-495 | 4.23 | 4.40 | 4.74 | 5.09 | 4.75 | 5.08 | 5.33 | 5.04 | 4.93 |
| hsa-miR-494 | 6.36 | 6.37 | 5.82 | 5.97 | 5.95 | 6.18 | 6.00 | 7.04 | 6.21 |
| ambi-miR-7066 | 1.42 | 2.73 | 2.52 | 2.66 | 2.48 | 2.62 | 2.58 | 2.70 | 2.98 |
| ambi-miR-7067 | 2.91 | 2.67 | 2.56 | 2.86 | 2.78 | 2.89 | 3.29 | 2.51 | 2.82 |
| ambi-miR-7068-1 | 3.08 | 2.93 | 3.14 | 3.16 | 3.04 | 3.18 | 3.40 | 3.30 | 3.38 |
| hsa-miR-496 | 2.19 | 1.03 | 2.52 | 1.64 | 1.37 | 1.78 | 1.71 | 1.43 | 1.35 |
| ambi-miR-7070 | 4.80 | 4.49 | 4.44 | 4.71 | 4.46 | 4.95 | 4.97 | 4.79 | 4.84 |
| hsa-miR-492 | 1.90 | 0.28 | 1.55 | 1.79 | 2.29 | 1.89 | 1.77 | 2.16 | 1.88 |
| hsa-miR-490 | 1.90 | 1.15 | 1.97 | 1.88 | 1.75 | 1.74 | 1.68 | 1.62 | 1.94 |
| hsa-miR-497 | 7.68 | 7.50 | 7.68 | 7.74 | 7.71 | 8.36 | 7.61 | 7.99 | 7.80 |
| ambi-miR-7074 | 2.28 | 1.98 | 2.74 | 1.88 | 1.53 | 1.70 | 1.64 | 1.95 | 2.33 |
| ambi-miR-7075 | 3.77 | 3.48 | 4.30 | 3.67 | 4.13 | 4.14 | 3.86 | 3.91 | 3.92 |
| ambi-miR-7076 | 4.32 | 4.34 | 4.59 | 4.80 | 4.75 | 5.12 | 4.53 | 4.85 | 4.65 |
| hsa-miR-501 | 2.36 | 3.06 | 2.18 | 2.00 | 2.48 | 2.28 | 2.01 | 2.16 | 2.33 |
| hsa-miR-502 | 3.27 | 2.78 | 3.41 | 3.34 | 3.29 | 3.30 | 3.24 | 3.60 | 3.20 |
| ambi-miR-7079 | 3.87 | 3.56 | 4.34 | 4.18 | 5.14 | 5.43 | 4.93 | 4.37 | 4.55 |
| ambi-miR-7080 | 1.67 | 2.33 | 2.66 | 2.33 | 2.48 | 1.93 | 2.16 | 2.56 | 2.46 |
| ambi-miR-7081 | 3.96 | 4.32 | 3.97 | 3.94 | 3.99 | 3.53 | 3.86 | 4.14 | 4.20 |
| hsa-miR-202-AS | 1.67 | 1.03 | 1.55 | 1.23 | 1.32 | 1.41 | 1.37 | 1.38 | 0.61 |
| ambi-miR-7083 | 7.82 | 7.44 | 7.85 | 8.00 | 8.25 | 7.91 | 7.96 | 7.58 | 7.42 |
| ambi-miR-7084 | 2.43 | 2.55 | 2.78 | 2.00 | 2.56 | 3.87 | 2.47 | 2.41 | 2.38 |
| ambi-miR-7085 | 4.27 | 3.88 | 4.40 | 4.98 | 4.46 | 4.80 | 4.21 | 4.59 | 4.33 |
| ambi-miR-7086 | 2.57 | 2.67 | 2.66 | 3.22 | 3.39 | 3.29 | 3.03 | 2.91 | 2.76 |
| hsa-miR-512-5p | 2.70 | 2.55 | 1.64 | 1.64 | 2.08 | 1.74 | 1.71 | 1.66 | 1.69 |
| hsa-miR-504 | 0.90 | 1.41 | 2.82 | 2.69 | 2.56 | 2.66 | 2.45 | 2.51 | 2.33 |
| ambi-miR-7089 | 2.36 | 1.28 | 2.56 | 2.08 | 1.82 | 1.89 | 2.11 | 1.57 | 1.76 |
| hsa-miR-511 | 1.29 | 2.61 | 1.81 | 2.26 | 1.21 | 1.70 | 1.71 | 1.83 | 2.10 |
| hsa-miR-452-AS | 3.30 | 3.51 | 3.02 | 2.69 | 3.04 | 3.18 | 3.46 | 3.38 | 3.16 |
| hsa-miR-503 | 6.54 | 6.76 | 6.75 | 6.34 | 6.41 | 6.56 | 6.59 | 6.35 | 5.90 |
| hsa-miR-485-5p | 2.91 | 3.31 | 2.74 | 3.10 | 2.81 | 3.14 | 3.31 | 3.27 | 2.73 |
| hsa-miR-499 | 0.56 | 1.28 | 1.46 | 2.00 | 2.08 | 1.74 | 1.92 | 2.20 | 2.10 |
| ambi-miR-7095 | 1.90 | 2.41 | 1.73 | 1.39 | 1.75 | 1.70 | 1.61 | 1.57 | 1.42 |
| hsa-miR-505 | 4.45 | 3.90 | 4.54 | 5.03 | 4.73 | 4.91 | 4.85 | 4.55 | 4.68 |
| ambi-miR-7097 | 3.23 | 2.33 | 2.89 | 2.69 | 2.60 | 2.38 | 2.26 | 2.26 | 2.38 |
| ambi-miR-7098 | 1.79 | 1.77 | 1.64 | 2.12 | 2.24 | 1.54 | 1.51 | 1.52 | 1.88 |
| hsa-miR-489 | 2.75 | 2.88 | 2.24 | 2.88 | 3.35 | 2.64 | 2.97 | 2.38 | 2.29 |
| ambi-miR-7100 | 2.81 | 3.48 | 3.11 | 3.39 | 3.25 | 3.46 | 4.07 | 3.66 | 3.27 |
| ambi-miR-7101 | 3.89 | 3.21 | 3.61 | 4.05 | 4.09 | 5.21 | 4.42 | 4.04 | 4.29 |
| hsa-miR-432-AS | 2.36 | 1.28 | 2.61 | 2.23 | 1.53 | 1.86 | 1.77 | 1.83 | 1.82 |
| ambi-miR-7103 | 3.08 | 1.41 | 2.89 | 2.19 | 2.60 | 2.22 | 2.14 | 2.61 | 2.57 |
| hsa-miR-500 | 4.03 | 3.97 | 4.33 | 4.94 | 4.64 | 4.79 | 4.37 | 4.70 | 4.52 |
| ambi-miR-7105 | 4.70 | 4.65 | 5.03 | 4.78 | 4.94 | 4.76 | 4.87 | 4.85 | 4.85 |

TABLE 5-continued

Normalized Array Data for Sixteen Normal Cervix Tissue Samples (NCX1-NCX16). TV, threshold value, miRNAs > TV, number of miRNAs expressed at greater than threshold value. %, percentage of miRNAs expressed at greater than threshold value.

| | NCX 10 | NCX 11 | NCX 12 | NCX 13 | NCX 14 | NCX 15 | NCX 16 | Mean (NCX) |
|---|---|---|---|---|---|---|---|---|
| TV | 2.84 | 3.15 | 2.15 | 2.76 | 3.18 | 3.09 | 3.79 | 2.87 |
| miRNAs > TV | 207 | 189 | 248 | 206 | 187 | 203 | 157 | 207 |
| % | 54.81 | 50.13 | 65.71 | 54.55 | 49.61 | 53.77 | 41.56 | 55.03 |
| miR Name | | | | | | | | |
| hsa-let-7a | 11.12 | 11.11 | 10.80 | 10.89 | 11.02 | 10.75 | 10.84 | 10.90 |
| hsa-let-7b | 11.12 | 11.27 | 10.80 | 10.99 | 11.33 | 11.05 | 11.05 | 11.00 |
| hsa-let-7c | 11.12 | 11.19 | 10.80 | 10.96 | 11.27 | 10.95 | 11.00 | 10.96 |
| hsa-let-7d | 10.23 | 9.85 | 10.17 | 9.59 | 9.53 | 9.26 | 9.58 | 9.78 |
| hsa-let-7e | 8.44 | 8.03 | 8.33 | 8.20 | 8.07 | 8.07 | 8.25 | 8.26 |
| hsa-let-7f | 9.06 | 8.86 | 9.31 | 8.33 | 8.14 | 7.88 | 8.57 | 8.64 |
| hsa-let-7g | 9.21 | 8.84 | 9.31 | 8.45 | 8.54 | 8.16 | 8.49 | 8.71 |
| hsa-let-7i | 9.09 | 8.62 | 8.74 | 8.56 | 8.78 | 8.50 | 8.47 | 8.68 |
| hsa-miR-1 | 6.32 | 5.56 | 6.86 | 5.06 | 4.81 | 4.92 | 5.34 | 5.45 |
| hsa-miR-100 | 9.64 | 9.27 | 9.80 | 9.29 | 9.31 | 8.69 | 9.17 | 9.26 |
| hsa-miR-101 | 4.71 | 5.04 | 5.53 | 4.59 | 4.17 | 3.97 | 3.94 | 4.47 |
| hsa-miR-103 | 8.37 | 7.95 | 8.42 | 8.19 | 8.07 | 7.99 | 8.03 | 8.29 |
| hsa-miR-105 | 1.37 | 2.65 | 1.57 | 1.11 | 1.38 | 1.31 | 1.73 | 1.64 |
| hsa-miR-106a | 7.54 | 7.46 | 7.83 | 7.48 | 7.25 | 7.25 | 7.19 | 7.48 |
| hsa-miR-106b | 6.54 | 6.51 | 6.36 | 6.19 | 6.05 | 6.40 | 5.97 | 6.37 |
| hsa-miR-107 | 8.29 | 7.86 | 8.27 | 7.93 | 8.04 | 8.02 | 7.92 | 8.22 |
| hsa-miR-10a | 7.47 | 7.17 | 7.31 | 6.87 | 6.57 | 5.84 | 6.48 | 7.07 |
| hsa-miR-10b | 7.94 | 8.04 | 8.37 | 8.16 | 7.36 | 7.13 | 7.83 | 7.87 |
| hsa-miR-122a | 3.26 | 3.76 | 2.79 | 3.87 | 3.04 | 3.49 | 4.05 | 3.37 |
| hsa-miR-124a | 3.79 | 2.85 | 2.62 | 2.91 | 2.26 | 4.55 | 2.24 | 3.31 |
| hsa-miR-125a | 9.20 | 9.27 | 9.37 | 9.36 | 8.49 | 8.87 | 8.87 | 8.95 |
| hsa-miR-125b | 10.61 | 10.46 | 10.64 | 10.37 | 10.58 | 10.01 | 9.93 | 10.34 |
| hsa-miR-126 | 9.39 | 9.70 | 9.40 | 9.34 | 9.36 | 9.26 | 9.38 | 9.43 |
| hsa-miR-126-AS | 5.38 | 5.75 | 5.98 | 5.16 | 4.71 | 4.70 | 4.06 | 5.34 |
| hsa-miR-127 | 4.33 | 3.53 | 4.43 | 2.98 | 4.34 | 4.30 | 4.18 | 4.34 |
| hsa-miR-128a | 5.36 | 5.30 | 5.34 | 5.48 | 5.27 | 5.09 | 4.65 | 5.25 |
| hsa-miR-129 | 2.38 | 2.81 | 2.57 | 2.98 | 2.53 | 2.72 | 1.92 | 2.59 |
| hsa-miR-130a | 7.87 | 7.84 | 8.56 | 7.70 | 7.55 | 7.42 | 7.50 | 7.75 |
| hsa-miR-130b | 4.69 | 4.40 | 4.88 | 4.45 | 4.45 | 4.70 | 4.36 | 4.71 |
| hsa-miR-132 | 5.93 | 5.32 | 5.65 | 5.66 | 5.48 | 5.14 | 5.49 | 5.61 |
| hsa-miR-133a | 7.67 | 6.94 | 7.95 | 7.28 | 7.08 | 7.19 | 6.67 | 7.18 |
| hsa-miR-134 | 4.73 | 4.75 | 4.60 | 4.25 | 4.72 | 5.29 | 4.87 | 4.92 |
| hsa-miR-135a | 2.14 | 1.92 | 2.48 | 1.37 | 1.66 | 2.36 | 1.52 | 2.06 |
| hsa-miR-135b | 1.37 | 0.89 | 1.67 | 1.80 | 1.59 | 3.28 | 1.84 | |
| hsa-miR-136 | 1.65 | 0.89 | 1.81 | 1.80 | 0.64 | 1.24 | 2.51 | 1.65 |
| hsa-miR-137 | 2.38 | 2.21 | 1.90 | 0.92 | 1.00 | 1.66 | 2.38 | 2.07 |
| hsa-miR-138 | 1.72 | 2.07 | 2.45 | 2.06 | 1.48 | 2.27 | 2.09 | 2.17 |
| hsa-miR-139 | 4.86 | 5.47 | 5.60 | 5.38 | 4.88 | 3.18 | 4.84 | 4.80 |
| hsa-miR-140 | 5.16 | 5.45 | 5.35 | 4.99 | 4.73 | 4.95 | 5.04 | 5.05 |
| hsa-miR-141 | 5.11 | 5.18 | 4.49 | 3.47 | 4.01 | 3.83 | 3.92 | 5.26 |
| hsa-miR-142-3p | 2.75 | 3.15 | 2.76 | 2.98 | 3.26 | 3.72 | 3.39 | 3.12 |
| hsa-miR-142-5p | 3.90 | 3.12 | 3.97 | 3.27 | 3.87 | 3.40 | 3.25 | 3.58 |
| hsa-miR-143 | 10.44 | 10.35 | 10.64 | 10.25 | 10.48 | 10.30 | 9.69 | 10.36 |
| hsa-miR-144 | 1.85 | 1.57 | 1.41 | 1.31 | 2.20 | 1.38 | 0.23 | 1.41 |
| hsa-miR-145 | 11.12 | 11.40 | 10.80 | 10.99 | 11.38 | 10.99 | 11.12 | 11.03 |
| hsa-miR-146a | 5.71 | 6.22 | 5.64 | 5.31 | 5.59 | 5.54 | 5.58 | 5.83 |
| hsa-miR-147 | 2.46 | 1.75 | 1.95 | 2.01 | 2.80 | 1.79 | 3.41 | 2.25 |
| hsa-miR-148a | 6.46 | 6.55 | 6.37 | 5.91 | 5.87 | 5.68 | 5.87 | 6.41 |
| hsa-miR-148b | 4.82 | 3.90 | 4.76 | 3.94 | 3.97 | 4.24 | 3.84 | 4.25 |
| hsa-miR-149 | 3.56 | 3.69 | 4.25 | 4.01 | 3.97 | 3.59 | 3.91 | 3.99 |
| hsa-miR-150 | 5.86 | 6.30 | 6.33 | 6.02 | 6.17 | 5.20 | 5.53 | 6.02 |
| hsa-miR-151 | 5.88 | 5.76 | 5.92 | 5.95 | 5.82 | 5.69 | 5.50 | 5.83 |
| hsa-miR-152 | 6.88 | 6.81 | 7.00 | 6.73 | 6.70 | 7.07 | 6.84 | 7.02 |
| hsa-miR-153 | 2.08 | 2.27 | 2.51 | 2.64 | 2.83 | 2.52 | 2.56 | 2.47 |
| hsa-miR-154 | 4.86 | 4.38 | 5.16 | 4.36 | 4.60 | 5.01 | 4.48 | 4.91 |
| hsa-miR-155 | 5.61 | 5.47 | 5.24 | 5.33 | 5.55 | 4.84 | 5.34 | 5.41 |
| hsa-miR-15a | 6.59 | 6.59 | 6.77 | 6.25 | 6.18 | 6.11 | 6.39 | 6.51 |
| hsa-miR-15b | 6.97 | 6.91 | 7.09 | 6.91 | 6.66 | 6.71 | 6.80 | 6.84 |
| hsa-miR-16 | 9.68 | 9.78 | 9.72 | 9.85 | 9.51 | 9.56 | 9.57 | 9.68 |
| hsa-miR-17-3p | 4.24 | 4.00 | 4.70 | 4.04 | 4.10 | 4.23 | 3.98 | 4.26 |
| hsa-miR-17-5p | 7.44 | 7.43 | 7.60 | 7.42 | 7.24 | 7.15 | 7.32 | 7.38 |
| hsa-miR-18a | 3.95 | 4.30 | 3.93 | 4.04 | 3.24 | 4.32 | 3.55 | 4.14 |
| hsa-miR-181a | 7.14 | 6.82 | 6.58 | 6.83 | 6.49 | 6.56 | 6.66 | 6.74 |
| hsa-miR-181b | 6.31 | 5.77 | 5.74 | 6.03 | 5.68 | 5.89 | 5.52 | 5.96 |
| hsa-miR-181c | 4.47 | 4.06 | 4.21 | 4.82 | 4.42 | 4.29 | 3.22 | 4.10 |
| hsa-miR-182 | 4.58 | 3.60 | 3.54 | 3.65 | 3.80 | 3.40 | 3.55 | 4.49 |
| hsa-miR-182-AS | 2.38 | 1.84 | 1.67 | 2.11 | 2.20 | 0.25 | 2.98 | 1.78 |
| hsa-miR-183 | 2.89 | 2.07 | 1.99 | 2.11 | 2.38 | 2.23 | 0.56 | 2.50 |

TABLE 5-continued

Normalized Array Data for Sixteen Normal Cervix Tissue Samples (NCX1-NCX16). TV, threshold value, miRNAs > TV, number of miRNAs expressed at greater than threshold value. %, percentage of miRNAs expressed at greater than threshold value.

| | | | | | | | | |
|---|---|---|---|---|---|---|---|---|
| hsa-miR-184 | 3.78 | 4.12 | 3.25 | 4.22 | 3.88 | 4.44 | 3.89 | 3.78 |
| hsa-miR-185 | 5.30 | 4.98 | 5.08 | 5.13 | 5.12 | 5.79 | 5.35 | 5.46 |
| hsa-miR-186 | 4.66 | 4.53 | 4.98 | 4.24 | 3.77 | 3.46 | 3.36 | 4.23 |
| hsa-miR-187 | 5.50 | 4.41 | 5.93 | 5.31 | 6.17 | 4.71 | 3.97 | 5.26 |
| hsa-miR-188 | 3.05 | 2.99 | 3.41 | 3.41 | 3.07 | 3.55 | 3.81 | 3.35 |
| hsa-miR-189 | 4.37 | 4.22 | 4.71 | 4.56 | 4.01 | 4.09 | 3.89 | 4.39 |
| hsa-miR-190 | 1.91 | 1.84 | 2.03 | 2.20 | 1.66 | 0.95 | 1.52 | 1.68 |
| hsa-miR-191 | 7.89 | 7.73 | 8.20 | 8.04 | 7.87 | 7.48 | 7.46 | 7.92 |
| hsa-miR-192 | 4.69 | 4.76 | 5.02 | 4.83 | 4.05 | 4.11 | 3.53 | 4.44 |
| hsa-miR-193a | 4.48 | 4.77 | 5.01 | 4.63 | 3.94 | 4.39 | 4.13 | 4.35 |
| hsa-miR-194 | 4.83 | 4.91 | 5.19 | 5.53 | 4.66 | 4.33 | 4.40 | 4.87 |
| hsa-miR-195 | 9.36 | 9.57 | 9.61 | 9.05 | 9.07 | 8.93 | 9.09 | 9.22 |
| hsa-miR-196a | 5.39 | 4.86 | 4.94 | 4.61 | 4.78 | 4.96 | 5.17 | 4.98 |
| hsa-miR-196b | 6.77 | 6.41 | 6.74 | 6.12 | 6.45 | 6.50 | 6.56 | 6.59 |
| hsa-miR-197 | 4.84 | 5.06 | 5.29 | 5.23 | 5.36 | 4.30 | 4.98 | 4.95 |
| hsa-miR-198 | 4.67 | 5.04 | 4.09 | 5.11 | 4.66 | 5.45 | 5.09 | 4.69 |
| hsa-miR-199a | 8.96 | 8.32 | 9.06 | 8.86 | 8.62 | 8.62 | 7.59 | 8.64 |
| hsa-miR-199a-AS | 9.16 | 8.58 | 9.30 | 8.61 | 8.90 | 8.63 | 8.21 | 8.86 |
| hsa-miR-199b | 6.93 | 6.73 | 6.87 | 5.81 | 6.86 | 6.78 | 5.63 | 6.77 |
| hsa-miR-19a | 4.12 | 4.37 | 4.88 | 3.99 | 3.36 | 3.67 | 2.01 | 4.00 |
| hsa-miR-19b | 7.64 | 7.97 | 8.26 | 7.90 | 7.39 | 7.55 | 6.79 | 7.70 |
| hsa-miR-20a | 6.32 | 6.52 | 6.97 | 6.33 | 5.95 | 6.07 | 6.28 | 6.38 |
| hsa-miR-200a | 6.20 | 5.65 | 5.09 | 4.12 | 5.25 | 4.65 | 4.82 | 5.97 |
| hsa-miR-200b | 7.30 | 6.58 | 6.32 | 5.28 | 6.52 | 5.20 | 5.98 | 6.92 |
| hsa-miR-200c | 7.89 | 7.45 | 7.10 | 6.16 | 7.42 | 6.14 | 7.16 | 7.79 |
| hsa-miR-203 | 4.61 | 5.58 | 6.62 | 4.37 | 7.46 | 6.02 | 6.45 | 6.86 |
| hsa-miR-204 | 5.53 | 5.44 | 6.08 | 5.87 | 5.35 | 4.57 | 4.10 | 4.99 |
| hsa-miR-205 | 4.30 | 7.54 | 8.11 | 6.48 | 8.57 | 6.99 | 7.39 | 7.72 |
| hsa-miR-206 | 3.18 | 3.18 | 2.74 | 3.55 | 3.56 | 3.88 | 3.25 | 3.19 |
| hsa-miR-208 | 1.91 | 0.71 | 2.15 | 1.96 | 2.32 | 0.51 | 2.67 | 1.71 |
| hsa-miR-21 | 9.36 | 8.98 | 9.09 | 8.39 | 8.72 | 8.57 | 8.94 | 9.11 |
| hsa-miR-210 | 5.31 | 5.37 | 5.86 | 4.82 | 5.47 | 5.22 | 4.57 | 5.53 |
| hsa-miR-211 | 1.79 | 1.84 | 1.90 | 1.50 | 1.75 | 1.02 | 1.92 | 1.97 |
| hsa-miR-212 | 3.39 | 2.65 | 2.67 | 2.91 | 2.63 | 3.11 | 3.51 | 3.01 |
| hsa-miR-213 | 2.54 | 2.21 | 1.72 | 1.80 | 1.57 | 2.40 | 2.38 | 2.08 |
| hsa-miR-214 | 8.43 | 8.04 | 8.52 | 8.51 | 7.92 | 7.92 | 8.31 | 8.24 |
| hsa-miR-215 | 2.14 | 2.39 | 1.90 | 2.73 | 2.20 | 1.97 | 1.92 | 2.00 |
| hsa-miR-216 | 1.97 | 1.66 | 1.99 | 2.48 | 2.80 | 2.79 | 2.09 | 1.99 |
| hsa-miR-217 | 2.75 | 2.00 | 1.81 | 1.91 | 1.48 | 1.66 | 0.47 | 1.91 |
| hsa-miR-218 | 5.79 | 5.84 | 6.00 | 5.14 | 5.07 | 4.98 | 5.60 | 5.63 |
| hsa-miR-219 | 2.54 | 2.50 | 3.39 | 2.86 | 2.63 | 1.91 | 2.86 | 2.42 |
| hsa-miR-22 | 7.63 | 7.51 | 8.02 | 7.29 | 7.66 | 8.23 | 8.13 | 8.17 |
| hsa-miR-220 | 2.29 | 1.28 | 1.81 | 2.37 | 2.38 | 1.31 | 2.38 | 1.84 |
| hsa-miR-221 | 8.53 | 7.91 | 8.57 | 8.06 | 8.31 | 8.07 | 7.73 | 8.28 |
| hsa-miR-222 | 7.79 | 7.42 | 8.01 | 7.67 | 7.70 | 7.35 | 7.09 | 7.70 |
| hsa-miR-223 | 6.17 | 6.38 | 6.25 | 5.71 | 5.74 | 5.87 | 5.72 | 6.18 |
| hsa-miR-224 | 5.37 | 5.00 | 5.78 | 4.85 | 5.17 | 5.68 | 5.46 | 5.61 |
| hsa-miR-23a | 9.30 | 9.59 | 9.66 | 9.55 | 9.32 | 8.85 | 9.22 | 9.43 |
| hsa-miR-23b | 9.90 | 9.88 | 10.17 | 10.11 | 9.80 | 9.29 | 9.77 | 9.91 |
| hsa-miR-24 | 9.78 | 9.78 | 9.87 | 9.75 | 9.70 | 9.60 | 9.79 | 9.80 |
| hsa-miR-25 | 6.69 | 6.69 | 6.83 | 6.59 | 6.45 | 6.26 | 6.53 | 6.57 |
| hsa-miR-26a | 11.06 | 11.15 | 10.80 | 10.97 | 10.99 | 10.49 | 10.98 | 10.84 |
| hsa-miR-26b | 7.87 | 7.77 | 8.64 | 7.53 | 7.27 | 6.81 | 7.58 | 7.64 |
| hsa-miR-27a | 8.73 | 9.04 | 8.82 | 8.69 | 8.72 | 8.56 | 8.41 | 8.74 |
| hsa-miR-27b | 9.34 | 9.28 | 9.46 | 9.31 | 9.06 | 8.86 | 9.0 | 9.21 |
| hsa-miR-28 | 6.15 | 5.92 | 6.62 | 6.01 | 5.93 | 5.65 | 6.07 | 6.02 |
| hsa-miR-296 | 2.54 | 2.81 | 2.51 | 2.11 | 3.45 | 2.63 | 3.16 | 2.66 |
| hsa-miR-299-5p | 4.75 | 4.55 | 4.97 | 4.32 | 4.64 | 4.40 | 4.28 | 4.76 |
| hsa-miR-29a | 9.70 | 9.68 | 10.16 | 9.43 | 9.40 | 9.13 | 9.05 | 9.42 |
| hsa-miR-29b | 6.80 | 7.45 | 7.89 | 6.98 | 6.18 | 6.23 | 5.94 | 6.89 |
| hsa-miR-29c | 7.03 | 7.68 | 7.88 | 7.10 | 6.04 | 6.08 | 6.30 | 6.80 |
| hsa-miR-301 | 2.65 | 2.77 | 2.11 | 2.06 | 0.64 | 2.40 | 1.30 | 2.21 |
| hsa-miR-302a | 2.08 | 2.00 | 2.42 | 1.96 | 1.75 | 2.23 | 0.85 | 2.08 |
| hsa-miR-302b | 1.14 | 1.84 | 1.72 | 1.44 | 2.20 | 1.38 | 1.07 | 1.64 |
| hsa-miR-302b-AS | 2.14 | 1.66 | 1.72 | 1.31 | 1.75 | 0.75 | 2.77 | 1.63 |
| hsa-miR-302c | 1.85 | 2.21 | 1.95 | 1.62 | 2.32 | 2.52 | 1.07 | 1.88 |
| hsa-miR-302c-AS | 3.85 | 3.40 | 3.04 | 3.71 | 4.06 | 3.78 | 3.82 | 3.56 |
| hsa-miR-302d | 1.51 | 2.33 | 1.77 | 2.25 | 2.38 | 2.56 | 3.12 | 2.07 |
| hsa-miR-30a-3p | 4.15 | 4.47 | 4.14 | 3.84 | 3.65 | 3.88 | 3.89 | 4.10 |
| hsa-miR-30a-5p | 7.99 | 8.15 | 8.34 | 7.87 | 7.81 | 7.84 | 7.86 | 8.11 |
| hsa-miR-30b | 7.21 | 7.41 | 8.19 | 7.24 | 6.98 | 6.63 | 6.13 | 7.26 |
| hsa-miR-30c | 7.60 | 7.54 | 7.89 | 7.51 | 7.68 | 7.32 | 6.81 | 7.57 |
| hsa-miR-30d | 8.21 | 8.33 | 8.46 | 8.28 | 8.06 | 7.88 | 8.05 | 8.17 |
| hsa-miR-30e-3p | 4.42 | 4.06 | 4.34 | 4.18 | 4.47 | 3.97 | 3.46 | 4.10 |
| hsa-miR-30e-5p | 7.30 | 7.58 | 7.73 | 7.48 | 6.84 | 7.22 | 6.77 | 7.42 |
| hsa-miR-31 | 6.80 | 7.03 | 6.30 | 6.11 | 6.90 | 5.99 | 6.58 | 6.98 |

TABLE 5-continued

Normalized Array Data for Sixteen Normal Cervix Tissue Samples (NCX1-NCX16). TV, threshold value, miRNAs > TV, number of miRNAs expressed at greater than threshold value. %, percentage of miRNAs expressed at greater than threshold value.

| | | | | | | | | |
|---|---|---|---|---|---|---|---|---|
| hsa-miR-32 | 1.79 | 1.84 | 2.26 | 1.37 | 2.58 | 1.91 | 0.85 | 1.95 |
| hsa-miR-320 | 8.37 | 8.15 | 8.31 | 8.74 | 8.14 | 8.34 | 8.18 | 8.37 |
| hsa-miR-323 | 1.91 | 2.45 | 1.99 | 1.56 | 2.63 | 2.79 | 1.41 | 2.26 |
| hsa-miR-324-3p | 5.82 | 5.34 | 5.59 | 5.42 | 6.03 | 5.92 | 5.46 | 5.71 |
| hsa-miR-324-5p | 3.26 | 2.39 | 3.20 | 2.40 | 3.29 | 3.26 | 3.22 | 3.18 |
| hsa-miR-325 | 2.33 | 2.21 | 2.29 | 2.61 | 2.63 | 1.52 | 2.17 | 2.26 |
| hsa-miR-326 | 1.65 | 2.73 | 2.36 | 2.48 | 2.67 | 2.27 | 2.09 | 2.44 |
| hsa-miR-328 | 3.95 | 3.98 | 4.29 | 4.48 | 4.31 | 3.20 | 3.74 | 3.79 |
| hsa-miR-33 | 1.72 | 1.66 | 1.86 | 2.06 | 1.75 | 1.38 | 0.56 | 1.62 |
| hsa-miR-330 | 2.78 | 2.73 | 2.36 | 2.67 | 2.67 | 2.36 | 3.22 | 2.77 |
| hsa-miR-331 | 5.09 | 5.41 | 4.91 | 5.37 | 5.05 | 4.69 | 5.35 | 5.15 |
| hsa-miR-335 | 4.96 | 4.79 | 5.43 | 4.42 | 4.73 | 4.85 | 4.38 | 4.70 |
| hsa-miR-337 | 2.61 | 1.66 | 2.19 | 1.96 | 1.57 | 1.91 | 2.51 | 2.17 |
| hsa-miR-338 | 3.00 | 3.12 | 3.16 | 2.51 | 1.91 | 1.72 | 1.83 | 2.53 |
| hsa-miR-339 | 5.11 | 5.16 | 5.40 | 5.83 | 5.04 | 4.79 | 4.72 | 5.05 |
| hsa-miR-340 | 2.68 | 2.21 | 2.45 | 2.25 | 2.48 | 1.31 | 1.41 | 2.09 |
| hsa-miR-342 | 7.45 | 7.15 | 7.80 | 7.56 | 7.40 | 6.83 | 7.10 | 7.31 |
| hsa-miR-345 | 4.28 | 3.80 | 4.45 | 4.42 | 3.87 | 3.09 | 3.33 | 4.19 |
| hsa-miR-346 | 1.58 | 2.14 | 1.99 | 1.86 | 1.57 | 2.02 | 2.09 | 2.00 |
| hsa-miR-34a | 7.65 | 7.53 | 7.66 | 7.74 | 7.37 | 7.08 | 6.85 | 7.48 |
| hsa-miR-34b | 5.09 | 4.99 | 4.63 | 4.52 | 4.22 | 3.92 | 3.81 | 4.58 |
| hsa-miR-34c | 4.29 | 3.40 | 2.57 | 1.91 | 2.80 | 2.63 | 2.17 | 3.44 |
| hsa-miR-361 | 7.06 | 7.09 | 7.12 | 7.27 | 6.78 | 6.60 | 7.00 | 6.99 |
| hsa-miR-365 | 3.55 | 3.09 | 4.11 | 3.30 | 2.87 | 2.66 | 3.02 | 3.41 |
| hsa-miR-367 | 2.29 | 1.57 | 1.25 | 1.44 | 1.91 | 0.75 | 2.01 | 1.55 |
| hsa-miR-368 | 6.93 | 6.67 | 7.07 | 6.29 | 6.66 | 7.01 | 6.74 | 6.97 |
| hsa-miR-369-3p | 2.54 | 0.89 | 1.81 | 1.44 | 0.73 | 1.79 | 0.56 | 1.48 |
| hsa-miR-370 | 4.87 | 4.94 | 4.36 | 4.68 | 5.06 | 4.52 | 4.94 | 4.69 |
| hsa-miR-371 | 2.14 | 2.27 | 1.95 | 1.69 | 2.43 | 1.09 | 1.52 | 1.75 |
| hsa-miR-372 | 2.03 | 1.57 | 1.77 | 1.04 | 0.82 | 1.38 | 1.52 | 1.56 |
| hsa-miR-373 | 1.65 | 2.33 | 2.07 | 2.33 | 1.91 | 2.79 | 3.05 | 2.04 |
| hsa-miR-373-AS | 2.71 | 3.57 | 3.47 | 3.15 | 3.53 | 3.77 | 3.25 | 3.41 |
| hsa-miR-374 | 3.20 | 3.31 | 3.86 | 2.84 | 3.01 | 2.84 | 2.72 | 3.03 |
| hsa-miR-375 | 4.06 | 3.45 | 2.64 | 1.69 | 3.42 | 2.36 | 3.72 | 4.01 |
| hsa-miR-376a | 5.08 | 4.83 | 5.68 | 4.28 | 4.30 | 5.09 | 4.86 | 5.17 |
| hsa-miR-377 | 3.42 | 3.71 | 3.63 | 3.32 | 2.80 | 3.31 | 2.77 | 3.49 |
| hsa-miR-378 | 4.10 | 3.57 | 4.31 | 3.47 | 3.49 | 3.74 | 3.97 | 3.94 |
| hsa-miR-379 | 5.21 | 5.35 | 5.27 | 5.05 | 5.07 | 5.54 | 5.61 | 5.46 |
| hsa-miR-380-3p | 2.03 | 1.48 | 1.46 | 1.96 | 0.73 | 1.85 | 0.75 | 1.51 |
| hsa-miR-380-5p | 1.14 | 1.08 | 1.62 | 1.37 | 2.48 | 0.95 | 2.17 | 1.59 |
| hsa-miR-381 | 4.26 | 4.14 | 4.61 | 4.24 | 3.91 | 4.62 | 3.79 | 4.38 |
| hsa-miR-382 | 3.75 | 3.79 | 4.02 | 3.78 | 3.81 | 4.60 | 4.82 | 4.36 |
| hsa-miR-383 | 2.42 | 2.77 | 2.42 | 2.93 | 3.16 | 2.59 | 3.02 | 2.52 |
| hsa-miR-384 | 1.91 | 0.71 | 1.46 | 1.11 | 1.38 | 1.38 | 0.75 | 1.27 |
| hsa-miR-422a | 4.89 | 4.63 | 5.89 | 4.35 | 4.49 | 4.35 | 4.74 | 5.04 |
| hsa-miR-422b | 6.44 | 6.35 | 6.87 | 6.19 | 6.28 | 6.13 | 6.34 | 6.55 |
| hsa-miR-423 | 6.24 | 6.17 | 6.16 | 6.51 | 6.26 | 5.92 | 5.87 | 6.19 |
| hsa-miR-424 | 6.10 | 5.58 | 5.75 | 3.91 | 4.75 | 5.79 | 5.48 | 5.71 |
| hsa-miR-425 | 3.59 | 3.66 | 4.22 | 3.98 | 3.38 | 3.09 | 2.94 | 3.78 |
| hsa-miR-429 | 4.86 | 4.01 | 3.95 | 2.81 | 3.62 | 3.26 | 3.89 | 4.49 |
| hsa-miR-448 | 2.19 | 1.75 | 1.51 | 1.44 | 2.38 | 1.66 | 0.65 | 1.61 |
| hsa-miR-449 | 3.02 | 1.84 | 2.42 | 1.44 | 0.57 | 3.24 | 3.28 | 2.44 |
| hsa-miR-450 | 2.81 | 3.03 | 2.54 | 2.29 | 2.38 | 3.36 | 2.38 | 2.65 |
| hsa-miR-7 | 2.68 | 2.89 | 2.83 | 2.25 | 1.48 | 2.63 | 3.05 | 2.69 |
| hsa-miR-9 | 1.85 | 2.07 | 2.54 | 1.91 | 1.09 | 1.85 | 1.73 | 2.04 |
| hsa-miR-9-AS | 3.77 | 3.92 | 3.93 | 2.91 | 3.31 | 3.18 | 3.33 | 3.46 |
| hsa-miR-92 | 7.34 | 7.39 | 7.33 | 7.47 | 7.34 | 7.21 | 6.73 | 7.13 |
| hsa-miR-93 | 6.96 | 6.40 | 6.75 | 6.53 | 6.67 | 6.88 | 6.67 | 6.83 |
| hsa-miR-95 | 3.18 | 3.09 | 3.57 | 3.40 | 3.29 | 3.11 | 3.44 | 3.32 |
| hsa-miR-96 | 3.34 | 3.62 | 3.70 | 3.53 | 3.49 | 1.09 | 3.39 | 3.38 |
| hsa-miR-98 | 6.16 | 5.70 | 5.91 | 5.82 | 5.47 | 5.39 | 5.45 | 5.66 |
| hsa-miR-99a | 10.35 | 10.16 | 10.66 | 10.09 | 10.27 | 9.82 | 9.86 | 10.12 |
| hsa-miR-99b | 7.37 | 7.12 | 7.61 | 7.51 | 7.38 | 7.10 | 7.30 | 7.37 |
| mmu-let-7d-AS | 2.42 | 1.57 | 2.03 | 1.80 | 2.63 | 2.72 | 2.17 | 1.96 |
| mmu-miR-101b | 1.72 | 2.39 | 3.49 | 1.62 | 1.99 | 1.52 | 2.32 | 2.01 |
| mmu-miR-106a | 6.84 | 6.88 | 7.13 | 6.85 | 6.58 | 6.67 | 6.63 | 6.81 |
| mmu-miR-129-3p | 1.91 | 1.38 | 2.07 | 2.48 | 2.67 | 1.85 | 3.81 | 2.26 |
| mmu-miR-140-AS | 7.34 | 7.32 | 7.53 | 7.72 | 7.27 | 7.30 | 6.85 | 7.26 |
| mmu-miR-151 | 3.83 | 3.42 | 4.88 | 3.93 | 3.31 | 3.35 | 3.64 | 4.04 |
| mmu-miR-155 | 3.49 | 3.38 | 3.51 | 2.81 | 3.10 | 2.59 | 3.41 | 3.07 |
| mmu-miR-17-3p | 2.42 | 3.18 | 3.42 | 2.25 | 1.83 | 2.72 | 1.92 | 2.73 |
| mmu-miR-192 | 4.52 | 4.37 | 4.88 | 4.90 | 4.02 | 3.62 | 3.53 | 4.28 |
| mmu-miR-199b | 6.71 | 6.15 | 6.88 | 6.03 | 6.21 | 5.83 | 4.91 | 6.23 |
| mmu-miR-201 | 1.51 | 1.84 | 1.62 | 2.55 | 1.83 | 0.95 | 1.07 | 1.60 |
| mmu-miR-202 | 4.20 | 4.30 | 3.82 | 4.80 | 4.58 | 5.05 | 4.67 | 4.21 |
| mmu-miR-207 | 2.58 | 2.99 | 2.29 | 1.91 | 1.66 | 2.36 | 2.62 | 2.34 |

TABLE 5-continued

Normalized Array Data for Sixteen Normal Cervix Tissue Samples (NCX1-NCX16). TV, threshold value, miRNAs > TV, number of miRNAs expressed at greater than threshold value. %, percentage of miRNAs expressed at greater than threshold value.

| | | | | | | | | |
|---|---|---|---|---|---|---|---|---|
| mmu-miR-211 | 1.37 | 1.66 | 1.90 | 1.44 | 1.75 | 1.66 | 2.51 | 1.68 |
| mmu-miR-215 | 1.72 | 1.48 | 1.62 | 2.20 | 1.99 | 1.45 | 0.96 | 1.69 |
| mmu-miR-217 | 1.85 | 2.14 | 1.67 | 1.91 | 2.53 | 2.36 | 2.09 | 1.88 |
| mmu-miR-290 | 3.14 | 3.36 | 2.62 | 3.41 | 3.65 | 3.55 | 3.55 | 3.14 |
| mmu-miR-291-3p | 1.58 | 2.27 | 1.46 | 1.80 | 2.72 | 1.91 | 1.83 | 1.83 |
| mmu-miR-291-5p | 2.14 | 2.00 | 1.99 | 1.91 | 2.20 | 2.48 | 2.38 | 2.13 |
| mmu-miR-292-3p | 1.22 | 1.92 | 1.77 | 1.91 | 1.48 | 2.72 | 2.24 | 1.97 |
| mmu-miR-292-5p | 2.61 | 2.99 | 2.36 | 2.81 | 2.43 | 3.11 | 3.05 | 2.52 |
| mmu-miR-293 | 1.97 | 1.92 | 1.77 | 2.16 | 1.00 | 1.97 | 1.83 | 1.88 |
| mmu-miR-294 | 2.84 | 2.00 | 2.54 | 1.96 | 1.83 | 2.40 | 2.51 | 2.14 |
| mmu-miR-295 | 1.72 | 1.92 | 1.72 | 1.80 | 1.99 | 1.72 | 1.18 | 1.79 |
| mmu-miR-297 | 1.14 | 2.00 | 1.62 | 2.16 | 2.26 | 2.02 | 2.81 | 1.76 |
| mmu-miR-298 | 4.67 | 4.98 | 4.30 | 4.86 | 4.88 | 5.22 | 4.80 | 4.63 |
| mmu-miR-300 | 3.14 | 2.81 | 3.43 | 2.91 | 3.18 | 3.31 | 3.09 | 3.16 |
| mmu-miR-322 | 1.91 | 2.27 | 1.41 | 1.80 | 2.13 | 2.18 | 2.17 | 1.86 |
| mmu-miR-424 | 5.07 | 4.47 | 4.50 | 2.96 | 3.40 | 5.07 | 4.13 | 4.58 |
| mmu-miR-325 | 1.07 | 2.21 | 2.03 | 2.44 | 1.99 | 2.56 | 3.22 | 2.12 |
| mmu-miR-329 | 2.61 | 1.75 | 1.57 | 1.50 | 2.80 | 2.44 | 2.90 | 2.20 |
| mmu-miR-330 | 2.38 | 2.33 | 1.99 | 1.80 | 2.13 | 2.76 | 2.17 | 2.10 |
| mmu-miR-337 | 2.24 | 2.21 | 1.86 | 2.20 | 2.53 | 1.59 | 1.73 | 1.95 |
| mmu-miR-341 | 2.58 | 2.27 | 2.57 | 1.86 | 1.91 | 2.52 | 1.83 | 2.35 |
| mmu-miR-344 | 1.07 | 1.18 | 1.72 | 2.01 | 2.38 | 1.31 | 2.09 | 1.51 |
| mmu-miR-345 | 2.38 | 3.12 | 2.69 | 2.91 | 2.53 | 1.52 | 3.02 | 2.57 |
| mmu-miR-346 | 2.29 | 1.92 | 2.11 | 2.40 | 2.53 | 1.31 | 2.51 | 2.02 |
| mmu-miR-34b | 3.20 | 2.73 | 2.39 | 2.29 | 2.53 | 2.40 | 2.67 | 2.75 |
| mmu-miR-350 | 1.91 | 2.00 | 1.77 | 1.80 | 1.66 | 1.52 | 2.32 | 1.96 |
| mmu-miR-351 | 2.08 | 2.33 | 2.03 | 2.33 | 1.83 | 2.79 | 2.09 | 2.13 |
| mmu-miR-376a | 3.12 | 2.45 | 3.33 | 2.20 | 2.76 | 3.11 | 2.62 | 2.95 |
| mmu-miR-376b | 1.97 | 2.55 | 2.07 | 2.20 | 2.72 | 2.81 | 2.86 | 2.31 |
| mmu-miR-380-3p | 2.81 | 2.89 | 2.59 | 2.84 | 2.38 | 2.27 | 1.62 | 2.55 |
| mmu-miR-383 | 2.92 | 2.50 | 2.48 | 2.70 | 3.31 | 3.26 | 2.67 | 2.53 |
| mmu-miR-384 | 1.29 | 1.28 | 1.30 | 1.17 | 2.13 | 1.79 | 2.94 | 1.49 |
| mmu-miR-409 | 3.69 | 3.55 | 3.69 | 2.73 | 3.81 | 5.08 | 4.22 | 4.37 |
| hsa-miR-410 | 2.54 | 2.45 | 2.72 | 2.11 | 2.13 | 3.48 | 1.92 | 2.88 |
| mmu-miR-411 | 2.14 | 2.39 | 2.48 | 1.96 | 2.20 | 2.44 | 2.62 | 2.55 |
| hsa-miR-412 | 1.51 | 1.66 | 1.62 | 1.96 | 2.48 | 1.45 | 0.75 | 1.61 |
| mmu-miR-429 | 1.79 | 1.18 | 1.77 | 2.01 | 2.13 | 2.23 | 2.51 | 1.89 |
| mmu-miR-7b | 1.85 | 1.57 | 1.95 | 2.25 | 2.26 | 2.18 | 3.22 | 2.19 |
| rno-miR-151-AS | 7.24 | 7.22 | 7.37 | 7.27 | 7.26 | 6.97 | 7.17 | 7.19 |
| rno-miR-20-AS | 1.79 | 1.18 | 1.35 | 1.24 | 1.00 | 1.66 | 2.67 | 1.82 |
| rno-miR-297 | 1.91 | 1.92 | 1.67 | 1.44 | 1.57 | 0.56 | 1.62 | 1.48 |
| rno-miR-327 | 3.63 | 4.01 | 3.22 | 3.83 | 3.78 | 4.10 | 3.79 | 3.57 |
| rno-miR-333 | 1.91 | 1.38 | 2.07 | 1.50 | 2.38 | 1.09 | 2.72 | 1.94 |
| rno-miR-336 | 3.26 | 3.33 | 3.26 | 3.02 | 4.15 | 3.87 | 4.18 | 3.49 |
| rno-miR-343 | 2.42 | 1.84 | 1.57 | 2.29 | 0.73 | 1.31 | 2.32 | 1.85 |
| rno-miR-344 | 1.51 | 1.48 | 1.90 | 1.86 | 0.82 | 0.56 | 2.01 | 1.44 |
| rno-miR-346 | 1.91 | 2.27 | 2.19 | 2.51 | 2.76 | 1.79 | 2.38 | 2.31 |
| rao-miR-347 | 2.42 | 3.92 | 2.48 | 1.44 | 2.94 | 2.44 | 2.56 | 2.33 |
| rno-miR-349 | 1.00 | 2.21 | 1.62 | 1.96 | 2.53 | 1.79 | 0.75 | 1.47 |
| rno-miR-352 | 6.12 | 5.88 | 6.21 | 6.04 | 5.59 | 5.42 | 5.60 | 5.78 |
| rno-miR-421 | 1.79 | 1.28 | 1.90 | 2.20 | 1.75 | 1.72 | 3.79 | 1.87 |
| rno-miR-7-AS | 2.46 | 2.21 | 2.74 | 2.29 | 1.19 | 1.24 | 1.83 | 2.15 |
| hsa-miR-522 | 0.47 | 0.40 | 1.77 | 1.74 | 2.13 | 0.40 | 2.17 | 1.61 |
| hsa-miR-519b | 0.92 | 1.08 | 1.19 | 1.96 | 2.06 | 2.56 | 0.39 | 1.64 |
| hsa-miR-520c | 1.51 | 1.66 | 1.41 | 2.29 | 2.38 | 0.62 | 2.32 | 1.69 |
| hsa-miR-519e | 1.37 | 1.92 | 1.51 | 2.20 | 2.53 | 1.31 | 1.62 | 1.60 |
| hsa-miR-519d | 1.14 | 2.07 | 1.72 | 2.16 | 1.48 | 1.79 | 1.62 | 1.83 |
| hsa-miR-520b | 1.58 | 1.38 | 1.95 | 2.25 | 2.06 | 2.92 | 2.62 | 1.84 |
| hsa-miR-519c | 2.08 | 1.48 | 1.67 | 2.20 | 1.83 | 2.13 | 1.73 | 1.73 |
| hsa-miR-526b-AS | 1.72 | 1.18 | 1.62 | 0.92 | 1.57 | 1.38 | 0.85 | 1.49 |
| hsa-miR-520e | 1.07 | 1.75 | 1.46 | 0.98 | 2.06 | 1.45 | 3.12 | 1.81 |
| hsa-miR-520a | 1.44 | 1.48 | 1.46 | 1.44 | 1.19 | 2.48 | 1.30 | 1.47 |
| hsa-miR-520d | 2.29 | 2.14 | 1.81 | 2.16 | 2.26 | 2.36 | 1.52 | 1.94 |
| hsa-miR-520h | 0.92 | 0.89 | 1.51 | 1.91 | 1.75 | 1.72 | 2.38 | 1.75 |
| hsa-miR-517a | 1.44 | 0.89 | 1.77 | 1.11 | 2.32 | 1.38 | 2.38 | 1.74 |
| hsa-miR-518e | 1.65 | 1.66 | 1.51 | 0.85 | 1.75 | 1.24 | 1.30 | 1.52 |
| hsa-miR-521 | 1.79 | 1.57 | 1.67 | 2.01 | 2.32 | 1.72 | 1.83 | 1.92 |
| hsa-miR-523 | 1.44 | 1.75 | 1.67 | 2.73 | 1.66 | 2.23 | 3.25 | 1.94 |
| hsa-miR-518f | 2.19 | 1.84 | 1.41 | 2.11 | 1.09 | 2.59 | 2.17 | 1.80 |
| hsa-miR-518c | 1.79 | 1.84 | 1.46 | 2.16 | 1.57 | 0.51 | 1.62 | 1.67 |
| hsa-miR-518b | 1.22 | 1.18 | 1.77 | 1.24 | 1.48 | 1.38 | 1.92 | 1.66 |
| hsa-miR-518d | 1.07 | 2.00 | 1.57 | 1.69 | 2.20 | 1.97 | 2.72 | 1.72 |
| hsa-miR-525-AS | 2.38 | 1.08 | 1.35 | 1.50 | 1.83 | 1.16 | 2.51 | 1.45 |
| hsa-miR-524 | 1.79 | 1.66 | 1.77 | 1.86 | 2.63 | 2.59 | 3.22 | 2.00 |
| hsa-miR-518a | 2.33 | 2.21 | 1.35 | 1.62 | 2.32 | 0.88 | 3.33 | 1.67 |
| hsa-miR-515-3p | 1.51 | 2.55 | 1.25 | 1.62 | 1.99 | 0.75 | 1.18 | 1.72 |

TABLE 5-continued

Normalized Array Data for Sixteen Normal Cervix Tissue Samples (NCX1-NCX16). TV, threshold value, miRNAs > TV, number of miRNAs expressed at greater than threshold value. %, percentage of miRNAs expressed at greater than threshold value.

| | | | | | | | | |
|---|---|---|---|---|---|---|---|---|
| hsa-miR-516-3p | 1.58 | 1.28 | 1.72 | 2.06 | 2.06 | 2.81 | 3.05 | 2.00 |
| ambi-miR-7026 | 0.53 | 0.47 | 1.57 | 1.86 | 1.83 | 2.08 | 1.52 | 1.46 |
| ambi-miR-7027 | 3.20 | 2.73 | 3.02 | 2.55 | 2.94 | 3.78 | 2.72 | 3.14 |
| hsa-miR-512-3p | 2.14 | 2.81 | 1.86 | 2.70 | 2.72 | 2.69 | 2.72 | 2.32 |
| ambi-miR-7029 | 7.02 | 6.03 | 6.51 | 7.25 | 5.88 | 7.60 | 6.57 | 6.99 |
| hsa-miR-491 | 3.84 | 3.74 | 3.62 | 4.22 | 4.07 | 4.73 | 3.75 | 3.91 |
| hsa-miR-506 | 1.58 | 2.50 | 1.81 | 2.37 | 1.75 | 1.85 | 2.67 | 1.97 |
| hsa-miR-514 | 1.85 | 0.47 | 1.77 | 2.06 | 1.57 | 0.62 | 3.16 | 1.46 |
| hsa-miR-509 | 2.03 | 2.33 | 1.99 | 2.51 | 1.91 | 2.48 | 2.62 | 2.20 |
| hsa-miR-508 | 2.24 | 2.14 | 1.46 | 1.80 | 2.63 | 1.59 | 1.83 | 1.73 |
| hsa-miR-507 | 0.72 | 0.71 | 1.51 | 1.56 | 0.91 | 2.40 | 2.86 | 1.63 |
| ambi-miR-7036 | 3.00 | 3.09 | 2.72 | 2.89 | 2.20 | 3.29 | 3.22 | 2.83 |
| hsa-miR-193b | 6.80 | 6.33 | 6.68 | 5.86 | 6.74 | 6.59 | 5.74 | 6.65 |
| ambi-miR-7038-1 | 2.33 | 1.28 | 1.77 | 1.31 | 1.19 | 2.13 | 0.85 | 1.81 |
| ambi-miR-7039 | 4.98 | 4.43 | 4.35 | 4.14 | 5.23 | 4.74 | 4.22 | 4.60 |
| hsa-miR-488 | 1.14 | 2.33 | 1.81 | 1.62 | 1.83 | 1.66 | 0.47 | 1.76 |
| hsa-miR-510 | 2.03 | 1.92 | 1.90 | 1.91 | 2.38 | 2.59 | 1.92 | 2.00 |
| hsa-miR-517-AS | 1.97 | 2.39 | 1.95 | 2.40 | 2.67 | 2.44 | 2.81 | 2.14 |
| hsa-miR-518f-AS | 1.51 | 2.65 | 1.57 | 2.81 | 0.49 | 1.79 | 3.36 | 1.93 |
| hsa-miR-518c-AS | 3.62 | 4.11 | 3.11 | 4.33 | 4.14 | 4.32 | 3.75 | 3.66 |
| hsa-miR-526c | 1.72 | 2.21 | 1.62 | 2.37 | 2.20 | 2.56 | 2.98 | 1.87 |
| hsa-miR-526b | 1.97 | 3.03 | 2.42 | 3.18 | 3.04 | 3.55 | 3.41 | 2.65 |
| hsa-miR-520a-AS | 1.22 | 1.48 | 1.51 | 1.69 | 0.64 | 2.02 | 1.41 | 1.37 |
| hsa-miR-525 | 1.91 | 2.14 | 1.81 | 2.44 | 1.48 | 2.81 | 2.90 | 1.99 |
| hsa-miR-524-AS | 2.19 | 3.12 | 1.90 | 2.55 | 1.19 | 2.48 | 3.09 | 2.40 |
| hsa-miR-520d-AS | 2.08 | 2.33 | 1.95 | 2.44 | 1.75 | 2.27 | 3.36 | 1.92 |
| hsa-miR-527 | 2.89 | 2.33 | 1.99 | 2.98 | 2.32 | 3.16 | 3.51 | 2.52 |
| hsa-miR-515-5p | 1.00 | 1.18 | 1.86 | 1.04 | 1.29 | 1.91 | 1.52 | 1.55 |
| hsa-miR-519e-AS | 1.44 | 1.08 | 1.77 | 2.25 | 1.83 | 2.90 | 1.92 | 1.83 |
| ambi-miR-7054 | 2.19 | 2.33 | 1.62 | 1.62 | 1.29 | 1.16 | 1.52 | 1.67 |
| ambi-miR-7055 | 2.65 | 2.00 | 1.95 | 2.40 | 2.63 | 2.40 | 2.62 | 2.12 |
| hsa-miR-498 | 2.42 | 2.39 | 1.99 | 2.48 | 1.48 | 2.72 | 2.32 | 2.21 |
| hsa-miR-513 | 3.69 | 4.55 | 3.86 | 4.57 | 4.80 | 4.98 | 4.24 | 4.21 |
| ambi-miR-7058 | 6.25 | 5.92 | 5.41 | 6.28 | 6.07 | 6.38 | 5.68 | 5.98 |
| ambi-miR-7059-1 | 1.29 | 2.73 | 1.57 | 1.04 | 1.75 | 1.45 | 1.41 | 1.71 |
| hsa-miR-452 | 4.55 | 4.58 | 4.56 | 4.65 | 4.83 | 5.00 | 5.07 | 4.82 |
| hsa-miR-493 | 2.78 | 1.84 | 2.54 | 2.16 | 2.48 | 1.59 | 2.86 | 2.37 |
| ambi-miR-7062 | 1.79 | 2.96 | 2.19 | 2.37 | 2.26 | 2.56 | 2.86 | 2.46 |
| hsa-miR-432 | 4.53 | 4.54 | 4.33 | 4.55 | 4.63 | 5.27 | 4.98 | 4.88 |
| hsa-miR-495 | 4.60 | 3.97 | 4.87 | 4.16 | 4.33 | 4.73 | 4.20 | 4.65 |
| hsa-miR-494 | 5.60 | 5.92 | 5.69 | 6.10 | 6.23 | 6.70 | 6.05 | 6.14 |
| ambi-miR-7066 | 2.42 | 2.27 | 2.45 | 2.55 | 2.94 | 2.90 | 2.67 | 2.55 |
| ambi-miR-7067 | 1.97 | 2.45 | 2.48 | 2.58 | 2.63 | 3.22 | 2.94 | 2.72 |
| ambi-miR-7068-1 | 3.09 | 2.45 | 2.91 | 2.91 | 2.83 | 2.97 | 2.72 | 3.03 |
| hsa-miR-496 | 1.44 | 1.75 | 1.62 | 1.80 | 2.20 | 2.02 | 1.83 | 1.73 |
| ambi-miR-7070 | 4.32 | 3.88 | 4.14 | 3.64 | 4.11 | 4.39 | 4.10 | 4.44 |
| hsa-miR-492 | 1.65 | 2.21 | 1.77 | 2.29 | 2.58 | 2.32 | 1.62 | 1.87 |
| hsa-miR-490 | 1.22 | 2.39 | 1.46 | 1.62 | 1.29 | 1.79 | 3.09 | 1.78 |
| hsa-miR-497 | 7.64 | 7.65 | 8.01 | 7.33 | 7.67 | 7.56 | 7.03 | 7.69 |
| ambi-miR-7074 | 1.44 | 2.00 | 1.81 | 2.06 | 1.66 | 2.27 | 1.30 | 1.91 |
| ambi-miR-7075 | 4.14 | 3.71 | 4.24 | 3.97 | 3.99 | 3.91 | 3.64 | 3.92 |
| ambi-miR-7076 | 4.73 | 4.04 | 5.10 | 4.85 | 4.67 | 4.38 | 4.05 | 4.61 |
| hsa-miR-501 | 2.19 | 2.69 | 2.11 | 2.01 | 1.29 | 1.85 | 2.09 | 2.19 |
| hsa-miR-502 | 3.26 | 3.15 | 3.26 | 3.46 | 2.72 | 2.81 | 3.22 | 3.21 |
| ambi-miR-7079 | 4.57 | 4.19 | 4.15 | 3.13 | 2.91 | 3.89 | 2.77 | 4.12 |
| ambi-miR-7080 | 2.38 | 3.09 | 2.19 | 2.33 | 3.16 | 2.18 | 2.81 | 2.42 |
| ambi-miR-7081 | 4.39 | 3.76 | 3.81 | 3.35 | 4.66 | 4.50 | 2.24 | 3.91 |
| hsa-miR-202-AS | 1.58 | 0.99 | 1.57 | 1.91 | 1.29 | 1.79 | 2.09 | 1.46 |
| ambi-miR-7083 | 7.64 | 6.67 | 6.87 | 6.28 | 7.29 | 7.78 | 7.67 | 7.53 |
| ambi-miR-7084 | 1.65 | 2.55 | 1.95 | 1.56 | 2.53 | 1.52 | 2.81 | 2.38 |
| ambi-miR-7085 | 4.38 | 3.93 | 4.74 | 4.34 | 4.67 | 4.35 | 3.31 | 4.35 |
| ambi-miR-7086 | 2.89 | 2.60 | 2.59 | 3.11 | 3.01 | 2.69 | 1.62 | 2.81 |
| hsa-miR-512-5p | 2.24 | 1.08 | 1.57 | 2.37 | 2.13 | 2.23 | 3.19 | 2.01 |
| hsa-miR-504 | 2.54 | 2.27 | 2.36 | 2.61 | 2.48 | 2.36 | 1.18 | 2.26 |
| ambi-miR-7089 | 2.08 | 1.28 | 2.26 | 1.50 | 2.48 | 2.84 | 3.02 | 2.06 |
| hsa-miR-511 | 1.44 | 1.18 | 1.99 | 1.04 | 0.57 | 2.02 | 0.85 | 1.60 |
| hsa-miR-452-AS | 2.78 | 3.03 | 3.17 | 2.48 | 3.26 | 3.20 | 3.19 | 3.12 |
| hsa-miR-503 | 6.38 | 5.55 | 4.78 | 4.10 | 5.49 | 7.35 | 6.33 | 6.14 |
| hsa-miR-485-5p | 2.89 | 3.12 | 2.33 | 3.16 | 3.36 | 3.46 | 2.38 | 3.00 |
| hsa-miR-499 | 2.46 | 1.57 | 2.15 | 2.67 | 1.66 | 2.13 | 2.72 | 1.92 |
| ambi-miR-7095 | 1.65 | 1.57 | 1.81 | 1.31 | 1.91 | 1.45 | 2.24 | 1.71 |
| hsa-miR-505 | 4.73 | 4.71 | 5.13 | 4.93 | 4.92 | 4.29 | 4.28 | 4.67 |
| ambi-miR-7097 | 1.79 | 2.27 | 2.54 | 1.91 | 2.53 | 1.85 | 2.01 | 2.37 |
| ambi-miR-7098 | 1.44 | 2.21 | 1.62 | 1.24 | 1.57 | 1.45 | 2.81 | 1.77 |
| hsa-miR-489 | 2.71 | 3.03 | 2.29 | 1.69 | 2.38 | 1.59 | 1.52 | 2.47 |
| ambi-miR-7100 | 3.12 | 3.33 | 3.69 | 2.76 | 3.07 | 2.84 | 2.51 | 3.24 |

TABLE 5-continued

Normalized Array Data for Sixteen Normal Cervix Tissue Samples (NCX1-NCX16). TV, threshold value, miRNAs > TV, number of miRNAs expressed at greater than threshold value. %, percentage of miRNAs expressed at greater than threshold value.

| ambi-miR-7101 | 4.46 | 4.01 | 4.48 | 4.07 | 3.87 | 4.51 | 3.44 | 4.10 |
| hsa-miR-432-AS | 2.03 | 1.84 | 1.46 | 1.62 | 2.26 | 1.45 | 3.05 | 1.94 |
| ambi-miR-7103 | 2.81 | 2.77 | 2.11 | 2.84 | 2.83 | 3.24 | 2.72 | 2.56 |
| hsa-miR-500 | 4.66 | 3.60 | 4.76 | 4.43 | 4.48 | 4.33 | 4.06 | 4.41 |
| ambi-miR-7105 | 4.87 | 5.06 | 5.29 | 5.02 | 4.97 | 4.45 | 4.31 | 4.84 |

To identify miRNAs enriched or uniquely expressed in the normal cervix, the inventors performed a global comparison of miRNA expression between the 16 normal cervix samples and a reference set of human tissues. miRNA expression in 33 different human tissues was determined using the same microarray platform described above. The human reference set consisted of FirstChoice® Total RNA samples (Ambion) isolated from 33 distinct tissues: adipose, adrenal, aorta, bladder, bone marrow, brain, breast, colon, duodenum, esophagus, fallopian tube, heart, ileum, jejunum, kidney, liver, lung, lymph node, muscle, ovary, pancreas, pituitary, placenta, prostate, small intestine, spleen, stomach, testis, thymus, thyroid, trachea, uterus, and vena cava.

The inventors observed that mean expression levels for 103 human miRNAs in the normal cervix samples were significantly different from the mean expression levels in the 33 reference human tissues (Table 6). These include 94 miRNAs previously identified in humans (hsa-miRNAs) and nine new human miRNAs (ambi-miRs). Of these, 41 miRNAs expressed at higher levels in the cervix samples showed an expression increase greater than 2-fold; whereas, 25 miRNAs expressed at lower levels in the cervix samples showed an expression decrease greater than 2-fold. Several human miRNAs (hsa-miR-205, -196b, -203, -503, -196a, -99a, -187 and Ambi-miR-7083 and -7101) were enriched by at least five-fold ($\Delta H(NCX-REF)>1.6$) in normal cervix samples compared to the reference tissues; whereas, two human miRNAs (hsa-miR-7 and -215) were underexpressed by at least five-fold ($\Delta H(NCX-REF)<-1.6$) in the normal cervix samples.

TABLE 6 miRNAs with Significantly Different Expression in 16 Normal Cervix Samples vs 33 Different Human Tissues. NCX, normal cervix. REF, 33 human tissues reference set.

| miRNA | Mean (NCX) | Mean (REF) | ΔH NCX − REF | Fold Change (NCX vs REF) | p-value (NCX vs REF) |
|---|---|---|---|---|---|
| hsa-let-7a | 10.90 | 10.54 | 0.35 | 1.43 | 0.001022 |
| hsa-let-7b | 11.00 | 10.15 | 0.85 | 2.33 | 2.91E−06 |
| hsa-let-7c | 10.96 | 10.25 | 0.71 | 2.03 | 6.08E−06 |
| hsa-let-7i | 8.68 | 8.34 | 0.34 | 1.40 | 0.012744 |
| hsa-miR-100 | 9.26 | 8.10 | 1.17 | 3.21 | 1.81E−06 |
| hsa-miR-101 | 4.45 | 4.93 | −0.48 | 1.62 | 0.009598 |
| hsa-miR-106a | 7.47 | 7.96 | −0.48 | 1.62 | 0.006077 |
| hsa-miR-125a | 8.95 | 8.14 | 0.80 | 2.24 | 7.2E−05 |
| hsa-miR-125b | 10.33 | 8.84 | 1.49 | 4.44 | 5.2E−10 |
| hsa-miR-126-AS | 5.33 | 5.90 | −0.57 | 1.77 | 0.00412 |
| hsa-miR-127 | 4.32 | 2.95 | 1.37 | 3.92 | 3.16E−06 |
| hsa-miR-130a | 7.75 | 6.91 | 0.85 | 2.33 | 3.21E−05 |
| hsa-miR-134 | 4.91 | 3.37 | 1.53 | 4.63 | 3.23E−07 |
| hsa-miR-142-3p | 3.04 | 3.78 | −0.74 | 2.09 | 0.013448 |
| hsa-miR-143 | 10.36 | 9.72 | 0.64 | 1.89 | 0.013777 |
| hsa-miR-145 | 11.03 | 10.07 | 0.96 | 2.60 | 0.000148 |
| hsa-miR-148b | 4.23 | 5.04 | −0.81 | 2.24 | 9.76E−09 |
| hsa-miR-149 | 3.96 | 3.19 | 0.77 | 2.15 | 0.000335 |
| hsa-miR-151 | 5.82 | 5.46 | 0.36 | 1.44 | 0.000376 |
| hsa-miR-152 | 7.02 | 6.46 | 0.55 | 1.74 | 9.59E−05 |
| hsa-miR-154 | 4.90 | 3.85 | 1.05 | 2.85 | 9.68E−05 |
| hsa-miR-15a | 6.50 | 7.37 | −0.87 | 2.39 | 3.53E−07 |
| hsa-miR-15b | 6.84 | 7.65 | −0.81 | 2.25 | 1.86E−05 |
| hsa-miR-16 | 9.68 | 9.99 | −0.31 | 1.37 | 0.015778 |
| hsa-miR-17-5p | 7.38 | 7.84 | −0.46 | 1.59 | 0.005901 |
| hsa-miR-181a | 6.73 | 7.45 | −0.72 | 2.05 | 0.001346 |
| hsa-miR-185 | 5.45 | 6.06 | −0.61 | 1.84 | 0.000244 |
| hsa-miR-186 | 4.21 | 4.92 | −0.72 | 2.05 | 4.13E−05 |
| hsa-miR-187 | 5.25 | 3.60 | 1.65 | 5.21 | 0.000782 |
| hsa-miR-192 | 4.43 | 5.87 | −1.45 | 4.24 | 0.015567 |
| hsa-miR-193a | 4.33 | 3.56 | 0.77 | 2.16 | 0.000147 |
| hsa-miR-195 | 9.22 | 8.14 | 1.08 | 2.93 | 5.37E−07 |
| hsa-miR-196a | 4.97 | 2.99 | 1.98 | 7.26 | 0.000277 |
| hsa-miR-196b | 6.58 | 3.33 | 3.25 | 25.77 | 1.83E−08 |
| hsa-miR-199a | 8.64 | 7.51 | 1.13 | 3.08 | 1.95E−05 |
| hsa-miR-199a-AS | 8.86 | 8.24 | 0.61 | 1.85 | 0.008817 |
| hsa-miR-199b | 6.76 | 5.56 | 1.20 | 3.31 | 0.000616 |
| hsa-miR-19a | 3.97 | 5.21 | −1.24 | 3.44 | 2.48E−05 |
| hsa-miR-20a | 6.38 | 7.08 | −0.70 | 2.01 | 0.000188 |
| hsa-miR-203 | 6.85 | 4.57 | 2.28 | 9.77 | 4.72E−05 |
| hsa-miR-205 | 7.72 | 3.69 | 4.03 | 56.10 | 3.38E−06 |
| hsa-miR-21 | 9.10 | 9.62 | −0.51 | 1.67 | 0.006949 |
| hsa-miR-214 | 8.24 | 6.80 | 1.43 | 4.20 | 9.49E−08 |
| hsa-miR-215 | 1.74 | 3.46 | −1.72 | 5.56 | 0.005969 |
| hsa-miR-22 | 8.17 | 8.64 | −0.46 | 1.59 | 0.014943 |
| hsa-miR-221 | 8.28 | 7.73 | 0.55 | 1.73 | 0.015073 |
| hsa-miR-223 | 6.18 | 7.11 | −0.93 | 2.53 | 0.002949 |
| hsa-miR-23b | 9.91 | 9.49 | 0.42 | 1.53 | 0.009 |
| hsa-miR-24 | 9.80 | 9.13 | 0.67 | 1.95 | 1.73E−05 |
| hsa-miR-25 | 6.56 | 6.98 | −0.42 | 1.52 | 0.006356 |
| hsa-miR-26a | 10.83 | 10.48 | 0.36 | 1.43 | 0.00039 |
| hsa-miR-26b | 7.64 | 8.13 | −0.49 | 1.64 | 0.003271 |
| hsa-miR-299-5p | 4.74 | 3.44 | 1.30 | 3.68 | 2.36E−07 |
| hsa-miR-29b | 6.89 | 7.48 | −0.59 | 1.81 | 0.000533 |
| hsa-miR-29c | 6.79 | 7.66 | −0.87 | 2.39 | 5.13E−06 |
| hsa-miR-302c-AS | 3.49 | 2.93 | 0.56 | 1.76 | 0.001188 |
| hsa-miR-30a-3p | 4.08 | 4.90 | −0.82 | 2.28 | 5.54E−06 |
| hsa-miR-30a-5p | 8.11 | 8.69 | −0.58 | 1.78 | 5.94E−05 |
| hsa-miR-30b | 7.25 | 8.15 | −0.90 | 2.46 | 1E−06 |
| hsa-miR-30c | 7.56 | 8.28 | −0.72 | 2.05 | 1.25E−05 |
| hsa-miR-30e-3p | 4.08 | 4.59 | −0.51 | 1.67 | 7.66E−05 |
| hsa-miR-30e-5p | 7.41 | 7.89 | −0.48 | 1.61 | 0.000371 |
| hsa-miR-31 | 6.97 | 5.71 | 1.26 | 3.52 | 0.005863 |
| hsa-miR-320 | 8.37 | 7.63 | 0.74 | 2.09 | 2.91E−07 |
| hsa-miR-324-3p | 5.71 | 5.01 | 0.70 | 2.02 | 3.75E−08 |
| hsa-miR-335 | 4.69 | 6.06 | −1.37 | 3.93 | 1.04E−06 |
| hsa-miR-338 | 2.36 | 3.40 | −1.04 | 2.84 | 0.004285 |
| hsa-miR-342 | 7.31 | 7.71 | −0.40 | 1.49 | 0.014704 |
| hsa-miR-34a | 7.48 | 6.70 | 0.78 | 2.19 | 5.3E−05 |
| hsa-miR-361 | 6.99 | 6.64 | 0.35 | 1.41 | 0.006748 |
| hsa-miR-365 | 3.36 | 4.01 | −0.65 | 1.92 | 0.009203 |
| hsa-miR-367 | 1.12 | 1.54 | −0.43 | 1.53 | 0.005012 |
| hsa-miR-368 | 6.97 | 5.80 | 1.17 | 3.23 | 9.53E−06 |

TABLE 6-continued miRNAs with Significantly Different Expression in 16 Normal Cervix Samples vs 33 Different Human Tissues. NCX, normal cervix. REF, 33 human tissues reference set.

| miRNA | Mean (NCX) | Mean (REF) | ΔH NCX − REF | Fold Change (NCX vs REF) | p-value (NCX vs REF) |
|---|---|---|---|---|---|
| hsa-miR-370 | 4.68 | 4.22 | 0.46 | 1.58 | 0.000226 |
| hsa-miR-374 | 2.95 | 3.96 | −1.00 | 2.73 | 6.11E−05 |
| hsa-miR-376a | 5.16 | 4.49 | 0.67 | 1.95 | 0.009825 |
| hsa-miR-379 | 5.45 | 4.48 | 0.97 | 2.64 | 9.16E−06 |
| hsa-miR-381 | 4.36 | 3.34 | 1.02 | 2.77 | 2.66E−06 |
| hsa-miR-423 | 6.19 | 5.85 | 0.34 | 1.41 | 0.012001 |
| hsa-miR-424 | 5.70 | 4.33 | 1.38 | 3.96 | 0.000364 |
| hsa-miR-450 | 2.52 | 2.02 | 0.50 | 1.66 | 0.014789 |
| hsa-miR-7 | 2.55 | 4.48 | −1.94 | 6.94 | 3.65E−05 |
| hsa-miR-93 | 6.82 | 7.22 | −0.40 | 1.49 | 0.011372 |
| hsa-miR-95 | 3.26 | 4.51 | −1.25 | 3.48 | 0.000314 |
| hsa-miR-96 | 3.31 | 4.14 | −0.83 | 2.30 | 0.003532 |
| hsa-miR-99a | 10.12 | 8.30 | 1.82 | 6.17 | 2.24E−09 |
| hsa-miR-99b | 7.37 | 6.67 | 0.70 | 2.02 | 4.52E−05 |
| ambi-miR-7027 | 3.07 | 2.59 | 0.48 | 1.61 | 0.006012 |
| ambi-miR-7029 | 6.99 | 8.25 | −1.26 | 3.52 | 0.003885 |
| hsa-miR-509 | 1.97 | 3.00 | −1.04 | 2.82 | 0.01444 |
| hsa-miR-193b | 6.64 | 5.80 | 0.84 | 2.32 | 0.003545 |
| ambi-miR-7039 | 4.59 | 3.78 | 0.81 | 2.25 | 2.68E−05 |
| hsa-miR-526b | 2.51 | 3.04 | −0.53 | 1.69 | 0.014724 |
| hsa-miR-498 | 2.00 | 2.87 | −0.87 | 2.39 | 0.001218 |
| hsa-miR-452 | 4.81 | 4.10 | 0.71 | 2.04 | 0.002909 |
| ambi-miR-7062 | 2.28 | 2.67 | −0.38 | 1.47 | 0.011083 |
| ambi-miR-7070 | 4.42 | 3.26 | 1.16 | 3.19 | 1.19E−05 |
| hsa-miR-497 | 7.68 | 6.53 | 1.16 | 3.17 | 1.31E−08 |
| ambi-miR-7079 | 4.10 | 5.01 | −0.92 | 2.50 | 0.004187 |
| ambi-miR-7083 | 7.52 | 5.23 | 2.29 | 9.92 | 4.03E−11 |
| ambi-miR-7085 | 4.33 | 3.12 | 1.22 | 3.38 | 3.3E−10 |
| hsa-miR-503 | 6.13 | 4.12 | 2.01 | 7.45 | 6.42E−07 |
| ambi-miR-7101 | 4.08 | 2.39 | 1.68 | 5.39 | 1.53E−08 |

Example 3

MicroRNA Expression Profiling Distinguishes Normal and Cancerous Cervix Tissue Samples miRNAs potentially relevant to carcinogenesis frequently exhibit differential expression in cancer versus normal samples collected from the same tissue type. In addition, miRNAs with differential expression in normal and cancerous samples may be used in the diagnosis of pre-cancerous and cancerous lesions. To identify miRNAs that may be useful for diagnosis of the most common type of cervical cancer (cervical squamous cell carcinoma), the inventors used the microarray platform described in Example 2 to compare global miRNA expression in nine cervical squamous cell carcinomas and nine paired normal adjacent tissue samples from the same patients. The results are shown below in Table 7. On average, 244 miRNAs were detected above background (>2.32) in normal adjacent tissues from cancer patients and 208 miRNAs were detected above background (>2.64) in cervical tumors.

The miRNA expression data from the nine Ca and nine NAT samples (Table 7) were normalized together with the data from the 16 NCX samples (Table 5). Mean miRNA expression levels are altered in the nine squamous cell carcinomas (Ca) when compared to miRNA expression levels in the adjacent normal cervical samples (NAT) and in the 16 normal cervix samples (NCX) (Table 8).

TABLE 7

Normalized Array Data for miRNA Expression in Nine Cervical Tumor Tissue Samples (Ca1-Ca9) and Nine Cervical Normal Adjacent Tissue Samples (NAT1-NAT-9). TV, threshold value. miRNAs > TV, miRNAs greater than threshold value. %, Percentage of miRNAs greater than threshold value.

| | Ca 1 | Ca 2 | Ca 3 | Ca 4 | Ca 5 | Ca 6 | Ca 7 | Ca 8 | Ca 9 | Mean (Ca) |
|---|---|---|---|---|---|---|---|---|---|---|
| TV | 2.78 | 2.64 | 2.13 | 2.83 | 2.70 | 2.62 | 2.73 | 2.68 | 3.30 | 2.64 |
| miRNAs > TV | 192 | 205 | 258 | 196 | 210 | 213 | 209 | 222 | 170 | 208 |
| % | 50.91 | 54.29 | 68.31 | 51.95 | 55.58 | 56.62 | 55.32 | 58.96 | 45.19 | 55.24 |
| miR Name | | | | | | | | | | |
| hsa-let-7a | 10.47 | 10.86 | 10.30 | 10.45 | 10.03 | 9.82 | 9.71 | 10.31 | 9.53 | 10.17 |
| hsa-let-7b | 10.57 | 10.99 | 9.84 | 10.57 | 9.86 | 10.17 | 9.96 | 10.27 | 9.20 | 10.16 |
| hsa-let-7c | 9.96 | 10.63 | 9.82 | 10.23 | 9.75 | 9.62 | 9.52 | 10.10 | 8.85 | 9.83 |
| hsa-let-7d | 9.31 | 9.42 | 9.17 | 9.12 | 8.71 | 8.45 | 8.42 | 9.01 | 8.06 | 8.85 |
| hsa-let-7e | 7.20 | 7.66 | 7.31 | 7.69 | 6.95 | 7.13 | 6.85 | 7.27 | 6.63 | 7.19 |
| hsa-let-7f | 7.80 | 8.22 | 8.55 | 8.11 | 7.47 | 7.31 | 7.09 | 7.91 | 6.83 | 7.70 |
| hsa-let-7g | 7.50 | 8.33 | 7.98 | 7.80 | 7.50 | 7.16 | 6.78 | 7.84 | 6.70 | 7.51 |
| hsa-let-7i | 8.31 | 8.43 | 8.40 | 8.38 | 8.13 | 7.91 | 8.10 | 8.28 | 7.48 | 8.16 |
| hsa-miR-1 | 1.95 | 2.79 | 2.13 | 2.17 | 2.87 | 2.56 | 1.73 | 2.68 | 1.52 | 2.27 |
| hsa-miR-100 | 5.73 | 7.61 | 7.08 | 7.15 | 7.76 | 7.27 | 6.92 | 8.03 | 6.36 | 7.10 |
| hsa-miR-101 | 2.84 | 3.19 | 3.45 | 2.43 | 2.75 | 3.11 | 2.80 | 3.42 | 2.49 | 2.94 |
| hsa-miR-103 | 8.81 | 8.53 | 7.99 | 8.67 | 7.88 | 8.09 | 8.08 | 7.98 | 7.85 | 8.21 |
| hsa-miR-105 | 1.82 | 0.57 | 1.69 | 2.35 | 1.61 | 1.78 | 1.64 | 1.18 | 3.14 | 1.75 |
| hsa-miR-106a | 8.77 | 7.66 | 7.97 | 8.34 | 8.58 | 8.10 | 8.58 | 7.83 | 8.54 | 8.26 |
| hsa-miR-106b | 7.58 | 7.25 | 7.02 | 6.96 | 6.90 | 6.75 | 7.03 | 6.93 | 7.14 | 7.06 |
| hsa-miR-107 | 8.78 | 8.56 | 7.87 | 8.56 | 7.81 | 8.01 | 8.07 | 7.87 | 7.75 | 8.14 |

TABLE 7-continued

Normalized Array Data for miRNA Expression in Nine Cervical Tumor Tissue Samples (Ca1-Ca9) and
Nine Cervical Normal Adjacent Tissue Samples (NAT1-NAT-9). TV, threshold value. miRNAs >
TV, miRNAs greater than threshold value. %, Percentage of miRNAs greater than threshold value.

| | | | | | | | | | | |
|---|---|---|---|---|---|---|---|---|---|---|
| hsa-miR-10a | 5.83 | 6.64 | 5.08 | 5.10 | 7.28 | 6.34 | 5.97 | 6.41 | 7.19 | 6.20 |
| hsa-miR-10b | 5.95 | 6.01 | 6.18 | 6.53 | 7.24 | 6.57 | 6.14 | 7.05 | 6.55 | 6.47 |
| hsa-miR-122a | 4.20 | 3.78 | 4.90 | 3.97 | 2.98 | 3.21 | 3.57 | 2.91 | 3.70 | 3.69 |
| hsa-miR-124a | 1.67 | 1.90 | 1.26 | 2.17 | 1.41 | 2.62 | 2.80 | 1.72 | 2.91 | 2.05 |
| hsa-miR-125a | 7.25 | 7.91 | 6.73 | 7.82 | 8.26 | 8.44 | 7.96 | 8.28 | 7.25 | 7.77 |
| hsa-miR-125b | 7.36 | 8.99 | 8.31 | 8.88 | 9.59 | 9.27 | 9.01 | 9.67 | 8.15 | 8.80 |
| hsa-miR-126 | 8.43 | 8.42 | 8.17 | 8.54 | 9.01 | 8.67 | 8.16 | 9.25 | 7.80 | 8.50 |
| hsa-miR-126-AS | 3.25 | 3.32 | 4.22 | 3.41 | 4.57 | 4.20 | 3.23 | 5.17 | 3.21 | 3.84 |
| hsa-miR-127 | 2.78 | 2.89 | 2.05 | 2.65 | 3.78 | 3.61 | 3.33 | 4.39 | 3.14 | 3.18 |
| hsa-miR-128a | 5.27 | 5.57 | 5.11 | 5.05 | 5.31 | 5.02 | 5.24 | 5.13 | 5.20 | 5.21 |
| hsa-miR-129 | 2.64 | 2.52 | 3.60 | 2.35 | 2.83 | 2.82 | 2.98 | 1.79 | 3.18 | 2.74 |
| hsa-miR-130a | 5.85 | 6.78 | 5.83 | 6.14 | 6.33 | 6.04 | 6.63 | 6.59 | 6.58 | 6.31 |
| hsa-miR-130b | 5.47 | 6.23 | 5.91 | 5.37 | 4.92 | 5.18 | 5.91 | 4.75 | 5.84 | 5.51 |
| hsa-miR-132 | 5.54 | 5.93 | 5.66 | 5.69 | 5.70 | 5.89 | 5.57 | 5.70 | 4.77 | 5.61 |
| hsa-miR-133a | 3.51 | 4.18 | 3.45 | 4.24 | 5.65 | 5.57 | 4.63 | 4.13 | 3.83 | 4.35 |
| hsa-miR-134 | 2.84 | 3.46 | 2.86 | 3.35 | 3.58 | 3.69 | 3.33 | 3.70 | 2.66 | 3.27 |
| hsa-miR-135a | 2.64 | 2.32 | 2.05 | 2.26 | 1.41 | 1.78 | 2.40 | 1.18 | 1.84 | 1.99 |
| hsa-miR-135b | 2.29 | 1.99 | 2.05 | 2.71 | 2.55 | 2.06 | 1.37 | 2.36 | 3.36 | 2.31 |
| hsa-miR-136 | 1.36 | 1.80 | 1.87 | 1.18 | 1.30 | 1.97 | 1.28 | 1.92 | 2.55 | 1.69 |
| hsa-miR-137 | 1.95 | 1.90 | 2.20 | 0.90 | 1.79 | 1.67 | 2.10 | 2.10 | 3.18 | 1.98 |
| hsa-miR-138 | 1.82 | 2.69 | 2.46 | 2.51 | 2.12 | 2.15 | 2.45 | 1.92 | 2.91 | 2.34 |
| hsa-miR-139 | 2.56 | 3.69 | 2.05 | 2.88 | 4.20 | 3.04 | 4.19 | 4.59 | 3.49 | 3.41 |
| hsa-miR-140 | 3.07 | 3.87 | 4.26 | 3.56 | 4.60 | 4.30 | 4.18 | 4.77 | 3.42 | 4.00 |
| hsa-miR-141 | 6.50 | 6.95 | 6.14 | 6.45 | 6.38 | 5.53 | 6.53 | 6.54 | 8.86 | 6.65 |
| hsa-miR-142-3p | 3.29 | 3.05 | 4.69 | 3.41 | 3.39 | 2.82 | 3.26 | 4.34 | 3.30 | 3.51 |
| hsa-miR-142-5p | 3.01 | 3.05 | 3.18 | 2.58 | 3.83 | 3.84 | 2.94 | 2.61 | 4.01 | 3.23 |
| hsa-miR-143 | 7.43 | 8.51 | 7.76 | 8.40 | 9.53 | 9.82 | 8.65 | 9.14 | 7.95 | 8.58 |
| hsa-miR-144 | 1.36 | 2.46 | 1.69 | 1.59 | 0.70 | 0.87 | 2.17 | 1.10 | 0.11 | 1.34 |
| hsa-miR-145 | 8.59 | 9.90 | 8.52 | 9.79 | 10.55 | 10.58 | 9.54 | 10.07 | 8.57 | 9.57 |
| hsa-miR-146a | 6.30 | 6.86 | 6.63 | 7.21 | 6.71 | 6.31 | 6.53 | 7.32 | 5.65 | 6.61 |
| hsa-miR-147 | 2.71 | 2.58 | 2.90 | 1.59 | 2.04 | 1.88 | 2.29 | 0.87 | 1.63 | 2.06 |
| hsa-miR-148a | 5.02 | 6.61 | 6.39 | 6.24 | 5.99 | 5.92 | 5.32 | 6.70 | 5.41 | 5.96 |
| hsa-miR-148b | 4.51 | 4.75 | 4.56 | 4.68 | 4.48 | 4.40 | 3.88 | 4.82 | 4.72 | 4.53 |
| hsa-miR-149 | 3.29 | 3.19 | 3.18 | 3.71 | 3.60 | 4.56 | 4.54 | 3.74 | 4.80 | 3.85 |
| hsa-miR-150 | 5.45 | 6.47 | 7.17 | 7.11 | 7.69 | 7.27 | 6.62 | 8.86 | 5.85 | 6.94 |
| hsa-miR-151 | 5.86 | 5.15 | 5.07 | 5.54 | 5.71 | 5.93 | 5.65 | 5.47 | 5.87 | 5.58 |
| hsa-miR-152 | 5.24 | 6.63 | 5.94 | 5.96 | 6.24 | 6.61 | 6.35 | 6.46 | 6.71 | 6.24 |
| hsa-miR-153 | 2.39 | 1.90 | 2.05 | 1.72 | 2.19 | 2.15 | 2.23 | 2.36 | 2.03 | 2.11 |
| hsa-miR-154 | 1.82 | 3.29 | 2.82 | 3.28 | 3.39 | 3.89 | 3.35 | 4.06 | 2.86 | 3.19 |
| hsa-miR-155 | 7.58 | 7.74 | 7.46 | 7.49 | 6.28 | 6.48 | 6.56 | 7.08 | 6.15 | 6.98 |
| hsa-miR-15a | 6.53 | 6.52 | 6.72 | 6.73 | 6.57 | 6.53 | 6.11 | 6.83 | 6.73 | 6.58 |
| hsa-miR-15b | 8.51 | 8.80 | 7.98 | 8.66 | 7.82 | 7.72 | 7.81 | 7.71 | 8.51 | 8.17 |
| hsa-miR-16 | 10.25 | 10.47 | 9.83 | 10.44 | 9.90 | 9.87 | 9.82 | 10.14 | 10.33 | 10.12 |
| hsa-miR-17-3p | 4.95 | 3.80 | 4.03 | 4.43 | 4.49 | 4.02 | 4.70 | 4.07 | 4.24 | 4.30 |
| hsa-miR-17-5p | 8.68 | 7.52 | 7.82 | 8.32 | 8.27 | 7.88 | 8.44 | 7.52 | 8.37 | 8.09 |
| hsa-miR-18a | 5.69 | 4.73 | 5.46 | 5.08 | 5.55 | 5.19 | 6.01 | 5.19 | 6.26 | 5.46 |
| hsa-miR-181a | 7.24 | 7.36 | 7.15 | 7.32 | 6.89 | 7.52 | 7.08 | 7.50 | 6.90 | 7.22 |
| hsa-miR-181b | 6.81 | 6.46 | 6.26 | 6.62 | 6.06 | 6.17 | 6.92 | 6.25 | 5.97 | 6.39 |
| hsa-miR-181c | 2.56 | 3.43 | 3.79 | 3.16 | 3.92 | 4.43 | 3.64 | 4.14 | 3.86 | 3.66 |
| hsa-miR-182 | 6.76 | 6.65 | 6.52 | 6.40 | 6.31 | 5.80 | 6.09 | 6.07 | 6.23 | 6.32 |
| hsa-miR-182-AS | 1.82 | 2.08 | 2.13 | 2.43 | 1.30 | 1.97 | 1.96 | 1.98 | 0.71 | 1.82 |
| hsa-miR-183 | 5.30 | 4.71 | 4.66 | 4.92 | 4.67 | 4.26 | 4.65 | 4.52 | 4.93 | 4.74 |
| hsa-miR-184 | 3.91 | 3.01 | 5.03 | 3.71 | 3.36 | 3.27 | 3.82 | 2.99 | 3.27 | 3.60 |
| hsa-miR-185 | 6.51 | 6.70 | 6.34 | 6.06 | 5.58 | 5.80 | 6.11 | 5.81 | 6.22 | 6.13 |
| hsa-miR-186 | 3.07 | 4.10 | 3.90 | 3.12 | 3.52 | 3.56 | 2.84 | 3.74 | 2.66 | 3.39 |
| hsa-miR-187 | 4.66 | 1.90 | 3.87 | 2.98 | 4.27 | 3.94 | 2.98 | 4.78 | 4.02 | 3.71 |
| hsa-miR-188 | 3.69 | 3.40 | 4.14 | 3.44 | 3.26 | 3.92 | 4.20 | 3.33 | 3.76 | 3.68 |
| hsa-miR-189 | 2.84 | 3.69 | 3.49 | 3.41 | 3.52 | 3.97 | 3.41 | 3.79 | 3.52 | 3.52 |
| hsa-miR-190 | 1.20 | 1.47 | 1.16 | 0.90 | 0.89 | 1.88 | 1.37 | 0.66 | 0.93 | 1.16 |
| hsa-miR-191 | 7.83 | 8.85 | 7.50 | 8.13 | 8.04 | 7.89 | 7.40 | 7.60 | 7.70 | 7.88 |
| hsa-miR-192 | 3.51 | 3.95 | 4.21 | 3.95 | 4.78 | 4.13 | 4.42 | 4.63 | 3.63 | 4.14 |
| hsa-miR-193a | 5.34 | 4.94 | 3.91 | 4.75 | 3.99 | 4.22 | 5.16 | 4.48 | 5.56 | 4.71 |
| hsa-miR-194 | 4.25 | 4.60 | 4.61 | 4.44 | 5.13 | 4.69 | 4.74 | 4.90 | 4.15 | 4.61 |
| hsa-miR-195 | 6.03 | 7.53 | 6.32 | 7.45 | 7.81 | 7.50 | 7.25 | 7.86 | 6.77 | 7.17 |
| hsa-miR-196a | 5.42 | 3.40 | 2.46 | 3.62 | 4.27 | 4.13 | 4.23 | 4.72 | 5.32 | 4.17 |
| hsa-miR-196b | 5.06 | 5.59 | 4.62 | 5.42 | 5.49 | 4.81 | 4.91 | 5.42 | 4.45 | 5.08 |
| hsa-miR-197 | 4.94 | 6.05 | 4.62 | 5.33 | 5.23 | 5.02 | 5.05 | 4.77 | 5.56 | 5.17 |
| hsa-miR-198 | 5.13 | 4.74 | 5.96 | 5.19 | 5.02 | 5.14 | 5.43 | 4.57 | 5.54 | 5.19 |
| hsa-miR-199a | 7.01 | 8.31 | 7.51 | 7.92 | 8.13 | 8.65 | 7.72 | 7.93 | 7.18 | 7.82 |
| hsa-miR-199a-AS | 7.26 | 8.30 | 7.98 | 8.01 | 8.44 | 8.38 | 7.67 | 8.27 | 7.35 | 7.96 |
| hsa-miR-199b | 3.80 | 5.64 | 5.52 | 5.40 | 6.03 | 6.12 | 4.85 | 6.47 | 4.75 | 5.40 |
| hsa-miR-19a | 3.69 | 3.43 | 4.58 | 3.24 | 4.29 | 3.88 | 4.16 | 4.38 | 4.94 | 4.06 |
| hsa-miR-19b | 7.48 | 7.28 | 7.36 | 7.43 | 8.05 | 7.64 | 7.78 | 7.76 | 8.37 | 7.68 |
| hsa-miR-20a | 6.77 | 6.27 | 6.48 | 6.74 | 7.46 | 6.61 | 7.22 | 6.75 | 7.21 | 6.83 |
| hsa-miR-200a | 6.11 | 7.56 | 6.18 | 5.99 | 7.62 | 6.22 | 6.06 | 6.82 | 6.90 | 6.61 |
| hsa-miR-200b | 7.75 | 8.83 | 7.67 | 7.65 | 9.18 | 7.99 | 7.56 | 8.19 | 8.00 | 8.09 |

TABLE 7-continued

Normalized Array Data for miRNA Expression in Nine Cervical Tumor Tissue Samples (Ca1-Ca9) and
Nine Cervical Normal Adjacent Tissue Samples (NAT1-NAT-9). TV, threshold value. miRNAs >
TV, miRNAs greater than threshold value. %, Percentage of miRNAs greater than threshold value.

| | | | | | | | | | | |
|---|---|---|---|---|---|---|---|---|---|---|
| hsa-miR-200c | 9.88 | 9.54 | 8.65 | 9.75 | 9.45 | 8.33 | 9.19 | 8.79 | 10.55 | 9.35 |
| hsa-miR-203 | 7.92 | 8.96 | 9.01 | 9.09 | 7.67 | 8.46 | 8.37 | 9.09 | 8.80 | 8.60 |
| hsa-miR-204 | 1.52 | 2.08 | 2.34 | 2.71 | 2.55 | 3.07 | 2.10 | 2.94 | 2.12 | 2.38 |
| hsa-miR-205 | 11.09 | 11.07 | 10.23 | 11.19 | 11.19 | 10.75 | 11.12 | 10.73 | 11.43 | 10.98 |
| hsa-miR-206 | 2.71 | 3.01 | 4.22 | 2.83 | 2.75 | 2.68 | 2.88 | 2.68 | 2.86 | 2.96 |
| hsa-miR-208 | 2.07 | 1.80 | 2.13 | 1.72 | 1.51 | 1.33 | 1.28 | 1.42 | 1.52 | 1.64 |
| hsa-miR-21 | 10.73 | 10.42 | 10.74 | 10.54 | 11.10 | 11.21 | 10.62 | 10.99 | 11.54 | 10.88 |
| hsa-miR-210 | 6.69 | 6.98 | 5.75 | 6.86 | 5.33 | 6.36 | 5.74 | 5.98 | 7.77 | 6.39 |
| hsa-miR-211 | 1.36 | 2.08 | 1.69 | 2.58 | 2.12 | 1.56 | 1.96 | 2.40 | 2.28 | 2.01 |
| hsa-miR-212 | 3.21 | 3.43 | 3.37 | 3.08 | 2.55 | 3.11 | 2.88 | 2.88 | 2.91 | 3.05 |
| hsa-miR-213 | 2.39 | 2.32 | 1.69 | 2.43 | 1.97 | 2.96 | 2.55 | 2.49 | 2.35 | 2.35 |
| hsa-miR-214 | 7.11 | 7.96 | 6.92 | 7.86 | 7.62 | 7.82 | 7.17 | 7.05 | 6.54 | 7.34 |
| hsa-miR-215 | 2.78 | 2.25 | 2.90 | 2.88 | 2.19 | 2.30 | 2.35 | 2.31 | 2.42 | 2.49 |
| hsa-miR-216 | 1.20 | 2.25 | 1.96 | 2.35 | 2.61 | 2.37 | 2.80 | 2.45 | 2.91 | 2.32 |
| hsa-miR-217 | 2.39 | 1.69 | 2.20 | 2.17 | 2.04 | 1.67 | 1.64 | 1.79 | 1.04 | 1.85 |
| hsa-miR-218 | 3.58 | 3.05 | 3.52 | 3.20 | 4.23 | 3.56 | 3.47 | 4.55 | 3.14 | 3.59 |
| hsa-miR-219 | 2.07 | 1.90 | 1.87 | 1.72 | 2.19 | 2.44 | 1.89 | 2.26 | 2.12 | 2.05 |
| hsa-miR-22 | 7.86 | 8.25 | 7.67 | 7.83 | 8.28 | 8.84 | 8.54 | 8.28 | 8.52 | 8.23 |
| hsa-miR-220 | 1.36 | 1.69 | 0.65 | 2.17 | 2.12 | 1.10 | 1.96 | 1.72 | 0.51 | 1.48 |
| hsa-miR-221 | 7.63 | 7.70 | 8.38 | 8.64 | 8.37 | 8.99 | 8.52 | 8.01 | 8.13 | 8.27 |
| hsa-miR-222 | 7.18 | 6.86 | 7.79 | 7.95 | 7.91 | 8.43 | 8.24 | 7.60 | 7.59 | 7.73 |
| hsa-miR-223 | 6.73 | 5.93 | 8.76 | 7.50 | 7.86 | 7.30 | 7.56 | 8.23 | 6.98 | 7.43 |
| hsa-miR-224 | 7.41 | 8.56 | 7.08 | 7.32 | 6.79 | 8.23 | 6.43 | 7.67 | 7.46 | 7.44 |
| hsa-miR-23a | 9.81 | 9.59 | 9.35 | 9.40 | 9.33 | 9.69 | 9.53 | 9.67 | 9.42 | 9.53 |
| hsa-miR-23b | 9.31 | 9.84 | 9.32 | 9.72 | 9.56 | 9.99 | 9.26 | 9.83 | 9.38 | 9.58 |
| hsa-miR-24 | 9.94 | 9.37 | 8.85 | 9.47 | 9.40 | 9.99 | 9.62 | 9.46 | 9.27 | 9.48 |
| hsa-miR-25 | 7.55 | 7.22 | 7.40 | 7.18 | 7.23 | 6.73 | 6.80 | 7.11 | 7.07 | 7.14 |
| hsa-miR-26a | 9.67 | 10.16 | 9.49 | 10.13 | 10.26 | 10.10 | 9.56 | 10.18 | 9.64 | 9.91 |
| hsa-miR-26b | 6.08 | 6.21 | 6.64 | 6.27 | 6.27 | 5.94 | 5.60 | 6.65 | 5.54 | 6.13 |
| hsa-miR-27a | 8.88 | 8.32 | 8.48 | 8.48 | 8.82 | 9.15 | 9.16 | 9.07 | 9.06 | 8.82 |
| hsa-miR-27b | 7.55 | 8.30 | 8.15 | 8.56 | 8.59 | 9.13 | 8.19 | 8.80 | 8.39 | 8.41 |
| hsa-miR-28 | 5.19 | 4.97 | 5.07 | 5.20 | 5.46 | 5.68 | 5.08 | 5.05 | 5.31 | 5.22 |
| hsa-miR-296 | 2.90 | 2.64 | 1.58 | 2.88 | 3.71 | 3.65 | 3.93 | 3.21 | 4.17 | 3.19 |
| hsa-miR-299-5p | 2.64 | 3.26 | 2.34 | 3.12 | 3.34 | 3.79 | 2.73 | 3.83 | 1.84 | 2.99 |
| hsa-miR-29a | 7.91 | 8.59 | 8.28 | 8.13 | 8.53 | 8.53 | 8.21 | 8.90 | 7.62 | 8.30 |
| hsa-miR-29b | 4.35 | 6.45 | 6.30 | 5.23 | 5.61 | 5.81 | 5.88 | 6.80 | 5.08 | 5.72 |
| hsa-miR-29c | 3.44 | 6.26 | 5.76 | 5.00 | 5.25 | 5.26 | 4.74 | 6.44 | 5.04 | 5.24 |
| hsa-miR-301 | 2.90 | 2.89 | 2.73 | 2.58 | 1.51 | 1.78 | 2.64 | 2.40 | 3.33 | 2.53 |
| hsa-miR-302a | 2.07 | 2.32 | 1.96 | 1.96 | 2.45 | 2.30 | 1.64 | 2.36 | 2.82 | 2.21 |
| hsa-miR-302b | 0.74 | 2.08 | 3.87 | 2.26 | 0.62 | 1.22 | 1.64 | 0.41 | 0.18 | 1.45 |
| hsa-miR-302b-AS | 1.82 | 2.32 | 1.48 | 1.72 | 1.09 | 1.45 | 1.81 | 1.49 | 0.93 | 1.57 |
| hsa-miR-302c | 2.29 | 2.32 | 1.58 | 2.07 | 1.51 | 2.06 | 1.00 | 1.02 | 1.52 | 1.71 |
| hsa-miR-302c-AS | 4.08 | 3.91 | 5.10 | 3.85 | 2.95 | 3.41 | 3.55 | 2.96 | 3.44 | 3.69 |
| hsa-miR-302d | 1.82 | 1.69 | 2.05 | 1.32 | 1.79 | 1.97 | 1.73 | 1.10 | 1.40 | 1.65 |
| hsa-miR-30a-3p | 2.29 | 2.46 | 3.49 | 2.35 | 3.20 | 2.68 | 2.91 | 3.27 | 2.91 | 2.84 |
| hsa-miR-30a-5p | 7.15 | 7.46 | 7.27 | 7.83 | 7.67 | 7.55 | 7.22 | 7.69 | 7.23 | 7.45 |
| hsa-miR-30b | 6.56 | 6.58 | 6.66 | 6.32 | 7.08 | 7.02 | 6.10 | 6.57 | 6.11 | 6.56 |
| hsa-miR-30c | 7.18 | 7.88 | 7.12 | 9.25 | 7.71 | 7.49 | 7.13 | 7.53 | 7.65 | 7.66 |
| hsa-miR-30d | 7.83 | 7.42 | 7.03 | 7.29 | 7.86 | 8.13 | 7.40 | 7.78 | 7.03 | 7.53 |
| hsa-miR-30e-3p | 3.80 | 4.07 | 3.68 | 4.42 | 4.10 | 3.41 | 2.64 | 3.57 | 3.18 | 3.65 |
| hsa-miR-30e-5p | 6.61 | 7.48 | 6.84 | 8.23 | 7.19 | 6.90 | 6.90 | 7.46 | 7.24 | 7.20 |
| hsa-miR-31 | 10.02 | 8.54 | 9.01 | 9.02 | 8.47 | 8.56 | 9.81 | 8.03 | 8.20 | 8.85 |
| hsa-miR-32 | 1.82 | 1.99 | 1.26 | 2.65 | 2.61 | 2.56 | 2.55 | 2.21 | 2.35 | 2.22 |
| hsa-miR-320 | 8.48 | 7.94 | 7.70 | 8.37 | 7.57 | 7.36 | 7.28 | 7.41 | 7.35 | 7.72 |
| hsa-miR-323 | 2.18 | 1.90 | 1.87 | 1.72 | 2.55 | 2.44 | 3.01 | 2.72 | 2.03 | 2.27 |
| hsa-miR-324-3p | 5.80 | 5.34 | 5.28 | 5.59 | 5.89 | 5.65 | 5.60 | 5.51 | 5.24 | 5.55 |
| hsa-miR-324-5p | 3.54 | 2.75 | 3.01 | 3.53 | 3.73 | 3.75 | 3.62 | 3.54 | 2.66 | 3.35 |
| hsa-miR-325 | 2.56 | 2.39 | 3.47 | 2.07 | 1.79 | 2.30 | 1.28 | 0.66 | 2.28 | 2.09 |
| hsa-miR-326 | 1.95 | 3.09 | 2.27 | 2.88 | 2.75 | 2.23 | 3.04 | 2.85 | 2.49 | 2.62 |
| hsa-miR-328 | 2.56 | 3.32 | 2.13 | 3.20 | 3.78 | 3.33 | 3.04 | 3.59 | 2.91 | 3.09 |
| hsa-miR-33 | 0.89 | 2.25 | 1.26 | 2.35 | 1.41 | 0.98 | 2.10 | 1.34 | 1.84 | 1.60 |
| hsa-miR-330 | 4.82 | 4.68 | 3.21 | 3.08 | 2.87 | 2.68 | 3.39 | 3.02 | 3.49 | 3.47 |
| hsa-miR-331 | 5.29 | 5.79 | 4.55 | 4.81 | 5.54 | 5.10 | 5.53 | 5.36 | 5.44 | 5.27 |
| hsa-miR-335 | 3.29 | 3.66 | 4.20 | 3.12 | 3.83 | 2.96 | 3.13 | 2.99 | 3.14 | 3.37 |
| hsa-miR-337 | 1.82 | 1.90 | 2.27 | 2.17 | 1.97 | 1.22 | 1.55 | 1.57 | 1.84 | 1.81 |
| hsa-miR-338 | 1.82 | 2.32 | 2.20 | 2.43 | 1.88 | 2.06 | 1.46 | 2.40 | 2.03 | 2.07 |
| hsa-miR-339 | 5.53 | 5.57 | 4.87 | 5.52 | 5.72 | 5.13 | 5.89 | 5.35 | 5.77 | 5.48 |
| hsa-miR-340 | 2.56 | 2.17 | 1.87 | 2.35 | 2.39 | 2.30 | 2.35 | 1.92 | 2.12 | 2.23 |
| hsa-miR-342 | 7.51 | 7.78 | 7.67 | 7.84 | 7.43 | 7.46 | 7.23 | 7.53 | 7.24 | 7.52 |
| hsa-miR-345 | 5.04 | 4.74 | 4.00 | 4.18 | 4.66 | 4.42 | 4.88 | 4.64 | 5.12 | 4.63 |
| hsa-miR-346 | 1.95 | 2.08 | 1.96 | 1.85 | 2.45 | 1.00 | 1.78 | 3.42 | 1.40 | 1.99 |
| hsa-miR-34a | 7.67 | 8.32 | 7.09 | 7.19 | 6.93 | 7.61 | 6.56 | 7.18 | 6.25 | 7.20 |
| hsa-miR-34b | 3.82 | 4.64 | 4.49 | 4.07 | 4.12 | 4.40 | 4.53 | 4.46 | 3.85 | 4.27 |
| hsa-miR-34c | 1.52 | 2.17 | 2.98 | 3.91 | 4.37 | 3.47 | 4.50 | 3.12 | 3.30 | 3.26 |
| hsa-miR-361 | 5.86 | 6.72 | 6.08 | 7.05 | 6.41 | 6.25 | 6.14 | 6.46 | 7.14 | 6.46 |
| hsa-miR-365 | 3.25 | 3.43 | 3.08 | 2.94 | 3.34 | 3.52 | 3.33 | 3.63 | 3.14 | 3.29 |

TABLE 7-continued

Normalized Array Data for miRNA Expression in Nine Cervical Tumor Tissue Samples (Ca1-Ca9) and
Nine Cervical Normal Adjacent Tissue Samples (NAT1-NAT-9). TV, threshold value. miRNAs >
TV, miRNAs greater than threshold value. %, Percentage of miRNAs greater than threshold value.

| | | | | | | | | | | |
|---|---|---|---|---|---|---|---|---|---|---|
| hsa-miR-367 | 1.20 | 1.99 | 2.05 | 1.72 | 1.79 | 1.88 | 1.55 | 1.49 | 2.66 | 1.82 |
| hsa-miR-368 | 3.07 | 4.79 | 4.39 | 4.21 | 5.29 | 5.09 | 4.64 | 5.42 | 3.68 | 4.51 |
| hsa-miR-369-3p | 2.29 | 0.99 | 1.78 | 1.72 | 0.70 | 1.45 | 2.17 | 1.18 | 2.03 | 1.59 |
| hsa-miR-370 | 4.71 | 5.15 | 4.59 | 4.78 | 5.67 | 5.69 | 5.45 | 5.19 | 5.23 | 5.16 |
| hsa-miR-371 | 1.52 | 1.23 | 1.16 | 1.59 | 1.51 | 1.88 | 1.73 | 1.79 | 1.16 | 1.51 |
| hsa-miR-372 | 1.82 | 1.11 | 1.16 | 1.72 | 1.88 | 1.56 | 1.09 | 1.26 | 1.63 | 1.47 |
| hsa-miR-373 | 2.18 | 1.90 | 2.68 | 2.26 | 0.99 | 1.22 | 1.55 | 1.64 | 4.08 | 2.06 |
| hsa-miR-373-AS | 3.72 | 3.26 | 4.57 | 3.56 | 4.34 | 4.34 | 4.38 | 4.17 | 4.51 | 4.09 |
| hsa-miR-374 | 2.18 | 2.52 | 3.42 | 2.51 | 2.55 | 3.21 | 2.10 | 2.91 | 2.20 | 2.62 |
| hsa-miR-375 | 2.64 | 2.97 | 1.96 | 3.67 | 4.44 | 2.15 | 3.01 | 4.06 | 2.86 | 3.08 |
| hsa-miR-376a | 1.67 | 3.01 | 4.07 | 2.77 | 3.68 | 3.27 | 2.94 | 3.88 | 2.49 | 3.09 |
| hsa-miR-377 | 1.95 | 2.25 | 1.96 | 2.26 | 2.32 | 1.88 | 2.17 | 2.72 | 2.61 | 2.24 |
| hsa-miR-378 | 3.16 | 3.82 | 3.97 | 3.44 | 4.19 | 4.56 | 4.26 | 4.49 | 3.44 | 3.93 |
| hsa-miR-379 | 5.28 | 4.45 | 5.09 | 5.13 | 4.60 | 4.79 | 4.67 | 4.35 | 4.41 | 4.75 |
| hsa-miR-380-3p | 1.67 | 1.35 | 1.87 | 0.77 | 1.88 | 2.06 | 1.46 | 1.18 | 2.42 | 1.63 |
| hsa-miR-380-5p | 2.64 | 1.69 | 1.58 | 1.46 | 1.70 | 0.98 | 1.55 | 1.92 | 2.66 | 1.80 |
| hsa-miR-381 | 2.71 | 2.84 | 3.27 | 3.20 | 3.48 | 3.47 | 3.53 | 3.23 | 3.07 | 3.20 |
| hsa-miR-382 | 3.37 | 3.60 | 3.91 | 3.41 | 3.43 | 3.73 | 3.15 | 3.88 | 2.99 | 3.50 |
| hsa-miR-383 | 2.90 | 2.39 | 3.01 | 2.65 | 2.32 | 2.23 | 2.35 | 2.10 | 2.61 | 2.51 |
| hsa-miR-384 | 1.36 | 1.47 | 1.58 | 0.77 | 0.62 | 1.45 | 2.10 | 0.80 | 1.63 | 1.31 |
| hsa-miR-422a | 3.33 | 3.94 | 5.06 | 4.71 | 4.43 | 4.66 | 4.62 | 4.98 | 3.63 | 4.37 |
| hsa-miR-422b | 5.61 | 6.04 | 6.62 | 6.47 | 6.19 | 6.63 | 6.59 | 6.83 | 5.57 | 6.28 |
| hsa-miR-423 | 6.65 | 7.08 | 6.24 | 6.66 | 6.73 | 6.28 | 6.61 | 6.58 | 6.59 | 6.60 |
| hsa-miR-424 | 2.78 | 3.29 | 4.53 | 3.78 | 3.31 | 4.07 | 4.17 | 4.69 | 3.27 | 3.77 |
| hsa-miR-425 | 3.89 | 4.88 | 3.70 | 3.85 | 4.32 | 3.97 | 3.66 | 3.64 | 3.74 | 3.96 |
| hsa-miR-429 | 4.82 | 5.95 | 5.27 | 4.72 | 6.75 | 5.29 | 5.06 | 5.74 | 5.41 | 5.45 |
| hsa-miR-448 | 1.82 | 1.90 | 1.05 | 1.03 | 1.41 | 0.87 | 1.28 | 2.61 | 1.28 | 1.47 |
| hsa-miR-449 | 2.29 | 2.25 | 1.96 | 2.17 | 1.61 | 1.88 | 2.88 | 2.57 | 2.66 | 2.25 |
| hsa-miR-450 | 2.48 | 2.32 | 2.13 | 2.17 | 1.61 | 1.67 | 1.81 | 1.64 | 0.93 | 1.86 |
| hsa-miR-7 | 3.01 | 2.75 | 4.76 | 3.08 | 2.61 | 2.78 | 3.55 | 3.09 | 3.83 | 3.27 |
| hsa-miR-9 | 3.12 | 2.52 | 3.08 | 1.59 | 2.45 | 2.50 | 2.03 | 2.68 | 3.36 | 2.59 |
| hsa-miR-9-AS | 3.66 | 3.05 | 3.68 | 2.83 | 3.64 | 2.87 | 2.45 | 3.31 | 3.68 | 3.24 |
| hsa-miR-92 | 7.89 | 7.18 | 7.03 | 7.76 | 8.03 | 7.65 | 7.58 | 7.42 | 7.90 | 7.60 |
| hsa-miR-93 | 8.83 | 8.04 | 7.87 | 8.38 | 7.77 | 7.84 | 8.00 | 7.66 | 7.66 | 8.00 |
| hsa-miR-95 | 3.37 | 4.41 | 4.00 | 3.41 | 3.60 | 4.06 | 4.15 | 4.27 | 3.33 | 3.85 |
| hsa-miR-96 | 3.58 | 3.82 | 4.47 | 3.50 | 4.18 | 3.18 | 3.57 | 4.24 | 4.21 | 3.86 |
| hsa-miR-98 | 5.19 | 5.31 | 5.82 | 5.54 | 4.62 | 5.05 | 4.70 | 5.17 | 4.22 | 5.07 |
| hsa-miR-99a | 5.82 | 8.07 | 7.70 | 7.89 | 8.47 | 7.80 | 7.95 | 8.75 | 7.45 | 7.77 |
| hsa-miR-99b | 6.33 | 6.40 | 5.47 | 6.46 | 6.56 | 6.55 | 6.63 | 6.35 | 5.92 | 6.30 |
| mmu-let-7d-AS | 2.07 | 1.58 | 1.87 | 1.85 | 1.88 | 2.06 | 1.96 | 1.42 | 1.52 | 1.80 |
| mmu-miR-101b | 1.52 | 2.08 | 1.69 | 1.32 | 0.62 | 1.33 | 1.00 | 0.35 | 0.61 | 1.17 |
| mmu-miR-106a | 7.76 | 6.76 | 7.27 | 7.54 | 7.86 | 7.31 | 7.80 | 7.15 | 7.70 | 7.46 |
| mmu-miR-129-3p | 2.56 | 2.52 | 1.69 | 2.07 | 1.70 | 2.06 | 2.50 | 2.45 | 2.28 | 2.20 |
| mmu-miR-140-AS | 5.61 | 6.39 | 5.89 | 6.17 | 6.54 | 6.32 | 6.10 | 6.72 | 5.48 | 6.14 |
| mmu-miR-151 | 3.29 | 2.58 | 3.24 | 3.44 | 3.75 | 3.56 | 3.39 | 3.54 | 3.65 | 3.38 |
| mmu-miR-155 | 4.08 | 4.50 | 5.32 | 4.61 | 3.43 | 2.50 | 3.18 | 4.57 | 2.12 | 3.81 |
| mmu-miR-17-3p | 3.16 | 3.05 | 2.77 | 2.83 | 2.83 | 3.00 | 3.21 | 2.85 | 3.14 | 2.98 |
| mmu-miR-192 | 3.29 | 3.64 | 4.16 | 3.38 | 4.46 | 3.71 | 3.89 | 4.49 | 2.95 | 3.78 |
| mmu-miR-199b | 3.69 | 5.45 | 5.49 | 5.08 | 5.83 | 6.10 | 4.85 | 6.00 | 4.75 | 5.25 |
| mmu-miR-201 | 1.20 | 1.23 | 1.37 | 1.32 | 0.80 | 1.56 | 1.00 | 1.02 | 2.20 | 1.30 |
| mmu-miR-202 | 4.85 | 4.17 | 5.16 | 3.98 | 4.60 | 4.56 | 5.42 | 4.38 | 3.68 | 4.53 |
| mmu-miR-207 | 2.56 | 2.46 | 1.96 | 1.72 | 1.79 | 1.56 | 2.29 | 1.34 | 2.35 | 2.00 |
| mmu-miR-211 | 1.82 | 1.58 | 0.84 | 1.46 | 1.88 | 0.98 | 1.73 | 1.10 | 2.28 | 1.52 |
| mmu-miR-215 | 2.18 | 2.17 | 1.37 | 1.32 | 2.26 | 1.56 | 0.74 | 1.72 | 1.63 | 1.66 |
| mmu-miR-217 | 2.18 | 1.90 | 1.87 | 1.96 | 1.61 | 0.76 | 1.46 | 1.42 | 1.74 | 1.66 |
| mmu-miR-290 | 3.16 | 3.05 | 4.34 | 3.38 | 4.37 | 4.50 | 4.84 | 3.91 | 5.05 | 4.07 |
| mmu-miR-291-3p | 1.20 | 1.23 | 1.16 | 1.85 | 2.19 | 1.78 | 2.17 | 1.79 | 2.35 | 1.75 |
| mmu-miR-291-5p | 1.82 | 1.80 | 2.13 | 1.85 | 3.26 | 3.00 | 3.33 | 2.72 | 2.82 | 2.52 |
| mmu-miR-292-3p | 1.95 | 2.46 | 1.96 | 2.71 | 1.20 | 1.67 | 2.29 | 2.31 | 2.55 | 2.12 |
| mmu-miR-292-5p | 2.90 | 2.64 | 3.52 | 2.98 | 2.83 | 3.11 | 2.98 | 2.65 | 3.07 | 2.96 |
| mmu-miR-293 | 2.48 | 0.88 | 1.78 | 1.46 | 1.09 | 2.06 | 2.10 | 1.34 | 2.72 | 1.77 |
| mmu-miR-294 | 2.56 | 1.99 | 1.78 | 1.72 | 1.51 | 2.30 | 1.89 | 2.49 | 1.16 | 1.93 |
| mmu-miR-295 | 1.95 | 0.99 | 1.69 | 1.59 | 1.09 | 1.45 | 1.37 | 0.80 | 0.71 | 1.29 |
| mmu-miR-297 | 0.74 | 1.47 | 2.13 | 1.18 | 1.41 | 1.45 | 1.46 | 1.72 | 0.61 | 1.35 |
| mmu-miR-298 | 4.78 | 4.47 | 5.69 | 4.64 | 5.01 | 5.07 | 5.40 | 4.86 | 5.29 | 5.02 |
| mmu-miR-300 | 2.90 | 2.89 | 2.73 | 2.71 | 3.02 | 2.87 | 3.15 | 2.57 | 2.99 | 2.87 |
| mmu-miR-322 | 1.20 | 1.90 | 0.65 | 2.58 | 1.30 | 2.50 | 2.45 | 1.85 | 2.61 | 1.89 |
| mmu-miR-424 | 2.18 | 2.39 | 2.77 | 3.16 | 2.75 | 3.07 | 3.46 | 3.63 | 1.94 | 2.82 |
| mmu-miR-325 | 2.84 | 2.39 | 2.40 | 1.96 | 1.79 | 2.06 | 1.73 | 3.16 | 1.16 | 2.17 |
| mmu-miR-329 | 2.64 | 2.64 | 2.20 | 2.26 | 2.39 | 2.06 | 1.96 | 1.72 | 1.40 | 2.14 |
| mmu-miR-330 | 3.01 | 2.84 | 2.46 | 2.35 | 2.50 | 1.78 | 3.10 | 1.98 | 2.82 | 2.54 |
| mmu-miR-337 | 2.64 | 1.58 | 1.78 | 1.72 | 2.19 | 1.33 | 1.46 | 2.10 | 1.40 | 1.80 |
| mmu-miR-341 | 2.18 | 1.58 | 2.27 | 2.26 | 2.50 | 1.88 | 2.68 | 2.40 | 1.28 | 2.12 |
| mmu-miR-344 | 2.56 | 1.23 | 1.48 | 1.46 | 0.99 | 1.78 | 1.19 | 2.10 | 2.49 | 1.70 |
| mmu-miR-345 | 2.39 | 2.75 | 2.57 | 2.71 | 3.20 | 2.62 | 3.18 | 2.94 | 3.14 | 2.83 |
| mmu-miR-346 | 1.95 | 1.69 | 2.77 | 2.07 | 1.51 | 1.78 | 1.89 | 1.34 | 1.28 | 1.81 |

TABLE 7-continued

Normalized Array Data for miRNA Expression in Nine Cervical Tumor Tissue Samples (Ca1-Ca9) and
Nine Cervical Normal Adjacent Tissue Samples (NAT1-NAT-9). TV, threshold value. miRNAs >
TV, miRNAs greater than threshold value. %, Percentage of miRNAs greater than threshold value.

| | | | | | | | | | | |
|---|---|---|---|---|---|---|---|---|---|---|
| mmu-miR-34b | 2.29 | 2.52 | 3.08 | 2.71 | 2.45 | 2.44 | 3.07 | 2.49 | 3.70 | 2.75 |
| mmu-miR-350 | 2.29 | 1.99 | 1.78 | 2.51 | 2.04 | 1.45 | 1.28 | 1.64 | 1.16 | 1.80 |
| mmu-miR-351 | 2.39 | 2.17 | 2.20 | 2.71 | 2.39 | 2.44 | 2.45 | 2.31 | 3.03 | 2.45 |
| mmu-miR-376a | 1.67 | 1.47 | 0.84 | 1.96 | 2.04 | 2.06 | 1.64 | 1.85 | 1.94 | 1.72 |
| mmu-miR-376b | 2.39 | 2.25 | 2.40 | 2.65 | 1.88 | 2.06 | 1.73 | 1.57 | 2.55 | 2.16 |
| mmu-miR-380-3p | 2.39 | 2.69 | 3.54 | 3.12 | 1.88 | 1.78 | 2.29 | 0.87 | 1.84 | 2.27 |
| mmu-miR-383 | 2.48 | 2.39 | 3.27 | 2.83 | 2.61 | 2.37 | 2.50 | 3.07 | 2.72 | 2.69 |
| mmu-miR-384 | 1.36 | 1.35 | 1.78 | 0.90 | 1.61 | 1.88 | 2.17 | 2.04 | 2.91 | 1.78 |
| mmu-miR-409 | 3.01 | 3.76 | 3.42 | 3.83 | 4.01 | 4.37 | 3.67 | 4.19 | 3.27 | 3.73 |
| hsa-miR-410 | 1.67 | 1.90 | 1.87 | 2.43 | 2.79 | 2.56 | 2.73 | 2.40 | 2.86 | 2.36 |
| mmu-miR-411 | 2.64 | 2.08 | 1.58 | 2.83 | 2.32 | 1.67 | 1.64 | 2.26 | 2.12 | 2.13 |
| hsa-miR-412 | 0.89 | 1.99 | 1.78 | 2.17 | 2.04 | 1.56 | 1.55 | 0.35 | 2.03 | 1.60 |
| mmu-miR-429 | 1.67 | 1.47 | 1.87 | 1.59 | 2.45 | 1.67 | 1.73 | 2.36 | 1.84 | 1.85 |
| mmu-miR-7b | 3.07 | 2.52 | 2.63 | 2.43 | 2.70 | 2.50 | 2.29 | 2.85 | 3.18 | 2.69 |
| rno-miR-151-AS | 6.95 | 6.29 | 6.12 | 6.71 | 6.92 | 6.98 | 6.64 | 6.51 | 6.70 | 6.65 |
| rno-miR-20-AS | 2.18 | 0.88 | 1.05 | 1.96 | 0.62 | 1.33 | 1.28 | 1.42 | 2.03 | 1.42 |
| rno-miR-297 | 1.36 | 1.90 | 0.94 | 1.72 | 1.09 | 1.45 | 1.19 | 1.26 | 1.74 | 1.41 |
| rno-miR-327 | 4.04 | 3.51 | 4.91 | 3.74 | 3.48 | 3.54 | 3.92 | 3.47 | 3.77 | 3.82 |
| rno-miR-333 | 0.74 | 2.32 | 1.58 | 1.46 | 0.99 | 0.98 | 2.03 | 1.92 | 1.63 | 1.52 |
| rno-miR-336 | 3.37 | 3.43 | 2.86 | 3.24 | 2.98 | 3.04 | 2.73 | 2.75 | 3.07 | 3.05 |
| rno-miR-343 | 1.67 | 1.69 | 0.84 | 1.72 | 2.45 | 0.87 | 2.35 | 3.23 | 2.77 | 1.95 |
| rno-miR-344 | 1.36 | 1.99 | 1.96 | 2.17 | 1.41 | 1.56 | 1.64 | 2.53 | 2.61 | 1.92 |
| rno-miR-346 | 3.51 | 2.46 | 2.34 | 2.17 | 2.95 | 2.56 | 2.55 | 3.09 | 2.49 | 2.68 |
| rno-miR-347 | 2.64 | 2.75 | 2.20 | 2.58 | 2.45 | 3.36 | 3.41 | 3.49 | 4.83 | 3.08 |
| rno-miR-349 | 1.20 | 0.99 | 1.48 | 2.26 | 1.97 | 1.97 | 1.73 | 1.92 | 1.28 | 1.65 |
| rno-miR-352 | 5.25 | 5.29 | 5.80 | 5.28 | 4.49 | 4.66 | 4.51 | 4.94 | 3.76 | 4.89 |
| rno-miR-421 | 1.67 | 2.17 | 1.96 | 2.07 | 1.51 | 1.56 | 1.37 | 1.72 | 0.93 | 1.66 |
| rno-miR-7-AS | 2.07 | 2.89 | 2.27 | 1.85 | 2.79 | 2.15 | 2.91 | 2.85 | 3.03 | 2.53 |
| hsa-miR-522 | 1.67 | 1.35 | 2.46 | 2.17 | 1.41 | 1.45 | 2.23 | 0.19 | 1.28 | 1.58 |
| hsa-miR-519b | 1.04 | 2.32 | 1.26 | 2.35 | 1.79 | 1.97 | 1.73 | 2.26 | 2.66 | 1.93 |
| hsa-miR-520c | 2.64 | 2.25 | 2.05 | 2.43 | 1.61 | 1.88 | 1.73 | 1.72 | 2.61 | 2.10 |
| hsa-miR-519e | 1.20 | 1.80 | 1.37 | 2.65 | 1.70 | 2.23 | 1.73 | 1.26 | 2.03 | 1.77 |
| hsa-miR-519d | 2.78 | 2.39 | 2.13 | 1.85 | 2.32 | 1.78 | 2.23 | 1.79 | 1.84 | 2.12 |
| hsa-miR-520b | 1.36 | 1.69 | 2.34 | 1.85 | 1.70 | 2.15 | 1.96 | 1.64 | 2.12 | 1.87 |
| hsa-miR-519c | 1.36 | 1.23 | 2.13 | 1.32 | 0.45 | 1.33 | 1.89 | 2.10 | 1.16 | 1.44 |
| hsa-miR-526b-AS | 1.04 | 2.25 | 1.69 | 1.85 | 1.30 | 1.67 | 1.81 | 1.49 | 2.28 | 1.71 |
| hsa-miR-520e | 1.95 | 1.69 | 1.78 | 1.96 | 1.20 | 1.97 | 1.37 | 1.10 | 2.03 | 1.67 |
| hsa-miR-520a | 1.52 | 1.23 | 1.05 | 2.07 | 0.89 | 1.97 | 1.96 | 2.72 | 2.82 | 1.80 |
| hsa-miR-520d | 2.84 | 2.52 | 2.63 | 1.96 | 2.65 | 1.97 | 2.23 | 1.92 | 3.21 | 2.44 |
| hsa-miR-520h | 0.60 | 1.35 | 1.16 | 1.85 | 2.12 | 1.88 | 1.28 | 2.04 | 2.82 | 1.68 |
| hsa-miR-517a | 2.07 | 1.99 | 2.13 | 1.59 | 1.61 | 1.97 | 2.64 | 2.68 | 1.74 | 2.05 |
| hsa-miR-518e | 1.36 | 1.47 | 1.48 | 0.90 | 1.20 | 1.45 | 1.00 | 1.57 | 1.84 | 1.36 |
| hsa-miR-521 | 2.56 | 2.17 | 2.68 | 1.85 | 2.19 | 1.33 | 2.17 | 0.59 | 2.55 | 2.01 |
| hsa-miR-523 | 2.07 | 1.69 | 2.13 | 2.43 | 1.79 | 1.88 | 1.89 | 1.85 | 2.20 | 1.99 |
| hsa-miR-518f | 1.82 | 1.11 | 1.48 | 1.72 | 2.04 | 1.33 | 2.40 | 2.26 | 1.40 | 1.73 |
| hsa-miR-518c | 2.18 | 2.08 | 1.48 | 1.18 | 1.88 | 1.78 | 1.28 | 2.16 | 1.74 | 1.75 |
| hsa-miR-518b | 2.39 | 2.46 | 1.26 | 2.26 | 2.19 | 2.37 | 2.55 | 2.36 | 2.72 | 2.29 |
| hsa-miR-518d | 0.74 | 1.90 | 1.05 | 1.85 | 2.04 | 1.56 | 1.64 | 2.04 | 1.28 | 1.57 |
| hsa-miR-525-AS | 1.36 | 1.69 | 1.78 | 1.85 | 1.70 | 1.97 | 1.89 | 1.42 | 1.74 | 1.71 |
| hsa-miR-524 | 1.52 | 1.58 | 1.48 | 2.07 | 1.97 | 1.88 | 2.03 | 2.40 | 2.66 | 1.96 |
| hsa-miR-518a | 2.07 | 0.67 | 1.69 | 0.90 | 2.55 | 1.56 | 2.10 | 2.65 | 2.35 | 1.84 |
| hsa-miR-515-3p | 2.07 | 1.69 | 1.37 | 1.85 | 1.79 | 1.78 | 1.46 | 1.49 | 0.93 | 1.60 |
| hsa-miR-516-3p | 2.64 | 1.58 | 2.46 | 2.43 | 1.09 | 1.78 | 1.64 | 1.34 | 2.20 | 1.91 |
| ambi-miR-7026 | 1.67 | 1.47 | 2.46 | 1.59 | 1.88 | 1.45 | 1.73 | 1.49 | 2.77 | 1.84 |
| ambi-miR-7027 | 3.33 | 4.53 | 2.34 | 3.20 | 3.23 | 4.22 | 2.80 | 4.22 | 3.74 | 3.51 |
| hsa-miR-512-3p | 2.29 | 2.64 | 3.91 | 2.77 | 2.12 | 2.56 | 2.40 | 1.98 | 1.74 | 2.49 |
| ambi-miR-7029 | 4.51 | 2.97 | 5.46 | 5.79 | 6.15 | 6.37 | 5.90 | 6.15 | 4.88 | 5.35 |
| hsa-miR-491 | 3.87 | 3.97 | 4.64 | 3.76 | 4.50 | 4.26 | 4.71 | 4.20 | 5.15 | 4.34 |
| hsa-miR-506 | 2.39 | 2.25 | 2.34 | 2.17 | 2.19 | 2.30 | 1.81 | 2.78 | 2.61 | 2.32 |
| hsa-miR-514 | 1.82 | 1.35 | 1.05 | 1.59 | 0.99 | 1.22 | 0.66 | 2.36 | 1.28 | 1.37 |
| hsa-miR-509 | 2.18 | 1.99 | 2.73 | 2.35 | 1.70 | 2.30 | 2.17 | 1.64 | 2.77 | 2.20 |
| hsa-miR-508 | 1.67 | 1.90 | 1.48 | 2.58 | 1.70 | 1.97 | 1.00 | 1.34 | 1.63 | 1.70 |
| hsa-miR-507 | 1.36 | 1.80 | 1.05 | 1.18 | 1.61 | 1.67 | 1.28 | 2.45 | 2.28 | 1.63 |
| ambi-miR-7036 | 2.56 | 2.52 | 2.98 | 2.51 | 2.19 | 2.62 | 2.17 | 2.26 | 2.20 | 2.45 |
| hsa-miR-193b | 6.83 | 7.29 | 5.53 | 6.65 | 5.83 | 6.62 | 6.66 | 6.10 | 6.10 | 6.40 |
| ambi-miR-7038-1 | 1.82 | 1.99 | 2.27 | 2.35 | 1.30 | 0.98 | 1.55 | 0.80 | 2.42 | 1.72 |
| ambi-miR-7039 | 5.32 | 5.11 | 4.35 | 5.15 | 4.60 | 5.59 | 5.23 | 4.82 | 4.42 | 4.95 |
| hsa-miR-488 | 2.29 | 1.11 | 1.96 | 1.72 | 2.04 | 1.33 | 1.55 | 2.65 | 1.63 | 1.81 |
| hsa-miR-510 | 0.89 | 1.99 | 2.13 | 1.72 | 2.12 | 2.50 | 2.10 | 2.36 | 2.55 | 2.04 |
| hsa-miR-517-AS | 1.20 | 1.47 | 2.40 | 0.90 | 1.70 | 2.68 | 2.10 | 2.57 | 2.20 | 1.91 |
| hsa-miR-518f-AS | 1.82 | 2.17 | 1.05 | 1.85 | 0.89 | 1.45 | 1.96 | 1.98 | 2.28 | 1.72 |
| hsa-miR-518c-AS | 4.00 | 3.35 | 5.04 | 3.83 | 4.04 | 4.17 | 4.42 | 3.91 | 4.41 | 4.13 |
| hsa-miR-526c | 1.36 | 2.08 | 2.05 | 1.59 | 1.61 | 2.56 | 2.35 | 2.04 | 1.52 | 1.91 |
| hsa-miR-526b | 3.12 | 3.19 | 4.39 | 3.35 | 2.50 | 3.21 | 3.13 | 2.26 | 3.21 | 3.15 |
| hsa-miR-520a-AS | 2.07 | 0.88 | 1.37 | 1.59 | 1.09 | 1.45 | 1.73 | 1.85 | 1.28 | 1.48 |
| hsa-miR-525 | 2.96 | 2.25 | 3.32 | 2.35 | 1.88 | 2.06 | 2.68 | 2.10 | 2.72 | 2.48 |

TABLE 7-continued

Normalized Array Data for miRNA Expression in Nine Cervical Tumor Tissue Samples (Ca1-Ca9) and Nine Cervical Normal Adjacent Tissue Samples (NAT1-NAT-9). TV, threshold value. miRNAs > TV, miRNAs greater than threshold value. %, Percentage of miRNAs greater than threshold value.

| | | | | | | | | | | |
|---|---|---|---|---|---|---|---|---|---|---|
| hsa-miR-524-AS | 2.48 | 1.99 | 2.40 | 1.96 | 2.65 | 2.30 | 2.60 | 2.53 | 2.66 | 2.40 |
| hsa-miR-520d-AS | 1.52 | 1.69 | 2.13 | 2.71 | 2.45 | 1.45 | 2.55 | 2.68 | 2.35 | 2.17 |
| hsa-miR-527 | 2.64 | 2.32 | 3.05 | 2.43 | 2.79 | 2.62 | 3.13 | 3.12 | 3.44 | 2.84 |
| hsa-miR-515-5p | 2.07 | 1.90 | 1.26 | 1.59 | 2.55 | 2.23 | 2.17 | 2.88 | 2.55 | 2.13 |
| hsa-miR-519e-AS | 2.29 | 2.08 | 2.27 | 1.85 | 1.70 | 2.68 | 1.96 | 1.92 | 2.42 | 2.13 |
| ambi-miR-7054 | 1.67 | 1.90 | 1.37 | 2.17 | 1.97 | 1.78 | 2.50 | 1.79 | 2.03 | 1.91 |
| ambi-miR-7055 | 2.39 | 2.25 | 2.46 | 2.51 | 1.30 | 3.07 | 2.40 | 2.36 | 2.49 | 2.36 |
| hsa-miR-498 | 2.48 | 2.32 | 3.12 | 2.58 | 2.32 | 3.04 | 2.80 | 3.04 | 3.21 | 2.77 |
| hsa-miR-513 | 4.35 | 3.86 | 5.44 | 4.32 | 5.08 | 5.10 | 5.44 | 4.44 | 5.39 | 4.83 |
| ambi-miR-7058 | 6.76 | 6.61 | 6.25 | 6.32 | 5.95 | 5.66 | 5.98 | 6.04 | 5.87 | 6.16 |
| ambi-miR-7059-1 | 1.36 | 1.23 | 1.58 | 1.96 | 1.61 | 1.67 | 1.37 | 2.26 | 1.52 | 1.62 |
| hsa-miR-452 | 4.91 | 6.25 | 4.84 | 5.16 | 4.69 | 5.47 | 4.79 | 5.57 | 5.86 | 5.28 |
| hsa-miR-493 | 1.04 | 2.25 | 1.78 | 1.72 | 2.26 | 2.50 | 1.09 | 2.72 | 2.82 | 2.02 |
| ambi-miR-7062 | 3.87 | 3.43 | 3.35 | 2.35 | 2.98 | 2.96 | 3.43 | 2.82 | 3.49 | 3.19 |
| hsa-miR-432 | 4.35 | 4.49 | 5.14 | 4.44 | 3.99 | 4.14 | 4.30 | 4.17 | 3.70 | 4.30 |
| hsa-miR-495 | 2.78 | 3.23 | 3.32 | 3.31 | 3.36 | 3.21 | 2.91 | 3.52 | 3.91 | 3.28 |
| hsa-miR-494 | 6.14 | 5.26 | 6.94 | 5.76 | 7.00 | 6.58 | 6.70 | 5.60 | 6.48 | 6.27 |
| ambi-miR-7066 | 1.82 | 2.52 | 1.96 | 1.46 | 1.79 | 1.67 | 1.73 | 2.49 | 0.82 | 1.81 |
| ambi-miR-7067 | 2.29 | 1.80 | 2.46 | 2.71 | 2.19 | 2.44 | 2.03 | 2.26 | 3.07 | 2.36 |
| ambi-miR-7068-1 | 2.48 | 2.17 | 2.94 | 2.51 | 2.75 | 2.15 | 2.35 | 2.61 | 2.28 | 2.47 |
| hsa-miR-496 | 1.82 | 1.11 | 1.05 | 1.32 | 0.70 | 1.56 | 2.29 | 2.36 | 1.16 | 1.49 |
| ambi-miR-7070 | 2.29 | 3.05 | 2.05 | 2.83 | 3.46 | 3.49 | 2.73 | 3.97 | 2.61 | 2.94 |
| hsa-miR-492 | 2.48 | 2.17 | 3.24 | 2.43 | 2.39 | 3.00 | 2.88 | 1.92 | 3.63 | 2.68 |
| hsa-miR-490 | 2.07 | 1.99 | 1.37 | 1.72 | 2.32 | 2.06 | 1.96 | 1.98 | 1.74 | 1.92 |
| hsa-miR-497 | 4.75 | 6.10 | 4.77 | 6.11 | 6.45 | 6.16 | 6.33 | 6.53 | 5.33 | 5.84 |
| ambi-miR-7074 | 2.07 | 2.08 | 2.34 | 2.43 | 2.79 | 2.50 | 2.23 | 2.04 | 2.72 | 2.36 |
| ambi-miR-7075 | 2.71 | 4.25 | 3.18 | 3.28 | 3.50 | 3.18 | 3.18 | 3.55 | 3.14 | 3.33 |
| ambi-miR-7076 | 4.31 | 4.96 | 4.66 | 5.23 | 5.05 | 4.52 | 4.67 | 4.58 | 4.50 | 4.72 |
| hsa-miR-501 | 3.41 | 3.16 | 3.32 | 3.16 | 2.55 | 2.44 | 1.96 | 2.40 | 2.82 | 2.80 |
| hsa-miR-502 | 3.07 | 3.09 | 3.66 | 3.74 | 3.36 | 3.11 | 3.23 | 3.44 | 3.07 | 3.31 |
| ambi-miR-7079 | 6.46 | 4.68 | 6.81 | 5.48 | 5.09 | 4.30 | 4.24 | 5.52 | 6.16 | 5.42 |
| ambi-miR-7080 | 1.52 | 1.99 | 3.27 | 2.58 | 2.61 | 2.23 | 2.03 | 2.36 | 2.03 | 2.29 |
| ambi-miR-7081 | 3.29 | 3.80 | 3.40 | 3.44 | 4.25 | 4.39 | 3.43 | 4.25 | 3.49 | 3.75 |
| hsa-miR-202-AS | 1.82 | 1.80 | 1.37 | 1.18 | 1.20 | 1.10 | 1.64 | 0.87 | 1.52 | 1.39 |
| ambi-miR-7083 | 5.94 | 6.59 | 6.07 | 6.93 | 6.74 | 6.82 | 7.20 | 6.50 | 6.26 | 6.56 |
| ambi-miR-7084 | 1.95 | 1.90 | 2.57 | 2.94 | 2.45 | 2.44 | 2.10 | 2.78 | 2.61 | 2.42 |
| ambi-miR-7085 | 2.48 | 3.40 | 3.80 | 3.41 | 3.18 | 3.07 | 3.89 | 3.78 | 3.39 | 3.38 |
| ambi-miR-7086 | 2.48 | 3.01 | 3.01 | 2.98 | 2.65 | 2.56 | 3.95 | 2.31 | 3.14 | 2.90 |
| hsa-miR-512-5p | 1.52 | 2.08 | 1.05 | 1.72 | 1.79 | 1.78 | 2.03 | 1.98 | 1.52 | 1.72 |
| hsa-miR-504 | 2.18 | 1.99 | 1.69 | 0.90 | 1.88 | 2.30 | 2.29 | 2.45 | 1.63 | 1.92 |
| ambi-miR-7089 | 2.39 | 2.52 | 2.13 | 2.07 | 2.12 | 2.56 | 2.35 | 2.82 | 1.74 | 2.30 |
| hsa-miR-511 | 1.04 | 2.25 | 1.48 | 1.96 | 1.51 | 2.23 | 1.55 | 1.85 | 2.03 | 1.77 |
| hsa-miR-452-AS | 3.37 | 4.30 | 3.49 | 3.31 | 2.95 | 3.47 | 2.40 | 3.21 | 3.88 | 3.38 |
| hsa-miR-503 | 6.07 | 5.02 | 5.05 | 5.78 | 5.41 | 5.69 | 5.88 | 5.52 | 5.14 | 5.51 |
| hsa-miR-485-5p | 2.56 | 2.89 | 3.49 | 2.83 | 3.11 | 3.39 | 3.66 | 2.99 | 3.39 | 3.15 |
| hsa-miR-499 | 2.56 | 1.80 | 2.27 | 2.17 | 1.61 | 2.15 | 1.64 | 2.26 | 1.84 | 2.03 |
| ambi-miR-7095 | 2.07 | 1.47 | 2.05 | 1.18 | 1.79 | 1.56 | 2.03 | 1.49 | 1.04 | 1.63 |
| hsa-miR-505 | 3.77 | 4.03 | 4.05 | 4.41 | 3.81 | 4.25 | 3.49 | 4.57 | 2.95 | 3.93 |
| ambi-miR-7097 | 2.39 | 2.32 | 1.78 | 1.72 | 2.32 | 2.30 | 2.50 | 2.65 | 3.18 | 2.35 |
| ambi-miR-7098 | 2.18 | 2.08 | 0.84 | 1.18 | 1.61 | 1.67 | 1.46 | 1.42 | 1.84 | 1.59 |
| hsa-miR-489 | 1.52 | 2.58 | 2.40 | 2.71 | 2.39 | 2.37 | 1.28 | 1.64 | 1.94 | 2.09 |
| ambi-miR-7100 | 1.82 | 1.80 | 2.05 | 2.43 | 2.26 | 2.23 | 2.03 | 3.27 | 2.35 | 2.25 |
| ambi-miR-7101 | 1.67 | 2.17 | 1.05 | 2.35 | 2.55 | 2.68 | 2.55 | 3.16 | 2.91 | 2.34 |
| hsa-miR-432-AS | 1.82 | 1.80 | 1.37 | 1.03 | 1.09 | 1.22 | 2.03 | 1.72 | 2.61 | 1.63 |
| ambi-miR-7103 | 3.29 | 3.40 | 4.87 | 3.64 | 1.88 | 2.68 | 2.23 | 2.31 | 2.82 | 3.01 |
| hsa-miR-500 | 4.22 | 4.88 | 4.38 | 4.76 | 4.80 | 4.35 | 4.34 | 4.34 | 3.77 | 4.43 |
| ambi-miR-7105 | 4.76 | 5.03 | 4.83 | 5.00 | 5.21 | 4.83 | 4.85 | 5.24 | 5.08 | 4.98 |

| | NAT 1 | NAT 2 | NAT 3 | NAT 4 | NAT 5 | NAT 6 | NAT 7 | NAT 8 | NAT 9 | Mean (NAT) |
|---|---|---|---|---|---|---|---|---|---|---|
| TV | 2.77 | 3.22 | 2.55 | 2.10 | 1.97 | 2.10 | 1.81 | 2.15 | 2.20 | 2.32 |
| miRNAs > TV | 222 | 192 | 232 | 240 | 271 | 253 | 283 | 254 | 246 | 244 |
| % | 58.96 | 50.91 | 61.56 | 63.64 | 71.95 | 67.01 | 75.06 | 67.27 | 65.19 | 64.62 |
| miR Name | | | | | | | | | | |
| hsa-let-7a | 10.69 | 10.47 | 10.82 | 10.95 | 10.79 | 10.50 | 10.01 | 10.68 | 10.68 | 10.62 |
| hsa-let-7b | 10.61 | 10.70 | 10.98 | 10.95 | 10.72 | 10.85 | 10.01 | 10.61 | 10.53 | 10.66 |
| hsa-let-7c | 10.61 | 10.60 | 10.87 | 10.95 | 10.85 | 10.60 | 10.01 | 10.69 | 10.64 | 10.65 |
| hsa-let-7d | 9.44 | 9.12 | 9.32 | 10.16 | 9.68 | 9.15 | 9.52 | 9.49 | 9.41 | 9.48 |
| hsa-let-7e | 8.22 | 8.13 | 8.31 | 8.68 | 7.98 | 7.83 | 8.61 | 7.58 | 7.82 | 8.13 |
| hsa-let-7f | 8.69 | 7.93 | 8.37 | 9.03 | 8.69 | 8.14 | 8.31 | 8.48 | 8.32 | 8.44 |
| hsa-let-7g | 8.18 | 7.63 | 8.08 | 8.91 | 8.37 | 8.07 | 8.27 | 8.41 | 8.09 | 8.23 |
| hsa-let-7i | 8.25 | 8.24 | 8.58 | 8.82 | 8.41 | 8.05 | 8.48 | 8.62 | 8.31 | 8.42 |
| hsa-miR-1 | 5.46 | 5.10 | 5.16 | 5.64 | 5.59 | 4.90 | 5.31 | 4.31 | 4.55 | 5.11 |
| hsa-miR-100 | 8.39 | 8.01 | 8.66 | 9.16 | 9.00 | 9.42 | 8.71 | 9.31 | 9.07 | 8.86 |

TABLE 7-continued

Normalized Array Data for miRNA Expression in Nine Cervical Tumor Tissue Samples (Ca1-Ca9) and
Nine Cervical Normal Adjacent Tissue Samples (NAT1-NAT-9). TV, threshold value. miRNAs >
TV, miRNAs greater than threshold value. %, Percentage of miRNAs greater than threshold value.

| | | | | | | | | | | |
|---|---|---|---|---|---|---|---|---|---|---|
| hsa-miR-101 | 3.40 | 3.16 | 3.54 | 4.33 | 4.24 | 4.28 | 3.70 | 4.59 | 4.79 | 4.00 |
| hsa-miR-103 | 7.62 | 8.01 | 8.17 | 8.34 | 8.02 | 7.97 | 8.38 | 8.22 | 7.93 | 8.07 |
| hsa-miR-105 | 2.05 | 1.25 | 1.50 | 2.01 | 1.85 | 1.82 | 2.14 | 1.39 | 1.91 | 1.77 |
| hsa-miR-106a | 7.27 | 7.23 | 7.68 | 7.81 | 7.68 | 7.81 | 7.43 | 7.89 | 7.78 | 7.62 |
| hsa-miR-106b | 5.74 | 5.90 | 6.28 | 6.38 | 6.16 | 6.21 | 5.98 | 6.70 | 6.48 | 6.20 |
| hsa-miR-107 | 7.60 | 7.94 | 8.18 | 8.30 | 7.97 | 7.88 | 8.33 | 8.14 | 7.93 | 8.03 |
| hsa-miR-10a | 5.77 | 5.56 | 5.96 | 6.97 | 6.64 | 8.13 | 7.23 | 6.42 | 6.13 | 6.53 |
| hsa-miR-10b | 7.22 | 6.86 | 7.37 | 8.32 | 8.09 | 8.44 | 9.39 | 7.91 | 7.57 | 7.91 |
| hsa-miR-122a | 5.31 | 4.28 | 4.01 | 2.42 | 2.99 | 2.71 | 2.68 | 2.96 | 2.69 | 3.34 |
| hsa-miR-124a | 2.41 | 1.84 | 2.99 | 2.88 | 1.73 | 1.99 | 2.01 | 2.55 | 1.87 | 2.25 |
| hsa-miR-125a | 8.63 | 8.64 | 8.65 | 8.95 | 9.27 | 9.51 | 9.57 | 8.91 | 8.67 | 8.98 |
| hsa-miR-125b | 9.75 | 9.79 | 10.03 | 10.19 | 10.51 | 10.85 | 10.01 | 10.36 | 10.13 | 10.18 |
| hsa-miR-126 | 9.32 | 9.24 | 9.28 | 9.77 | 10.02 | 9.70 | 9.84 | 10.02 | 9.82 | 9.67 |
| hsa-miR-126-AS | 3.92 | 4.22 | 4.71 | 5.36 | 6.06 | 5.56 | 5.60 | 6.10 | 5.85 | 5.27 |
| hsa-miR-127 | 3.16 | 3.90 | 4.22 | 4.14 | 5.01 | 3.37 | 4.64 | 5.06 | 4.91 | 4.27 |
| hsa-miR-128a | 4.82 | 4.81 | 5.11 | 5.43 | 5.17 | 5.15 | 5.76 | 5.15 | 4.92 | 5.15 |
| hsa-miR-129 | 2.85 | 2.53 | 2.41 | 2.10 | 2.44 | 2.93 | 2.70 | 2.63 | 2.55 | 2.57 |
| hsa-miR-130a | 6.64 | 6.50 | 6.63 | 7.25 | 6.89 | 6.80 | 7.35 | 7.30 | 7.23 | 6.95 |
| hsa-miR-130b | 5.04 | 4.93 | 5.19 | 4.51 | 4.58 | 3.90 | 4.68 | 4.52 | 4.67 | 4.67 |
| hsa-miR-132 | 5.09 | 5.73 | 5.80 | 5.14 | 5.24 | 5.41 | 6.33 | 5.56 | 5.26 | 5.51 |
| hsa-miR-133a | 6.43 | 7.44 | 7.01 | 7.24 | 7.15 | 6.96 | 7.95 | 5.87 | 6.32 | 6.93 |
| hsa-miR-134 | 3.59 | 4.24 | 4.38 | 4.68 | 4.79 | 3.67 | 4.38 | 4.73 | 4.96 | 4.38 |
| hsa-miR-135a | 1.74 | 1.84 | 2.41 | 2.52 | 2.44 | 3.05 | 1.87 | 2.15 | 2.47 | 2.28 |
| hsa-miR-135b | 1.57 | 1.25 | 2.33 | 1.86 | 1.39 | 1.55 | 1.61 | 1.39 | 1.31 | 1.59 |
| hsa-miR-136 | 2.18 | 1.84 | 2.07 | 1.81 | 1.25 | 1.20 | 1.59 | 2.07 | 1.55 | 1.73 |
| hsa-miR-137 | 0.67 | 2.16 | 1.86 | 1.75 | 2.36 | 1.41 | 1.93 | 2.49 | 1.78 | 1.82 |
| hsa-miR-138 | 2.98 | 2.16 | 2.79 | 2.01 | 2.44 | 2.61 | 1.81 | 2.55 | 2.24 | 2.40 |
| hsa-miR-139 | 4.86 | 4.59 | 4.46 | 4.63 | 5.06 | 4.52 | 5.45 | 4.81 | 3.62 | 4.67 |
| hsa-miR-140 | 4.00 | 4.30 | 4.38 | 4.65 | 5.24 | 5.25 | 5.51 | 5.60 | 5.53 | 4.94 |
| hsa-miR-141 | 4.49 | 4.24 | 5.77 | 5.54 | 4.83 | 5.17 | 3.18 | 5.65 | 5.51 | 4.93 |
| hsa-miR-142-3p | 3.81 | 3.28 | 3.42 | 2.83 | 2.86 | 2.42 | 2.14 | 3.19 | 2.72 | 2.96 |
| hsa-miR-142-5p | 2.69 | 2.73 | 2.25 | 3.78 | 3.93 | 4.15 | 3.39 | 3.31 | 4.41 | 3.41 |
| hsa-miR-143 | 9.82 | 10.52 | 10.39 | 10.58 | 10.84 | 10.60 | 10.01 | 10.39 | 10.29 | 10.38 |
| hsa-miR-144 | 1.74 | 1.45 | 1.24 | 1.69 | 1.67 | 1.62 | 1.68 | 1.45 | 1.60 | 1.57 |
| hsa-miR-145 | 11.33 | 11.88 | 11.70 | 10.95 | 11.07 | 11.09 | 10.01 | 10.83 | 10.70 | 11.06 |
| hsa-miR-146a | 5.67 | 5.50 | 6.62 | 6.21 | 6.06 | 5.65 | 5.24 | 6.06 | 5.84 | 5.87 |
| hsa-miR-147 | 3.10 | 2.01 | 1.86 | 1.52 | 1.91 | 1.62 | 1.70 | 1.81 | 1.87 | 1.93 |
| hsa-miR-148a | 5.74 | 5.37 | 6.05 | 6.65 | 6.17 | 6.23 | 5.93 | 6.67 | 6.39 | 6.13 |
| hsa-miR-148b | 4.26 | 4.13 | 4.47 | 5.05 | 4.62 | 4.48 | 4.97 | 5.17 | 4.65 | 4.65 |
| hsa-miR-149 | 4.30 | 4.01 | 4.30 | 4.92 | 4.81 | 3.99 | 3.97 | 4.86 | 4.76 | 4.44 |
| hsa-miR-150 | 6.30 | 5.94 | 6.34 | 6.74 | 7.26 | 7.00 | 6.60 | 7.47 | 6.45 | 6.68 |
| hsa-miR-151 | 5.47 | 5.35 | 5.51 | 5.89 | 5.89 | 5.95 | 5.98 | 5.76 | 5.87 | 5.74 |
| hsa-miR-152 | 6.23 | 7.12 | 7.12 | 7.27 | 7.01 | 6.63 | 7.26 | 7.26 | 7.25 | 7.02 |
| hsa-miR-153 | 1.74 | 2.29 | 1.97 | 2.01 | 2.08 | 1.69 | 2.33 | 2.49 | 2.30 | 2.10 |
| hsa-miR-154 | 3.35 | 4.43 | 4.32 | 4.42 | 4.96 | 3.72 | 4.27 | 5.43 | 5.16 | 4.45 |
| hsa-miR-155 | 6.02 | 5.71 | 6.27 | 5.76 | 5.64 | 4.96 | 5.05 | 5.76 | 4.74 | 5.55 |
| hsa-miR-15a | 6.07 | 6.08 | 6.49 | 7.02 | 6.77 | 6.36 | 6.90 | 6.81 | 6.57 | 6.56 |
| hsa-miR-15b | 6.99 | 6.93 | 7.66 | 7.86 | 7.32 | 7.63 | 7.34 | 7.32 | 6.93 | 7.33 |
| hsa-miR-16 | 9.52 | 9.48 | 9.88 | 9.95 | 9.80 | 10.17 | 9.87 | 9.85 | 9.66 | 9.80 |
| hsa-miR-17-3p | 3.72 | 3.74 | 3.96 | 4.28 | 3.71 | 4.23 | 4.01 | 4.22 | 4.26 | 4.02 |
| hsa-miR-17-5p | 7.16 | 6.95 | 7.48 | 7.71 | 7.31 | 7.62 | 7.19 | 7.64 | 7.54 | 7.40 |
| hsa-miR-18a | 2.61 | 4.26 | 4.55 | 4.14 | 4.12 | 3.61 | 3.82 | 4.99 | 4.32 | 4.05 |
| hsa-miR-181a | 6.53 | 7.04 | 7.22 | 7.16 | 6.93 | 7.26 | 7.17 | 7.26 | 6.75 | 7.03 |
| hsa-miR-181b | 5.40 | 5.86 | 6.09 | 5.65 | 5.56 | 5.92 | 6.23 | 5.88 | 5.45 | 5.78 |
| hsa-miR-181c | 3.56 | 3.56 | 3.12 | 3.75 | 3.62 | 4.68 | 4.01 | 4.33 | 4.32 | 3.88 |
| hsa-miR-182 | 4.86 | 4.79 | 5.42 | 5.53 | 4.92 | 4.15 | 2.63 | 4.80 | 4.70 | 4.65 |
| hsa-miR-182-AS | 2.18 | 0.48 | 2.25 | 1.75 | 1.73 | 1.75 | 1.52 | 1.56 | 1.78 | 1.67 |
| hsa-miR-183 | 2.98 | 3.22 | 3.45 | 3.64 | 3.28 | 2.74 | 2.36 | 3.58 | 3.40 | 3.18 |
| hsa-miR-184 | 4.52 | 3.90 | 4.89 | 3.27 | 3.58 | 3.14 | 2.94 | 3.45 | 3.55 | 3.69 |
| hsa-miR-185 | 5.55 | 5.84 | 6.29 | 5.68 | 5.40 | 5.60 | 5.27 | 5.75 | 5.75 | 5.68 |
| hsa-miR-186 | 3.59 | 3.84 | 3.42 | 4.16 | 4.67 | 4.21 | 4.22 | 4.67 | 4.35 | 4.13 |
| hsa-miR-187 | 1.57 | 2.73 | 2.84 | 2.01 | 2.36 | 4.71 | 3.22 | 2.82 | 2.03 | 2.70 |
| hsa-miR-188 | 4.09 | 3.81 | 3.36 | 2.90 | 3.45 | 3.51 | 4.41 | 3.46 | 3.62 | 3.62 |
| hsa-miR-189 | 2.92 | 4.32 | 4.21 | 4.65 | 4.30 | 4.56 | 5.01 | 4.21 | 4.11 | 4.26 |
| hsa-miR-190 | 0.67 | 0.84 | 1.97 | 1.58 | 1.60 | 1.55 | 1.70 | 1.66 | 1.51 | 1.45 |
| hsa-miR-191 | 7.37 | 7.56 | 7.78 | 8.09 | 7.91 | 8.09 | 8.14 | 7.80 | 7.58 | 7.81 |
| hsa-miR-192 | 3.10 | 3.60 | 3.79 | 4.08 | 3.70 | 4.79 | 4.15 | 3.93 | 3.76 | 3.88 |
| hsa-miR-193a | 4.48 | 3.81 | 4.65 | 4.94 | 4.49 | 4.72 | 4.40 | 4.76 | 5.03 | 4.59 |
| hsa-miR-194 | 3.81 | 4.04 | 4.65 | 4.48 | 4.51 | 5.28 | 5.02 | 4.39 | 4.17 | 4.48 |
| hsa-miR-195 | 8.25 | 8.38 | 8.24 | 8.85 | 8.92 | 9.28 | 9.35 | 8.93 | 8.95 | 8.80 |
| hsa-miR-196a | 3.05 | 3.60 | 3.45 | 4.66 | 4.77 | 2.25 | 6.69 | 4.58 | 4.49 | 4.17 |
| hsa-miR-196b | 5.66 | 5.43 | 5.53 | 6.35 | 6.25 | 2.15 | 7.29 | 6.21 | 6.07 | 5.66 |
| hsa-miR-197 | 4.99 | 4.82 | 5.28 | 5.28 | 5.36 | 4.94 | 5.62 | 4.83 | 3.82 | 4.99 |
| hsa-miR-198 | 6.06 | 5.57 | 4.94 | 4.09 | 4.71 | 5.00 | 4.30 | 4.47 | 6.01 | 5.02 |
| hsa-miR-199a | 7.66 | 8.07 | 8.31 | 8.56 | 8.21 | 8.39 | 8.46 | 8.57 | 8.65 | 8.32 |
| hsa-miR-199a-AS | 8.46 | 8.02 | 8.24 | 9.18 | 8.81 | 8.49 | 8.96 | 8.92 | 8.84 | 8.66 |

TABLE 7-continued

Normalized Array Data for miRNA Expression in Nine Cervical Tumor Tissue Samples (Ca1-Ca9) and Nine Cervical Normal Adjacent Tissue Samples (NAT1-NAT-9). TV, threshold value. miRNAs > TV, miRNAs greater than threshold value. %, Percentage of miRNAs greater than threshold value.

| | | | | | | | | | | |
|---|---|---|---|---|---|---|---|---|---|---|
| hsa-miR-199b | 5.91 | 5.85 | 6.46 | 6.94 | 6.69 | 5.53 | 5.46 | 7.50 | 7.49 | 6.43 |
| hsa-miR-19a | 2.61 | 3.28 | 3.23 | 3.75 | 3.62 | 3.24 | 3.03 | 4.59 | 4.12 | 3.50 |
| hsa-miR-19b | 6.43 | 6.90 | 7.26 | 7.41 | 7.26 | 7.56 | 6.87 | 7.92 | 7.87 | 7.28 |
| hsa-miR-20a | 6.00 | 5.84 | 6.34 | 6.52 | 6.68 | 6.64 | 6.15 | 6.89 | 6.73 | 6.42 |
| hsa-miR-200a | 4.65 | 4.43 | 5.83 | 5.85 | 5.37 | 5.49 | 3.09 | 5.91 | 5.62 | 5.14 |
| hsa-miR-200b | 7.02 | 6.42 | 7.58 | 7.66 | 7.19 | 7.55 | 4.56 | 7.30 | 6.95 | 6.91 |
| hsa-miR-200c | 8.11 | 7.96 | 8.95 | 8.70 | 8.31 | 8.36 | 5.95 | 8.41 | 8.26 | 8.11 |
| hsa-miR-203 | 9.16 | 9.12 | 9.10 | 9.66 | 9.33 | 5.50 | 4.62 | 9.46 | 9.46 | 8.38 |
| hsa-miR-204 | 4.23 | 3.84 | 4.11 | 4.72 | 4.39 | 4.83 | 5.38 | 4.45 | 4.48 | 4.49 |
| hsa-miR-205 | 9.62 | 9.25 | 10.28 | 10.14 | 10.17 | 6.41 | 3.99 | 10.26 | 10.27 | 8.93 |
| hsa-miR-206 | 3.90 | 3.56 | 3.26 | 2.15 | 2.66 | 2.46 | 2.80 | 2.68 | 2.62 | 2.90 |
| hsa-miR-208 | 1.57 | 2.16 | 1.63 | 1.81 | 1.39 | 1.82 | 1.54 | 1.66 | 1.65 | 1.69 |
| hsa-miR-21 | 9.52 | 9.79 | 10.01 | 9.42 | 9.74 | 8.70 | 9.63 | 10.10 | 9.99 | 9.65 |
| hsa-miR-210 | 5.83 | 5.53 | 6.33 | 6.67 | 5.49 | 5.08 | 4.68 | 6.51 | 6.56 | 5.85 |
| hsa-miR-211 | 1.02 | 1.45 | 0.85 | 2.06 | 2.40 | 1.82 | 1.79 | 2.46 | 2.20 | 1.78 |
| hsa-miR-212 | 3.21 | 3.33 | 3.30 | 3.25 | 3.21 | 2.96 | 3.66 | 3.12 | 2.93 | 3.22 |
| hsa-miR-213 | 2.77 | 2.01 | 2.33 | 1.81 | 2.13 | 2.05 | 1.99 | 2.46 | 1.55 | 2.12 |
| hsa-miR-214 | 7.68 | 8.14 | 8.33 | 8.11 | 8.09 | 7.77 | 8.52 | 7.68 | 7.77 | 8.01 |
| hsa-miR-215 | 3.44 | 3.28 | 2.48 | 2.59 | 2.62 | 2.80 | 3.39 | 2.70 | 2.42 | 2.86 |
| hsa-miR-216 | 1.74 | 2.16 | 2.62 | 1.86 | 2.52 | 2.34 | 1.89 | 2.15 | 2.14 | 2.16 |
| hsa-miR-217 | 2.77 | 2.89 | 2.33 | 2.10 | 1.97 | 1.82 | 1.95 | 1.86 | 1.95 | 2.18 |
| hsa-miR-218 | 5.27 | 4.73 | 5.07 | 5.85 | 6.02 | 5.72 | 5.52 | 5.91 | 6.09 | 5.58 |
| hsa-miR-219 | 2.30 | 2.63 | 2.07 | 2.35 | 2.18 | 2.10 | 2.86 | 2.23 | 2.33 | 2.34 |
| hsa-miR-22 | 7.87 | 8.40 | 8.42 | 8.58 | 8.58 | 7.65 | 9.07 | 8.73 | 8.66 | 8.44 |
| hsa-miR-220 | 1.57 | 2.63 | 0.97 | 1.75 | 1.39 | 1.62 | 1.59 | 1.66 | 1.60 | 1.64 |
| hsa-miR-221 | 8.43 | 8.21 | 8.72 | 8.86 | 8.35 | 8.50 | 8.96 | 8.42 | 8.40 | 8.54 |
| hsa-miR-222 | 7.89 | 7.73 | 8.31 | 8.49 | 7.75 | 8.09 | 8.54 | 7.77 | 7.89 | 8.05 |
| hsa-miR-223 | 6.79 | 6.38 | 6.88 | 7.22 | 6.71 | 5.74 | 5.56 | 7.57 | 6.89 | 6.64 |
| hsa-miR-224 | 6.07 | 6.48 | 6.82 | 7.18 | 6.53 | 4.99 | 5.16 | 6.32 | 6.32 | 6.21 |
| hsa-miR-23a | 9.29 | 9.70 | 9.85 | 9.91 | 9.87 | 9.14 | 9.81 | 9.73 | 9.52 | 9.65 |
| hsa-miR-23b | 9.62 | 10.35 | 10.28 | 10.25 | 10.26 | 9.87 | 10.01 | 9.97 | 9.75 | 10.04 |
| hsa-miR-24 | 9.35 | 9.81 | 9.80 | 9.83 | 9.97 | 9.88 | 10.01 | 9.83 | 9.81 | 9.81 |
| hsa-miR-25 | 6.33 | 6.06 | 6.55 | 6.96 | 6.88 | 6.98 | 6.72 | 6.88 | 6.62 | 6.66 |
| hsa-miR-26a | 10.64 | 10.29 | 10.61 | 10.95 | 11.00 | 11.09 | 10.01 | 10.73 | 10.69 | 10.67 |
| hsa-miR-26b | 7.31 | 6.64 | 7.10 | 7.93 | 7.70 | 7.34 | 7.16 | 7.42 | 7.19 | 7.31 |
| hsa-miR-27a | 8.82 | 8.53 | 8.87 | 9.52 | 9.26 | 8.83 | 8.91 | 9.27 | 9.21 | 9.02 |
| hsa-miR-27b | 8.90 | 8.88 | 9.01 | 9.65 | 9.26 | 9.67 | 9.61 | 9.26 | 9.02 | 9.25 |
| hsa-miR-28 | 5.70 | 5.75 | 5.67 | 6.33 | 6.21 | 6.06 | 6.43 | 5.92 | 6.03 | 6.01 |
| hsa-miR-296 | 3.16 | 2.73 | 3.07 | 2.70 | 3.67 | 3.62 | 3.26 | 3.35 | 3.87 | 3.27 |
| hsa-miR-299-5p | 3.52 | 4.36 | 4.01 | 4.45 | 5.07 | 3.75 | 4.73 | 4.92 | 4.70 | 4.39 |
| hsa-miR-29a | 8.51 | 8.46 | 8.68 | 9.25 | 8.97 | 9.25 | 8.86 | 9.49 | 9.60 | 9.01 |
| hsa-miR-29b | 5.09 | 5.24 | 6.10 | 6.25 | 6.12 | 6.21 | 5.86 | 7.09 | 6.93 | 6.10 |
| hsa-miR-29c | 5.16 | 5.49 | 5.88 | 6.14 | 5.94 | 6.42 | 5.43 | 6.79 | 6.95 | 6.02 |
| hsa-miR-301 | 1.20 | 1.45 | 1.97 | 2.27 | 1.97 | 2.05 | 2.01 | 2.52 | 1.87 | 1.92 |
| hsa-miR-302a | 2.05 | 2.63 | 2.16 | 2.39 | 2.27 | 2.38 | 2.10 | 2.26 | 1.78 | 2.23 |
| hsa-miR-302b | 1.57 | 1.25 | 1.37 | 1.86 | 1.32 | 1.41 | 1.45 | 1.28 | 1.51 | 1.45 |
| hsa-miR-302b-AS | 2.41 | 3.28 | 1.37 | 1.69 | 1.32 | 1.75 | 1.61 | 1.45 | 1.46 | 1.82 |
| hsa-miR-302c | 1.90 | 0.84 | 2.16 | 2.06 | 1.73 | 1.93 | 1.81 | 1.86 | 1.74 | 1.78 |
| hsa-miR-302c-AS | 5.64 | 4.95 | 4.38 | 2.15 | 2.62 | 2.85 | 2.30 | 3.25 | 3.63 | 3.53 |
| hsa-miR-302d | 2.30 | 1.45 | 1.37 | 1.69 | 0.90 | 1.41 | 1.68 | 1.71 | 1.91 | 1.60 |
| hsa-miR-30a-3p | 3.16 | 3.52 | 3.59 | 4.52 | 4.49 | 4.80 | 4.70 | 4.24 | 4.13 | 4.13 |
| hsa-miR-30a-5p | 7.39 | 7.65 | 7.65 | 8.10 | 8.13 | 8.44 | 8.36 | 8.13 | 8.12 | 8.00 |
| hsa-miR-30b | 6.74 | 6.45 | 6.75 | 7.77 | 7.64 | 7.41 | 7.42 | 7.55 | 7.29 | 7.22 |
| hsa-miR-30c | 6.98 | 7.27 | 7.39 | 8.09 | 7.81 | 8.30 | 8.12 | 7.78 | 7.59 | 7.70 |
| hsa-miR-30d | 7.43 | 7.65 | 7.72 | 8.09 | 8.35 | 8.41 | 8.40 | 8.15 | 8.02 | 8.03 |
| hsa-miR-30e-3p | 3.21 | 3.60 | 3.56 | 4.25 | 4.33 | 4.52 | 4.22 | 4.35 | 4.21 | 4.03 |
| hsa-miR-30e-5p | 6.60 | 6.63 | 7.00 | 7.22 | 7.20 | 7.33 | 7.17 | 7.59 | 7.40 | 7.13 |
| hsa-miR-31 | 7.56 | 7.75 | 8.16 | 8.05 | 7.81 | 7.11 | 4.47 | 8.07 | 8.07 | 7.45 |
| hsa-miR-32 | 2.69 | 1.65 | 2.48 | 2.01 | 2.44 | 2.34 | 2.39 | 2.03 | 2.10 | 2.24 |
| hsa-miR-320 | 8.26 | 8.30 | 8.88 | 8.69 | 8.01 | 8.07 | 8.03 | 7.76 | 8.54 | 8.28 |
| hsa-miR-323 | 0.84 | 2.29 | 1.97 | 2.39 | 2.69 | 2.15 | 2.07 | 2.68 | 2.45 | 2.17 |
| hsa-miR-324-3p | 5.82 | 6.12 | 5.96 | 5.91 | 6.17 | 5.98 | 6.16 | 5.73 | 5.95 | 5.98 |
| hsa-miR-324-5p | 2.51 | 3.56 | 3.59 | 3.50 | 4.07 | 3.76 | 4.20 | 3.88 | 4.25 | 3.70 |
| hsa-miR-325 | 3.76 | 3.10 | 3.07 | 1.39 | 1.79 | 1.88 | 1.63 | 1.56 | 1.78 | 2.22 |
| hsa-miR-326 | 2.18 | 2.81 | 3.12 | 2.86 | 2.62 | 2.42 | 2.86 | 2.60 | 2.39 | 2.65 |
| hsa-miR-328 | 3.48 | 3.90 | 3.48 | 3.78 | 4.27 | 4.17 | 5.12 | 3.79 | 3.57 | 3.95 |
| hsa-miR-33 | 0.25 | 0.65 | 2.16 | 1.58 | 1.32 | 1.41 | 1.63 | 1.45 | 1.74 | 1.36 |
| hsa-miR-330 | 2.98 | 3.38 | 2.84 | 2.81 | 2.92 | 2.15 | 2.43 | 3.06 | 2.69 | 2.81 |
| hsa-miR-331 | 4.86 | 5.55 | 5.36 | 4.98 | 5.67 | 5.23 | 6.12 | 5.34 | 4.53 | 5.29 |
| hsa-miR-335 | 3.76 | 3.43 | 3.42 | 4.03 | 4.12 | 5.15 | 5.24 | 3.79 | 3.76 | 4.08 |
| hsa-miR-337 | 2.61 | 2.01 | 1.50 | 2.06 | 1.97 | 1.69 | 1.93 | 2.15 | 2.10 | 2.00 |
| hsa-miR-338 | 0.84 | 2.42 | 2.25 | 2.70 | 2.48 | 2.15 | 1.81 | 2.60 | 2.20 | 2.16 |
| hsa-miR-339 | 5.04 | 4.99 | 5.33 | 5.24 | 5.56 | 5.52 | 5.58 | 5.35 | 5.25 | 5.32 |
| hsa-miR-340 | 1.74 | 2.29 | 2.16 | 2.49 | 1.97 | 2.42 | 2.77 | 2.15 | 2.03 | 2.23 |
| hsa-miR-342 | 7.24 | 6.96 | 7.35 | 7.51 | 7.19 | 7.63 | 7.75 | 6.95 | 7.01 | 7.29 |
| hsa-miR-345 | 3.05 | 3.71 | 3.93 | 4.14 | 4.19 | 4.80 | 4.25 | 4.53 | 4.59 | 4.13 |

TABLE 7-continued

Normalized Array Data for miRNA Expression in Nine Cervical Tumor Tissue Samples (Ca1-Ca9) and Nine Cervical Normal Adjacent Tissue Samples (NAT1-NAT9). TV, threshold value. miRNAs > TV, miRNAs greater than threshold value. %, Percentage of miRNAs greater than threshold value.

| | | | | | | | | | | |
|---|---|---|---|---|---|---|---|---|---|---|
| hsa-miR-346 | 2.41 | 2.73 | 1.50 | 1.96 | 2.23 | 1.99 | 2.07 | 2.07 | 1.46 | 2.05 |
| hsa-miR-34a | 6.30 | 6.68 | 7.28 | 6.75 | 6.46 | 7.33 | 6.61 | 7.27 | 7.06 | 6.86 |
| hsa-miR-34b | 3.72 | 3.47 | 3.77 | 3.68 | 3.65 | 5.62 | 3.41 | 4.34 | 4.07 | 3.97 |
| hsa-miR-34c | 2.51 | 1.84 | 2.48 | 1.91 | 2.32 | 6.06 | 2.22 | 2.49 | 2.20 | 2.67 |
| hsa-miR-361 | 6.29 | 6.46 | 6.77 | 7.10 | 6.88 | 7.01 | 7.35 | 6.68 | 6.66 | 6.80 |
| hsa-miR-365 | 3.40 | 3.38 | 3.71 | 4.17 | 4.40 | 3.26 | 4.41 | 4.06 | 4.02 | 3.87 |
| hsa-miR-367 | 1.20 | 2.42 | 1.63 | 1.96 | 1.60 | 2.15 | 2.07 | 1.50 | 1.69 | 1.80 |
| hsa-miR-368 | 5.53 | 5.78 | 6.01 | 6.70 | 7.06 | 5.24 | 6.18 | 7.08 | 6.95 | 6.28 |
| hsa-miR-369-3p | 1.57 | 2.73 | 1.10 | 2.06 | 2.40 | 1.82 | 1.79 | 2.23 | 2.17 | 1.98 |
| hsa-miR-370 | 5.29 | 5.49 | 5.73 | 4.23 | 5.95 | 5.23 | 5.30 | 5.23 | 5.06 | 5.28 |
| hsa-miR-371 | 1.02 | 0.48 | 1.24 | 1.69 | 1.32 | 0.98 | 1.81 | 1.06 | 1.51 | 1.23 |
| hsa-miR-372 | 0.52 | 1.25 | 2.07 | 1.33 | 1.53 | 1.62 | 1.77 | 1.99 | 1.55 | 1.51 |
| hsa-miR-373 | 2.30 | 2.53 | 2.07 | 1.81 | 1.99 | 1.75 | 1.76 | 1.55 | 1.94 |
| hsa-miR-373-AS | 4.57 | 3.81 | 3.64 | 4.38 | 4.63 | 3.92 | 4.63 | 4.22 | 4.28 | 4.23 |
| hsa-miR-374 | 2.85 | 3.16 | 2.99 | 2.46 | 3.79 | 3.33 | 3.28 | 3.92 | 3.21 | 3.22 |
| hsa-miR-375 | 3.72 | 3.56 | 3.81 | 4.17 | 4.27 | 2.71 | 2.07 | 4.42 | 3.96 | 3.63 |
| hsa-miR-376a | 4.02 | 4.43 | 4.82 | 4.90 | 5.37 | 3.30 | 4.54 | 5.57 | 5.40 | 4.71 |
| hsa-miR-377 | 2.41 | 2.81 | 2.94 | 3.54 | 3.68 | 1.75 | 2.56 | 4.23 | 3.94 | 3.10 |
| hsa-miR-378 | 3.78 | 4.01 | 4.46 | 3.89 | 4.50 | 4.56 | 4.50 | 4.40 | 3.92 | 4.22 |
| hsa-miR-379 | 5.33 | 5.46 | 5.06 | 5.17 | 5.44 | 4.33 | 4.85 | 5.43 | 5.34 | 5.16 |
| hsa-miR-380-3p | 1.20 | 1.25 | 2.25 | 1.46 | 1.97 | 1.55 | 1.66 | 1.61 | 1.69 | 1.63 |
| hsa-miR-380-5p | 1.74 | 2.01 | 1.63 | 1.52 | 2.08 | 1.34 | 1.70 | 1.39 | 1.78 | 1.69 |
| hsa-miR-381 | 3.95 | 3.78 | 4.08 | 3.98 | 4.69 | 3.75 | 3.86 | 4.94 | 5.13 | 4.24 |
| hsa-miR-382 | 3.78 | 4.79 | 4.70 | 4.64 | 4.70 | 3.12 | 4.21 | 4.81 | 4.84 | 4.40 |
| hsa-miR-383 | 3.16 | 2.89 | 2.79 | 2.06 | 2.08 | 1.99 | 1.95 | 1.86 | 1.46 | 2.25 |
| hsa-miR-384 | 1.20 | 1.65 | 2.07 | 1.33 | 1.67 | 1.75 | 1.49 | 1.12 | 1.41 | 1.52 |
| hsa-miR-422a | 4.70 | 4.66 | 4.96 | 5.88 | 5.16 | 4.83 | 4.86 | 5.15 | 4.82 | 5.00 |
| hsa-miR-422b | 6.42 | 6.54 | 6.67 | 6.80 | 6.80 | 6.71 | 6.80 | 6.56 | 6.36 | 6.63 |
| hsa-miR-423 | 6.29 | 6.28 | 6.81 | 6.34 | 6.34 | 6.36 | 6.65 | 6.07 | 5.75 | 6.32 |
| hsa-miR-424 | 4.09 | 4.20 | 4.70 | 4.73 | 5.60 | 5.48 | 4.94 | 5.82 | 5.62 | 5.02 |
| hsa-miR-425 | 3.16 | 3.47 | 3.71 | 4.09 | 4.02 | 4.06 | 4.52 | 3.89 | 3.74 | 3.85 |
| hsa-miR-429 | 3.78 | 3.38 | 4.67 | 4.52 | 4.63 | 4.58 | 1.99 | 4.64 | 4.27 | 4.05 |
| hsa-miR-448 | 2.30 | 2.01 | 2.79 | 2.06 | 1.91 | 1.62 | 1.56 | 1.50 | 1.21 | 1.89 |
| hsa-miR-449 | 2.18 | 1.84 | 1.97 | 2.01 | 1.97 | 2.10 | 1.85 | 1.66 | 1.74 | 1.92 |
| hsa-miR-450 | 2.61 | 2.29 | 2.74 | 2.06 | 2.13 | 2.29 | 2.15 | 2.37 | 2.33 | 2.33 |
| hsa-miR-7 | 3.21 | 3.16 | 2.74 | 2.86 | 3.04 | 2.38 | 2.07 | 3.04 | 2.45 | 2.77 |
| hsa-miR-9 | 1.90 | 2.16 | 2.33 | 2.31 | 2.48 | 2.25 | 2.34 | 2.33 | 1.99 | 2.23 |
| hsa-miR-9-AS | 3.21 | 1.65 | 2.79 | 3.78 | 3.98 | 3.24 | 3.75 | 3.60 | 3.62 | 3.29 |
| hsa-miR-92 | 7.02 | 6.99 | 7.31 | 7.20 | 7.28 | 7.86 | 7.13 | 7.39 | 7.38 | 7.28 |
| hsa-miR-93 | 6.81 | 6.97 | 7.52 | 7.26 | 7.04 | 7.40 | 7.22 | 7.21 | 7.10 | 7.17 |
| hsa-miR-95 | 4.73 | 3.87 | 3.89 | 4.02 | 4.22 | 3.60 | 3.13 | 4.20 | 4.14 | 3.98 |
| hsa-miR-96 | 3.21 | 3.38 | 3.19 | 3.60 | 3.12 | 3.86 | 3.64 | 3.02 | 3.41 |
| hsa-miR-98 | 5.94 | 5.53 | 5.40 | 5.94 | 5.63 | 5.69 | 5.77 | 5.63 | 5.50 | 5.67 |
| hsa-miR-99a | 8.98 | 9.00 | 9.45 | 9.79 | 9.72 | 9.66 | 9.31 | 10.04 | 9.88 | 9.54 |
| hsa-miR-99b | 6.83 | 7.11 | 7.20 | 7.49 | 7.21 | 7.21 | 8.00 | 6.99 | 6.94 | 7.22 |
| mmu-let-7d-AS | 3.05 | 1.84 | 2.25 | 2.10 | 1.85 | 2.67 | 1.79 | 2.40 | 3.18 | 2.35 |
| mmu-miR-101b | 1.74 | 2.16 | 1.63 | 2.01 | 1.39 | 1.62 | 1.63 | 1.28 | 1.87 | 1.70 |
| mmu-miR-106a | 6.54 | 6.32 | 6.71 | 7.12 | 6.96 | 7.09 | 6.66 | 7.28 | 7.15 | 6.87 |
| mmu-miR-129-3p | 2.05 | 1.04 | 2.33 | 2.35 | 2.27 | 2.05 | 2.44 | 1.81 | 1.87 | 2.02 |
| mmu-miR-140-AS | 6.45 | 6.93 | 6.97 | 6.86 | 7.10 | 7.45 | 7.51 | 7.21 | 7.26 | 7.08 |
| mmu-miR-151 | 2.98 | 3.47 | 2.94 | 4.77 | 4.03 | 3.77 | 3.94 | 3.79 | 3.98 | 3.74 |
| mmu-miR-155 | 3.78 | 3.22 | 3.48 | 3.84 | 3.35 | 2.10 | 2.17 | 3.66 | 2.78 | 3.15 |
| mmu-miR-17-3p | 2.98 | 2.97 | 2.99 | 3.13 | 2.72 | 2.74 | 2.72 | 2.60 | 2.93 | 2.86 |
| mmu-miR-192 | 2.41 | 3.22 | 3.30 | 3.90 | 3.57 | 4.56 | 3.86 | 3.79 | 3.60 | 3.58 |
| mmu-miR-199b | 5.64 | 5.39 | 5.96 | 6.52 | 6.45 | 5.84 | 5.83 | 6.81 | 6.85 | 6.14 |
| mmu-miR-201 | 0.38 | 2.73 | 2.16 | 1.81 | 2.02 | 1.93 | 1.81 | 1.28 | 1.91 | 1.78 |
| mmu-miR-202 | 5.28 | 4.53 | 4.48 | 3.46 | 4.35 | 4.14 | 3.64 | 4.23 | 4.24 | 4.26 |
| mmu-miR-207 | 0.38 | 2.63 | 2.07 | 2.93 | 1.79 | 1.93 | 1.68 | 1.86 | 1.69 | 1.88 |
| mmu-miR-211 | 0.67 | 2.81 | 2.68 | 1.64 | 1.53 | 1.93 | 1.91 | 1.81 | 1.69 | 1.85 |
| mmu-miR-215 | 2.18 | 2.53 | 1.86 | 1.69 | 1.39 | 1.34 | 1.56 | 1.66 | 1.26 | 1.72 |
| mmu-miR-217 | 1.57 | 2.29 | 1.97 | 1.69 | 1.53 | 1.34 | 1.61 | 1.71 | 1.91 | 1.74 |
| mmu-miR-290 | 4.38 | 3.78 | 3.39 | 3.48 | 4.24 | 4.15 | 3.89 | 4.12 | 4.49 | 3.99 |
| mmu-miR-291-3p | 1.20 | 1.04 | 1.75 | 1.58 | 0.97 | 1.34 | 1.54 | 1.56 | 1.71 | 1.39 |
| mmu-miR-291-5p | 2.05 | 2.89 | 1.63 | 3.55 | 3.51 | 3.51 | 3.53 | 3.19 | 3.90 | 3.08 |
| mmu-miR-292-3p | 2.61 | 2.01 | 2.07 | 1.75 | 1.39 | 1.20 | 1.72 | 1.45 | 1.74 | 1.77 |
| mmu-miR-292-5p | 3.48 | 3.33 | 2.74 | 2.35 | 2.99 | 2.83 | 2.74 | 2.93 | 3.27 | 2.96 |
| mmu-miR-293 | 2.05 | 1.45 | 1.37 | 2.01 | 1.85 | 1.62 | 2.03 | 2.07 | 2.14 | 1.84 |
| mmu-miR-294 | 2.61 | 2.81 | 2.84 | 2.59 | 2.86 | 1.99 | 2.33 | 2.23 | 2.30 | 2.51 |
| mmu-miR-295 | 2.30 | 1.65 | 1.37 | 1.52 | 1.73 | 1.05 | 1.70 | 1.99 | 1.26 | 1.62 |
| mmu-miR-297 | 2.51 | 0.84 | 1.24 | 1.69 | 1.60 | 1.55 | 1.56 | 1.71 | 1.11 | 1.54 |
| mmu-miR-298 | 5.72 | 4.76 | 4.64 | 4.13 | 4.87 | 5.19 | 4.47 | 4.84 | 5.28 | 4.88 |
| mmu-miR-300 | 3.16 | 2.42 | 2.99 | 3.15 | 3.57 | 3.05 | 3.07 | 3.65 | 3.95 | 3.22 |
| mmu-miR-322 | 1.02 | 2.29 | 1.63 | 1.86 | 2.13 | 1.93 | 2.17 | 2.19 | 1.78 | 1.89 |
| mmu-miR-424 | 3.16 | 2.73 | 3.42 | 3.60 | 4.58 | 4.77 | 4.18 | 4.87 | 4.75 | 4.01 |
| mmu-miR-325 | 3.16 | 3.16 | 2.07 | 1.75 | 2.18 | 1.82 | 1.68 | 1.99 | 2.30 | 2.23 |
| mmu-miR-329 | 1.57 | 2.53 | 1.63 | 2.10 | 2.23 | 2.25 | 2.10 | 1.86 | 2.17 | 2.05 |

TABLE 7-continued

Normalized Array Data for miRNA Expression in Nine Cervical Tumor Tissue Samples (Ca1-Ca9) and
Nine Cervical Normal Adjacent Tissue Samples (NAT1-NAT-9). TV, threshold value. miRNAs >
TV, miRNAs greater than threshold value. %, Percentage of miRNAs greater than threshold value.

| | | | | | | | | | | |
|---|---|---|---|---|---|---|---|---|---|---|
| mmu-miR-330 | 2.41 | 2.01 | 2.25 | 2.01 | 2.36 | 2.38 | 2.20 | 1.95 | 2.39 | 2.22 |
| mmu-miR-337 | 1.74 | 1.45 | 1.37 | 1.91 | 2.02 | 1.69 | 1.77 | 2.07 | 1.69 | 1.75 |
| mmu-miR-341 | 2.92 | 2.01 | 1.86 | 1.91 | 2.44 | 1.82 | 2.03 | 2.26 | 2.39 | 2.18 |
| mmu-miR-344 | 2.30 | 1.04 | 1.24 | 1.52 | 1.79 | 1.93 | 1.63 | 1.50 | 1.55 | 1.61 |
| mmu-miR-345 | 2.41 | 2.53 | 1.97 | 2.86 | 2.72 | 2.98 | 2.75 | 2.60 | 3.14 | 2.66 |
| mmu-miR-346 | 0.52 | 2.81 | 1.86 | 2.06 | 1.79 | 2.20 | 2.08 | 1.90 | 1.83 | 1.89 |
| mmu-miR-34b | 2.69 | 2.29 | 3.07 | 2.52 | 2.44 | 3.75 | 1.91 | 2.07 | 2.33 | 2.57 |
| mmu-miR-350 | 1.39 | 0.65 | 1.86 | 1.91 | 2.18 | 1.55 | 1.63 | 1.90 | 1.99 | 1.67 |
| mmu-miR-351 | 2.18 | 2.29 | 2.33 | 2.10 | 2.32 | 2.46 | 2.28 | 2.07 | 2.42 | 2.27 |
| mmu-miR-376a | 2.30 | 2.29 | 2.48 | 2.52 | 3.47 | 1.93 | 2.58 | 3.55 | 3.36 | 2.72 |
| mmu-miR-376b | 2.30 | 2.16 | 2.68 | 2.01 | 1.60 | 1.99 | 1.77 | 1.45 | 1.83 | 1.98 |
| mmu-miR-380-3p | 3.48 | 3.10 | 2.16 | 2.10 | 2.23 | 2.67 | 2.28 | 2.58 | 2.03 | 2.51 |
| mmu-miR-383 | 3.26 | 3.22 | 2.74 | 2.10 | 1.97 | 1.99 | 2.03 | 1.95 | 2.30 | 2.40 |
| mmu-miR-384 | 2.05 | 1.04 | 1.24 | 1.69 | 1.67 | 1.93 | 1.75 | 2.30 | 1.31 | 1.66 |
| mmu-miR-409 | 3.87 | 5.05 | 5.06 | 4.83 | 4.88 | 2.96 | 4.48 | 5.00 | 4.74 | 4.54 |
| hsa-miR-410 | 3.05 | 2.01 | 2.41 | 3.73 | 3.57 | 2.34 | 3.32 | 3.61 | 4.12 | 3.13 |
| mmu-miR-411 | 1.39 | 2.97 | 2.68 | 2.49 | 3.23 | 2.15 | 2.93 | 2.52 | 2.58 | 2.55 |
| hsa-miR-412 | 2.05 | 0.65 | 1.63 | 1.86 | 1.67 | 1.88 | 1.63 | 1.61 | 1.36 | 1.59 |
| mmu-miR-429 | 0.52 | 1.84 | 1.97 | 2.01 | 1.46 | 1.69 | 1.61 | 1.56 | 1.36 | 1.56 |
| mmu-miR-7b | 2.85 | 2.81 | 2.48 | 1.52 | 1.79 | 2.29 | 1.79 | 1.76 | 1.91 | 2.13 |
| rno-miR-151-AS | 6.61 | 6.78 | 6.95 | 7.25 | 7.19 | 7.24 | 7.20 | 7.08 | 7.05 | 7.04 |
| rno-miR-20-AS | 1.20 | 2.81 | 2.25 | 1.81 | 1.32 | 1.34 | 1.45 | 1.39 | 1.41 | 1.66 |
| rno-miR-297 | 1.57 | 2.63 | 1.50 | 1.39 | 1.91 | 2.20 | 1.63 | 1.61 | 1.69 | 1.79 |
| rno-miR-327 | 4.88 | 4.24 | 3.30 | 2.68 | 3.17 | 3.42 | 2.96 | 2.73 | 3.85 | 3.47 |
| rno-miR-333 | 2.41 | 1.65 | 1.24 | 1.91 | 1.46 | 1.69 | 1.85 | 2.07 | 1.91 | 1.80 |
| rno-miR-336 | 3.59 | 3.47 | 3.30 | 4.07 | 2.48 | 3.85 | 2.37 | 2.73 | 2.55 | 3.16 |
| rno-miR-343 | 2.51 | 2.16 | 1.75 | 2.46 | 1.79 | 1.99 | 1.68 | 1.45 | 2.17 | 2.00 |
| rno-miR-344 | 1.90 | 2.29 | 1.37 | 1.58 | 1.18 | 1.69 | 1.52 | 1.90 | 1.55 | 1.67 |
| rno-miR-346 | 2.41 | 3.87 | 2.41 | 1.96 | 2.66 | 2.98 | 1.79 | 2.75 | 2.33 | 2.57 |
| rno-miR-347 | 3.56 | 3.56 | 2.68 | 2.76 | 3.80 | 2.85 | 3.15 | 3.74 | 3.68 | 3.31 |
| rno-miR-349 | 1.74 | 2.16 | 1.75 | 1.58 | 1.04 | 1.75 | 1.77 | 1.45 | 1.36 | 1.62 |
| rno-miR-352 | 5.70 | 5.28 | 5.46 | 6.08 | 5.49 | 5.40 | 5.67 | 5.38 | 5.30 | 5.53 |
| rno-miR-421 | 2.69 | 2.81 | 0.97 | 1.64 | 1.32 | 1.48 | 1.47 | 1.34 | 1.51 | 1.69 |
| rno-miR-7-AS | 1.90 | 3.04 | 2.68 | 2.93 | 2.18 | 2.46 | 2.27 | 2.26 | 1.95 | 2.41 |
| hsa-miR-522 | 2.77 | 1.65 | 2.41 | 1.58 | 1.39 | 1.55 | 1.54 | 1.45 | 1.26 | 1.73 |
| hsa-miR-519b | 1.90 | 1.25 | 2.07 | 1.69 | 1.60 | 1.88 | 1.59 | 1.28 | 1.65 | 1.66 |
| hsa-miR-520c | 2.18 | 2.01 | 2.68 | 1.86 | 1.73 | 1.62 | 2.08 | 1.61 | 1.99 | 1.97 |
| hsa-miR-519e | 1.39 | 2.97 | 0.97 | 1.64 | 1.32 | 1.48 | 1.59 | 1.50 | 1.11 | 1.55 |
| hsa-miR-519d | 2.05 | 1.84 | 2.16 | 1.75 | 1.39 | 1.88 | 1.70 | 1.61 | 1.51 | 1.77 |
| hsa-miR-520b | 2.30 | 2.42 | 2.25 | 1.52 | 1.46 | 1.27 | 1.75 | 1.66 | 1.51 | 1.79 |
| hsa-miR-519c | 1.20 | 1.65 | 1.37 | 1.64 | 1.32 | 1.82 | 1.47 | 1.99 | 1.65 | 1.57 |
| hsa-miR-526b-AS | 1.02 | 2.16 | 1.50 | 1.46 | 1.60 | 1.48 | 1.66 | 1.56 | 1.91 | 1.59 |
| hsa-miR-520e | 0.67 | 0.48 | 2.07 | 1.91 | 1.53 | 1.62 | 1.59 | 1.12 | 1.69 | 1.41 |
| hsa-miR-520a | 0.67 | 1.84 | 1.10 | 1.64 | 1.67 | 1.62 | 1.56 | 1.50 | 1.41 | 1.45 |
| hsa-miR-520d | 3.10 | 2.42 | 1.97 | 1.81 | 1.79 | 2.20 | 1.75 | 1.45 | 1.74 | 2.02 |
| hsa-miR-520h | 1.39 | 0.65 | 1.86 | 1.64 | 1.85 | 1.93 | 1.70 | 0.95 | 1.87 | 1.54 |
| hsa-miR-517a | 2.51 | 2.29 | 1.63 | 1.96 | 2.13 | 1.75 | 1.91 | 2.07 | 2.03 | 2.03 |
| hsa-miR-518e | 1.20 | 1.65 | 2.25 | 1.64 | 1.32 | 1.62 | 1.61 | 1.39 | 1.21 | 1.54 |
| hsa-miR-521 | 2.30 | 2.29 | 2.48 | 1.64 | 1.79 | 1.55 | 1.72 | 1.66 | 1.99 | 1.94 |
| hsa-miR-523 | 1.57 | 1.25 | 1.63 | 1.58 | 1.60 | 1.75 | 1.61 | 1.39 | 1.74 | 1.57 |
| hsa-miR-518f | 0.52 | 0.48 | 1.86 | 1.69 | 1.53 | 1.93 | 1.61 | 1.61 | 1.65 | 1.43 |
| hsa-miR-518c | 2.61 | 2.42 | 2.25 | 1.46 | 1.60 | 1.69 | 1.52 | 1.90 | 1.78 | 1.91 |
| hsa-miR-518b | 1.90 | 0.84 | 2.16 | 2.06 | 2.02 | 1.93 | 1.85 | 1.86 | 2.10 | 1.86 |
| hsa-miR-518d | 1.90 | 0.65 | 1.63 | 1.64 | 1.18 | 1.88 | 1.45 | 1.66 | 1.51 | 1.50 |
| hsa-miR-525-AS | 2.51 | 2.01 | 1.75 | 1.75 | 1.46 | 1.48 | 1.68 | 1.76 | 1.83 | 1.80 |
| hsa-miR-524 | 1.90 | 2.42 | 1.50 | 1.96 | 1.32 | 1.99 | 1.63 | 1.56 | 1.69 | 1.78 |
| hsa-miR-518a | 1.90 | 2.29 | 2.16 | 1.64 | 1.25 | 1.88 | 1.66 | 1.81 | 1.69 | 1.81 |
| hsa-miR-515-3p | 1.39 | 0.65 | 1.24 | 1.64 | 1.73 | 2.05 | 1.61 | 1.66 | 1.65 | 1.51 |
| hsa-miR-516-3p | 1.57 | 1.04 | 2.16 | 1.52 | 1.73 | 1.34 | 1.72 | 1.71 | 1.65 | 1.61 |
| ambi-miR-7026 | 0.84 | 0.84 | 2.68 | 1.52 | 1.73 | 1.48 | 1.52 | 1.45 | 1.69 | 1.53 |
| ambi-miR-7027 | 3.16 | 2.97 | 3.15 | 3.68 | 3.73 | 2.54 | 2.22 | 3.73 | 4.02 | 3.24 |
| hsa-miR-512-3p | 2.61 | 2.97 | 2.90 | 1.91 | 2.18 | 2.34 | 1.93 | 1.34 | 1.87 | 2.23 |
| ambi-miR-7029 | 6.56 | 5.72 | 7.94 | 7.87 | 7.26 | 8.74 | 5.87 | 7.59 | 7.32 | 7.21 |
| hsa-miR-491 | 4.09 | 4.04 | 3.75 | 3.53 | 3.81 | 4.19 | 3.96 | 3.95 | 4.39 | 3.97 |
| hsa-miR-506 | 2.18 | 2.81 | 2.16 | 1.86 | 2.08 | 2.05 | 1.99 | 1.90 | 1.69 | 2.08 |
| hsa-miR-514 | 0.67 | 1.65 | 1.10 | 1.81 | 1.67 | 1.41 | 1.59 | 1.50 | 1.41 | 1.42 |
| hsa-miR-509 | 2.51 | 2.16 | 1.75 | 1.91 | 1.97 | 2.25 | 1.66 | 1.86 | 1.69 | 1.97 |
| hsa-miR-508 | 1.90 | 1.45 | 2.07 | 1.81 | 1.39 | 1.41 | 1.49 | 1.61 | 1.95 | 1.68 |
| hsa-miR-507 | 2.18 | 1.45 | 1.63 | 1.64 | 1.53 | 1.75 | 1.40 | 1.56 | 1.16 | 1.59 |
| ambi-miR-7036 | 3.16 | 2.53 | 2.79 | 3.71 | 2.59 | 3.26 | 2.08 | 2.86 | 2.69 | 2.85 |
| hsa-miR-193b | 6.41 | 6.54 | 6.90 | 7.13 | 6.86 | 5.88 | 7.14 | 6.83 | 6.71 | 6.71 |
| ambi-miR-7038-1 | 2.61 | 2.97 | 1.86 | 1.58 | 1.79 | 1.88 | 1.52 | 1.61 | 1.60 | 1.93 |
| ambi-miR-7039 | 4.82 | 4.60 | 4.95 | 4.18 | 3.96 | 5.30 | 5.26 | 4.83 | 4.08 | 4.67 |
| hsa-miR-488 | 2.61 | 1.04 | 1.75 | 1.81 | 1.73 | 1.88 | 1.79 | 1.81 | 1.74 | 1.79 |
| hsa-miR-510 | 2.18 | 1.25 | 2.55 | 1.96 | 1.91 | 1.88 | 1.91 | 2.19 | 2.03 | 1.98 |
| hsa-miR-517-AS | 2.05 | 3.10 | 2.62 | 1.58 | 1.91 | 1.88 | 1.99 | 1.90 | 1.78 | 2.09 |

TABLE 7-continued

Normalized Array Data for miRNA Expression in Nine Cervical Tumor Tissue Samples (Ca1-Ca9) and Nine Cervical Normal Adjacent Tissue Samples (NAT1-NAT-9). TV, threshold value. miRNAs > TV, miRNAs greater than threshold value. %, Percentage of miRNAs greater than threshold value.

| | | | | | | | | | | |
|---|---|---|---|---|---|---|---|---|---|---|
| hsa-miR-518f-AS | 1.57 | 2.29 | 1.50 | 1.64 | 1.53 | 1.69 | 1.59 | 1.61 | 1.65 | 1.67 |
| hsa-miR-518c-AS | 4.70 | 3.90 | 3.61 | 2.70 | 3.62 | 3.91 | 3.22 | 3.56 | 3.96 | 3.69 |
| hsa-miR-526c | 2.61 | 0.65 | 1.75 | 1.75 | 1.79 | 2.10 | 1.93 | 1.90 | 2.06 | 1.84 |
| hsa-miR-526b | 4.17 | 3.64 | 2.90 | 2.10 | 2.40 | 2.96 | 2.51 | 2.60 | 2.76 | 2.89 |
| hsa-miR-520a-AS | 2.30 | 2.16 | 1.50 | 1.39 | 1.53 | 1.41 | 1.59 | 1.50 | 1.74 | 1.68 |
| hsa-miR-525 | 3.21 | 3.22 | 2.33 | 2.01 | 2.08 | 2.10 | 1.77 | 2.07 | 2.45 | 2.36 |
| hsa-miR-524-AS | 3.26 | 2.97 | 2.33 | 2.93 | 2.66 | 2.71 | 2.70 | 2.37 | 3.40 | 2.81 |
| hsa-miR-520d-AS | 2.05 | 1.25 | 1.86 | 1.86 | 1.85 | 1.34 | 1.79 | 1.99 | 2.27 | 1.81 |
| hsa-miR-527 | 3.05 | 2.73 | 2.33 | 1.96 | 2.13 | 2.88 | 1.97 | 2.30 | 2.47 | 2.42 |
| hsa-miR-515-5p | 1.20 | 2.53 | 1.75 | 1.86 | 2.02 | 1.93 | 2.12 | 1.95 | 2.17 | 1.95 |
| hsa-miR-519e-AS | 2.51 | 2.89 | 1.75 | 1.58 | 2.08 | 2.25 | 2.08 | 2.26 | 2.24 | 2.18 |
| ambi-miR-7054 | 1.39 | 2.42 | 1.24 | 1.75 | 1.97 | 1.69 | 1.56 | 1.39 | 1.16 | 1.62 |
| ambi-miR-7055 | 2.51 | 3.10 | 2.55 | 2.06 | 2.23 | 2.54 | 2.27 | 1.95 | 2.53 | 2.41 |
| hsa-miR-498 | 3.26 | 3.04 | 2.84 | 3.45 | 3.26 | 2.91 | 3.15 | 3.02 | 3.08 | 3.11 |
| hsa-miR-513 | 5.04 | 4.04 | 3.98 | 3.78 | 4.63 | 4.80 | 4.19 | 4.59 | 5.11 | 4.46 |
| ambi-miR-7058 | 6.48 | 6.18 | 6.56 | 6.55 | 6.01 | 6.94 | 6.04 | 5.90 | 6.47 | 6.35 |
| ambi-miR-7059-1 | 1.74 | 0.84 | 1.63 | 1.69 | 1.73 | 1.41 | 1.79 | 1.76 | 1.83 | 1.60 |
| hsa-miR-452 | 4.56 | 4.56 | 5.23 | 5.34 | 5.20 | 3.88 | 3.72 | 5.27 | 5.46 | 4.80 |
| hsa-miR-493 | 2.41 | 1.84 | 1.97 | 2.01 | 2.84 | 1.20 | 2.88 | 2.55 | 2.27 | 2.22 |
| ambi-miR-7062 | 2.69 | 2.89 | 2.41 | 2.68 | 2.55 | 2.38 | 2.50 | 2.23 | 2.42 | 2.53 |
| hsa-miR-432 | 5.18 | 5.51 | 5.07 | 4.82 | 4.97 | 3.48 | 4.73 | 4.79 | 4.73 | 4.81 |
| hsa-miR-495 | 4.15 | 4.28 | 4.29 | 4.97 | 4.89 | 3.57 | 4.45 | 4.94 | 4.88 | 4.49 |
| hsa-miR-494 | 6.44 | 6.04 | 5.89 | 5.87 | 6.27 | 5.92 | 5.74 | 6.33 | 6.72 | 6.14 |
| ambi-miR-7066 | 1.74 | 2.89 | 2.84 | 2.65 | 1.85 | 2.10 | 2.08 | 2.49 | 2.33 | 2.33 |
| ambi-miR-7067 | 2.69 | 3.22 | 2.62 | 2.93 | 2.32 | 1.88 | 2.27 | 2.68 | 2.72 | 2.59 |
| ambi-miR-7068-1 | 3.05 | 3.56 | 3.26 | 3.35 | 3.50 | 1.99 | 3.20 | 3.53 | 4.17 | 3.29 |
| hsa-miR-496 | 1.74 | 0.48 | 2.25 | 1.69 | 1.60 | 2.15 | 1.66 | 1.66 | 2.14 | 1.71 |
| ambi-miR-7070 | 3.63 | 4.36 | 4.26 | 4.79 | 5.22 | 3.18 | 4.54 | 5.14 | 4.80 | 4.44 |
| hsa-miR-492 | 2.51 | 1.84 | 1.75 | 2.06 | 2.13 | 2.46 | 1.83 | 2.23 | 2.14 | 2.10 |
| hsa-miR-490 | 2.30 | 2.01 | 0.61 | 1.46 | 1.53 | 2.10 | 1.68 | 1.61 | 1.60 | 1.66 |
| hsa-miR-497 | 6.39 | 6.92 | 6.69 | 6.98 | 7.03 | 7.21 | 7.56 | 7.39 | 7.55 | 7.08 |
| ambi-miR-7074 | 2.51 | 2.42 | 1.63 | 1.75 | 1.79 | 1.82 | 1.81 | 2.03 | 1.60 | 1.93 |
| ambi-miR-7075 | 3.35 | 3.52 | 3.36 | 3.89 | 3.58 | 4.06 | 3.91 | 3.90 | 3.79 | 3.71 |
| ambi-miR-7076 | 3.76 | 4.36 | 4.82 | 4.20 | 4.52 | 4.54 | 5.75 | 4.59 | 4.61 | 4.57 |
| hsa-miR-501 | 2.51 | 2.53 | 2.62 | 2.15 | 2.23 | 1.93 | 3.59 | 1.95 | 1.55 | 2.34 |
| hsa-miR-502 | 3.76 | 3.71 | 2.55 | 3.01 | 3.23 | 3.53 | 4.26 | 2.73 | 2.47 | 3.25 |
| ambi-miR-7079 | 3.56 | 3.74 | 4.61 | 5.00 | 4.22 | 4.81 | 3.83 | 4.55 | 4.23 | 4.28 |
| ambi-miR-7080 | 2.85 | 2.63 | 2.62 | 1.91 | 2.08 | 1.99 | 1.85 | 2.03 | 2.27 | 2.25 |
| ambi-miR-7081 | 4.09 | 4.06 | 4.21 | 4.12 | 4.44 | 4.87 | 3.44 | 4.86 | 5.12 | 4.36 |
| hsa-miR-202-AS | 1.39 | 1.25 | 1.75 | 1.69 | 1.73 | 1.62 | 1.59 | 1.45 | 1.31 | 1.53 |
| ambi-miR-7083 | 6.13 | 6.98 | 7.32 | 7.70 | 7.49 | 5.39 | 7.35 | 7.22 | 5.98 | 6.84 |
| ambi-miR-7084 | 1.39 | 1.25 | 2.25 | 2.15 | 1.67 | 4.74 | 2.05 | 1.71 | 1.83 | 2.11 |
| ambi-miR-7085 | 3.66 | 3.78 | 4.46 | 4.25 | 4.68 | 4.47 | 4.42 | 4.53 | 4.49 | 4.30 |
| ambi-miR-7086 | 2.41 | 2.29 | 2.79 | 3.01 | 2.36 | 3.05 | 3.34 | 2.55 | 2.17 | 2.67 |
| hsa-miR-512-5p | 2.51 | 1.45 | 1.86 | 1.58 | 1.85 | 1.55 | 1.63 | 1.39 | 1.74 | 1.73 |
| hsa-miR-504 | 2.51 | 1.84 | 1.63 | 2.49 | 2.08 | 2.34 | 2.14 | 2.40 | 2.47 | 2.21 |
| ambi-miR-7089 | 2.30 | 2.01 | 1.63 | 1.91 | 1.97 | 2.20 | 1.97 | 2.23 | 2.14 | 2.04 |
| hsa-miR-511 | 1.90 | 1.45 | 1.97 | 1.91 | 1.85 | 2.10 | 1.75 | 1.86 | 1.95 | 1.86 |
| hsa-miR-452-AS | 3.16 | 3.04 | 3.23 | 3.56 | 3.51 | 1.88 | 2.17 | 3.76 | 3.48 | 3.09 |
| hsa-miR-503 | 5.08 | 6.08 | 6.41 | 5.88 | 5.92 | 5.20 | 6.03 | 6.02 | 5.92 | 5.84 |
| hsa-miR-485-5p | 3.52 | 2.97 | 3.07 | 2.97 | 3.06 | 3.03 | 3.06 | 3.51 | 3.73 | 3.21 |
| hsa-miR-499 | 2.77 | 0.33 | 1.63 | 1.69 | 1.85 | 1.99 | 1.99 | 1.61 | 1.65 | 1.72 |
| ambi-miR-7095 | 1.74 | 2.16 | 1.37 | 1.64 | 1.53 | 1.41 | 1.63 | 1.39 | 1.36 | 1.58 |
| hsa-miR-505 | 4.25 | 4.50 | 4.49 | 5.06 | 4.96 | 4.67 | 5.23 | 4.93 | 4.58 | 4.74 |
| ambi-miR-7097 | 1.90 | 2.16 | 1.75 | 2.46 | 2.44 | 2.64 | 2.87 | 2.07 | 2.76 | 2.34 |
| ambi-miR-7098 | 1.74 | 0.84 | 1.75 | 2.01 | 1.73 | 2.29 | 2.03 | 2.03 | 2.06 | 1.83 |
| hsa-miR-489 | 2.92 | 2.01 | 2.25 | 2.97 | 2.13 | 2.42 | 2.14 | 2.30 | 2.42 | 2.39 |
| ambi-miR-7100 | 2.18 | 2.81 | 2.79 | 3.30 | 3.06 | 2.25 | 1.99 | 3.39 | 3.49 | 2.81 |
| ambi-miR-7101 | 2.92 | 3.38 | 3.19 | 3.79 | 3.88 | 3.85 | 3.35 | 4.66 | 4.75 | 3.75 |
| hsa-miR-432-AS | 1.20 | 1.04 | 2.07 | 2.06 | 1.60 | 1.62 | 1.66 | 1.61 | 1.83 | 1.63 |
| ambi-miR-7103 | 4.38 | 3.60 | 2.84 | 2.01 | 1.67 | 1.99 | 2.03 | 2.15 | 1.95 | 2.51 |
| hsa-miR-500 | 4.32 | 4.18 | 4.40 | 4.44 | 4.45 | 4.93 | 6.00 | 4.45 | 4.38 | 4.62 |
| ambi-miR-7105 | 4.09 | 4.01 | 4.52 | 5.15 | 4.92 | 4.88 | 5.07 | 4.94 | 4.98 | 4.73 |

TABLE 8 miRNAs Differentially Expressed Among Normal Cervix (NCX), Normal Adjacent Cervical Tissue (NAT), and Cervical Cancer (Ca) Samples

| miRNA | Mean NCX | Mean NAT | Mean Ca | p-value ANOVA | ΔH NCX − Ca | Fold Change NCX vs Ca | p-value NCX vs Ca | Flag* NCX vs Ca |
|---|---|---|---|---|---|---|---|---|
| hsa-let-7a | 10.90 | 10.62 | 10.17 | 9.62E−06 | 0.73 | 2.08 | 8.59E−06 | 1 |
| hsa-let-7b | 11.00 | 10.66 | 10.16 | 1.96E−05 | 0.84 | 2.32 | 2.34E−05 | 1 |
| hsa-let-7c | 10.96 | 10.65 | 9.83 | 2.28E−08 | 1.13 | 3.10 | 9.89E−08 | 1 |
| hsa-let-7d | 9.78 | 9.48 | 8.85 | 1.98E−06 | 0.93 | 2.54 | 2.43E−06 | 1 |
| hsa-let-7e | 8.26 | 8.13 | 7.19 | 7.88E−10 | 1.07 | 2.93 | 2.6E−10 | 1 |
| hsa-let-7f | 8.64 | 8.44 | 7.70 | 7.56E−05 | 0.94 | 2.56 | 0.000101 | 1 |
| hsa-let-7g | 8.71 | 8.23 | 7.51 | 2.67E−07 | 1.20 | 3.31 | 5.53E−07 | 1 |
| hsa-let-7i | 8.68 | 8.42 | 8.16 | 2.82E−05 | 0.52 | 1.69 | 1.63E−05 | 1 |
| hsa-miR-1 | 5.45 | 5.11 | 2.27 | 5.36E−13 | 3.18 | 24.02 | 6.62E−11 | 1 |
| hsa-miR-100 | 9.26 | 8.86 | 7.10 | 8.34E−12 | 2.16 | 8.68 | 9.04E−11 | 1 |
| hsa-miR-101 | 4.47 | 4.00 | 2.94 | 3.89E−07 | 1.53 | 4.60 | 2.24E−07 | 1 |
| hsa-miR-106a | 7.48 | 7.62 | 8.26 | 2.23E−07 | −0.79 | 2.20 | 4.46E−07 | 1 |
| hsa-miR-106b | 6.37 | 6.20 | 7.06 | 3.49E−08 | −0.69 | 2.00 | 2.11E−07 | 1 |
| hsa-miR-10a | 7.07 | 6.53 | 6.20 | 0.014656 | 0.86 | 2.37 | 0.003802 | 1 |
| hsa-miR-10b | 7.87 | 7.91 | 6.47 | 4.21E−07 | 1.40 | 4.06 | 2.12E−08 | 1 |
| hsa-miR-124a | 3.31 | 2.25 | 2.05 | 0.0003 | 1.26 | 3.51 | 0.001072 | 1 |
| hsa-miR-125a | 8.95 | 8.98 | 7.77 | 2.96E−07 | 1.18 | 3.25 | 1.75E−06 | 1 |
| hsa-miR-125b | 10.34 | 10.18 | 8.80 | 1.1E−08 | 1.53 | 4.62 | 1.13E−07 | 1 |
| hsa-miR-126 | 9.43 | 9.67 | 8.50 | 1.01E−09 | 0.93 | 2.53 | 4.41E−08 | 1 |
| hsa-miR-126-AS | 5.34 | 5.27 | 3.84 | 1.6E−05 | 1.50 | 4.47 | 5.97E−06 | 1 |
| hsa-miR-127 | 4.34 | 4.27 | 3.18 | 0.000239 | 1.17 | 3.21 | 9.87E−05 | 1 |
| hsa-miR-130a | 7.75 | 6.95 | 6.31 | 1.47E−09 | 1.45 | 4.24 | 1.19E−08 | 1 |
| hsa-miR-130b | 4.71 | 4.67 | 5.51 | 9.52E−06 | −0.80 | 2.22 | 1.47E−05 | 1 |
| hsa-miR-133a | 7.18 | 6.93 | 4.35 | 1.06E−11 | 2.82 | 16.83 | 1.55E−10 | 1 |
| hsa-miR-134 | 4.92 | 4.38 | 3.27 | 8.32E−11 | 1.64 | 5.17 | 3.91E−11 | 1 |
| hsa-miR-135b | 1.84 | 1.59 | 2.31 | 0.010775 | −0.47 | 1.60 | 0.04138 | 1 |
| hsa-miR-139 | 4.80 | 4.67 | 3.41 | 9.87E−05 | 1.39 | 4.03 | 0.000172 | 1 |
| hsa-miR-140 | 5.05 | 4.94 | 4.00 | 1.51E−05 | 1.05 | 2.86 | 1.43E−06 | 1 |
| hsa-miR-141 | 5.26 | 4.93 | 6.65 | 0.001274 | −1.39 | 4.02 | 0.003113 | 1 |
| hsa-miR-143 | 10.36 | 10.38 | 8.58 | 3.07E−10 | 1.78 | 5.94 | 2.09E−08 | 1 |
| hsa-miR-145 | 11.03 | 11.06 | 9.57 | 5.05E−07 | 1.46 | 4.31 | 1.45E−06 | 1 |
| hsa-miR-146a | 5.83 | 5.87 | 6.61 | 0.00014 | −0.78 | 2.18 | 0.0001 | 1 |
| hsa-miR-149 | 3.99 | 4.44 | 3.85 | 0.011345 | 0.14 | 1.15 | 0.43343 | 0 |
| hsa-miR-150 | 6.02 | 6.68 | 6.94 | 0.002355 | −0.92 | 2.50 | 0.002482 | 1 |
| hsa-miR-152 | 7.02 | 7.02 | 6.24 | 6.51E−06 | 0.78 | 2.18 | 7.42E−06 | 1 |
| hsa-miR-153 | 2.47 | 2.10 | 2.11 | 0.001355 | 0.36 | 1.43 | 0.002775 | 1 |
| hsa-miR-154 | 4.91 | 4.45 | 3.19 | 7.78E−08 | 1.72 | 5.57 | 2.22E−08 | 1 |
| hsa-miR-155 | 5.41 | 5.55 | 6.98 | 3.45E−09 | −1.57 | 4.80 | 5.3E−09 | 1 |
| hsa-miR-15b | 6.84 | 7.33 | 8.17 | 1.18E−10 | −1.33 | 3.78 | 2.77E−10 | 1 |
| hsa-miR-16 | 9.68 | 9.80 | 10.12 | 3.65E−05 | −0.44 | 1.55 | 1.17E−05 | 1 |
| hsa-miR-17-5p | 7.38 | 7.40 | 8.09 | 6.01E−07 | −0.71 | 2.03 | 1.46E−06 | 1 |
| hsa-miR-18a | 4.14 | 4.05 | 5.46 | 1.34E−06 | −1.32 | 3.76 | 7.94E−07 | 1 |
| hsa-miR-181a | 6.74 | 7.03 | 7.22 | 0.000501 | −0.48 | 1.62 | 0.000357 | 1 |
| hsa-miR-181b | 5.96 | 5.78 | 6.39 | 0.000244 | −0.43 | 1.54 | 0.001442 | 1 |
| hsa-miR-182 | 4.49 | 4.65 | 6.32 | 1.93E−06 | −1.83 | 6.23 | 7.24E−07 | 1 |
| hsa-miR-183 | 2.50 | 3.18 | 4.74 | 3.9E−09 | −2.23 | 9.33 | 3.79E−08 | 1 |
| hsa-miR-185 | 5.46 | 5.68 | 6.13 | 5.8E−05 | −0.67 | 1.96 | 3.58E−05 | 1 |
| hsa-miR-186 | 4.23 | 4.13 | 3.39 | 0.000738 | 0.84 | 2.31 | 0.000532 | 1 |
| hsa-miR-187 | 5.26 | 2.70 | 3.71 | 4.56E−08 | 1.55 | 4.71 | 7.52E−05 | 1 |
| hsa-miR-189 | 4.39 | 4.26 | 3.52 | 5.45E−05 | 0.87 | 2.40 | 2.18E−06 | 1 |
| hsa-miR-190 | 1.68 | 1.45 | 1.16 | 0.010554 | 0.52 | 1.68 | 0.002674 | 1 |
| hsa-miR-192 | 4.44 | 3.88 | 4.14 | 0.009286 | 0.31 | 1.36 | 0.079731 | 0 |
| hsa-miR-195 | 9.22 | 8.80 | 7.17 | 2.02E−12 | 2.05 | 7.78 | 2.68E−11 | 1 |
| hsa-miR-196b | 6.59 | 5.66 | 5.08 | 0.000192 | 1.50 | 4.49 | 1.84E−10 | 1 |
| hsa-miR-199a | 8.64 | 8.32 | 7.82 | 0.000102 | 0.82 | 2.28 | 9.89E−05 | 1 |
| hsa-miR-199a-AS | 8.86 | 8.66 | 7.96 | 9.7E−06 | 0.90 | 2.45 | 6.36E−06 | 1 |
| hsa-miR-199b | 6.77 | 6.43 | 5.40 | 9.98E−05 | 1.37 | 3.92 | 1.74E−05 | 1 |
| hsa-miR-20a | 6.38 | 6.42 | 6.83 | 0.006239 | −0.45 | 1.57 | 0.0021 | 1 |
| hsa-miR-200a | 5.97 | 5.14 | 6.61 | 0.004995 | −0.64 | 1.89 | 0.089772 | 0 |
| hsa-miR-200b | 6.92 | 6.91 | 8.09 | 0.003739 | −1.17 | 3.23 | 0.0013 | 1 |
| hsa-miR-200c | 7.79 | 8.11 | 9.35 | 0.000193 | −1.56 | 4.76 | 6.48E−05 | 1 |
| hsa-miR-203 | 6.86 | 8.38 | 8.60 | 0.008118 | −1.74 | 5.69 | 0.002106 | 1 |
| hsa-miR-204 | 4.99 | 4.49 | 2.38 | 6.34E−11 | 2.61 | 13.56 | 1.66E−09 | 1 |
| hsa-miR-205 | 7.72 | 8.93 | 10.98 | 3.09E−05 | −3.26 | 25.94 | 1.01E−07 | 1 |
| hsa-miR-21 | 9.11 | 9.65 | 10.88 | 1.53E−11 | −1.77 | 5.88 | 4.43E−11 | 1 |
| hsa-miR-210 | 5.53 | 5.85 | 6.39 | 0.014084 | −0.86 | 2.36 | 0.003763 | 1 |
| hsa-miR-214 | 8.24 | 8.01 | 7.34 | 5.35E−06 | 0.90 | 2.46 | 7.58E−06 | 1 |
| hsa-miR-215 | 2.00 | 2.86 | 2.49 | 1.77E−05 | −0.48 | 1.62 | 0.00393 | 1 |
| hsa-miR-218 | 5.63 | 5.58 | 3.59 | 1.77E−12 | 2.04 | 7.69 | 3.17E−11 | 1 |
| hsa-miR-223 | 6.18 | 6.64 | 7.43 | 0.000137 | −1.25 | 3.48 | 4.46E−05 | 1 |
| hsa-miR-224 | 5.61 | 6.21 | 7.44 | 5.01E−08 | −1.83 | 6.23 | 8.13E−09 | 1 |

TABLE 8-continued miRNAs Differentially Expressed Among Normal Cervix (NCX), Normal Adjacent Cervical Tissue (NAT), and Cervical Cancer (Ca) Samples

| | | | | | | | | |
|---|---|---|---|---|---|---|---|---|
| hsa-miR-23b | 9.91 | 10.04 | 9.58 | 0.001341 | 0.33 | 1.39 | 0.003883 | 1 |
| hsa-miR-24 | 9.80 | 9.81 | 9.48 | 0.00332 | 0.31 | 1.37 | 0.00341 | 1 |
| hsa-miR-25 | 6.57 | 6.66 | 7.14 | 8E−06 | −0.58 | 1.78 | 8.04E−07 | 1 |
| hsa-miR-26a | 10.84 | 10.67 | 9.91 | 2.64E−08 | 0.92 | 2.52 | 1.04E−08 | 1 |
| hsa-miR-26b | 7.64 | 7.31 | 6.13 | 1.55E−08 | 1.51 | 4.52 | 7.59E−08 | 1 |
| hsa-miR-27b | 9.21 | 9.25 | 8.41 | 9.19E−07 | 0.80 | 2.23 | 2.57E−06 | 1 |
| hsa-miR-28 | 6.02 | 6.01 | 5.22 | 3.73E−08 | 0.80 | 2.22 | 9.8E−08 | 1 |
| hsa-miR-296 | 2.66 | 3.27 | 3.19 | 0.010234 | −0.53 | 1.70 | 0.028655 | 1 |
| hsa-miR-299-5p | 4.76 | 4.39 | 2.99 | 1.64E−09 | 1.77 | 5.87 | 2.08E−09 | 1 |
| hsa-miR-29a | 9.42 | 9.01 | 8.30 | 6.59E−08 | 1.12 | 3.08 | 2.39E−08 | 1 |
| hsa-miR-29b | 6.89 | 6.10 | 5.72 | 0.000374 | 1.16 | 3.20 | 0.000258 | 1 |
| hsa-miR-29c | 6.80 | 6.02 | 5.24 | 3.71E−05 | 1.55 | 4.72 | 3.51E−05 | 1 |
| hsa-miR-302d | 2.07 | 1.60 | 1.65 | 0.020075 | 0.42 | 1.52 | 0.034949 | 1 |
| hsa-miR-30a-3p | 4.10 | 4.13 | 2.84 | 7.16E−08 | 1.26 | 3.52 | 1.77E−08 | 1 |
| hsa-miR-30a-5p | 8.11 | 8.00 | 7.45 | 3.12E−05 | 0.66 | 1.93 | 7.15E−06 | 1 |
| hsa-miR-30b | 7.26 | 7.22 | 6.56 | 0.003418 | 0.70 | 2.02 | 0.002078 | 1 |
| hsa-miR-30d | 8.17 | 8.03 | 7.53 | 8.99E−05 | 0.64 | 1.89 | 2.07E−05 | 1 |
| hsa-miR-31 | 6.98 | 7.45 | 8.85 | 2.3E−05 | −1.88 | 6.52 | 5.22E−07 | 1 |
| hsa-miR-320 | 8.37 | 8.28 | 7.72 | 7.6E−05 | 0.65 | 1.92 | 2.42E−05 | 1 |
| hsa-miR-324-3p | 5.71 | 5.98 | 5.55 | 0.001082 | 0.17 | 1.18 | 0.108804 | 0 |
| hsa-miR-328 | 3.79 | 3.95 | 3.09 | 0.000914 | 0.70 | 2.01 | 0.001159 | 1 |
| hsa-miR-330 | 2.77 | 2.81 | 3.47 | 0.002538 | −0.70 | 2.01 | 0.002491 | 1 |
| hsa-miR-335 | 4.70 | 4.08 | 3.37 | 2.17E−06 | 1.33 | 3.80 | 1.39E−07 | 1 |
| hsa-miR-339 | 5.05 | 5.32 | 5.48 | 0.003199 | −0.43 | 1.54 | 0.002785 | 1 |
| hsa-miR-34a | 7.48 | 6.86 | 7.20 | 0.004662 | 0.28 | 1.32 | 0.130504 | 0 |
| hsa-miR-361 | 6.99 | 6.80 | 6.46 | 0.001312 | 0.53 | 1.71 | 0.000413 | 1 |
| hsa-miR-365 | 3.41 | 3.87 | 3.29 | 0.009438 | 0.11 | 1.12 | 0.47858 | 0 |
| hsa-miR-368 | 6.97 | 6.28 | 4.51 | 8.88E−11 | 2.47 | 11.77 | 8.13E−11 | 1 |
| hsa-miR-370 | 4.69 | 5.28 | 5.16 | 0.001678 | −0.47 | 1.60 | 0.004143 | 1 |
| hsa-miR-371 | 1.75 | 1.23 | 1.51 | 0.010158 | 0.24 | 1.27 | 0.13033 | 0 |
| hsa-miR-373-AS | 3.41 | 4.23 | 4.09 | 9.34E−06 | −0.69 | 1.99 | 0.000251 | 1 |
| hsa-miR-376a | 5.17 | 4.71 | 3.09 | 5.15E−08 | 2.08 | 8.02 | 3.55E−08 | 1 |
| hsa-miR-377 | 3.49 | 3.10 | 2.24 | 2.03E−05 | 1.25 | 3.50 | 1.55E−07 | 1 |
| hsa-miR-379 | 5.46 | 5.16 | 4.75 | 4.95E−05 | 0.71 | 2.02 | 1.08E−05 | 1 |
| hsa-miR-381 | 4.38 | 4.24 | 3.20 | 1.71E−07 | 1.18 | 3.26 | 2.2E−08 | 1 |
| hsa-miR-382 | 4.36 | 4.40 | 3.50 | 9.8E−05 | 0.87 | 2.38 | 2E−05 | 1 |
| hsa-miR-423 | 6.19 | 6.32 | 6.60 | 0.002864 | −0.41 | 1.51 | 0.000542 | 1 |
| hsa-miR-424 | 5.71 | 5.02 | 3.77 | 6.19E−07 | 1.94 | 6.99 | 7.46E−07 | 1 |
| hsa-miR-429 | 4.49 | 4.05 | 5.45 | 0.00259 | −0.96 | 2.60 | 0.006491 | 1 |
| hsa-miR-450 | 2.65 | 2.33 | 1.86 | 0.00018 | 0.79 | 2.20 | 0.000259 | 1 |
| hsa-miR-92 | 7.13 | 7.28 | 7.60 | 0.001184 | −0.48 | 1.61 | 0.00055 | 1 |
| hsa-miR-93 | 6.83 | 7.17 | 8.00 | 3.58E−11 | −1.18 | 3.24 | 5.61E−10 | 1 |
| hsa-miR-95 | 3.32 | 3.98 | 3.85 | 5.6E−05 | −0.53 | 1.69 | 0.000188 | 1 |
| hsa-miR-98 | 5.66 | 5.67 | 5.07 | 0.000297 | 0.59 | 1.80 | 0.000841 | 1 |
| hsa-miR-99a | 10.12 | 9.54 | 7.77 | 4.93E−12 | 2.35 | 10.50 | 1.71E−10 | 1 |
| hsa-miR-99b | 7.37 | 7.22 | 6.30 | 3.06E−09 | 1.07 | 2.93 | 3.19E−09 | 1 |
| hsa-miR-520d | 1.94 | 2.02 | 2.44 | 0.020504 | −0.50 | 1.64 | 0.004272 | 1 |
| hsa-miR-518b | 1.66 | 1.86 | 2.29 | 0.00531 | −0.62 | 1.86 | 0.00214 | 1 |
| ambi-miR-7029 | 6.99 | 7.21 | 5.35 | 8.66E−05 | 1.64 | 5.14 | 9.18E−05 | 1 |
| hsa-miR-491 | 3.91 | 3.97 | 4.34 | 0.01061 | −0.43 | 1.54 | 0.007043 | 1 |
| hsa-miR-515-5p | 1.55 | 1.95 | 2.13 | 0.00377 | −0.59 | 1.80 | 0.002857 | 1 |
| hsa-miR-498 | 2.21 | 3.11 | 2.77 | 1.72E−06 | −0.56 | 1.75 | 0.002128 | 1 |
| ambi-miR-7062 | 2.46 | 2.53 | 3.19 | 6.18E−05 | −0.73 | 2.08 | 0.000163 | 1 |
| hsa-miR-432 | 4.88 | 4.81 | 4.30 | 0.005479 | 0.58 | 1.78 | 0.000437 | 1 |
| hsa-miR-495 | 4.65 | 4.49 | 3.28 | 1.05E−08 | 1.37 | 3.93 | 9.65E−09 | 1 |
| ambi-miR-7066 | 2.55 | 2.33 | 1.81 | 0.000726 | 0.75 | 2.11 | 0.000283 | 1 |
| ambi-miR-7068-1 | 3.03 | 3.29 | 2.47 | 0.000142 | 0.56 | 1.75 | 2.03E−05 | 1 |
| ambi-miR-7070 | 4.44 | 4.44 | 2.94 | 2.73E−07 | 1.50 | 4.47 | 1.38E−07 | 1 |
| hsa-miR-492 | 1.87 | 2.10 | 2.68 | 0.001236 | −0.81 | 2.24 | 0.001266 | 1 |
| hsa-miR-497 | 7.69 | 7.08 | 5.84 | 3.75E−10 | 1.85 | 6.34 | 2.85E−09 | 1 |
| ambi-miR-7074 | 1.91 | 1.93 | 2.36 | 0.00895 | −0.45 | 1.56 | 0.004949 | 1 |
| ambi-miR-7075 | 3.92 | 3.71 | 3.33 | 0.000198 | 0.59 | 1.81 | 0.000132 | 1 |
| hsa-miR-501 | 2.19 | 2.34 | 2.80 | 0.013752 | −0.61 | 1.84 | 0.002164 | 1 |
| ambi-miR-7079 | 4.12 | 4.28 | 5.42 | 0.000812 | −1.29 | 3.64 | 0.000998 | 1 |
| ambi-miR-7083 | 7.53 | 6.84 | 6.56 | 0.00091 | 0.97 | 2.62 | 9.45E−05 | 1 |
| ambi-miR-7085 | 4.35 | 4.30 | 3.38 | 4.31E−06 | 0.97 | 2.65 | 1.04E−05 | 1 |
| hsa-miR-505 | 4.67 | 4.74 | 3.93 | 4.47E−05 | 0.74 | 2.09 | 0.000142 | 1 |
| ambi-miR-7100 | 3.24 | 2.81 | 2.25 | 5.49E−05 | 0.99 | 2.69 | 7.78E−06 | 1 |
| ambi-miR-7101 | 4.10 | 3.75 | 2.34 | 8.71E−08 | 1.76 | 5.81 | 6.71E−08 | 1 |

TABLE 8-continued miRNAs Differentially Expressed Among Normal Cervix (NCX), Normal Adjacent Cervical Tissue (NAT), and Cervical Cancer (Ca) Samples

| miRNA | ΔH NAT − Ca | Fold Change NAT vs CA | p-value NAT vs Ca | Flag* NAT vs Ca | ΔH NAT − NCX | Fold Change NAT vs NCX | p-value NAT vs NCX | Flag* NAT vs NCX |
|---|---|---|---|---|---|---|---|---|
| hsa-let-7a | 0.46 | 1.58 | 0.015243 | 1 | −0.28 | 1.32 | 0.011975 | 1 |
| hsa-let-7b | 0.50 | 1.66 | 0.022416 | 1 | −0.34 | 1.40 | 0.008776 | 1 |
| hsa-let-7c | 0.82 | 2.26 | 0.000541 | 1 | −0.32 | 1.37 | 0.007383 | 1 |
| hsa-let-7d | 0.63 | 1.87 | 0.004004 | 1 | −0.31 | 1.36 | 0.021385 | 0 |
| hsa-let-7e | 0.94 | 2.56 | 4.62E−05 | 1 | −0.13 | 1.14 | 0.216576 | 0 |
| hsa-let-7f | 0.74 | 2.10 | 0.003563 | 1 | −0.20 | 1.22 | 0.243771 | 0 |
| hsa-let-7g | 0.71 | 2.04 | 0.004455 | 1 | −0.48 | 1.62 | 0.002158 | 1 |
| hsa-let-7i | 0.26 | 1.30 | 0.061383 | 0 | −0.27 | 1.30 | 0.004328 | 1 |
| hsa-miR-1 | 2.85 | 17.22 | 7.99E−10 | 1 | −0.33 | 1.39 | 0.242419 | 0 |
| hsa-miR-100 | 1.76 | 5.80 | 1.21E−05 | 1 | −0.40 | 1.50 | 0.008496 | 1 |
| hsa-miR-101 | 1.06 | 2.89 | 0.000247 | 1 | −0.46 | 1.59 | 0.06104 | 0 |
| hsa-miR-106a | −0.64 | 1.90 | 0.000669 | 1 | 0.14 | 1.16 | 0.11028 | 0 |
| hsa-miR-106b | −0.86 | 2.36 | 5.1E−06 | 1 | −0.16 | 1.18 | 0.130659 | 0 |
| hsa-miR-10a | 0.33 | 1.39 | 0.398991 | 0 | −0.54 | 1.71 | 0.060318 | 0 |
| hsa-miR-10b | 1.44 | 4.22 | 0.000167 | 1 | 0.04 | 1.04 | 0.86805 | 0 |
| hsa-miR-124a | 0.20 | 1.22 | 0.44417 | 0 | −1.06 | 2.87 | 0.003334 | 1 |
| hsa-miR-125a | 1.21 | 3.35 | 7.62E−05 | 1 | 0.03 | 1.03 | 0.850416 | 0 |
| hsa-miR-125b | 1.38 | 3.96 | 0.000123 | 1 | −0.16 | 1.17 | 0.22021 | 0 |
| hsa-miR-126 | 1.17 | 3.22 | 7.44E−06 | 1 | 0.24 | 1.27 | 0.009991 | 1 |
| hsa-miR-126-AS | 1.42 | 4.14 | 0.00111 | 1 | −0.07 | 1.08 | 0.783743 | 0 |
| hsa-miR-127 | 1.09 | 2.98 | 0.004356 | 1 | −0.08 | 1.08 | 0.766118 | 0 |
| hsa-miR-130a | 0.65 | 1.91 | 0.001093 | 1 | −0.80 | 2.23 | 6.87E−05 | 1 |
| hsa-miR-130b | −0.84 | 2.31 | 0.001 | 1 | −0.04 | 1.04 | 0.729348 | 0 |
| hsa-miR-133a | 2.58 | 13.13 | 1.14E−06 | 1 | −0.25 | 1.28 | 0.29185 | 0 |
| hsa-miR-134 | 1.11 | 3.03 | 6.43E−05 | 1 | −0.54 | 1.71 | 0.0024 | 1 |
| hsa-miR-135b | −0.72 | 2.05 | 0.004128 | 1 | −0.25 | 1.28 | 0.199291 | 0 |
| hsa-miR-139 | 1.26 | 3.52 | 0.00143 | 1 | −0.14 | 1.15 | 0.608109 | 0 |
| hsa-miR-140 | 0.94 | 2.56 | 0.00383 | 1 | −0.11 | 1.12 | 0.526241 | 0 |
| hsa-miR-141 | −1.72 | 5.59 | 0.000753 | 1 | −0.33 | 1.39 | 0.433299 | 0 |
| hsa-miR-143 | 1.81 | 6.08 | 1.14E−05 | 1 | 0.02 | 1.02 | 0.840388 | 0 |
| hsa-miR-145 | 1.49 | 4.46 | 0.000354 | 1 | 0.03 | 1.03 | 0.849024 | 0 |
| hsa-miR-146a | −0.74 | 2.10 | 0.003667 | 1 | 0.04 | 1.04 | 0.798434 | 0 |
| hsa-miR-149 | 0.59 | 1.80 | 0.030786 | 1 | 0.45 | 1.57 | 0.001649 | 1 |
| hsa-miR-150 | −0.26 | 1.30 | 0.492727 | 0 | 0.65 | 1.92 | 0.000498 | 1 |
| hsa-miR-152 | 0.78 | 2.18 | 0.001101 | 1 | 0.00 | 1.00 | 0.989967 | 0 |
| hsa-miR-153 | −0.01 | 1.01 | 0.911482 | 0 | −0.37 | 1.45 | 0.003765 | 1 |
| hsa-miR-154 | 1.26 | 3.52 | 0.000932 | 1 | −0.46 | 1.58 | 0.036815 | 0 |
| hsa-miR-155 | −1.43 | 4.20 | 6.31E−05 | 1 | 0.13 | 1.14 | 0.386352 | 0 |
| hsa-miR-15b | −0.84 | 2.31 | 0.000359 | 1 | 0.49 | 1.63 | 9.76E−05 | 1 |
| hsa-miR-16 | −0.32 | 1.38 | 0.012464 | 1 | 0.11 | 1.12 | 0.106486 | 0 |
| hsa-miR-17-5p | −0.69 | 1.99 | 0.000675 | 1 | 0.02 | 1.02 | 0.79936 | 0 |
| hsa-miR-18a | −1.41 | 4.11 | 9.49E−05 | 1 | −0.09 | 1.09 | 0.699746 | 0 |
| hsa-miR-181a | −0.18 | 1.20 | 0.130289 | 0 | 0.30 | 1.35 | 0.018762 | 0 |
| hsa-miR-181b | −0.61 | 1.83 | 0.000709 | 1 | −0.18 | 1.19 | 0.129553 | 0 |
| hsa-miR-182 | −1.67 | 5.31 | 4.7E−05 | 1 | 0.16 | 1.17 | 0.640337 | 0 |
| hsa-miR-183 | −1.55 | 4.72 | 9.87E−08 | 1 | 0.68 | 1.98 | 0.0264 | 0 |
| hsa-miR-185 | −0.45 | 1.56 | 0.010668 | 1 | 0.23 | 1.25 | 0.07405 | 0 |
| hsa-miR-186 | 0.74 | 2.09 | 0.003986 | 1 | −0.10 | 1.10 | 0.625592 | 0 |
| hsa-miR-187 | −1.01 | 2.75 | 0.033105 | 1 | −2.56 | 12.95 | 4.22E−08 | 1 |
| hsa-miR-189 | 0.74 | 2.09 | 0.00377 | 1 | −0.14 | 1.15 | 0.464329 | 0 |
| hsa-miR-190 | 0.29 | 1.34 | 0.13868 | 0 | −0.22 | 1.25 | 0.175009 | 0 |
| hsa-miR-192 | −0.26 | 1.29 | 0.236471 | 0 | −0.56 | 1.76 | 0.00339 | 1 |
| hsa-miR-195 | 1.63 | 5.08 | 1.02E−05 | 1 | −0.43 | 1.53 | 0.001786 | 1 |
| hsa-miR-196b | 0.58 | 1.78 | 0.261415 | 0 | −0.92 | 2.52 | 0.018425 | 0 |
| hsa-miR-199a | 0.50 | 1.65 | 0.024973 | 1 | −0.32 | 1.38 | 0.032228 | 0 |
| hsa-miR-199a-AS | 0.70 | 2.01 | 0.002385 | 1 | −0.20 | 1.22 | 0.175687 | 0 |
| hsa-miR-199b | 1.03 | 2.79 | 0.015601 | 1 | −0.34 | 1.40 | 0.180953 | 0 |
| hsa-miR-20a | −0.41 | 1.51 | 0.032556 | 1 | 0.04 | 1.04 | 0.763735 | 0 |
| hsa-miR-200a | −1.47 | 4.36 | 0.001268 | 1 | −0.83 | 2.30 | 0.046462 | 0 |
| hsa-miR-200b | −1.18 | 3.25 | 0.006012 | 1 | 0.00 | 1.00 | 0.991458 | 0 |
| hsa-miR-200c | −1.24 | 3.44 | 0.003982 | 1 | 0.33 | 1.38 | 0.355729 | 0 |
| hsa-miR-203 | −0.22 | 1.24 | 0.743944 | 0 | 1.52 | 4.57 | 0.033847 | 0 |
| hsa-miR-204 | 2.11 | 8.24 | 5.19E−08 | 1 | −0.50 | 1.65 | 0.075662 | 0 |
| hsa-miR-205 | −2.04 | 7.72 | 0.015248 | 1 | 1.21 | 3.36 | 0.092096 | 0 |
| hsa-miR-21 | −1.22 | 3.40 | 6.23E−06 | 1 | 0.55 | 1.73 | 0.002685 | 1 |
| hsa-miR-210 | −0.53 | 1.70 | 0.144968 | 0 | 0.33 | 1.39 | 0.216869 | 0 |
| hsa-miR-214 | 0.67 | 1.96 | 0.003073 | 1 | −0.23 | 1.26 | 0.075271 | 0 |
| hsa-miR-215 | 0.37 | 1.45 | 0.037795 | 0 | 0.85 | 2.35 | 3.25E−05 | 1 |
| hsa-miR-218 | 1.99 | 7.28 | 1.83E−07 | 1 | −0.05 | 1.06 | 0.749189 | 0 |
| hsa-miR-223 | −0.79 | 2.20 | 0.039494 | 0 | 0.46 | 1.58 | 0.042502 | 0 |
| hsa-miR-224 | −1.23 | 3.42 | 0.001657 | 1 | 0.60 | 1.82 | 0.0117 | 1 |

TABLE 8-continued miRNAs Differentially Expressed Among Normal Cervix (NCX), Normal Adjacent
Cervical Tissue (NAT), and Cervical Cancer (Ca) Samples

| miRNA | | | | | | | | |
|---|---|---|---|---|---|---|---|---|
| hsa-miR-23b | 0.46 | 1.59 | 0.002108 | 1 | 0.13 | 1.14 | 0.219651 | 0 |
| hsa-miR-24 | 0.33 | 1.39 | 0.023963 | 1 | 0.01 | 1.01 | 0.858987 | 0 |
| hsa-miR-25 | −0.48 | 1.62 | 0.002677 | 1 | 0.10 | 1.10 | 0.319939 | 0 |
| hsa-miR-26a | 0.76 | 2.13 | 0.000163 | 1 | −0.17 | 1.18 | 0.148275 | 0 |
| hsa-miR-26b | 1.18 | 3.24 | 6.76E−06 | 1 | −0.33 | 1.39 | 0.096304 | 0 |
| hsa-miR-27b | 0.85 | 2.33 | 0.000295 | 1 | 0.05 | 1.05 | 0.654817 | 0 |
| hsa-miR-28 | 0.79 | 2.20 | 6.33E−06 | 1 | −0.01 | 1.01 | 0.929022 | 0 |
| hsa-miR-296 | 0.08 | 1.09 | 0.78112 | 0 | 0.61 | 1.85 | 0.00053 | 1 |
| hsa-miR-299-5p | 1.40 | 4.07 | 0.000139 | 1 | −0.37 | 1.44 | 0.032411 | 0 |
| hsa-miR-29a | 0.71 | 2.03 | 0.001787 | 1 | −0.42 | 1.51 | 0.007002 | 1 |
| hsa-miR-29b | 0.37 | 1.45 | 0.284654 | 0 | −0.79 | 2.21 | 0.004827 | 1 |
| hsa-miR-29c | 0.78 | 2.18 | 0.046282 | 0 | −0.77 | 2.17 | 0.006631 | 1 |
| hsa-miR-302d | −0.05 | 1.05 | 0.775881 | 0 | −0.47 | 1.60 | 0.025228 | 0 |
| hsa-miR-30a-3p | 1.29 | 3.62 | 6.36E−05 | 1 | 0.03 | 1.03 | 0.876348 | 0 |
| hsa-miR-30a-5p | 0.54 | 1.72 | 0.001615 | 1 | −0.11 | 1.12 | 0.388696 | 0 |
| hsa-miR-30b | 0.67 | 1.95 | 0.003136 | 1 | −0.03 | 1.03 | 0.879898 | 0 |
| hsa-miR-30d | 0.50 | 1.64 | 0.012288 | 1 | −0.14 | 1.15 | 0.222424 | 0 |
| hsa-miR-31 | −1.40 | 4.06 | 0.006742 | 1 | 0.47 | 1.61 | 0.197151 | 0 |
| hsa-miR-320 | 0.56 | 1.76 | 0.009972 | 1 | −0.09 | 1.10 | 0.394436 | 0 |
| hsa-miR-324-3p | 0.43 | 1.54 | 0.000209 | 1 | 0.26 | 1.30 | 0.009605 | 1 |
| hsa-miR-328 | 0.86 | 2.36 | 0.00282 | 1 | 0.16 | 1.17 | 0.415978 | 0 |
| hsa-miR-330 | −0.66 | 1.94 | 0.031868 | 1 | 0.04 | 1.04 | 0.771205 | 0 |
| hsa-miR-335 | 0.71 | 2.03 | 0.017404 | 1 | −0.63 | 1.87 | 0.009017 | 1 |
| hsa-miR-339 | −0.17 | 1.18 | 0.21493 | 0 | 0.26 | 1.30 | 0.029979 | 0 |
| hsa-miR-34a | −0.34 | 1.41 | 0.179225 | 0 | −0.62 | 1.86 | 0.000113 | 1 |
| hsa-miR-361 | 0.35 | 1.41 | 0.076527 | 0 | −0.19 | 1.21 | 0.092505 | 0 |
| hsa-miR-365 | 0.57 | 1.77 | 0.003141 | 1 | 0.46 | 1.58 | 0.021064 | 0 |
| hsa-miR-368 | 1.78 | 5.90 | 9.85E−05 | 1 | −0.69 | 1.99 | 0.002487 | 1 |
| hsa-miR-370 | 0.12 | 1.12 | 0.590414 | 0 | 0.59 | 1.80 | 0.001394 | 1 |
| hsa-miR-371 | −0.27 | 1.31 | 0.115045 | 0 | −0.51 | 1.67 | 0.006384 | 1 |
| hsa-miR-373-AS | 0.14 | 1.15 | 0.495744 | 0 | 0.83 | 2.28 | 7.1E−06 | 1 |
| hsa-miR-376a | 1.62 | 5.05 | 0.000269 | 1 | −0.46 | 1.59 | 0.082456 | 0 |
| hsa-miR-377 | 0.86 | 2.37 | 0.008208 | 1 | −0.39 | 1.48 | 0.132348 | 0 |
| hsa-miR-379 | 0.40 | 1.50 | 0.029153 | 1 | −0.30 | 1.35 | 0.031118 | 0 |
| hsa-miR-381 | 1.04 | 2.83 | 9.54E−05 | 1 | −0.14 | 1.15 | 0.436383 | 0 |
| hsa-miR-382 | 0.90 | 2.46 | 0.000964 | 1 | 0.03 | 1.04 | 0.866807 | 0 |
| hsa-miR-423 | −0.28 | 1.32 | 0.04673 | 0 | 0.13 | 1.14 | 0.254892 | 0 |
| hsa-miR-424 | 1.25 | 3.51 | 0.000778 | 1 | −0.69 | 1.99 | 0.025304 | 0 |
| hsa-miR-429 | −1.40 | 4.04 | 0.001464 | 1 | −0.44 | 1.55 | 0.230225 | 0 |
| hsa-miR-450 | 0.47 | 1.60 | 0.01585 | 1 | −0.32 | 1.38 | 0.045827 | 0 |
| hsa-miR-92 | −0.32 | 1.38 | 0.039582 | 0 | 0.16 | 1.17 | 0.149912 | 0 |
| hsa-miR-93 | −0.83 | 2.30 | 3.24E−05 | 1 | 0.34 | 1.41 | 0.000628 | 1 |
| hsa-miR-95 | 0.13 | 1.14 | 0.525755 | 0 | 0.66 | 1.93 | 2.37E−05 | 1 |
| hsa-miR-98 | 0.60 | 1.83 | 0.003268 | 1 | 0.02 | 1.02 | 0.877474 | 0 |
| hsa-miR-99a | 1.77 | 5.88 | 2.55E−05 | 1 | −0.58 | 1.79 | 6.91E−05 | 1 |
| hsa-miR-99b | 0.92 | 2.52 | 5.67E−05 | 1 | −0.15 | 1.16 | 0.19189 | 0 |
| hsa-miR-520d | −0.41 | 1.51 | 0.081113 | 0 | 0.08 | 1.09 | 0.615708 | 0 |
| hsa-miR-518b | −0.43 | 1.53 | 0.040292 | 0 | 0.20 | 1.22 | 0.283243 | 0 |
| ambi-miR-7029 | 1.85 | 6.38 | 0.00165 | 1 | 0.22 | 1.24 | 0.520839 | 0 |
| hsa-miR-491 | −0.37 | 1.45 | 0.04579 | 0 | 0.06 | 1.06 | 0.620906 | 0 |
| hsa-miR-515-5p | −0.19 | 1.20 | 0.379519 | 0 | 0.40 | 1.49 | 0.015358 | 0 |
| hsa-miR-498 | 0.35 | 1.41 | 0.019316 | 1 | 0.90 | 2.47 | 2.16E−06 | 1 |
| ambi-miR-7062 | −0.66 | 1.93 | 0.001036 | 1 | 0.07 | 1.07 | 0.580049 | 0 |
| hsa-miR-432 | 0.51 | 1.66 | 0.041701 | 0 | −0.07 | 1.07 | 0.679418 | 0 |
| hsa-miR-495 | 1.21 | 3.34 | 1.12E−05 | 1 | −0.16 | 1.18 | 0.371675 | 0 |
| ambi-miR-7066 | 0.53 | 1.69 | 0.030487 | 1 | −0.22 | 1.25 | 0.172483 | 0 |
| ambi-miR-7068-1 | 0.82 | 2.27 | 0.001419 | 1 | 0.26 | 1.30 | 0.131392 | 0 |
| ambi-miR-7070 | 1.50 | 4.46 | 0.000157 | 1 | 0.00 | 1.00 | 0.99131 | 0 |
| hsa-miR-492 | −0.58 | 1.78 | 0.011987 | 1 | 0.23 | 1.26 | 0.226341 | 0 |
| hsa-miR-497 | 1.24 | 3.46 | 0.00027 | 1 | −0.61 | 1.83 | 0.000215 | 1 |
| ambi-miR-7074 | −0.43 | 1.53 | 0.008942 | 1 | 0.02 | 1.02 | 0.905055 | 0 |
| ambi-miR-7075 | 0.38 | 1.46 | 0.036183 | 1 | −0.22 | 1.24 | 0.043131 | 0 |
| hsa-miR-501 | −0.46 | 1.59 | 0.087541 | 0 | 0.15 | 1.16 | 0.449912 | 0 |
| ambi-miR-7079 | −1.13 | 3.10 | 0.005324 | 1 | 0.16 | 1.17 | 0.580437 | 0 |
| ambi-miR-7083 | 0.28 | 1.32 | 0.37084 | 0 | −0.69 | 1.99 | 0.016519 | 0 |
| ambi-miR-7085 | 0.93 | 2.52 | 0.000151 | 1 | −0.05 | 1.05 | 0.763632 | 0 |
| hsa-miR-505 | 0.81 | 2.26 | 0.000753 | 1 | 0.08 | 1.08 | 0.577705 | 0 |
| ambi-miR-7100 | 0.56 | 1.75 | 0.031741 | 1 | −0.43 | 1.54 | 0.034031 | 0 |
| ambi-miR-7101 | 1.41 | 4.09 | 0.000245 | 1 | −0.35 | 1.42 | 0.129315 | 0 |

*Significant differential expression is indicated by a Flag = 1

The inventors identified 107 human miRNAs (96 hsa-miRNAs and 11 ambi-miRNAs) whose average expression levels were significantly different between the nine squamous cell carcinomas (Ca) and the nine samples from adjacent normal regions of the cervixes (NAT) in the same patients (Table 8, Flag (NAT vs Ca)=1). Among these miRNAs, 53 were down-regulated (ΔH(NAT−Ca)>0.69), and 21 were up-regulated (ΔH(NAT−Ca)<−0.69) by at least 2-fold in Ca samples, when compared to their expression in NAT samples (Fold Change NAT vs Ca≥2.0). Eleven miRNAs (hsa-miR-1, -133a, -204, -218, -143, -368, -99a, -100, -195, -376a, and ambi-miR-7029) were down-regulated by more than 5-fold in Ca samples versus NAT samples (ΔH(NAT−Ca)>1.6). Three miRNAs (hsa-miR-205, -141, and -182) were up-regulated more than 5-fold in Ca samples versus NAT samples (ΔH(NAT−Ca)<−1.6).

The inventors identified 133 human miRNAs (121 hsa-miRNAs and 12 ambi-miRNAs) whose average expression levels were significantly different between the nine cervical tumor samples (Ca) and the sixteen normal cervical samples (NCX) (Table 8, Flag (NCX vs Ca)=1). Among these miRNAs, 70 were down-regulated (ΔH(NCX−Ca)>0.69) and 27 were up-regulated (ΔH(NCX−Ca)<−0.69), by at least 2-fold in Ca samples, when compared to their expression in NCX samples (Fold Change NCX vs Ca≥2.0). Seventeen miRNAs (hsa-miR-1, -133a, -204, -368, -99a, -100, -376a, -195, -218, -424, -497, -143, -299-5p, -154, -134, and ambi-miR-7101 and -7029) were down-regulated by more than 5-fold in Ca samples versus NCX samples (ΔH(NCX−Ca)>1.6). Seven miRNAs (hsa-miR-205, -183, -31, -224, -182, -21, and -203) were up-regulated more than 5-fold in Ca samples versus NCX sample (ΔH(NCX−Ca)<−1.6).

Overall, 103 human miRNAs were significantly differentially expressed between the cancer samples (Ca) and both the normal cervix samples (NCX) and the normal adjacent tissue samples (NAT). Thirty human miRNAs were significantly differentially expressed between Ca and NCX samples that were not significantly differentially expressed between Ca and NAT samples. Four distinct human miRNAs were significantly differentially expressed between Ca and NAT samples that were not significantly differentially expressed between Ca and NCX samples.

Unsupervised hierarchical clustering analysis (as determined by ANOVA) on the global miRNA expression in the 34 samples (16 NCX, 9 Ca, and 9 NAT) showed a clear segregation of the cancer samples away from the two normal tissue sample groups. Additional clustering and principal component analyses on all expressed miRNAs also showed clear segregation of the cancer samples from the two normal tissue sample groups. Similar results were obtained for principal component analysis of the miRNAs that were differentially expressed among the three groups.

The data described in this example demonstrate that miRNA expression analysis can be used to distinguish a cancerous cervical tissue sample from a normal, non-cancerous cervical tissue sample. The inventors have shown that specific miRNAs are differentially expressed (up-regulated or down-regulated) in cancerous cervical tissue as opposed to normal cervical tissues. Comparing the expression levels of these specific miRNAs in a cervical tissue sample that is suspected of being cancerous with their expression levels in a reference non-cancerous cervical tissue sample can indicate whether or not the suspect tissue sample is cancerous.

Example 4

23 miRNA Biomarkers for Cervical Squamous Cell Carcinoma

Microarray profiling of cervical squamous cell carcinomas and normal primary tissues, using the microarrays described in Example 2, identified 103 mis-regulated (differentially expressed) miRNAs between the cervical cancer samples and both normal sample types (Table 8). The inventors identified 23 miRNAs that were differentially expressed, with at least a 5-fold change, between the Ca and NCX or NAT samples and a p-value<0.0001. These 23 miRNAs whose expression is significantly affected in cervical cancer represent novel biomarkers and therapeutic targets for cervical squamous cell carcinoma. Their identity and associated array data are summarized in Table 9.

TABLE 9

Top 23 miRNAs Identified on mirVana ™ miRNA Bioarrays V1 (Ambion) as Differentially Expressed in Cervical Squamous Cell Carcinoma.

| miRNA | Mean NCX | Mean NAT | Mean Ca | ΔH NCX − Ca | Fold Change NCX vs Ca | p-value NCX vs Ca | ΔH NAT − Ca | Fold Change NAT vs Ca | p-value NAT vs Ca |
|---|---|---|---|---|---|---|---|---|---|
| hsa-miR-1 | 5.45 | 5.11 | 2.27 | 3.18 | 24.02 | 6.62E−11 | 2.85 | 17.22 | 7.99E−10 |
| hsa-miR-100 | 9.26 | 8.86 | 7.10 | 2.16 | 8.68 | 9.04E−11 | 1.76 | 5.80 | 1.21E−05 |
| hsa-miR-133a | 7.18 | 6.93 | 4.35 | 2.82 | 16.83 | 1.55E−10 | 2.58 | 13.13 | 1.14E−06 |
| hsa-miR-134 | 4.92 | 4.38 | 3.27 | 1.64 | 5.17 | 3.91E−11 | 1.11 | 3.03 | 6.43E−05 |
| hsa-miR-143 | 10.36 | 10.38 | 8.58 | 1.78 | 5.94 | 2.09E−08 | 1.81 | 6.08 | 1.14E−05 |
| hsa-miR-154 | 4.91 | 4.45 | 3.19 | 1.72 | 5.57 | 2.22E−08 | 1.26 | 3.52 | 0.000932 |
| hsa-miR-182 | 4.49 | 4.65 | 6.32 | −1.83 | 6.23 | 7.24E−07 | −1.67 | 5.31 | 4.7E−05 |
| hsa-miR-183 | 2.50 | 3.18 | 4.74 | −2.23 | 9.33 | 3.79E−08 | −1.55 | 4.72 | 9.87E−08 |
| hsa-miR-195 | 9.22 | 8.80 | 7.17 | 2.05 | 7.78 | 2.68E−11 | 1.63 | 5.08 | 1.02E−05 |
| hsa-miR-204 | 4.99 | 4.49 | 2.38 | 2.61 | 13.56 | 1.66E−09 | 2.11 | 8.24 | 5.19E−08 |
| hsa-miR-205 | 7.72 | 8.93 | 10.98 | −3.26 | 25.94 | 1.01E−07 | −2.04 | 7.72 | 0.015248 |
| hsa-miR-21 | 9.11 | 9.65 | 10.88 | −1.77 | 5.88 | 4.43E−11 | −1.22 | 3.40 | 6.23E−06 |
| hsa-miR-218 | 5.63 | 5.58 | 3.59 | 2.04 | 7.69 | 3.17E−11 | 1.99 | 7.28 | 1.83E−07 |
| hsa-miR-224 | 5.61 | 6.21 | 7.44 | −1.83 | 6.23 | 8.13E−09 | −1.23 | 3.42 | 0.001657 |
| hsa-miR-299-5p | 4.76 | 4.39 | 2.99 | 1.77 | 5.87 | 2.08E−09 | 1.40 | 4.07 | 0.000139 |
| hsa-miR-31 | 6.98 | 7.45 | 8.85 | −1.88 | 6.52 | 5.22E−07 | −1.40 | 4.06 | 0.006742 |
| hsa-miR-368 | 6.97 | 6.28 | 4.51 | 2.47 | 11.77 | 8.13E−11 | 1.78 | 5.90 | 9.85E−05 |
| hsa-miR-376a | 5.17 | 4.71 | 3.09 | 2.08 | 8.02 | 3.55E−08 | 1.62 | 5.05 | 0.000269 |
| hsa-miR-424 | 5.71 | 5.02 | 3.77 | 1.94 | 6.99 | 7.46E−07 | 1.25 | 3.51 | 0.000778 |
| hsa-miR-99a | 10.12 | 9.54 | 7.77 | 2.35 | 10.50 | 1.71E−10 | 1.77 | 5.88 | 2.55E−05 |
| ambi-miR-7029 | 6.99 | 7.21 | 5.35 | 1.64 | 5.14 | 9.18E−05 | 1.85 | 6.38 | 0.00165 |
| hsa-miR-497 | 7.69 | 7.08 | 5.84 | 1.85 | 6.34 | 2.85E−09 | 1.24 | 3.46 | 0.00027 |
| ambi-miR-7101 | 4.10 | 3.75 | 2.34 | 1.76 | 5.81 | 6.71E−08 | 1.41 | 4.09 | 0.000245 |

Example 5

Microarray Data Validation by qRT-PCR

To verify array data, the inventors performed real-time qRT-PCR reactions for 12 of the top 23 miRNAs in Table 9 with very distinct expression patterns between cervical squamous cell carcinomas (Ca) and normal adjacent tissues (NAT) or normal cervix (NCX) samples (hsa-miR-1, -15b, -133a, -143, -205, -21, -204, -195, -100, -99a, -368, and -183) and one miRNA with no significant change (hsa-miR-16), which was used for normalization. qRT-PCR reactions were performed using TaqMan® MicroRNA Assays (Applied Biosystems; Foster City, Calif., USA) according to the manufacturer's instructions. Reactions included 15 ng of total RNA per reaction and were incubated in the 7900HT Fast Real-Time PCR System (Applied Biosystems). Initial data analysis was done using the 7500 Fast System SDS 2.3 software. The inventors analyzed the 34 samples previously profiled (16 NCX and 9 paired Ca and NAT samples).

Figure 2A:
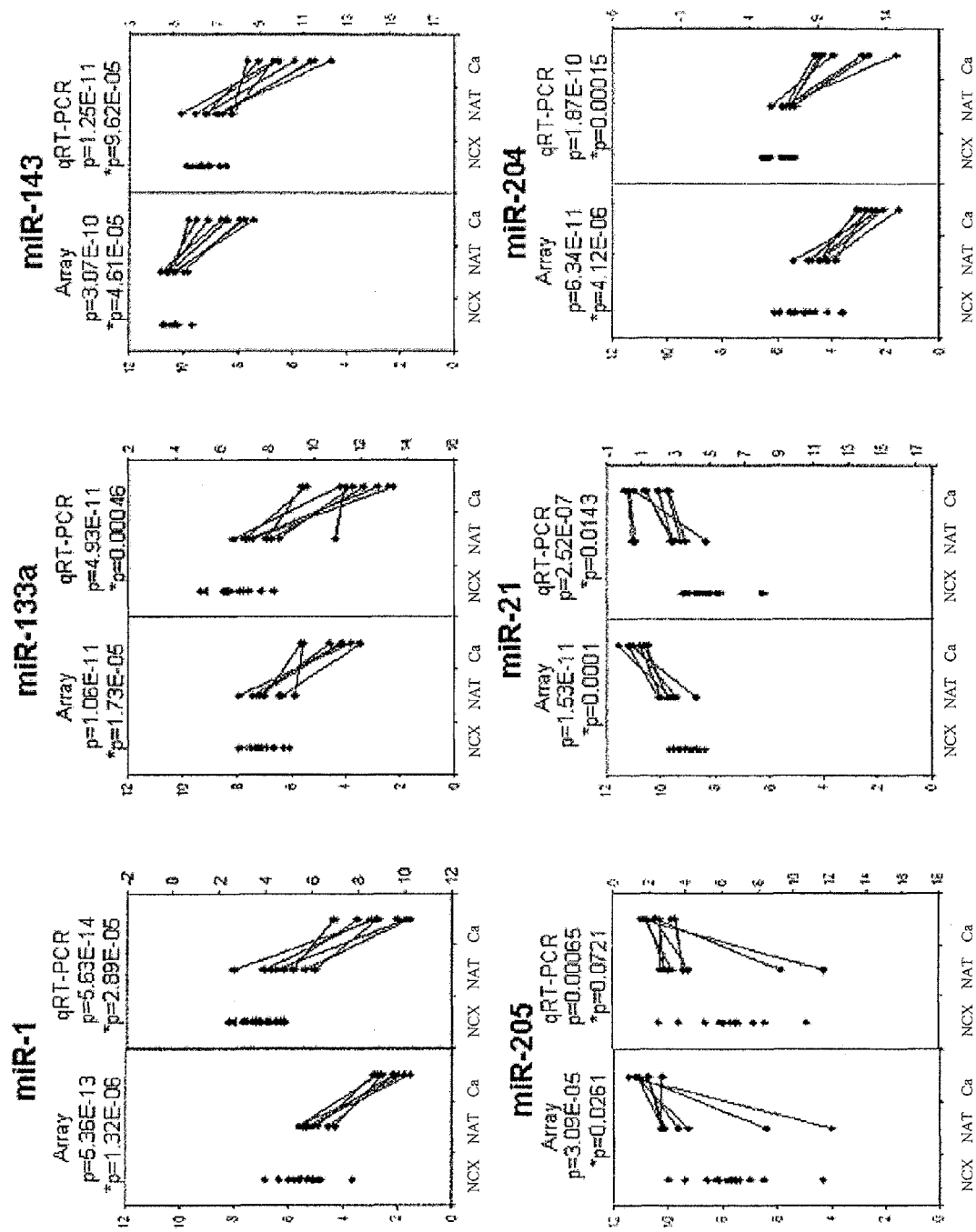
FIGS. 2A-2B Comparison between array and qRT-PCR data. Real time RT-PCR were performed using 15 ng of total RNA input from the 34 samples previously profiled (16 NCX and 9 paired Ca and NAT samples). miRNA expression data obtained with primer sets specific for the indicated miRNAs were normalized to miR-16 expression level for each sample (miRNA Ct-miR-16 Ct). The graphs show the individual normalized miRNA expression levels determined by array or qRT-PCR and associated p-values (p (ANOVA) and *p (pairwise t-test)).
Figure 2B:
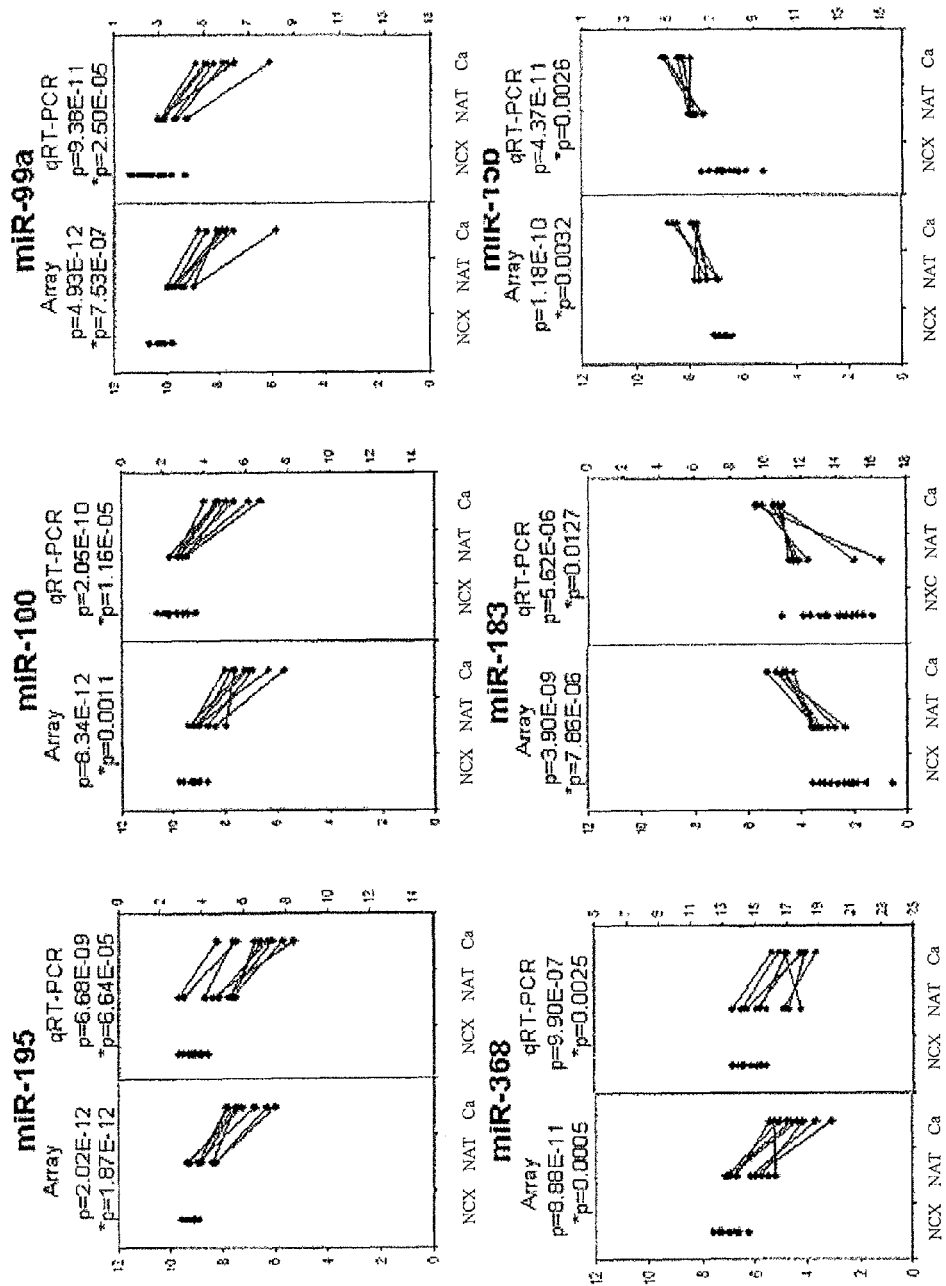

As illustrated in FIGS. 2A-2B, the relative variations of miRNA expression levels were very similar for qRT-PCR and array data. All 34 samples showed the expected miRNA expression patterns characteristic of normal cervix, normal adjacent tissue and squamous cell carcinoma, thus validating the array data. This was further confirmed after performing pair wise comparisons between qRT-PCR and array data for each paired Ca-NAT sample.

Example 6 miRNA Expression in Precancerous Cervical Squamous Intraepithelial Lesions

The inventors sought to determine if the top 23 misregulated miRNAs in cervical cancer (Table 9) could distinguish precancerous cervical squamous epithelial lesions from normal cervical samples. The inventors evaluated miRNA expression in three cervical squamous intraepithelial lesions (SILs) (also known as cervical intraepithelial neoplasias, CINs) (Table 10). Pathological analysis classified two lesions (SIL1, SIL2) as low grade (LSIL) and one (SIL3) as high grade (HSIL).

TABLE 10

Histology and HPV (Human Papillomavirus) Status for Three Cervical Cancer Precursor Lesions. CIN, cervical intraepithelial neoplasia.

| Sample ID | Age | Race | Diagnosis | Histological Diagnosis (Richart et al., 1967) | HPV 16/18 Status |
|---|---|---|---|---|---|
| SIL1 | 36 | Caucasian | CIN | CIN I-II | not available |
| SIL2 | 30 | Caucasian | CIN | CIN I-II | not available |
| SIL3 | 25 | Caucasian | CIN | CIN III | not available | miRNA expression analysis was carried out as described in Example 2, except that 7 µg of total RNA from each SIL sample were hybridized to the arrays. To avoid introducing a bias due to the differences in the mass input amounts for array analysis of the various samples (SIL, NCX, Ca, NAT) the inventors used the non parametric "rank product" method (Breitling et al., 2004) for identifying differentially expressed genes. Rank Product (RP) uses fold-change to assign ranks for all features in a dataset, providing reliable and sensitive results. Importantly, RP does not depend on the variance calculation for every gene and therefore is powerful when a small number of replicates is available. The robustness of this method has been demonstrated in previous studies where the list of genes generated from RP and a Student's T-test at a false discovery rate-corrected p-value of 5% were found in agreement (Breitling et al., 2004).

Using the RP method, 29 human miRNAs were identified as the most differentially expressed miRNAs between the SILs and the sixteen normal cervix samples, based on the rank value and an estimated percentage of false positive (PFP) of 5%. (Table 11). Among those, 15 miRNAs were down-regulated (Table 11, FC (NCX/SIL)>1) and 14 miRNAs were up-regulated in SILs (Table 11, FC(SIL/NCX)>1) compared to NCX. Interestingly, 11 out of the 15 miRNAs down-regulated in SILs were among the miRNAs down-regulated by at least 2-fold in Ca versus NCX (miR-1, -133a, -187, -204, -145, -143, -125a, -376a, -505, -100, and -99a). It is also noteworthy that miR-1, which is the most significantly down-regulated miRNA in the cervical cancers of our series, was also the most down-regulated miRNA in SILs. Among the 14 miRNAs up-regulated in SILs compared to the normal cervix samples, eight miRNAs (miR-141, -205, -146a, -200b, -182, -203, -21, and -31) were also up-regulated by at least 2-fold in the Ca samples compared to NCX samples. The presence of numerous identical miRNAs differentially expressed between Ca and NCX samples and between SIL and NCX samples, suggests that misregulation of these miRNAs is likely an early event in cervical tumorigenesis.

TABLE 11 miRNAs Differentially Expressed Between Squamous Intraepithelial Lesions (SILs) and Normal Cervix (NCX) Samples. RP/Rsum, Computed Rank Product/Sum of miRNA Probes on Array (377); FC, Fold Change; FC (NCX/SIL), miRNA expression is higher in normal cervix samples; FC (SIL/NCX), miRNA expression is higher in squamous intraepithelial lesions; pfp percentage of false positive.

| miRNA | RP/Rsum | FC (NCX/SIL) | pfp | P value |
|---|---|---|---|---|
| hsa-miR-1 | 1.7496 | 29.1 | 0 | 0 |
| hsa-miR-133a | 2.1106 | 25.6 | 0 | 0 |
| hsa-miR-124a | 10.0096 | 7.0 | 0 | 0 |
| hsa-miR-187 | 12.0012 | 6.0 | 0 | 0 |
| hsa-miR-204 | 13.9261 | 5.5 | 0 | 0 |
| hsa-miR-145 | 16.6001 | 4.8 | 0 | 0 |
| hsa-miR-143 | 18.1237 | 4.4 | 0 | 0 |
| hsa-miR-325 | 24.6184 | 3.8 | 0.001 | 0 |
| hsa-miR-500 | 24.6936 | 3.9 | 9.00E−04 | 0 |
| hsa-miR-196a | 28.1128 | 3.8 | 0.0025 | 1.00E−04 |
| hsa-miR-125a | 31.4805 | 3.4 | 0.0062 | 2.00E−04 |
| hsa-miR-376a | 34.1794 | 3.3 | 0.0093 | 3.00E−04 |
| hsa-miR-505 | 37.0398 | 3.1 | 0.015 | 6.00E−04 |
| hsa-miR-100 | 38.4455 | 3.2 | 0.0171 | 8.00E−04 |
| hsa-miR-99a | 42.0798 | 3.0 | 0.0258 | 0.0013 |

| miRNA | RP/Rsum | FC (SIL/NCX) | pfp | P value |
|---|---|---|---|---|
| hsa-miR-141 | 5.8787 | 9.2 | 0 | 0 |
| hsa-miR-200a | 6.0647 | 8.9 | 0 | 0 |
| ambi-miR-7029 | 7.5704 | 7.3 | 0 | 0 |
| hsa-miR-223 | 8.9032 | 6.9 | 0 | 0 |
| hsa-miR-205 | 9.544 | 7.1 | 0 | 0 |
| hsa-miR-146a | 10.4209 | 6.0 | 0 | 0 |
| hsa-miR-429 | 12.5128 | 6.1 | 0.0025 | 1.00E−04 |
| hsa-miR-200b | 13.589 | 6.0 | 0.0044 | 1.00E−04 |
| hsa-miR-182 | 16.8691 | 5.0 | 0.012 | 3.00E−04 |
| hsa-miR-142-5p | 18.1534 | 4.2 | 0.0155 | 4.00E−04 |

TABLE 11-continued miRNAs Differentially Expressed Between Squamous Intraepithelial Lesions (SILs) and Normal Cervix (NCX) Samples. RP/Rsum, Computed Rank Product/Sum of miRNA Probes on Array (377); FC, Fold Change; FC (NCX/SIL), miRNA expression is higher in normal cervix samples; FC (SIL/NCX), miRNA expression is higher in squamous intraepithelial lesions; pfp percentage of false positive.

| hsa-miR-203 | 18.208  | 3.7 | 0.0142 | 4.00E−04 |
| hsa-miR-21  | 21.2961 | 4.0 | 0.0238 | 8.00E−04 |
| hsa-miR-31  | 21.4027 | 4.0 | 0.0229 | 8.00E−04 |
| hsa-miR-513 | 21.8734 | 3.7 | 0.0253 | 0.001    |

The data described in this example demonstrate that miRNA expression analysis can be used to distinguish a pre-cancerous cervical squamous intraepithelial lesion (SIL) or a cervical intraepithelial neoplasia (CIN) from normal non-cancerous cervical tissue. Specific miRNAs are differentially expressed (up-regulated or down-regulated) in cervical SILs (CINs). Comparing the expression levels of these specific miRNAs in a cervical tissue sample that is suspected of being pre-cancerous with their expression levels in a reference non-cancerous cervical tissue sample can indicate whether or not the suspect tissue is pre-cancerous.

Example 7 miRNA Expression in Cervical Carcinoma-Derived Cell Lines

The inventors determined miRNA expression profiles of five cervical cancer-derived cell lines using the same microarray platform described in Example 2. To compare miRNA expression profiles, miRNA expression data from the five cervical cancer cell lines (CL) were normalized together with the data described in earlier examples from the nine pairs of cervical tumors (Ca) and normal adjacent tissue specimens (NAT) and from the sixteen normal cervix samples (NCX) (Table 12).

TABLE 12 miRNAs Differentially Expressed Among Five Cervical Cancer-Derived Cell Lines, Nine Cervical Cancer Samples (Ca), Nine Paired Normal Adjacent Tissue Samples (NAT), and Sixteen Normal Cervix Tissue Samples (NCX). FC; Fold Change

| miRNA | Mean CL | Mean NCX | Mean NAT | Mean Ca | ΔH CL vs NCX | FC CL vs NCX | p-value CL vs NCX | Flag CL vs NCX |
| --- | --- | --- | --- | --- | --- | --- | --- | --- |
| hsa-let-7a | 9.99 | 10.91 | 10.64 | 10.19 | −0.92 | 2.51 | 1.17258E−06 | 1 |
| hsa-let-7b | 9.69 | 11.01 | 10.68 | 10.18 | −1.32 | 3.76 | 4.61978E−06 | 1 |
| hsa-let-7c | 9.26 | 10.98 | 10.66 | 9.86 | −1.71 | 5.54 | 1.00313E−08 | 1 |
| hsa-let-7d | 8.94 | 9.79 | 9.49 | 8.88 | −0.85 | 2.34 | 1.71325E−05 | 1 |
| hsa-let-7e | 7.94 | 8.28 | 8.14 | 7.21 | −0.34 | 1.40 | 0.135766933 | 0 |
| hsa-let-7f | 7.91 | 8.65 | 8.45 | 7.72 | −0.74 | 2.09 | 0.003283921 | 1 |
| hsa-let-7g | 7.61 | 8.72 | 8.24 | 7.54 | −1.12 | 3.05 | 7.21271E−06 | 1 |
| hsa-let-7i | 8.06 | 8.69 | 8.43 | 8.18 | −0.63 | 1.88 | 0.003322803 | 1 |
| hsa-miR-1 | 1.81 | 5.46 | 5.13 | 2.25 | −3.65 | 38.52 | 3.82415E−09 | 1 |
| hsa-miR-100 | 7.68 | 9.28 | 8.87 | 7.13 | −1.60 | 4.93 | 2.06806E−06 | 1 |
| hsa-miR-101 | 3.55 | 4.48 | 4.01 | 2.95 | −0.93 | 2.53 | 0.006473943 | 1 |
| hsa-miR-105 | 2.50 | 1.54 | 1.67 | 1.66 | 0.96 | 2.60 | 0.001579242 | 1 |
| hsa-miR-106a | 8.44 | 7.49 | 7.63 | 8.29 | 0.95 | 2.60 | 2.80259E−06 | 1 |
| hsa-miR-106b | 8.12 | 6.38 | 6.22 | 7.09 | 1.74 | 5.70 | 1.54019E−10 | 1 |
| hsa-miR-10a | 5.92 | 7.08 | 6.55 | 6.23 | −1.16 | 3.19 | 0.005059754 | 1 |
| hsa-miR-10b | 5.68 | 7.88 | 7.92 | 6.49 | −2.20 | 9.01 | 2.34952E−08 | 1 |
| hsa-miR-124a | 2.07 | 3.30 | 2.20 | 2.00 | −1.23 | 3.42 | 0.008540615 | 1 |
| hsa-miR-125a | 8.02 | 8.96 | 8.99 | 7.79 | −0.94 | 2.55 | 0.001651966 | 1 |
| hsa-miR-125b | 7.36 | 10.35 | 10.19 | 8.83 | −2.98 | 19.76 | 1.51232E−09 | 1 |
| hsa-miR-126 | 4.64 | 9.44 | 9.68 | 8.52 | −4.80 | 120.87 | 2.00347E−15 | 1 |
| hsa-miR-126-AS | 1.74 | 5.35 | 5.28 | 3.86 | −3.61 | 37.08 | 6.43116E−11 | 1 |
| hsa-miR-127 | 2.15 | 4.35 | 4.28 | 3.19 | −2.20 | 9.04 | 6.58949E−08 | 1 |
| hsa-miR-128a | 5.73 | 5.26 | 5.16 | 5.23 | 0.46 | 1.59 | 0.00380461 | 1 |
| hsa-miR-130a | 8.13 | 7.77 | 6.97 | 6.33 | 0.36 | 1.44 | 0.205782804 | 0 |
| hsa-miR-130b | 6.32 | 4.72 | 4.68 | 5.53 | 1.60 | 4.95 | 3.25172E−11 | 1 |
| hsa-miR-132 | 4.81 | 5.62 | 5.52 | 5.63 | −0.81 | 2.25 | 0.006000262 | 1 |
| hsa-miR-133a | 2.36 | 7.19 | 6.94 | 4.38 | −4.83 | 125.51 | 1.83597E−11 | 1 |
| hsa-miR-134 | 2.09 | 4.93 | 4.39 | 3.29 | −2.84 | 17.10 | 2.14893E−13 | 1 |
| hsa-miR-135b | 1.91 | 1.75 | 1.46 | 2.28 | 0.16 | 1.17 | 0.58389938 | 0 |
| hsa-miR-138 | 4.41 | 2.12 | 2.35 | 2.32 | 2.29 | 9.88 | 4.9646E−05 | 1 |
| hsa-miR-139 | 2.93 | 4.81 | 4.68 | 3.42 | −1.88 | 6.57 | 0.000461652 | 1 |
| hsa-miR-140 | 3.57 | 5.06 | 4.95 | 4.02 | −1.50 | 4.46 | 1.55297E−06 | 1 |
| hsa-miR-142-3p | 1.81 | 3.11 | 2.95 | 3.52 | −1.30 | 3.66 | 8.17751E−06 | 1 |
| hsa-miR-142-5p | 1.76 | 3.59 | 3.40 | 3.24 | −1.83 | 6.22 | 6.76277E−10 | 1 |
| hsa-miR-143 | 2.20 | 10.37 | 10.40 | 8.60 | −8.17 | 3524.68 | 2.19343E−21 | 1 |
| hsa-miR-145 | 2.34 | 11.04 | 11.08 | 9.59 | −8.71 | 6027.90 | 5.18209E−20 | 1 |
| hsa-miR-146a | 2.45 | 5.84 | 5.88 | 6.64 | −3.39 | 29.75 | 5.38207E−14 | 1 |
| hsa-miR-148a | 4.89 | 6.42 | 6.15 | 5.98 | −1.53 | 4.61 | 0.000301763 | 1 |
| hsa-miR-148b | 5.09 | 4.26 | 4.66 | 4.55 | 0.83 | 2.28 | 0.000427998 | 1 |
| hsa-miR-150 | 2.12 | 6.04 | 6.69 | 6.97 | −3.92 | 50.37 | 1.5846E−13 | 1 |
| hsa-miR-151 | 6.15 | 5.84 | 5.75 | 5.61 | 0.31 | 1.37 | 0.003594843 | 1 |
| hsa-miR-152 | 6.21 | 7.03 | 7.03 | 6.26 | −0.82 | 2.27 | 2.81463E−07 | 1 |
| hsa-miR-153 | 2.12 | 2.44 | 2.04 | 2.08 | −0.33 | 1.38 | 0.108816949 | 0 |
| hsa-miR-154 | 1.47 | 4.92 | 4.46 | 3.20 | −3.46 | 31.70 | 1.65629E−11 | 1 |
| hsa-miR-155 | 5.14 | 5.42 | 5.56 | 7.01 | −0.29 | 1.33 | 0.497848019 | 0 |
| hsa-miR-15a | 7.25 | 6.52 | 6.58 | 6.61 | 0.73 | 2.08 | 0.000321889 | 1 |

TABLE 12-continued miRNAs Differentially Expressed Among Five Cervical Cancer-Derived Cell Lines, Nine
Cervical Cancer Samples (Ca), Nine Paired Normal Adjacent Tissue Samples (NAT), and Sixteen
Normal Cervix Tissue Samples (NCX). FC; Fold Change

| | | | | | | | | |
|---|---|---|---|---|---|---|---|---|
| hsa-miR-15b | 8.28 | 6.85 | 7.35 | 8.19 | 1.43 | 4.17 | 1.04496E−11 | 1 |
| hsa-miR-16 | 9.90 | 9.69 | 9.81 | 10.14 | 0.21 | 1.23 | 0.015593653 | 1 |
| hsa-miR-17-3p | 5.29 | 4.27 | 4.02 | 4.32 | 1.02 | 2.76 | 1.29121E−06 | 1 |
| hsa-miR-17-5p | 8.19 | 7.39 | 7.41 | 8.11 | 0.80 | 2.22 | 2.46377E−06 | 1 |
| hsa-miR-18a | 6.09 | 4.14 | 4.05 | 5.48 | 1.95 | 7.04 | 2.17437E−07 | 1 |
| hsa-miR-181a | 7.28 | 6.75 | 7.05 | 7.24 | 0.54 | 1.71 | 0.02628498 | 1 |
| hsa-miR-181b | 7.08 | 5.97 | 5.80 | 6.41 | 1.11 | 3.02 | 0.00044532 | 1 |
| hsa-miR-181c | 4.57 | 4.11 | 3.89 | 3.67 | 0.46 | 1.59 | 0.020579145 | 1 |
| hsa-miR-182 | 7.14 | 4.49 | 4.65 | 6.34 | 2.65 | 14.09 | 7.57599E−07 | 1 |
| hsa-miR-183 | 5.31 | 2.46 | 3.18 | 4.76 | 2.85 | 17.26 | 9.98684E−07 | 1 |
| hsa-miR-184 | 2.77 | 3.78 | 3.69 | 3.62 | −1.01 | 2.76 | 5.30924E−05 | 1 |
| hsa-miR-185 | 6.33 | 5.47 | 5.69 | 6.15 | 0.86 | 2.37 | 2.30288E−05 | 1 |
| hsa-miR-186 | 4.06 | 4.24 | 4.14 | 3.41 | −0.17 | 1.19 | 0.469642053 | 0 |
| hsa-miR-187 | 1.19 | 5.27 | 2.66 | 3.71 | −4.08 | 59.33 | 2.18548E−10 | 1 |
| hsa-miR-188 | 4.79 | 3.35 | 3.62 | 3.70 | 1.44 | 4.22 | 9.22828E−08 | 1 |
| hsa-miR-189 | 3.39 | 4.40 | 4.26 | 3.53 | −1.01 | 2.75 | 3.90592E−05 | 1 |
| hsa-miR-190 | 1.53 | 1.58 | 1.32 | 1.02 | −0.05 | 1.06 | 0.790124832 | 0 |
| hsa-miR-192 | 3.78 | 4.45 | 3.88 | 4.16 | −0.67 | 1.96 | 0.0117373 | 1 |
| hsa-miR-194 | 4.28 | 4.88 | 4.49 | 4.64 | −0.60 | 1.83 | 0.002283553 | 1 |
| hsa-miR-195 | 5.10 | 9.23 | 8.81 | 7.19 | −4.14 | 62.57 | 4.23922E−19 | 1 |
| hsa-miR-196a | 5.82 | 4.99 | 4.17 | 4.19 | 0.83 | 2.29 | 0.002694126 | 1 |
| hsa-miR-196b | 4.38 | 6.60 | 5.67 | 5.11 | −2.22 | 9.19 | 1.55374E−11 | 1 |
| hsa-miR-198 | 4.35 | 4.70 | 5.03 | 5.21 | −0.35 | 1.42 | 0.1332213 | 0 |
| hsa-miR-199a | 2.13 | 8.65 | 8.33 | 7.84 | −6.52 | 679.14 | 1.83555E−16 | 1 |
| hsa-miR-199a-AS | 2.54 | 8.87 | 8.67 | 7.99 | −6.33 | 562.02 | 3.21649E−16 | 1 |
| hsa-miR-199b | 1.98 | 6.78 | 6.44 | 5.42 | −4.80 | 121.21 | 1.66836E−14 | 1 |
| hsa-miR-19a | 5.65 | 4.01 | 3.50 | 4.08 | 1.64 | 5.17 | 0.00028546 | 1 |
| hsa-miR-19b | 8.11 | 7.71 | 7.29 | 7.71 | 0.40 | 1.49 | 0.042429839 | 0 |
| hsa-miR-20a | 6.91 | 6.40 | 6.44 | 6.86 | 0.51 | 1.67 | 0.01473628 | 1 |
| hsa-miR-200a | 4.09 | 5.98 | 5.15 | 6.63 | −1.90 | 6.66 | 0.025359211 | 1 |
| hsa-miR-200b | 5.18 | 6.93 | 6.93 | 8.12 | −1.75 | 5.75 | 0.041123295 | 0 |
| hsa-miR-200c | 5.75 | 7.80 | 8.13 | 9.37 | −2.05 | 7.75 | 0.017233123 | 1 |
| hsa-miR-203 | 4.57 | 6.87 | 8.39 | 8.62 | −2.30 | 9.99 | 0.011750278 | 1 |
| hsa-miR-204 | 1.90 | 5.00 | 4.50 | 2.36 | −3.10 | 22.23 | 5.285E−08 | 1 |
| hsa-miR-205 | 5.80 | 7.73 | 8.95 | 11.00 | −1.93 | 6.91 | 0.114971754 | 0 |
| hsa-miR-206 | 2.21 | 3.19 | 2.88 | 2.97 | −0.98 | 2.67 | 0.000129379 | 1 |
| hsa-miR-21 | 10.64 | 9.12 | 9.67 | 10.90 | 1.52 | 4.58 | 1.55273E−07 | 1 |
| hsa-miR-210 | 6.60 | 5.54 | 5.87 | 6.41 | 1.06 | 2.88 | 0.011451334 | 1 |
| hsa-miR-213 | 1.62 | 2.03 | 2.05 | 2.34 | −0.41 | 1.51 | 0.054223209 | 0 |
| hsa-miR-214 | 3.19 | 8.25 | 8.02 | 7.36 | −5.06 | 158.19 | 1.41242E−17 | 1 |
| hsa-miR-215 | 1.85 | 1.94 | 2.84 | 2.48 | −0.10 | 1.10 | 0.669928978 | 0 |
| hsa-miR-218 | 3.63 | 5.64 | 5.59 | 3.61 | −2.01 | 7.46 | 8.63202E−07 | 1 |
| hsa-miR-222 | 8.62 | 7.71 | 8.06 | 7.75 | 0.90 | 2.47 | 0.000965119 | 1 |
| hsa-miR-223 | 2.34 | 6.19 | 6.65 | 7.45 | −3.85 | 47.07 | 4.01105E−14 | 1 |
| hsa-miR-224 | 5.94 | 5.62 | 6.22 | 7.46 | 0.32 | 1.37 | 0.577286744 | 0 |
| hsa-miR-23b | 9.13 | 9.93 | 10.05 | 9.60 | −0.80 | 2.22 | 2.06649E−05 | 1 |
| hsa-miR-24 | 9.25 | 9.81 | 9.82 | 9.51 | −0.56 | 1.75 | 2.85758E−05 | 1 |
| hsa-miR-25 | 7.58 | 6.58 | 6.68 | 7.17 | 1.00 | 2.73 | 2.50502E−07 | 1 |
| hsa-miR-26a | 8.94 | 10.85 | 10.68 | 9.94 | −1.91 | 6.76 | 2.18482E−10 | 1 |
| hsa-miR-26b | 5.90 | 7.65 | 7.32 | 6.16 | −1.75 | 5.77 | 8.59969E−07 | 1 |
| hsa-miR-27a | 9.14 | 8.75 | 9.04 | 8.85 | 0.38 | 1.47 | 0.00582862 | 1 |
| hsa-miR-27b | 8.41 | 9.22 | 9.27 | 8.43 | −0.81 | 2.25 | 2.44159E−05 | 1 |
| hsa-miR-28 | 5.47 | 6.03 | 6.03 | 5.25 | −0.57 | 1.77 | 0.000538298 | 1 |
| hsa-miR-296 | 3.41 | 2.64 | 3.27 | 3.19 | 0.77 | 2.16 | 0.000887969 | 1 |
| hsa-miR-299-5p | 2.18 | 4.77 | 4.40 | 2.99 | −2.58 | 13.24 | 8.64446E−12 | 1 |
| hsa-miR-29a | 9.34 | 9.44 | 9.02 | 8.32 | −0.10 | 1.10 | 0.575888506 | 0 |
| hsa-miR-29b | 7.51 | 6.90 | 6.11 | 5.75 | 0.61 | 1.84 | 0.069571767 | 0 |
| hsa-miR-29c | 5.59 | 6.81 | 6.04 | 5.27 | −1.22 | 3.38 | 0.000857257 | 1 |
| hsa-miR-301 | 4.39 | 2.16 | 1.84 | 2.52 | 2.23 | 9.31 | 8.49028E−06 | 1 |
| hsa-miR-302a | 1.26 | 2.03 | 2.17 | 2.18 | −0.77 | 2.16 | 0.005771406 | 1 |
| hsa-miR-30a-3p | 5.61 | 4.11 | 4.13 | 2.84 | 1.50 | 4.48 | 4.16271E−08 | 1 |
| hsa-miR-30a-5p | 8.73 | 8.12 | 8.01 | 7.48 | 0.61 | 1.83 | 0.002611571 | 1 |
| hsa-miR-30b | 6.76 | 7.27 | 7.24 | 6.58 | −0.51 | 1.67 | 0.076511595 | 0 |
| hsa-miR-30d | 7.93 | 8.18 | 8.04 | 7.55 | −0.25 | 1.28 | 0.1214696 | 0 |
| hsa-miR-30e-3p | 4.72 | 4.11 | 4.04 | 3.67 | 0.60 | 1.83 | 0.000660312 | 1 |
| hsa-miR-31 | 9.12 | 6.99 | 7.46 | 8.88 | 2.13 | 8.44 | 1.91471E−06 | 1 |
| hsa-miR-320 | 8.24 | 8.38 | 8.30 | 7.74 | −0.15 | 1.16 | 0.290505753 | 0 |
| hsa-miR-324-3p | 5.11 | 5.73 | 5.99 | 5.57 | −0.61 | 1.85 | 0.002964343 | 1 |
| hsa-miR-324-5p | 4.19 | 3.17 | 3.70 | 3.36 | 1.02 | 2.78 | 0.001172378 | 1 |
| hsa-miR-326 | 1.89 | 2.41 | 2.63 | 2.61 | −0.52 | 1.68 | 0.034306803 | 1 |
| hsa-miR-328 | 2.74 | 3.80 | 3.96 | 3.10 | −1.06 | 2.90 | 0.000266512 | 1 |
| hsa-miR-330 | 3.61 | 2.76 | 2.79 | 3.49 | 0.85 | 2.35 | 0.001159597 | 1 |
| hsa-miR-335 | 5.00 | 4.71 | 4.08 | 3.38 | 0.29 | 1.33 | 0.350364555 | 0 |
| hsa-miR-339 | 5.05 | 5.06 | 5.33 | 5.51 | −0.02 | 1.02 | 0.910800962 | 0 |
| hsa-miR-342 | 6.40 | 7.32 | 7.30 | 7.55 | −0.93 | 2.53 | 1.30738E−06 | 1 |
| hsa-miR-34a | 7.28 | 7.49 | 6.87 | 7.23 | −0.21 | 1.24 | 0.187836999 | 0 |

TABLE 12-continued miRNAs Differentially Expressed Among Five Cervical Cancer-Derived Cell Lines, Nine Cervical Cancer Samples (Ca), Nine Paired Normal Adjacent Tissue Samples (NAT), and Sixteen Normal Cervix Tissue Samples (NCX). FC; Fold Change

| | | | | | | | | |
|---|---|---|---|---|---|---|---|---|
| hsa-miR-361 | 6.50 | 7.00 | 6.82 | 6.48 | −0.51 | 1.66 | 0.010542824 | 1 |
| hsa-miR-365 | 5.01 | 3.41 | 3.87 | 3.31 | 1.60 | 4.93 | 2.41083E−05 | 1 |
| hsa-miR-368 | 1.82 | 6.99 | 6.30 | 4.53 | −5.16 | 174.81 | 1.34846E−16 | 1 |
| hsa-miR-370 | 3.82 | 4.70 | 5.29 | 5.19 | −0.88 | 2.42 | 2.20094E−05 | 1 |
| hsa-miR-371 | 1.93 | 1.66 | 1.07 | 1.41 | 0.28 | 1.32 | 0.205890133 | 0 |
| hsa-miR-373-AS | 3.78 | 3.41 | 4.24 | 4.11 | 0.37 | 1.45 | 0.035829035 | 1 |
| hsa-miR-375 | 2.11 | 4.01 | 3.63 | 3.09 | −1.90 | 6.67 | 0.001461287 | 1 |
| hsa-miR-376a | 1.12 | 5.18 | 4.72 | 3.09 | −4.06 | 57.70 | 3.07283E−11 | 1 |
| hsa-miR-377 | 2.02 | 3.49 | 3.08 | 2.21 | −1.47 | 4.36 | 2.16415E−06 | 1 |
| hsa-miR-379 | 2.86 | 5.47 | 5.17 | 4.78 | −2.60 | 13.52 | 1.54188E−13 | 1 |
| hsa-miR-381 | 2.16 | 4.39 | 4.25 | 3.21 | −2.23 | 9.30 | 5.1954E−10 | 1 |
| hsa-miR-382 | 1.98 | 4.37 | 4.41 | 3.52 | −2.39 | 10.91 | 4.71258E−09 | 1 |
| hsa-miR-383 | 1.59 | 2.49 | 2.18 | 2.50 | −0.90 | 2.45 | 0.000556195 | 1 |
| hsa-miR-423 | 6.46 | 6.20 | 6.33 | 6.63 | 0.26 | 1.29 | 0.069079765 | 0 |
| hsa-miR-424 | 3.39 | 5.72 | 5.03 | 3.78 | −2.33 | 10.32 | 3.72795E−06 | 1 |
| hsa-miR-429 | 3.48 | 4.50 | 4.05 | 5.47 | −1.01 | 2.76 | 0.153711126 | 0 |
| hsa-miR-450 | 2.10 | 2.63 | 2.28 | 1.81 | −0.53 | 1.71 | 0.032076794 | 1 |
| hsa-miR-7 | 4.83 | 2.66 | 2.75 | 3.28 | 2.16 | 8.70 | 2.25351E−05 | 1 |
| hsa-miR-92 | 7.36 | 7.14 | 7.30 | 7.63 | 0.22 | 1.24 | 0.126864644 | 0 |
| hsa-miR-93 | 8.48 | 6.84 | 7.19 | 8.03 | 1.64 | 5.16 | 1.50603E−11 | 1 |
| hsa-miR-95 | 3.15 | 3.32 | 3.98 | 3.87 | −0.17 | 1.18 | 0.56292993 | 0 |
| hsa-miR-96 | 5.75 | 3.38 | 3.41 | 3.88 | 2.37 | 10.70 | 1.80468E−06 | 1 |
| hsa-miR-98 | 5.26 | 5.67 | 5.69 | 5.09 | −0.41 | 1.50 | 0.014821661 | 1 |
| hsa-miR-99a | 6.47 | 10.13 | 9.55 | 7.79 | −3.66 | 38.75 | 1.73369E−10 | 1 |
| hsa-miR-99b | 7.04 | 7.39 | 7.24 | 6.32 | −0.34 | 1.41 | 0.12606875 | 0 |
| hsa-miR-410 | 2.25 | 2.86 | 3.12 | 2.33 | −0.61 | 1.85 | 0.03898867 | 1 |
| hsa-miR-522 | 3.02 | 1.51 | 1.62 | 1.49 | 1.52 | 4.56 | 0.019262647 | 1 |
| hsa-miR-520d | 1.50 | 1.87 | 1.94 | 2.42 | −0.38 | 1.46 | 0.072828238 | 0 |
| hsa-miR-518b | 1.72 | 1.57 | 1.77 | 2.26 | 0.15 | 1.17 | 0.594786543 | 0 |
| ambi-miR-7029 | 1.66 | 7.00 | 7.22 | 5.37 | −5.35 | 209.78 | 3.62222E−13 | 1 |
| hsa-miR-491 | 4.27 | 3.92 | 3.97 | 4.36 | 0.35 | 1.42 | 0.033448437 | 1 |
| hsa-miR-509 | 1.64 | 2.15 | 1.89 | 2.17 | −0.51 | 1.67 | 0.00486388 | 1 |
| ambi-miR-7036 | 1.95 | 2.81 | 2.83 | 2.44 | −0.86 | 2.37 | 0.004226539 | 1 |
| hsa-miR-193b | 7.45 | 6.66 | 6.72 | 6.42 | 0.79 | 2.20 | 0.016824316 | 1 |
| hsa-miR-524-AS | 2.00 | 2.36 | 2.79 | 2.38 | −0.36 | 1.43 | 0.208631744 | 0 |
| hsa-miR-515-5p | 2.13 | 1.44 | 1.87 | 2.09 | 0.69 | 2.00 | 0.004290557 | 1 |
| hsa-miR-519e-AS | 2.47 | 1.75 | 2.11 | 2.10 | 0.72 | 2.05 | 0.00883769 | 1 |
| hsa-miR-498 | 2.27 | 2.16 | 3.11 | 2.77 | 0.10 | 1.11 | 0.633478617 | 0 |
| hsa-miR-513 | 4.76 | 4.22 | 4.47 | 4.85 | 0.54 | 1.72 | 0.033217171 | 1 |
| ambi-miR-7062 | 3.29 | 2.42 | 2.49 | 3.20 | 0.87 | 2.39 | 0.000309653 | 1 |
| hsa-miR-432 | 3.03 | 4.89 | 4.82 | 4.32 | −1.86 | 6.44 | 1.04598E−09 | 1 |
| hsa-miR-495 | 1.64 | 4.66 | 4.50 | 3.30 | −3.02 | 20.49 | 4.41648E−11 | 1 |
| ambi-miR-7066 | 1.76 | 2.53 | 2.28 | 1.75 | −0.77 | 2.17 | 0.000961526 | 1 |
| ambi-miR-7067 | 1.88 | 2.71 | 2.56 | 2.34 | −0.83 | 2.28 | 0.002027711 | 1 |
| ambi-miR-7068-1 | 1.23 | 3.03 | 3.28 | 2.46 | −1.79 | 6.00 | 1.27449E−07 | 1 |
| ambi-miR-7070 | 1.89 | 4.45 | 4.44 | 2.95 | −2.56 | 12.95 | 1.73207E−10 | 1 |
| hsa-miR-492 | 2.03 | 1.80 | 2.04 | 2.67 | 0.23 | 1.26 | 0.455020614 | 0 |
| hsa-miR-497 | 3.52 | 7.70 | 7.09 | 5.86 | −4.18 | 65.14 | 5.55959E−16 | 1 |
| ambi-miR-7074 | 2.62 | 1.84 | 1.84 | 2.34 | 0.78 | 2.18 | 0.019048309 | 1 |
| ambi-miR-7075 | 2.82 | 3.93 | 3.71 | 3.35 | −1.11 | 3.03 | 2.91216E−06 | 1 |
| ambi-miR-7079 | 2.72 | 4.13 | 4.29 | 5.44 | −1.41 | 4.08 | 0.010883261 | 1 |
| ambi-miR-7083 | 4.79 | 7.54 | 6.85 | 6.59 | −2.75 | 15.60 | 3.97052E−06 | 1 |
| ambi-miR-7085 | 3.09 | 4.36 | 4.31 | 3.39 | −1.27 | 3.56 | 0.00010135 | 1 |
| ambi-miR-7086 | 4.23 | 2.80 | 2.64 | 2.91 | 1.43 | 4.17 | 0.000431178 | 1 |
| hsa-miR-503 | 5.24 | 6.15 | 5.85 | 5.53 | −0.91 | 2.48 | 0.02892035 | 1 |
| hsa-miR-505 | 4.59 | 4.68 | 4.75 | 3.95 | −0.09 | 1.09 | 0.57775453 | 0 |
| ambi-miR-7100 | 2.20 | 3.24 | 2.78 | 2.22 | −1.03 | 2.81 | 9.26051E−05 | 1 |
| ambi-miR-7101 | 2.09 | 4.11 | 3.76 | 2.31 | −2.02 | 7.55 | 5.97147E−08 | 1 |

| miRNA | ΔH CL vs NAT | FC CL vs NAT | p-value CL vs NAT | Flag CL vs NAT | ΔH CL vs Ca | FC CL vs Ca | p-value CL vs Ca | Flag CL vs Ca |
|---|---|---|---|---|---|---|---|---|
| hsa-let-7a | −0.65 | 1.91 | 0.002564156 | 1 | −0.20 | 1.22 | 0.408622193 | 0 |
| hsa-let-7b | −0.99 | 2.69 | 0.002830398 | 1 | −0.50 | 1.64 | 0.171044287 | 0 |
| hsa-let-7c | −1.40 | 4.05 | 4.91843E−05 | 1 | −0.59 | 1.81 | 0.07499268 | 0 |
| hsa-let-7d | −0.55 | 1.73 | 0.009512494 | 1 | 0.07 | 1.07 | 0.785132203 | 0 |
| hsa-let-7e | −0.20 | 1.23 | 0.546555934 | 0 | 0.73 | 2.07 | 0.046196278 | 0 |
| hsa-let-7f | −0.54 | 1.72 | 0.021784695 | 1 | 0.19 | 1.21 | 0.531964694 | 0 |
| hsa-let-7g | −0.63 | 1.88 | 0.012387609 | 1 | 0.07 | 1.07 | 0.816115287 | 0 |
| hsa-let-7i | −0.37 | 1.45 | 0.181899088 | 0 | −0.12 | 1.13 | 0.669938425 | 0 |
| hsa-miR-1 | −3.32 | 27.64 | 2.00372E−08 | 1 | −0.44 | 1.55 | 0.132899703 | 0 |
| hsa-miR-100 | −1.19 | 3.30 | 0.005694202 | 1 | 0.55 | 1.74 | 0.224775916 | 0 |
| hsa-miR-101 | −0.46 | 1.59 | 0.203682031 | 0 | 0.60 | 1.82 | 0.055732231 | 0 |
| hsa-miR-105 | 0.83 | 2.30 | 0.017527241 | 1 | 0.83 | 2.30 | 0.086176225 | 0 |

TABLE 12-continued miRNAs Differentially Expressed Among Five Cervical Cancer-Derived Cell Lines, Nine Cervical Cancer Samples (Ca), Nine Paired Normal Adjacent Tissue Samples (NAT), and Sixteen Normal Cervix Tissue Samples (NCX). FC; Fold Change

| | | | | | | | |
|---|---|---|---|---|---|---|---|
| hsa-miR-106a | 0.81 | 2.24 | 0.001580081 | 1 | 0.15 | 1.17 0.527869905 | 0 |
| hsa-miR-106b | 1.90 | 6.71 | 4.45187E−07 | 1 | 1.03 | 2.81 7.94937E−05 | 1 |
| hsa-miR-10a | −0.62 | 1.87 | 0.249709156 | 0 | −0.31 | 1.36 0.55761954 | 0 |
| hsa-miR-10b | −2.24 | 9.37 | 0.000174992 | 1 | −0.81 | 2.24 0.020759589 | 1 |
| hsa-miR-124a | −0.13 | 1.14 | 0.610942253 | 0 | 0.07 | 1.07 0.825943217 | 0 |
| hsa-miR-125a | −0.97 | 2.63 | 0.010290547 | 1 | 0.23 | 1.26 0.547660553 | 0 |
| hsa-miR-125b | −2.83 | 16.94 | 6.69813E−06 | 1 | −1.46 | 4.32 0.009761948 | 1 |
| hsa-miR-126 | −5.04 | 154.13 | 1.41255E−09 | 1 | −3.88 | 48.29 8.32735E−08 | 1 |
| hsa-miR-126-AS | −3.54 | 34.44 | 1.27765E−06 | 1 | −2.12 | 8.36 7.59077E−05 | 1 |
| hsa-miR-127 | −2.13 | 8.38 | 4.80286E−05 | 1 | −1.04 | 2.82 0.009006179 | 1 |
| hsa-miR-128a | 0.57 | 1.76 | 0.007532189 | 1 | 0.49 | 1.64 0.002929175 | 1 |
| hsa-miR-130a | 1.16 | 3.20 | 0.003096519 | 1 | 1.80 | 6.04 0.000106276 | 1 |
| hsa-miR-130b | 1.64 | 5.16 | 1.71419E−06 | 1 | 0.79 | 2.20 0.007077483 | 1 |
| hsa-miR-132 | −0.71 | 2.03 | 0.081087439 | 0 | −0.82 | 2.27 0.042851307 | 0 |
| hsa-miR-133a | −4.59 | 98.12 | 3.48512E−07 | 1 | −2.02 | 7.53 0.001764406 | 1 |
| hsa-miR-134 | −2.30 | 10.00 | 8.38805E−07 | 1 | −1.20 | 3.33 7.1367E−05 | 1 |
| hsa-miR-135b | 0.45 | 1.57 | 0.108684941 | 0 | −0.36 | 1.44 0.298588113 | 0 |
| hsa-miR-138 | 2.05 | 7.80 | 0.00444813 | 1 | 2.09 | 8.07 0.003905859 | 1 |
| hsa-miR-139 | −1.75 | 5.73 | 0.003869851 | 1 | −0.49 | 1.63 0.41652404 | 0 |
| hsa-miR-140 | −1.39 | 3.99 | 0.003243831 | 1 | −0.45 | 1.58 0.229185331 | 0 |
| hsa-miR-142-3p | −1.13 | 3.10 | 0.004072312 | 1 | −1.71 | 5.52 0.00032376 | 1 |
| hsa-miR-142-5p | −1.64 | 5.17 | 0.000654177 | 1 | −1.48 | 4.39 0.000140237 | 1 |
| hsa-miR-143 | −8.19 | 3611.68 | 1.20011E−13 | 1 | −6.40 | 600.17 1.98343E−09 | 1 |
| hsa-miR-145 | −8.74 | 6240.79 | 5.82229E−12 | 1 | −7.26 | 1414.69 1.14504E−09 | 1 |
| hsa-miR-146a | −3.43 | 30.98 | 4.17614E−09 | 1 | −4.19 | 65.79 2.34555E−09 | 1 |
| hsa-miR-148a | −1.26 | 3.51 | 0.015346304 | 1 | −1.09 | 2.97 0.044294998 | 0 |
| hsa-miR-148b | 0.43 | 1.54 | 0.03781447 | 0 | 0.53 | 1.70 0.004486178 | 1 |
| hsa-miR-150 | −4.58 | 97.14 | 4.78549E−09 | 1 | −4.85 | 127.67 5.46053E−07 | 1 |
| hsa-miR-151 | 0.40 | 1.49 | 0.016309379 | 1 | 0.55 | 1.73 0.005690752 | 1 |
| hsa-miR-152 | −0.82 | 2.27 | 0.00058475 | 1 | −0.05 | 1.06 0.805456909 | 0 |
| hsa-miR-153 | 0.08 | 1.08 | 0.736937712 | 0 | 0.04 | 1.04 0.867324584 | 0 |
| hsa-miR-154 | −3.00 | 19.99 | 5.23142E−06 | 1 | −1.74 | 5.67 0.000728255 | 1 |
| hsa-miR-155 | −0.42 | 1.53 | 0.491586137 | 0 | −1.87 | 6.48 0.010771346 | 1 |
| hsa-miR-15a | 0.67 | 1.96 | 0.010596657 | 1 | 0.64 | 1.90 0.003606718 | 1 |
| hsa-miR-15b | 0.94 | 2.55 | 0.000148959 | 1 | 0.09 | 1.09 0.702117193 | 0 |
| hsa-miR-16 | 0.09 | 1.10 | 0.461554909 | 0 | −0.24 | 1.27 0.129958328 | 0 |
| hsa-miR-17-3p | 1.27 | 3.55 | 1.51532E−06 | 1 | 0.97 | 2.62 0.000297975 | 1 |
| hsa-miR-17-5p | 0.78 | 2.17 | 0.001578005 | 1 | 0.08 | 1.08 0.757523816 | 0 |
| hsa-miR-18a | 2.04 | 7.70 | 8.73636E−05 | 1 | 0.61 | 1.84 0.039550432 | 1 |
| hsa-miR-181a | 0.23 | 1.26 | 0.398873106 | 0 | 0.04 | 1.04 0.880408981 | 0 |
| hsa-miR-181b | 1.28 | 3.60 | 0.002890922 | 1 | 0.66 | 1.94 0.086682478 | 0 |
| hsa-miR-181c | 0.69 | 1.99 | 0.011080834 | 1 | 0.90 | 2.46 0.004103805 | 1 |
| hsa-miR-182 | 2.49 | 12.04 | 6.17572E−05 | 1 | 0.80 | 2.23 0.000968959 | 1 |
| hsa-miR-183 | 2.14 | 8.47 | 2.50383E−06 | 1 | 0.55 | 1.74 0.021123146 | 1 |
| hsa-miR-184 | −0.92 | 2.52 | 0.020419376 | 1 | −0.84 | 2.33 0.028295762 | 0 |
| hsa-miR-185 | 0.64 | 1.89 | 0.003357543 | 1 | 0.18 | 1.20 0.401570526 | 0 |
| hsa-miR-186 | −0.07 | 1.07 | 0.734671749 | 0 | 0.66 | 1.93 0.016423569 | 1 |
| hsa-miR-187 | −1.47 | 4.36 | 0.007772722 | 1 | −2.53 | 12.49 0.000163213 | 1 |
| hsa-miR-188 | 1.17 | 3.22 | 0.000816505 | 1 | 1.09 | 2.98 0.000548352 | 1 |
| hsa-miR-189 | −0.87 | 2.39 | 0.013603201 | 1 | −0.14 | 1.15 0.487108945 | 0 |
| hsa-miR-190 | 0.21 | 1.24 | 0.390558273 | 0 | 0.51 | 1.67 0.037952429 | 1 |
| hsa-miR-192 | −0.11 | 1.11 | 0.736350941 | 0 | −0.38 | 1.46 0.223147494 | 0 |
| hsa-miR-194 | −0.22 | 1.24 | 0.385520786 | 0 | −0.36 | 1.43 0.070919825 | 0 |
| hsa-miR-195 | −3.71 | 40.97 | 6.14258E−10 | 1 | −2.10 | 8.14 2.10883E−05 | 1 |
| hsa-miR-196a | 1.64 | 5.17 | 0.02833625 | 1 | 1.62 | 5.06 0.008101535 | 1 |
| hsa-miR-196b | −1.29 | 3.63 | 0.082926301 | 0 | −0.73 | 2.07 0.008323833 | 1 |
| hsa-miR-198 | −0.67 | 1.96 | 0.097498873 | 0 | −0.86 | 2.37 0.007107716 | 1 |
| hsa-miR-199a | −6.20 | 494.45 | 7.31672E−11 | 1 | −5.71 | 302.14 1.49322E−09 | 1 |
| hsa-miR-199a-AS | −6.13 | 460.97 | 2.34691E−10 | 1 | −5.45 | 231.79 1.54312E−09 | 1 |
| hsa-miR-199b | −4.46 | 86.45 | 8.68444E−08 | 1 | −3.44 | 31.24 1.71423E−06 | 1 |
| hsa-miR-19a | 2.16 | 8.65 | 4.31416E−05 | 1 | 1.57 | 4.81 0.000330652 | 1 |
| hsa-miR-19b | 0.82 | 2.28 | 0.009387699 | 1 | 0.41 | 1.50 0.074727832 | 0 |
| hsa-miR-20a | 0.47 | 1.60 | 0.097058425 | 0 | 0.05 | 1.05 0.86056343 | 0 |
| hsa-miR-200a | −1.06 | 2.89 | 0.301256418 | 0 | −2.55 | 12.77 0.018139637 | 1 |
| hsa-miR-200b | −1.75 | 5.73 | 0.121392088 | 0 | −2.94 | 18.82 0.011484585 | 1 |
| hsa-miR-200c | −2.38 | 10.75 | 0.039122382 | 0 | −3.62 | 37.35 0.003490819 | 1 |
| hsa-miR-203 | −3.82 | 45.79 | 0.004799045 | 1 | −4.05 | 57.62 0.000119271 | 1 |
| hsa-miR-204 | −2.60 | 13.49 | 9.97564E−07 | 1 | −0.46 | 1.59 0.160067155 | 0 |
| hsa-miR-205 | −3.15 | 23.23 | 0.094490207 | 0 | −5.20 | 181.39 0.003096347 | 1 |
| hsa-miR-206 | −0.67 | 1.95 | 0.05445294 | 0 | −0.76 | 2.13 0.019626819 | 1 |
| hsa-miR-21 | 0.97 | 2.64 | 0.001185624 | 1 | −0.26 | 1.30 0.185574026 | 0 |
| hsa-miR-210 | 0.73 | 2.08 | 0.172153768 | 0 | 0.19 | 1.20 0.725839109 | 0 |
| hsa-miR-213 | −0.44 | 1.55 | 0.076540795 | 0 | −0.72 | 2.05 0.006000676 | 1 |
| hsa-miR-214 | −4.83 | 125.74 | 1.09298E−11 | 1 | −4.17 | 64.97 2.38826E−09 | 1 |
| hsa-miR-215 | −0.99 | 2.69 | 0.001666504 | 1 | −0.63 | 1.88 0.011311119 | 1 |
| hsa-miR-218 | −1.96 | 7.08 | 0.000229654 | 1 | 0.02 | 1.03 0.949339108 | 0 |

TABLE 12-continued miRNAs Differentially Expressed Among Five Cervical Cancer-Derived Cell Lines, Nine
Cervical Cancer Samples (Ca), Nine Paired Normal Adjacent Tissue Samples (NAT), and Sixteen
Normal Cervix Tissue Samples (NCX). FC; Fold Change

| | | | | | | | | |
|---|---|---|---|---|---|---|---|---|
| hsa-miR-222 | 0.55 | 1.74 | 0.085666914 | 0 | 0.87 | 2.38 | 0.022942193 | 0 |
| hsa-miR-223 | −4.31 | 74.48 | 8.07424E−09 | 1 | −5.11 | 165.86 | 1.18338E−08 | 1 |
| hsa-miR-224 | −0.29 | 1.33 | 0.72590801 | 0 | −1.53 | 4.61 | 0.075392183 | 0 |
| hsa-miR-23b | −0.93 | 2.52 | 0.000190145 | 1 | −0.47 | 1.61 | 0.020550201 | 1 |
| hsa-miR-24 | −0.57 | 1.77 | 0.001539146 | 1 | −0.26 | 1.29 | 0.206303311 | 0 |
| hsa-miR-25 | 0.90 | 2.47 | 0.000710397 | 1 | 0.41 | 1.51 | 0.047208289 | 0 |
| hsa-miR-26a | −1.75 | 5.73 | 5.81949E−06 | 1 | −1.00 | 2.72 | 0.000704867 | 1 |
| hsa-miR-26b | −1.42 | 4.15 | 1.91084E−05 | 1 | −0.26 | 1.29 | 0.264825843 | 0 |
| hsa-miR-27a | 0.10 | 1.11 | 0.62104518 | 0 | 0.29 | 1.34 | 0.149270954 | 0 |
| hsa-miR-27b | −0.86 | 2.36 | 0.001713904 | 1 | −0.02 | 1.02 | 0.930534106 | 0 |
| hsa-miR-28 | −0.56 | 1.75 | 0.003954264 | 1 | 0.22 | 1.24 | 0.120960033 | 0 |
| hsa-miR-296 | 0.14 | 1.15 | 0.559440544 | 0 | 0.22 | 1.25 | 0.588177213 | 0 |
| hsa-miR-299-5p | −2.22 | 9.17 | 8.45749E−06 | 1 | −0.81 | 2.25 | 0.037207215 | 0 |
| hsa-miR-29a | 0.32 | 1.37 | 0.215472392 | 0 | 1.02 | 2.76 | 0.000932502 | 1 |
| hsa-miR-29b | 1.40 | 4.07 | 0.003550866 | 1 | 1.76 | 5.84 | 0.001243472 | 1 |
| hsa-miR-29c | −0.44 | 1.56 | 0.195423205 | 0 | 0.32 | 1.38 | 0.473002447 | 0 |
| hsa-miR-301 | 2.55 | 12.76 | 1.47153E−06 | 1 | 1.87 | 6.48 | 0.000171342 | 1 |
| hsa-miR-302a | −0.91 | 2.49 | 0.003269396 | 1 | −0.92 | 2.52 | 0.005581583 | 1 |
| hsa-miR-30a-3p | 1.47 | 4.36 | 0.000293427 | 1 | 2.77 | 15.90 | 5.43344E−08 | 1 |
| hsa-miR-30a-5p | 0.72 | 2.05 | 0.007569169 | 1 | 1.25 | 3.50 | 3.23694E−05 | 1 |
| hsa-miR-30b | −0.48 | 1.62 | 0.093238229 | 0 | 0.17 | 1.19 | 0.442986905 | 0 |
| hsa-miR-30d | −0.11 | 1.11 | 0.64385759 | 0 | 0.38 | 1.46 | 0.13999398 | 0 |
| hsa-miR-30e-3p | 0.68 | 1.98 | 0.014957136 | 1 | 1.05 | 2.85 | 0.003054267 | 1 |
| hsa-miR-31 | 1.66 | 5.25 | 0.01168522 | 1 | 0.25 | 1.28 | 0.5059954 | 0 |
| hsa-miR-320 | −0.06 | 1.06 | 0.803938004 | 0 | 0.50 | 1.64 | 0.086826188 | 0 |
| hsa-miR-324-3p | −0.88 | 2.40 | 0.000929575 | 1 | −0.46 | 1.58 | 0.054810824 | 0 |
| hsa-miR-324-5p | 0.49 | 1.63 | 0.203625976 | 0 | 0.83 | 2.30 | 0.028072305 | 0 |
| hsa-miR-326 | −0.74 | 2.09 | 0.018838903 | 1 | −0.72 | 2.06 | 0.032319463 | 0 |
| hsa-miR-328 | −1.22 | 3.39 | 0.002008415 | 1 | −0.37 | 1.45 | 0.256066853 | 0 |
| hsa-miR-330 | 0.83 | 2.28 | 0.022063627 | 1 | 0.12 | 1.13 | 0.784395438 | 0 |
| hsa-miR-335 | 0.92 | 2.50 | 0.056332812 | 0 | 1.61 | 5.02 | 0.000877309 | 1 |
| hsa-miR-339 | −0.28 | 1.33 | 0.027547838 | 1 | −0.46 | 1.58 | 0.012750132 | 1 |
| hsa-miR-342 | −0.91 | 2.47 | 8.97736E−05 | 1 | −1.15 | 3.16 | 1.9368E−06 | 1 |
| hsa-miR-34a | 0.40 | 1.50 | 0.086483152 | 0 | 0.05 | 1.05 | 0.872377202 | 0 |
| hsa-miR-361 | −0.32 | 1.38 | 0.235159472 | 0 | 0.02 | 1.02 | 0.955596055 | 0 |
| hsa-miR-365 | 1.13 | 3.10 | 0.006874283 | 1 | 1.70 | 5.45 | 8.44234E−05 | 1 |
| hsa-miR-368 | −4.48 | 87.75 | 3.38864E−08 | 1 | −2.71 | 14.99 | 1.31584E−05 | 1 |
| hsa-miR-370 | −1.47 | 4.35 | 3.52893E−05 | 1 | −1.37 | 3.93 | 1.2933E−05 | 1 |
| hsa-miR-371 | 0.86 | 2.37 | 0.001357719 | 1 | 0.53 | 1.69 | 0.004253505 | 1 |
| hsa-miR-373-AS | −0.46 | 1.59 | 0.031106578 | 1 | −0.34 | 1.40 | 0.14850487 | 0 |
| hsa-miR-375 | −1.51 | 4.55 | 0.00259286 | 1 | −0.98 | 2.66 | 0.036365468 | 0 |
| hsa-miR-376a | −3.59 | 36.29 | 1.65581E−06 | 1 | −1.96 | 7.13 | 0.000521819 | 1 |
| hsa-miR-377 | −1.07 | 2.90 | 0.01970983 | 1 | −0.20 | 1.22 | 0.252806322 | 0 |
| hsa-miR-379 | −2.30 | 10.02 | 5.81312E−08 | 1 | −1.91 | 6.76 | 2.13163E−07 | 1 |
| hsa-miR-381 | −2.09 | 8.05 | 7.57949E−06 | 1 | −1.05 | 2.86 | 8.39637E−05 | 1 |
| hsa-miR-382 | −2.42 | 11.30 | 1.06896E−05 | 1 | −1.53 | 4.64 | 2.75985E−05 | 1 |
| hsa-miR-383 | −0.59 | 1.80 | 0.092925247 | 0 | −0.91 | 2.48 | 0.00156188 | 1 |
| hsa-miR-423 | 0.13 | 1.13 | 0.478565626 | 0 | −0.17 | 1.18 | 0.308298368 | 0 |
| hsa-miR-424 | −1.64 | 5.18 | 0.000658185 | 1 | −0.40 | 1.49 | 0.295865628 | 0 |
| hsa-miR-429 | −0.57 | 1.76 | 0.531543409 | 0 | −1.99 | 7.30 | 0.032765975 | 0 |
| hsa-miR-450 | −0.19 | 1.21 | 0.3720215 | 0 | 0.28 | 1.33 | 0.348374961 | 0 |
| hsa-miR-7 | 2.08 | 8.01 | 0.000951938 | 1 | 1.54 | 4.68 | 0.014016465 | 1 |
| hsa-miR-92 | 0.06 | 1.06 | 0.70820557 | 0 | −0.27 | 1.31 | 0.166735277 | 0 |
| hsa-miR-93 | 1.30 | 3.65 | 6.64559E−07 | 1 | 0.45 | 1.57 | 0.046468006 | 0 |
| hsa-miR-95 | −0.83 | 2.30 | 0.07643174 | 0 | −0.72 | 2.05 | 0.116093482 | 0 |
| hsa-miR-96 | 2.34 | 10.35 | 3.47237E−07 | 1 | 1.87 | 6.48 | 1.58105E−05 | 1 |
| hsa-miR-98 | −0.43 | 1.53 | 0.011085983 | 1 | 0.17 | 1.18 | 0.528087739 | 0 |
| hsa-miR-99a | −3.08 | 21.73 | 9.28027E−06 | 1 | −1.32 | 3.73 | 0.030040712 | 0 |
| hsa-miR-99b | −0.19 | 1.22 | 0.539575153 | 0 | 0.72 | 2.05 | 0.040375059 | 0 |
| hsa-miR-410 | −0.87 | 2.38 | 0.036886829 | 0 | −0.09 | 1.09 | 0.739616418 | 0 |
| hsa-miR-522 | 1.40 | 4.07 | 0.070263513 | 0 | 1.53 | 4.63 | 0.061064352 | 0 |
| hsa-miR-520d | −0.44 | 1.56 | 0.147379909 | 0 | −0.92 | 2.52 | 0.00432607 | 1 |
| hsa-miR-518b | −0.05 | 1.05 | 0.873268465 | 0 | −0.54 | 1.72 | 0.110312674 | 0 |
| ambi-miR-7029 | −5.56 | 260.63 | 4.28249E−08 | 1 | −3.72 | 41.09 | 7.1299E−06 | 1 |
| hsa-miR-491 | 0.30 | 1.35 | 0.091661144 | 0 | −0.09 | 1.10 | 0.69587552 | 0 |
| hsa-miR-509 | −0.25 | 1.28 | 0.167701698 | 0 | −0.53 | 1.71 | 0.027661107 | 0 |
| ambi-miR-7036 | −0.88 | 2.42 | 0.004928386 | 1 | −0.49 | 1.63 | 0.01880771 | 1 |
| hsa-miR-193b | 0.72 | 2.06 | 0.084513757 | 0 | 1.02 | 2.78 | 0.032211247 | 0 |
| hsa-miR-524-AS | −0.79 | 2.21 | 0.007754441 | 1 | −0.38 | 1.46 | 0.109201363 | 0 |
| hsa-miR-515-5p | 0.27 | 1.31 | 0.260180768 | 0 | 0.04 | 1.04 | 0.88336412 | 0 |
| hsa-miR-519e-AS | 0.35 | 1.42 | 0.128146687 | 0 | 0.37 | 1.45 | 0.059693136 | 0 |
| hsa-miR-498 | −0.84 | 2.32 | 4.60235E−05 | 1 | −0.50 | 1.65 | 0.020206169 | 1 |
| hsa-miR-513 | 0.29 | 1.33 | 0.241047983 | 0 | −0.09 | 1.09 | 0.758774837 | 0 |
| ambi-miR-7062 | 0.80 | 2.22 | 0.00042669 | 1 | 0.10 | 1.10 | 0.707610045 | 0 |
| hsa-miR-432 | −1.79 | 6.00 | 5.45133E−05 | 1 | −1.30 | 3.66 | 0.000109277 | 1 |
| hsa-miR-495 | −2.86 | 17.42 | 4.25236E−07 | 1 | −1.65 | 5.23 | 1.32828E−05 | 1 |

TABLE 12-continued miRNAs Differentially Expressed Among Five Cervical Cancer-Derived Cell Lines, Nine
Cervical Cancer Samples (Ca), Nine Paired Normal Adjacent Tissue Samples (NAT), and Sixteen
Normal Cervix Tissue Samples (NCX). FC; Fold Change

| | | | | | | | | |
|---|---|---|---|---|---|---|---|---|
| ambi-miR-7066 | −0.53 | 1.69 | 0.056367586 | 0 | 0.01 | 1.01 | 0.973973967 | 0 |
| ambi-miR-7067 | −0.68 | 1.97 | 0.04749556 | 0 | −0.46 | 1.59 | 0.150876999 | 0 |
| ambi-miR-7068-1 | −2.05 | 7.76 | 0.00016193 | 1 | −1.23 | 3.41 | 0.001025432 | 1 |
| ambi-miR-7070 | −2.56 | 12.91 | 8.73303E−06 | 1 | −1.06 | 2.88 | 0.00569231 | 1 |
| hsa-miR-492 | −0.01 | 1.01 | 0.970600957 | 0 | −0.64 | 1.90 | 0.083677666 | 0 |
| hsa-miR-497 | −3.57 | 35.62 | 2.0527E−09 | 1 | −2.34 | 10.39 | 1.97045E−05 | 1 |
| ambi-miR-7074 | 0.78 | 2.18 | 0.055468623 | 0 | 0.28 | 1.33 | 0.440054074 | 0 |
| ambi-miR-7075 | −0.89 | 2.43 | 0.001511717 | 1 | −0.52 | 1.69 | 0.076818689 | 0 |
| ambi-miR-7079 | −1.57 | 4.80 | 0.01306748 | 1 | −2.72 | 15.10 | 0.001223169 | 1 |
| ambi-miR-7083 | −2.06 | 7.86 | 0.00580768 | 1 | −1.79 | 6.02 | 0.004943006 | 1 |
| ambi-miR-7085 | −1.22 | 3.39 | 0.001465025 | 1 | −0.30 | 1.35 | 0.366910567 | 0 |
| ambi-miR-7086 | 1.59 | 4.89 | 0.002633915 | 1 | 1.32 | 3.75 | 0.010693738 | 1 |
| hsa-miR-503 | −0.61 | 1.84 | 0.029692919 | 1 | −0.29 | 1.34 | 0.219217668 | 0 |
| hsa-miR-505 | −0.16 | 1.18 | 0.350664693 | 0 | 0.64 | 1.90 | 0.021085413 | 1 |
| ambi-miR-7100 | −0.58 | 1.79 | 0.079960504 | 0 | −0.02 | 1.02 | 0.948236753 | 0 |
| ambi-miR-7101 | −1.67 | 5.29 | 0.000195791 | 1 | −0.22 | 1.25 | 0.522072423 | 0 |

*; F.C., Fold Change

On average, 186 miRNAs were detected above background in the cell lines, corresponding to 49.5% of the miRNAs present on the array. As more than 200 miRNAs were detected above background in the normal cervix, cervical cancer, and normal adjacent tissue specimens, this indicates that expression of some miRNAs is lost in the cell lines evaluated here. Thirty-three miRNAs expressed in normal cervix samples, 27 miRNAs expressed in cervical tumor samples, and 41 miRNAs expressed in normal adjacent tissue samples were not expressed above background levels in the cell lines.

One hundred and forty-five human miRNAs (130 hsa-miRNAs and 15 ambi-miR5) had significantly different expression levels between the cell lines and the normal cervix samples (Table 12; Flag (CL vs NCX)=1). Among these miRNAs, 83 were down-regulated and 39 were up-regulated by at least 2-fold in the CL samples (FC, CLvsNCX≥2.0). Of these, 48 miRNAs were down-regulated by more than 5-fold in the CL samples (ΔH(CL−NCX)<−1.6), 31 were down-regulated by more than 10-fold in the CL samples (ΔH(CL−NCX)<−2.3), and 10 (hsa-miR-145, -143, -199a, -199aAS, -368, -214, -126, -133a, 199b, and Ambi-miR 7029) were down-regulated by more than 100-fold in the CL samples (ΔH(CL−NCX)<−4.61) (Table 12). In contrast, 11 miRNAs were up-regulated by more than 5-fold in the cell lines compared to the normal cervix samples (ΔH(CL-NCX)>1.6), including 3 miRNAs (hsa-miR-183, -182, and -96) that were over-expressed by more than 10-fold (ΔH(CL−NCX)>2.3). Overall, 56 miRNAs were identified that had a differential expression of more than 2-fold between Ca and NCX samples or between CL and NCX samples.

Figure 3:
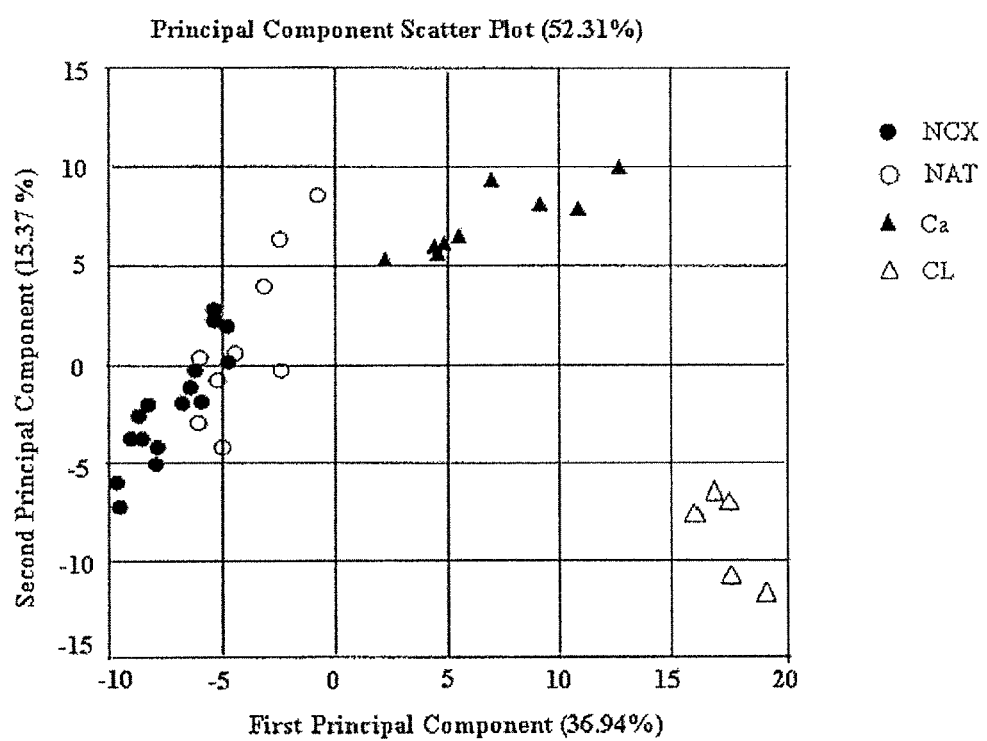
FIG. 3 Principal Component Analysis of miRNAs expressed in normal cervix sample (NCX), cancerous cervix samples (Ca) and paired normal adjacent cervix samples (NAT), and cervical cancer cell lines (CL).

Hierarchical clustering and principal component analysis on the global miRNA expression data showed a clear segregation between the cell line samples (CL), and the three tissue samples (Ca, NAT, NCX). Further, the normal cervix (NCX) and normal adjacent tissue samples (NAT) clustered away from the cervical tumor samples (Ca) and the cell lines (CL) (FIG. 3). This observation was confirmed by pair-wise comparison of Pearson correlation values, calculated using mean normalized data for the 377 individual miRNAs on the array (Table 13). Overall, the mean miRNA expression levels in cell lines correlated better with expression levels in cervical cancer samples than with expression levels in normal adjacent and normal tissue samples.

TABLE 13

Paired Pearson Correlation Values. Values were calculated
using mean normalized miRNA expression levels.

| | NCX | NAT | Ca | CL |
|---|---|---|---|---|
| NCX | 1 | 0.99 | 0.95 | 0.81 |
| NAT | | 1 | 0.97 | 0.82 |
| Ca | | | 1 | 0.87 |
| CL | | | | 1 |

Example 8 miRNA Expression Differences in Cervical Cancer Specimens and Cervical Cancer Cell Lines Associated with HPV Status Among the nine cervical cancer specimens (Ca) analyzed, 4 were identified as positive for HPV16, 3 were positive for HPV18, 1 was positive for both HPV16 and HPV18, and 1 was negative for both HPV16 and 18, as determined by RT-PCR, using specific primers for the E6 open reading frames of HPV 16 and HPV 18. To investigate whether miRNA expression profiles could help distinguish between HPV16-positive and HPV18-positive cervical cancers, a pair wise t-test comparison was performed between the four HPV16-positive cancers and the three HPV18-positive cancers. No statistically significant differences were observed between the microRNA expression profiles of HPV16-positive and HPV18-positive cervical cancers.

Similarly, a pair wise t-test comparison between the three cell lines that are HPV18-positive and the two cell lines that are HPV16-positive did not reveal any miRNAs with significantly different expression between the two groups.

Example 9

Identification of a Classifier for Cervical Cancer by qRT-PCR

Figure 4:
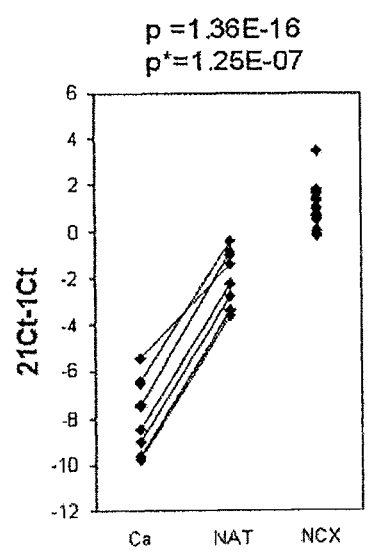
FIG. 4 Expression of miR-21 and miR-1 classifies normal and cancerous cervical tissues. Real time RT-PCR were performed with primer sets specific for miR-1 and miR-21 using 15 ng total RNA from 16 normal cervix (NCX), 9 cancerous cervix (Ca), or 9 normal adjacent cervix (NAT) samples. Raw Ct values were directly used to calculate the ratio of miR-21 to miR-1 expression, i.e., miR-21 Ct-miR1 Ct in the logarithmic space.

Analyses of global miRNA expression profiles (Table 5, Table 7), differentially expressed miRNAs (Table 8, Table 12), and the top 23 differentially expressed miRNA markers (Table 9) indicated that miRNA expression can distinguish normal and cancerous cervical tissues. To take this classification one step further, the minimal set of miRNAs that could discriminate between cancerous and non-cancerous tissues were identified by applying a quantitative RT-PCR analysis of mature miRNAs. The inventors found that the difference between raw Ct values of two miRNAs (miR-1 and -21) fulfilled the criteria (FIG. 4). qRT-PCR experiments performed on the 34 samples (NCX, CA, NAT) showed a perfect segregation between normal cervix (NCX), cervical cancer (Ca) and normal adjacent tissue (NAT) with a p-value of $1.36 \times 10^{-16}$.

Example 10

High Density Microarray Analysis of miRNAs in Normal Cervix and Cervical Cancer Samples miRNA Array Expression Analysis:

microRNA-containing fractions were recovered from 10 μg of total RNA isolated from each RNA sample, using the FlashPage fractionation system (Ambion, Inc.). Purified small RNAs were enzymatically biotinylated at the 3'-termini and hybridized to a custom-made Affymetrix based microRNA array, Asuragen's DiscovArrays V.1 containing probes for 14,215 verified and candidate miRNAs from a number of sources including Sanger miRBase v9.2 database (http:microrna.sanger.ac.uk/sequences/) and published reports. Hybridization, washing, staining, imaging, and signal extraction were performed as recommended by the manufacturer, except that the 20X GeneChip® Eukaryotic Hybridization Control cocktail was omitted.

Array Data Processing:

The signal processing implemented for the Ambion miR-CHIP is a multi-step process involving probe specific signal detection calls, background estimate and correction, constant variance stabilization and either array scaling or global normalization. For an overview of miRNA processing and analysis, see Davison et al. (2006). For more details, see supplementary information.

Probe Specific Signal Detection Calls:

Each probe on an array is assayed for detection based on a Wilcoxon rank-sum test of the miRNA probe signal compared to the distribution of signals from GC-content matched anti-genomic probes. If the resulting p-value for the probes is ≤0.06 then it is considered "Detected above background." Probes with p-values>0.06 have insufficient signal to discriminate from the background and are thus considered not detected.

Background Estimate and Correction:

The same set of anti-genomic probes used to determine detection calls are used to estimate GC-content matched background signals. Each miRNA probe signal has a GC-content matched background estimate subtracted from its value. This GC-specific background contribution is estimated by the median signal from the distribution of GC-matched anti-genomic probes.

Constant Variance Stabilization:

Probes with low signal often exhibit a high degree of variability once transformed into logarithmic scales. To stabilize this low signal variability we add a constant value of 16 to the background corrected signal. This technique is commonly performed on microarray data. It was the recommended data preprocessing method by Affymetrix and Illumina in the MicroArray Quality Control (MAQC) project.

Normalization:

The data were normalized with the VSN method (Huber et al., 2002; Szafranska et al., 2007). Briefly, VSN is a global normalization process that stabilizes the variance evenly across the entire range of expression. Differences in VSN transformed expression are denoted by Log 2 diff and were used for all subsequent data analyses. Differences in normalized expression values between samples (Log 2 diff) can be transformed to a generalized fold change via exponentiation base 2. These values will exhibit a compression for small differences in expression.

Nine cervical cancer specimens (Ca1-Ca9) and four normal cervix samples (NCX3, NCX10, NCX13, and a new normal cervix sample—NCX17) were analyzed by the DiscovArray™ miRNA Expression Profiling Service (Asuragen). The DiscovArray™ microarray contains probes for 994 miRNAs from Sanger miRBase V9.2 (Griffiths-Jones et al., 2006) (467 human miRNAs, 234 rat miRNAs, 293 mouse miRNAs) and 12,894 predicted human miRNAs (see world wide web page at asuragen.com/services/discovarray.html).

One hundred forty four miRNAs were significantly differentially expressed between NCX and Ca samples by at least 2-fold (Table 14). Of those, 136 were down-regulated (Log 2 Diff Ca vs NCX≤−1.0) and 8 were up-regulated (Log 2 Diff Ca vs NCX≥1.0) in Ca samples compared to NCX samples. Sixty-three (63) miRNAs were down-regulated in Ca samples by more than 5-fold (Log 2 Diff Ca vs NCX≤−2.3) with a p-value<0.0001. Seventeen of those miRNAs were down-regulated by over 10-fold in Ca samples (Log 2 Diff Ca vs NCX≤−3.3).

TABLE 14 miRNAs Differentially Expressed Among Nine Cervical Cancer Samples (Ca) and Four Normal Cervix Tissue Samples (NCX) Following Expression Analysis on High-Density Microarrays. FC; Fold Change.

| miRNA[a] | Ca 8 | Ca 9 | Ca 5 | Ca 7 | Ca 6 | Ca 4 | Ca 3 | Ca 2 | Ca 1 | Mean (Ca) | % Ca | NCX 17 |
|---|---|---|---|---|---|---|---|---|---|---|---|---|
| hsa-miR-133b | 5.05 | 4.50 | 6.56 | 5.58 | 6.52 | 4.91 | 2.50 | 5.95 | 3.17 | 4.97 | 22.2 | 8.68 |
| hsa-miR-133a | 5.8 | 5.03 | 7.38 | 5.71 | 7.33 | 5.07 | 4.61 | 6.35 | 3.61 | 5.66 | 33.3 | 9.47 |
| hsa-miR-204 | 6.09 | 3.53 | 5.74 | 4.48 | 5.57 | 4.56 | 3.87 | 3.11 | 2.92 | 4.43 | 0 | 9.09 |
| hsa-miR-497 | 6.16 | 3.94 | 6.05 | 4.66 | 4.37 | 5.33 | 3.65 | 6.01 | 2.03 | 4.69 | 0 | 9.14 |
| hsa-miR-368 | 9.35 | 6.36 | 7.39 | 7.75 | 7.77 | 7.50 | 6.98 | 8.11 | 4.89 | 7.35 | 88.8 | 11.2 |
| hsa-miR-455 | 5.57 | 5.00 | 4.99 | 6.23 | 4.53 | 5.33 | 5.40 | 6.50 | 3.28 | 5.20 | 33.3 | 8.49 |
| hsa-miR-497 | 7.45 | 5.76 | 6.47 | 7.07 | 6.04 | 6.62 | 5.95 | 7.49 | 5.36 | 6.47 | 22.2 | 10.1 |
| hsa-asg-13254_st1 | 7.63 | 5.25 | 6.68 | 6.18 | 6.96 | 6.48 | 6.08 | 7.05 | 3.40 | 6.19 | 77.7 | 10.3 |
| hsa-miR-299-5p | 7.50 | 5.49 | 6.61 | 5.88 | 6.49 | 5.29 | 5.99 | 6.88 | 4.29 | 6.05 | 66.6 | 9.86 |
| hsa-asg-14176_st1 | 6.29 | 5.40 | 5.82 | 5.81 | 5.07 | 5.87 | 6.35 | 6.04 | 4.14 | 5.64 | 11.1 | 9.00 |
| hsa-miR-495 | 7.80 | 5.00 | 7.49 | 7.24 | 6.89 | 6.17 | 6.46 | 7.52 | 4.06 | 6.51 | 77.7 | 10.3 |

TABLE 14-continued miRNAs Differentially Expressed Among Nine Cervical Cancer Samples (Ca) and Four Normal Cervix Tissue Samples (NCX) Following Expression Analysis on High-Density Microarrays. FC; Fold Change.

| | | | | | | | | | | | | |
|---|---|---|---|---|---|---|---|---|---|---|---|---|
| hsa-miR-381 | 5.14 | 3.85 | 4.55 | 4.20 | 4.76 | 3.92 | 3.48 | 4.88 | 2.92 | 4.19 | 0 | 7.41 |
| hsa-miR-487b | 7.75 | 5.84 | 7.55 | 7.03 | 7.22 | 6.90 | 6.77 | 8.04 | 5.66 | 6.97 | 100 | 10.9 |
| hsa-miR-411 | 6.81 | 4.66 | 5.53 | 5.88 | 5.85 | 4.10 | 5.09 | 5.61 | 2.92 | 5.16 | 22.2 | 9.10 |
| hsa-miR-184 | 3.79 | 2.93 | 3.96 | 3.96 | 2.02 | 4.69 | 3.62 | 2.80 | 2.54 | 3.37 | 0 | 6.97 |
| hsa-asg-5021__st1 | 7.57 | 5.55 | 6.84 | 6.69 | 7.45 | 6.37 | 5.80 | 7.53 | 4.33 | 6.46 | 77.7 | 10.3 |
| hsa-miR-154 | 5.82 | 3.73 | 4.88 | 4.83 | 4.53 | 4.02 | 4.96 | 4.10 | 3.17 | 4.45 | 0 | 7.38 |
| hsa-miR-127 | 9.31 | 6.76 | 8.65 | 8.08 | 8.28 | 8.05 | 7.92 | 8.67 | 6.35 | 8.01 | 88.8 | 11.64 |
| hsa-miR-574 | 8.36 | 7.36 | 7.80 | 8.34 | 8.66 | 7.99 | 7.46 | 8.71 | 7.21 | 7.99 | 100 | 10.8 |
| hsa-miR-134 | 6.67 | 5.18 | 5.96 | 5.98 | 6.30 | 5.69 | 6.08 | 6.46 | 4.96 | 5.92 | 22.2 | 9.31 |
| hsa-miR-376a | 6.83 | 2.68 | 6.22 | 5.69 | 4.43 | 4.97 | 5.28 | 5.72 | 4.14 | 5.11 | 11.1 | 8.97 |
| hsa-miR-542-5p | 4.87 | 4.08 | 5.19 | 3.58 | 4.47 | 4.75 | 4.10 | 5.61 | 3.98 | 4.51 | 0 | 7.73 |
| hsa-miR-376a | 6.87 | 2.85 | 5.93 | 6.34 | 5.99 | 5.07 | 5.40 | 6.75 | 4.68 | 5.54 | 44.4 | 9.38 |
| hsa-asg-5617__st1 | 5.12 | 3.39 | 4.62 | 4.20 | 5.79 | 3.62 | 4.05 | 3.53 | 3.50 | 4.20 | 0 | 7.37 |
| hsa-miR-124a | 2.93 | 3.73 | 3.20 | 5.22 | 3.08 | 3.39 | 3.41 | 2.33 | 3.50 | 3.42 | 0 | 7.50 |
| hsa-asg-14172__st1 | 4.60 | 3.17 | 4.28 | 3.73 | 4.15 | 2.87 | 3.48 | 4.65 | 2.86 | 3.75 | 0 | 7.05 |
| hsa-miR-432 | 7.13 | 4.70 | 7.02 | 6.47 | 6.37 | 6.40 | 6.66 | 7.08 | 5.20 | 6.34 | 77.7 | 9.84 |
| hsa-asg-13304__st2 | 5.33 | 5.77 | 2.91 | 5.37 | 5.03 | 5.29 | 5.23 | 5.95 | 4.06 | 4.99 | 11.1 | 7.97 |
| hsa-miR-214 | 8.95 | 7.93 | 9.05 | 8.91 | 9.41 | 9.08 | 8.64 | 9.83 | 8.15 | 8.88 | 100 | 11.4 |
| hsa-asg-13297__st1 | 3.39 | 2.93 | 3.26 | 3.24 | 4.53 | 2.59 | 2.85 | 3.26 | 3.50 | 3.28 | 0 | 6.76 |
| hsa-miR-218 | 9.64 | 7.22 | 8.84 | 8.85 | 8.15 | 7.87 | 7.17 | 8.33 | 8.00 | 8.23 | 100 | 11.3 |
| hsa-miR-503 | 8.30 | 7.70 | 8.31 | 8.56 | 7.52 | 8.53 | 7.96 | 8.60 | 8.85 | 8.26 | 100 | 11.3 |
| hsa-miR-485-5p | 3.39 | 3.85 | 2.91 | 3.82 | 4.50 | 4.35 | 2.24 | 3.40 | 3.40 | 3.54 | 0 | 6.50 |
| hsa-miR157__st2 | 9.05 | 7.95 | 8.61 | 9.92 | 8.93 | 8.59 | 8.57 | 9.28 | 7.07 | 8.66 | 100 | 11.5 |
| hsa-miR-329 | 4.31 | 3.67 | 3.26 | 4.35 | 4.84 | 3.39 | 3.75 | 3.40 | 2.8 | 3.75 | 0 | 6.89 |
| hsa-miR-503 | 8.36 | 7.54 | 8.25 | 8.76 | 7.70 | 8.37 | 7.88 | 8.54 | 8.72 | 8.24 | 100 | 11.2 |
| hsa-asg-10202__st2 | 3.34 | 2.80 | 4.01 | 3.42 | 1.84 | 3.26 | 3.58 | 4.50 | 2.28 | 3.23 | 0 | 6.53 |
| hsa-miR-1 | 9.28 | 8.71 | 10.22 | 9.27 | 10.0 | 8.34 | 7.53 | 9.74 | 7.33 | 8.94 | 100 | 11.6 |
| hsa-miR-379 | 8.61 | 6.85 | 8.01 | 7.53 | 7.61 | 7.10 | 7.21 | 7.65 | 6.82 | 7.49 | 100 | 10.9 |
| hsa-miR-369-5p | 5.86 | 3.91 | 4.93 | 4.83 | 3.99 | 4.10 | 3.99 | 4.61 | 3.71 | 4.44 | 0 | 7.28 |
| hsa-miR-494 | 7.92 | 6.28 | 7.64 | 7.04 | 7.27 | 6.85 | 6.86 | 7.53 | 5.88 | 7.03 | 100 | 10.6 |
| hsa-asg-13284__st1 | 4.01 | 4.00 | 4.59 | 3.30 | 4.15 | 3.83 | 3.84 | 4.78 | 3.50 | 4.00 | 0 | 7.12 |
| hsa-asg-9687__st1 | 4.44 | 4.73 | 5.09 | 4.88 | 4.56 | 4.75 | 4.25 | 4.68 | 4.29 | 4.63 | 0 | 7.218 |
| hsa-miR-433 | 4.05 | 3.53 | 4.11 | 4.08 | 4.50 | 2.45 | 4.25 | 5.16 | 3.17 | 3.92 | 0 | 7.04 |
| hsa-miR-565 | 8.26 | 6.75 | 6.94 | 7.51 | 7.79 | 7.30 | 6.58 | 7.11 | 5.36 | 7.07 | 44.4 | 10.0 |
| hsa-miR-124a | 4.20 | 3.39 | 3.52 | 5.53 | 4.03 | 3.62 | 3.93 | 2.96 | 3.71 | 3.88 | 0 | 7.87 |
| hsa-asg-562__st1 | 10.39 | 9.63 | 10.09 | 11.23 | 10.5 | 10.3 | 9.79 | 10.8 | 8.46 | 10.14 | 100 | 12.9 |
| hsa-miR-329 | 4.01 | 3.60 | 4.55 | 3.68 | 4.43 | 3.26 | 4.86 | 4.68 | 3.50 | 4.07 | 0 | 7.12 |
| hsa-asg-279__st2 | 4.98 | 4.64 | 4.44 | 4.78 | 5.20 | 4.56 | 4.85 | 5.21 | 4.50 | 4.80 | 0 | 7.13 |
| hsa-miR-376a | 6.16 | 3.53 | 5.24 | 4.88 | 5.07 | 4.56 | 4.30 | 5.31 | 3.71 | 4.75 | 11.1 | 8.34 |
| hsa-asg-8411__st2 | 4.20 | 3.32 | 4.85 | 4.69 | 5.16 | 4.86 | 4.53 | 4.65 | 4.26 | 4.50 | 0 | 6.52 |
| hsa-asg-7472__st2 | 4.76 | 3.24 | 3.81 | 3.52 | 3.91 | 3.83 | 2.59 | 3.78 | 3.05 | 3.61 | 0 | 6.42 |
| hsa-asg-13279__st1 | 6.00 | 5.00 | 5.07 | 4.80 | 4.73 | 5.07 | 5.5 | 7.13 | 3.40 | 5.19 | 11.1 | 7.67 |
| hsa-miR-189 | 6.33 | 5.27 | 5.82 | 6.11 | 6.12 | 5.41 | 5.20 | 6.85 | 4.99 | 5.79 | 11.1 | 8.34 |
| hsa-miR-504 | 3.28 | 4.30 | 3.64 | 2.75 | 2.51 | 3.50 | 3.62 | 1.48 | 3.11 | 3.13 | 0 | 5.55 |
| hsa-miR-487a | 4.63 | 3.53 | 3.52 | 4.04 | 3.19 | 3.00 | 4.10 | 3.11 | 3.28 | 3.60 | 0 | 6.28 |
| hsa-miR-494 | 7.29 | 5.77 | 6.95 | 6.29 | 6.69 | 6.24 | 6.06 | 6.84 | 6.39 | 6.39 | 88.8 | 9.44 |
| hsa-miR-329 | 4.24 | 3.24 | 5.45 | 4.66 | 5.11 | 3.92 | 4.53 | 3.53 | 3.80 | 4.28 | 0 | 7.10 |
| hsa-cand206__st1 | 4.79 | 3.91 | 4.82 | 4.88 | 4.50 | 4.35 | 4.30 | 4.68 | 3.50 | 4.41 | 0 | 7.05 |
| hsa-miR-211 | 2.43 | 3.24 | 3.06 | 2.55 | 3.52 | 3.39 | 3.25 | 2.65 | 2.54 | 2.96 | 0 | 7.09 |
| hsa-cand345__st1 | 4.41 | 4.73 | 4.55 | 4.04 | 4.47 | 4.80 | 4.80 | 4.54 | 4.14 | 4.50 | 0 | 6.78 |
| hsa-asg-9696__st1 | 8.71 | 7.69 | 8.39 | 9.25 | 8.15 | 8.62 | 7.96 | 8.46 | 7.78 | 8.34 | 100 | 10.5 |
| hsa-miR-130a | 10.0 | 9.17 | 9.39 | 9.91 | 8.99 | 9.32 | 8.78 | 10.0 | 8.85 | 9.39 | 100 | 11.5 |
| hsa-miR-485-3p | 4.65 | 3.24 | 4.82 | 4.42 | 4.26 | 4.35 | 4.93 | 5.92 | 2.67 | 4.36 | 0 | 7.25 |
| hsa-asg-13166__st2 | 5.24 | 4.23 | 5.64 | 5.39 | 4.98 | 4.19 | 4.93 | 5.92 | 3.28 | 4.87 | 0 | 7.95 |

TABLE 14-continued miRNAs Differentially Expressed Among Nine Cervical Cancer Samples (Ca) and Four Normal Cervix Tissue Samples (NCX) Following Expression Analysis on High-Density Microarrays. FC; Fold Change.

| Name | | | | | | | | | | | | FC |
|---|---|---|---|---|---|---|---|---|---|---|---|---|
| hsa-miR-99b | 10.1 | 9.16 | 9.90 | 10.3 | 9.95 | 10.0 | 9.08 | 10.6 | 9.84 | 9.89 | 100 | 12.2 |
| hsa-miR-299-3p | 4.13 | 3.91 | 2.54 | 3.68 | 2.77 | 3.62 | 4.15 | 4.75 | 2.28 | 3.54 | 0 | 6.13 |
| hsa-miR-594_st2 | 8.65 | 7.10 | 6.76 | 9.07 | 7.91 | 7.78 | 7.58 | 8.07 | 6.75 | 7.74 | 66.6 | 10.3 |
| hsa-miR-99b | 10.4 | 8.97 | 9.97 | 10.4 | 10.1 | 10.1 | 9.28 | 10.6 | 9.77 | 9.98 | 100 | 12.1 |
| hsa-miR-539 | 5.35 | 3.73 | 4.93 | 4.66 | 4.62 | 3.72 | 3.48 | 4.61 | 3.05 | 4.24 | 0 | 6.67 |
| hsa-miR-369-5p | 4.87 | 3.32 | 4.59 | 4.85 | 4.62 | 4.19 | 3.93 | 4.78 | 3.23 | 4.26 | 0 | 7.04 |
| hsa-asg-10883_st1 | 7.96 | 5.75 | 6.91 | 6.96 | 8.27 | 7.18 | 6.51 | 8.14 | 5.85 | 7.06 | 88.8 | 9.16 |
| hsa-miR-382 | 8.27 | 6.56 | 7.58 | 7.89 | 8.08 | 7.98 | 7.70 | 8.47 | 6.86 | 7.71 | 100 | 9.63 |
| hsa-miR-424 | 8.79 | 7.33 | 7.74 | 8.38 | 7.17 | 7.15 | 7.47 | 7.93 | 6.00 | 7.53 | 100 | 9.73 |
| hsa-miR-130a | 10.2 | 9.21 | 9.39 | 10.0 | 8.95 | 9.27 | 8.96 | 10.3 | 9.04 | 9.49 | 100 | 11.4 |
| hsa-miR-485-3p | 4.91 | 3.67 | 4.33 | 4.48 | 4.65 | 3.62 | 4.35 | 5.16 | 3.71 | 4.32 | 0 | 6.83 |
| hsa-miR-585 | 3.97 | 2.76 | 2.47 | 2.94 | 3.63 | 2.45 | 3.01 | 3.40 | 2.16 | 2.98 | 0 | 5.40 |
| hsa-miR-493-5p | 7.31 | 6.23 | 7.88 | 7.03 | 8.48 | 6.99 | 7.49 | 8.53 | 5.88 | 7.31 | 100 | 9.39 |
| hsa-miR-487a | 4.98 | 3.39 | 4.82 | 4.48 | 5.03 | 4.62 | 4.69 | 5.00 | 3.80 | 4.53 | 0 | 7.19 |
| hsa-asg-12964_st2 | 2.43 | 4.08 | 3.06 | 3.73 | 3.31 | 3.14 | 3.41 | 2.96 | 3.28 | 3.26 | 0 | 4.70 |
| hsa-asg-4557_st2 | 5.67 | 5.61 | 5.49 | 5.39 | 5.16 | 5.41 | 5.70 | 5.11 | 5.03 | 5.40 | 22.2 | 7.20 |
| hsa-miR-320 | 9.93 | 9.70 | 9.94 | 9.86 | 9.63 | 10.8 | 9.85 | 10.4 | 10.7 | 10.11 | 100 | 12.0 |
| hsa-miR-539 | 4.65 | 3.53 | 4.85 | 3.52 | 4.62 | 4.19 | 2.85 | 4.65 | 3.23 | 4.01 | 0 | 5.59 |
| hsa-miR-499 | 3.65 | 4.33 | 3.40 | 2.75 | 4.07 | 3.26 | 3.18 | 4.00 | 4.79 | 3.71 | 0 | 4.64 |
| hsa-miR-499 | 4.74 | 4.13 | 3.52 | 4.20 | 3.52 | 3.50 | 4.25 | 4.20 | 2.8 | 3.87 | 0 | 5.53 |
| hsa-asg-10674_st1 | 5.40 | 4.50 | 5.59 | 5.41 | 5.52 | 5.16 | 4.72 | 5.44 | 4.94 | 5.19 | 0 | 7.38 |
| hsa-asg-14230_st1 | 5.28 | 4.87 | 5.24 | 4.64 | 3.99 | 4.10 | 3.99 | 5.11 | 4.84 | 4.67 | 22.2 | 6.65 |
| hsa-miR-324-3p | 6.92 | 5.80 | 6.61 | 6.50 | 6.31 | 7.29 | 6.77 | 6.88 | 7.06 | 6.68 | 0 | 8.34 |
| hsa-miR-628 | 6.40 | 5.44 | 5.87 | 6.18 | 6.30 | 6.54 | 6.08 | 7.09 | 5.28 | 6.13 | 66.6 | 8.15 |
| hsa-asg-13237_st1 | 5.95 | 4.94 | 4.41 | 4.28 | 5.40 | 4.56 | 4.76 | 5.06 | 3.17 | 4.72 | 0 | 5.88 |
| hsa-miR-299-3p | 4.28 | 3.24 | 3.58 | 3.63 | 3.08 | 3.92 | 3.55 | 4.05 | 3.45 | 3.64 | 0 | 5.83 |
| hsa-asg-13230_st2 | 5.49 | 4.58 | 5.33 | 5.28 | 5.07 | 5.78 | 5.11 | 7.09 | 4.50 | 5.36 | 33.3 | 7.12 |
| hsa-miR-422b | 9.95 | 8.11 | 7.87 | 9.48 | 8.66 | 9.40 | 9.91 | 9.10 | 7.62 | 8.90 | 100 | 10.6 |
| hsa-miR-493-3p | 4.60 | 3.05 | 4.48 | 3.13 | 3.77 | 3.83 | 5.43 | 5.00 | 3.85 | 4.12 | 0 | 6.665 |
| hsa-miR-450 | 6.67 | 6.31 | 5.57 | 6.18 | 4.89 | 4.69 | 5.52 | 6.01 | 4.94 | 5.64 | 22.2 | 6.91 |
| hsa-miR-196b | 9.57 | 8.93 | 8.64 | 8.86 | 8.56 | 8.96 | 8.12 | 9.84 | 8.92 | 100 | 10.6 |
| hsa-miR-654 | 3.50 | 4.70 | 4.79 | 5.09 | 4.37 | 5.02 | 4.80 | 4.00 | 4.36 | 4.51 | 0 | 7.20 |
| hsa-miR-361 | 10.9 | 11.27 | 9.79 | 10.5 | 10.1 | 11.1 | 10.2 | 11.4 | 9.70 | 10.59 | 100 | 12.2 |
| hsa-miR-505 | 7.48 | 6.43 | 6.84 | 7.19 | 7.13 | 7.24 | 7.56 | 7.23 | 6.92 | 7.11 | 100 | 8.69 |
| hsa-miR-370 | 5.35 | 4.75 | 4.96 | 4.95 | 5.20 | 5.48 | 4.88 | 5.14 | 3.61 | 4.92 | 0 | 7.15 |
| hsa-asg-8067_st2 | 3.70 | 4.48 | 5.24 | 5.50 | 3.58 | 4.19 | 4.10 | 3.66 | 4.81 | 4.36 | 0 | 6.62 |
| hsa-miR-338 | 3.75 | 3.79 | 3.52 | 3.68 | 2.70 | 3.14 | 4.40 | 4.75 | 2.92 | 3.63 | 0 | 4.98 |
| hsa-asg-11199_st2 | 10.5 | 10.70 | 10.6 | 11.0 | 10.8 | 10.7 | 10.3 | 11.0 | 11.1 | 10.77 | 100 | 12.9 |
| hsa-asg-12346_st2 | 5.91 | 5.86 | 6.13 | 6.38 | 5.76 | 6.57 | 6.27 | 6.28 | 6.53 | 6.19 | 0 | 7.31 |
| hsa-miR-422a | 8.55 | 7.11 | 6.85 | 8.18 | 7.44 | 8.02 | 8.65 | 7.61 | 6.47 | 7.65 | 66.6 | 9.09 |
| hsa-miR-140 | 6.57 | 5.20 | 5.99 | 5.56 | 4.91 | 5.29 | 5.83 | 5.98 | 4.06 | 5.49 | 33.3 | 7.22 |
| hsa-asg-11883_st1 | 6.80 | 5.91 | 6.49 | 6.50 | 6.34 | 6.08 | 6.38 | 6.95 | 6.45 | 6.43 | 88.8 | 8.42 |
| hsa-miR-28 | 9.32 | 9.91 | 9.65 | 9.82 | 9.69 | 9.42 | 9.28 | 10.0 | 10.0 | 9.6 | 100 | 11.5 |
| hsa-miR-500 | 7.45 | 6.64 | 7.33 | 7.11 | 6.83 | 7.64 | 7.56 | 8.15 | 6.75 | 7.27 | 100 | 8.62 |
| Hsa-miR102_st2 | 7.35 | 6.74 | 7.73 | 7.42 | 6.38 | 7.91 | 7.65 | 8.30 | 6.72 | 7.36 | 100 | 8.9 |
| hsa-asg-2027_st1 | 3.84 | 2.93 | 3.96 | 4.12 | 3.99 | 4.10 | 2.85 | 2.49 | 2.92 | 3.47 | 0 | 4.41 |
| hsa-asg-3145_st1 | 4.71 | 5.11 | 5.12 | 5.37 | 5.20 | 4.56 | 4.96 | 4.91 | 4.59 | 4.95 | 0 | 6.28 |
| hsa-asg-7465_st2 | 5.60 | 4.37 | 4.37 | 4.91 | 5.11 | 4.56 | 5.03 | 5.38 | 5.14 | 4.94 | 0 | 5.56 |
| hsa-asg-9681_st1 | 5.28 | 5.11 | 5.41 | 5.62 | 4.98 | 4.62 | 4.76 | 5.21 | 4.43 | 5.05 | 0 | 6.53 |
| hsa-asg-3376_st1 | 5.37 | 4.23 | 5.09 | 4.83 | 4.53 | 4.75 | 4.72 | 4.82 | 4.36 | 4.74 | 0 | 6.65 |

TABLE 14-continued miRNAs Differentially Expressed Among Nine Cervical Cancer Samples (Ca) and Four Normal Cervix Tissue Samples (NCX) Following Expression Analysis on High-Density Microarrays. FC; Fold Change.

| | | | | | | | | | | | | |
|---|---|---|---|---|---|---|---|---|---|---|---|---|
| Hsa-cand283__st1 | 3.88 | 3.85 | 3.86 | 3.58 | 4.26 | 2.87 | 4.48 | 3.66 | 2.92 | 3.71 | 0 | 6.02 |
| hsa-asg-2301__st2 | 6.44 | 6.84 | 5.68 | 6.59 | 5.45 | 5.90 | 6.15 | 6.90 | 5.32 | 6.14 | 66.6 | 7.39 |
| Hsa-cand207__st1 | 4.13 | 3.85 | 3.52 | 3.68 | 3.77 | 3.72 | 4.30 | 4.00 | 3.98 | 3.88 | 0 | 5.53 |
| hsa-miR-598 | 5.33 | 4.66 | 5.17 | 5.58 | 4.84 | 5.41 | 5.62 | 5.63 | 5.48 | 5.30 | 0 | 6.76 |
| hsa-asg-10278__st2 | 3.39 | 3.32 | 3.58 | 3.91 | 3.02 | 4.10 | 3.78 | 3.26 | 3.40 | 3.53 | 0 | 4.38 |
| hsa-miR-30a-3p | 7.31 | 7.20 | 7.86 | 7.71 | 7.22 | 7.64 | 7.82 | 7.78 | 6.90 | 7.49 | 100 | 8.90 |
| hsa-miR-331 | 6.40 | 6.69 | 6.33 | 6.54 | 6.20 | 5.33 | 6.47 | 7.65 | 5.92 | 6.39 | 55.5 | 7.48 |
| hsa-asg-11181__st1 | 5.12 | 4.30 | 4.91 | 5.00 | 4.68 | 5.59 | 5.34 | 4.97 | 5.43 | 5.04 | 0 | 5.86 |
| hsa-miR-489 | 5.44 | 5.89 | 5.35 | 5.14 | 5.87 | 5.25 | 5.52 | 6.19 | 4.10 | 5.41 | 22.2 | 6.96 |
| hsa-asg-7023__st2 | 4.13 | 3.46 | 3.81 | 3.52 | 3.52 | 4.27 | 3.81 | 3.26 | 3.50 | 3.70 | 0 | 5.34 |
| hsa-miR-149 | 4.76 | 5.66 | 4.69 | 5.66 | 4.86 | 4.86 | 4.53 | 4.46 | 4.53 | 4.89 | 0 | 6.41 |
| hsa-asg-3597__st2 | 5.74 | 5.41 | 5.41 | 5.39 | 5.09 | 5.20 | 5.28 | 3.89 | 5.01 | 5.16 | 0 | 7.22 |
| hsa-miR-324-5p | 8.17 | 7.18 | 6.99 | 7.98 | 7.08 | 8.13 | 7.98 | 8.29 | 8.10 | 7.77 | 100 | 8.80 |
| hsa-miR-151 | 9.28 | 9.52 | 9.30 | 9.49 | 9.34 | 9.04 | 9.04 | 9.23 | 9.56 | 9.31 | 100 | 10.8 |
| hsa-asg-5304__st1 | 8.83 | 9.84 | 9.09 | 9.12 | 9.36 | 9.42 | 9.16 | 9.72 | 9.02 | 9.28 | 100 | 10.4 |
| Hsa-cand720__st1 | 5.35 | 6.37 | 5.07 | 5.58 | 5.28 | 5.29 | 5.51 | 5.55 | 4.62 | 5.40 | 11.1 | 6.84 |
| hsa-miR-17-3p | 5.29 | 5.30 | 5.28 | 5.07 | 4.53 | 4.42 | 4.53 | 5.36 | 4.94 | 4.97 | 11.1 | 6.00 |
| hsa-miR-30d | 11.6 | 11.0 | 11.4 | 11.6 | 11.9 | 11.8 | 11.6 | 12.4 | 12.0 | 11.74 | 100 | 12.9 |
| hsa-asg-13308__st2 | 8.76 | 9.82 | 9.01 | 9.05 | 9.37 | 9.08 | 9.03 | 9.51 | 9.06 | 9.19 | 100 | 10.3 |
| hsa-asg-3038__st2 | 4.65 | 5.27 | 5.12 | 5.34 | 4.78 | 4.69 | 4.61 | 4.54 | 5.46 | 4.94 | 0 | 6.30 |
| hsa-asg-13966__st2 | 4.87 | 5.01 | 4.99 | 4.54 | 5.22 | 5.45 | 5.03 | 4.29 | 4.65 | 4.89 | 0 | 5.74 |
| hsa-asg-13189__st1 | 6.89 | 7.40 | 6.91 | 7.29 | 6.71 | 7.19 | 7.55 | 6.98 | 7.29 | 7.13 | 100 | 8.02 |
| hsa-miR-340 | 5.29 | 4.77 | 4.66 | 4.95 | 4.93 | 4.69 | 4.93 | 5.51 | 4.46 | 4.91 | 0 | 5.34 |
| hsa-miR-30a-5p | 11.3 | 10.7 | 11.1 | 11.1 | 11.1 | 11.2 | 11.2 | 11.7 | 11.2 | 11.21 | 100 | 12.2 |
| hsa-asg-11938__st1 | 4.28 | 5.25 | 4.79 | 4.45 | 5.20 | 5.52 | 5.80 | 4.68 | 4.99 | 4.99 | 11.1 | 6.15 |
| hsa-asg-5740__st2 | 3.60 | 4.90 | 4.20 | 4.69 | 4.62 | 4.35 | 4.76 | 4.46 | 4.62 | 4.47 | 0 | 5.76 |
| hsa-asg-8477__st1 | 6.84 | 7.79 | 6.43 | 7.41 | 7.32 | 6.94 | 7.09 | 6.73 | 6.71 | 7.03 | 100 | 8.20 |
| hsa-miR-194 | 8.43 | 7.44 | 8.05 | 8.07 | 7.38 | 7.45 | 7.71 | 8.17 | 7.20 | 7.77 | 100 | 8.97 |
| hsa-asg-12325__st2 | 5.18 | 5.77 | 5.12 | 5.00 | 5.62 | 5.41 | 5.25 | 5.31 | 6.03 | 5.41 | 11.1 | 6.41 |
| hsa-miR-10b | 11.4 | 11.3 | 11.8 | 11.3 | 11.0 | 11.1 | 10.9 | 11.3 | 10.5 | 11.22 | 100 | 12.4 |
| hsa-asg-12356__st1 | 6.89 | 7.03 | 6.70 | 6.84 | 6.41 | 7.02 | 6.52 | 6.85 | 6.35 | 6.73 | 88.8 | 8.16 |
| hsa-asg-6758__st1 | 3.97 | 3.32 | 3.52 | 3.87 | 3.77 | 4.02 | 3.87 | 4.20 | 3.28 | 3.76 | 0 | 5.23 |
| hsa-asg-522__st1 | 4.09 | 4.23 | 3.86 | 4.04 | 3.31 | 4.49 | 4.35 | 4.00 | 4.43 | 4.09 | 0 | 5.19 |
| hsa-asg-4564__st2 | 5.94 | 5.56 | 5.35 | 5.79 | 5.52 | 5.37 | 5.16 | 5.19 | 5.60 | 5.50 | 0 | 6.70 |
| hsa-asg-6951__st2 | 6.45 | 6.60 | 6.56 | 6.75 | 6.09 | 6.67 | 6.50 | 6.46 | 6.89 | 6.55 | 77.7 | 7.25 |
| hsa-asg-9920__st1 | 7.01 | 7.17 | 6.25 | 7.34 | 6.98 | 7.09 | 7.18 | 6.32 | 6.60 | 6.88 | 11.1 | 8.14 |
| hsa-asg-13613__st2 | 6.74 | 7.29 | 6.51 | 7.52 | 6.73 | 6.66 | 7.22 | 6.72 | 6.52 | 6.88 | 88.8 | 8.13 |
| hsa-asg-11688__st1 | 4.82 | 4.70 | 4.82 | 5.91 | 4.47 | 5.07 | 4.86 | 5.31 | 6.00 | 5.10 | 22.2 | 4.34 |
| hsa-miR-18b | 7.10 | 7.92 | 6.64 | 7.24 | 5.97 | 6.84 | 7.25 | 7.26 | 7.28 | 7.06 | 88.8 | 5.93 |
| hsa-miR-18a | 7.41 | 8.27 | 7.03 | 7.77 | 6.33 | 6.84 | 7.65 | 7.55 | 7.47 | 7.37 | 88.8 | 6.23 |
| hsa-asg-3711__st2 | 7.01 | 7.62 | 6.94 | 7.52 | 5.77 | 6.95 | 7.49 | 7.94 | 7.58 | 7.20 | 88.8 | 6.05 |
| hsa-miR-183 | 9.78 | 10.5 | 9.80 | 10.5 | 9.41 | 10.5 | 10.4 | 10.7 | 10.6 | 10.27 | 100 | 8.97 |
| hsa-asg-2919__st1 | 5.18 | 5.09 | 6.11 | 6.70 | 5.16 | 5.41 | 4.90 | 4.15 | 5.76 | 5.38 | 11.1 | 3.34 |

TABLE 14-continued miRNAs Differentially Expressed Among Nine Cervical Cancer Samples (Ca) and Four Normal Cervix Tissue Samples (NCX) Following Expression Analysis on High-Density Microarrays. FC; Fold Change.

| | | | | | | | | | | | | |
|---|---|---|---|---|---|---|---|---|---|---|---|---|
| hsa-asg-924_st1 | 8.96 | 8.34 | 8.87 | 10.1 | 8.25 | 8.39 | 9.67 | 9.63 | 8.92 | 9.02 | 100 | 7.61 |
| Hsa-cand317_st1 | 7.01 | 6.63 | 7.18 | 8.78 | 6.64 | 7.00 | 8.27 | 7.73 | 7.19 | 7.38 | 100 | 5.44 |

| miRNA[a] | NCX 10 | NCX 3 | NCX 16 | Mean (NCX) | % NCX | Ttest (Ca vs NCX) | Log2 Diff (Ca vs NCX) | Fold change |
|---|---|---|---|---|---|---|---|---|
| hsa-miR-133b | 11.2 | 10.9 | 10.49 | 10.32 | 100 | $3.6 \times 10^{-5}$ | −5.34 | 40.78 |
| hsa-miR-133a | 11.8 | 11.50 | 11.15 | 10.99 | 100 | $1.3 \times 10^{-5}$ | −5.33 | 40.27 |
| hsa-miR-204 | 10.1 | 9.700 | 9.85 | 9.70 | 100 | $3.3 \times 10^{-6}$ | −5.27 | 38.61 |
| hsa-miR-497 | 9.43 | 10.28 | 8.719 | 9.39 | 100 | $4.8 \times 10^{-5}$ | −4.70 | 25.99 |
| hsa-miR-368 | 11.6 | 11.36 | 11.34 | 11.39 | 100 | $5.1 \times 10^{-5}$ | −4.04 | 16.45 |
| hsa-miR-455 | 8.64 | 10.11 | 8.966 | 9.05 | 100 | $1.7 \times 10^{-5}$ | −3.84 | 14.39 |
| hsa-miR-497 | 10.1 | 10.89 | 9.529 | 10.18 | 100 | $2.8 \times 10^{-6}$ | −3.71 | 13.11 |
| hsa-asg-13254_st1 | 9.58 | 9.347 | 10.22 | 9.87 | 100 | $1.6 \times 10^{-4}$ | −3.67 | 12.77 |
| hsa-miR-299-5p | 9.74 | 9.526 | 9.619 | 9.68 | 100 | $1.3 \times 10^{-5}$ | −3.63 | 12.44 |
| hsa-asg-14176_st1 | 9.48 | 9.707 | 8.855 | 9.26 | 100 | $1.1 \times 10^{-6}$ | −3.61 | 12.23 |
| hsa-miR-495 | 9.78 | 10.20 | 10.14 | 10.11 | 100 | $1.7 \times 10^{-4}$ | −3.59 | 12.06 |
| hsa-miR-381 | 8.10 | 7.779 | 7.832 | 7.78 | 100 | $1.2 \times 10^{-6}$ | −3.58 | 12.02 |
| hsa-miR-487b | 9.84 | 10.35 | 10.91 | 10.52 | 100 | $6.9 \times 10^{-6}$ | −3.54 | 11.66 |
| hsa-miR-411 | 8.61 | 8.512 | 8.547 | 8.69 | 100 | $9.4 \times 10^{-5}$ | −3.52 | 11.53 |
| hsa-miR-184 | 7.11 | 6.968 | 6.371 | 6.85 | 100 | $7.9 \times 10^{-6}$ | −3.48 | 11.20 |
| hsa-asg-5021_st1 | 9.58 | 9.473 | 10.23 | 9.90 | 100 | $8.6 \times 10^{-5}$ | −3.44 | 10.90 |
| hsa-miR-154 | 8.53 | 7.583 | 8.071 | 7.89 | 100 | $7.2 \times 10^{-6}$ | −3.44 | 10.85 |
| hsa-miR-127 | 11.2 | 10.89 | 11.77 | 11.40 | 100 | $2.7 \times 10^{-5}$ | −3.38 | 10.46 |
| hsa-miR-574 | 11.6 | 11.13 | 11.41 | 11.26 | 100 | $4.3 \times 10^{-7}$ | −3.27 | 9.66 |
| hsa-miR-134 | 8.83 | 8.819 | 9.609 | 9.14 | 100 | $5.6 \times 10^{-7}$ | −3.21 | 9.31 |
| hsa-miR-376a | 7.91 | 8.29 | 8.116 | 8.32 | 100 | $4.4 \times 10^{-4}$ | −3.21 | 9.26 |
| hsa-miR-542-5p | 7.58 | 7.449 | 7.910 | 7.66 | 100 | $1.4 \times 10^{-6}$ | −3.15 | 8.88 |
| hsa-miR-376a | 8.45 | 8.408 | 8.39 | 8.66 | 100 | $6.1 \times 10^{-4}$ | −3.11 | 8.65 |
| hsa-asg-5617_st1 | 7.04 | 7.163 | 7.698 | 7.31 | 100 | $1.8 \times 10^{-5}$ | −3.11 | 8.64 |
| hsa-miR-124a | 6.80 | 6.134 | 5.699 | 6.53 | 50 | $3.9 \times 10^{-5}$ | −3.11 | 8.64 |
| hsa-asg-14172_st1 | 7.21 | 6.494 | 6.719 | 6.86 | 100 | $4.5 \times 10^{-6}$ | −3.11 | 8.64 |
| hsa-miR-432 | 8.95 | 9.03 | 9.981 | 9.45 | 100 | $3.5 \times 10^{-5}$ | −3.11 | 8.63 |
| hsa-asg-13304_st2 | 8.47 | 8.050 | 7.570 | 8.01 | 100 | $7.9 \times 10^{-5}$ | −3.01 | 8.09 |
| hsa-miR-214 | 12.0 | 11.73 | 12.28 | 11.88 | 100 | $1.4 \times 10^{-6}$ | −2.99 | 7.98 |
| hsa-asg-13297_st1 | 3.75 | 6.352 | 8.257 | 6.28 | 75 | $7.7 \times 10^{-4}$ | −2.99 | 7.96 |
| hsa-miR-218 | 11.3 | 10.98 | 11.17 | 11.21 | 100 | $1.6 \times 10^{-5}$ | −2.98 | 7.91 |
| hsa-miR-503 | 10.9 | 11.08 | 11.541 | 11.22 | 100 | $9.9 \times 10^{-8}$ | −2.96 | 7.78 |
| hsa-miR-485-5p | 6.29 | 5.833 | 7.282 | 6.47 | 50 | $1.6 \times 10^{-5}$ | −2.93 | 7.63 |
| hsa-miR157_st2 | 11.5 | 11.49 | 11.85 | 11.60 | 100 | $2.2 \times 10^{-5}$ | −2.93 | 7.63 |
| hsa-miR-329 | 6.38 | 6.474 | 6.942 | 6.67 | 100 | $3.2 \times 10^{-6}$ | −2.91 | 7.56 |
| hsa-miR-503 | 10.8 | 11.08 | 11.35 | 11.15 | 100 | $7.8 \times 10^{-8}$ | −2.91 | 7.54 |
| hsa-asg-10202_st2 | 6.62 | 5.353 | 6.046 | 6.14 | 50 | $5.5 \times 10^{-5}$ | −2.90 | 7.51 |
| hsa-miR-1 | 12.1 | 12.09 | 11.57 | 11.85 | 100 | $2.3 \times 10^{-4}$ | −2.90 | 7.50 |
| hsa-miR-379 | 10.0 | 9.978 | 10.49 | 10.38 | 100 | $2.6 \times 10^{-6}$ | −2.89 | 7.41 |
| hsa-miR-369-5p | 7.18 | 6.821 | 7.978 | 7.31 | 100 | $1.2 \times 10^{-5}$ | −2.87 | 7.33 |
| hsa-miR-494 | 9.48 | 9.360 | 10.03 | 9.87 | 100 | $1.2 \times 10^{-5}$ | −2.83 | 7.15 |
| hsa-asg-13284_st1 | 7.31 | 6.264 | 6.612 | 6.82 | 75 | $7.9 \times 10^{-7}$ | −2.82 | 7.07 |
| hsa-asg-9687_st1 | 7.46 | 7.151 | 7.998 | 7.45 | 100 | $9.5 \times 10^{-9}$ | −2.81 | 7.06 |
| hsa-miR-433 | 6.41 | 5.977 | 7.532 | 6.74 | 75 | $7.0 \times 10^{-5}$ | −2.81 | 7.03 |
| hsa-miR-565 | 10.2 | 8.865 | 10.29 | 9.87 | 100 | $1.0 \times 10^{-4}$ | −2.80 | 6.97 |
| hsa-miR-124a | 7.21 | 5.723 | 5.913 | 6.68 | 100 | $1.4 \times 10^{-4}$ | −2.79 | 6.95 |
| hsa-asg-562_st1 | 12.8 | 12.85 | 13.1 | 12.94 | 100 | $3.0 \times 10^{-5}$ | −2.79 | 6.94 |
| hsa-miR-329 | 6.84 | 6.474 | 6.830 | 6.81 | 100 | $2.4 \times 10^{-6}$ | −2.74 | 6.72 |
| hsa-asg-279_st2 | 8.27 | 7.606 | 7.087 | 7.52 | 50 | $1.1 \times 10^{-7}$ | −2.72 | 6.61 |

TABLE 14-continued miRNAs Differentially Expressed Among Nine Cervical Cancer Samples (Ca) and Four Normal Cervix Tissue Samples (NCX) Following Expression Analysis on High-Density Microarrays. FC; Fold Change.

| Name | | | | | | | | |
|---|---|---|---|---|---|---|---|---|
| hsa-miR-376a | 7.12 | 7.223 | 7.169 | 7.46 | 100 | $1.0 \times 10^{-4}$ | −2.70 | 6.53 |
| hsa-asg-8411_st2 | 7.55 | 7.036 | 7.6989 | 7.20 | 100 | $4.0 \times 10^{-6}$ | −2.69 | 6.48 |
| hsa-asg-7472_st2 | 6.50 | 5.771 | 6.414 | 6.27 | 75 | $6.5 \times 10^{-6}$ | −2.66 | 6.34 |
| hsa-asg-13279_st1 | 7.85 | 7.709 | 8.111 | 7.83 | 100 | $3.5 \times 10^{-4}$ | −2.64 | 6.25 |
| hsa-miR-189 | 8.64 | 8.241 | 8.467 | 8.42 | 100 | $5.0 \times 10^{-6}$ | −2.63 | 6.19 |
| hsa-miR-504 | 6.42 | 5.245 | 5.842 | 5.76 | 25 | $1.0 \times 10^{-4}$ | −2.62 | 6.18 |
| hsa-miR-487a | 6.06 | 6.330 | 6.265 | 6.23 | 100 | $1.4 \times 10^{-6}$ | −2.62 | 6.18 |
| hsa-miR-494 | 8.66 | 8.536 | 9.223 | 8.96 | 100 | $1.1 \times 10^{-5}$ | −2.57 | 5.96 |
| hsa-miR-329 | 6.48 | 6.587 | 7.235 | 6.85 | 100 | $4.0 \times 10^{-5}$ | −2.57 | 5.94 |
| hsa-cand206_st1 | 6.57 | 7.113 | 7.211 | 6.98 | 100 | $6.2 \times 10^{-7}$ | −2.56 | 5.92 |
| hsa-miR-211 | 5.34 | 3.471 | 6.152 | 5.51 | 50 | $5.2 \times 10^{-4}$ | −2.55 | 5.86 |
| hsa-cand345_st1 | 7.00 | 6.852 | 7.485 | 7.03 | 100 | $1.2 \times 10^{-8}$ | −2.52 | 5.76 |
| hsa-asg-9696_st1 | 11.1 | 10.78 | 10.90 | 10.85 | 100 | $1.3 \times 10^{-6}$ | −2.51 | 5.70 |
| hsa-miR-130a | 12.2 | 11.78 | 11.89 | 11.88 | 100 | $2.0 \times 10^{-6}$ | −2.48 | 5.60 |
| hsa-miR-485-3p | 6.48 | 6.454 | 7.074 | 6.81 | 100 | $4.8 \times 10^{-4}$ | −2.44 | 5.46 |
| hsa-asg-13166_st2 | 6.75 | 7.138 | 7.373 | 7.30 | 100 | $2.2 \times 10^{-4}$ | −2.43 | 5.40 |
| hsa-miR-99b | 12.3 | 12.14 | 12.48 | 12.32 | 100 | $1.5 \times 10^{-6}$ | −2.42 | 5.35 |
| hsa-miR-299-3p | 5.13 | 6.532 | 6.046 | 5.96 | 75 | $2.9 \times 10^{-4}$ | −2.41 | 5.34 |
| hsa-miR-594_st2 | 10.6 | 9.359 | 10.23 | 10.15 | 100 | $2.1 \times 10^{-4}$ | −2.41 | 5.32 |
| hsa-miR-99b | 12.5 | 12.27 | 12.54 | 12.38 | 100 | $5.3 \times 10^{-6}$ | −2.40 | 5.28 |
| hsa-miR-539 | 6.06 | 6.241 | 7.583 | 6.63 | 100 | $2.3 \times 10^{-4}$ | −2.39 | 5.25 |
| hsa-miR-369-5p | 6.46 | 5.787 | 7.313 | 6.65 | 75 | $7.9 \times 10^{-5}$ | −2.38 | 5.21 |
| hsa-asg-10883_st1 | 10.3 | 9.277 | 8.876 | 9.42 | 100 | $8.5 \times 10^{-4}$ | −2.36 | 5.13 |
| hsa-miR-382 | 9.67 | 10.25 | 10.68 | 10.06 | 100 | $4.2 \times 10^{-5}$ | −2.35 | 5.10 |
| hsa-miR-424 | 10.1 | 9.929 | 9.468 | 9.83 | 100 | $2.1 \times 10^{-4}$ | −2.29 | 4.91 |
| hsa-miR-130a | 12.1 | 11.79 | 11.66 | 11.77 | 100 | $1.1 \times 10^{-5}$ | −2.27 | 4.83 |
| hsa-miR-485-3p | 6.15 | 6.352 | 6.962 | 6.57 | 100 | $1.6 \times 10^{-5}$ | −2.25 | 4.76 |
| hsa-miR-585 | 5.55 | 4.359 | 5.502 | 5.20 | 25 | $5.8 \times 10^{-5}$ | −2.22 | 4.67 |
| hsa-miR-493-5p | 9.61 | 9.438 | 9.699 | 9.53 | 100 | $6.1 \times 10^{-4}$ | −2.21 | 4.65 |
| hsa-miR-487a | 6.16 | 6.925 | 6.625 | 6.72 | 100 | $3.1 \times 10^{-5}$ | −2.18 | 4.56 |
| hsa-asg-12964_st2 | 5.64 | 5.374 | 6.100 | 5.45 | 25 | $1.6 \times 10^{-5}$ | −2.18 | 4.54 |
| hsa-asg-4557_st2 | 7.79 | 7.714 | 7.570 | 7.57 | 100 | $1.8 \times 10^{-8}$ | −2.16 | 4.49 |
| hsa-miR-320 | 12.3 | 12.27 | 12.42 | 12.27 | 100 | $1.9 \times 10^{-6}$ | −2.16 | 4.49 |
| hsa-miR-539 | 6.07 | 6.264 | 6.787 | 6.17 | 50 | $2.5 \times 10^{-4}$ | −2.16 | 4.48 |
| hsa-miR-499 | 6.81 | 5.656 | 6.357 | 5.86 | 50 | $4.9 \times 10^{-4}$ | −2.15 | 4.44 |
| hsa-miR-499 | 7.23 | 5.311 | 5.991 | 6.01 | 75 | $2.4 \times 10^{-4}$ | −2.14 | 4.40 |
| hsa-asg-10674_st1 | 7.60 | 6.932 | 7.351 | 7.31 | 100 | $8.6 \times 10^{-7}$ | −2.12 | 4.36 |
| hsa-asg-14230_st1 | 6.66 | 6.939 | 6.932 | 6.79 | 100 | $8.6 \times 10^{-6}$ | −2.12 | 4.34 |
| hsa-miR-324-3p | 9.23 | 8.688 | 8.936 | 8.80 | 25 | $4.7 \times 10^{-6}$ | −2.11 | 4.32 |
| hsa-miR-628 | 7.98 | 8.047 | 8.802 | 8.24 | 100 | $2.7 \times 10^{-5}$ | −2.11 | 4.31 |
| hsa-asg-13237_st1 | 7.51 | 7.138 | 6.753 | 6.82 | 100 | $7.6 \times 10^{-4}$ | −2.09 | 4.27 |
| hsa-miR-299-3p | 5.47 | 5.755 | 5.893 | 5.73 | 25 | $5.9 \times 10^{-7}$ | −2.09 | 4.26 |
| hsa-asg-13230_st2 | 7.74 | 6.852 | 8.085 | 7.45 | 100 | $5.1 \times 10^{-4}$ | −2.08 | 4.25 |
| hsa-miR-422b | 11.2 | 11.15 | 10.91 | 10.97 | 100 | $8.5 \times 10^{-4}$ | −2.06 | 4.19 |
| hsa-miR-493-3p | 5.63 | 6.444 | 5.981 | 6.18 | 50 | $6.9 \times 10^{-4}$ | −2.05 | 4.14 |
| hsa-miR-450 | 7.82 | 7.818 | 8.192 | 7.68 | 100 | $3.2 \times 10^{-4}$ | −2.04 | 4.12 |
| hsa-miR-196b | 11.4 | 10.91 | 10.91 | 10.96 | 100 | $1.8 \times 10^{-5}$ | −2.03 | 4.11 |
| hsa-miR-654 | 6.03 | 5.892 | 7.028 | 6.54 | 50 | $8.9 \times 10^{-5}$ | −2.02 | 4.06 |
| hsa-miR-361 | 12.7 | 12.65 | 12.74 | 12.60 | 100 | $1.0 \times 10^{-4}$ | −2.00 | 4.01 |
| hsa-miR-505 | 8.98 | 8.744 | 9.85 | 9.06 | 100 | $6.4 \times 10^{-6}$ | −1.95 | 3.86 |
| hsa-miR-370 | 6.56 | 6.454 | 7.074 | 6.81 | 75 | $6.1 \times 10^{-5}$ | −1.88 | 3.68 |
| hsa-asg-8067_st2 | 6.02 | 5.739 | 6.594 | 6.24 | 50 | $4.7 \times 10^{-4}$ | −1.87 | 3.67 |

TABLE 14-continued miRNAs Differentially Expressed Among Nine Cervical Cancer Samples (Ca) and Four Normal Cervix Tissue Samples (NCX) Following Expression Analysis on High-Density Microarrays. FC; Fold Change.

| | | | | | | | | |
|---|---|---|---|---|---|---|---|---|
| hsa-miR-338 | 6.16 | 4.743 | 6.028 | 5.48 | 75 | $8.4 \times 10^{-4}$ | −1.85 | 3.60 |
| hsa-asg-11199__st2 | 12.6 | 12.18 | 12.60 | 12.59 | 100 | $4.3 \times 10^{-7}$ | −1.81 | 3.52 |
| hsa-asg-12346__st2 | 8.22 | 7.882 | 8.499 | 7.97 | 75 | $5.6 \times 10^{-6}$ | −1.78 | 3.44 |
| hsa-miR-422a | 9.56 | 9.652 | 9.455 | 9.44 | 100 | $8.8 \times 10^{-4}$ | −1.78 | 3.44 |
| hsa-miR-140 | 7.65 | 7.062 | 7.161 | 7.27 | 100 | $6.9 \times 10^{-4}$ | −1.78 | 3.44 |
| hsa-asg-11883__st1 | 8.03 | 8.096 | 8.296 | 8.21 | 100 | $5.9 \times 10^{-7}$ | −1.77 | 3.42 |
| hsa-miR-28 | 11.4 | 11.26 | 11.62 | 11.46 | 100 | $2.7 \times 10^{-7}$ | −1.77 | 3.42 |
| hsa-miR-500 | 9.47 | 8.756 | 9.282 | 9.03 | 100 | $6.5 \times 10^{-5}$ | −1.75 | 3.37 |
| Hsa-miR102__st2 | 9.60 | 8.561 | 9.282 | 9.08 | 100 | $4.6 \times 10^{-4}$ | −1.72 | 3.31 |
| hsa-asg-2027__st1 | 5.58 | 5.787 | 5.009 | 5.19 | 25 | $9.7 \times 10^{-4}$ | −1.72 | 3.31 |
| hsa-asg-3145__st1 | 6.82 | 6.241 | 7.306 | 6.66 | 75 | $6.5 \times 10^{-6}$ | −1.71 | 3.27 |
| hsa-asg-7465__st2 | 7.75 | 6.373 | 6.731 | 6.60 | 100 | $7.6 \times 10^{-4}$ | −1.66 | 3.16 |
| hsa-asg-9681__st1 | 6.75 | 6.641 | 6.902 | 6.70 | 100 | $5.7 \times 10^{-6}$ | −1.65 | 3.14 |
| hsa-asg-3376__st1 | 6.18 | 6.758 | 6.009 | 6.40 | 100 | $8.5 \times 10^{-6}$ | −1.65 | 3.14 |
| Hsa-cand283__st1 | 5.53 | 4.237 | 5.652 | 5.36 | 75 | $9.4 \times 10^{-4}$ | −1.65 | 3.14 |
| hsa-asg-2301__st2 | 7.98 | 7.499 | 8.253 | 7.78 | 100 | $4.0 \times 10^{-4}$ | −1.63 | 3.10 |
| Hsa-cand207__st1 | 4.75 | 5.723 | 5.972 | 5.49 | 75 | $8.6 \times 10^{-6}$ | −1.60 | 3.04 |
| hsa-miR-598 | 7.29 | 6.352 | 7.194 | 6.90 | 100 | $1.9 \times 10^{-5}$ | −1.59 | 3.02 |
| hsa-asg-10278__st2 | 5.33 | 5.332 | 5.321 | 5.09 | 75 | $3.2 \times 10^{-5}$ | −1.55 | 2.94 |
| hsa-miR-30a-3p | 8.63 | 8.913 | 9.556 | 9.00 | 100 | $2.2 \times 10^{-5}$ | −1.50 | 2.83 |
| hsa-miR-331 | 7.94 | 7.919 | 8.239 | 7.89 | 100 | $9.0 \times 10^{-4}$ | −1.49 | 2.82 |
| hsa-asg-11181__st1 | 6.96 | 6.434 | 6.861 | 6.53 | 50 | $1.1 \times 10^{-4}$ | −1.48 | 2.80 |
| hsa-miR-489 | 6.51 | 7.211 | 6.922 | 6.90 | 100 | $7.1 \times 10^{-4}$ | −1.48 | 2.79 |
| hsa-asg-7023__st2 | 5.61 | 4.509 | 5.213 | 5.16 | 25 | $4.4 \times 10^{-5}$ | −1.46 | 2.76 |
| hsa-miR-149 | 6.24 | 5.949 | 6.736 | 6.33 | 75 | $1.5 \times 10^{-4}$ | −1.44 | 2.71 |
| hsa-asg-3597__st2 | 6.15 | 6.319 | 6.679 | 6.59 | 100 | $6.6 \times 10^{-4}$ | −1.43 | 2.69 |
| hsa-miR-324-5p | 9.60 | 9.105 | 9.179 | 9.17 | 100 | $4.9 \times 10^{-4}$ | −1.40 | 2.64 |
| hsa-miR-151 | 10.8 | 10.45 | 10.69 | 10.69 | 100 | $9.8 \times 10^{-8}$ | −1.38 | 2.60 |
| hsa-asg-5304__st1 | 10.6 | 10.71 | 10.86 | 10.65 | 100 | $1.1 \times 10^{-5}$ | −1.36 | 2.56 |
| Hsa-cand720__st1 | 6.28 | 6.805 | 7.009 | 6.73 | 100 | $3.2 \times 10^{-4}$ | −1.33 | 2.51 |
| hsa-miR-17-3p | 7.27 | 5.787 | 6.082 | 6.28 | 100 | $7.9 \times 10^{-4}$ | −1.31 | 2.48 |
| hsa-miR-30d | 13.2 | 13.05 | 13.00 | 13.05 | 100 | $3.8 \times 10^{-5}$ | −1.30 | 2.47 |
| hsa-asg-13308__st2 | 10.5 | 10.34 | 10.78 | 10.49 | 100 | $1.4 \times 10^{-5}$ | −1.30 | 2.47 |
| hsa-asg-3038__st2 | 6.67 | 6.083 | 5.913 | 6.24 | 75 | $6.8 \times 10^{-5}$ | −1.30 | 2.46 |
| hsa-asg-13966__st2 | 6.18 | 6.383 | 6.407 | 6.18 | 75 | $6.1 \times 10^{-5}$ | −1.28 | 2.43 |
| hsa-asg-13189__st1 | 8.74 | 8.164 | 8.705 | 8.41 | 100 | $2.3 \times 10^{-5}$ | −1.27 | 2.41 |
| hsa-miR-340 | 6.13 | 6.569 | 6.497 | 6.13 | 50 | $3.8 \times 10^{-4}$ | −1.22 | 2.33 |
| hsa-miR-30a-5p | 12.5 | 12.34 | 12.50 | 12.42 | 100 | $3.3 \times 10^{-6}$ | −1.20 | 2.30 |
| hsa-asg-11938__st1 | 6.34 | 6.182 | 6.028 | 6.17 | 75 | $8.1 \times 10^{-4}$ | −1.17 | 2.26 |
| hsa-asg-5740__st2 | 5.34 | 6.005 | 5.449 | 5.64 | 25 | $2.4 \times 10^{-4}$ | −1.17 | 2.25 |
| hsa-asg-8477__st1 | 8.35 | 7.837 | 8.312 | 8.17 | 100 | $3.8 \times 10^{-4}$ | −1.14 | 2.21 |
| hsa-miR-194 | 9.05 | 8.867 | 8.668 | 8.89 | 100 | $4.0 \times 10^{-4}$ | −1.12 | 2.17 |
| hsa-asg-12325__st2 | 6.70 | 6.341 | 6.497 | 6.48 | 75 | $8.4 \times 10^{-5}$ | −1.07 | 2.10 |
| hsa-miR-10b | 12.3 | 12.13 | 12.33 | 12.29 | 100 | $9.9 \times 10^{-5}$ | −1.07 | 2.10 |
| hsa-asg-12356__st1 | 7.43 | 7.464 | 8.174 | 7.80 | 100 | $1.1 \times 10^{-4}$ | −1.07 | 2.09 |

TABLE 14-continued miRNAs Differentially Expressed Among Nine Cervical Cancer Samples (Ca) and Four Normal Cervix Tissue Samples (NCX) Following Expression Analysis on High-Density Microarrays. FC; Fold Change.

| | | | | | | | | |
|---|---|---|---|---|---|---|---|---|
| hsa-asg-6758_st1 | 4.90 | 4.863 | 4.284 | 4.82 | 25 | $2.9 \times 10^{-4}$ | −1.05 | 2.08 |
| hsa-asg-522_st1 | 5.27 | 4.804 | 5.276 | 5.13 | 25 | $2.6 \times 10^{-4}$ | −1.04 | 2.06 |
| hsa-asg-4564_st2 | 6.78 | 6.241 | 6.327 | 6.51 | 75 | $4.9 \times 10^{-5}$ | −1.01 | 2.01 |
| hsa-asg-6951_st2 | 7.53 | 7.414 | 8.069 | 7.56 | 100 | $5.7 \times 10^{-5}$ | −1.01 | 2.01 |
| hsa-asg-9920_st1 | 7.92 | 7.623 | 7.861 | 7.89 | 100 | $6.3 \times 10^{-4}$ | −1.00 | 2.00 |
| hsa-asg-13613_st2 | 8.00 | 7.637 | 7.756 | 7.88 | 100 | $4.1 \times 10^{-4}$ | −1.00 | 2.00 |
| hsa-asg-11688_st1 | 3.65 | 3.648 | 3.353 | 3.75 | 0 | $9.6 \times 10^{-4}$ | 1.35 | 2.56 |
| hsa-miR-18b | 5.47 | 6.018 | 4.642 | 5.51 | 25 | $8.3 \times 10^{-4}$ | 1.54 | 2.91 |
| hsa-miR-18a | 5.50 | 6.194 | 4.856 | 5.69 | 25 | $6.4 \times 10^{-4}$ | 1.67 | 3.19 |
| hsa-asg-3711_st2 | 5.04 | 5.673 | 5.197 | 5.49 | 0 | $5.5 \times 10^{-4}$ | 1.71 | 3.27 |
| hsa-miR-183 | 8.35 | 9.072 | 7.698 | 8.52 | 100 | $1.7 \times 10^{-4}$ | 1.74 | 3.35 |
| hsa-asg-2919_st1 | 3.23 | 3.409 | 3.524 | 3.37 | 0 | $2.5 \times 10^{-4}$ | 2.01 | 4.02 |
| hsa-asg-924_st1 | 6.22 | 7.126 | 5.699 | 6.66 | 50 | $2.1 \times 10^{-4}$ | 2.36 | 5.14 |
| Hsa-cand317_st1 | 3.80 | 4.614 | 3.974 | 4.45 | 25 | $3.9 \times 10^{-5}$ | 2.92 | 7.61 |

[a]Multiple entries for a single miRNA represent data from different microarray probes.

Example 11

Agilent Human microRNA Microarray Analysis of miRNAs in Normal Cervix and Cervical Cancer Samples miRNA Array Expression Analysis:

miRNA expression in six cervical cancer specimens (Ca1-4, Ca6, and Ca8) and six normal cervix samples (NCX1-3, NCX10, NCX13, and NCX16) were further evaluated using the Human miRNA Microarray (V2) (Agilent Technologies, Inc.; Santa Clara, Calif., USA). The Human miRNA Microarray contains probes for 723 human and 76 human viral microRNAs from the Sanger database v.10.1. Samples for miRNA profiling studies were processed by Asuragen Services (Asuragen, Inc.; Austin, Tex., USA). Total RNA from each sample (200 ng) was dephosphorylated and the pCp-Cy3 labeling molecule was ligated to the 3' end of the RNA molecules. The labeled RNA was purified using a Bio-Spin P-6 column (Bio-Rad Laboratories Inc.; Hercules, Calif., USA). Array hybridization, washing, staining, imaging, and signal extraction were performed according to Agilent's recommended procedures.

miRNA Array Signal Processing:

The signal processing implemented for the Agilent miRNA array is a multi-step process involving probe specific signal detection calls, background correction, and global normalization. For each probe, the contribution of signal due to background was estimated and removed by the Agilent Feature Extraction software as part of the data file output. Similarly, detection calls were based on the Agilent Feature Extraction software. Arrays within a specific analysis experiment were normalized together according to the VSN method described by Huber et al., 2002.

Background Estimate and Correction and Probe Detection:

Three types of data are provided to evaluate each hybridization. The "Total Gene Signal" is the total probe signal multiplied by the number of probes per gene and is calculated after the background effects have been accounted for. The "Total Gene Error" is the square root of the square of the total probe error multiplied by the number of probes per gene. The "Total Probe Error" is the robust average for each replicated probe multiplied by the total number of probe replicates. The "Detection Call" is a binary number that indicates if the gene was detected on the miRNA microarray. Probes detected at least once across all samples in the experiment were considered for statistical analysis.

Global Normalization:

The inventors have found that the Variance Stabilization Normalization (VSN) algorithm provides an ideal balance of accuracy and precision while optimizing sensitivity and specificity of signal. One advantage of VSN, is that it accommodates negative values by using the generalized $\log_2$ transformation.

Generalized $\log_2$ Transformed:

The post-normalized data scale is reported as generalized $\log_2$ data. The distribution of microarray data is typically log normal (i.e, it tends to follow a normal distribution pattern after log transformation). A normal distributed data is amendable to classical statistical treatments, including t-tests and one-way or two-way ANOVA.

For statistical hypothesis testing, a two-sample t-Test, with assumption of equal variance, was applied. This test is used to define which probes are considered to be significantly differentially expressed, or "significant", based on false discovery rate set at 0.05.

A total of 382 human miRNAs were expressed above background level in the normal cervix samples, representing 53% of the miRNAs present on the arrays. A total of 337 miRNAs were expressed above background level in the tumor samples, representing 46.6% of the miRNAs present on the arrays.

A total of 202 human miRNAs were significantly differentially expressed between NCX and Ca samples (Table 15). Among these, 129 were down-regulated (Log 2 diff (NCX vs Ca)≥1) and 41 were up-regulated (Log 2 diff (NCX vs Ca)≤1) by more than 2-fold in Ca samples compared to NCX samples. Thirty-three miRNAs were down-regulated in Ca samples by more than 5-fold (Log 2 diff (NCX vs Ca)≥2.3) with a Student t-test p-value≤0.001. Of those, 7 miRNAs (hsa-miR-204, -133b, -1, -133a, -885-5p, -99a, and -143) were down-regulated in Ca samples by more than 10-fold (Log 2 diff (NCX vs Ca)≥3.3). Among the miRNAs up-regulated in Ca samples, 11 miRNAs (hsa-miR-205, -135b, -182, -31, -31*, -96, -224, -141, -21*, -183, and -944) were up-regulated by more than 5-fold compared to NCX with a Student t-test p-value≤0.005.

TABLE 15 miRNAs Differentially Expressed Among Six Cervical Cancer Samples (Ca) and Six Normal Cervix Tissue Samples (NCX) Following Expression Analysis on Agilent Human miRNA Microarrays. Positive Log2Diff (NCX vs Ca) values represent miRNAs down-regulated in cancer samples

| miRNA Probe ID | NCX 13 | NCX 2 | NCX 1 | NCX 16 | NCX 3 | NCX 10 | Mean (NCX) | % NCX | Ca6 | Ca8 |
|---|---|---|---|---|---|---|---|---|---|---|
| hsa-miR-204 | 11.4 | 10.02 | 8.44 | 10.05 | 9.99 | 10.34 | 10.05 | 100 | 6.26 | 5.96 |
| hsa-miR-133b | 11.8 | 10.50 | 9.92 | 12.31 | 12.36 | 12.28 | 11.53 | 100 | 8.63 | 6.94 |
| hsa-miR-1 | 10.4 | 8.67 | 8.64 | 10.94 | 10.63 | 10.79 | 10.01 | 100 | 6.59 | 4.87 |
| hsa-miR-133a | 8.88 | 8.03 | 7.46 | 9.79 | 9.89 | 9.74 | 8.96 | 100 | 6.19 | 4.39 |
| hsa-miR-205 | 9.70 | 12.73 | 13.60 | 11.55 | 12.22 | 6.28 | 11.01 | 100 | 14.40 | 14.77 |
| hsa-miR-885-5p | 4.28 | 4.61 | 5.64 | 6.83 | 5.93 | 5.93 | 5.54 | 100 | 2.28 | 3.63 |
| hsa-miR-99a | 14.9 | 13.89 | 13.77 | 14.77 | 14.26 | 14.61 | 14.38 | 100 | 10.46 | 12.12 |
| hsa-miR-143 | 14.5 | 13.17 | 13.37 | 14.72 | 14.15 | 13.96 | 13.98 | 100 | 11.76 | 10.81 |
| hsa-miR-145* | 11.0 | 9.39 | 9.77 | 10.89 | 10.65 | 10.60 | 10.39 | 100 | 8.10 | 7.42 |
| hsa-miR-100 | 13.7 | 12.58 | 12.97 | 13.89 | 13.30 | 13.70 | 13.37 | 100 | 10.21 | 11.29 |
| hsa-miR-218 | 10.1 | 9.73 | 10.44 | 10.96 | 10.16 | 10.34 | 10.29 | 100 | 7.43 | 8.03 |
| hsa-miR-195 | 13.8 | 13.23 | 13.41 | 14.62 | 14.28 | 14.35 | 13.96 | 100 | 11.09 | 11.79 |
| hsa-miR-517* | 5.73 | 4.33 | 4.17 | 5.64 | 4.84 | 4.53 | 4.87 | 100 | 2.46 | 2.42 |
| hsa-miR-139-5p | 8.92 | 8.25 | 8.38 | 9.22 | 8.18 | 8.14 | 8.51 | 100 | 5.75 | 6.87 |
| hsa-miR-211 | 2.40 | 3.58 | 7.92 | 6.36 | 2.98 | 5.29 | 4.75 | 50 | 0.86 | 3.96 |
| hsa-miR-145 | 15.2 | 14.72 | 14.58 | 15.31 | 15.34 | 14.98 | 15.02 | 100 | 13.40 | 12.44 |
| hsa-miR-376c | 10.5 | 9.89 | 11.22 | 11.77 | 10.95 | 10.95 | 10.90 | 100 | 8.39 | 8.96 |
| hsa-miR-135b | 6.72 | 6.62 | 6.91 | 7.33 | 6.76 | 7.12 | 6.91 | 100 | 9.74 | 9.18 |
| hsa-miR-381 | 8.97 | 8.12 | 9.23 | 9.92 | 9.14 | 8.89 | 9.04 | 100 | 6.83 | 7.23 |
| hsa-miR-136* | 8.49 | 7.98 | 9.20 | 9.66 | 8.68 | 8.70 | 8.79 | 100 | 6.58 | 6.98 |
| hsa-miR-99a* | 6.22 | 5.15 | 5.36 | 5.79 | 5.88 | 6.03 | 5.74 | 100 | 2.05 | 4.28 |
| hsa-miR-125b-2* | 9.12 | 8.02 | 8.11 | 8.83 | 8.80 | 9.04 | 8.66 | 100 | 5.73 | 6.72 |
| hsa-miR-182 | 1.75 | 1.82 | 2.90 | 2.56 | 3.02 | 1.95 | 2.33 | 17 | 3.82 | 4.75 |
| hsa-miR-31 | 7.53 | 9.07 | 10.00 | 8.48 | 8.79 | 8.26 | 8.69 | 100 | 10.41 | 9.98 |
| hsa-miR-31* | 4.60 | 6.08 | 7.32 | 6.23 | 6.83 | 5.95 | 6.17 | 100 | 8.68 | 8.17 |
| hsa-miR-376a | 10.5 | 9.72 | 11.20 | 11.77 | 10.85 | 10.77 | 10.81 | 100 | 8.45 | 8.90 |
| hsa-miR-497 | 12.1 | 11.46 | 12.04 | 12.83 | 12.38 | 12.31 | 12.20 | 100 | 9.55 | 10.30 |
| hsa-miR-299-5p | 8.33 | 7.77 | 8.64 | 9.40 | 8.60 | 8.26 | 8.50 | 100 | 6.48 | 6.74 |
| hsa-miR-125b | 15.4 | 15.09 | 14.71 | 15.03 | 15.15 | 14.88 | 15.06 | 100 | 12.72 | 13.56 |
| hsa-miR-96 | 5.38 | 5.71 | 7.61 | 6.21 | 7.27 | 6.69 | 6.48 | 100 | 8.29 | 9.09 |
| hsa-miR-411 | 7.10 | 6.31 | 7.90 | 8.34 | 7.41 | 7.14 | 7.37 | 100 | 5.41 | 5.72 |
| hsa-miR-451 | 15.2 | 14.00 | 13.54 | 15.36 | 15.19 | 14.15 | 14.58 | 100 | 13.31 | 12.70 |
| hsa-miR-143* | 8.61 | 7.32 | 7.81 | 9.60 | 8.95 | 8.45 | 8.46 | 100 | 6.89 | 5.75 |

TABLE 15-continued miRNAs Differentially Expressed Among Six Cervical Cancer Samples (Ca) and
Six Normal Cervix Tissue Samples (NCX) Following Expression Analysis on Agilent
Human miRNA Microarrays. Positive Log2Diff (NCX vs Ca) values represent miRNAs
down-regulated in cancer samples

| miRNA | | | | | | | | | | |
|---|---|---|---|---|---|---|---|---|---|---|
| hsa-miR-135a | 2.82 | 5.08 | 4.25 | 5.36 | 3.34 | 1.06 | 3.65 | 50 | 2.08 | 2.54 |
| hsa-miR-299-3p | 6.71 | 5.95 | 7.28 | 7.54 | 7.21 | 6.66 | 6.89 | 100 | 4.82 | 5.48 |
| hsa-miR-224 | 8.60 | 8.78 | 9.58 | 10.22 | 9.17 | 8.58 | 9.15 | 100 | 12.52 | 11.88 |
| hsa-miR-495 | 7.99 | 6.77 | 8.48 | 9.30 | 8.71 | 8.35 | 8.27 | 100 | 6.03 | 6.83 |
| hsa-miR-141 | 6.86 | 8.85 | 10.72 | 9.02 | 10.40 | 9.68 | 9.26 | 100 | 10.15 | 11.70 |
| hsa-miR-375 | 3.74 | 5.63 | 7.58 | 6.94 | 7.53 | 6.82 | 6.37 | 100 | 2.10 | 5.33 |
| hsa-miR-21* | 5.28 | 6.10 | 7.23 | 6.75 | 7.28 | 6.79 | 6.57 | 100 | 9.60 | 9.16 |
| hsa-miR-654-3p | 8.03 | 7.58 | 9.34 | 9.75 | 8.87 | 8.61 | 8.70 | 100 | 7.11 | 7.36 |
| hsa-miR-455-5p | 8.45 | 8.37 | 9.60 | 10.30 | 9.94 | 9.86 | 9.42 | 100 | 7.17 | 7.70 |
| hsa-miR-379 | 6.94 | 6.41 | 7.82 | 8.42 | 7.48 | 7.32 | 7.40 | 100 | 5.42 | 6.03 |
| hsa-miR-337-3p | 5.33 | 5.21 | 6.94 | 7.39 | 6.42 | 5.95 | 6.21 | 100 | 4.18 | 4.55 |
| hsa-miR-154 | 7.38 | 7.06 | 7.95 | 8.78 | 7.96 | 7.95 | 7.84 | 100 | 6.11 | 6.63 |
| hsa-miR-886-5p | 4.09 | 4.70 | 3.75 | 3.15 | 3.19 | 4.14 | 3.84 | 100 | 2.42 | 2.51 |
| hsa-miR-183 | 3.86 | 4.32 | 5.91 | 4.75 | 5.48 | 5.14 | 4.91 | 100 | 6.57 | 7.47 |
| hsa-miR-424 | 11.7 | 12.23 | 13.68 | 14.41 | 14.05 | 14.09 | 13.37 | 100 | 10.75 | 11.43 |
| hsa-miR-410 | 4.87 | 4.67 | 6.29 | 7.25 | 6.55 | 5.72 | 5.89 | 100 | 5.03 | 5.14 |
| hsa-miR-944 | −0.59 | 1.39 | 2.68 | 1.94 | 2.78 | 0.80 | 1.50 | 0 | 2.73 | 3.83 |
| hsa-miR-337-5p | 7.49 | 7.33 | 8.79 | 9.18 | 8.55 | 8.02 | 8.22 | 100 | 6.37 | 7.27 |
| hsa-miR-129-3p | 5.81 | 3.67 | 4.34 | 6.18 | 4.54 | 5.15 | 4.95 | 83 | 3.34 | 3.35 |
| hsa-miR-328 | 6.44 | 5.92 | 4.49 | 5.86 | 5.29 | 5.50 | 5.58 | 100 | 3.80 | 3.65 |
| hsa-let-7e* | 5.04 | 3.86 | 4.16 | 5.13 | 4.69 | 4.60 | 4.58 | 100 | 3.03 | 3.09 |
| hsa-miR-21 | 13.28 | 13.35 | 13.77 | 14.33 | 13.98 | 14.25 | 13.83 | 100 | 16.36 | 15.84 |
| hsa-miR-149 | 7.86 | 7.20 | 8.03 | 8.05 | 7.23 | 7.02 | 7.57 | 100 | 7.00 | 6.39 |
| hsa-miR-127-3p | 9.21 | 9.18 | 10.40 | 10.69 | 10.10 | 9.94 | 9.92 | 100 | 8.20 | 8.82 |
| hsa-miR-30a* | 7.07 | 5.45 | 6.82 | 8.33 | 6.96 | 6.95 | 6.93 | 100 | 4.70 | 5.32 |
| hsa-miR-142-3p | 10.37 | 10.03 | 11.54 | 11.17 | 11.00 | 9.91 | 10.67 | 100 | 12.29 | 13.00 |
| hsa-miR-10b | 13.09 | 10.66 | 11.49 | 12.61 | 11.67 | 11.91 | 11.91 | 100 | 9.74 | 10.05 |
| hsa-miR-140-3p | 12.35 | 10.84 | 10.80 | 11.98 | 11.16 | 11.47 | 11.43 | 100 | 9.20 | 9.83 |
| hsa-miR-155 | 7.52 | 6.60 | 7.17 | 7.53 | 7.86 | 7.55 | 7.37 | 100 | 8.79 | 9.55 |
| hsa-miR-144* | 5.99 | 4.72 | 4.62 | 6.31 | 5.68 | 4.45 | 5.29 | 100 | 4.06 | 3.28 |
| hsa-miR-329 | 5.73 | 4.34 | 6.10 | 7.05 | 5.87 | 5.42 | 5.75 | 100 | 4.18 | 4.39 |
| hsa-miR-873 | 5.89 | 2.11 | 2.83 | 3.88 | 3.79 | 3.60 | 3.68 | 67 | 2.37 | 2.28 |
| hsa-miR-18a | 4.55 | 3.87 | 4.57 | 5.40 | 5.43 | 4.70 | 4.75 | 83 | 6.26 | 6.56 |
| hsa-miR-431* | 2.79 | 2.45 | 3.26 | 3.76 | 3.23 | 3.01 | 3.08 | 17 | 4.48 | 4.84 |
| hsa-let-7e | 12.95 | 11.8 | 12.27 | 13.51 | 12.93 | 12.98 | 12.74 | 100 | 11.42 | 11.30 |
| hsa-miR-154* | 5.98 | 4.88 | 6.66 | 6.68 | 6.41 | 5.81 | 6.07 | 100 | 4.77 | 4.67 |
| hsa-miR-886-3p | 12.14 | 11.1 | 11.00 | 11.73 | 11.11 | 11.85 | 11.50 | 100 | 9.42 | 10.80 |
| hsa-miR-199b-5p | 12.14 | 12.0 | 13.13 | 13.38 | 12.79 | 12.66 | 12.70 | 100 | 11.44 | 11.30 |

TABLE 15-continued miRNAs Differentially Expressed Among Six Cervical Cancer Samples (Ca) and
Six Normal Cervix Tissue Samples (NCX) Following Expression Analysis on Agilent
Human miRNA Microarrays. Positive Log2Diff (NCX vs Ca) values represent miRNAs
down-regulated in cancer samples

| miRNA | | | | | | | | | | |
|---|---|---|---|---|---|---|---|---|---|---|
| hsa-miR-377 | 9.05 | 8.44 | 10.06 | 10.13 | 9.83 | 9.45 | 9.49 | 100 | 8.03 | 8.56 |
| hsa-miR-136 | 8.43 | 8.60 | 10.43 | 10.13 | 9.57 | 8.58 | 9.29 | 100 | 7.72 | 8.19 |
| hsa-miR-543 | 5.70 | 5.02 | 6.86 | 7.35 | 6.84 | 6.38 | 6.36 | 100 | 4.95 | 5.34 |
| hsa-miR-26a | 15.39 | 14.1 | 14.07 | 14.92 | 14.21 | 14.59 | 14.55 | 100 | 12.43 | 12.61 |
| hsa-miR-369-5p | 4.60 | 4.24 | 5.79 | 6.56 | 5.55 | 5.11 | 5.31 | 100 | 3.70 | 3.99 |
| hsa-miR-488 | 2.77 | 0.46 | 2.46 | 4.22 | 4.13 | 2.89 | 2.82 | 33 | 2.61 | 0.27 |
| hsa-miR-195* | 4.99 | 4.53 | 4.15 | 4.96 | 4.97 | 4.85 | 4.74 | 100 | 3.05 | 3.50 |
| hsa-miR-101* | 5.93 | 5.17 | 4.90 | 5.70 | 5.05 | 5.10 | 5.31 | 100 | 3.38 | 2.59 |
| hsa-miR-485-5p | 3.44 | 3.08 | 3.83 | 4.75 | 4.00 | 3.78 | 3.81 | 83 | 1.86 | 2.67 |
| hsa-miR-455-3p | 9.69 | 10.0 | 11.38 | 12.65 | 11.97 | 11.52 | 11.21 | 100 | 10.05 | 9.57 |
| hsa-miR-483-3p | 5.75 | 5.14 | 4.04 | 4.92 | 4.16 | 4.39 | 4.73 | 100 | 3.67 | 3.37 |
| hsa-miR-130a | 12.75 | 11.8 | 12.10 | 13.11 | 12.50 | 12.82 | 12.52 | 100 | 10.18 | 11.28 |
| hsa-miR-487b | 8.30 | 7.75 | 9.07 | 10.16 | 9.12 | 8.77 | 8.86 | 100 | 7.44 | 7.67 |
| hsa-miR-433 | 2.36 | 3.17 | 3.94 | 4.84 | 4.11 | 3.85 | 3.71 | 67 | 3.38 | 2.93 |
| hsa-miR-141* | 1.33 | 2.65 | 2.53 | 2.66 | 3.19 | 2.75 | 2.52 | 0 | 3.78 | 4.21 |
| hsa-miR-376b | 5.74 | 4.84 | 8.07 | 7.92 | 7.47 | 6.72 | 6.79 | 100 | 5.07 | 5.88 |
| hsa-let-7c | 15.50 | 14.9 | 14.87 | 15.38 | 15.42 | 15.28 | 15.23 | 100 | 13.34 | 13.93 |
| hsa-miR-142-5p | 8.04 | 7.70 | 9.51 | 8.65 | 8.80 | 7.52 | 8.37 | 100 | 10.06 | 8.94 |
| hsa-miR-190 | 5.82 | 4.47 | 5.70 | 5.29 | 4.88 | 4.78 | 5.15 | 100 | 3.12 | 2.80 |
| hsa-miR-200c | 6.98 | 9.15 | 9.91 | 8.84 | 9.55 | 9.14 | 8.93 | 100 | 9.78 | 10.49 |
| hsa-miR-539 | 3.42 | 3.35 | 4.60 | 6.17 | 4.75 | 4.13 | 4.40 | 67 | 3.59 | 3.34 |
| hsa-miR-125a-5p | 11.01 | 9.98 | 9.75 | 10.69 | 10.13 | 10.15 | 10.29 | 100 | 8.94 | 8.76 |
| hsa-miR-15b* | 2.09 | 0.56 | 1.61 | 3.07 | 2.16 | 2.78 | 2.05 | 33 | 2.78 | 2.89 |
| hsa-miR-18b | 4.77 | 4.38 | 4.76 | 4.86 | 5.02 | 4.25 | 4.67 | 100 | 5.47 | 5.96 |
| hsa-miR-574-3p | 9.08 | 9.02 | 8.42 | 9.69 | 9.10 | 9.24 | 9.09 | 100 | 7.91 | 7.73 |
| hsa-miR-656 | 3.10 | 2.35 | 4.67 | 5.32 | 4.06 | 3.27 | 3.80 | 50 | 3.25 | 2.67 |
| hsa-miR-214 | 12.81 | 11.4 | 11.50 | 12.74 | 12.18 | 12.52 | 12.19 | 100 | 11.22 | 10.48 |
| hsa-miR-99b | 9.73 | 9.06 | 8.73 | 10.50 | 9.80 | 9.73 | 9.59 | 100 | 8.53 | 8.39 |
| hsa-miR-486-5p | 7.70 | 7.44 | 6.85 | 7.83 | 7.63 | 6.79 | 7.37 | 100 | 6.51 | 5.94 |
| hsa-miR-223 | 11.13 | 11.2 | 11.40 | 11.89 | 11.48 | 11.07 | 11.37 | 100 | 13.09 | 14.00 |
| hsa-miR-542-3p | 5.85 | 6.30 | 7.77 | 8.82 | 8.45 | 7.80 | 7.50 | 100 | 5.76 | 6.31 |
| hsa-miR-199b-3p | 15.23 | 14.0 | 14.62 | 15.25 | 14.75 | 15.03 | 14.82 | 100 | 13.71 | 13.10 |
| hsa-miR-196b | 10.21 | 9.55 | 9.88 | 10.74 | 10.19 | 10.48 | 10.18 | 100 | 8.09 | 8.52 |
| hsa-miR-146b-5p | 8.17 | 8.00 | 8.05 | 8.91 | 9.28 | 9.73 | 8.69 | 100 | 10.45 | 10.49 |
| hsa-miR-140-5p | 10.09 | 8.72 | 9.07 | 10.39 | 9.67 | 9.92 | 9.64 | 100 | 8.01 | 8.62 |
| hsa-miR-29c* | 9.29 | 8.15 | 8.03 | 9.05 | 8.37 | 8.48 | 8.56 | 100 | 6.62 | 7.21 |
| hsa-miR-499-5p | 6.16 | 4.07 | 4.56 | 5.37 | 5.07 | 5.62 | 5.14 | 83 | 3.64 | 2.94 |
| hsa-miR-29a | 15.29 | 14.6 | 14.32 | 15.16 | 14.68 | 14.95 | 14.84 | 100 | 13.14 | 13.72 |

TABLE 15-continued miRNAs Differentially Expressed Among Six Cervical Cancer Samples (Ca) and
Six Normal Cervix Tissue Samples (NCX) Following Expression Analysis on Agilent
Human miRNA Microarrays. Positive Log2Diff (NCX vs Ca) values represent miRNAs
down-regulated in cancer samples

| | | | | | | | | | | |
|---|---|---|---|---|---|---|---|---|---|---|
| hsa-miR-650 | 4.56 | 3.59 | 3.72 | 3.63 | 3.73 | 3.27 | 3.75 | 100 | 5.36 | 5.52 |
| hsa-miR-101 | 13.11 | 11.6 | 11.56 | 11.74 | 11.59 | 11.84 | 11.92 | 100 | 9.52 | 10.45 |
| hsa-miR-32 | 4.51 | 3.96 | 6.01 | 4.53 | 4.70 | 3.32 | 4.50 | 100 | 4.82 | 5.65 |
| hsa-miR-30a | 10.51 | 9.44 | 10.44 | 11.81 | 10.59 | 10.59 | 10.56 | 100 | 8.94 | 9.21 |
| hsa-miR-210 | 7.06 | 7.92 | 8.51 | 7.09 | 8.29 | 7.32 | 7.70 | 100 | 8.97 | 8.95 |
| hsa-miR-450a | 6.40 | 6.25 | 8.18 | 8.72 | 8.37 | 7.81 | 7.62 | 100 | 5.89 | 6.25 |
| hsa-miR-26b | 14.71 | 13.5 | 13.55 | 14.72 | 13.98 | 14.32 | 14.14 | 100 | 12.16 | 12.61 |
| hsa-miR-126* | 9.37 | 8.07 | 8.95 | 9.81 | 8.35 | 8.27 | 8.80 | 100 | 6.60 | 7.26 |
| hsa-miR-10a | 11.07 | 9.04 | 10.40 | 11.09 | 10.60 | 11.10 | 10.55 | 100 | 9.33 | 9.07 |
| hsa-miR-29c | 14.55 | 13.2 | 13.37 | 13.82 | 13.39 | 13.54 | 13.65 | 100 | 11.41 | 12.47 |
| hsa-miR-377* | 2.59 | 1.68 | 3.44 | 4.17 | 3.35 | 3.32 | 3.09 | 67 | 2.24 | 2.39 |
| hsa-miR-29b-2* | 3.69 | 2.87 | 2.89 | 3.80 | 3.22 | 2.87 | 3.22 | 67 | 0.63 | 1.72 |
| hsa-miR-183* | 1.35 | 2.84 | 2.83 | 1.95 | 2.23 | 2.70 | 2.32 | 0 | 3.22 | 3.89 |
| hsa-miR-93 | 9.30 | 8.34 | 8.93 | 9.71 | 9.49 | 9.36 | 9.19 | 100 | 10.28 | 10.31 |
| hsa-miR-146a | 8.08 | 7.14 | 8.51 | 8.61 | 8.26 | 8.13 | 8.12 | 100 | 8.67 | 10.20 |
| hsa-miR-28-5p | 10.96 | 9.59 | 9.77 | 11.13 | 10.47 | 10.38 | 10.38 | 100 | 9.52 | 8.60 |
| hsa-miR-429 | 6.29 | 7.67 | 9.00 | 8.24 | 8.60 | 9.07 | 8.15 | 100 | 9.54 | 9.81 |
| hsa-miR-432 | 5.36 | 5.60 | 6.78 | 7.46 | 6.86 | 6.32 | 6.40 | 100 | 5.26 | 5.69 |
| hsa-miR-889 | 1.99 | 1.27 | 3.17 | 4.00 | 3.19 | 2.32 | 2.66 | 17 | 0.26 | 1.69 |
| hsa-miR-382 | 5.35 | 4.72 | 6.57 | 7.11 | 6.27 | 5.84 | 5.98 | 100 | 4.99 | 5.12 |
| hsa-miR-200b | 7.75 | 9.18 | 10.33 | 9.84 | 9.96 | 10.36 | 9.57 | 100 | 10.98 | 11.26 |
| hsa-miR-126 | 12.89 | 12.2 | 12.58 | 13.91 | 12.82 | 12.81 | 12.87 | 100 | 11.37 | 12.07 |
| hsa-miR-424* | 5.67 | 7.06 | 6.92 | 7.25 | 7.17 | 7.38 | 6.91 | 100 | 4.69 | 5.17 |
| hsa-miR-106a | 5.59 | 4.97 | 5.04 | 6.00 | 5.83 | 5.63 | 5.51 | 100 | 5.99 | 6.03 |
| hsa-let-7b | 15.89 | 15.5 | 15.29 | 15.67 | 15.89 | 15.52 | 15.64 | 100 | 14.85 | 15.01 |
| hsa-miR-26b* | 4.21 | 3.05 | 3.41 | 4.71 | 4.08 | 4.16 | 3.94 | 100 | 2.70 | 2.85 |
| hsa-miR-505 | 8.42 | 8.11 | 7.73 | 8.98 | 8.24 | 8.17 | 8.28 | 100 | 6.85 | 7.38 |
| hsa-miR-214* | 8.39 | 6.85 | 7.19 | 7.97 | 7.61 | 7.85 | 7.64 | 100 | 7.18 | 6.28 |
| hsa-miR-542-5p | 5.63 | 5.91 | 7.42 | 8.38 | 7.97 | 7.43 | 7.12 | 100 | 5.61 | 6.47 |
| hsa-miR-144 | 9.08 | 7.90 | 8.91 | 9.58 | 9.78 | 7.88 | 8.85 | 100 | 7.97 | 7.46 |
| hsa-miR-151-5p | 11.84 | 10.6 | 10.93 | 11.92 | 11.17 | 11.31 | 11.31 | 100 | 10.27 | 9.93 |
| hsa-miR-361-5p | 10.86 | 9.45 | 9.84 | 10.87 | 10.09 | 10.36 | 10.24 | 100 | 8.73 | 9.11 |
| hsa-miR-629* | 3.79 | 5.28 | 5.31 | 4.19 | 3.98 | 3.71 | 4.38 | 83 | 4.86 | 5.25 |
| hsa-miR-10b* | 6.35 | 4.42 | 5.42 | 6.10 | 5.35 | 5.88 | 5.59 | 100 | 3.84 | 4.27 |
| hsa-miR-30b | 13.31 | 11.8 | 12.16 | 13.17 | 12.45 | 12.58 | 12.58 | 100 | 11.64 | 11.29 |
| hsa-miR-15b | 11.61 | 10.3 | 10.87 | 12.01 | 11.35 | 11.38 | 11.26 | 100 | 11.82 | 12.35 |
| hsa-miR-184 | 3.50 | 5.38 | 4.13 | 4.22 | 5.06 | 5.10 | 4.56 | 83 | 3.63 | 4.39 |
| hsa-miR-106b* | 0.85 | 1.06 | 1.16 | 2.22 | 1.48 | 1.30 | 1.34 | 0 | 1.77 | 2.22 |

TABLE 15-continued miRNAs Differentially Expressed Among Six Cervical Cancer Samples (Ca) and Six Normal Cervix Tissue Samples (NCX) Following Expression Analysis on Agilent Human miRNA Microarrays. Positive Log2Diff (NCX vs Ca) values represent miRNAs down-regulated in cancer samples

| | | | | | | | | | | |
|---|---|---|---|---|---|---|---|---|---|---|
| hsa-miR-199a-5p | 13.58 | 12.2 | 12.57 | 14.07 | 13.54 | 13.85 | 13.31 | 100 | 12.86 | 11.96 |
| hsa-miR-490-3p | 3.32 | 4.15 | 2.09 | 2.49 | 3.38 | 3.46 | 3.15 | 33 | 1.65 | 2.91 |
| hsa-miR-100* | 1.97 | 0.58 | 2.24 | 2.58 | 2.56 | 3.00 | 2.15 | 17 | 1.74 | 0.58 |
| hsa-miR-152 | 8.64 | 8.37 | 9.20 | 9.90 | 9.15 | 9.24 | 9.08 | 100 | 8.45 | 8.23 |
| hsa-miR-130b | 6.24 | 6.44 | 6.44 | 7.40 | 7.16 | 6.97 | 6.77 | 100 | 7.71 | 7.59 |
| hsa-miR-23b | 14.85 | 13.5 | 14.23 | 15.09 | 14.32 | 14.34 | 14.40 | 100 | 13.85 | 13.40 |
| hsa-miR-27b | 14.96 | 13.5 | 13.96 | 14.97 | 14.41 | 14.43 | 14.38 | 100 | 13.92 | 13.42 |
| hsa-miR-492 | 3.04 | 4.07 | 3.97 | 2.66 | 3.59 | 2.91 | 3.37 | 0 | 5.04 | 3.79 |
| hsa-miR-485-3p | 3.67 | 3.06 | 4.48 | 4.83 | 4.09 | 3.73 | 3.98 | 67 | 3.47 | 3.36 |
| hsa-miR-505* | 5.58 | 5.28 | 5.09 | 6.37 | 5.63 | 5.67 | 5.61 | 100 | 4.02 | 5.03 |
| hsa-miR-320 | 11.24 | 10.6 | 10.28 | 11.47 | 11.26 | 11.25 | 11.03 | 100 | 10.01 | 10.05 |
| hsa-miR-335 | 7.52 | 7.16 | 6.59 | 7.90 | 7.13 | 7.27 | 7.26 | 100 | 5.39 | 5.41 |
| hsa-miR-630 | 8.16 | 9.09 | 8.66 | 7.15 | 8.66 | 8.89 | 8.44 | 100 | 8.78 | 8.74 |
| hsa-miR-181d | 7.27 | 6.67 | 6.67 | 6.73 | 6.26 | 6.60 | 6.70 | 100 | 5.67 | 5.75 |
| hsa-miR-425 | 8.20 | 7.50 | 8.25 | 8.74 | 8.28 | 8.00 | 8.16 | 100 | 8.84 | 8.62 |
| hsa-miR-628-5p | 3.63 | 3.26 | 3.66 | 4.73 | 4.07 | 4.05 | 3.90 | 67 | 2.81 | 2.66 |
| hsa-miR-29b-1* | 5.77 | 5.23 | 5.42 | 6.13 | 6.00 | 6.04 | 5.76 | 100 | 4.99 | 5.17 |
| hsa-miR-106b | 10.72 | 9.89 | 10.12 | 11.08 | 10.89 | 10.89 | 10.60 | 100 | 10.94 | 11.19 |
| hsa-miR-181c | 9.38 | 7.58 | 7.38 | 8.21 | 7.77 | 8.24 | 8.09 | 100 | 7.27 | 7.02 |
| hsa-miR-29a* | 4.63 | 3.94 | 4.15 | 4.92 | 4.25 | 4.16 | 4.34 | 100 | 3.14 | 3.08 |
| hsa-miR-513c | 4.09 | 4.96 | 5.06 | 4.19 | 4.42 | 4.20 | 4.48 | 100 | 4.94 | 4.69 |
| hsa-miR-374b | 10.47 | 9.31 | 9.82 | 11.01 | 10.07 | 10.27 | 10.16 | 100 | 9.13 | 9.04 |
| hsa-miR-215 | 7.24 | 6.09 | 5.69 | 6.40 | 6.46 | 6.45 | 6.39 | 100 | 5.36 | 5.89 |
| hsa-miR-24-1* | 7.28 | 6.19 | 6.89 | 8.11 | 7.17 | 7.06 | 7.12 | 100 | 6.91 | 6.48 |
| hsa-miR-151-3p | 9.08 | 8.23 | 8.36 | 9.18 | 8.69 | 8.73 | 8.71 | 100 | 8.21 | 7.60 |
| hsa-miR-197 | 8.18 | 8.02 | 7.30 | 8.08 | 7.47 | 7.45 | 7.75 | 100 | 7.03 | 6.87 |
| hsa-miR-30c-2* | 4.94 | 5.64 | 5.08 | 5.67 | 5.22 | 5.54 | 5.35 | 100 | 4.73 | 4.83 |
| hsa-miR-330-3p | 4.75 | 4.60 | 5.01 | 4.47 | 4.42 | 4.39 | 4.61 | 100 | 4.77 | 5.20 |
| hsa-let-7g | 14.21 | 13.2 | 13.47 | 14.66 | 14.02 | 14.33 | 13.99 | 100 | 12.75 | 13.17 |
| hsa-miR-20a* | 7.19 | 5.79 | 5.94 | 6.65 | 6.25 | 6.42 | 6.37 | 100 | 5.30 | 4.95 |
| hsa-miR-655 | 2.09 | 1.84 | 0.84 | 2.60 | 2.26 | 1.38 | 1.83 | 17 | 0.65 | 1.10 |
| hsa-miR-93* | 2.93 | 2.11 | 2.22 | 2.87 | 2.53 | 2.90 | 2.60 | 33 | 3.05 | 2.94 |
| hsa-miR-766 | 4.78 | 5.69 | 4.56 | 5.14 | 4.91 | 5.20 | 5.05 | 100 | 5.87 | 6.04 |
| hsa-miR-186 | 9.73 | 8.95 | 8.98 | 9.61 | 9.02 | 8.84 | 9.19 | 100 | 7.84 | 8.04 |
| hsa-miR-17 | 9.61 | 9.13 | 9.05 | 9.88 | 9.63 | 9.52 | 9.47 | 100 | 9.90 | 9.90 |
| hsa-miR-374b* | 3.80 | 3.11 | 3.20 | 3.51 | 2.65 | 3.07 | 3.22 | 67 | 1.33 | 2.63 |
| hsa-let-7i | 14.01 | 13.1 | 13.22 | 14.31 | 13.85 | 14.07 | 13.77 | 100 | 12.95 | 13.29 |
| hsa-miR-194 | 7.35 | 6.18 | 6.09 | 6.61 | 6.38 | 6.39 | 6.50 | 100 | 5.41 | 5.72 |

TABLE 15-continued miRNAs Differentially Expressed Among Six Cervical Cancer Samples (Ca) and
Six Normal Cervix Tissue Samples (NCX) Following Expression Analysis on Agilent
Human miRNA Microarrays. Positive Log2Diff (NCX vs Ca) values represent miRNAs
down-regulated in cancer samples

| | | | | | | | | | | |
|---|---|---|---|---|---|---|---|---|---|---|
| hsa-miR-602 | 3.95 | 4.78 | 4.68 | 3.62 | 3.83 | 3.80 | 4.11 | 67 | 4.40 | 5.07 |
| hsa-miR-212 | 6.58 | 5.47 | 6.22 | 6.21 | 6.38 | 5.98 | 6.14 | 100 | 6.67 | 6.76 |
| hsa-miR-940 | 9.36 | 9.95 | 10.05 | 8.62 | 9.43 | 9.22 | 9.44 | 100 | 10.79 | 9.77 |
| hsa-let-7a | 16.08 | 15.6 | 15.78 | 15.67 | 15.84 | 15.52 | 15.75 | 100 | 15.03 | 15.31 |
| hsa-let-7d* | 4.43 | 4.36 | 3.13 | 4.07 | 3.68 | 3.76 | 3.91 | 100 | 3.68 | 2.46 |
| hsa-miR-768-3p | 12.02 | 11.6 | 11.24 | 12.12 | 11.99 | 12.26 | 11.87 | 100 | 11.46 | 11.57 |
| hsa-miR-744 | 7.06 | 6.33 | 6.72 | 7.64 | 6.92 | 7.03 | 6.95 | 100 | 6.17 | 6.29 |
| hsa-miR-512-3p | 4.77 | 5.08 | 4.16 | 4.58 | 4.36 | 4.61 | 4.59 | 83 | 3.44 | 4.44 |
| hsa-miR-30b* | 5.25 | 5.40 | 5.25 | 5.39 | 4.97 | 5.44 | 5.28 | 100 | 4.82 | 5.04 |
| hsa-miR-374a | 11.09 | 10.1 | 10.91 | 11.58 | 10.70 | 10.93 | 10.90 | 100 | 10.16 | 10.19 |
| hsa-miR-99b* | 3.80 | 4.23 | 4.45 | 4.42 | 4.05 | 3.73 | 4.11 | 83 | 5.25 | 5.23 |
| hsa-miR-193a-5p | 8.08 | 7.08 | 6.97 | 7.78 | 7.29 | 7.60 | 7.47 | 100 | 6.88 | 6.42 |
| hsa-let-7f | 15.48 | 14.5 | 15.10 | 15.23 | 15.22 | 14.98 | 15.09 | 100 | 14.14 | 14.38 |
| hsa-miR-28-3p | 5.44 | 4.46 | 4.35 | 4.90 | 4.80 | 4.48 | 4.74 | 100 | 4.30 | 3.89 |
| hsa-miR-654-5p | 4.58 | 5.27 | 5.21 | 5.42 | 5.39 | 5.30 | 5.20 | 100 | 4.53 | 4.33 |
| hsa-miR-345 | 4.97 | 5.00 | 5.04 | 4.11 | 4.21 | 4.47 | 4.63 | 100 | 4.98 | 5.27 |
| hsa-miR-501-5p | 5.72 | 5.30 | 5.55 | 5.72 | 5.57 | 5.63 | 5.58 | 100 | 5.71 | 5.87 |

| miRNA Probe ID | Ca4 | Ca1 | Ca2 | Ca3 | Mean (Ca) | % Ca | Ttest (NCX vs CA) | Log2 Diff (NCX vs Ca) | FC |
|---|---|---|---|---|---|---|---|---|---|
| hsa-miR-204 | 4.06 | 1.80 | 3.31 | 3.53 | 4.15 | 33 | 2.30E−05 | 5.90 | 59.66 |
| hsa-miR-133b | 5.35 | 5.65 | 7.38 | 5.50 | 6.58 | 100 | 2.86E−05 | 4.96 | 31.12 |
| hsa-miR-1 | 5.22 | 4.21 | 6.15 | 4.22 | 5.21 | 100 | 1.07E−05 | 4.80 | 27.89 |
| hsa-miR-133a | 4.55 | 4.03 | 5.13 | 3.29 | 4.60 | 67 | 2.05E−05 | 4.37 | 20.63 |
| hsa-miR-205 | 15.32 | 15.76 | 15.69 | 14.78 | 15.12 | 100 | 4.12E−03 | −4.11 | 17.23 |
| hsa-miR-885-5p | 2.01 | 1.17 | −0.22 | 1.55 | 1.73 | 0 | 1.54E−04 | 3.80 | 13.97 |
| hsa-miR-99a | 11.03 | 8.33 | 11.25 | 10.90 | 10.68 | 100 | 5.78E−05 | 3.70 | 12.98 |
| hsa-miR-143 | 10.86 | 9.47 | 10.96 | 9.70 | 10.59 | 100 | 1.37E−05 | 3.39 | 10.48 |
| hsa-miR-145* | 7.44 | 6.30 | 7.08 | 6.24 | 7.10 | 100 | 8.71E−06 | 3.29 | 9.78 |
| hsa-miR-100 | 9.56 | 8.54 | 10.87 | 10.07 | 10.09 | 100 | 2.67E−05 | 3.28 | 9.71 |
| hsa-miR-218 | 6.55 | 7.49 | 6.82 | 6.04 | 7.06 | 100 | 2.42E−06 | 3.23 | 9.38 |
| hsa-miR-195 | 10.44 | 9.83 | 11.43 | 9.91 | 10.75 | 100 | 1.18E−05 | 3.21 | 9.27 |
| hsa-miR-517* | 1.87 | 0.71 | 2.79 | −0.15 | 1.68 | 0 | 1.64E−04 | 3.19 | 9.12 |
| hsa-miR-139-5p | 5.02 | 4.72 | 5.01 | 4.63 | 5.33 | 100 | 1.05E−05 | 3.18 | 9.07 |
| hsa-miR-211 | 1.28 | 1.03 | 1.15 | 1.72 | 1.67 | 0 | 1.12E−02 | 3.09 | 8.50 |
| hsa-miR-145 | 12.07 | 10.78 | 12.26 | 10.79 | 11.96 | 100 | 3.44E−05 | 3.07 | 8.38 |
| hsa-miR-376c | 7.45 | 6.23 | 8.49 | 7.57 | 7.85 | 100 | 7.68E−05 | 3.05 | 8.27 |
| hsa-miR-135b | 8.10 | 11.35 | 10.40 | 10.57 | 9.89 | 100 | 1.01E−04 | −2.98 | 7.89 |

TABLE 15-continued miRNAs Differentially Expressed Among Six Cervical Cancer Samples (Ca) and Six Normal Cervix Tissue Samples (NCX) Following Expression Analysis on Agilent Human miRNA Microarrays. Positive Log2Diff (NCX vs Ca) values represent miRNAs down-regulated in cancer samples

| | | | | | | | | | |
|---|---|---|---|---|---|---|---|---|---|
| hsa-miR-381 | 5.08 | 5.05 | 6.50 | 5.90 | 6.10 | 100 | 5.58E−05 | 2.94 | 7.70 |
| hsa-miR-136* | 5.12 | 4.41 | 6.55 | 5.45 | 5.85 | 83 | 1.02E−04 | 2.94 | 7.66 |
| hsa-miR-99a* | 3.16 | 0.84 | 3.30 | 3.20 | 2.81 | 33 | 2.00E−04 | 2.94 | 7.65 |
| hsa-miR-125b-2* | 5.84 | 4.33 | 5.76 | 6.23 | 5.77 | 83 | 1.82E−05 | 2.89 | 7.40 |
| hsa-miR-182 | 4.59 | 6.33 | 5.80 | 5.94 | 5.21 | 100 | 9.10E−05 | −2.87 | 7.33 |
| hsa-miR-31 | 11.74 | 13.68 | 11.36 | 12.18 | 11.56 | 100 | 1.15E−03 | −2.87 | 7.31 |
| hsa-miR-31* | 7.93 | 10.16 | 9.14 | 9.99 | 9.01 | 100 | 3.34E−04 | −2.85 | 7.19 |
| hsa-miR-376a | 7.71 | 6.20 | 8.78 | 7.85 | 7.98 | 100 | 1.94E−04 | 2.82 | 7.08 |
| hsa-miR-497 | 10.06 | 7.97 | 10.18 | 8.38 | 9.41 | 100 | 9.51E−05 | 2.79 | 6.92 |
| hsa-miR-299-5p | 5.22 | 4.67 | 6.01 | 5.35 | 5.74 | 100 | 3.80E−05 | 2.76 | 6.75 |
| hsa-miR-125b | 11.99 | 10.73 | 12.62 | 12.25 | 12.31 | 100 | 4.35E−05 | 2.74 | 6.69 |
| hsa-miR-96 | 9.03 | 9.34 | 9.79 | 9.55 | 9.18 | 100 | 6.77E−05 | −2.70 | 6.51 |
| hsa-miR-411 | 4.47 | 3.24 | 5.21 | 4.22 | 4.71 | 67 | 2.17E−04 | 2.66 | 6.30 |
| hsa-miR-451 | 11.67 | 11.81 | 9.85 | 12.31 | 11.94 | 100 | 1.06E−03 | 2.64 | 6.25 |
| hsa-miR-143* | 6.00 | 5.30 | 5.96 | 5.13 | 5.84 | 100 | 9.29E−05 | 2.62 | 6.15 |
| hsa-miR-135a | 1.58 | −0.56 | 0.42 | 0.30 | 1.06 | 0 | 9.77E−03 | 2.59 | 6.04 |
| hsa-miR-299-3p | 3.40 | 3.46 | 4.46 | 4.35 | 4.33 | 50 | 7.97E−05 | 2.56 | 5.91 |
| hsa-miR-224 | 10.31 | 11.71 | 12.93 | 10.91 | 11.71 | 100 | 3.25E−04 | −2.56 | 5.88 |
| hsa-miR-495 | 5.08 | 4.41 | 6.11 | 5.83 | 5.71 | 100 | 4.02E−04 | 2.55 | 5.87 |
| hsa-miR-141 | 11.57 | 12.25 | 13.08 | 11.92 | 11.78 | 100 | 4.35E−03 | −2.52 | 5.74 |
| hsa-miR-375 | 5.27 | 4.06 | 4.90 | 1.47 | 3.86 | 67 | 2.01E−02 | 2.52 | 5.72 |
| hsa-miR-21* | 8.19 | 9.16 | 8.75 | 9.43 | 9.05 | 100 | 5.94E−05 | −2.48 | 5.56 |
| hsa-miR-654-3p | 5.50 | 4.91 | 6.61 | 5.89 | 6.23 | 100 | 6.96E−04 | 2.46 | 5.52 |
| hsa-miR-455-5p | 6.88 | 5.77 | 7.62 | 6.81 | 6.99 | 100 | 2.44E−04 | 2.43 | 5.39 |
| hsa-miR-379 | 4.80 | 4.14 | 4.94 | 4.54 | 4.98 | 83 | 1.08E−04 | 2.42 | 5.35 |
| hsa-miR-337-3p | 3.86 | 2.07 | 4.59 | 3.57 | 3.80 | 33 | 9.84E−04 | 2.40 | 5.29 |
| hsa-miR-154 | 4.64 | 3.97 | 6.25 | 5.13 | 5.45 | 100 | 6.25E−04 | 2.39 | 5.25 |
| hsa-miR-886-5p | −0.35 | 0.47 | 1.94 | 1.76 | 1.46 | 0 | 1.15E−03 | 2.38 | 5.21 |
| hsa-miR-183 | 6.73 | 8.01 | 7.38 | 7.49 | 7.27 | 100 | 9.66E−05 | −2.36 | 5.14 |
| hsa-miR-424 | 11.30 | 10.59 | 11.03 | 10.95 | 11.01 | 100 | 5.09E−04 | 2.36 | 5.14 |
| hsa-miR-410 | 2.28 | 3.15 | 1.56 | 4.04 | 3.53 | 50 | 8.55E−03 | 2.36 | 5.13 |
| hsa-miR-944 | 3.61 | 3.98 | 4.85 | 3.98 | 3.83 | 17 | 2.70E−03 | −2.33 | 5.03 |
| hsa-miR-337-5p | 5.43 | 3.64 | 6.90 | 5.87 | 5.91 | 83 | 3.50E−03 | 2.31 | 4.97 |
| hsa-miR-129-3p | 2.68 | 2.16 | 1.97 | 2.41 | 2.65 | 0 | 4.97E−04 | 2.30 | 4.92 |
| hsa-miR-328 | 3.14 | 2.23 | 4.13 | 2.85 | 3.30 | 17 | 1.73E−04 | 2.29 | 4.88 |
| hsa-let-7e* | 3.08 | 0.71 | 2.93 | 0.99 | 2.31 | 33 | 1.13E−03 | 2.27 | 4.83 |

TABLE 15-continued miRNAs Differentially Expressed Among Six Cervical Cancer Samples (Ca) and Six Normal Cervix Tissue Samples (NCX) Following Expression Analysis on Agilent Human miRNA Microarrays. Positive Log2Diff (NCX vs Ca) values represent miRNAs down-regulated in cancer samples

| | | | | | | | | | |
|---|---|---|---|---|---|---|---|---|---|
| hsa-miR-21 | 15.80 | 16.37 | 15.90 | 16.27 | 16.09 | 100 | 8.77E−07 | −2.26 | 4.80 |
| hsa-miR-149 | 4.88 | 3.74 | 5.01 | 4.93 | 5.32 | 83 | 1.46E−03 | 2.24 | 4.72 |
| hsa-miR-127-3p | 7.11 | 6.43 | 8.27 | 7.31 | 7.69 | 100 | 5.01E−04 | 2.23 | 4.69 |
| hsa-miR-30a* | 5.02 | 2.90 | 4.85 | 5.44 | 4.71 | 83 | 1.89E−03 | 2.23 | 4.68 |
| hsa-miR-142-3p | 12.63 | 12.27 | 13.30 | 13.81 | 12.88 | 100 | 1.24E−04 | −2.21 | 4.64 |
| hsa-miR-10b | 9.76 | 9.64 | 9.54 | 9.51 | 9.71 | 100 | 1.13E−04 | 2.20 | 4.60 |
| hsa-miR-140-3p | 8.79 | 8.68 | 9.65 | 9.33 | 9.25 | 100 | 4.17E−05 | 2.19 | 4.55 |
| hsa-miR-155 | 9.04 | 10.23 | 9.90 | 9.75 | 9.54 | 100 | 1.75E−05 | −2.17 | 4.51 |
| hsa-miR-144* | 2.97 | 2.16 | 2.46 | 3.92 | 3.14 | 17 | 7.51E−04 | 2.15 | 4.45 |
| hsa-miR-329 | 3.52 | 1.83 | 4.20 | 3.46 | 3.60 | 33 | 2.24E−03 | 2.15 | 4.45 |
| hsa-miR-873 | 0.79 | 1.89 | 0.40 | 1.64 | 1.56 | 0 | 6.20E−03 | 2.12 | 4.36 |
| hsa-miR-18a | 6.57 | 7.64 | 6.54 | 7.58 | 6.86 | 100 | 1.08E−04 | −2.10 | 4.30 |
| hsa-miR-431* | 4.51 | 6.66 | 6.22 | 4.42 | 5.19 | 83 | 7.83E−04 | −2.10 | 4.29 |
| hsa-let-7e | 9.96 | 10.71 | 10.77 | 9.75 | 10.65 | 100 | 2.30E−04 | 2.09 | 4.25 |
| hsa-miR-154* | 3.12 | 2.54 | 4.16 | 4.69 | 3.99 | 33 | 1.40E−03 | 2.08 | 4.22 |
| hsa-miR-886-3p | 8.46 | 7.67 | 10.87 | 9.37 | 9.43 | 100 | 3.63E−03 | 2.07 | 4.20 |
| hsa-miR-199b-5p | 10.23 | 8.96 | 11.31 | 10.56 | 10.63 | 100 | 9.09E−04 | 2.06 | 4.17 |
| hsa-miR-377 | 6.52 | 5.88 | 8.16 | 7.45 | 7.43 | 100 | 2.13E−03 | 2.06 | 4.17 |
| hsa-miR-136 | 6.96 | 4.95 | 8.18 | 7.41 | 7.23 | 100 | 7.17E−03 | 2.05 | 4.16 |
| hsa-miR-543 | 3.20 | 3.36 | 4.23 | 4.74 | 4.31 | 67 | 2.12E−03 | 2.05 | 4.15 |
| hsa-miR-26a | 12.66 | 12.47 | 12.84 | 12.02 | 12.50 | 100 | 6.74E−06 | 2.05 | 4.14 |
| hsa-miR-369-5p | 2.72 | 2.83 | 3.44 | 2.94 | 3.27 | 17 | 4.85E−04 | 2.04 | 4.12 |
| hsa-miR-488 | 0.51 | −0.21 | 0.71 | 0.96 | 0.81 | 0 | 1.47E−02 | 2.02 | 4.04 |
| hsa-miR-195* | 2.42 | 2.95 | 3.37 | 1.19 | 2.75 | 17 | 3.30E−04 | 2.00 | 3.99 |
| hsa-miR-101* | 3.25 | 3.85 | 3.88 | 2.96 | 3.32 | 17 | 1.95E−05 | 1.99 | 3.98 |
| hsa-miR-485-5p | 2.10 | 0.48 | 2.60 | 1.33 | 1.84 | 0 | 7.13E−04 | 1.97 | 3.92 |
| hsa-miR-455-3p | 8.64 | 8.47 | 9.62 | 9.14 | 9.25 | 100 | 3.75E−03 | 1.97 | 3.91 |
| hsa-miR-483-3p | 2.70 | 1.58 | 2.00 | 3.32 | 2.77 | 0 | 1.10E−03 | 1.96 | 3.90 |
| hsa-miR-130a | 10.37 | 10.07 | 11.65 | 9.83 | 10.56 | 100 | 2.65E−04 | 1.96 | 3.88 |
| hsa-miR-487b | 6.14 | 6.58 | 7.39 | 6.40 | 6.94 | 100 | 1.09E−03 | 1.92 | 3.80 |
| hsa-miR-433 | 1.25 | −0.50 | 1.77 | 1.95 | 1.80 | 0 | 1.56E−02 | 1.91 | 3.77 |
| hsa-miR-141* | 4.04 | 5.78 | 4.53 | 4.22 | 4.43 | 67 | 5.81E−04 | −1.91 | 3.75 |
| hsa-miR-376b | 4.63 | 3.18 | 5.49 | 5.08 | 4.89 | 83 | 1.50E−02 | 1.91 | 3.75 |
| hsa-let-7c | 12.81 | 13.37 | 13.79 | 12.75 | 13.33 | 100 | 7.41E−06 | 1.90 | 3.74 |
| hsa-miR-142-5p | 10.07 | 9.64 | 11.06 | 11.87 | 10.27 | 100 | 4.66E−03 | −1.90 | 3.74 |
| hsa-miR-190 | 3.15 | 2.55 | 5.00 | 2.90 | 3.25 | 17 | 1.14E−03 | 1.90 | 3.74 |
| hsa-miR-200c | 10.71 | 12.14 | 11.41 | 10.39 | 10.82 | 100 | 5.62E−03 | −1.89 | 3.72 |

TABLE 15-continued miRNAs Differentially Expressed Among Six Cervical Cancer Samples (Ca) and Six Normal Cervix Tissue Samples (NCX) Following Expression Analysis on Agilent Human miRNA Microarrays. Positive Log2Diff (NCX vs Ca) values represent miRNAs down-regulated in cancer samples

| | | | | | | | | | |
|---|---|---|---|---|---|---|---|---|---|
| hsa-miR-539 | 2.35 | 1.15 | 3.12 | 1.56 | 2.52 | 0 | 9.58E−03 | 1.88 | 3.69 |
| hsa-miR-125a-5p | 8.50 | 8.19 | 8.56 | 7.48 | 8.41 | 100 | 6.43E−05 | 1.88 | 3.68 |
| hsa-miR-15b* | 4.39 | 4.74 | 4.99 | 3.73 | 3.92 | 83 | 5.40E−03 | −1.87 | 3.67 |
| hsa-miR-18b | 6.54 | 7.60 | 6.01 | 7.63 | 6.54 | 100 | 7.25E−04 | −1.86 | 3.64 |
| hsa-miR-574-3p | 5.97 | 7.17 | 7.74 | 6.92 | 7.24 | 100 | 2.96E−04 | 1.85 | 3.60 |
| hsa-miR-656 | 1.51 | 0.56 | 1.46 | 2.31 | 1.96 | 0 | 1.18E−02 | 1.84 | 3.57 |
| hsa-miR-214 | 10.04 | 9.84 | 10.73 | 9.88 | 10.36 | 100 | 2.75E−04 | 1.83 | 3.56 |
| hsa-miR-99b | 6.99 | 8.03 | 8.02 | 6.74 | 7.79 | 100 | 1.02E−03 | 1.81 | 3.50 |
| hsa-miR-486-5p | 5.58 | 5.39 | 4.50 | 5.50 | 5.57 | 100 | 2.62E−04 | 1.80 | 3.49 |
| hsa-miR-223 | 12.92 | 12.90 | 11.26 | 14.81 | 13.16 | 100 | 5.20E−03 | −1.79 | 3.46 |
| hsa-miR-542-3p | 4.83 | 5.17 | 6.33 | 5.83 | 5.71 | 100 | 7.90E−03 | 1.79 | 3.46 |
| hsa-miR-199b-3p | 12.64 | 12.34 | 13.67 | 12.78 | 13.04 | 100 | 1.35E−04 | 1.78 | 3.43 |
| hsa-miR-196b | 8.25 | 8.98 | 9.18 | 7.43 | 8.41 | 100 | 2.03E−04 | 1.77 | 3.41 |
| hsa-miR-146b-5p | 10.02 | 10.51 | 10.28 | 10.99 | 10.46 | 100 | 2.74E−04 | −1.77 | 3.40 |
| hsa-miR-140-5p | 7.01 | 7.13 | 8.55 | 7.98 | 7.88 | 100 | 9.73E−04 | 1.76 | 3.39 |
| hsa-miR-29c* | 6.18 | 5.84 | 8.31 | 6.68 | 6.81 | 100 | 1.61E−03 | 1.76 | 3.38 |
| hsa-miR-499-5p | 3.22 | 3.61 | 4.00 | 2.96 | 3.39 | 0 | 5.62E−04 | 1.75 | 3.36 |
| hsa-miR-29a | 12.30 | 12.86 | 13.58 | 13.05 | 13.11 | 100 | 4.93E−05 | 1.73 | 3.33 |
| hsa-miR-650 | 4.75 | 5.10 | 6.64 | 5.54 | 5.48 | 100 | 2.55E−04 | −1.73 | 3.32 |
| hsa-miR-101 | 9.85 | 10.46 | 10.83 | 10.12 | 10.20 | 100 | 2.47E−04 | 1.72 | 3.29 |
| hsa-miR-32 | 5.65 | 6.31 | 7.51 | 7.23 | 6.19 | 100 | 1.26E−02 | −1.69 | 3.23 |
| hsa-miR-30a | 8.68 | 8.13 | 8.66 | 9.67 | 8.88 | 100 | 1.19E−03 | 1.68 | 3.21 |
| hsa-miR-210 | 9.46 | 9.88 | 10.36 | 8.63 | 9.38 | 100 | 1.09E−03 | −1.67 | 3.19 |
| hsa-miR-450a | 5.78 | 5.07 | 6.83 | 5.89 | 5.95 | 100 | 6.64E−03 | 1.67 | 3.18 |
| hsa-miR-26b | 11.96 | 12.94 | 12.74 | 12.44 | 12.47 | 100 | 8.62E−05 | 1.66 | 3.17 |
| hsa-miR-126* | 7.02 | 7.18 | 7.57 | 7.22 | 7.14 | 100 | 3.32E−04 | 1.66 | 3.16 |
| hsa-miR-10a | 7.96 | 9.38 | 10.07 | 7.65 | 8.91 | 100 | 7.99E−03 | 1.64 | 3.12 |
| hsa-miR-29c | 11.62 | 10.88 | 13.49 | 12.23 | 12.01 | 100 | 3.18E−03 | 1.64 | 3.11 |
| hsa-miR-377* | 1.59 | 0.65 | 1.98 | −0.07 | 1.46 | 0 | 1.18E−02 | 1.63 | 3.09 |
| hsa-miR-29b-2* | 1.22 | 0.25 | 3.57 | 2.25 | 1.61 | 17 | 1.12E−02 | 1.62 | 3.07 |
| hsa-miR-183* | 3.71 | 4.69 | 3.85 | 4.14 | 3.92 | 67 | 4.56E−04 | −1.60 | 3.03 |
| hsa-miR-93 | 10.54 | 12.07 | 10.75 | 10.77 | 10.79 | 100 | 7.69E−04 | −1.60 | 3.03 |
| hsa-miR-146a | 10.02 | 9.48 | 10.16 | 9.71 | 9.71 | 100 | 5.65E−04 | −1.58 | 3.00 |
| hsa-miR-28-5p | 8.23 | 9.20 | 8.78 | 8.47 | 8.80 | 100 | 5.78E−04 | 1.58 | 3.00 |
| hsa-miR-429 | 8.63 | 9.64 | 11.03 | 9.72 | 9.73 | 100 | 1.36E−02 | −1.58 | 2.99 |
| hsa-miR-432 | 4.37 | 4.08 | 5.07 | 4.50 | 4.83 | 67 | 3.42E−03 | 1.57 | 2.97 |

TABLE 15-continued miRNAs Differentially Expressed Among Six Cervical Cancer Samples (Ca) and Six Normal Cervix Tissue Samples (NCX) Following Expression Analysis on Agilent Human miRNA Microarrays. Positive Log2Diff (NCX vs Ca) values represent miRNAs down-regulated in cancer samples

| | | | | | | | | | |
|---|---|---|---|---|---|---|---|---|---|
| hsa-miR-889 | 2.02 | 0.80 | 0.36 | 1.39 | 1.09 | 0 | 1.05E−02 | 1.57 | 2.97 |
| hsa-miR-382 | 3.87 | 3.79 | 4.77 | 4.01 | 4.43 | 67 | 4.74E−03 | 1.55 | 2.93 |
| hsa-miR-200b | 10.26 | 11.15 | 12.41 | 10.63 | 11.12 | 100 | 1.19E−02 | −1.54 | 2.92 |
| hsa-miR-126 | 10.73 | 11.65 | 11.34 | 10.97 | 11.35 | 100 | 5.53E−04 | 1.51 | 2.86 |
| hsa-miR-424* | 5.99 | 6.17 | 5.36 | 5.21 | 5.43 | 100 | 1.45E−03 | 1.48 | 2.79 |
| hsa-miR-106a | 7.78 | 8.30 | 6.60 | 7.15 | 6.98 | 100 | 5.85E−03 | −1.47 | 2.77 |
| hsa-let-7b | 12.79 | 14.35 | 14.70 | 13.39 | 14.18 | 100 | 3.13E−03 | 1.46 | 2.75 |
| hsa-miR-26b* | 2.20 | 3.13 | 2.33 | 1.76 | 2.50 | 0 | 1.07E−03 | 1.44 | 2.72 |
| hsa-miR-505 | 6.26 | 7.03 | 6.69 | 6.87 | 6.85 | 100 | 8.92E−05 | 1.43 | 2.69 |
| hsa-miR-214* | 6.08 | 5.31 | 6.92 | 5.62 | 6.23 | 100 | 3.55E−03 | 1.41 | 2.66 |
| hsa-miR-542-5p | 5.50 | 5.08 | 6.16 | 5.46 | 5.71 | 100 | 1.80E−02 | 1.41 | 2.66 |
| hsa-miR-144 | 8.21 | 6.54 | 6.20 | 8.48 | 7.48 | 100 | 2.08E−02 | 1.38 | 2.60 |
| hsa-miR-151-5p | 9.79 | 10.62 | 9.58 | 9.45 | 9.94 | 100 | 4.73E−04 | 1.37 | 2.59 |
| hsa-miR-361-5p | 9.64 | 8.13 | 9.10 | 8.51 | 8.87 | 100 | 1.48E−03 | 1.37 | 2.59 |
| hsa-miR-629* | 6.26 | 6.55 | 5.43 | 6.08 | 5.74 | 100 | 6.72E−03 | −1.36 | 2.57 |
| hsa-miR-10b* | 4.29 | 4.85 | 3.88 | 4.34 | 4.25 | 33 | 1.84E−03 | 1.34 | 2.53 |
| hsa-miR-30b | 10.58 | 11.88 | 11.33 | 10.81 | 11.25 | 100 | 1.47E−03 | 1.33 | 2.51 |
| hsa-miR-15b | 12.40 | 13.36 | 13.17 | 12.09 | 12.53 | 100 | 4.26E−03 | −1.27 | 2.42 |
| hsa-miR-184 | 3.67 | 2.45 | 2.68 | 2.92 | 3.29 | 17 | 1.29E−02 | 1.27 | 2.42 |
| hsa-miR-106b* | 3.48 | 2.72 | 2.35 | 3.11 | 2.61 | 17 | 2.82E−03 | −1.26 | 2.40 |
| hsa-miR-199a-5p | 11.82 | 11.07 | 12.88 | 11.68 | 12.05 | 100 | 1.22E−02 | 1.26 | 2.40 |
| hsa-miR-490-3p | 1.44 | 1.30 | 2.22 | 2.05 | 1.93 | 0 | 1.04E−02 | 1.22 | 2.33 |
| hsa-miR-100* | 0.12 | 0.69 | 1.02 | 1.53 | 0.95 | 0 | 1.75E−02 | 1.21 | 2.31 |
| hsa-miR-152 | 7.03 | 7.06 | 8.76 | 7.73 | 7.88 | 100 | 8.14E−03 | 1.21 | 2.31 |
| hsa-miR-130b | 6.81 | 8.12 | 9.26 | 8.34 | 7.97 | 100 | 1.12E−02 | −1.20 | 2.29 |
| hsa-miR-23b | 13.13 | 12.51 | 13.50 | 12.83 | 13.21 | 100 | 2.30E−03 | 1.19 | 2.29 |
| hsa-miR-27b | 12.88 | 12.50 | 13.32 | 13.09 | 13.19 | 100 | 2.72E−03 | 1.19 | 2.28 |
| hsa-miR-492 | 4.68 | 4.00 | 4.69 | 5.17 | 4.56 | 50 | 4.90E−03 | −1.19 | 2.28 |
| hsa-miR-485-3p | 2.19 | 2.35 | 2.85 | 2.56 | 2.79 | 0 | 5.56E−03 | 1.18 | 2.27 |
| hsa-miR-505* | 3.72 | 4.86 | 4.37 | 4.63 | 4.44 | 83 | 1.61E−03 | 1.17 | 2.25 |
| hsa-miR-320 | 9.29 | 10.54 | 9.65 | 9.65 | 9.87 | 100 | 1.12E−03 | 1.16 | 2.24 |
| hsa-miR-335 | 5.57 | 6.83 | 6.94 | 6.50 | 6.11 | 100 | 7.54E−03 | 1.16 | 2.23 |
| hsa-miR-630 | 9.61 | 9.81 | 9.90 | 10.41 | 9.54 | 100 | 1.84E−02 | −1.11 | 2.15 |
| hsa-miR-181d | 5.17 | 5.44 | 5.96 | 5.63 | 5.60 | 100 | 8.38E−05 | 1.10 | 2.14 |
| hsa-miR-425 | 8.54 | 9.87 | 10.51 | 8.97 | 9.22 | 100 | 1.53E−02 | −1.06 | 2.09 |
| hsa-miR-628-5p | 2.55 | 2.31 | 3.77 | 2.90 | 2.83 | 0 | 4.41E−03 | 1.06 | 2.09 |
| hsa-miR-29b-1* | 4.42 | 4.85 | 4.05 | 4.75 | 4.71 | 100 | 8.06E−04 | 1.06 | 2.08 |
| hsa-miR-106b | 11.15 | 12.70 | 12.12 | 11.77 | 11.65 | 100 | 1.12E−02 | −1.05 | 2.07 |

TABLE 15-continued miRNAs Differentially Expressed Among Six Cervical Cancer Samples (Ca) and Six Normal Cervix Tissue Samples (NCX) Following Expression Analysis on Agilent Human miRNA Microarrays. Positive Log2Diff (NCX vs Ca) values represent miRNAs down-regulated in cancer samples

| miRNA | | | | | | | | | |
|---|---|---|---|---|---|---|---|---|---|
| hsa-miR-181c | 7.09 | 6.59 | 7.39 | 6.88 | 7.04 | 100 | 7.40E−03 | 1.05 | 2.07 |
| hsa-miR-29a* | 2.97 | 3.15 | 4.02 | 3.42 | 3.30 | 50 | 6.71E−04 | 1.05 | 2.07 |
| hsa-miR-513c | 6.11 | 6.13 | 5.73 | 5.51 | 5.52 | 100 | 6.08E−03 | −1.03 | 2.05 |
| hsa-miR-374b | 9.05 | 8.94 | 9.51 | 9.17 | 9.14 | 100 | 2.18E−03 | 1.02 | 2.03 |
| hsa-miR-215 | 4.71 | 4.90 | 5.60 | 5.89 | 5.39 | 83 | 6.67E−03 | 1.00 | 2.00 |
| hsa-miR-24-1* | 5.80 | 5.38 | 6.46 | 5.85 | 6.15 | 100 | 1.77E−02 | 0.97 | 1.96 |
| hsa-miR-151-3p | 6.97 | 8.70 | 7.51 | 7.52 | 7.75 | 100 | 8.32E−03 | 0.96 | 1.94 |
| hsa-miR-197 | 6.07 | 6.49 | 7.73 | 6.57 | 6.79 | 100 | 6.48E−03 | 0.96 | 1.94 |
| hsa-miR-30c-2* | 3.93 | 3.81 | 4.28 | 4.78 | 4.39 | 67 | 1.62E−03 | 0.96 | 1.94 |
| hsa-miR-330-3p | 5.06 | 6.62 | 6.44 | 5.31 | 5.57 | 100 | 1.55E−02 | −0.96 | 1.94 |
| hsa-let-7g | 12.58 | 13.30 | 13.81 | 12.68 | 13.05 | 100 | 9.15E−03 | 0.94 | 1.92 |
| hsa-miR-20a* | 5.28 | 5.67 | 5.93 | 5.48 | 5.43 | 100 | 3.63E−03 | 0.94 | 1.92 |
| hsa-miR-655 | −0.03 | 1.25 | 1.24 | 1.15 | 0.90 | 0 | 1.77E−02 | 0.94 | 1.92 |
| hsa-miR-93* | 3.30 | 4.33 | 3.89 | 3.69 | 3.53 | 83 | 5.08E−03 | −0.94 | 1.92 |
| hsa-miR-766 | 5.34 | 5.72 | 6.48 | 6.40 | 5.98 | 100 | 2.95E−03 | −0.93 | 1.90 |
| hsa-miR-186 | 7.65 | 8.72 | 9.45 | 7.89 | 8.27 | 100 | 1.64E−02 | 0.92 | 1.89 |
| hsa-miR-17 | 10.36 | 11.58 | 9.87 | 10.47 | 10.35 | 100 | 1.44E−02 | −0.88 | 1.84 |
| hsa-miR-374b* | 2.10 | 2.04 | 3.19 | 2.84 | 2.36 | 50 | 2.05E−02 | 0.87 | 1.83 |
| hsa-let-7i | 12.06 | 13.21 | 13.11 | 12.87 | 12.91 | 100 | 9.49E−03 | 0.85 | 1.81 |
| hsa-miR-194 | 5.51 | 5.49 | 5.81 | 5.92 | 5.64 | 100 | 1.80E−03 | 0.86 | 1.81 |
| hsa-miR-602 | 5.50 | 4.94 | 4.89 | 4.77 | 4.93 | 83 | 8.39E−03 | −0.82 | 1.76 |
| hsa-miR-212 | 6.70 | 7.34 | 7.09 | 7.07 | 6.94 | 100 | 1.93E−03 | −0.80 | 1.74 |
| hsa-miR-940 | 9.83 | 10.33 | 9.87 | 10.85 | 10.24 | 100 | 2.05E−02 | −0.80 | 1.74 |
| hsa-let-7a | 14.20 | 15.44 | 15.44 | 14.41 | 14.97 | 100 | 7.87E−03 | 0.78 | 1.72 |
| hsa-let-7d* | 2.87 | 3.45 | 3.29 | 3.06 | 3.14 | 17 | 1.62E−02 | 0.77 | 1.70 |
| hsa-miR-768-3p | 10.55 | 10.57 | 11.60 | 10.86 | 11.10 | 100 | 1.33E−02 | 0.77 | 1.70 |
| hsa-miR-744 | 5.81 | 6.22 | 6.17 | 6.70 | 6.23 | 100 | 6.63E−03 | 0.72 | 1.65 |
| hsa-miR-512-3p | 4.41 | 4.07 | 3.15 | 3.76 | 3.88 | 17 | 1.71E−02 | 0.71 | 1.64 |
| hsa-miR-30b* | 4.18 | 4.49 | 4.34 | 4.59 | 4.58 | 83 | 7.05E−04 | 0.71 | 1.63 |
| hsa-miR-374a | 9.70 | 9.84 | 10.80 | 10.45 | 10.19 | 100 | 1.74E−02 | 0.71 | 1.63 |
| hsa-miR-99b* | 4.86 | 4.40 | 4.03 | 5.07 | 4.81 | 83 | 1.55E−02 | −0.69 | 1.62 |
| hsa-miR-193a-5p | 6.85 | 7.18 | 6.98 | 6.57 | 6.81 | 100 | 1.06E−02 | 0.65 | 1.57 |
| hsa-let-7f | 14.30 | 15.08 | 14.92 | 14.11 | 14.49 | 100 | 1.89E−02 | 0.60 | 1.52 |
| hsa-miR-28-3p | 4.22 | 4.21 | 4.27 | 3.93 | 4.14 | 100 | 7.51E−03 | 0.60 | 1.52 |
| hsa-miR-654-5p | 5.13 | 4.31 | 4.51 | 4.93 | 4.62 | 100 | 1.17E−02 | 0.57 | 1.49 |
| hsa-miR-345 | 5.17 | 5.24 | 5.37 | 5.18 | 5.20 | 100 | 1.04E−02 | −0.57 | 1.48 |
| hsa-miR-501-5p | 6.30 | 6.29 | 5.95 | 6.03 | 6.03 | 100 | 3.34E−03 | −0.44 | 1.36 |

REFERENCES

The following references, to the extent that they provide exemplary procedural or other details supplementary to those set forth herein, are specifically incorporated herein by reference.

U.S. Pat. No. 4,337,063
U.S. Pat. No. 4,404,289
U.S. Pat. No. 4,405,711
U.S. Pat. No. 4,659,774
U.S. Pat. No. 4,682,195
U.S. Pat. No. 4,683,202
U.S. Pat. No. 4,704,362
U.S. Pat. No. 4,816,571
U.S. Pat. No. 4,959,463
U.S. Pat. No. 5,141,813
U.S. Pat. No. 5,143,854
U.S. Pat. No. 5,202,231
U.S. Pat. No. 5,214,136
U.S. Pat. No. 5,221,619
U.S. Pat. No. 5,223,618
U.S. Pat. No. 5,242,974
U.S. Pat. No. 5,264,566
U.S. Pat. No. 5,268,486
U.S. Pat. No. 5,288,644
U.S. Pat. No. 5,324,633
U.S. Pat. No. 5,378,825
U.S. Pat. No. 5,384,261
U.S. Pat. No. 5,405,783
U.S. Pat. No. 5,412,087
U.S. Pat. No. 5,424,186
U.S. Pat. No. 5,428,148
U.S. Pat. No. 5,429,807
U.S. Pat. No. 5,432,049
U.S. Pat. No. 5,436,327
U.S. Pat. No. 5,445,934
U.S. Pat. No. 5,446,137
U.S. Pat. No. 5,466,786
U.S. Pat. No. 5,468,613
U.S. Pat. No. 5,470,710
U.S. Pat. No. 5,470,967
U.S. Pat. No. 5,472,672
U.S. Pat. No. 5,480,980
U.S. Pat. No. 5,492,806
U.S. Pat. No. 5,503,980
U.S. Pat. No. 5,510,270
U.S. Pat. No. 5,525,464
U.S. Pat. No. 5,527,681
U.S. Pat. No. 5,529,756
U.S. Pat. No. 5,532,128
U.S. Pat. No. 5,545,531
U.S. Pat. No. 5,547,839
U.S. Pat. No. 5,554,501
U.S. Pat. No. 5,554,744
U.S. Pat. No. 5,556,752
U.S. Pat. No. 5,561,071
U.S. Pat. No. 5,571,639
U.S. Pat. No. 5,574,146
U.S. Pat. No. 5,580,726
U.S. Pat. No. 5,580,732
U.S. Pat. No. 5,583,013
U.S. Pat. No. 5,593,839
U.S. Pat. No. 5,599,672
U.S. Pat. No. 5,599,695
U.S. Pat. No. 5,602,240
U.S. Pat. No. 5,602,244
U.S. Pat. No. 5,610,289
U.S. Pat. No. 5,610,287
U.S. Pat. No. 5,614,617
U.S. Pat. No. 5,623,070
U.S. Pat. No. 5,624,711
U.S. Pat. No. 5,631,134
U.S. Pat. No. 5,637,683
U.S. Pat. No. 5,639,603
U.S. Pat. No. 5,645,897
U.S. Pat. No. 5,652,099
U.S. Pat. No. 5,654,413
U.S. Pat. No. 5,658,734
U.S. Pat. No. 5,661,028
U.S. Pat. No. 5,665,547
U.S. Pat. No. 5,667,972
U.S. Pat. No. 5,670,663
U.S. Pat. No. 5,672,697
U.S. Pat. No. 5,681,947
U.S. Pat. No. 5,695,940
U.S. Pat. No. 5,700,637
U.S. Pat. No. 5,700,922
U.S. Pat. No. 5,705,629
U.S. Pat. No. 5,708,154
U.S. Pat. No. 5,714,606
U.S. Pat. No. 5,728,525
U.S. Pat. No. 5,744,305
U.S. Pat. No. 5,763,167
U.S. Pat. No. 5,777,092
U.S. Pat. No. 5,792,847
U.S. Pat. No. 5,800,992
U.S. Pat. No. 5,807,522
U.S. Pat. No. 5,830,645
U.S. Pat. No. 5,837,196
U.S. Pat. No. 5,847,219
U.S. Pat. No. 5,858,988
U.S. Pat. No. 5,859,221
U.S. Pat. No. 5,871,928
U.S. Pat. No. 5,872,232
U.S. Pat. No. 5,876,932
U.S. Pat. No. 5,886,165
U.S. Pat. No. 5,919,626
U.S. Pat. No. 6,004,755
U.S. Pat. No. 6,087,102
U.S. Pat. No. 6,251,666
U.S. Pat. No. 6,368,799
U.S. Pat. No. 6,383,749
U.S. Pat. No. 6,617,112
U.S. Pat. No. 6,638,717
U.S. Pat. No. 6,720,138
U.S. Pat. No. 6,723,509
U.S. Pat. No. 5,770,358
U.S. Pat. No. 5,789,162
U.S. Pat. No. 5,708,153
U.S. Pat. No. 6,040,193
U.S. Pat. No. 5,800,992
U.S. patent application Ser. No. 09/545,207
U.S. patent application Ser. No. 10/667,126
U.S. patent application Ser. No. 11/273,640
ALTS Group (The Atypical Squamous Cells of Undetermined Significance/Low-Grade Squamous Intraepithelial Lesions Triage Study), *J. Natl. Cancer Inst.*, 92(5):397-402, 2000.
Bagga et al., *Cell,* 122(4):553-563, 2005.
Beaucage, and Lyer, *Tetrahedron,* 48:2223-2311, 1992.
Bentwich et al., *Nat. Genet.,* 37(7):766-770, 2005.
Berezikov et al, *Cell,* 120(1):21-24, 2005.
Bergeron et al., *Obstet. Gynecol.,* 95:821-827, 2000.

Bosch and de Sanjose, *Curr. Oncol. Rep.,* 4(2):175-183, 2002.
Breitling et al., *FEBS Letters,* 513:83-92, 2004.
Calin and Croce, *Nat. Rev. Cancer,* 6(11):857-866, 2006.
Carrington and Ambros, *Science,* 301(5631):336-338, 2003.
Carrington et al. *Science,* 301(5631):336-338, 2003.
Clifford et al., *Br. J. Cancer,* 88(1):63-73, 2003
Cummins et al., In: *IRT: Nucleosides and nucleosides,* La Jolla Calif., 72, 1996.
Davison et al., *Meth. Enzymol.,* 411:14-34, 2006.
de Cremoux et al., *Amer. J. Clin. Pathol.,* 120:492-499, 2003.
Denli et al., *Trends Biochem. Sci.,* 28:196, 2003.
EP 266,032
EP 373 203
EP 785 280
EP 799 897
Esquela-Kerscher and Slack, *Nat. Rev. Cancer,* 6(4):259-269, 2006.
Fodor et al., *Science,* 251:767-777 (1991)
Froehler et al., *Nucleic Acids Res.,* 14(13):5399-5407, 1986.
Gillam et al., *J. Biol. Chem.,* 253:2532, 1978.
Gillam et al., *Nucleic Acids Res.,* 6:2973, 1979.
Gillison et al., *J. Natl. Cancer. Inst.,* 92(9):709-720, 2000.
Griffey et al., *J Mass Spectrom,* 32(3):305-13, 1997.
Griffiths-Jones et al., *Nucleic Acids Res.,* 34:D140-D144, 2006.
Huber et al., *Bioinformatics,* 18:Suppl 1:S96-104, 2002.
Itakura and Riggs, *Science,* 209:1401-1405, 1980.
Itakura et al., *J. Biol. Chem.,* 250:4592, 1975.
Jemal et al., *CA Cancer J. Clin.,* 57:43-66, 2007.
Khorana, *Science,* 203, 614 1979.
Kornberg and Baker, In: *DNA Replication,* 2d Ed., Freeman, San Francisco, 1992.
Lagos-Quintana et al., *Science,* 294(5543):853-858, 2001.
Lau et al., *Science,* 294(5543):858-862, 2001.
Lee and Ambros, *Science,* 294(5543):862-864, 2001.
Lee et al., *EMBO J.* 21:4663-70, 2002.
Lim et al., *Nature,* 433(7027):769-773, 2005.
Logsdon et al., *Cancer Res.,* 63(10):2649-2657. 2003.
Olsen et al., *Dev. Biol.,* 216:671, 1999.
Parkin et al., *CA Cancer J. Clin.,* 55(2):74-108, 2005.
Pisani et al., *Int. J. Cancer,* 83:18-29, 1999.
Pisani et al., *Int. J. Cancer,* 97(1):72-81, 2002.
Richart et al., *Clin. Obstet. Gynecol.,* 10:748-784, 1967.
Rose et al., *Transplantation,* 82(4):570-573, 2006.
Sambrook et al., In: *DNA microaarays: a molecular cloning manual,* Cold Spring Harbor Laboratory Press, Cold Spring Harbor, N.Y., 2003.
Sambrook et al., In: *Molecular cloning: a laboratory manual,* $2^{nd}$ Ed., Cold Spring Harbor Laboratory Press, Cold Spring Harbor, N.Y., 1989.
Sambrook et al., In: *Molecular cloning: a laboratory manual,* $3^{rd}$ Ed., Cold Spring Harbor Laboratory Press, Cold Spring Harbor, N.Y., 2001.
Seggerson et al., *Dev. Biol.,* 243:215, 2002.
Shingara et al., *RNA,* (9):1461-1470, 2005.
Szafeanska et al., *Oncogene,* 26(30):4442-4452, 2007.
U.K. Patent 1,529,202
UK 8 803 000
WO 0168255
WO 03020898
WO 03022421
WO 03023058
WO 03029485
WO 03040410
WO 03053586
WO 03066906
WO 03067217
WO 03076928
WO 03087297
WO 03091426
WO 03093810
WO 03100448
WO 04020085
WO 04027093
WO 09923256
WO 09936760
WO 93/17126
WO 95/11995
WO 95/21265
WO 95/21944
WO 95/35505
WO 96/31622
WO 97/10365
WO 97/27317
WO 9743450
WO 99/35505
WO 0138580
WO 03100012
Xie, et al., *Nature,* 434(7031):338-345, 2005.
zur Hausen, *Nat. Rev. Cancer,* 2(5):342-350, 2002.

---

What is claimed is:

1. A method for identifying a biomarker indicative of cervical precancer or cancer in a patient comprising generating an expression profile comprising measuring expression of at least three miRNAs in a cervical sample from a patient suspected of having a pre-cancerous or cancerous cervical condition, wherein expression of hsa-miR-21 is measured using a nucleic acid probe comprising a sequence that is at least 95% identical or complementary to each of SEQ ID NO:183, expression of hsa-miR-143 is measured using a nucleic acid probe comprising a sequence that is at least 95% identical or complementary to each of SEQ ID NO:123, and expression of hsa-miR-218 is measured using a nucleic acid probe comprising a sequence that is at least 95% identical or complementary to each of SEQ ID NO:192,
and identifying the patient as having biomarkers indicative of cervical precancer or cancer after measuring an increase in hsa-miR-21 expression and decreases in hsa-miR-143 and hsa-miR-218 expression compared to an expression profile of a normal cervical sample or a reference sample.

2. The method of claim 1, comprising measuring one or more miRNA that is hsa-miR-1 (SEQ ID NO:87), hsa-miR-224 (SEQ ID NO:199), hsa-miR-15b (SEQ ID NO:139), or hsa-miR-21* (SEQ ID NO:486).

3. The method of claim 1, wherein the patient is identified as having a biomarker indicative of cervical cancer based on measuring a increased expression of hsa-miR-21 in the patient's sample.

4. The method of claim 2, wherein the expression profile shows decreased expression of hsa-miR-1 or increased expression of hsa-miR-224, hsa-miR-15b, or hsa-miR-21* in the sample relative to the expression level of normal sample.

5. The method of claim 4, wherein decreased expression of hsa-miR-1 is measured in the sample relative to the normal sample.

6. The method of claim 1, wherein the sample from the patient is isolated RNA, fresh tissue or cells, frozen tissue or cells, fixed tissue or cells, or embedded tissue or cells.

7. The method of claim 1, wherein the cervical precancer is cervical squamous intraepithelial lesion or cervical intraepithelial neoplasia.

8. The method of claim 1, wherein the cervical cancer is cervical squamous cell carcinoma.

9. The method of claim 1, further comprising obtaining the cervical sample from the patient.

10. The method of claim 1, further comprising labeling miRNA from the cervical sample.

11. The method of claim 10, further comprising hybridizing the labeled miRNA to one or more miRNA probes.

12. The method of claim 1, wherein the expression profile of the one or more miRNA involves an amplification assay.

13. The method of claim 12, wherein the one or more miRNA is all or part of one or more of hsa-miR-1, hsa-miR-15b, hsa-miR-133a, hsa-miR-205, hsa-miR-21, hsa-miR-204, hsa-miR-195, hsa-miR-100, hsa-miR-99a, hsa-miR-368, hsa-miR-183, hsa-miR-224, hsa-miR-21* or combination thereof.

14. A method for identifying a biomarker indicative of cervical precancer or cancer in a patient comprising:
a) measuring an expression profile of at least three miRNAs that includes has-miR-21 in a cervical sample from a patient suspected of having a pre-cancerous or cancerous cervical condition, wherein hybridization or amplification of miRNA is used to measure the expression profile, wherein expression of hsa-miR-21 is measured using a nucleic acid probe comprising a sequence that at least 95% identical or complementary to each of SEQ ID NO:183, expression of hsa-miR-143 is measured using a nucleic acid probe comprising a sequence that is at least 95% identical or complementary to each of SEQ ID NO:123, and expression of hsa-miR-218 is measured using a nucleic acid probe comprising a sequence that is at least 95% identical or complementary to each of SEQ ID NO:192, and
b) identifying the patient as having biomarkers indicative of cervical precancer or cancer after measuring an increase in hsa-miR-21 expression and decreases in hsa-miR-143 and hsa-miR-218 expression compared to an expression profile of a normal cervical sample.

15. The method of claim 14, wherein the expression profile includes one or more of hsa-miR-1, hsa-miR-15b, hsa-miR-133a, hsa-miR-205, hsa-miR-204, hsa-miR-195, hsa-miR-100, hsa-miR-99a, hsa-miR-368, hsa-miR-183, hsa-miR-224, hsa-miR-21* or combination thereof.

16. The method of claim 14, wherein measuring the expression profile involves miRNA hybridization or amplification.

17. A method for identifying a biomarker indicative of cervical precancer or cancer in a patient comprising:
a) measuring increased hsa-miR-21 and reduced hsa-miR-143 and hsa-miR-218 expression in a cervical sample from a patient suspected of having a pre-cancerous or cancerous cervical condition compared to an expression profile of a reference cervical sample, wherein expression of hsa-miR-21 is measured using a nucleic acid probe comprising a sequence that is at least 95% identical or complementary to each of SEQ ID NO:183, expression of hsa-miR-143 is measured using a nucleic acid probe comprising a sequence that is at least 95% identical or complementary to each of SEQ ID NO:123, and expression of hsa-miR-218 is measured using a nucleic acid probe comprising a sequence that is at least 95% identical or complementary to each of SEQ ID NO:192; and b) identifying the patient as having biomarkers indicative of cervical precancer or cancer.

18. The method of claim 17, wherein the expression profile includes one or more of hsa-miR-1, hsa-miR-15b, hsa-miR-133a, hsa-miR-205, hsa-miR-204, hsa-miR-195, hsa-miR-100, hsa-miR-99a, hsa-miR-368, hsa-miR-183, hsa-miR-224, hsa-miR-21* or combination thereof.

19. The method of claim 17, wherein measuring the expression profile involves miRNA amplification.

* * * * *

UNITED STATES PATENT AND TRADEMARK OFFICE
CERTIFICATE OF CORRECTION

PATENT NO. : 9,080,215 B2  
APPLICATION NO. : 13/735760  
DATED : July 14, 2015  
INVENTOR(S) : Sylvie Beaudenon-Huibregtse Page 1 of 1

It is certified that error appears in the above-identified patent and that said Letters Patent is hereby corrected as shown below:

In the Claims

In Claim 14 column 354, line 36, delete "has-miR-21" and insert --hsa-miR-21-- therefor.

In Claim 14 column 354, line 41, insert --is-- between "that" and "at".

Signed and Sealed this
Twenty-fourth Day of November, 2015

Michelle K. Lee
*Director of the United States Patent and Trademark Office*

SEQUENCE LISTING

```
<160> NUMBER OF SEQ ID NOS: 562

<210> SEQ ID NO 1
<211> LENGTH: 21
<212> TYPE: RNA
<213> ORGANISM: Artificial
<220> FEATURE:
<223> OTHER INFORMATION: Synthetic

<400> SEQUENCE: 1
aaauggugcc cuagugacua c                                                 21

<210> SEQ ID NO 2
<211> LENGTH: 23
<212> TYPE: RNA
<213> ORGANISM: Artificial
<220> FEATURE:
<223> OTHER INFORMATION: Synthetic
```

```
<400> SEQUENCE: 2
ggaaaccguu accauuacug agu                                          23

<210> SEQ ID NO 3
<211> LENGTH: 23
<212> TYPE: RNA
<213> ORGANISM: Artificial
<220> FEATURE:
<223> OTHER INFORMATION: Synthetic

<400> SEQUENCE: 3
gccgagacua gagucacauc cug                                          23

<210> SEQ ID NO 4
<211> LENGTH: 22
<212> TYPE: RNA
<213> ORGANISM: Artificial
<220> FEATURE:
<223> OTHER INFORMATION: Synthetic

<400> SEQUENCE: 4
ucucugggcc ugugucuuag gc                                           22

<210> SEQ ID NO 5
<211> LENGTH: 22
<212> TYPE: RNA
<213> ORGANISM: Artificial
<220> FEATURE:
<223> OTHER INFORMATION: Synthetic

<400> SEQUENCE: 5
gucauacacg gcucccucu cu                                            22

<210> SEQ ID NO 6
<211> LENGTH: 19
<212> TYPE: RNA
<213> ORGANISM: Artificial
<220> FEATURE:
<223> OTHER INFORMATION: Synthetic

<400> SEQUENCE: 6
acacaccugg uuaaccucu                                               19

<210> SEQ ID NO 7
<211> LENGTH: 20
<212> TYPE: RNA
<213> ORGANISM: Artificial
<220> FEATURE:
<223> OTHER INFORMATION: Synthetic

<400> SEQUENCE: 7
uaugucugcu gaccaucacc                                              20

<210> SEQ ID NO 8
<211> LENGTH: 21
<212> TYPE: RNA
<213> ORGANISM: Artificial
<220> FEATURE:
<223> OTHER INFORMATION: Synthetic

<400> SEQUENCE: 8
ccacagcacu gccuggucag a                                            21

<210> SEQ ID NO 9
```

```
<211> LENGTH: 24
<212> TYPE: RNA
<213> ORGANISM: Artificial
<220> FEATURE:
<223> OTHER INFORMATION: Synthetic

<400> SEQUENCE: 9
cugguuucac augguggcuu agau                                          24

<210> SEQ ID NO 10
<211> LENGTH: 22
<212> TYPE: RNA
<213> ORGANISM: Artificial
<220> FEATURE:
<223> OTHER INFORMATION: Synthetic

<400> SEQUENCE: 10
aauugcacgg uauccaucug ua                                            22

<210> SEQ ID NO 11
<211> LENGTH: 21
<212> TYPE: RNA
<213> ORGANISM: Artificial
<220> FEATURE:
<223> OTHER INFORMATION: Synthetic

<400> SEQUENCE: 11
gcaguccaug ggcauauaca c                                             21

<210> SEQ ID NO 12
<211> LENGTH: 22
<212> TYPE: RNA
<213> ORGANISM: Artificial
<220> FEATURE:
<223> OTHER INFORMATION: Synthetic

<400> SEQUENCE: 12
acaagucagg cucuugggac cu                                            22

<210> SEQ ID NO 13
<211> LENGTH: 20
<212> TYPE: RNA
<213> ORGANISM: Artificial
<220> FEATURE:
<223> OTHER INFORMATION: Synthetic

<400> SEQUENCE: 13
ucaucgucuc aaaugagucu                                               20

<210> SEQ ID NO 14
<211> LENGTH: 21
<212> TYPE: RNA
<213> ORGANISM: Artificial
<220> FEATURE:
<223> OTHER INFORMATION: Synthetic

<400> SEQUENCE: 14
caagcucgcu ucuauggguc u                                             21

<210> SEQ ID NO 15
<211> LENGTH: 22
<212> TYPE: RNA
<213> ORGANISM: Artificial
<220> FEATURE:
<223> OTHER INFORMATION: Synthetic

<400> SEQUENCE: 15
```
gggcccuggc uccaucuccu uu					22

<210> SEQ ID NO 16
<211> LENGTH: 22
<212> TYPE: RNA
<213> ORGANISM: Artificial
<220> FEATURE:
<223> OTHER INFORMATION: Synthetic

<400> SEQUENCE: 16
uauagauuua aauacguaug ua					22

<210> SEQ ID NO 17
<211> LENGTH: 22
<212> TYPE: RNA
<213> ORGANISM: Artificial
<220> FEATURE:
<223> OTHER INFORMATION: Synthetic

<400> SEQUENCE: 17
gacagcacga cacugccuuc au					22

<210> SEQ ID NO 18
<211> LENGTH: 22
<212> TYPE: RNA
<213> ORGANISM: Artificial
<220> FEATURE:
<223> OTHER INFORMATION: Synthetic

<400> SEQUENCE: 18
ugccugucua cacuugcugu gc					22

<210> SEQ ID NO 19
<211> LENGTH: 22
<212> TYPE: RNA
<213> ORGANISM: Artificial
<220> FEATURE:
<223> OTHER INFORMATION: Synthetic

<400> SEQUENCE: 19
uggccuuggg ucagagaggg cu					22

<210> SEQ ID NO 20
<211> LENGTH: 22
<212> TYPE: RNA
<213> ORGANISM: Artificial
<220> FEATURE:
<223> OTHER INFORMATION: Synthetic

<400> SEQUENCE: 20
cccucgagga gcucacaguc ua					22

<210> SEQ ID NO 21
<211> LENGTH: 22
<212> TYPE: RNA
<213> ORGANISM: Artificial
<220> FEATURE:
<223> OTHER INFORMATION: Synthetic

<400> SEQUENCE: 21
ccucagcugu guucuuggua uc					22

<210> SEQ ID NO 22
<211> LENGTH: 22
<212> TYPE: RNA

<213> ORGANISM: Artificial
<220> FEATURE:
<223> OTHER INFORMATION: Synthetic

<400> SEQUENCE: 22
ggaacggcuu cauacaggag uu                                              22

<210> SEQ ID NO 23
<211> LENGTH: 22
<212> TYPE: RNA
<213> ORGANISM: Artificial
<220> FEATURE:
<223> OTHER INFORMATION: Synthetic

<400> SEQUENCE: 23
gggcagagag caagaaguau ca                                              22

<210> SEQ ID NO 24
<211> LENGTH: 22
<212> TYPE: RNA
<213> ORGANISM: Artificial
<220> FEATURE:
<223> OTHER INFORMATION: Synthetic

<400> SEQUENCE: 24
ugcugagggg cagagaucag ac                                              22

<210> SEQ ID NO 25
<211> LENGTH: 22
<212> TYPE: RNA
<213> ORGANISM: Artificial
<220> FEATURE:
<223> OTHER INFORMATION: Synthetic

<400> SEQUENCE: 25
uggauggagg uugagagggc ug                                              22

<210> SEQ ID NO 26
<211> LENGTH: 22
<212> TYPE: RNA
<213> ORGANISM: Artificial
<220> FEATURE:
<223> OTHER INFORMATION: Synthetic

<400> SEQUENCE: 26
uggcggugga gagagggaau gu                                              22

<210> SEQ ID NO 27
<211> LENGTH: 22
<212> TYPE: RNA
<213> ORGANISM: Artificial
<220> FEATURE:
<223> OTHER INFORMATION: Synthetic

<400> SEQUENCE: 27
ugguuuuugg uuuccagagc ag                                              22

<210> SEQ ID NO 28
<211> LENGTH: 22
<212> TYPE: RNA
<213> ORGANISM: Artificial
<220> FEATURE:
<223> OTHER INFORMATION: Synthetic

<400> SEQUENCE: 28
aaucauucac ggacaacacu uu                                              22

<210> SEQ ID NO 29
<211> LENGTH: 23
<212> TYPE: RNA
<213> ORGANISM: Artificial
<220> FEATURE:
<223> OTHER INFORMATION: Synthetic

<400> SEQUENCE: 29
ugaggggcag agagcgagac uuu                                          23

<210> SEQ ID NO 30
<211> LENGTH: 24
<212> TYPE: RNA
<213> ORGANISM: Artificial
<220> FEATURE:
<223> OTHER INFORMATION: Synthetic

<400> SEQUENCE: 30
cugguuucac augguggcuu agau                                         24

<210> SEQ ID NO 31
<211> LENGTH: 17
<212> TYPE: RNA
<213> ORGANISM: Artificial
<220> FEATURE:
<223> OTHER INFORMATION: Synthetic

<400> SEQUENCE: 31
acacucaaac ugcugac                                                 17

<210> SEQ ID NO 32
<211> LENGTH: 20
<212> TYPE: RNA
<213> ORGANISM: Artificial
<220> FEATURE:
<223> OTHER INFORMATION: Synthetic

<400> SEQUENCE: 32
uaugucugcu gaccaucacc                                              20

<210> SEQ ID NO 33
<211> LENGTH: 25
<212> TYPE: RNA
<213> ORGANISM: Artificial
<220> FEATURE:
<223> OTHER INFORMATION: Synthetic

<400> SEQUENCE: 33
ugaccgauuu cuccuggugu ucaga                                        25

<210> SEQ ID NO 34
<211> LENGTH: 22
<212> TYPE: RNA
<213> ORGANISM: Artificial
<220> FEATURE:
<223> OTHER INFORMATION: Synthetic

<400> SEQUENCE: 34
uuagggcccu ggcuccaucu cc                                           22

<210> SEQ ID NO 35
<211> LENGTH: 22
<212> TYPE: RNA
<213> ORGANISM: Artificial
<220> FEATURE:

-continued

<223> OTHER INFORMATION: Synthetic

<400> SEQUENCE: 35
uacccagagc augcagugug aa          22

<210> SEQ ID NO 36
<211> LENGTH: 22
<212> TYPE: RNA
<213> ORGANISM: Artificial
<220> FEATURE:
<223> OTHER INFORMATION: Synthetic

<400> SEQUENCE: 36
cuuggcaccu agcaagcacu ca          22

<210> SEQ ID NO 37
<211> LENGTH: 22
<212> TYPE: RNA
<213> ORGANISM: Artificial
<220> FEATURE:
<223> OTHER INFORMATION: Synthetic

<400> SEQUENCE: 37
cacuagauug ugagcuccug ga          22

<210> SEQ ID NO 38
<211> LENGTH: 22
<212> TYPE: RNA
<213> ORGANISM: Artificial
<220> FEATURE:
<223> OTHER INFORMATION: Synthetic

<400> SEQUENCE: 38
uuuccacagg auguggggg gg          22

<210> SEQ ID NO 39
<211> LENGTH: 22
<212> TYPE: RNA
<213> ORGANISM: Artificial
<220> FEATURE:
<223> OTHER INFORMATION: Synthetic

<400> SEQUENCE: 39
cuggcucuua aaggcacgag ag          22

<210> SEQ ID NO 40
<211> LENGTH: 22
<212> TYPE: RNA
<213> ORGANISM: Artificial
<220> FEATURE:
<223> OTHER INFORMATION: Synthetic

<400> SEQUENCE: 40
aaacaugguu ccgucaagca cc          22

<210> SEQ ID NO 41
<211> LENGTH: 22
<212> TYPE: RNA
<213> ORGANISM: Artificial
<220> FEATURE:
<223> OTHER INFORMATION: Synthetic

<400> SEQUENCE: 41
acaagucagg cucuugggac cu          22

```
<210> SEQ ID NO 42
<211> LENGTH: 20
<212> TYPE: RNA
<213> ORGANISM: Artificial
<220> FEATURE:
<223> OTHER INFORMATION: Synthetic

<400> SEQUENCE: 42
uugggaacau uuugcaugua                                                   20

<210> SEQ ID NO 43
<211> LENGTH: 22
<212> TYPE: RNA
<213> ORGANISM: Artificial
<220> FEATURE:
<223> OTHER INFORMATION: Synthetic

<400> SEQUENCE: 43
gagcugguaa aauggaacca aa                                                22

<210> SEQ ID NO 44
<211> LENGTH: 22
<212> TYPE: RNA
<213> ORGANISM: Artificial
<220> FEATURE:
<223> OTHER INFORMATION: Synthetic

<400> SEQUENCE: 44
uacuucagaa ucuccaggag ua                                                22

<210> SEQ ID NO 45
<211> LENGTH: 22
<212> TYPE: RNA
<213> ORGANISM: Artificial
<220> FEATURE:
<223> OTHER INFORMATION: Synthetic

<400> SEQUENCE: 45
ugcuuggcac cuagcaagca cu                                                22

<210> SEQ ID NO 46
<211> LENGTH: 22
<212> TYPE: RNA
<213> ORGANISM: Artificial
<220> FEATURE:
<223> OTHER INFORMATION: Synthetic

<400> SEQUENCE: 46
auuucagugg agugaaguuc ag                                                22

<210> SEQ ID NO 47
<211> LENGTH: 22
<212> TYPE: RNA
<213> ORGANISM: Artificial
<220> FEATURE:
<223> OTHER INFORMATION: Synthetic

<400> SEQUENCE: 47
uguagcaggc cagagaauga gg                                                22

<210> SEQ ID NO 48
<211> LENGTH: 22
<212> TYPE: RNA
<213> ORGANISM: Artificial
<220> FEATURE:
<223> OTHER INFORMATION: Synthetic
```

```
<400> SEQUENCE: 48
aagcucacag ucuaguugug uu                                      22

<210> SEQ ID NO 49
<211> LENGTH: 22
<212> TYPE: RNA
<213> ORGANISM: Artificial
<220> FEATURE:
<223> OTHER INFORMATION: Synthetic

<400> SEQUENCE: 49
cgagguugcc cuuuguauau uc                                      22

<210> SEQ ID NO 50
<211> LENGTH: 22
<212> TYPE: RNA
<213> ORGANISM: Artificial
<220> FEATURE:
<223> OTHER INFORMATION: Synthetic

<400> SEQUENCE: 50
gcauuugcug gugguggcag gg                                      22

<210> SEQ ID NO 51
<211> LENGTH: 22
<212> TYPE: RNA
<213> ORGANISM: Artificial
<220> FEATURE:
<223> OTHER INFORMATION: Synthetic

<400> SEQUENCE: 51
gggaugggca agguagaacu ca                                      22

<210> SEQ ID NO 52
<211> LENGTH: 22
<212> TYPE: RNA
<213> ORGANISM: Artificial
<220> FEATURE:
<223> OTHER INFORMATION: Synthetic

<400> SEQUENCE: 52
cagauucgau ucuaggggaa ua                                      22

<210> SEQ ID NO 53
<211> LENGTH: 22
<212> TYPE: RNA
<213> ORGANISM: Artificial
<220> FEATURE:
<223> OTHER INFORMATION: Synthetic

<400> SEQUENCE: 53
caggugaggu ucuugggagc cu                                      22

<210> SEQ ID NO 54
<211> LENGTH: 22
<212> TYPE: RNA
<213> ORGANISM: Artificial
<220> FEATURE:
<223> OTHER INFORMATION: Synthetic

<400> SEQUENCE: 54
uaugucugcu gaccaucacc uu                                      22

<210> SEQ ID NO 55
<211> LENGTH: 22
```

```
<212> TYPE: RNA
<213> ORGANISM: Artificial
<220> FEATURE:
<223> OTHER INFORMATION: Synthetic

<400> SEQUENCE: 55
aauggauuug uaggaggaag gg                                             22

<210> SEQ ID NO 56
<211> LENGTH: 22
<212> TYPE: RNA
<213> ORGANISM: Artificial
<220> FEATURE:
<223> OTHER INFORMATION: Synthetic

<400> SEQUENCE: 56
acuagauugu gagcuccugg ag                                             22

<210> SEQ ID NO 57
<211> LENGTH: 22
<212> TYPE: RNA
<213> ORGANISM: Artificial
<220> FEATURE:
<223> OTHER INFORMATION: Synthetic

<400> SEQUENCE: 57
uauguaacau gguccacuaa cu                                             22

<210> SEQ ID NO 58
<211> LENGTH: 22
<212> TYPE: RNA
<213> ORGANISM: Artificial
<220> FEATURE:
<223> OTHER INFORMATION: Synthetic

<400> SEQUENCE: 58
ugcaguccau gggcauauac ac                                             22

<210> SEQ ID NO 59
<211> LENGTH: 22
<212> TYPE: RNA
<213> ORGANISM: Artificial
<220> FEATURE:
<223> OTHER INFORMATION: Synthetic

<400> SEQUENCE: 59
ucagguggcc aggugcauau cu                                             22

<210> SEQ ID NO 60
<211> LENGTH: 22
<212> TYPE: RNA
<213> ORGANISM: Artificial
<220> FEATURE:
<223> OTHER INFORMATION: Synthetic

<400> SEQUENCE: 60
uuugaugaga acaucugggg cc                                             22

<210> SEQ ID NO 61
<211> LENGTH: 22
<212> TYPE: RNA
<213> ORGANISM: Artificial
<220> FEATURE:
<223> OTHER INFORMATION: Synthetic

<400> SEQUENCE: 61
```

-continued

| | |
|---|---|
| caggaacagc aggguuguga gg | 22 |

```
<210> SEQ ID NO 62
<211> LENGTH: 22
<212> TYPE: RNA
<213> ORGANISM: Artificial
<220> FEATURE:
<223> OTHER INFORMATION: Synthetic

<400> SEQUENCE: 62
```

| | |
|---|---|
| gaaagcugug uuggagaggc ag | 22 |

```
<210> SEQ ID NO 63
<211> LENGTH: 22
<212> TYPE: RNA
<213> ORGANISM: Artificial
<220> FEATURE:
<223> OTHER INFORMATION: Synthetic

<400> SEQUENCE: 63
```

| | |
|---|---|
| aaccguggcu uucgauuguu ac | 22 |

```
<210> SEQ ID NO 64
<211> LENGTH: 22
<212> TYPE: RNA
<213> ORGANISM: Artificial
<220> FEATURE:
<223> OTHER INFORMATION: Synthetic

<400> SEQUENCE: 64
```

| | |
|---|---|
| agagguugcc cuuggugaau uc | 22 |

```
<210> SEQ ID NO 65
<211> LENGTH: 22
<212> TYPE: RNA
<213> ORGANISM: Artificial
<220> FEATURE:
<223> OTHER INFORMATION: Synthetic

<400> SEQUENCE: 65
```

| | |
|---|---|
| uggagacgcg gcccuguugg ag | 22 |

```
<210> SEQ ID NO 66
<211> LENGTH: 22
<212> TYPE: RNA
<213> ORGANISM: Artificial
<220> FEATURE:
<223> OTHER INFORMATION: Synthetic

<400> SEQUENCE: 66
```

| | |
|---|---|
| uuucuagggc acagacagug ca | 22 |

```
<210> SEQ ID NO 67
<211> LENGTH: 22
<212> TYPE: RNA
<213> ORGANISM: Artificial
<220> FEATURE:
<223> OTHER INFORMATION: Synthetic

<400> SEQUENCE: 67
```

| | |
|---|---|
| gggagccagg aaguauugau gu | 22 |

```
<210> SEQ ID NO 68
<211> LENGTH: 22
<212> TYPE: RNA
<213> ORGANISM: Artificial
```

```
<220> FEATURE:
<223> OTHER INFORMATION: Synthetic

<400> SEQUENCE: 68
ccugcuaugc aacauauug cc                                              22

<210> SEQ ID NO 69
<211> LENGTH: 22
<212> TYPE: RNA
<213> ORGANISM: Artificial
<220> FEATURE:
<223> OTHER INFORMATION: Synthetic

<400> SEQUENCE: 69
uugggaacau uuugcaugua ua                                             22

<210> SEQ ID NO 70
<211> LENGTH: 22
<212> TYPE: RNA
<213> ORGANISM: Artificial
<220> FEATURE:
<223> OTHER INFORMATION: Synthetic

<400> SEQUENCE: 70
uuggggacau uuugcauuca ua                                             22

<210> SEQ ID NO 71
<211> LENGTH: 22
<212> TYPE: RNA
<213> ORGANISM: Artificial
<220> FEATURE:
<223> OTHER INFORMATION: Synthetic

<400> SEQUENCE: 71
ucaaaacgug aggcgcugcu au                                             22

<210> SEQ ID NO 72
<211> LENGTH: 22
<212> TYPE: RNA
<213> ORGANISM: Artificial
<220> FEATURE:
<223> OTHER INFORMATION: Synthetic

<400> SEQUENCE: 72
uguuuuuggg gguggguggc cc                                             22

<210> SEQ ID NO 73
<211> LENGTH: 21
<212> TYPE: RNA
<213> ORGANISM: Artificial
<220> FEATURE:
<223> OTHER INFORMATION: Synthetic

<400> SEQUENCE: 73
uaacaugguc cacuaacucu c                                              21

<210> SEQ ID NO 74
<211> LENGTH: 21
<212> TYPE: RNA
<213> ORGANISM: Artificial
<220> FEATURE:
<223> OTHER INFORMATION: Synthetic

<400> SEQUENCE: 74
ugggauggua aaccgcuucu u                                              21
```

```
<210> SEQ ID NO 75
<211> LENGTH: 21
<212> TYPE: RNA
<213> ORGANISM: Artificial
<220> FEATURE:
<223> OTHER INFORMATION: Synthetic

<400> SEQUENCE: 75
ugggagaagg cguuuacuc u                                              21

<210> SEQ ID NO 76
<211> LENGTH: 21
<212> TYPE: RNA
<213> ORGANISM: Artificial
<220> FEATURE:
<223> OTHER INFORMATION: Synthetic

<400> SEQUENCE: 76
ugccaacaua uugccaucuu u                                             21

<210> SEQ ID NO 77
<211> LENGTH: 21
<212> TYPE: RNA
<213> ORGANISM: Artificial
<220> FEATURE:
<223> OTHER INFORMATION: Synthetic

<400> SEQUENCE: 77
agccaggaag uauugauguu u                                             21

<210> SEQ ID NO 78
<211> LENGTH: 21
<212> TYPE: RNA
<213> ORGANISM: Artificial
<220> FEATURE:
<223> OTHER INFORMATION: Synthetic

<400> SEQUENCE: 78
ugucagaggu gacaggggcc a                                             21

<210> SEQ ID NO 79
<211> LENGTH: 22
<212> TYPE: RNA
<213> ORGANISM: Artificial
<220> FEATURE:
<223> OTHER INFORMATION: Synthetic

<400> SEQUENCE: 79
ugagguagua gguuguauag uu                                            22

<210> SEQ ID NO 80
<211> LENGTH: 22
<212> TYPE: RNA
<213> ORGANISM: Artificial
<220> FEATURE:
<223> OTHER INFORMATION: Synthetic

<400> SEQUENCE: 80
ugagguagua gguugugugg uu                                            22

<210> SEQ ID NO 81
<211> LENGTH: 22
<212> TYPE: RNA
<213> ORGANISM: Artificial
<220> FEATURE:
<223> OTHER INFORMATION: Synthetic
```

```
<400> SEQUENCE: 81
ugagguagua gguuguaugg uu                                            22

<210> SEQ ID NO 82
<211> LENGTH: 21
<212> TYPE: RNA
<213> ORGANISM: Artificial
<220> FEATURE:
<223> OTHER INFORMATION: Synthetic

<400> SEQUENCE: 82
agagguagua gguugcauag u                                             21

<210> SEQ ID NO 83
<211> LENGTH: 21
<212> TYPE: RNA
<213> ORGANISM: Artificial
<220> FEATURE:
<223> OTHER INFORMATION: Synthetic

<400> SEQUENCE: 83
ugagguagga gguuguauag u                                             21

<210> SEQ ID NO 84
<211> LENGTH: 22
<212> TYPE: RNA
<213> ORGANISM: Artificial
<220> FEATURE:
<223> OTHER INFORMATION: Synthetic

<400> SEQUENCE: 84
ugagguagua gauuguauag uu                                            22

<210> SEQ ID NO 85
<211> LENGTH: 21
<212> TYPE: RNA
<213> ORGANISM: Artificial
<220> FEATURE:
<223> OTHER INFORMATION: Synthetic

<400> SEQUENCE: 85
ugagguagua guuuguacag u                                             21

<210> SEQ ID NO 86
<211> LENGTH: 21
<212> TYPE: RNA
<213> ORGANISM: Artificial
<220> FEATURE:
<223> OTHER INFORMATION: Synthetic

<400> SEQUENCE: 86
ugagguagua guuugugcug u                                             21

<210> SEQ ID NO 87
<211> LENGTH: 21
<212> TYPE: RNA
<213> ORGANISM: Artificial
<220> FEATURE:
<223> OTHER INFORMATION: Synthetic

<400> SEQUENCE: 87
uggaauguaa agaaguaugu a                                             21

<210> SEQ ID NO 88
```

```
<211> LENGTH: 22
<212> TYPE: RNA
<213> ORGANISM: Artificial
<220> FEATURE:
<223> OTHER INFORMATION: Synthetic

<400> SEQUENCE: 88
aacccguaga uccgaacuug ug                                              22

<210> SEQ ID NO 89
<211> LENGTH: 22
<212> TYPE: RNA
<213> ORGANISM: Artificial
<220> FEATURE:
<223> OTHER INFORMATION: Synthetic

<400> SEQUENCE: 89
uacaguacug ugauaacuga ag                                              22

<210> SEQ ID NO 90
<211> LENGTH: 22
<212> TYPE: RNA
<213> ORGANISM: Artificial
<220> FEATURE:
<223> OTHER INFORMATION: Synthetic

<400> SEQUENCE: 90
aaugcaccug ggcaaggauu ca                                              22

<210> SEQ ID NO 91
<211> LENGTH: 23
<212> TYPE: RNA
<213> ORGANISM: Artificial
<220> FEATURE:
<223> OTHER INFORMATION: Synthetic

<400> SEQUENCE: 91
agcagcauug uacagggcua uga                                             23

<210> SEQ ID NO 92
<211> LENGTH: 20
<212> TYPE: RNA
<213> ORGANISM: Artificial
<220> FEATURE:
<223> OTHER INFORMATION: Synthetic

<400> SEQUENCE: 92
ucaaaugcuc agacuccugu                                                 20

<210> SEQ ID NO 93
<211> LENGTH: 24
<212> TYPE: RNA
<213> ORGANISM: Artificial
<220> FEATURE:
<223> OTHER INFORMATION: Synthetic

<400> SEQUENCE: 93
aaaagugcuu acagugcagg uagc                                            24

<210> SEQ ID NO 94
<211> LENGTH: 21
<212> TYPE: RNA
<213> ORGANISM: Artificial
<220> FEATURE:
<223> OTHER INFORMATION: Synthetic

<400> SEQUENCE: 94
```
uaaagugcug acagugcaga u                                    21

<210> SEQ ID NO 95
<211> LENGTH: 23
<212> TYPE: RNA
<213> ORGANISM: Artificial
<220> FEATURE:
<223> OTHER INFORMATION: Synthetic

<400> SEQUENCE: 95
agcagcauug uacagggcua uca                                  23

<210> SEQ ID NO 96
<211> LENGTH: 23
<212> TYPE: RNA
<213> ORGANISM: Artificial
<220> FEATURE:
<223> OTHER INFORMATION: Synthetic

<400> SEQUENCE: 96
uacccuguag auccgaauuu gug                                  23

<210> SEQ ID NO 97
<211> LENGTH: 22
<212> TYPE: RNA
<213> ORGANISM: Artificial
<220> FEATURE:
<223> OTHER INFORMATION: Synthetic

<400> SEQUENCE: 97
uacccuguag aaccgaauuu gu                                   22

<210> SEQ ID NO 98
<211> LENGTH: 23
<212> TYPE: RNA
<213> ORGANISM: Artificial
<220> FEATURE:
<223> OTHER INFORMATION: Synthetic

<400> SEQUENCE: 98
uggaguguga caauggguguu ugu                                 23

<210> SEQ ID NO 99
<211> LENGTH: 22
<212> TYPE: RNA
<213> ORGANISM: Artificial
<220> FEATURE:
<223> OTHER INFORMATION: Synthetic

<400> SEQUENCE: 99
uuaaggcacg cggugaaugc ca                                   22

<210> SEQ ID NO 100
<211> LENGTH: 23
<212> TYPE: RNA
<213> ORGANISM: Artificial
<220> FEATURE:
<223> OTHER INFORMATION: Synthetic

<400> SEQUENCE: 100
ucccugagac ccuuuaaccu gug                                  23

<210> SEQ ID NO 101
<211> LENGTH: 22
<212> TYPE: RNA

```
<213> ORGANISM: Artificial
<220> FEATURE:
<223> OTHER INFORMATION: Synthetic

<400> SEQUENCE: 101
ucccugagac ccuaacuugu ga                                              22

<210> SEQ ID NO 102
<211> LENGTH: 21
<212> TYPE: RNA
<213> ORGANISM: Artificial
<220> FEATURE:
<223> OTHER INFORMATION: Synthetic

<400> SEQUENCE: 102
cauuauuacu uuugguacgc g                                               21

<210> SEQ ID NO 103
<211> LENGTH: 21
<212> TYPE: RNA
<213> ORGANISM: Artificial
<220> FEATURE:
<223> OTHER INFORMATION: Synthetic

<400> SEQUENCE: 103
cgcguaccaa aaguaauaau g                                               21

<210> SEQ ID NO 104
<211> LENGTH: 22
<212> TYPE: RNA
<213> ORGANISM: Artificial
<220> FEATURE:
<223> OTHER INFORMATION: Synthetic

<400> SEQUENCE: 104
ucggauccgu cugagcuugg cu                                              22

<210> SEQ ID NO 105
<211> LENGTH: 22
<212> TYPE: RNA
<213> ORGANISM: Artificial
<220> FEATURE:
<223> OTHER INFORMATION: Synthetic

<400> SEQUENCE: 105
ucacagugaa ccggucucuu uu                                              22

<210> SEQ ID NO 106
<211> LENGTH: 21
<212> TYPE: RNA
<213> ORGANISM: Artificial
<220> FEATURE:
<223> OTHER INFORMATION: Synthetic

<400> SEQUENCE: 106
cuuuuugcgg ucugggcuug c                                               21

<210> SEQ ID NO 107
<211> LENGTH: 22
<212> TYPE: RNA
<213> ORGANISM: Artificial
<220> FEATURE:
<223> OTHER INFORMATION: Synthetic

<400> SEQUENCE: 107
cagugcaaug uuaaaagggc au                                              22
```

```
<210> SEQ ID NO 108
<211> LENGTH: 22
<212> TYPE: RNA
<213> ORGANISM: Artificial
<220> FEATURE:
<223> OTHER INFORMATION: Synthetic

<400> SEQUENCE: 108
cagugcaaug augaaagggc au                                              22

<210> SEQ ID NO 109
<211> LENGTH: 22
<212> TYPE: RNA
<213> ORGANISM: Artificial
<220> FEATURE:
<223> OTHER INFORMATION: Synthetic

<400> SEQUENCE: 109
uaacagucua cagccauggu cg                                              22

<210> SEQ ID NO 110
<211> LENGTH: 22
<212> TYPE: RNA
<213> ORGANISM: Artificial
<220> FEATURE:
<223> OTHER INFORMATION: Synthetic

<400> SEQUENCE: 110 uuggucccu ucaaccagcu gu                                               22

<210> SEQ ID NO 111
<211> LENGTH: 21
<212> TYPE: RNA
<213> ORGANISM: Artificial
<220> FEATURE:
<223> OTHER INFORMATION: Synthetic

<400> SEQUENCE: 111 uuggucccu ucaaccagcu a                                                21

<210> SEQ ID NO 112
<211> LENGTH: 21
<212> TYPE: RNA
<213> ORGANISM: Artificial
<220> FEATURE:
<223> OTHER INFORMATION: Synthetic

<400> SEQUENCE: 112
ugugacuggu ugaccagagg g                                               21

<210> SEQ ID NO 113
<211> LENGTH: 23
<212> TYPE: RNA
<213> ORGANISM: Artificial
<220> FEATURE:
<223> OTHER INFORMATION: Synthetic

<400> SEQUENCE: 113
uauggcuuuu uauuccuaug uga                                             23

<210> SEQ ID NO 114
<211> LENGTH: 22
<212> TYPE: RNA
<213> ORGANISM: Artificial
<220> FEATURE:
```

```
<223> OTHER INFORMATION: Synthetic

<400> SEQUENCE: 114
uauggcuuuu cauuccuaug ug                                              22

<210> SEQ ID NO 115
<211> LENGTH: 23
<212> TYPE: RNA
<213> ORGANISM: Artificial
<220> FEATURE:
<223> OTHER INFORMATION: Synthetic

<400> SEQUENCE: 115
acuccauuug uuuugaugau gga                                             23

<210> SEQ ID NO 116
<211> LENGTH: 22
<212> TYPE: RNA
<213> ORGANISM: Artificial
<220> FEATURE:
<223> OTHER INFORMATION: Synthetic

<400> SEQUENCE: 116
uauugcuuaa gaauacgcgu ag                                              22

<210> SEQ ID NO 117
<211> LENGTH: 17
<212> TYPE: RNA
<213> ORGANISM: Artificial
<220> FEATURE:
<223> OTHER INFORMATION: Synthetic

<400> SEQUENCE: 117
agcugguguu gugaauc                                                    17

<210> SEQ ID NO 118
<211> LENGTH: 18
<212> TYPE: RNA
<213> ORGANISM: Artificial
<220> FEATURE:
<223> OTHER INFORMATION: Synthetic

<400> SEQUENCE: 118
ucuacagugc acgugucu                                                   18

<210> SEQ ID NO 119
<211> LENGTH: 21
<212> TYPE: RNA
<213> ORGANISM: Artificial
<220> FEATURE:
<223> OTHER INFORMATION: Synthetic

<400> SEQUENCE: 119
agugguuuua cccuauggua g                                               21

<210> SEQ ID NO 120
<211> LENGTH: 22
<212> TYPE: RNA
<213> ORGANISM: Artificial
<220> FEATURE:
<223> OTHER INFORMATION: Synthetic

<400> SEQUENCE: 120
uaacacuguc ugguaaagau gg                                              22
```

```
<210> SEQ ID NO 121
<211> LENGTH: 23
<212> TYPE: RNA
<213> ORGANISM: Artificial
<220> FEATURE:
<223> OTHER INFORMATION: Synthetic

<400> SEQUENCE: 121
uguaguguuu ccuacuuuau gga                                              23

<210> SEQ ID NO 122
<211> LENGTH: 20
<212> TYPE: RNA
<213> ORGANISM: Artificial
<220> FEATURE:
<223> OTHER INFORMATION: Synthetic

<400> SEQUENCE: 122
cauaaaguag aaagcacuac                                                  20

<210> SEQ ID NO 123
<211> LENGTH: 22
<212> TYPE: RNA
<213> ORGANISM: Artificial
<220> FEATURE:
<223> OTHER INFORMATION: Synthetic

<400> SEQUENCE: 123
ugagaugaag cacuguagcu ca                                               22

<210> SEQ ID NO 124
<211> LENGTH: 22
<212> TYPE: RNA
<213> ORGANISM: Artificial
<220> FEATURE:
<223> OTHER INFORMATION: Synthetic

<400> SEQUENCE: 124
uacaguauag augauguacu ag                                               22

<210> SEQ ID NO 125
<211> LENGTH: 24
<212> TYPE: RNA
<213> ORGANISM: Artificial
<220> FEATURE:
<223> OTHER INFORMATION: Synthetic

<400> SEQUENCE: 125
guccaguuuu cccaggaauc ccuu                                             24

<210> SEQ ID NO 126
<211> LENGTH: 22
<212> TYPE: RNA
<213> ORGANISM: Artificial
<220> FEATURE:
<223> OTHER INFORMATION: Synthetic

<400> SEQUENCE: 126
ugagaacuga auuccauggg uu                                               22

<210> SEQ ID NO 127
<211> LENGTH: 20
<212> TYPE: RNA
<213> ORGANISM: Artificial
<220> FEATURE:
<223> OTHER INFORMATION: Synthetic
```

```
<400> SEQUENCE: 127
gugugaggaa augcuucugc                                        20

<210> SEQ ID NO 128
<211> LENGTH: 22
<212> TYPE: RNA
<213> ORGANISM: Artificial
<220> FEATURE:
<223> OTHER INFORMATION: Synthetic

<400> SEQUENCE: 128
ucagugcacu acagaacuuu gu                                     22

<210> SEQ ID NO 129
<211> LENGTH: 22
<212> TYPE: RNA
<213> ORGANISM: Artificial
<220> FEATURE:
<223> OTHER INFORMATION: Synthetic

<400> SEQUENCE: 129
ucagugcauc acagaacuuu gu                                     22

<210> SEQ ID NO 130
<211> LENGTH: 22
<212> TYPE: RNA
<213> ORGANISM: Artificial
<220> FEATURE:
<223> OTHER INFORMATION: Synthetic

<400> SEQUENCE: 130
ucuggcuccg ugucuucacu cc                                     22

<210> SEQ ID NO 131
<211> LENGTH: 22
<212> TYPE: RNA
<213> ORGANISM: Artificial
<220> FEATURE:
<223> OTHER INFORMATION: Synthetic

<400> SEQUENCE: 131
ucucccaacc cuuguaccag ug                                     22

<210> SEQ ID NO 132
<211> LENGTH: 22
<212> TYPE: RNA
<213> ORGANISM: Artificial
<220> FEATURE:
<223> OTHER INFORMATION: Synthetic

<400> SEQUENCE: 132
acuagacuga agcuccuuga gg                                     22

<210> SEQ ID NO 133
<211> LENGTH: 22
<212> TYPE: RNA
<213> ORGANISM: Artificial
<220> FEATURE:
<223> OTHER INFORMATION: Synthetic

<400> SEQUENCE: 133
ucagugcaug acagaacuug gg                                     22

<210> SEQ ID NO 134
<211> LENGTH: 20
```

```
<212> TYPE: RNA
<213> ORGANISM: Artificial
<220> FEATURE:
<223> OTHER INFORMATION: Synthetic

<400> SEQUENCE: 134
uugcauaguc acaaaaguga                                            20

<210> SEQ ID NO 135
<211> LENGTH: 22
<212> TYPE: RNA
<213> ORGANISM: Artificial
<220> FEATURE:
<223> OTHER INFORMATION: Synthetic

<400> SEQUENCE: 135
uagguuaucc guguugccuu cg                                         22

<210> SEQ ID NO 136
<211> LENGTH: 22
<212> TYPE: RNA
<213> ORGANISM: Artificial
<220> FEATURE:
<223> OTHER INFORMATION: Synthetic

<400> SEQUENCE: 136
uuaaugcuaa ucgugauagg gg                                         22

<210> SEQ ID NO 137
<211> LENGTH: 22
<212> TYPE: RNA
<213> ORGANISM: Artificial
<220> FEATURE:
<223> OTHER INFORMATION: Synthetic

<400> SEQUENCE: 137
agcaccaugc aguccauggg ca                                         22

<210> SEQ ID NO 138
<211> LENGTH: 22
<212> TYPE: RNA
<213> ORGANISM: Artificial
<220> FEATURE:
<223> OTHER INFORMATION: Synthetic

<400> SEQUENCE: 138
uagcagcaca uaaugguuug ug                                         22

<210> SEQ ID NO 139
<211> LENGTH: 22
<212> TYPE: RNA
<213> ORGANISM: Artificial
<220> FEATURE:
<223> OTHER INFORMATION: Synthetic

<400> SEQUENCE: 139
uagcagcaca ucaugguuua ca                                         22

<210> SEQ ID NO 140
<211> LENGTH: 22
<212> TYPE: RNA
<213> ORGANISM: Artificial
<220> FEATURE:
<223> OTHER INFORMATION: Synthetic

<400> SEQUENCE: 140
```

```
uagcagcacg uaaauauugg cg                                              22

<210> SEQ ID NO 141
<211> LENGTH: 20
<212> TYPE: RNA
<213> ORGANISM: Artificial
<220> FEATURE:
<223> OTHER INFORMATION: Synthetic

<400> SEQUENCE: 141
acugcaguga aggcacuugu                                                 20

<210> SEQ ID NO 142
<211> LENGTH: 24
<212> TYPE: RNA
<213> ORGANISM: Artificial
<220> FEATURE:
<223> OTHER INFORMATION: Synthetic

<400> SEQUENCE: 142
caaagugcuu acagugcagg uagu                                            24

<210> SEQ ID NO 143
<211> LENGTH: 23
<212> TYPE: RNA
<213> ORGANISM: Artificial
<220> FEATURE:
<223> OTHER INFORMATION: Synthetic

<400> SEQUENCE: 143
aacauucaac gcugucggug agu                                             23

<210> SEQ ID NO 144
<211> LENGTH: 22
<212> TYPE: RNA
<213> ORGANISM: Artificial
<220> FEATURE:
<223> OTHER INFORMATION: Synthetic

<400> SEQUENCE: 144
aacauucauu gcugucggug gg                                              22

<210> SEQ ID NO 145
<211> LENGTH: 22
<212> TYPE: RNA
<213> ORGANISM: Artificial
<220> FEATURE:
<223> OTHER INFORMATION: Synthetic

<400> SEQUENCE: 145
aacauucaac cugucgguga gu                                              22

<210> SEQ ID NO 146
<211> LENGTH: 22
<212> TYPE: RNA
<213> ORGANISM: Artificial
<220> FEATURE:
<223> OTHER INFORMATION: Synthetic

<400> SEQUENCE: 146
uuuggcaaug guagaacuca ca                                              22

<210> SEQ ID NO 147
<211> LENGTH: 22
<212> TYPE: RNA
<213> ORGANISM: Artificial
```

```
<220> FEATURE:
<223> OTHER INFORMATION: Synthetic

<400> SEQUENCE: 147
ugugaguucu accauugcca aa                                          22

<210> SEQ ID NO 148
<211> LENGTH: 23
<212> TYPE: RNA
<213> ORGANISM: Artificial
<220> FEATURE:
<223> OTHER INFORMATION: Synthetic

<400> SEQUENCE: 148
uauggcacug guagaauuca cug                                         23

<210> SEQ ID NO 149
<211> LENGTH: 22
<212> TYPE: RNA
<213> ORGANISM: Artificial
<220> FEATURE:
<223> OTHER INFORMATION: Synthetic

<400> SEQUENCE: 149
uggacggaga acugauaagg gu                                          22

<210> SEQ ID NO 150
<211> LENGTH: 18
<212> TYPE: RNA
<213> ORGANISM: Artificial
<220> FEATURE:
<223> OTHER INFORMATION: Synthetic

<400> SEQUENCE: 150
uggagagaaa ggcaguuc                                               18

<210> SEQ ID NO 151
<211> LENGTH: 23
<212> TYPE: RNA
<213> ORGANISM: Artificial
<220> FEATURE:
<223> OTHER INFORMATION: Synthetic

<400> SEQUENCE: 151
caaagaauuc uccuuuuggg cuu                                         23

<210> SEQ ID NO 152
<211> LENGTH: 21
<212> TYPE: RNA
<213> ORGANISM: Artificial
<220> FEATURE:
<223> OTHER INFORMATION: Synthetic

<400> SEQUENCE: 152
ucgugucuug uguugcagcc g                                           21

<210> SEQ ID NO 153
<211> LENGTH: 22
<212> TYPE: RNA
<213> ORGANISM: Artificial
<220> FEATURE:
<223> OTHER INFORMATION: Synthetic

<400> SEQUENCE: 153
caucccuugc augguggagg gu                                          22
```

```
<210> SEQ ID NO 154
<211> LENGTH: 23
<212> TYPE: RNA
<213> ORGANISM: Artificial
<220> FEATURE:
<223> OTHER INFORMATION: Synthetic

<400> SEQUENCE: 154
gugccuacug agcugauauc agu                                              23

<210> SEQ ID NO 155
<211> LENGTH: 22
<212> TYPE: RNA
<213> ORGANISM: Artificial
<220> FEATURE:
<223> OTHER INFORMATION: Synthetic

<400> SEQUENCE: 155
uaaggugcau cuagugcaga ua                                               22

<210> SEQ ID NO 156
<211> LENGTH: 22
<212> TYPE: RNA
<213> ORGANISM: Artificial
<220> FEATURE:
<223> OTHER INFORMATION: Synthetic

<400> SEQUENCE: 156
uaaggugcau cuagugcagu ua                                               22

<210> SEQ ID NO 157
<211> LENGTH: 22
<212> TYPE: RNA
<213> ORGANISM: Artificial
<220> FEATURE:
<223> OTHER INFORMATION: Synthetic

<400> SEQUENCE: 157
ugauauguuu gauauauuag gu                                               22

<210> SEQ ID NO 158
<211> LENGTH: 22
<212> TYPE: RNA
<213> ORGANISM: Artificial
<220> FEATURE:
<223> OTHER INFORMATION: Synthetic

<400> SEQUENCE: 158
caacggaauc ccaaaagcag cu                                               22

<210> SEQ ID NO 159
<211> LENGTH: 21
<212> TYPE: RNA
<213> ORGANISM: Artificial
<220> FEATURE:
<223> OTHER INFORMATION: Synthetic

<400> SEQUENCE: 159
cugaccuaug aauugacagc c                                                21

<210> SEQ ID NO 160
<211> LENGTH: 21
<212> TYPE: RNA
<213> ORGANISM: Artificial
<220> FEATURE:
<223> OTHER INFORMATION: Synthetic
```

<400> SEQUENCE: 160
aacuggccua caaagucccca g                                            21

<210> SEQ ID NO 161
<211> LENGTH: 24
<212> TYPE: RNA
<213> ORGANISM: Artificial
<220> FEATURE:
<223> OTHER INFORMATION: Synthetic

<400> SEQUENCE: 161
aacuggcccu caaagucccg cuuu                                          24

<210> SEQ ID NO 162
<211> LENGTH: 22
<212> TYPE: RNA
<213> ORGANISM: Artificial
<220> FEATURE:
<223> OTHER INFORMATION: Synthetic

<400> SEQUENCE: 162
uguaacagca acuccaugug ga                                            22

<210> SEQ ID NO 163
<211> LENGTH: 21
<212> TYPE: RNA
<213> ORGANISM: Artificial
<220> FEATURE:
<223> OTHER INFORMATION: Synthetic

<400> SEQUENCE: 163
uagcagcaca gaaauauugg c                                             21

<210> SEQ ID NO 164
<211> LENGTH: 21
<212> TYPE: RNA
<213> ORGANISM: Artificial
<220> FEATURE:
<223> OTHER INFORMATION: Synthetic

<400> SEQUENCE: 164
uagguaguuu cauguuguug g                                             21

<210> SEQ ID NO 165
<211> LENGTH: 21
<212> TYPE: RNA
<213> ORGANISM: Artificial
<220> FEATURE:
<223> OTHER INFORMATION: Synthetic

<400> SEQUENCE: 165
uagguaguuu ccuguuguug g                                             21

<210> SEQ ID NO 166
<211> LENGTH: 22
<212> TYPE: RNA
<213> ORGANISM: Artificial
<220> FEATURE:
<223> OTHER INFORMATION: Synthetic

<400> SEQUENCE: 166
uucaccaccu ucuccaccca gc                                            22

<210> SEQ ID NO 167

```
<211> LENGTH: 19
<212> TYPE: RNA
<213> ORGANISM: Artificial
<220> FEATURE:
<223> OTHER INFORMATION: Synthetic

<400> SEQUENCE: 167
gguccagagg ggagauagg                                                      19

<210> SEQ ID NO 168
<211> LENGTH: 23
<212> TYPE: RNA
<213> ORGANISM: Artificial
<220> FEATURE:
<223> OTHER INFORMATION: Synthetic

<400> SEQUENCE: 168
cccaguguuc agacuaccug uuc                                                 23

<210> SEQ ID NO 169
<211> LENGTH: 23
<212> TYPE: RNA
<213> ORGANISM: Artificial
<220> FEATURE:
<223> OTHER INFORMATION: Synthetic

<400> SEQUENCE: 169
gaacagguag ucugaacacu ggg                                                 23

<210> SEQ ID NO 170
<211> LENGTH: 23
<212> TYPE: RNA
<213> ORGANISM: Artificial
<220> FEATURE:
<223> OTHER INFORMATION: Synthetic

<400> SEQUENCE: 170
cccaguguuu agacuaucug uuc                                                 23

<210> SEQ ID NO 171
<211> LENGTH: 23
<212> TYPE: RNA
<213> ORGANISM: Artificial
<220> FEATURE:
<223> OTHER INFORMATION: Synthetic

<400> SEQUENCE: 171
ugugcaaauc uaugcaaaac uga                                                 23

<210> SEQ ID NO 172
<211> LENGTH: 23
<212> TYPE: RNA
<213> ORGANISM: Artificial
<220> FEATURE:
<223> OTHER INFORMATION: Synthetic

<400> SEQUENCE: 172
ugugcaaauc caugcaaaac uga                                                 23

<210> SEQ ID NO 173
<211> LENGTH: 22
<212> TYPE: RNA
<213> ORGANISM: Artificial
<220> FEATURE:
<223> OTHER INFORMATION: Synthetic

<400> SEQUENCE: 173
```

```
caucuuaccg gacagugcug ga                                              22
```

<210> SEQ ID NO 174
<211> LENGTH: 23
<212> TYPE: RNA
<213> ORGANISM: Artificial
<220> FEATURE:
<223> OTHER INFORMATION: Synthetic

<400> SEQUENCE: 174

```
uaauacugcc ugguaaugau gac                                             23
```

<210> SEQ ID NO 175
<211> LENGTH: 22
<212> TYPE: RNA
<213> ORGANISM: Artificial
<220> FEATURE:
<223> OTHER INFORMATION: Synthetic

<400> SEQUENCE: 175

```
uaauacugcc ggguaaugau gg                                              22
```

<210> SEQ ID NO 176
<211> LENGTH: 22
<212> TYPE: RNA
<213> ORGANISM: Artificial
<220> FEATURE:
<223> OTHER INFORMATION: Synthetic

<400> SEQUENCE: 176

```
uuuucccaug cccuauaccu cu                                              22
```

<210> SEQ ID NO 177
<211> LENGTH: 22
<212> TYPE: RNA
<213> ORGANISM: Artificial
<220> FEATURE:
<223> OTHER INFORMATION: Synthetic

<400> SEQUENCE: 177

```
gugaaauguu uaggaccacu ag                                              22
```

<210> SEQ ID NO 178
<211> LENGTH: 22
<212> TYPE: RNA
<213> ORGANISM: Artificial
<220> FEATURE:
<223> OTHER INFORMATION: Synthetic

<400> SEQUENCE: 178

```
uucccuuugu cauccuaugc cu                                              22
```

<210> SEQ ID NO 179
<211> LENGTH: 22
<212> TYPE: RNA
<213> ORGANISM: Artificial
<220> FEATURE:
<223> OTHER INFORMATION: Synthetic

<400> SEQUENCE: 179

```
uccuucauuc caccggaguc ug                                              22
```

<210> SEQ ID NO 180
<211> LENGTH: 22
<212> TYPE: RNA

```
<213> ORGANISM: Artificial
<220> FEATURE:
<223> OTHER INFORMATION: Synthetic

<400> SEQUENCE: 180
uggaauguaa ggaagugugu gg                                              22

<210> SEQ ID NO 181
<211> LENGTH: 22
<212> TYPE: RNA
<213> ORGANISM: Artificial
<220> FEATURE:
<223> OTHER INFORMATION: Synthetic

<400> SEQUENCE: 181
auaagacgag caaaaagcuu gu                                              22

<210> SEQ ID NO 182
<211> LENGTH: 23
<212> TYPE: RNA
<213> ORGANISM: Artificial
<220> FEATURE:
<223> OTHER INFORMATION: Synthetic

<400> SEQUENCE: 182
uaaagugcuu auagugcagg uag                                             23

<210> SEQ ID NO 183
<211> LENGTH: 22
<212> TYPE: RNA
<213> ORGANISM: Artificial
<220> FEATURE:
<223> OTHER INFORMATION: Synthetic

<400> SEQUENCE: 183
uagcuuauca gacugauguu ga                                              22

<210> SEQ ID NO 184
<211> LENGTH: 22
<212> TYPE: RNA
<213> ORGANISM: Artificial
<220> FEATURE:
<223> OTHER INFORMATION: Synthetic

<400> SEQUENCE: 184
cugugcgugu gacagcggcu ga                                              22

<210> SEQ ID NO 185
<211> LENGTH: 22
<212> TYPE: RNA
<213> ORGANISM: Artificial
<220> FEATURE:
<223> OTHER INFORMATION: Synthetic

<400> SEQUENCE: 185
uucccuuugu cauccuucgc cu                                              22

<210> SEQ ID NO 186
<211> LENGTH: 21
<212> TYPE: RNA
<213> ORGANISM: Artificial
<220> FEATURE:
<223> OTHER INFORMATION: Synthetic

<400> SEQUENCE: 186
uaacagucuc cagucacggc c                                               21
```

```
<210> SEQ ID NO 187
<211> LENGTH: 22
<212> TYPE: RNA
<213> ORGANISM: Artificial
<220> FEATURE:
<223> OTHER INFORMATION: Synthetic

<400> SEQUENCE: 187
accaucgacc guugauugua cc                                               22

<210> SEQ ID NO 188
<211> LENGTH: 21
<212> TYPE: RNA
<213> ORGANISM: Artificial
<220> FEATURE:
<223> OTHER INFORMATION: Synthetic

<400> SEQUENCE: 188
acagcaggca cagacaggca g                                                21

<210> SEQ ID NO 189
<211> LENGTH: 21
<212> TYPE: RNA
<213> ORGANISM: Artificial
<220> FEATURE:
<223> OTHER INFORMATION: Synthetic

<400> SEQUENCE: 189
augaccuaug aauugacaga c                                                21

<210> SEQ ID NO 190
<211> LENGTH: 21
<212> TYPE: RNA
<213> ORGANISM: Artificial
<220> FEATURE:
<223> OTHER INFORMATION: Synthetic

<400> SEQUENCE: 190
uaaucucagc uggcaacugu g                                                21

<210> SEQ ID NO 191
<211> LENGTH: 24
<212> TYPE: RNA
<213> ORGANISM: Artificial
<220> FEATURE:
<223> OTHER INFORMATION: Synthetic

<400> SEQUENCE: 191
uacugcauca ggaacugauu ggau                                             24

<210> SEQ ID NO 192
<211> LENGTH: 21
<212> TYPE: RNA
<213> ORGANISM: Artificial
<220> FEATURE:
<223> OTHER INFORMATION: Synthetic

<400> SEQUENCE: 192
uugugcuuga ucuaaccaug u                                                21

<210> SEQ ID NO 193
<211> LENGTH: 21
<212> TYPE: RNA
<213> ORGANISM: Artificial
<220> FEATURE:
```

```
<223> OTHER INFORMATION: Synthetic

<400> SEQUENCE: 193
ugauugucca aacgcaauuc u                                              21

<210> SEQ ID NO 194
<211> LENGTH: 22
<212> TYPE: RNA
<213> ORGANISM: Artificial
<220> FEATURE:
<223> OTHER INFORMATION: Synthetic

<400> SEQUENCE: 194
aagcugccag uugaagaacu gu                                             22

<210> SEQ ID NO 195
<211> LENGTH: 21
<212> TYPE: RNA
<213> ORGANISM: Artificial
<220> FEATURE:
<223> OTHER INFORMATION: Synthetic

<400> SEQUENCE: 195
ccacaccgua ucugacacuu u                                              21

<210> SEQ ID NO 196
<211> LENGTH: 23
<212> TYPE: RNA
<213> ORGANISM: Artificial
<220> FEATURE:
<223> OTHER INFORMATION: Synthetic

<400> SEQUENCE: 196
agcuacauug ucugcugggu uuc                                            23

<210> SEQ ID NO 197
<211> LENGTH: 24
<212> TYPE: RNA
<213> ORGANISM: Artificial
<220> FEATURE:
<223> OTHER INFORMATION: Synthetic

<400> SEQUENCE: 197
agcuacaucu ggcuacuggg ucuc                                           24

<210> SEQ ID NO 198
<211> LENGTH: 21
<212> TYPE: RNA
<213> ORGANISM: Artificial
<220> FEATURE:
<223> OTHER INFORMATION: Synthetic

<400> SEQUENCE: 198
ugucaguuug ucaaauaccc c                                              21

<210> SEQ ID NO 199
<211> LENGTH: 23
<212> TYPE: RNA
<213> ORGANISM: Artificial
<220> FEATURE:
<223> OTHER INFORMATION: Synthetic

<400> SEQUENCE: 199
caagucacua gugguuccgu uua                                            23
```

```
<210> SEQ ID NO 200
<211> LENGTH: 21
<212> TYPE: RNA
<213> ORGANISM: Artificial
<220> FEATURE:
<223> OTHER INFORMATION: Synthetic

<400> SEQUENCE: 200
aucacauugc cagggauuuc c                                              21

<210> SEQ ID NO 201
<211> LENGTH: 21
<212> TYPE: RNA
<213> ORGANISM: Artificial
<220> FEATURE:
<223> OTHER INFORMATION: Synthetic

<400> SEQUENCE: 201
aucacauugc cagggauuac c                                              21

<210> SEQ ID NO 202
<211> LENGTH: 22
<212> TYPE: RNA
<213> ORGANISM: Artificial
<220> FEATURE:
<223> OTHER INFORMATION: Synthetic

<400> SEQUENCE: 202
uggcucaguu cagcaggaac ag                                             22

<210> SEQ ID NO 203
<211> LENGTH: 22
<212> TYPE: RNA
<213> ORGANISM: Artificial
<220> FEATURE:
<223> OTHER INFORMATION: Synthetic

<400> SEQUENCE: 203
cauugcacuu gucucggucu ga                                             22

<210> SEQ ID NO 204
<211> LENGTH: 21
<212> TYPE: RNA
<213> ORGANISM: Artificial
<220> FEATURE:
<223> OTHER INFORMATION: Synthetic

<400> SEQUENCE: 204
uucaaguaau ccaggauagg c                                              21

<210> SEQ ID NO 205
<211> LENGTH: 22
<212> TYPE: RNA
<213> ORGANISM: Artificial
<220> FEATURE:
<223> OTHER INFORMATION: Synthetic

<400> SEQUENCE: 205
uucaaguaau ucaggauagg uu                                             22

<210> SEQ ID NO 206
<211> LENGTH: 21
<212> TYPE: RNA
<213> ORGANISM: Artificial
<220> FEATURE:
<223> OTHER INFORMATION: Synthetic
```

```
<400> SEQUENCE: 206
uucacagugg cuaaguuccg c                                              21

<210> SEQ ID NO 207
<211> LENGTH: 21
<212> TYPE: RNA
<213> ORGANISM: Artificial
<220> FEATURE:
<223> OTHER INFORMATION: Synthetic

<400> SEQUENCE: 207
uucacagugg cuaaguucug c                                              21

<210> SEQ ID NO 208
<211> LENGTH: 22
<212> TYPE: RNA
<213> ORGANISM: Artificial
<220> FEATURE:
<223> OTHER INFORMATION: Synthetic

<400> SEQUENCE: 208
aaggagcuca cagucuauug ag                                             22

<210> SEQ ID NO 209
<211> LENGTH: 21
<212> TYPE: RNA
<213> ORGANISM: Artificial
<220> FEATURE:
<223> OTHER INFORMATION: Synthetic

<400> SEQUENCE: 209 agggccccccc cucaauccug u                                             21

<210> SEQ ID NO 210
<211> LENGTH: 22
<212> TYPE: RNA
<213> ORGANISM: Artificial
<220> FEATURE:
<223> OTHER INFORMATION: Synthetic

<400> SEQUENCE: 210
uaugugggau gguaaaccgc uu                                             22

<210> SEQ ID NO 211
<211> LENGTH: 22
<212> TYPE: RNA
<213> ORGANISM: Artificial
<220> FEATURE:
<223> OTHER INFORMATION: Synthetic

<400> SEQUENCE: 211
ugguuuaccg ucccacauac au                                             22

<210> SEQ ID NO 212
<211> LENGTH: 21
<212> TYPE: RNA
<213> ORGANISM: Artificial
<220> FEATURE:
<223> OTHER INFORMATION: Synthetic

<400> SEQUENCE: 212
uagcaccauc ugaaaucggu u                                              21

<210> SEQ ID NO 213
<211> LENGTH: 23
```

```
<212> TYPE: RNA
<213> ORGANISM: Artificial
<220> FEATURE:
<223> OTHER INFORMATION: Synthetic

<400> SEQUENCE: 213
uagcaccauu ugaaaucagu guu                                              23

<210> SEQ ID NO 214
<211> LENGTH: 20
<212> TYPE: RNA
<213> ORGANISM: Artificial
<220> FEATURE:
<223> OTHER INFORMATION: Synthetic

<400> SEQUENCE: 214
uagcaccauu ugaaaucggu                                                  20

<210> SEQ ID NO 215
<211> LENGTH: 23
<212> TYPE: RNA
<213> ORGANISM: Artificial
<220> FEATURE:
<223> OTHER INFORMATION: Synthetic

<400> SEQUENCE: 215
cagugcaaua guauugucaa agc                                              23

<210> SEQ ID NO 216
<211> LENGTH: 22
<212> TYPE: RNA
<213> ORGANISM: Artificial
<220> FEATURE:
<223> OTHER INFORMATION: Synthetic

<400> SEQUENCE: 216
uaaacgugga uguacuugcu uu                                               22

<210> SEQ ID NO 217
<211> LENGTH: 23
<212> TYPE: RNA
<213> ORGANISM: Artificial
<220> FEATURE:
<223> OTHER INFORMATION: Synthetic

<400> SEQUENCE: 217
acuuuaacau ggaagugcuu ucu                                              23

<210> SEQ ID NO 218
<211> LENGTH: 23
<212> TYPE: RNA
<213> ORGANISM: Artificial
<220> FEATURE:
<223> OTHER INFORMATION: Synthetic

<400> SEQUENCE: 218
agaaagcacu uccauguuaa agu                                              23

<210> SEQ ID NO 219
<211> LENGTH: 22
<212> TYPE: RNA
<213> ORGANISM: Artificial
<220> FEATURE:
<223> OTHER INFORMATION: Synthetic

<400> SEQUENCE: 219
```

```
uuuaacaugg ggguaccugc ug                                              22

<210> SEQ ID NO 220
<211> LENGTH: 22
<212> TYPE: RNA
<213> ORGANISM: Artificial
<220> FEATURE:
<223> OTHER INFORMATION: Synthetic

<400> SEQUENCE: 220
cagcagguac ccccauguua aa                                              22

<210> SEQ ID NO 221
<211> LENGTH: 23
<212> TYPE: RNA
<213> ORGANISM: Artificial
<220> FEATURE:
<223> OTHER INFORMATION: Synthetic

<400> SEQUENCE: 221
uaagugcuuc cauguuugag ugu                                             23

<210> SEQ ID NO 222
<211> LENGTH: 22
<212> TYPE: RNA
<213> ORGANISM: Artificial
<220> FEATURE:
<223> OTHER INFORMATION: Synthetic

<400> SEQUENCE: 222
cuuucagucg gauguuugca gc                                              22

<210> SEQ ID NO 223
<211> LENGTH: 22
<212> TYPE: RNA
<213> ORGANISM: Artificial
<220> FEATURE:
<223> OTHER INFORMATION: Synthetic

<400> SEQUENCE: 223
uguaaacauc cucgacugga ag                                              22

<210> SEQ ID NO 224
<211> LENGTH: 22
<212> TYPE: RNA
<213> ORGANISM: Artificial
<220> FEATURE:
<223> OTHER INFORMATION: Synthetic

<400> SEQUENCE: 224
uguaaacauc cuacacucag cu                                              22

<210> SEQ ID NO 225
<211> LENGTH: 23
<212> TYPE: RNA
<213> ORGANISM: Artificial
<220> FEATURE:
<223> OTHER INFORMATION: Synthetic

<400> SEQUENCE: 225
uguaaacauc cuacacucuc agc                                             23

<210> SEQ ID NO 226
<211> LENGTH: 22
<212> TYPE: RNA
<213> ORGANISM: Artificial
```

```
<220> FEATURE:
<223> OTHER INFORMATION: Synthetic

<400> SEQUENCE: 226
uguaaacauc cccgacugga ag                                          22

<210> SEQ ID NO 227
<211> LENGTH: 22
<212> TYPE: RNA
<213> ORGANISM: Artificial
<220> FEATURE:
<223> OTHER INFORMATION: Synthetic

<400> SEQUENCE: 227
cuuucagucg gauguuuaca gc                                          22

<210> SEQ ID NO 228
<211> LENGTH: 20
<212> TYPE: RNA
<213> ORGANISM: Artificial
<220> FEATURE:
<223> OTHER INFORMATION: Synthetic

<400> SEQUENCE: 228
uguaaacauc cuugacugga                                             20

<210> SEQ ID NO 229
<211> LENGTH: 21
<212> TYPE: RNA
<213> ORGANISM: Artificial
<220> FEATURE:
<223> OTHER INFORMATION: Synthetic

<400> SEQUENCE: 229
ggcaagaugc uggcauagcu g                                           21

<210> SEQ ID NO 230
<211> LENGTH: 21
<212> TYPE: RNA
<213> ORGANISM: Artificial
<220> FEATURE:
<223> OTHER INFORMATION: Synthetic

<400> SEQUENCE: 230
uauugcacau uacuaaguug c                                           21

<210> SEQ ID NO 231
<211> LENGTH: 23
<212> TYPE: RNA
<213> ORGANISM: Artificial
<220> FEATURE:
<223> OTHER INFORMATION: Synthetic

<400> SEQUENCE: 231
aaaagcuggg uugagagggc gaa                                         23

<210> SEQ ID NO 232
<211> LENGTH: 22
<212> TYPE: RNA
<213> ORGANISM: Artificial
<220> FEATURE:
<223> OTHER INFORMATION: Synthetic

<400> SEQUENCE: 232
gcacauuaca cggucgaccu cu                                          22
```

<210> SEQ ID NO 233
<211> LENGTH: 22
<212> TYPE: RNA
<213> ORGANISM: Artificial
<220> FEATURE:
<223> OTHER INFORMATION: Synthetic

<400> SEQUENCE: 233
ccacugcccc aggugcugcu gg                                          22

<210> SEQ ID NO 234
<211> LENGTH: 23
<212> TYPE: RNA
<213> ORGANISM: Artificial
<220> FEATURE:
<223> OTHER INFORMATION: Synthetic

<400> SEQUENCE: 234
cgcauccccu agggcauugg ugu                                         23

<210> SEQ ID NO 235
<211> LENGTH: 23
<212> TYPE: RNA
<213> ORGANISM: Artificial
<220> FEATURE:
<223> OTHER INFORMATION: Synthetic

<400> SEQUENCE: 235
ccuaguaggu guccaguaag ugu                                         23

<210> SEQ ID NO 236
<211> LENGTH: 20
<212> TYPE: RNA
<213> ORGANISM: Artificial
<220> FEATURE:
<223> OTHER INFORMATION: Synthetic

<400> SEQUENCE: 236
ccucugggcc cuuccuccag                                             20

<210> SEQ ID NO 237
<211> LENGTH: 22
<212> TYPE: RNA
<213> ORGANISM: Artificial
<220> FEATURE:
<223> OTHER INFORMATION: Synthetic

<400> SEQUENCE: 237
cuggcccucu cugcccuucc gu                                          22

<210> SEQ ID NO 238
<211> LENGTH: 22
<212> TYPE: RNA
<213> ORGANISM: Artificial
<220> FEATURE:
<223> OTHER INFORMATION: Synthetic

<400> SEQUENCE: 238
aacacaccug guuaaccucu uu                                          22

<210> SEQ ID NO 239
<211> LENGTH: 19
<212> TYPE: RNA
<213> ORGANISM: Artificial
<220> FEATURE:
<223> OTHER INFORMATION: Synthetic

```
<400> SEQUENCE: 239
gugcauugua guugcauug                                             19

<210> SEQ ID NO 240
<211> LENGTH: 23
<212> TYPE: RNA
<213> ORGANISM: Artificial
<220> FEATURE:
<223> OTHER INFORMATION: Synthetic

<400> SEQUENCE: 240
gcaaagcaca cggccugcag aga                                        23

<210> SEQ ID NO 241
<211> LENGTH: 21
<212> TYPE: RNA
<213> ORGANISM: Artificial
<220> FEATURE:
<223> OTHER INFORMATION: Synthetic

<400> SEQUENCE: 241
gccccugggc cuauccuaga a                                          21

<210> SEQ ID NO 242
<211> LENGTH: 23
<212> TYPE: RNA
<213> ORGANISM: Artificial
<220> FEATURE:
<223> OTHER INFORMATION: Synthetic

<400> SEQUENCE: 242
ucaagagcaa uaacgaaaaa ugu                                        23

<210> SEQ ID NO 243
<211> LENGTH: 23
<212> TYPE: RNA
<213> ORGANISM: Artificial
<220> FEATURE:
<223> OTHER INFORMATION: Synthetic

<400> SEQUENCE: 243
uccagcuccu auaugaugcc uuu                                        23

<210> SEQ ID NO 244
<211> LENGTH: 23
<212> TYPE: RNA
<213> ORGANISM: Artificial
<220> FEATURE:
<223> OTHER INFORMATION: Synthetic

<400> SEQUENCE: 244
uccagcauca gugauuuugu uga                                        23

<210> SEQ ID NO 245
<211> LENGTH: 21
<212> TYPE: RNA
<213> ORGANISM: Artificial
<220> FEATURE:
<223> OTHER INFORMATION: Synthetic

<400> SEQUENCE: 245
ucccuguccu ccaggagcuc a                                          21

<210> SEQ ID NO 246
```

```
<211> LENGTH: 23
<212> TYPE: RNA
<213> ORGANISM: Artificial
<220> FEATURE:
<223> OTHER INFORMATION: Synthetic

<400> SEQUENCE: 246
uccgucucag uuacuuuaua gcc                                              23

<210> SEQ ID NO 247
<211> LENGTH: 24
<212> TYPE: RNA
<213> ORGANISM: Artificial
<220> FEATURE:
<223> OTHER INFORMATION: Synthetic

<400> SEQUENCE: 247
ucucacacag aaaucgcacc cguc                                             24

<210> SEQ ID NO 248
<211> LENGTH: 21
<212> TYPE: RNA
<213> ORGANISM: Artificial
<220> FEATURE:
<223> OTHER INFORMATION: Synthetic

<400> SEQUENCE: 248
ugcugacucc uaguccaggg c                                                21

<210> SEQ ID NO 249
<211> LENGTH: 23
<212> TYPE: RNA
<213> ORGANISM: Artificial
<220> FEATURE:
<223> OTHER INFORMATION: Synthetic

<400> SEQUENCE: 249
ugucugcccg caugccugcc ucu                                              23

<210> SEQ ID NO 250
<211> LENGTH: 23
<212> TYPE: RNA
<213> ORGANISM: Artificial
<220> FEATURE:
<223> OTHER INFORMATION: Synthetic

<400> SEQUENCE: 250
uggcaguguc uuagcugguu guu                                              23

<210> SEQ ID NO 251
<211> LENGTH: 23
<212> TYPE: RNA
<213> ORGANISM: Artificial
<220> FEATURE:
<223> OTHER INFORMATION: Synthetic

<400> SEQUENCE: 251
uaggcagugu cauuagcuga uug                                              23

<210> SEQ ID NO 252
<211> LENGTH: 23
<212> TYPE: RNA
<213> ORGANISM: Artificial
<220> FEATURE:
<223> OTHER INFORMATION: Synthetic

<400> SEQUENCE: 252
```

-continued aggcagugua guuagcugau ugc                                          23

<210> SEQ ID NO 253
<211> LENGTH: 22
<212> TYPE: RNA
<213> ORGANISM: Artificial
<220> FEATURE:
<223> OTHER INFORMATION: Synthetic

<400> SEQUENCE: 253
uuaucagaau cuccaggggu ac                                           22

<210> SEQ ID NO 254
<211> LENGTH: 22
<212> TYPE: RNA
<213> ORGANISM: Artificial
<220> FEATURE:
<223> OTHER INFORMATION: Synthetic

<400> SEQUENCE: 254
uaaugccccu aaaaauccuu au                                           22

<210> SEQ ID NO 255
<211> LENGTH: 22
<212> TYPE: RNA
<213> ORGANISM: Artificial
<220> FEATURE:
<223> OTHER INFORMATION: Synthetic

<400> SEQUENCE: 255
aauugcacuu uagcaauggu ga                                           22

<210> SEQ ID NO 256
<211> LENGTH: 22
<212> TYPE: RNA
<213> ORGANISM: Artificial
<220> FEATURE:
<223> OTHER INFORMATION: Synthetic

<400> SEQUENCE: 256
acauagagga aauuccacgu uu                                           22

<210> SEQ ID NO 257
<211> LENGTH: 21
<212> TYPE: RNA
<213> ORGANISM: Artificial
<220> FEATURE:
<223> OTHER INFORMATION: Synthetic

<400> SEQUENCE: 257
aauaauacau gguugaucuu u                                            21

<210> SEQ ID NO 258
<211> LENGTH: 22
<212> TYPE: RNA
<213> ORGANISM: Artificial
<220> FEATURE:
<223> OTHER INFORMATION: Synthetic

<400> SEQUENCE: 258
agaucgaccg uguuauauuc gc                                           22

<210> SEQ ID NO 259
<211> LENGTH: 21
<212> TYPE: RNA

```
<213> ORGANISM: Artificial
<220> FEATURE:
<223> OTHER INFORMATION: Synthetic

<400> SEQUENCE: 259
gccugcuggg guggaaccug g                                             21

<210> SEQ ID NO 260
<211> LENGTH: 21
<212> TYPE: RNA
<213> ORGANISM: Artificial
<220> FEATURE:
<223> OTHER INFORMATION: Synthetic

<400> SEQUENCE: 260
gugccgccau cuuuugagug u                                             21

<210> SEQ ID NO 261
<211> LENGTH: 23
<212> TYPE: RNA
<213> ORGANISM: Artificial
<220> FEATURE:
<223> OTHER INFORMATION: Synthetic

<400> SEQUENCE: 261
aaagugcugc gacauuugag cgu                                           23

<210> SEQ ID NO 262
<211> LENGTH: 22
<212> TYPE: RNA
<213> ORGANISM: Artificial
<220> FEATURE:
<223> OTHER INFORMATION: Synthetic

<400> SEQUENCE: 262
acucaaaaug ggggcgcuuu cc                                            22

<210> SEQ ID NO 263
<211> LENGTH: 22
<212> TYPE: RNA
<213> ORGANISM: Artificial
<220> FEATURE:
<223> OTHER INFORMATION: Synthetic

<400> SEQUENCE: 263
ggaaagcgcc cccauuuuga gu                                            22

<210> SEQ ID NO 264
<211> LENGTH: 22
<212> TYPE: RNA
<213> ORGANISM: Artificial
<220> FEATURE:
<223> OTHER INFORMATION: Synthetic

<400> SEQUENCE: 264
uuauaauaca accugauaag ug                                            22

<210> SEQ ID NO 265
<211> LENGTH: 22
<212> TYPE: RNA
<213> ORGANISM: Artificial
<220> FEATURE:
<223> OTHER INFORMATION: Synthetic

<400> SEQUENCE: 265
uuuguucguu cggcucgcgu ga                                            22
```

<210> SEQ ID NO 266
<211> LENGTH: 21
<212> TYPE: RNA
<213> ORGANISM: Artificial
<220> FEATURE:
<223> OTHER INFORMATION: Synthetic

<400> SEQUENCE: 266
gguagauucu ccuucuauga g                                                   21

<210> SEQ ID NO 267
<211> LENGTH: 22
<212> TYPE: RNA
<213> ORGANISM: Artificial
<220> FEATURE:
<223> OTHER INFORMATION: Synthetic

<400> SEQUENCE: 267
aucacacaaa ggcaacuuuu gu                                                  22

<210> SEQ ID NO 268
<211> LENGTH: 22
<212> TYPE: RNA
<213> ORGANISM: Artificial
<220> FEATURE:
<223> OTHER INFORMATION: Synthetic

<400> SEQUENCE: 268
cuccugacuc cagguccugu gu                                                  22

<210> SEQ ID NO 269
<211> LENGTH: 19
<212> TYPE: RNA
<213> ORGANISM: Artificial
<220> FEATURE:
<223> OTHER INFORMATION: Synthetic

<400> SEQUENCE: 269
ugguagacua uggaacgua                                                      19

<210> SEQ ID NO 270
<211> LENGTH: 22
<212> TYPE: RNA
<213> ORGANISM: Artificial
<220> FEATURE:
<223> OTHER INFORMATION: Synthetic

<400> SEQUENCE: 270
uauguaauau gguccacauc uu                                                  22

<210> SEQ ID NO 271
<211> LENGTH: 22
<212> TYPE: RNA
<213> ORGANISM: Artificial
<220> FEATURE:
<223> OTHER INFORMATION: Synthetic

<400> SEQUENCE: 271
ugguugacca uagaacaugc gc                                                  22

<210> SEQ ID NO 272
<211> LENGTH: 22
<212> TYPE: RNA
<213> ORGANISM: Artificial
<220> FEATURE:

```
<223> OTHER INFORMATION: Synthetic

<400> SEQUENCE: 272
uauacaaggg caagcucucu gu                                      22

<210> SEQ ID NO 273
<211> LENGTH: 22
<212> TYPE: RNA
<213> ORGANISM: Artificial
<220> FEATURE:
<223> OTHER INFORMATION: Synthetic

<400> SEQUENCE: 273
gaaguuguuc gugguggauu cg                                      22

<210> SEQ ID NO 274
<211> LENGTH: 22
<212> TYPE: RNA
<213> ORGANISM: Artificial
<220> FEATURE:
<223> OTHER INFORMATION: Synthetic

<400> SEQUENCE: 274
agaucagaag gugauugugg cu                                      22

<210> SEQ ID NO 275
<211> LENGTH: 20
<212> TYPE: RNA
<213> ORGANISM: Artificial
<220> FEATURE:
<223> OTHER INFORMATION: Synthetic

<400> SEQUENCE: 275
auuccuagaa auuguucaua                                         20

<210> SEQ ID NO 276
<211> LENGTH: 21
<212> TYPE: RNA
<213> ORGANISM: Artificial
<220> FEATURE:
<223> OTHER INFORMATION: Synthetic

<400> SEQUENCE: 276
aauauaacac agauggccug u                                       21

<210> SEQ ID NO 277
<211> LENGTH: 21
<212> TYPE: RNA
<213> ORGANISM: Artificial
<220> FEATURE:
<223> OTHER INFORMATION: Synthetic

<400> SEQUENCE: 277
uaguagaccg uauagcguac g                                       21

<210> SEQ ID NO 278
<211> LENGTH: 23
<212> TYPE: RNA
<213> ORGANISM: Artificial
<220> FEATURE:
<223> OTHER INFORMATION: Synthetic

<400> SEQUENCE: 278
acuucaccug guccacuagc cgu                                     23
```

```
<210> SEQ ID NO 279
<211> LENGTH: 22
<212> TYPE: RNA
<213> ORGANISM: Artificial
<220> FEATURE:
<223> OTHER INFORMATION: Synthetic

<400> SEQUENCE: 279
cuggacuuag ggucagaagg cc                                              22

<210> SEQ ID NO 280
<211> LENGTH: 22
<212> TYPE: RNA
<213> ORGANISM: Artificial
<220> FEATURE:
<223> OTHER INFORMATION: Synthetic

<400> SEQUENCE: 280
cuggacuugg agucagaagg cc                                              22

<210> SEQ ID NO 281
<211> LENGTH: 22
<212> TYPE: RNA
<213> ORGANISM: Artificial
<220> FEATURE:
<223> OTHER INFORMATION: Synthetic

<400> SEQUENCE: 281
agcucggucu gaggccccuc ag                                              22

<210> SEQ ID NO 282
<211> LENGTH: 22
<212> TYPE: RNA
<213> ORGANISM: Artificial
<220> FEATURE:
<223> OTHER INFORMATION: Synthetic

<400> SEQUENCE: 282
cagcagcaau ucauguuuug aa                                              22

<210> SEQ ID NO 283
<211> LENGTH: 23
<212> TYPE: RNA
<213> ORGANISM: Artificial
<220> FEATURE:
<223> OTHER INFORMATION: Synthetic

<400> SEQUENCE: 283
aaugacacga ucacucccgu uga                                             23

<210> SEQ ID NO 284
<211> LENGTH: 22
<212> TYPE: RNA
<213> ORGANISM: Artificial
<220> FEATURE:
<223> OTHER INFORMATION: Synthetic

<400> SEQUENCE: 284
uaauacuguc ugguaaaacc gu                                              22

<210> SEQ ID NO 285
<211> LENGTH: 23
<212> TYPE: RNA
<213> ORGANISM: Artificial
<220> FEATURE:
<223> OTHER INFORMATION: Synthetic
```

```
<400> SEQUENCE: 285
ucuuggagua ggucauuggg ugg                                            23

<210> SEQ ID NO 286
<211> LENGTH: 23
<212> TYPE: RNA
<213> ORGANISM: Artificial
<220> FEATURE:
<223> OTHER INFORMATION: Synthetic

<400> SEQUENCE: 286
ccacccaaug accuacucca aga                                            23

<210> SEQ ID NO 287
<211> LENGTH: 22
<212> TYPE: RNA
<213> ORGANISM: Artificial
<220> FEATURE:
<223> OTHER INFORMATION: Synthetic

<400> SEQUENCE: 287
aucaugaugg gcuccucggu gu                                             22

<210> SEQ ID NO 288
<211> LENGTH: 22
<212> TYPE: RNA
<213> ORGANISM: Artificial
<220> FEATURE:
<223> OTHER INFORMATION: Synthetic

<400> SEQUENCE: 288
uugcauaugu aggauguccc au                                             22

<210> SEQ ID NO 289
<211> LENGTH: 22
<212> TYPE: RNA
<213> ORGANISM: Artificial
<220> FEATURE:
<223> OTHER INFORMATION: Synthetic

<400> SEQUENCE: 289
uggcagugua uuguuagcug gu                                             22

<210> SEQ ID NO 290
<211> LENGTH: 22
<212> TYPE: RNA
<213> ORGANISM: Artificial
<220> FEATURE:
<223> OTHER INFORMATION: Synthetic

<400> SEQUENCE: 290
uuuuugcgau guguuccuaa ua                                             22

<210> SEQ ID NO 291
<211> LENGTH: 22
<212> TYPE: RNA
<213> ORGANISM: Artificial
<220> FEATURE:
<223> OTHER INFORMATION: Synthetic

<400> SEQUENCE: 291
uguuugcaga ggaaacugag ac                                             22

<210> SEQ ID NO 292
<211> LENGTH: 22
```

```
<212> TYPE: RNA
<213> ORGANISM: Artificial
<220> FEATURE:
<223> OTHER INFORMATION: Synthetic

<400> SEQUENCE: 292
gucucaguuu ccucugcaaa ca                                              22

<210> SEQ ID NO 293
<211> LENGTH: 22
<212> TYPE: RNA
<213> ORGANISM: Artificial
<220> FEATURE:
<223> OTHER INFORMATION: Synthetic

<400> SEQUENCE: 293
uaugugccuu uggacuacau cg                                              22

<210> SEQ ID NO 294
<211> LENGTH: 22
<212> TYPE: RNA
<213> ORGANISM: Artificial
<220> FEATURE:
<223> OTHER INFORMATION: Synthetic

<400> SEQUENCE: 294
gucauacacg gcucccucu cu                                               22

<210> SEQ ID NO 295
<211> LENGTH: 22
<212> TYPE: RNA
<213> ORGANISM: Artificial
<220> FEATURE:
<223> OTHER INFORMATION: Synthetic

<400> SEQUENCE: 295
agaggcuggc cgugaugaau uc                                              22

<210> SEQ ID NO 296
<211> LENGTH: 22
<212> TYPE: RNA
<213> ORGANISM: Artificial
<220> FEATURE:
<223> OTHER INFORMATION: Synthetic

<400> SEQUENCE: 296
aaucauacag ggacauccag uu                                              22

<210> SEQ ID NO 297
<211> LENGTH: 22
<212> TYPE: RNA
<213> ORGANISM: Artificial
<220> FEATURE:
<223> OTHER INFORMATION: Synthetic

<400> SEQUENCE: 297
aaucguacag ggucauccac uu                                              22

<210> SEQ ID NO 298
<211> LENGTH: 21
<212> TYPE: RNA
<213> ORGANISM: Artificial
<220> FEATURE:
<223> OTHER INFORMATION: Synthetic

<400> SEQUENCE: 298
```
cccagauaau ggcacucuca a                                              21

<210> SEQ ID NO 299
<211> LENGTH: 23
<212> TYPE: RNA
<213> ORGANISM: Artificial
<220> FEATURE:
<223> OTHER INFORMATION: Synthetic

<400> SEQUENCE: 299
agugacauca cauauacggc agc                                            23

<210> SEQ ID NO 300
<211> LENGTH: 22
<212> TYPE: RNA
<213> ORGANISM: Artificial
<220> FEATURE:
<223> OTHER INFORMATION: Synthetic

<400> SEQUENCE: 300
caaccuggag gacuccaugc ug                                             22

<210> SEQ ID NO 301
<211> LENGTH: 23
<212> TYPE: RNA
<213> ORGANISM: Artificial
<220> FEATURE:
<223> OTHER INFORMATION: Synthetic

<400> SEQUENCE: 301 agugggaac ccuuccauga gga                                             23

<210> SEQ ID NO 302
<211> LENGTH: 23
<212> TYPE: RNA
<213> ORGANISM: Artificial
<220> FEATURE:
<223> OTHER INFORMATION: Synthetic

<400> SEQUENCE: 302
aggaccugcg ggacaagauu cuu                                            23

<210> SEQ ID NO 303
<211> LENGTH: 22
<212> TYPE: RNA
<213> ORGANISM: Artificial
<220> FEATURE:
<223> OTHER INFORMATION: Synthetic

<400> SEQUENCE: 303
uuguacaugg uaggcuuuca uu                                             22

<210> SEQ ID NO 304
<211> LENGTH: 21
<212> TYPE: RNA
<213> ORGANISM: Artificial
<220> FEATURE:
<223> OTHER INFORMATION: Synthetic

<400> SEQUENCE: 304
ugaaggucua cugugugcca g                                              21

<210> SEQ ID NO 305
<211> LENGTH: 21
<212> TYPE: RNA
<213> ORGANISM: Artificial

```
<220> FEATURE:
<223> OTHER INFORMATION: Synthetic

<400> SEQUENCE: 305
ugaaggucua cugugugcca g                                            21

<210> SEQ ID NO 306
<211> LENGTH: 24
<212> TYPE: RNA
<213> ORGANISM: Artificial
<220> FEATURE:
<223> OTHER INFORMATION: Synthetic

<400> SEQUENCE: 306
ugaaacauac acgggaaacc ucuu                                         24

<210> SEQ ID NO 307
<211> LENGTH: 23
<212> TYPE: RNA
<213> ORGANISM: Artificial
<220> FEATURE:
<223> OTHER INFORMATION: Synthetic

<400> SEQUENCE: 307
aaacaaacau ggugcacuuc uuu                                          23

<210> SEQ ID NO 308
<211> LENGTH: 17
<212> TYPE: RNA
<213> ORGANISM: Artificial
<220> FEATURE:
<223> OTHER INFORMATION: Synthetic

<400> SEQUENCE: 308
auuacauggc caaucuc                                                 17

<210> SEQ ID NO 309
<211> LENGTH: 21
<212> TYPE: RNA
<213> ORGANISM: Artificial
<220> FEATURE:
<223> OTHER INFORMATION: Synthetic

<400> SEQUENCE: 309
cagcagcaca cugugguuug u                                            21

<210> SEQ ID NO 310
<211> LENGTH: 23
<212> TYPE: RNA
<213> ORGANISM: Artificial
<220> FEATURE:
<223> OTHER INFORMATION: Synthetic

<400> SEQUENCE: 310
uuucaagcca gggggcguuu uuc                                          23

<210> SEQ ID NO 311
<211> LENGTH: 23
<212> TYPE: RNA
<213> ORGANISM: Artificial
<220> FEATURE:
<223> OTHER INFORMATION: Synthetic

<400> SEQUENCE: 311
uuaagacuug cagugauguu uaa                                          23
```

```
<210> SEQ ID NO 312
<211> LENGTH: 22
<212> TYPE: RNA
<213> ORGANISM: Artificial
<220> FEATURE:
<223> OTHER INFORMATION: Synthetic

<400> SEQUENCE: 312
augcaccugg gcaaggauuc ug                                                  22

<210> SEQ ID NO 313
<211> LENGTH: 22
<212> TYPE: RNA
<213> ORGANISM: Artificial
<220> FEATURE:
<223> OTHER INFORMATION: Synthetic

<400> SEQUENCE: 313
aauccuuugu cccuggguga ga                                                  22

<210> SEQ ID NO 314
<211> LENGTH: 21
<212> TYPE: RNA
<213> ORGANISM: Artificial
<220> FEATURE:
<223> OTHER INFORMATION: Synthetic

<400> SEQUENCE: 314
auccuugcua ucugggugcu a                                                   21

<210> SEQ ID NO 315
<211> LENGTH: 23
<212> TYPE: RNA
<213> ORGANISM: Artificial
<220> FEATURE:
<223> OTHER INFORMATION: Synthetic

<400> SEQUENCE: 315
uagcagcggg aacaguucug cag                                                 23

<210> SEQ ID NO 316
<211> LENGTH: 21
<212> TYPE: RNA
<213> ORGANISM: Artificial
<220> FEATURE:
<223> OTHER INFORMATION: Synthetic

<400> SEQUENCE: 316
agacccuggu cugcacucua u                                                   21

<210> SEQ ID NO 317
<211> LENGTH: 22
<212> TYPE: RNA
<213> ORGANISM: Artificial
<220> FEATURE:
<223> OTHER INFORMATION: Synthetic

<400> SEQUENCE: 317
gucaacacuu gcugguuucc uc                                                  22

<210> SEQ ID NO 318
<211> LENGTH: 21
<212> TYPE: RNA
<213> ORGANISM: Artificial
<220> FEATURE:
<223> OTHER INFORMATION: Synthetic
```

```
<400> SEQUENCE: 318
uaaggcaccc uucugaguag a                                              21

<210> SEQ ID NO 319
<211> LENGTH: 21
<212> TYPE: RNA
<213> ORGANISM: Artificial
<220> FEATURE:
<223> OTHER INFORMATION: Synthetic

<400> SEQUENCE: 319
uuuugcaccu uuuggaguga a                                              21

<210> SEQ ID NO 320
<211> LENGTH: 23
<212> TYPE: RNA
<213> ORGANISM: Artificial
<220> FEATURE:
<223> OTHER INFORMATION: Synthetic

<400> SEQUENCE: 320
ugauuguagc cuuuuggagu aga                                            23

<210> SEQ ID NO 321
<211> LENGTH: 23
<212> TYPE: RNA
<213> ORGANISM: Artificial
<220> FEATURE:
<223> OTHER INFORMATION: Synthetic

<400> SEQUENCE: 321
ugauugguac gucugugggu aga                                            23

<210> SEQ ID NO 322
<211> LENGTH: 23
<212> TYPE: RNA
<213> ORGANISM: Artificial
<220> FEATURE:
<223> OTHER INFORMATION: Synthetic

<400> SEQUENCE: 322
uacucaggag aguggcaauc aca                                            23

<210> SEQ ID NO 323
<211> LENGTH: 21
<212> TYPE: RNA
<213> ORGANISM: Artificial
<220> FEATURE:
<223> OTHER INFORMATION: Synthetic

<400> SEQUENCE: 323
gugucuuuug cucugcaguc a                                              21

<210> SEQ ID NO 324
<211> LENGTH: 22
<212> TYPE: RNA
<213> ORGANISM: Artificial
<220> FEATURE:
<223> OTHER INFORMATION: Synthetic

<400> SEQUENCE: 324
aagugcuguc auagcugagg uc                                             22

<210> SEQ ID NO 325
```

```
<211> LENGTH: 23
<212> TYPE: RNA
<213> ORGANISM: Artificial
<220> FEATURE:
<223> OTHER INFORMATION: Synthetic

<400> SEQUENCE: 325
cacucagccu ugagggcacu uuc                                              23

<210> SEQ ID NO 326
<211> LENGTH: 22
<212> TYPE: RNA
<213> ORGANISM: Artificial
<220> FEATURE:
<223> OTHER INFORMATION: Synthetic

<400> SEQUENCE: 326
uucacaggga ggugucauuu au                                               22

<210> SEQ ID NO 327
<211> LENGTH: 20
<212> TYPE: RNA
<213> ORGANISM: Artificial
<220> FEATURE:
<223> OTHER INFORMATION: Synthetic

<400> SEQUENCE: 327
auugacacuu cugugaguag                                                  20

<210> SEQ ID NO 328
<211> LENGTH: 21
<212> TYPE: RNA
<213> ORGANISM: Artificial
<220> FEATURE:
<223> OTHER INFORMATION: Synthetic

<400> SEQUENCE: 328
gagugccuuc uuuuggagcg u                                                21

<210> SEQ ID NO 329
<211> LENGTH: 24
<212> TYPE: RNA
<213> ORGANISM: Artificial
<220> FEATURE:
<223> OTHER INFORMATION: Synthetic

<400> SEQUENCE: 329
uucuccaaaa gaaagcacuu ucug                                             24

<210> SEQ ID NO 330
<211> LENGTH: 18
<212> TYPE: RNA
<213> ORGANISM: Artificial
<220> FEATURE:
<223> OTHER INFORMATION: Synthetic

<400> SEQUENCE: 330
ugcuuccuuu cagagggu                                                    18

<210> SEQ ID NO 331
<211> LENGTH: 23
<212> TYPE: RNA
<213> ORGANISM: Artificial
<220> FEATURE:
<223> OTHER INFORMATION: Synthetic

<400> SEQUENCE: 331
```

```
aucgugcauc ccuuuagagu guu                                          23

<210> SEQ ID NO 332
<211> LENGTH: 23
<212> TYPE: RNA
<213> ORGANISM: Artificial
<220> FEATURE:
<223> OTHER INFORMATION: Synthetic

<400> SEQUENCE: 332
aacacucuaa agggaugcac gau                                          23

<210> SEQ ID NO 333
<211> LENGTH: 21
<212> TYPE: RNA
<213> ORGANISM: Artificial
<220> FEATURE:
<223> OTHER INFORMATION: Synthetic

<400> SEQUENCE: 333
aaagcgcuuc ccuuugcugg a                                            21

<210> SEQ ID NO 334
<211> LENGTH: 22
<212> TYPE: RNA
<213> ORGANISM: Artificial
<220> FEATURE:
<223> OTHER INFORMATION: Synthetic

<400> SEQUENCE: 334
caaagcgcuc cccuuuagag gu                                           22

<210> SEQ ID NO 335
<211> LENGTH: 22
<212> TYPE: RNA
<213> ORGANISM: Artificial
<220> FEATURE:
<223> OTHER INFORMATION: Synthetic

<400> SEQUENCE: 335
caaagcgcuu cucuuuagag ug                                           22

<210> SEQ ID NO 336
<211> LENGTH: 22
<212> TYPE: RNA
<213> ORGANISM: Artificial
<220> FEATURE:
<223> OTHER INFORMATION: Synthetic

<400> SEQUENCE: 336
cacucuaaag agaagcgcuu ug                                           22

<210> SEQ ID NO 337
<211> LENGTH: 21
<212> TYPE: RNA
<213> ORGANISM: Artificial
<220> FEATURE:
<223> OTHER INFORMATION: Synthetic

<400> SEQUENCE: 337
caaagcgcuu cccuuuggag c                                            21

<210> SEQ ID NO 338
<211> LENGTH: 22
<212> TYPE: RNA
```

```
<213> ORGANISM: Artificial
<220> FEATURE:
<223> OTHER INFORMATION: Synthetic

<400> SEQUENCE: 338
aaagcgcuuc ccuucagagu gu                                              22

<210> SEQ ID NO 339
<211> LENGTH: 21
<212> TYPE: RNA
<213> ORGANISM: Artificial
<220> FEATURE:
<223> OTHER INFORMATION: Synthetic

<400> SEQUENCE: 339
aaagcgcuuc ucuuuagagg a                                               21

<210> SEQ ID NO 340
<211> LENGTH: 21
<212> TYPE: RNA
<213> ORGANISM: Artificial
<220> FEATURE:
<223> OTHER INFORMATION: Synthetic

<400> SEQUENCE: 340
uccucuaaag agaagcgcuu u                                               21

<210> SEQ ID NO 341
<211> LENGTH: 23
<212> TYPE: RNA
<213> ORGANISM: Artificial
<220> FEATURE:
<223> OTHER INFORMATION: Synthetic

<400> SEQUENCE: 341
aaagugcauc cuuuuagagg uuu                                             23

<210> SEQ ID NO 342
<211> LENGTH: 22
<212> TYPE: RNA
<213> ORGANISM: Artificial
<220> FEATURE:
<223> OTHER INFORMATION: Synthetic

<400> SEQUENCE: 342
aaagugcauc uuuuuagagg au                                              22

<210> SEQ ID NO 343
<211> LENGTH: 23
<212> TYPE: RNA
<213> ORGANISM: Artificial
<220> FEATURE:
<223> OTHER INFORMATION: Synthetic

<400> SEQUENCE: 343
caaagugccu cccuuuagag ugu                                             23

<210> SEQ ID NO 344
<211> LENGTH: 22
<212> TYPE: RNA
<213> ORGANISM: Artificial
<220> FEATURE:
<223> OTHER INFORMATION: Synthetic

<400> SEQUENCE: 344
aaagugccuc cuuuuagagu gu                                              22
```

<210> SEQ ID NO 345
<211> LENGTH: 22
<212> TYPE: RNA
<213> ORGANISM: Artificial
<220> FEATURE:
<223> OTHER INFORMATION: Synthetic

<400> SEQUENCE: 345
acacucuaaa aggaggcacu uu                                              22

<210> SEQ ID NO 346
<211> LENGTH: 22
<212> TYPE: RNA
<213> ORGANISM: Artificial
<220> FEATURE:
<223> OTHER INFORMATION: Synthetic

<400> SEQUENCE: 346
aaagugcuuc ccuuuggacu gu                                              22

<210> SEQ ID NO 347
<211> LENGTH: 22
<212> TYPE: RNA
<213> ORGANISM: Artificial
<220> FEATURE:
<223> OTHER INFORMATION: Synthetic

<400> SEQUENCE: 347
acaguccaaa gggaagcacu uu                                              22

<210> SEQ ID NO 348
<211> LENGTH: 21
<212> TYPE: RNA
<213> ORGANISM: Artificial
<220> FEATURE:
<223> OTHER INFORMATION: Synthetic

<400> SEQUENCE: 348
aaagugcuuc cuuuuagagg g                                               21

<210> SEQ ID NO 349
<211> LENGTH: 23
<212> TYPE: RNA
<213> ORGANISM: Artificial
<220> FEATURE:
<223> OTHER INFORMATION: Synthetic

<400> SEQUENCE: 349
aaagugcuuc cuuuuagagg guu                                             23

<210> SEQ ID NO 350
<211> LENGTH: 23
<212> TYPE: RNA
<213> ORGANISM: Artificial
<220> FEATURE:
<223> OTHER INFORMATION: Synthetic

<400> SEQUENCE: 350
aaagugcuuc ucuuuggugg guu                                             23

<210> SEQ ID NO 351
<211> LENGTH: 23
<212> TYPE: RNA
<213> ORGANISM: Artificial
<220> FEATURE:

```
<223> OTHER INFORMATION: Synthetic

<400> SEQUENCE: 351
aacccaccaa agagaagcac uuu                                              23

<210> SEQ ID NO 352
<211> LENGTH: 21
<212> TYPE: RNA
<213> ORGANISM: Artificial
<220> FEATURE:
<223> OTHER INFORMATION: Synthetic

<400> SEQUENCE: 352
aaagugcuuc cuuuuugagg g                                                21

<210> SEQ ID NO 353
<211> LENGTH: 22
<212> TYPE: RNA
<213> ORGANISM: Artificial
<220> FEATURE:
<223> OTHER INFORMATION: Synthetic

<400> SEQUENCE: 353
acaaagugcu ucccuuuaga gu                                               22

<210> SEQ ID NO 354
<211> LENGTH: 22
<212> TYPE: RNA
<213> ORGANISM: Artificial
<220> FEATURE:
<223> OTHER INFORMATION: Synthetic

<400> SEQUENCE: 354
aacgcacuuc ccuuuagagu gu                                               22

<210> SEQ ID NO 355
<211> LENGTH: 23
<212> TYPE: RNA
<213> ORGANISM: Artificial
<220> FEATURE:
<223> OTHER INFORMATION: Synthetic

<400> SEQUENCE: 355
aaaaugguuc ccuuuagagu guu                                              23

<210> SEQ ID NO 356
<211> LENGTH: 21
<212> TYPE: RNA
<213> ORGANISM: Artificial
<220> FEATURE:
<223> OTHER INFORMATION: Synthetic

<400> SEQUENCE: 356
aacgcgcuuc ccuauagagg g                                                21

<210> SEQ ID NO 357
<211> LENGTH: 21
<212> TYPE: RNA
<213> ORGANISM: Artificial
<220> FEATURE:
<223> OTHER INFORMATION: Synthetic

<400> SEQUENCE: 357
gaaggcgcuu cccuuuggag u                                                21
```

```
<210> SEQ ID NO 358
<211> LENGTH: 21
<212> TYPE: RNA
<213> ORGANISM: Artificial
<220> FEATURE:
<223> OTHER INFORMATION: Synthetic

<400> SEQUENCE: 358
acuccaaagg gaagcgccuu c                                              21

<210> SEQ ID NO 359
<211> LENGTH: 21
<212> TYPE: RNA
<213> ORGANISM: Artificial
<220> FEATURE:
<223> OTHER INFORMATION: Synthetic

<400> SEQUENCE: 359
cuccagaggg augcacuuuc u                                              21

<210> SEQ ID NO 360
<211> LENGTH: 21
<212> TYPE: RNA
<213> ORGANISM: Artificial
<220> FEATURE:
<223> OTHER INFORMATION: Synthetic

<400> SEQUENCE: 360
agaaagugca ucccucugga g                                              21

<210> SEQ ID NO 361
<211> LENGTH: 24
<212> TYPE: RNA
<213> ORGANISM: Artificial
<220> FEATURE:
<223> OTHER INFORMATION: Synthetic

<400> SEQUENCE: 361
cucuugaggg aagcacuuuc uguu                                           24

<210> SEQ ID NO 362
<211> LENGTH: 24
<212> TYPE: RNA
<213> ORGANISM: Artificial
<220> FEATURE:
<223> OTHER INFORMATION: Synthetic

<400> SEQUENCE: 362
aacagaaagu gcuucccuca agag                                           24

<210> SEQ ID NO 363
<211> LENGTH: 24
<212> TYPE: RNA
<213> ORGANISM: Artificial
<220> FEATURE:
<223> OTHER INFORMATION: Synthetic

<400> SEQUENCE: 363
cucuagaggg aagcgcuuuc uguu                                           24

<210> SEQ ID NO 364
<211> LENGTH: 21
<212> TYPE: RNA
<213> ORGANISM: Artificial
<220> FEATURE:
<223> OTHER INFORMATION: Synthetic
```

```
<400> SEQUENCE: 364
cugcaaaggg aagcccuuuc u                                              21

<210> SEQ ID NO 365
<211> LENGTH: 22
<212> TYPE: RNA
<213> ORGANISM: Artificial
<220> FEATURE:
<223> OTHER INFORMATION: Synthetic

<400> SEQUENCE: 365
ggagaaauua uccuuggugu gu                                             22

<210> SEQ ID NO 366
<211> LENGTH: 22
<212> TYPE: RNA
<213> ORGANISM: Artificial
<220> FEATURE:
<223> OTHER INFORMATION: Synthetic

<400> SEQUENCE: 366
ucggggauca ucaugucacg ag                                             22

<210> SEQ ID NO 367
<211> LENGTH: 22
<212> TYPE: RNA
<213> ORGANISM: Artificial
<220> FEATURE:
<223> OTHER INFORMATION: Synthetic

<400> SEQUENCE: 367
ggcuggcucg cgaugucugu uu                                             22

<210> SEQ ID NO 368
<211> LENGTH: 21
<212> TYPE: RNA
<213> ORGANISM: Artificial
<220> FEATURE:
<223> OTHER INFORMATION: Synthetic

<400> SEQUENCE: 368
cacgcucaug cacacaccca c                                              21

<210> SEQ ID NO 369
<211> LENGTH: 19
<212> TYPE: RNA
<213> ORGANISM: Artificial
<220> FEATURE:
<223> OTHER INFORMATION: Synthetic

<400> SEQUENCE: 369
ugggcguauc uguaugcua                                                 19

<210> SEQ ID NO 370
<211> LENGTH: 25
<212> TYPE: RNA
<213> ORGANISM: Artificial
<220> FEATURE:
<223> OTHER INFORMATION: Synthetic

<400> SEQUENCE: 370
cccaucuggg guggccugug acuuu                                          25

<210> SEQ ID NO 371
<211> LENGTH: 22
```

```
<212> TYPE: RNA
<213> ORGANISM: Artificial
<220> FEATURE:
<223> OTHER INFORMATION: Synthetic

<400> SEQUENCE: 371
uacgucaucg uugucaucgu ca                                              22

<210> SEQ ID NO 372
<211> LENGTH: 20
<212> TYPE: RNA
<213> ORGANISM: Artificial
<220> FEATURE:
<223> OTHER INFORMATION: Synthetic

<400> SEQUENCE: 372
ucuaguaaga guggcagucg                                                 20

<210> SEQ ID NO 373
<211> LENGTH: 22
<212> TYPE: RNA
<213> ORGANISM: Artificial
<220> FEATURE:
<223> OTHER INFORMATION: Synthetic

<400> SEQUENCE: 373
uggugggccg cagaacaugu gc                                              22

<210> SEQ ID NO 374
<211> LENGTH: 22
<212> TYPE: RNA
<213> ORGANISM: Artificial
<220> FEATURE:
<223> OTHER INFORMATION: Synthetic

<400> SEQUENCE: 374
uggaagacua gugauuuugu ug                                              22

<210> SEQ ID NO 375
<211> LENGTH: 23
<212> TYPE: RNA
<213> ORGANISM: Artificial
<220> FEATURE:
<223> OTHER INFORMATION: Synthetic

<400> SEQUENCE: 375
ucuuugguua ucuagcugua uga                                             23

<210> SEQ ID NO 376
<211> LENGTH: 21
<212> TYPE: RNA
<213> ORGANISM: Artificial
<220> FEATURE:
<223> OTHER INFORMATION: Synthetic

<400> SEQUENCE: 376
uauugcacuu gucccggccu g                                               21

<210> SEQ ID NO 377
<211> LENGTH: 22
<212> TYPE: RNA
<213> ORGANISM: Artificial
<220> FEATURE:
<223> OTHER INFORMATION: Synthetic

<400> SEQUENCE: 377
```
aaagugcugu ucgugcaggu ag         22

<210> SEQ ID NO 378
<211> LENGTH: 22
<212> TYPE: RNA
<213> ORGANISM: Artificial
<220> FEATURE:
<223> OTHER INFORMATION: Synthetic

<400> SEQUENCE: 378
uucaacgggu auuuauugag ca         22

<210> SEQ ID NO 379
<211> LENGTH: 22
<212> TYPE: RNA
<213> ORGANISM: Artificial
<220> FEATURE:
<223> OTHER INFORMATION: Synthetic

<400> SEQUENCE: 379
uuuggcacua gcacauuuuu gc         22

<210> SEQ ID NO 380
<211> LENGTH: 22
<212> TYPE: RNA
<213> ORGANISM: Artificial
<220> FEATURE:
<223> OTHER INFORMATION: Synthetic

<400> SEQUENCE: 380
ugagguagua aguuguauug uu         22

<210> SEQ ID NO 381
<211> LENGTH: 22
<212> TYPE: RNA
<213> ORGANISM: Artificial
<220> FEATURE:
<223> OTHER INFORMATION: Synthetic

<400> SEQUENCE: 381
aacccguaga uccgaucuug ug         22

<210> SEQ ID NO 382
<211> LENGTH: 22
<212> TYPE: RNA
<213> ORGANISM: Artificial
<220> FEATURE:
<223> OTHER INFORMATION: Synthetic

<400> SEQUENCE: 382
cacccguaga accgaccuug cg         22

<210> SEQ ID NO 383
<211> LENGTH: 23
<212> TYPE: RNA
<213> ORGANISM: Artificial
<220> FEATURE:
<223> OTHER INFORMATION: Synthetic

<400> SEQUENCE: 383
ucauacagcu agauaaccaa aga         23

<210> SEQ ID NO 384
<211> LENGTH: 21
<212> TYPE: RNA
<213> ORGANISM: Artificial

```
<220> FEATURE:
<223> OTHER INFORMATION: Synthetic

<400> SEQUENCE: 384
acuaugcaac cuacuaccuc u                                              21

<210> SEQ ID NO 385
<211> LENGTH: 22
<212> TYPE: RNA
<213> ORGANISM: Artificial
<220> FEATURE:
<223> OTHER INFORMATION: Synthetic

<400> SEQUENCE: 385
uacaguacug ugauagcuga ag                                             22

<210> SEQ ID NO 386
<211> LENGTH: 22
<212> TYPE: RNA
<213> ORGANISM: Artificial
<220> FEATURE:
<223> OTHER INFORMATION: Synthetic

<400> SEQUENCE: 386
caaagugcua acagugcagg ua                                             22

<210> SEQ ID NO 387
<211> LENGTH: 22
<212> TYPE: RNA
<213> ORGANISM: Artificial
<220> FEATURE:
<223> OTHER INFORMATION: Synthetic

<400> SEQUENCE: 387
aagcccuuac cccaaaaagc au                                             22

<210> SEQ ID NO 388
<211> LENGTH: 22
<212> TYPE: RNA
<213> ORGANISM: Artificial
<220> FEATURE:
<223> OTHER INFORMATION: Synthetic

<400> SEQUENCE: 388
cuaccauagg guaaaaccac ug                                             22

<210> SEQ ID NO 389
<211> LENGTH: 21
<212> TYPE: RNA
<213> ORGANISM: Artificial
<220> FEATURE:
<223> OTHER INFORMATION: Synthetic

<400> SEQUENCE: 389
cuagacugag gcuccuugag g                                              21

<210> SEQ ID NO 390
<211> LENGTH: 22
<212> TYPE: RNA
<213> ORGANISM: Artificial
<220> FEATURE:
<223> OTHER INFORMATION: Synthetic

<400> SEQUENCE: 390
uuaaugcuaa uugugauagg gg                                             22
```

<210> SEQ ID NO 391
<211> LENGTH: 21
<212> TYPE: RNA
<213> ORGANISM: Artificial
<220> FEATURE:
<223> OTHER INFORMATION: Synthetic

<400> SEQUENCE: 391
acugcaguga gggcacuugu a                                              21

<210> SEQ ID NO 392
<211> LENGTH: 18
<212> TYPE: RNA
<213> ORGANISM: Artificial
<220> FEATURE:
<223> OTHER INFORMATION: Synthetic

<400> SEQUENCE: 392
cugaccuaug aauugaca                                                  18

<210> SEQ ID NO 393
<211> LENGTH: 23
<212> TYPE: RNA
<213> ORGANISM: Artificial
<220> FEATURE:
<223> OTHER INFORMATION: Synthetic

<400> SEQUENCE: 393
cccaguguuu agacuaccug uuc                                            23

<210> SEQ ID NO 394
<211> LENGTH: 21
<212> TYPE: RNA
<213> ORGANISM: Artificial
<220> FEATURE:
<223> OTHER INFORMATION: Synthetic

<400> SEQUENCE: 394
uacucaguaa ggcauuguuc u                                              21

<210> SEQ ID NO 395
<211> LENGTH: 22
<212> TYPE: RNA
<213> ORGANISM: Artificial
<220> FEATURE:
<223> OTHER INFORMATION: Synthetic

<400> SEQUENCE: 395
agagguauag cgcaugggaa ga                                             22

<210> SEQ ID NO 396
<211> LENGTH: 23
<212> TYPE: RNA
<213> ORGANISM: Artificial
<220> FEATURE:
<223> OTHER INFORMATION: Synthetic

<400> SEQUENCE: 396
gcuucuccug gcucuccucc cuc                                            23

<210> SEQ ID NO 397
<211> LENGTH: 22
<212> TYPE: RNA
<213> ORGANISM: Artificial
<220> FEATURE:
<223> OTHER INFORMATION: Synthetic

```
<400> SEQUENCE: 397
uucccuuugu cauccuuugc cu                                    22

<210> SEQ ID NO 398
<211> LENGTH: 21
<212> TYPE: RNA
<213> ORGANISM: Artificial
<220> FEATURE:
<223> OTHER INFORMATION: Synthetic

<400> SEQUENCE: 398
augaccuaug auuugacaga c                                     21

<210> SEQ ID NO 399
<211> LENGTH: 24
<212> TYPE: RNA
<213> ORGANISM: Artificial
<220> FEATURE:
<223> OTHER INFORMATION: Synthetic

<400> SEQUENCE: 399
uacugcauca ggaacugacu ggau                                  24

<210> SEQ ID NO 400
<211> LENGTH: 23
<212> TYPE: RNA
<213> ORGANISM: Artificial
<220> FEATURE:
<223> OTHER INFORMATION: Synthetic

<400> SEQUENCE: 400
cucaaacuau gggggcacuu uuu                                   23

<210> SEQ ID NO 401
<211> LENGTH: 23
<212> TYPE: RNA
<213> ORGANISM: Artificial
<220> FEATURE:
<223> OTHER INFORMATION: Synthetic

<400> SEQUENCE: 401
aaagugcuuc cacuuugugu gcc                                   23

<210> SEQ ID NO 402
<211> LENGTH: 22
<212> TYPE: RNA
<213> ORGANISM: Artificial
<220> FEATURE:
<223> OTHER INFORMATION: Synthetic

<400> SEQUENCE: 402
caucaaagug gaggcccucu cu                                    22

<210> SEQ ID NO 403
<211> LENGTH: 23
<212> TYPE: RNA
<213> ORGANISM: Artificial
<220> FEATURE:
<223> OTHER INFORMATION: Synthetic

<400> SEQUENCE: 403
aagugccgcc agguuuugag ugu                                   23

<210> SEQ ID NO 404
```

```
<211> LENGTH: 22
<212> TYPE: RNA
<213> ORGANISM: Artificial
<220> FEATURE:
<223> OTHER INFORMATION: Synthetic

<400> SEQUENCE: 404
acucaaacug ggggcucuuu ug                                              22

<210> SEQ ID NO 405
<211> LENGTH: 22
<212> TYPE: RNA
<213> ORGANISM: Artificial
<220> FEATURE:
<223> OTHER INFORMATION: Synthetic

<400> SEQUENCE: 405
agugccgcag aguuguagu gu                                               22

<210> SEQ ID NO 406
<211> LENGTH: 22
<212> TYPE: RNA
<213> ORGANISM: Artificial
<220> FEATURE:
<223> OTHER INFORMATION: Synthetic

<400> SEQUENCE: 406
aaagugcuuc ccuuugugu gu                                               22

<210> SEQ ID NO 407
<211> LENGTH: 23
<212> TYPE: RNA
<213> ORGANISM: Artificial
<220> FEATURE:
<223> OTHER INFORMATION: Synthetic

<400> SEQUENCE: 407
aaagugcuac uacuuuugag ucu                                             23

<210> SEQ ID NO 408
<211> LENGTH: 21
<212> TYPE: RNA
<213> ORGANISM: Artificial
<220> FEATURE:
<223> OTHER INFORMATION: Synthetic

<400> SEQUENCE: 408
auguaugugu gcaugugcau g                                               21

<210> SEQ ID NO 409
<211> LENGTH: 22
<212> TYPE: RNA
<213> ORGANISM: Artificial
<220> FEATURE:
<223> OTHER INFORMATION: Synthetic

<400> SEQUENCE: 409
ggcagaggag ggcuguucuu cc                                              22

<210> SEQ ID NO 410
<211> LENGTH: 22
<212> TYPE: RNA
<213> ORGANISM: Artificial
<220> FEATURE:
<223> OTHER INFORMATION: Synthetic

<400> SEQUENCE: 410
```
uaugcaaggg caagcucucu uc                                    22

<210> SEQ ID NO 411
<211> LENGTH: 20
<212> TYPE: RNA
<213> ORGANISM: Artificial
<220> FEATURE:
<223> OTHER INFORMATION: Synthetic

<400> SEQUENCE: 411
aaacaugaag cgcugcaaca                                       20

<210> SEQ ID NO 412
<211> LENGTH: 23
<212> TYPE: RNA
<213> ORGANISM: Artificial
<220> FEATURE:
<223> OTHER INFORMATION: Synthetic

<400> SEQUENCE: 412
ccuaguaggu gcucaguaag ugu                                   23

<210> SEQ ID NO 413
<211> LENGTH: 22
<212> TYPE: RNA
<213> ORGANISM: Artificial
<220> FEATURE:
<223> OTHER INFORMATION: Synthetic

<400> SEQUENCE: 413
aacacaccca gcuaaccuuu uu                                    22

<210> SEQ ID NO 414
<211> LENGTH: 23
<212> TYPE: RNA
<213> ORGANISM: Artificial
<220> FEATURE:
<223> OTHER INFORMATION: Synthetic

<400> SEQUENCE: 414
gcaaagcaca gggccugcag aga                                   23

<210> SEQ ID NO 415
<211> LENGTH: 23
<212> TYPE: RNA
<213> ORGANISM: Artificial
<220> FEATURE:
<223> OTHER INFORMATION: Synthetic

<400> SEQUENCE: 415
uucagcuccu auaugaugcc uuu                                   23

<210> SEQ ID NO 416
<211> LENGTH: 21
<212> TYPE: RNA
<213> ORGANISM: Artificial
<220> FEATURE:
<223> OTHER INFORMATION: Synthetic

<400> SEQUENCE: 416
ucgaucgguc ggucggucag u                                     21

<210> SEQ ID NO 417
<211> LENGTH: 23
<212> TYPE: RNA

```
<213> ORGANISM: Artificial
<220> FEATURE:
<223> OTHER INFORMATION: Synthetic

<400> SEQUENCE: 417
ugaucuagcc aaagccugac ugu                                              23

<210> SEQ ID NO 418
<211> LENGTH: 21
<212> TYPE: RNA
<213> ORGANISM: Artificial
<220> FEATURE:
<223> OTHER INFORMATION: Synthetic

<400> SEQUENCE: 418
ugcugacccc uaguccagug c                                                21

<210> SEQ ID NO 419
<211> LENGTH: 23
<212> TYPE: RNA
<213> ORGANISM: Artificial
<220> FEATURE:
<223> OTHER INFORMATION: Synthetic

<400> SEQUENCE: 419
ugucugcccg agugccugcc ucu                                              23

<210> SEQ ID NO 420
<211> LENGTH: 23
<212> TYPE: RNA
<213> ORGANISM: Artificial
<220> FEATURE:
<223> OTHER INFORMATION: Synthetic

<400> SEQUENCE: 420
uaggcagugu aauuagcuga uug                                              23

<210> SEQ ID NO 421
<211> LENGTH: 23
<212> TYPE: RNA
<213> ORGANISM: Artificial
<220> FEATURE:
<223> OTHER INFORMATION: Synthetic

<400> SEQUENCE: 421
uucacaaagc ccauacacuu uca                                              23

<210> SEQ ID NO 422
<211> LENGTH: 24
<212> TYPE: RNA
<213> ORGANISM: Artificial
<220> FEATURE:
<223> OTHER INFORMATION: Synthetic

<400> SEQUENCE: 422
ucccugagga gcccuuugag ccug                                             24

<210> SEQ ID NO 423
<211> LENGTH: 21
<212> TYPE: RNA
<213> ORGANISM: Artificial
<220> FEATURE:
<223> OTHER INFORMATION: Synthetic

<400> SEQUENCE: 423
aucguagagg aaaauccacg u                                                21
```

<210> SEQ ID NO 424
<211> LENGTH: 22
<212> TYPE: RNA
<213> ORGANISM: Artificial
<220> FEATURE:
<223> OTHER INFORMATION: Synthetic

<400> SEQUENCE: 424
aucauagagg aacauccacu uu                                              22

<210> SEQ ID NO 425
<211> LENGTH: 22
<212> TYPE: RNA
<213> ORGANISM: Artificial
<220> FEATURE:
<223> OTHER INFORMATION: Synthetic

<400> SEQUENCE: 425
uauguaguau gguccacauc uu                                              22

<210> SEQ ID NO 426
<211> LENGTH: 22
<212> TYPE: RNA
<213> ORGANISM: Artificial
<220> FEATURE:
<223> OTHER INFORMATION: Synthetic

<400> SEQUENCE: 426
agaucagaag gugacugugg cu                                              22

<210> SEQ ID NO 427
<211> LENGTH: 20
<212> TYPE: RNA
<213> ORGANISM: Artificial
<220> FEATURE:
<223> OTHER INFORMATION: Synthetic

<400> SEQUENCE: 427
auuccuagaa auuguucaca                                                 20

<210> SEQ ID NO 428
<211> LENGTH: 23
<212> TYPE: RNA
<213> ORGANISM: Artificial
<220> FEATURE:
<223> OTHER INFORMATION: Synthetic

<400> SEQUENCE: 428
gaauguugcu cggugaaccc cuu                                             23

<210> SEQ ID NO 429
<211> LENGTH: 23
<212> TYPE: RNA
<213> ORGANISM: Artificial
<220> FEATURE:
<223> OTHER INFORMATION: Synthetic

<400> SEQUENCE: 429
aacacggucc acuaacccuc agu                                             23

<210> SEQ ID NO 430
<211> LENGTH: 22
<212> TYPE: RNA
<213> ORGANISM: Artificial
<220> FEATURE:

<223> OTHER INFORMATION: Synthetic

<400> SEQUENCE: 430
cagcagcaau ucauguuuug ga                                              22

<210> SEQ ID NO 431
<211> LENGTH: 22
<212> TYPE: RNA
<213> ORGANISM: Artificial
<220> FEATURE:
<223> OTHER INFORMATION: Synthetic

<400> SEQUENCE: 431
uaauacuguc ugguaaugcc gu                                              22

<210> SEQ ID NO 432
<211> LENGTH: 21
<212> TYPE: RNA
<213> ORGANISM: Artificial
<220> FEATURE:
<223> OTHER INFORMATION: Synthetic

<400> SEQUENCE: 432
uggaagacuu gugauuuugu u                                               21

<210> SEQ ID NO 433
<211> LENGTH: 22
<212> TYPE: RNA
<213> ORGANISM: Artificial
<220> FEATURE:
<223> OTHER INFORMATION: Synthetic

<400> SEQUENCE: 433
ccucaaggag ccucagucua gu                                              22

<210> SEQ ID NO 434
<211> LENGTH: 23
<212> TYPE: RNA
<213> ORGANISM: Artificial
<220> FEATURE:
<223> OTHER INFORMATION: Synthetic

<400> SEQUENCE: 434
uaaagugcuu auagugcagg uag                                             23

<210> SEQ ID NO 435
<211> LENGTH: 23
<212> TYPE: RNA
<213> ORGANISM: Artificial
<220> FEATURE:
<223> OTHER INFORMATION: Synthetic

<400> SEQUENCE: 435
auguaugugu gcauguaugc aug                                             23

<210> SEQ ID NO 436
<211> LENGTH: 19
<212> TYPE: RNA
<213> ORGANISM: Artificial
<220> FEATURE:
<223> OTHER INFORMATION: Synthetic

<400> SEQUENCE: 436
ccuugagggg caugagggu                                                  19

```
<210> SEQ ID NO 437
<211> LENGTH: 20
<212> TYPE: RNA
<213> ORGANISM: Artificial
<220> FEATURE:
<223> OTHER INFORMATION: Synthetic

<400> SEQUENCE: 437
guggugugcu aguuacuuuu                                              20

<210> SEQ ID NO 438
<211> LENGTH: 21
<212> TYPE: RNA
<213> ORGANISM: Artificial
<220> FEATURE:
<223> OTHER INFORMATION: Synthetic

<400> SEQUENCE: 438
ucacccuucc auaucuaguc u                                            21

<210> SEQ ID NO 439
<211> LENGTH: 20
<212> TYPE: RNA
<213> ORGANISM: Artificial
<220> FEATURE:
<223> OTHER INFORMATION: Synthetic

<400> SEQUENCE: 439
ucucccuccg ugugcccaga                                              20

<210> SEQ ID NO 440
<211> LENGTH: 23
<212> TYPE: RNA
<213> ORGANISM: Artificial
<220> FEATURE:
<223> OTHER INFORMATION: Synthetic

<400> SEQUENCE: 440
ugaucuagcc aaagccugac cgu                                          23

<210> SEQ ID NO 441
<211> LENGTH: 23
<212> TYPE: RNA
<213> ORGANISM: Artificial
<220> FEATURE:
<223> OTHER INFORMATION: Synthetic

<400> SEQUENCE: 441
ugucugccug agugccugcc ucu                                          23

<210> SEQ ID NO 442
<211> LENGTH: 19
<212> TYPE: RNA
<213> ORGANISM: Artificial
<220> FEATURE:
<223> OTHER INFORMATION: Synthetic

<400> SEQUENCE: 442
ugucccucug ggucgccca                                               19

<210> SEQ ID NO 443
<211> LENGTH: 22
<212> TYPE: RNA
<213> ORGANISM: Artificial
<220> FEATURE:
<223> OTHER INFORMATION: Synthetic
```

<400> SEQUENCE: 443
cagcccugcu gcuuaaccu cu                                          22

<210> SEQ ID NO 444
<211> LENGTH: 21
<212> TYPE: RNA
<213> ORGANISM: Artificial
<220> FEATURE:
<223> OTHER INFORMATION: Synthetic

<400> SEQUENCE: 444
agaguaguag guugcauagu a                                          21

<210> SEQ ID NO 445
<211> LENGTH: 21
<212> TYPE: RNA
<213> ORGANISM: Artificial
<220> FEATURE:
<223> OTHER INFORMATION: Synthetic

<400> SEQUENCE: 445
ggccucauua aauguuuguu g                                          21

<210> SEQ ID NO 446
<211> LENGTH: 21
<212> TYPE: RNA
<213> ORGANISM: Artificial
<220> FEATURE:
<223> OTHER INFORMATION: Synthetic

<400> SEQUENCE: 446
aacaaaauca cuagucuucc a                                          21

<210> SEQ ID NO 447
<211> LENGTH: 22
<212> TYPE: RNA
<213> ORGANISM: Artificial
<220> FEATURE:
<223> OTHER INFORMATION: Synthetic

<400> SEQUENCE: 447
cuauacgacc ugcugccuuu cu                                         22

<210> SEQ ID NO 448
<211> LENGTH: 22
<212> TYPE: RNA
<213> ORGANISM: Artificial
<220> FEATURE:
<223> OTHER INFORMATION: Synthetic

<400> SEQUENCE: 448
cuauacggcc uccuagcuuu cc                                         22

<210> SEQ ID NO 449
<211> LENGTH: 22
<212> TYPE: RNA
<213> ORGANISM: Artificial
<220> FEATURE:
<223> OTHER INFORMATION: Synthetic

<400> SEQUENCE: 449
caagcuugua ucuauaggua ug                                         22

<210> SEQ ID NO 450
<211> LENGTH: 22

```
<212> TYPE: RNA
<213> ORGANISM: Artificial
<220> FEATURE:
<223> OTHER INFORMATION: Synthetic

<400> SEQUENCE: 450
caguuaucac agugcugaug cu                                              22

<210> SEQ ID NO 451
<211> LENGTH: 22
<212> TYPE: RNA
<213> ORGANISM: Artificial
<220> FEATURE:
<223> OTHER INFORMATION: Synthetic

<400> SEQUENCE: 451
ccgcacugug gguacuugcu gc                                              22

<210> SEQ ID NO 452
<211> LENGTH: 22
<212> TYPE: RNA
<213> ORGANISM: Artificial
<220> FEATURE:
<223> OTHER INFORMATION: Synthetic

<400> SEQUENCE: 452
acagauucga uucuagggga au                                              22

<210> SEQ ID NO 453
<211> LENGTH: 24
<212> TYPE: RNA
<213> ORGANISM: Artificial
<220> FEATURE:
<223> OTHER INFORMATION: Synthetic

<400> SEQUENCE: 453
ucccugagac ccuuuaaccu guga                                            24

<210> SEQ ID NO 454
<211> LENGTH: 22
<212> TYPE: RNA
<213> ORGANISM: Artificial
<220> FEATURE:
<223> OTHER INFORMATION: Synthetic

<400> SEQUENCE: 454
ucacaaguca ggcucuuggg ac                                              22

<210> SEQ ID NO 455
<211> LENGTH: 21
<212> TYPE: RNA
<213> ORGANISM: Artificial
<220> FEATURE:
<223> OTHER INFORMATION: Synthetic

<400> SEQUENCE: 455
cauuauuacu uuugguacgc g                                               21

<210> SEQ ID NO 456
<211> LENGTH: 22
<212> TYPE: RNA
<213> ORGANISM: Artificial
<220> FEATURE:
<223> OTHER INFORMATION: Synthetic

<400> SEQUENCE: 456
```
ucggauccgu cugagcuugg cu                                    22

<210> SEQ ID NO 457
<211> LENGTH: 22
<212> TYPE: RNA
<213> ORGANISM: Artificial
<220> FEATURE:
<223> OTHER INFORMATION: Synthetic

<400> SEQUENCE: 457
aagcccuuac cccaaaaagc au                                    22

<210> SEQ ID NO 458
<211> LENGTH: 23
<212> TYPE: RNA
<213> ORGANISM: Artificial
<220> FEATURE:
<223> OTHER INFORMATION: Synthetic

<400> SEQUENCE: 458
uauggcuuuu uauuccuaug uga                                   23

<210> SEQ ID NO 459
<211> LENGTH: 23
<212> TYPE: RNA
<213> ORGANISM: Artificial
<220> FEATURE:
<223> OTHER INFORMATION: Synthetic

<400> SEQUENCE: 459
acuccauuug uuugaugau gga                                    23

<210> SEQ ID NO 460
<211> LENGTH: 22
<212> TYPE: RNA
<213> ORGANISM: Artificial
<220> FEATURE:
<223> OTHER INFORMATION: Synthetic

<400> SEQUENCE: 460
caucaucguc ucaaugagu cu                                     22

<210> SEQ ID NO 461
<211> LENGTH: 22
<212> TYPE: RNA
<213> ORGANISM: Artificial
<220> FEATURE:
<223> OTHER INFORMATION: Synthetic

<400> SEQUENCE: 461
ucuacagugc acgugucucc ag                                    22

<210> SEQ ID NO 462
<211> LENGTH: 21
<212> TYPE: RNA
<213> ORGANISM: Artificial
<220> FEATURE:
<223> OTHER INFORMATION: Synthetic

<400> SEQUENCE: 462
uaccacaggg uagaaccacg g                                     21

<210> SEQ ID NO 463
<211> LENGTH: 22
<212> TYPE: RNA
<213> ORGANISM: Artificial

```
<220> FEATURE:
<223> OTHER INFORMATION: Synthetic

<400> SEQUENCE: 463
cagugguuuu acccuauggu ag                                             22

<210> SEQ ID NO 464
<211> LENGTH: 22
<212> TYPE: RNA
<213> ORGANISM: Artificial
<220> FEATURE:
<223> OTHER INFORMATION: Synthetic

<400> SEQUENCE: 464
caucuuccag uacaguguug ga                                             22

<210> SEQ ID NO 465
<211> LENGTH: 23
<212> TYPE: RNA
<213> ORGANISM: Artificial
<220> FEATURE:
<223> OTHER INFORMATION: Synthetic

<400> SEQUENCE: 465
uguaguguuu ccuacuuuau gga                                            23

<210> SEQ ID NO 466
<211> LENGTH: 21
<212> TYPE: RNA
<213> ORGANISM: Artificial
<220> FEATURE:
<223> OTHER INFORMATION: Synthetic

<400> SEQUENCE: 466
cauaaaguag aaagcacuac u                                              21

<210> SEQ ID NO 467
<211> LENGTH: 22
<212> TYPE: RNA
<213> ORGANISM: Artificial
<220> FEATURE:
<223> OTHER INFORMATION: Synthetic

<400> SEQUENCE: 467
ggugcagugc ugcaucucug gu                                             22

<210> SEQ ID NO 468
<211> LENGTH: 20
<212> TYPE: RNA
<213> ORGANISM: Artificial
<220> FEATURE:
<223> OTHER INFORMATION: Synthetic

<400> SEQUENCE: 468
uacaguauag augauguacu                                                20

<210> SEQ ID NO 469
<211> LENGTH: 22
<212> TYPE: RNA
<213> ORGANISM: Artificial
<220> FEATURE:
<223> OTHER INFORMATION: Synthetic

<400> SEQUENCE: 469
ggauaucauc auauacugua ag                                             22
```

```
<210> SEQ ID NO 470
<211> LENGTH: 22
<212> TYPE: RNA
<213> ORGANISM: Artificial
<220> FEATURE:
<223> OTHER INFORMATION: Synthetic

<400> SEQUENCE: 470
ggauuccugg aaauacuguu cu                                                22

<210> SEQ ID NO 471
<211> LENGTH: 22
<212> TYPE: RNA
<213> ORGANISM: Artificial
<220> FEATURE:
<223> OTHER INFORMATION: Synthetic

<400> SEQUENCE: 471
ugagaacuga auuccauagg cu                                                22

<210> SEQ ID NO 472
<211> LENGTH: 21
<212> TYPE: RNA
<213> ORGANISM: Artificial
<220> FEATURE:
<223> OTHER INFORMATION: Synthetic

<400> SEQUENCE: 472
cuagacugaa gcuccuugag g                                                 21

<210> SEQ ID NO 473
<211> LENGTH: 22
<212> TYPE: RNA
<213> ORGANISM: Artificial
<220> FEATURE:
<223> OTHER INFORMATION: Synthetic

<400> SEQUENCE: 473
aaucauacac gguugaccua uu                                                22

<210> SEQ ID NO 474
<211> LENGTH: 22
<212> TYPE: RNA
<213> ORGANISM: Artificial
<220> FEATURE:
<223> OTHER INFORMATION: Synthetic

<400> SEQUENCE: 474
cgaaucauua uuugcugcuc ua                                                22

<210> SEQ ID NO 475
<211> LENGTH: 23
<212> TYPE: RNA
<213> ORGANISM: Artificial
<220> FEATURE:
<223> OTHER INFORMATION: Synthetic

<400> SEQUENCE: 475
caaagugcuu acagugcagg uag                                               23

<210> SEQ ID NO 476
<211> LENGTH: 22
<212> TYPE: RNA
<213> ORGANISM: Artificial
<220> FEATURE:
<223> OTHER INFORMATION: Synthetic
```

```
<400> SEQUENCE: 476
aacauucaac cgucgguga gu                                                 22

<210> SEQ ID NO 477
<211> LENGTH: 23
<212> TYPE: RNA
<213> ORGANISM: Artificial
<220> FEATURE:
<223> OTHER INFORMATION: Synthetic

<400> SEQUENCE: 477
aacauucauu guugucggug ggu                                               23

<210> SEQ ID NO 478
<211> LENGTH: 22
<212> TYPE: RNA
<213> ORGANISM: Artificial
<220> FEATURE:
<223> OTHER INFORMATION: Synthetic

<400> SEQUENCE: 478
gugaauuacc gaagggccau aa                                                22

<210> SEQ ID NO 479
<211> LENGTH: 22
<212> TYPE: RNA
<213> ORGANISM: Artificial
<220> FEATURE:
<223> OTHER INFORMATION: Synthetic

<400> SEQUENCE: 479
ugggucuuug cgggcgagau ga                                                22

<210> SEQ ID NO 480
<211> LENGTH: 22
<212> TYPE: RNA
<213> ORGANISM: Artificial
<220> FEATURE:
<223> OTHER INFORMATION: Synthetic

<400> SEQUENCE: 480
ccaauauugg cugugcugcu cc                                                22

<210> SEQ ID NO 481
<211> LENGTH: 22
<212> TYPE: RNA
<213> ORGANISM: Artificial
<220> FEATURE:
<223> OTHER INFORMATION: Synthetic

<400> SEQUENCE: 481
uucaccaccu ucuccaccca gc                                                22

<210> SEQ ID NO 482
<211> LENGTH: 23
<212> TYPE: RNA
<213> ORGANISM: Artificial
<220> FEATURE:
<223> OTHER INFORMATION: Synthetic

<400> SEQUENCE: 482
cccaguguuc agacuaccug uuc                                               23

<210> SEQ ID NO 483
```

```
<211> LENGTH: 22
<212> TYPE: RNA
<213> ORGANISM: Artificial
<220> FEATURE:
<223> OTHER INFORMATION: Synthetic

<400> SEQUENCE: 483
acaguagucu gcacauuggu ua                                                  22

<210> SEQ ID NO 484
<211> LENGTH: 23
<212> TYPE: RNA
<213> ORGANISM: Artificial
<220> FEATURE:
<223> OTHER INFORMATION: Synthetic

<400> SEQUENCE: 484
cccaguguuu agacuaucug uuc                                                 23

<210> SEQ ID NO 485
<211> LENGTH: 22
<212> TYPE: RNA
<213> ORGANISM: Artificial
<220> FEATURE:
<223> OTHER INFORMATION: Synthetic

<400> SEQUENCE: 485
acugcauuau gagcacuuaa ag                                                  22

<210> SEQ ID NO 486
<211> LENGTH: 21
<212> TYPE: RNA
<213> ORGANISM: Artificial
<220> FEATURE:
<223> OTHER INFORMATION: Synthetic

<400> SEQUENCE: 486
caacaccagu cgaugggcug u                                                   21

<210> SEQ ID NO 487
<211> LENGTH: 21
<212> TYPE: RNA
<213> ORGANISM: Artificial
<220> FEATURE:
<223> OTHER INFORMATION: Synthetic

<400> SEQUENCE: 487
uaacagucuc cagucacggc c                                                   21

<210> SEQ ID NO 488
<211> LENGTH: 22
<212> TYPE: RNA
<213> ORGANISM: Artificial
<220> FEATURE:
<223> OTHER INFORMATION: Synthetic

<400> SEQUENCE: 488
ugccugucua cacuugcugu gc                                                  22

<210> SEQ ID NO 489
<211> LENGTH: 22
<212> TYPE: RNA
<213> ORGANISM: Artificial
<220> FEATURE:
<223> OTHER INFORMATION: Synthetic

<400> SEQUENCE: 489
```

-continued ugccuacuga gcugauauca gu    22

<210> SEQ ID NO 490
<211> LENGTH: 22
<212> TYPE: RNA
<213> ORGANISM: Artificial
<220> FEATURE:
<223> OTHER INFORMATION: Synthetic

<400> SEQUENCE: 490 ccguucucc auuacuuggc uc    22

<210> SEQ ID NO 491
<211> LENGTH: 22
<212> TYPE: RNA
<213> ORGANISM: Artificial
<220> FEATURE:
<223> OTHER INFORMATION: Synthetic

<400> SEQUENCE: 491
cacuagauug ugagcuccug ga    22

<210> SEQ ID NO 492
<211> LENGTH: 22
<212> TYPE: RNA
<213> ORGANISM: Artificial
<220> FEATURE:
<223> OTHER INFORMATION: Synthetic

<400> SEQUENCE: 492
aaggagcuca cagucuauug ag    22

<210> SEQ ID NO 493
<211> LENGTH: 22
<212> TYPE: RNA
<213> ORGANISM: Artificial
<220> FEATURE:
<223> OTHER INFORMATION: Synthetic

<400> SEQUENCE: 493
acugauuucu uuugguguuc ag    22

<210> SEQ ID NO 494
<211> LENGTH: 24
<212> TYPE: RNA
<213> ORGANISM: Artificial
<220> FEATURE:
<223> OTHER INFORMATION: Synthetic

<400> SEQUENCE: 494
gcugguuuca uauggugguu uaga    24

<210> SEQ ID NO 495
<211> LENGTH: 22
<212> TYPE: RNA
<213> ORGANISM: Artificial
<220> FEATURE:
<223> OTHER INFORMATION: Synthetic

<400> SEQUENCE: 495
cugguuucac augguggcuu ag    22

<210> SEQ ID NO 496
<211> LENGTH: 22
<212> TYPE: RNA

```
<213> ORGANISM: Artificial
<220> FEATURE:
<223> OTHER INFORMATION: Synthetic

<400> SEQUENCE: 496
ugaccgauuu cuccuggugu uc                                              22

<210> SEQ ID NO 497
<211> LENGTH: 22
<212> TYPE: RNA
<213> ORGANISM: Artificial
<220> FEATURE:
<223> OTHER INFORMATION: Synthetic

<400> SEQUENCE: 497
uguaaacauc cucgacugga ag                                              22

<210> SEQ ID NO 498
<211> LENGTH: 22
<212> TYPE: RNA
<213> ORGANISM: Artificial
<220> FEATURE:
<223> OTHER INFORMATION: Synthetic

<400> SEQUENCE: 498
cuuucagucg gauguuugca gc                                              22

<210> SEQ ID NO 499
<211> LENGTH: 22
<212> TYPE: RNA
<213> ORGANISM: Artificial
<220> FEATURE:
<223> OTHER INFORMATION: Synthetic

<400> SEQUENCE: 499
cugggaggug gauguuuacu uc                                              22

<210> SEQ ID NO 500
<211> LENGTH: 22
<212> TYPE: RNA
<213> ORGANISM: Artificial
<220> FEATURE:
<223> OTHER INFORMATION: Synthetic

<400> SEQUENCE: 500
cugggagaag gcuguuuacu cu                                              22

<210> SEQ ID NO 501
<211> LENGTH: 22
<212> TYPE: RNA
<213> ORGANISM: Artificial
<220> FEATURE:
<223> OTHER INFORMATION: Synthetic

<400> SEQUENCE: 501
ugcuaugcca acauauugcc au                                              22

<210> SEQ ID NO 502
<211> LENGTH: 22
<212> TYPE: RNA
<213> ORGANISM: Artificial
<220> FEATURE:
<223> OTHER INFORMATION: Synthetic

<400> SEQUENCE: 502
uauugcacau uacuaaguug ca                                              22
```

<210> SEQ ID NO 503
<211> LENGTH: 22
<212> TYPE: RNA
<213> ORGANISM: Artificial
<220> FEATURE:
<223> OTHER INFORMATION: Synthetic

<400> SEQUENCE: 503
aacacaccug guuaaccucu uu                                              22

<210> SEQ ID NO 504
<211> LENGTH: 23
<212> TYPE: RNA
<213> ORGANISM: Artificial
<220> FEATURE:
<223> OTHER INFORMATION: Synthetic

<400> SEQUENCE: 504
gcaaagcaca cggccugcag aga                                             23

<210> SEQ ID NO 505
<211> LENGTH: 22
<212> TYPE: RNA
<213> ORGANISM: Artificial
<220> FEATURE:
<223> OTHER INFORMATION: Synthetic

<400> SEQUENCE: 505
cuccuauaug augccuuucu uc                                              22

<210> SEQ ID NO 506
<211> LENGTH: 21
<212> TYPE: RNA
<213> ORGANISM: Artificial
<220> FEATURE:
<223> OTHER INFORMATION: Synthetic

<400> SEQUENCE: 506
gaacggcuuc auacaggagu u                                               21

<210> SEQ ID NO 507
<211> LENGTH: 22
<212> TYPE: RNA
<213> ORGANISM: Artificial
<220> FEATURE:
<223> OTHER INFORMATION: Synthetic

<400> SEQUENCE: 507
gcugacuccu aguccagggc uc                                              22

<210> SEQ ID NO 508
<211> LENGTH: 22
<212> TYPE: RNA
<213> ORGANISM: Artificial
<220> FEATURE:
<223> OTHER INFORMATION: Synthetic

<400> SEQUENCE: 508
uuaucagaau cuccaggggu ac                                              22

<210> SEQ ID NO 509
<211> LENGTH: 22
<212> TYPE: RNA
<213> ORGANISM: Artificial
<220> FEATURE:

<223> OTHER INFORMATION: Synthetic

<400> SEQUENCE: 509
agaucgaccg uguuauauuc gc                                    22

<210> SEQ ID NO 510
<211> LENGTH: 22
<212> TYPE: RNA
<213> ORGANISM: Artificial
<220> FEATURE:
<223> OTHER INFORMATION: Synthetic

<400> SEQUENCE: 510
uuauaauaca accugauaag ug                                    22

<210> SEQ ID NO 511
<211> LENGTH: 22
<212> TYPE: RNA
<213> ORGANISM: Artificial
<220> FEATURE:
<223> OTHER INFORMATION: Synthetic

<400> SEQUENCE: 511
auauaauaca accugcuaag ug                                    22

<210> SEQ ID NO 512
<211> LENGTH: 22
<212> TYPE: RNA
<213> ORGANISM: Artificial
<220> FEATURE:
<223> OTHER INFORMATION: Synthetic

<400> SEQUENCE: 512
cuuagcaggu uguauuauca uu                                    22

<210> SEQ ID NO 513
<211> LENGTH: 22
<212> TYPE: RNA
<213> ORGANISM: Artificial
<220> FEATURE:
<223> OTHER INFORMATION: Synthetic

<400> SEQUENCE: 513
uuuguucguu cggcucgcgu ga                                    22

<210> SEQ ID NO 514
<211> LENGTH: 22
<212> TYPE: RNA
<213> ORGANISM: Artificial
<220> FEATURE:
<223> OTHER INFORMATION: Synthetic

<400> SEQUENCE: 514
aucauagagg aaaauccaug uu                                    22

<210> SEQ ID NO 515
<211> LENGTH: 21
<212> TYPE: RNA
<213> ORGANISM: Artificial
<220> FEATURE:
<223> OTHER INFORMATION: Synthetic

<400> SEQUENCE: 515
aacauagagg aaauuccacg u                                     21

```
<210> SEQ ID NO 516
<211> LENGTH: 22
<212> TYPE: RNA
<213> ORGANISM: Artificial
<220> FEATURE:
<223> OTHER INFORMATION: Synthetic

<400> SEQUENCE: 516
agagguugcc cuuggugaau uc                                               22

<210> SEQ ID NO 517
<211> LENGTH: 21
<212> TYPE: RNA
<213> ORGANISM: Artificial
<220> FEATURE:
<223> OTHER INFORMATION: Synthetic

<400> SEQUENCE: 517
aauauaacac agauggccug u                                                21

<210> SEQ ID NO 518
<211> LENGTH: 21
<212> TYPE: RNA
<213> ORGANISM: Artificial
<220> FEATURE:
<223> OTHER INFORMATION: Synthetic

<400> SEQUENCE: 518
caaaacguga ggcgcugcua u                                                21

<210> SEQ ID NO 519
<211> LENGTH: 22
<212> TYPE: RNA
<213> ORGANISM: Artificial
<220> FEATURE:
<223> OTHER INFORMATION: Synthetic

<400> SEQUENCE: 519
aucgggaaug ucguguccgc cc                                               22

<210> SEQ ID NO 520
<211> LENGTH: 22
<212> TYPE: RNA
<213> ORGANISM: Artificial
<220> FEATURE:
<223> OTHER INFORMATION: Synthetic

<400> SEQUENCE: 520
caggucgucu ugcagggcuu cu                                               22

<210> SEQ ID NO 521
<211> LENGTH: 22
<212> TYPE: RNA
<213> ORGANISM: Artificial
<220> FEATURE:
<223> OTHER INFORMATION: Synthetic

<400> SEQUENCE: 521
uuuugcgaug uguuccuaau au                                               22

<210> SEQ ID NO 522
<211> LENGTH: 22
<212> TYPE: RNA
<213> ORGANISM: Artificial
<220> FEATURE:
<223> OTHER INFORMATION: Synthetic
```

```
<400> SEQUENCE: 522
aaaccguuac cauuacugag uu                                            22

<210> SEQ ID NO 523
<211> LENGTH: 21
<212> TYPE: RNA
<213> ORGANISM: Artificial
<220> FEATURE:
<223> OTHER INFORMATION: Synthetic

<400> SEQUENCE: 523
gcaguccaug ggcauauaca c                                             21

<210> SEQ ID NO 524
<211> LENGTH: 22
<212> TYPE: RNA
<213> ORGANISM: Artificial
<220> FEATURE:
<223> OTHER INFORMATION: Synthetic

<400> SEQUENCE: 524
uaugugccuu uggacuacau cg                                            22

<210> SEQ ID NO 525
<211> LENGTH: 21
<212> TYPE: RNA
<213> ORGANISM: Artificial
<220> FEATURE:
<223> OTHER INFORMATION: Synthetic

<400> SEQUENCE: 525
ucacuccucu ccucccgucu u                                             21

<210> SEQ ID NO 526
<211> LENGTH: 22
<212> TYPE: RNA
<213> ORGANISM: Artificial
<220> FEATURE:
<223> OTHER INFORMATION: Synthetic

<400> SEQUENCE: 526
uccuguacug agcugccccg ag                                            22

<210> SEQ ID NO 527
<211> LENGTH: 21
<212> TYPE: RNA
<213> ORGANISM: Artificial
<220> FEATURE:
<223> OTHER INFORMATION: Synthetic

<400> SEQUENCE: 527
uugaaaggcu auuucuuggu c                                             21

<210> SEQ ID NO 528
<211> LENGTH: 22
<212> TYPE: RNA
<213> ORGANISM: Artificial
<220> FEATURE:
<223> OTHER INFORMATION: Synthetic

<400> SEQUENCE: 528
caaccuggag gacuccaugc ug                                            22

<210> SEQ ID NO 529
<211> LENGTH: 21
```

```
<212> TYPE: RNA
<213> ORGANISM: Artificial
<220> FEATURE:
<223> OTHER INFORMATION: Synthetic

<400> SEQUENCE: 529
cagcagcaca cugugguuug u                                              21

<210> SEQ ID NO 530
<211> LENGTH: 21
<212> TYPE: RNA
<213> ORGANISM: Artificial
<220> FEATURE:
<223> OTHER INFORMATION: Synthetic

<400> SEQUENCE: 530
uuaagacuug cagugauguu u                                              21

<210> SEQ ID NO 531
<211> LENGTH: 22
<212> TYPE: RNA
<213> ORGANISM: Artificial
<220> FEATURE:
<223> OTHER INFORMATION: Synthetic

<400> SEQUENCE: 531
aauccuuugu cccuggguga ga                                             22

<210> SEQ ID NO 532
<211> LENGTH: 22
<212> TYPE: RNA
<213> ORGANISM: Artificial
<220> FEATURE:
<223> OTHER INFORMATION: Synthetic

<400> SEQUENCE: 532
gggagccagg aaguauugau gu                                             22

<210> SEQ ID NO 533
<211> LENGTH: 22
<212> TYPE: RNA
<213> ORGANISM: Artificial
<220> FEATURE:
<223> OTHER INFORMATION: Synthetic

<400> SEQUENCE: 533
aagugcuguc auagcugagg uc                                             22

<210> SEQ ID NO 534
<211> LENGTH: 22
<212> TYPE: RNA
<213> ORGANISM: Artificial
<220> FEATURE:
<223> OTHER INFORMATION: Synthetic

<400> SEQUENCE: 534
uucucaagga ggugucguuu au                                             22

<210> SEQ ID NO 535
<211> LENGTH: 22
<212> TYPE: RNA
<213> ORGANISM: Artificial
<220> FEATURE:
<223> OTHER INFORMATION: Synthetic

<400> SEQUENCE: 535
```
ccucuagaug gaagcacugu cu					22

<210> SEQ ID NO 536
<211> LENGTH: 22
<212> TYPE: RNA
<213> ORGANISM: Artificial
<220> FEATURE:
<223> OTHER INFORMATION: Synthetic

<400> SEQUENCE: 536
ggagaaauua uccuuggugu gu					22

<210> SEQ ID NO 537
<211> LENGTH: 22
<212> TYPE: RNA
<213> ORGANISM: Artificial
<220> FEATURE:
<223> OTHER INFORMATION: Synthetic

<400> SEQUENCE: 537
ugugacagau ugauaacuga aa					22

<210> SEQ ID NO 538
<211> LENGTH: 22
<212> TYPE: RNA
<213> ORGANISM: Artificial
<220> FEATURE:
<223> OTHER INFORMATION: Synthetic

<400> SEQUENCE: 538
aaacauucgc ggugcacuuc uu					22

<210> SEQ ID NO 539
<211> LENGTH: 22
<212> TYPE: RNA
<213> ORGANISM: Artificial
<220> FEATURE:
<223> OTHER INFORMATION: Synthetic

<400> SEQUENCE: 539
cacgcucaug cacacaccca ca					22

<210> SEQ ID NO 540
<211> LENGTH: 23
<212> TYPE: RNA
<213> ORGANISM: Artificial
<220> FEATURE:
<223> OTHER INFORMATION: Synthetic

<400> SEQUENCE: 540
gacacgggcg acagcugcgg ccc					23

<210> SEQ ID NO 541
<211> LENGTH: 22
<212> TYPE: RNA
<213> ORGANISM: Artificial
<220> FEATURE:
<223> OTHER INFORMATION: Synthetic

<400> SEQUENCE: 541
augcugacau auuuacuaga gg					22

<210> SEQ ID NO 542
<211> LENGTH: 22
<212> TYPE: RNA
<213> ORGANISM: Artificial

```
<220> FEATURE:
<223> OTHER INFORMATION: Synthetic

<400> SEQUENCE: 542
guucucccaa cguaagccca gc                                              22

<210> SEQ ID NO 543
<211> LENGTH: 22
<212> TYPE: RNA
<213> ORGANISM: Artificial
<220> FEATURE:
<223> OTHER INFORMATION: Synthetic

<400> SEQUENCE: 543
aguauucugu accagggaag gu                                              22

<210> SEQ ID NO 544
<211> LENGTH: 21
<212> TYPE: RNA
<213> ORGANISM: Artificial
<220> FEATURE:
<223> OTHER INFORMATION: Synthetic

<400> SEQUENCE: 544
aggaggcagc gcucucagga c                                               21

<210> SEQ ID NO 545
<211> LENGTH: 22
<212> TYPE: RNA
<213> ORGANISM: Artificial
<220> FEATURE:
<223> OTHER INFORMATION: Synthetic

<400> SEQUENCE: 545
uaugucugcu gaccaucacc uu                                              22

<210> SEQ ID NO 546
<211> LENGTH: 22
<212> TYPE: RNA
<213> ORGANISM: Artificial
<220> FEATURE:
<223> OTHER INFORMATION: Synthetic

<400> SEQUENCE: 546
uggugggccg cagaacaugu gc                                              22

<210> SEQ ID NO 547
<211> LENGTH: 22
<212> TYPE: RNA
<213> ORGANISM: Artificial
<220> FEATURE:
<223> OTHER INFORMATION: Synthetic

<400> SEQUENCE: 547
auaauacaug guuaaccucu uu                                              22

<210> SEQ ID NO 548
<211> LENGTH: 21
<212> TYPE: RNA
<213> ORGANISM: Artificial
<220> FEATURE:
<223> OTHER INFORMATION: Synthetic

<400> SEQUENCE: 548
aauauuauac agucaaccuc u                                               21
```

```
<210> SEQ ID NO 549
<211> LENGTH: 22
<212> TYPE: RNA
<213> ORGANISM: Artificial
<220> FEATURE:
<223> OTHER INFORMATION: Synthetic

<400> SEQUENCE: 549
ugcggggcua gggcuaacag ca                                              22

<210> SEQ ID NO 550
<211> LENGTH: 22
<212> TYPE: RNA
<213> ORGANISM: Artificial
<220> FEATURE:
<223> OTHER INFORMATION: Synthetic

<400> SEQUENCE: 550
acuccagccc cacagccuca gc                                              22

<210> SEQ ID NO 551
<211> LENGTH: 28
<212> TYPE: RNA
<213> ORGANISM: Artificial
<220> FEATURE:
<223> OTHER INFORMATION: Synthetic

<400> SEQUENCE: 551
ucacaaugcu gacacucaaa cugcugac                                        28

<210> SEQ ID NO 552
<211> LENGTH: 21
<212> TYPE: RNA
<213> ORGANISM: Artificial
<220> FEATURE:
<223> OTHER INFORMATION: Synthetic

<400> SEQUENCE: 552
gcaggaacuu gugagucucc u                                               21

<210> SEQ ID NO 553
<211> LENGTH: 22
<212> TYPE: RNA
<213> ORGANISM: Artificial
<220> FEATURE:
<223> OTHER INFORMATION: Synthetic

<400> SEQUENCE: 553
uccauuacac uacccugccu cu                                              22

<210> SEQ ID NO 554
<211> LENGTH: 21
<212> TYPE: RNA
<213> ORGANISM: Artificial
<220> FEATURE:
<223> OTHER INFORMATION: Synthetic

<400> SEQUENCE: 554
cgcgggugcu uacugacccu u                                               21

<210> SEQ ID NO 555
<211> LENGTH: 23
<212> TYPE: RNA
<213> ORGANISM: Artificial
<220> FEATURE:
<223> OTHER INFORMATION: Synthetic
```

```
<400> SEQUENCE: 555
cgggucggag uuagcucaag cgg                                              23

<210> SEQ ID NO 556
<211> LENGTH: 21
<212> TYPE: RNA
<213> ORGANISM: Artificial
<220> FEATURE:
<223> OTHER INFORMATION: Synthetic

<400> SEQUENCE: 556
uuaauaucgg acaaccauug u                                                21

<210> SEQ ID NO 557
<211> LENGTH: 22
<212> TYPE: RNA
<213> ORGANISM: Artificial
<220> FEATURE:
<223> OTHER INFORMATION: Synthetic

<400> SEQUENCE: 557
acugcugagc uagcacuucc cg                                               22

<210> SEQ ID NO 558
<211> LENGTH: 21
<212> TYPE: RNA
<213> ORGANISM: Artificial
<220> FEATURE:
<223> OTHER INFORMATION: Synthetic

<400> SEQUENCE: 558
aaggcagggc ccccgcuccc c                                                21

<210> SEQ ID NO 559
<211> LENGTH: 22
<212> TYPE: RNA
<213> ORGANISM: Artificial
<220> FEATURE:
<223> OTHER INFORMATION: Synthetic

<400> SEQUENCE: 559
aaauuauugu acaucggaug ag                                               22

<210> SEQ ID NO 560
<211> LENGTH: 23
<212> TYPE: RNA
<213> ORGANISM: Artificial
<220> FEATURE:
<223> OTHER INFORMATION: Synthetic

<400> SEQUENCE: 560
uuuggcacua gcacauuuuu gcu                                              23

<210> SEQ ID NO 561
<211> LENGTH: 22
<212> TYPE: RNA
```

```
<213> ORGANISM: Artificial
<220> FEATURE:
<223> OTHER INFORMATION: Synthetic

<400> SEQUENCE: 561
caagcucgcu ucuauggguc ug                                              22

<210> SEQ ID NO 562
<211> LENGTH: 22
<212> TYPE: RNA
<213> ORGANISM: Artificial
<220> FEATURE:
<223> OTHER INFORMATION: Synthetic

<400> SEQUENCE: 562
caagcucgug ucugugguc cg                                               22
```